(12) United States Patent
Kim et al.

(10) Patent No.: US 12,029,739 B2
(45) Date of Patent: Jul. 9, 2024

(54) SHP2 INHIBITOR AND USE THEREOF

(71) Applicant: KANAPH THERAPEUTICS INC., Seoul (KR)

(72) Inventors: Miyeon Kim, Yongin-si (KR); Dohyun Park, Seoul (KR); Dongsu Kim, Hwaseong-si (KR); Kyeongjin Yoon, Seoul (KR); Sungpil Choi, Anyang-si (KR); Sang Kyun Lim, Seoul (KR); Eu Ddeum Chung, Seongnam-si (KR); Mijung Lee, Hwaseong-si (KR); Dahye Jeon, Suwon-si (KR); Soyeon Jang, Suwon-si (KR); Kyungik Lee, Incheon (KR); Jinhwan Kim, Hwaseong-si (KR); Eunji Kim, Seoul (KR); Jieun Min, Suwon-si (KR); Kangwoo Lee, Osan-si (KR); Jakyung Yoo, Yongin-si (KR)

(73) Assignee: KANAPH THERAPEUTICS INC., Seoul (KR)

( * ) Notice: Subject to any disclaimer, the term of this patent is extended or adjusted under 35 U.S.C. 154(b) by 0 days.

(21) Appl. No.: 18/407,400

(22) Filed: Jan. 8, 2024

(65) Prior Publication Data

US 2024/0189306 A1    Jun. 13, 2024

Related U.S. Application Data

(63) Continuation-in-part of application No. PCT/KR2022/009980, filed on Jul. 8, 2022.

(30) Foreign Application Priority Data

| Jul. 9, 2021 | (KR) | ......................... 10-2021-0090239 |
| Jul. 9, 2021 | (KR) | ......................... 10-2021-0090244 |
| Mar. 14, 2022 | (KR) | ......................... 10-2022-0031603 |

(51) Int. Cl.
| *A61K 31/497* | (2006.01) |
| *A61K 31/506* | (2006.01) |
| *A61K 31/517* | (2006.01) |
| *A61K 31/53* | (2006.01) |
| *A61K 31/551* | (2006.01) |
| *C07D 401/04* | (2006.01) |
| *C07D 401/14* | (2006.01) |
| *C07D 405/14* | (2006.01) |
| *C07D 471/10* | (2006.01) |
| *C07D 491/107* | (2006.01) |
| *C07D 519/00* | (2006.01) |

(52) U.S. Cl.
CPC .......... *A61K 31/497* (2013.01); *A61K 31/506* (2013.01); *A61K 31/517* (2013.01); *A61K 31/53* (2013.01); *A61K 31/551* (2013.01); *C07D 401/04* (2013.01); *C07D 401/14* (2013.01); *C07D 405/14* (2013.01); *C07D 471/10* (2013.01); *C07D 491/107* (2013.01); *C07D 519/00* (2013.01)

(58) Field of Classification Search
None
See application file for complete search history.

(56) References Cited

FOREIGN PATENT DOCUMENTS

| KR | 10-2019-0015756 A | 2/2019 |
| KR | 10-2019-0140931 A | 12/2019 |
| KR | 10-2020-0070295 A | 6/2020 |
| KR | 10-2021-0075110 A | 6/2021 |
| WO | WO 2017211303 A1 | 12/2017 |
| WO | WO 2018172984 A1 | 9/2018 |
| WO | WO 2019075265 A1 | 4/2019 |
| WO | WO 2020073949 A1 | 4/2020 |
| WO | WO 2021043077 A1 | 3/2021 |

OTHER PUBLICATIONS

International Search Report and Written Opinion, dated Oct. 19, 2022, for International Application No. PCT/KR2022/009980. (w/ English Translation) (24 pages).

*Primary Examiner* — Joseph R Kosack
*Assistant Examiner* — Jed A Kucharczk
(74) *Attorney, Agent, or Firm* — Seed IP Law Group LLP

(57) ABSTRACT

The present invention relates to an inhibitor of SHP2, a pharmaceutical composition for preventing or treating a disease related to SHP2 comprising the same, a method for treating and preventing a disease using the same, and a use thereof. Accordingly, the present invention can effectively prevent or treat diseases related to SHP2.

21 Claims, No Drawings

SHP2 INHIBITOR AND USE THEREOF

CROSS-REFERENCES TO RELATED APPLICATIONS

This application is a continuation application of International Patent Application No. PCT/KR2022/009980, filed Jul. 8, 2022, which claims priority to Korean Patent Application No. 10-2021-0090239, filed Jul. 9, 2021, and claims priority to Korean Patent Application No. 10-2021-0090244, filed Jul. 9, 2021, and claims priority to Korean Patent Application No. 10-2022-0031603, filed Mar. 14, 2022, which applications are incorporated herein by reference in their entireties.

TECHNICAL FIELD

The present invention relates to a compound as a SHP2 inhibitor, a stereoisomer or a solvate thereof, or a pharmaceutically acceptable salt thereof, and its use for the prevention or treatment of a disease associated with the abnormal activity of SHP2.

The present invention was supported by the National New Drug Development Project Support (HN22C0066) of the KOREA DRUG DEVELOPMENT FUND funded by the Ministry of Science and ICT, the Ministry of Trade, Industry and Energy, and the Ministry of Health and Welfare.

BACKGROUND ART

Src homology region 2 domain-containing phosphatase-2 (SHP2) is a protein tyrosine phosphatase (PTP), also referred to as PTPN11 (protein tyrosine phosphatase non-receptor type 11), PTP-1D (protein-tyrosine phosphatase 1D), or PTP-2C (protein-tyrosine phosphatase 2C). SHP2 is known as a signaling molecule that regulates various cellular functions, including cell growth, differentiation, cell cycle, and oncogenic transformation. SHP2, together with SHP1, consists of two tandem SH2 domains at the N-terminus. In the inactive state, the SH2 domain at the N-terminus binds to the PTP domain and blocks the substrate from binding to the active site, thereby inhibiting SHP2. Upon binding of the phospho-tyrosyl residue, the SH2 domain at the N-terminus is released from the PTP domain and the enzyme is activated.

Mutations in SHP2 are known to cause Noonan syndrome and Leopard syndrome and are known to be associated with cancer such as juvenile myelomonocytic leukemia, neuroblastoma, melanoma, acute myeloid leukemia, breast cancer, esophageal cancer, lung cancer, large intestine cancer, head cancer, squamous cell carcinoma of the head and neck, gastric carcinoma, anaplastic large cell lymphoma, glioblastoma, pancreatic cancer, biliary tract cancer, uterine cancer, endometrial cancer, liver cancer, and neurofibromatosis type 1.

Therefore, there is a need to develop a novel compound capable of inhibiting the activity of SHP2, a method for preparing the same, a pharmaceutical composition comprising the same, and a method for preventing or treating a disease associated with the abnormal activity of SHP2 using the same.

DETAILED DESCRIPTION OF INVENTION

There is provided a novel compound capable of inhibiting the activity of SHP2, a stereoisomer or a solvate thereof, or a pharmaceutically acceptable salt thereof.

There is provided a pharmaceutical composition for preventing or treating a disease associated with the abnormal activity of SHP2 using a novel compound capable of inhibiting the activity of SHP2, a stereoisomer or a solvate thereof, or a pharmaceutically acceptable salt thereof.

There is provided a method for preventing or treating a disease associated with the abnormal activity of SHP2 using a novel compound capable of inhibiting the activity of SHP2, a stereoisomer or a solvate thereof, or a pharmaceutically acceptable salt thereof.

There is provided a use of a novel compound capable of inhibiting the activity of SHP2, a stereoisomer or a solvate thereof, or a pharmaceutically acceptable salt thereof.

Each description and embodiment disclosed herein may also apply to each other description and embodiment. That is, all combinations of the various elements disclosed herein fall within the scope of the present application. In addition, it should not be construed that the scope of the present application is limited by the specific description set forth below.

In one aspect, there is provided a compound represented by Formula 1A, or a stereoisomer, solvate or pharmaceutically acceptable salt thereof:

[Formula 1A]

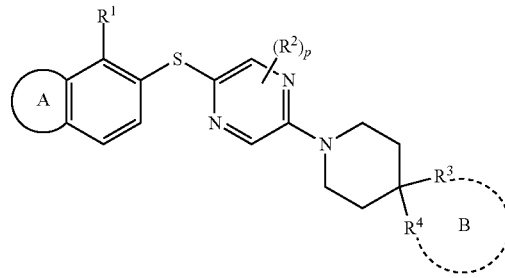

The compound represented by Formula 1A may have a structure in which a pyrazine ring and a fused ring of ring A and a benzene ring are connected via a sulfide group (—S—), and the pyrazine ring is connected with a piperidine ring.

In Formula 1A, $R^1$ is H, halogen, hydroxy, cyano or $C_1$-$C_6$ haloalkyl. In some embodiments, $R^1$ may be H, halogen or $C_1$-$C_6$ haloalkyl. In some embodiments, $R^1$ may be halogen or $C_1$-$C_3$ haloalkyl. In some embodiments, $R^1$ may be halogen. For example, $R^1$ may be F or Cl.

In Formula 1A, $R^2$ is selected from a group consisting of H, halogen, hydroxy, oxo, $C_1$-$C_{20}$ alkyl, $C_1$-$C_{20}$ alkoxy, $C_1$-$C_{20}$ haloalkyl, hydroxy-($C_1$-$C_{20}$ alkyl)-, $C_2$-$C_{20}$ alkoxyalkyl (for example, ($C_1$-$C_{10}$ alkoxy)-($C_1$-$C_{10}$ alkyl)-), $C_1$-$C_{20}$ alkyl substituted with an amine group (for example, $H_2N$—($C_1$-$C_{20}$ alkyl)-), an amine group (for example, —$NH_2$, —$NH(C_1$-$C_{20}$ alkyl), —$N(C_1$-$C_{20}$ alkyl$)_2$), an imine group (for example, =NH), nitro, cyano, amidino, —C(O)$NH_2$, —C(O)($C_1$-$C_{20}$ alkyl), —C(O)O($C_1$-$C_{20}$ alkyl), and carboxy or a salt thereof.

In some embodiments, $R^2$ may be selected from a group consisting of H, halogen, hydroxy, oxo, $C_1$-$C_6$ alkyl, $C_1$-$C_6$ alkoxy, $C_1$-$C_6$ haloalkyl, hydroxy-($C_1$-$C_6$ alkyl)-, ($C_1$-$C_6$ alkoxy)-($C_1$-$C_6$ alkyl)-, $H_2N$—($C_1$-$C_6$ alkyl)-, —$NH_2$, —$NH(C_1$-$C_6$ alkyl), —$N(C_1$-$C_6$ alkyl$)_2$, nitro, cyano, amidino, —C(O)$NH_2$, —C(O)($C_1$-$C_6$ alkyl), —C(O)O($C_1$-$C_6$ alkyl), and carboxy or a salt thereof. In some embodiments, $R^2$ may be selected from a group consisting of H, halogen, hydroxy, oxo, $C_1$-$C_3$ alkyl, $C_1$-$C_3$ alkoxy, $C_1$-$C_3$ haloalkyl, hydroxy-($C_1$-$C_3$ alkyl)-, ($C_1$-$C_3$ alkoxy)-($C_1$-$C_3$ alkyl)-, $H_2N$—($C_1$-$C_3$ alkyl)-, —$NH_2$, —$NH(C_1$-$C_3$ alkyl), —$N(C_1$-$C_3$ alkyl)$_2$, nitro, cyano, —$C(O)NH_2$, —$C(O)(C_1$-$C_3$ alkyl), —$C(O)O(C_1$-$C_3$ alkyl), and carboxy or a salt thereof. In some embodiments, $R^2$ may be selected from a group consisting of H, halogen, hydroxy, cyano, $C_1$-$C_6$ alkyl, $C_1$-$C_6$ alkoxy, hydroxy-($C_1$-$C_6$ alkyl)-, —$NH_2$, —$C(O)NH_2$ and —$C(O)(C_1$-$C_6$ alkyl). In some embodiments, $R^2$ may be selected from a group consisting of H, $C_1$-$C_3$ alkyl, hydroxy-($C_1$-$C_3$ alkyl)-, —$NH_2$, —$C(O)NH_2$ and —$C(O)(C_1$-$C_3$ alkyl).

In some embodiments, $R^2$ may include H, methyl, ethyl, propyl, butyl, hydroxymethyl, hydroxyethyl, hydroxypropyl, amino, methylcarbonyl(acetyl), ethylcarbonyl(propanoyl), carbamoyl, and the like. For example, $R^2$ may be H, —$CH_3$, —$CH_2OH$, —$NH_2$, —$C(O)NH_2$ or —$C(O)CH_3$.

In Formula 1A, p is an integer from 0 to 2. In some embodiments, when p is 2, two $R^2$ may be the same as or different from each other.

In Formula 1A, atoms constituting the pyrazine ring may have position numbers of

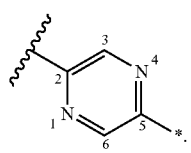

In this case,

indicates a binding position with the sulfur atom, and * indicates a binding position with the nitrogen atom of the piperidine ring.

In some embodiments, $R^2$ may be bonded at the position 3 and/or the position 6 of the pyrazine ring. For example, $R^2$ is halogen, hydroxy, $C_1$-$C_6$ alkyl, $C_1$-$C_6$ alkoxy, —$NH_2$ or cyano, and may be bonded at the position 3 of the pyrazine ring. In some embodiments, $R^2$ is hydroxy-($C_1$-$C_6$ alkyl)-, —$C(O)NH_2$ or —$C(O)(C_1$-$C_6$ alkyl)-, and may be bonded at the position 6 of the pyrazine ring. In some embodiments, when p is 2, $R^2$ may be bonded at the position 3 and the position 6 of the pyrazine ring, respectively.

In Formula 1A, $R^3$ and $R^4$ may be each independently H, $C_1$-$C_6$ alkyl, an amine group (for example, —$NH_2$, —$NH(C_1$-$C_6$ alkyl), —$N(C_1$-$C_6$ alkyl)$_2$) or $C_1$-$C_6$ alkyl substituted with an amine group (for example, $H_2N$—($C_1$-$C_6$ alkyl)-), or $R^3$ and $R^4$ may be connected to each other to form Ring B. For example, when $R^3$ and $R^4$ are connected to each other to form Ring B, a spiro-polycyclic ring including Ring B and the piperidine ring may be formed.

Ring B is a 3- to 8-membered cyclic ring group optionally containing one oxygen atom and optionally substituted. Ring B may be optionally fused with a cycloalkyl, aryl or heteroaryl ring. The cycloalkyl, aryl or heteroaryl ring fused with Ring B can be each optionally substituted.

In some embodiments, $R^3$ and $R^4$ may be each independently H, $C_1$-$C_3$ alkyl, —$NH_2$, —$NH(C_1$-$C_3$ alkyl), —$N(C_1$-$C_3$ alkyl)$_2$, or $H_2N$—($C_1$-$C_3$ alkyl)-. In some embodiments, one of $R^3$ and $R^4$ may be $C_1$-$C_3$ alkyl, and the other may be —$NH_2$ or $H_2N$—($C_1$-$C_3$ alkyl)-. In one embodiment, $R^3$ may be methyl or ethyl, $R^4$ may be amino, aminomethyl or aminoethyl. For example, $R^3$ may be methyl, and $R^4$ may be amino or aminomethyl.

In some embodiments, Ring B may be $C_3$-$C_8$ cycloalkyl or a 3- to 8-membered heterocycloalkyl ring optionally containing one oxygen atom. Ring B can be optionally substituted with at least one $R^B$. In some embodiments, Ring B may be $C_4$-$C_6$ cycloalkyl or a 4- to 6-membered heterocycloalkyl ring optionally containing one oxygen atom and optionally substituted with at least one $R^B$. For example, Ring B may be a cyclopentane ring or a tetrahydrofuran ring.

$R^B$ may be selected from a group consisting of deuterium, ($C_1$-$C_6$ alkyl), an amine group (for example, —$NH_2$, —$NH(C_1$-$C_6$ alkyl), —$N(C_1$-$C_6$ alkyl)$_2$) and $C_1$-$C_6$ alkyl substituted with an amine group (for example, $H_2N$—($C_1$-$C_6$ alkyl)-). In some embodiments, $R^B$ may be selected from a group consisting of deuterium, ($C_1$-$C_3$ alkyl), —$NH_2$, —$NH(C_1$-$C_3$ alkyl), —$N(C_1$-$C_3$ alkyl)$_2$, and $H_2N$—($C_1$-$C_3$ alkyl)-. In some embodiments, Ring B may be optionally substituted with at least one R B selected from deuterium, $C_1$-$C_3$ alkyl and —$NH_2$. For example, $R^B$ may be one or more selected from deuterium, methyl and —$NH_2$.

In some embodiments, Ring B may be optionally fused with Ring BB selected from $C_3$-$C_6$ cycloalkyl, $C_6$-$C_{10}$ aryl, and 5- to 10-membered heteroaryl containing one or two heteroatoms selected from N, O and S. In this case, Ring BB may be optionally substituted with at least one $R^{BB}$. In some embodiments, Ring BB may be selected from $C_3$-$C_6$ cycloalkyl, $C_6$-$C_{10}$ aryl, and 5- to 7-membered heteroaryl containing one or two heteroatoms selected from N, O and S. For example, Ring BB may be a $C_3$-$C_6$ cycloalkyl ring, a benzene ring, a pyridine ring or a thiazole ring.

In some embodiments, Ring B is a cyclopentane ring, and may be fused with Ring BB selected from a cyclopropane ring, a benzene ring, a pyridine ring and a thiazole ring. In some embodiments, Ring B is a tetrahydrofuran ring, and may be fused with Ring BB selected from a benzene ring and a pyridine ring.

$R^{BB}$ may be selected from a group consisting of halogen, hydroxy, oxo, $C_1$-$C_6$ alkyl, $C_1$-$C_6$ alkoxy, $C_1$-$C_6$ haloalkyl, hydroxy-($C_1$-$C_6$ alkyl)-, ($C_1$-$C_6$ alkoxy)-($C_1$-$C_6$ alkyl)-, $H_2N$—($C_1$-$C_6$ alkyl)-, —$NH_2$, —$NH(C_1$-$C_6$ alkyl), —$N(C_1$-$C_6$ alkyl)$_2$, nitro, cyano and amidino. In some embodiments, $R^{BB}$ may be selected from a group consisting of halogen, hydroxy, oxo, $C_1$-$C_3$ alkyl, $C_1$-$C_3$ alkoxy, $C_1$-$C_3$ haloalkyl, hydroxy-($C_1$-$C_3$ alkyl)-, ($C_1$-$C_3$ alkoxy)-($C_1$-$C_3$ alkyl)-, $H_2N$—($C_1$-$C_3$ alkyl)-, —$NH_2$, —$NH(C_1$-$C_3$ alkyl), —$N(C_1$-$C_3$ alkyl)$_2$, nitro and cyano. In some embodiments, $R^{BB}$ may be at least one selected from a group consisting of halogen, cyano, hydroxy, $C_1$-$C_3$ alkyl and $C_1$-$C_3$ alkoxy. For example, $R^{BB}$ may be one or more selected from a group consisting of halogen, cyano, hydroxy, methyl and methoxy.

In some embodiments,

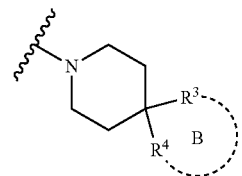

of Formula 1A may be selected from the following structures:

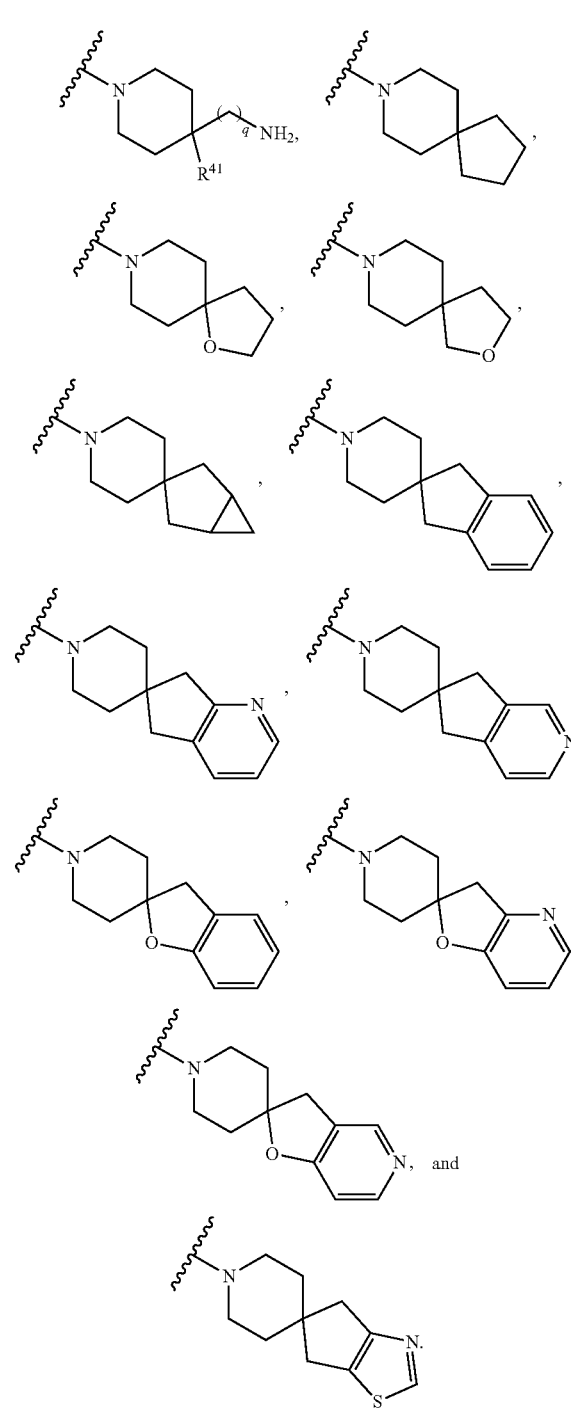

In the above structures, $R^{41}$ may be $C_1$-$C_3$ alkyl, and q may be an integer from 0 to 3. For example, $R^{41}$ may be methyl, and q may be 0 or 1.

Ring B in the above structures may be optionally substituted with at least one $R^B$ selected from deuterium, methyl and —$NH_2$. In addition, Ring BB may be optionally substituted with at least one $R^{BB}$ selected from a group consisting of halogen, cyano, hydroxy, methyl and methoxy.

For example,

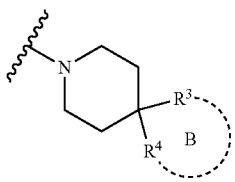

of Formula 1A may be selected from the following structures:

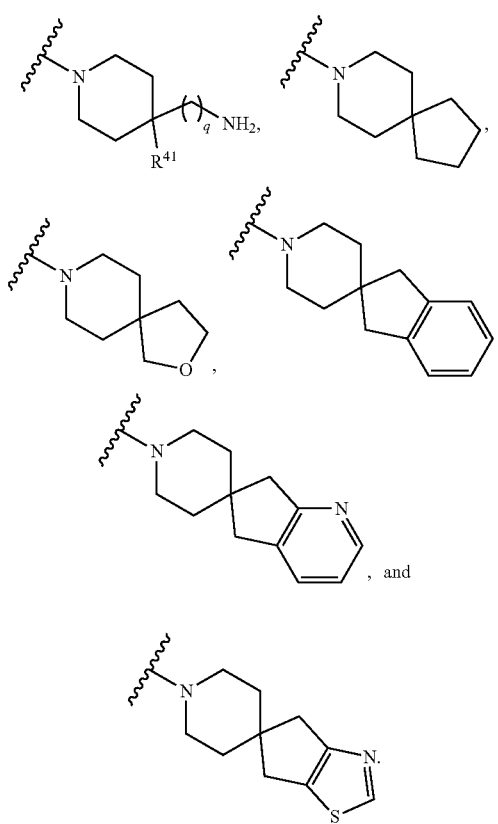

(In the above structures, $R^{41}$ is methyl, and q is 0 or 1.)

In this case, Ring B may be optionally substituted with at least one $R^B$ selected from methyl and —$NH_2$, and Ring BB may be optionally substituted with at least one $R^{BB}$ selected from a group consisting of halogen, cyano, hydroxy, methyl and methoxy.

In some embodiments,

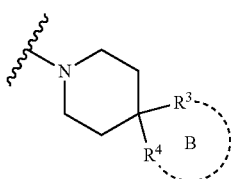

of Formula 1A may be selected from the following structures:
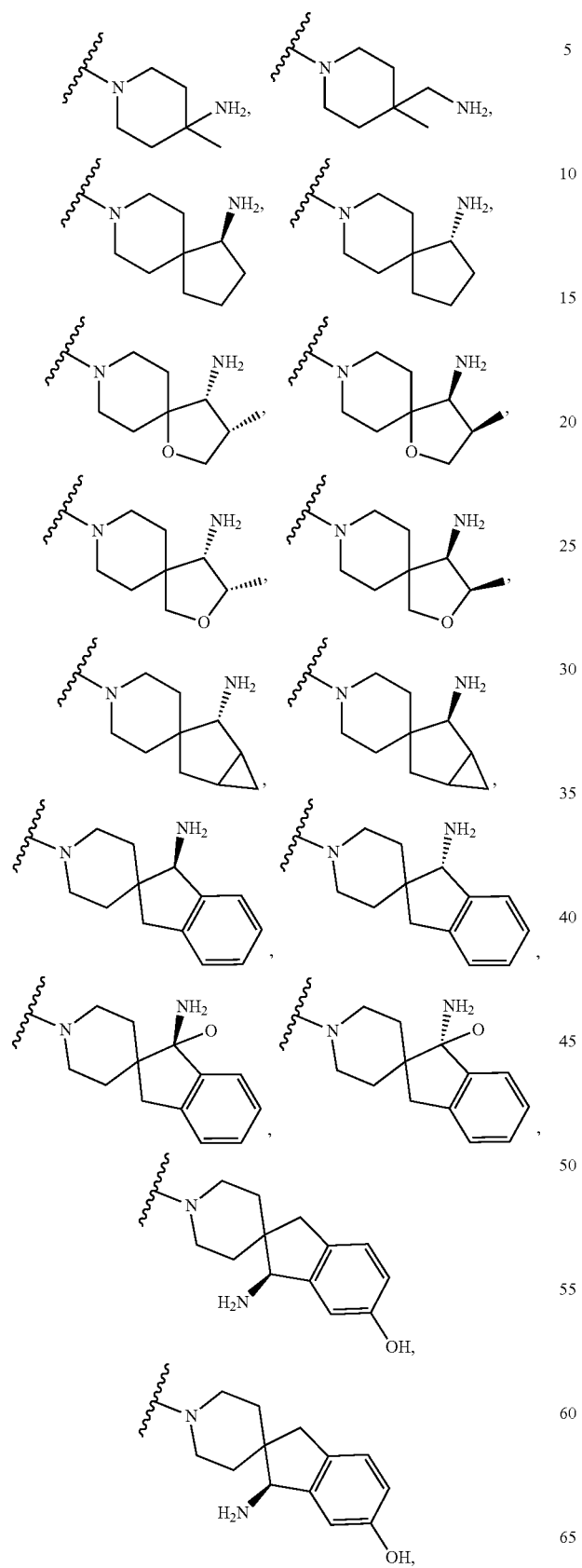
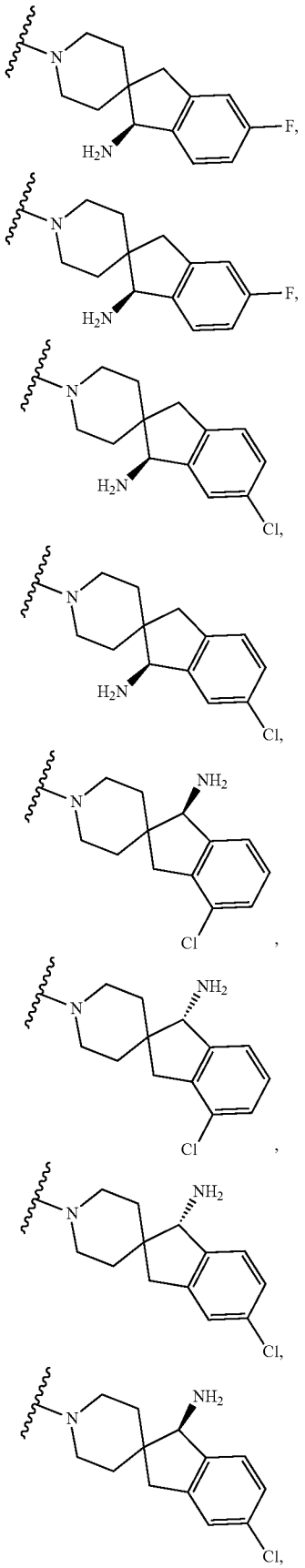

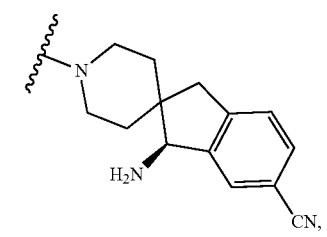
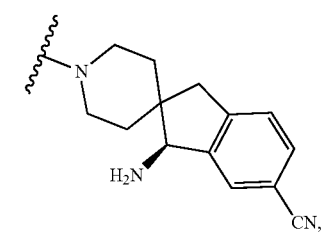
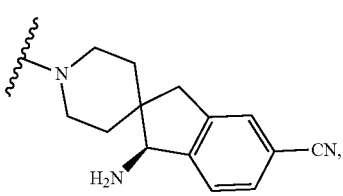
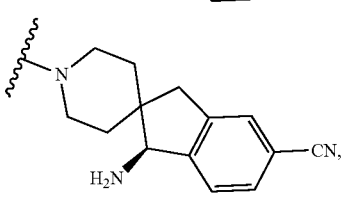
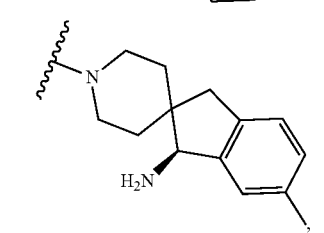
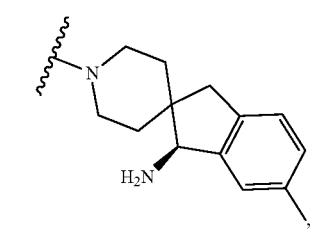
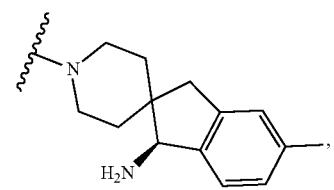
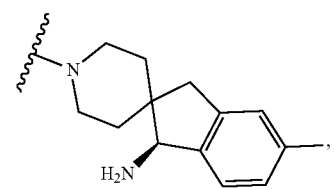
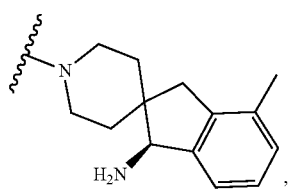
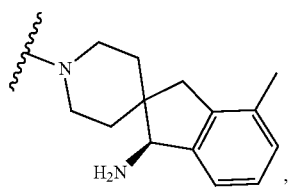
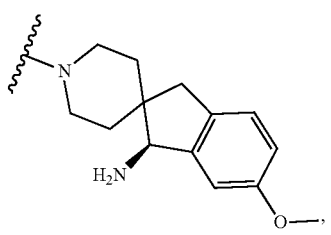
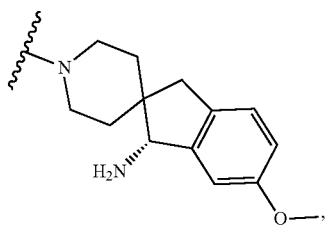
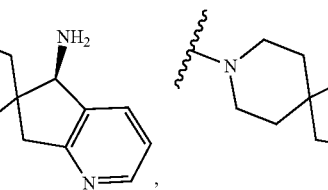
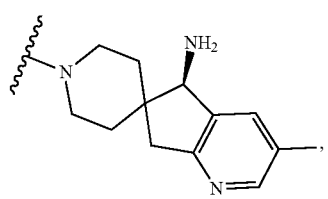
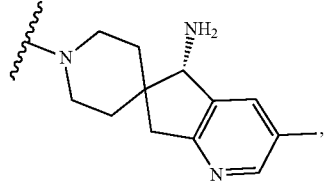
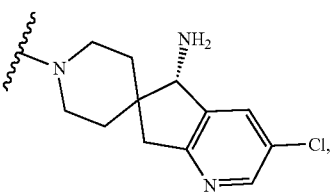

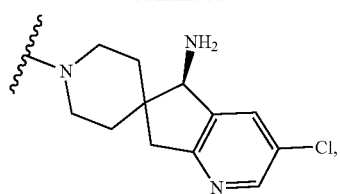
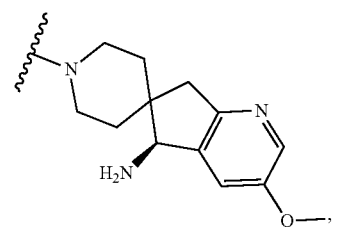
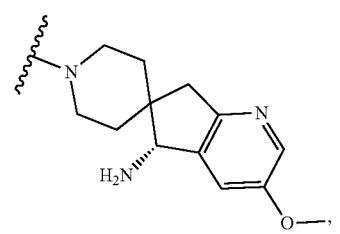
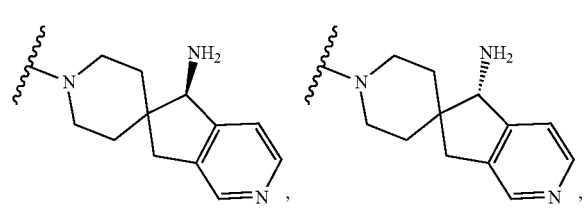
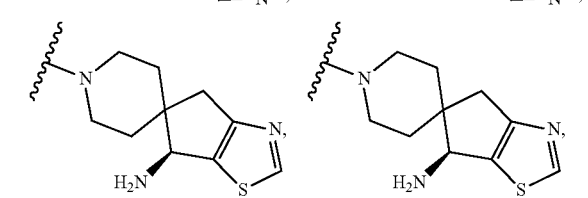
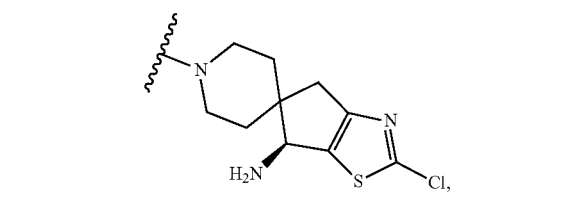
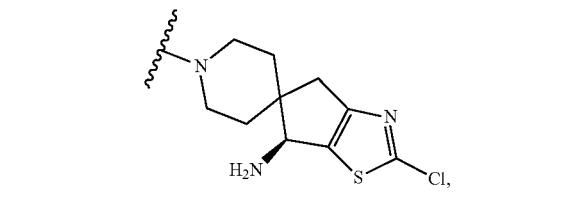
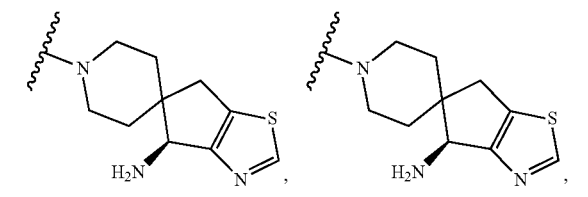
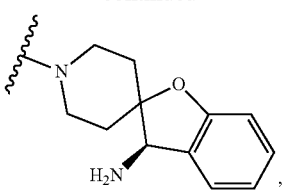
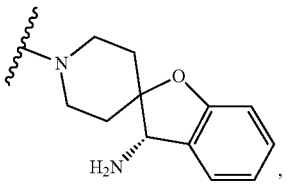
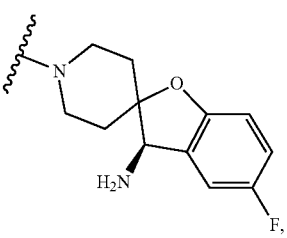
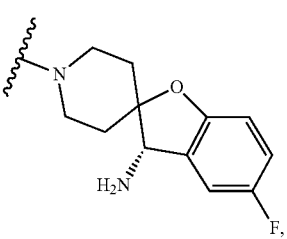
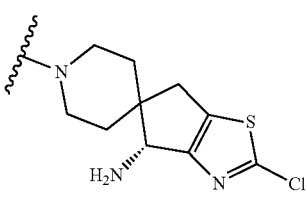
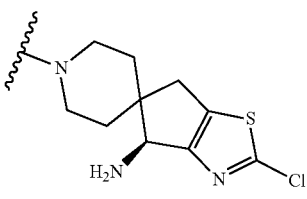
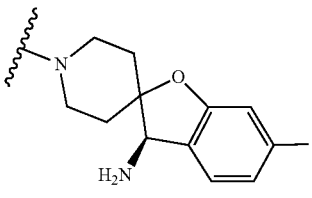
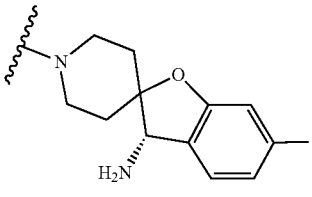

-continued
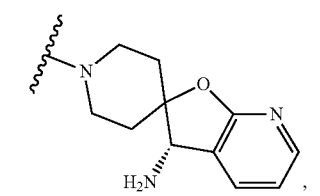,
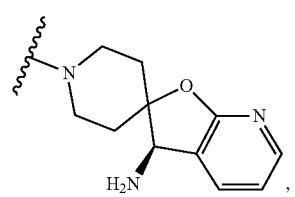,
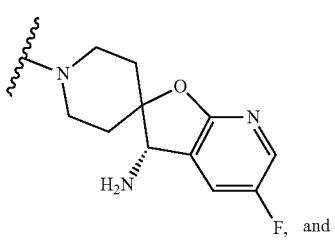F, and
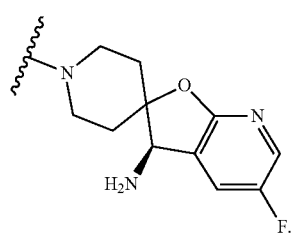F.
For example,
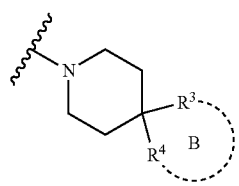
of Formula 1A may be selected from the following structures:
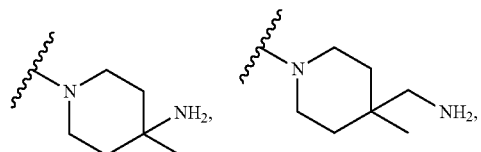
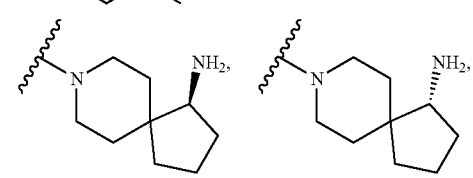
-continued
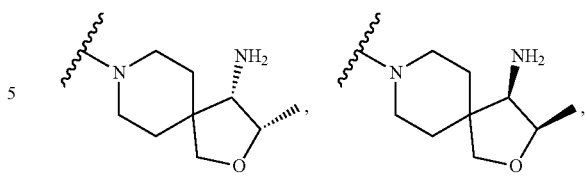,
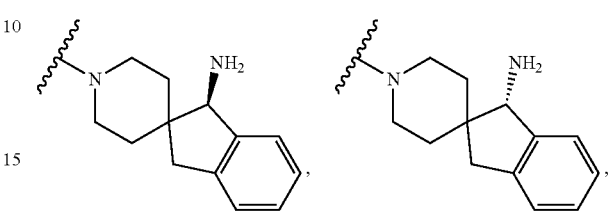,
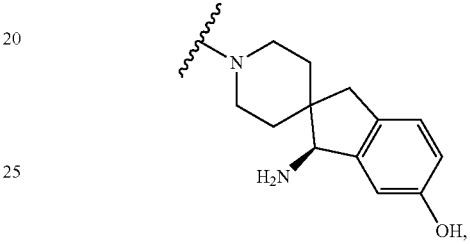OH,
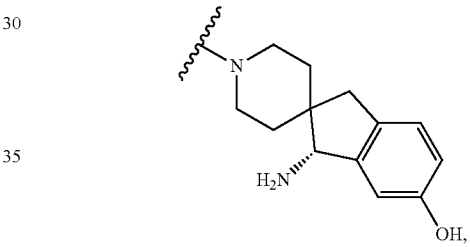OH,
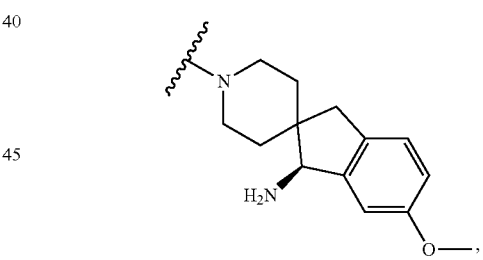,
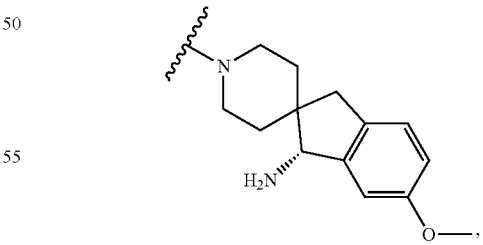,
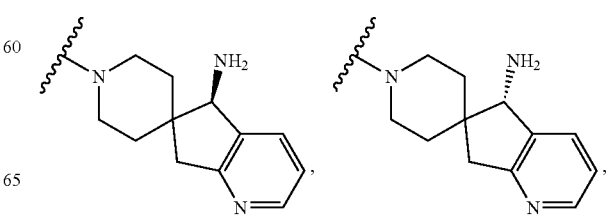, -continued

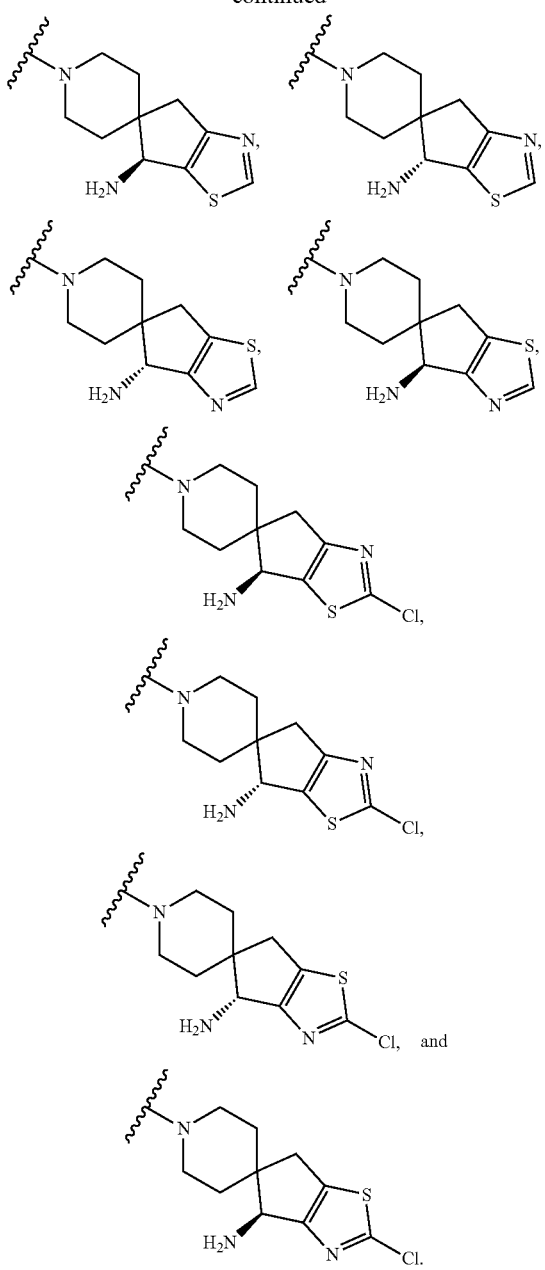

In addition,

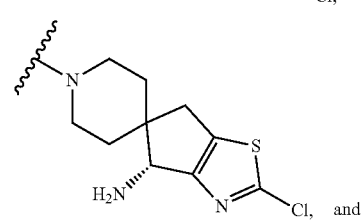

of Formula 1A may include a corresponding structure disclosed in International Patent Publication Nos. WO2019/183367, WO2020/063760, WO2020/201991, WO2020/081848, WO2020/073949, WO2021/197452, WO2021/147879, WO2020/049079, WO2021/218752, WO2021/218755, WO2022/017444, WO2021/115286, WO2021/088944, and the like, or a structure easily derived therefrom by those skilled in the art.

In Formula 1A,

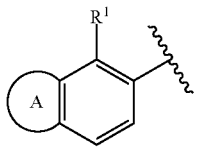

is selected from the following fused ring structures:

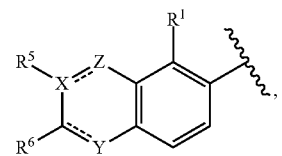

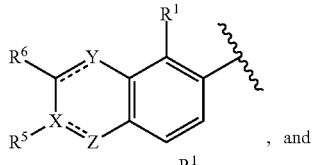
, and

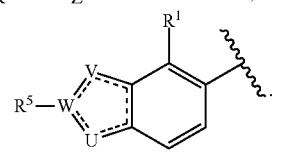
.

In the above fused ring structure, ===== is a single bond or a double bond in accordance with the valence that the ring element permits. (For example, a nitrogen atom allows 3 bonds and a carbon atom allows 4 bonds).

For example, when X is N, Y is N, and Z is C(O), ===== between X and Z is a single bond, and ===== between CR6 and Y is a double bond. For example, when W is C, U is N, and V is NR$^6$, ===== between V and W is a single bond, and ===== between W and U is a double bond, and thus ===== shared by the 5-membered ring and the 6-membered ring is a double bond. For example, when W and U are N, and V is CH, ===== between each of V and U and the respective carbon atoms shared by the 6-membered ring is a double bond, and ===== between W and V and ===== between W and U are single bonds, and thus ===== shared by the 5-membered ring and the 6-membered ring is a single bond.

In the above fused ring structures, X may be N or C, Y may be N, CH or CH$_2$, and Z may be C(O), S(O)$_2$, or N. In this case, when Z is N, X is C, and Y is CH, and when Z is S(O)$_2$, both X and Y are N.

In some embodiments, in the above fused ring structures, X may be N or C, Y may be N, CH or CH$_2$, and Z may be C(O) or S(O)$_2$. In this case, when Z is S(O)$_2$, both X and Y may be N.

In the above fused ring structures, U may be N, NR$^6$ or CHR$^6$, V may be CH, C(O), S, O, N or NR$^6$, and W may be N or C. In this case, when W is C, one of U and V is N, and the other is S, O or NR$^6$. In addition, when W is N, U is CHR$^6$, and V is C(O), or U is N, and V is CH. One or two of U, V and W is N.

In some embodiments, in the above fused ring structures, U may be N or NR$^6$, V may be CH, N or NR$^6$, and W may be N or C. In this case, when W is C, one of U and V is N, and the other is NR⁶. Also, when W is N, U is N, and V is CH.

In some embodiments,

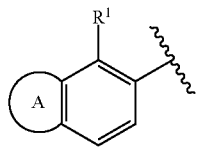

in Formula 1A may be selected from the following structures:

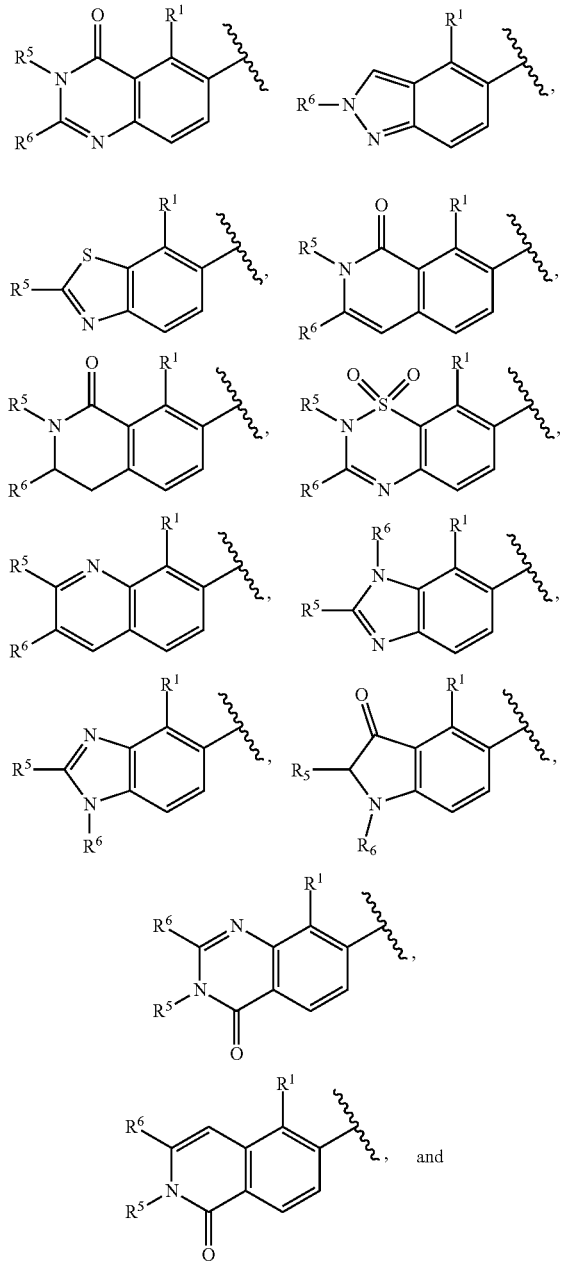

$R^5$ may be each independently selected from a group consisting of H, a halogen atom, a hydroxy group, a ketone group, $C_1$-$C_{20}$ alkyl, $C_1$-$C_{20}$ alkoxy, $C_2$-$C_{20}$ alkoxyalkyl, an amine group, $C_1$-$C_{20}$ alkyl substituted with an amine group, an imine group, nitro, cyano, amidino, a carboxyl group or a salt thereof, $C_1$-$C_{20}$ heteroalkyl, $C_3$-$C_{20}$ heterocycloalkyl, $C_6$-$C_{20}$ aryl, $C_6$-$C_{20}$ arylalkyl, $C_1$-$C_{20}$ heteroaryl, $C_1$-$C_{20}$ heteroarylalkyl, $C_1$-$C_{20}$ heteroaryloxy, $C_1$-$C_{20}$ heteroaryloxyalkyl, and $C_3$-$C_{20}$ heterocycloalkyl, and polycyclic $C_5$-$C_{12}$ heteroarylalkyl.

$R^5$ may be H, a $C_1$-$C_6$ alkyl group, a substituted or unsubstituted phenyl group, a substituted or unsubstituted benzyl group, a substituted or unsubstituted thiazolylalkyl group, a substituted or unsubstituted imidazolylalkyl group, a substituted or unsubstituted pyrrolidinylalkyl group, a substituted or unsubstituted pyridinylalkyl group, a substituted or unsubstituted pyrimidinylalkyl group, a substituted or unsubstituted pyrazinylalkyl group, a substituted or unsubstituted benzimidazolylalkyl group, or a substituted or unsubstituted pyrrolopyridinylalkyl group. The phenyl group, benzyl group, thiazolylalkyl group, imidazolylalkyl group, pyrrolidinylalkyl group, pyridinylalkyl group, pyrimidinylalkyl group, pyrazinylalkyl group, benzimidazolylalkyl group, or pyrrolopyridinylalkyl group may be unsubstituted or substituted with at least one substituent selected from a group consisting of halogen, $C_1$-$C_6$ alkyl substituted with a halogen atom, —CN, —NH$_2$, —NO$_2$, —OR$^a$, and —SO$_2$R$^a$. $C_1$-$C_6$ alkyl substituted with a halogen atom may be —CF$_3$. R$^a$ may be H, a halogen atom, or $C_1$-$C_6$ alkyl substituted with a halogen atom. —OR$^a$ may be —OCH$_3$. —SO$_2$R$^a$ may be —SO$_2$F.

In one embodiment, in the above fused ring structures, $R^5$ may be each independently selected from the following (i) to (vi):

(i) H, halogen, hydroxy, an amine group (such as —NH$_2$), an imine group (such as =NH), —C(O)NH$_2$, nitro, cyano, amidino, or carboxy or a salt thereof;

(ii) $C_1$-$C_{20}$ alkyl or $C_1$-$C_{20}$ alkoxy, which is optionally substituted with at least one substituent selected from a group consisting of halogen, hydroxy, $C_1$-$C_{20}$ alkyl, $C_1$-$C_{20}$ haloalkyl, $C_1$-$C_{20}$ alkoxy, $C_1$-$C_{20}$ haloalkoxy, an amine group (for example, —NR'R"), a carbonyl group (for example, R'C(O)—), a sulfonyl group (for example, R'S(O)$_2$—), an alkylsulfonylamine group (for example, R'S(O)$_2$NR"—), an aminocarbonyl group or an alkylaminocarbonyl group (for example, R"R'NC(O)—), and R'C(O)NR"—;

(iii) $C_6$-$C_{20}$ aryl, ($C_6$-$C_{12}$ aryl)-($C_1$-$C_8$ alkyl)-, $C_6$-$C_{20}$ aryloxy, ($C_6$-$C_{12}$ aryloxy)-($C_1$-$C_8$ alkyl)-, $C_6$-$C_{20}$ arylcarbonyl, ($C_6$-$C_{12}$ arylcarbonyl)-($C_1$-$C_8$ alkyl)-, —CONH—($C_6$-$C_{12}$ aryl), —CONH—($C_1$-$C_8$ alkyl)-($C_6$-$C_{12}$ aryl), —NHCO—($C_6$-$C_{12}$ aryl), or —NHCO—($C_1$-$C_8$ alkyl)-($C_6$-$C_{12}$ aryl);

(iv) heteroaryl, heteroaryl-($C_1$-$C_8$ alkyl)-, heteroaryloxy, heteroaryloxy-($C_1$-$C_8$ alkyl)-, heteroarylcarbonyl, heteroaryl carbonyl-($C_1$-$C_8$ alkyl)-, —CONH-heteroaryl, —CONH—($C_1$-$C_8$ alkyl)-heteroaryl, —NHCO-heteroaryl, or —NHCO—($C_1$-$C_8$ alkyl)-heteroaryl (wherein the heteroaryl ring may be 4- to 10-membered heteroaryl containing at least one heteroatoms selected from N, O and S; or the heteroaryl ring may be a $C_1$ to $C_{20}$ heteroaryl ring);

(v) heterocycloalkyl, heterocycloalkyl-($C_1$-$C_8$ alkyl)-, heterocycloalkyloxy, heterocycloalkyloxy-($C_1$-$C_8$ alkyl)-, heterocycloalkylcarbonyl, heterocycloalkylcarbonyl-($C_1$-$C_8$ alkyl)-, —CONH-heterocycloalkyl, —CONH—($C_1$-$C_8$ alkyl)-heterocycloalkyl, —NHCO— heterocycloalkyl, or —NHCO—($C_1$-$C_8$ alkyl)-heterocycloalkyl (wherein the heterocycloalkyl ring may be 3- to 10-membered fully saturated or partially unsaturated heterocycloalkyl containing at least one heteroatoms selected from N, O and S; or the heterocycloalkyl ring may be $C_3$ to $C_{20}$ heterocycloalkyl); and (vi) $C_3$-$C_{10}$ cycloalkyl, ($C_3$-$C_{10}$ cycloalkyl)-($C_1$-$C_8$ alkyl)-, $C_3$-$C_{10}$ cycloalkyloxy, ($C_3$-$C_{10}$ cycloalkyloxy)-($C_1$-$C_8$ alkyl)-, $C_3$-$C_{10}$ cycloalkylcarbonyl, ($C_3$-$C_{10}$ cycloalkylcarbonyl)-($C_1$-$C_8$ alkyl)-, —CONH—($C_3$-$C_{10}$ cycloalkyl), —CONH—($C_1$-$C_8$ alkyl)-($C_3$-$C_{10}$ cycloalkyl), —NHCO—($C_3$-$C_{10}$ cycloalkyl), or —NHCO—($C_1$-$C_8$ alkyl)-($C_3$-$C_{10}$ cycloalkyl).

R' and R" are each independently H or $C_1$-$C_{10}$ alkyl. In some embodiments, R' and R" can be each independently H or $C_1$-$C_6$ alkyl. For example, R' and R" may be each independently H or $C_1$-$C_3$ alkyl. Also, R' and R" may be each independently H, methyl or ethyl.

The aryl ring, heteroaryl ring, heterocycloalkyl ring and cycloalkyl ring described in (iii) to (vi) above may be each optionally substituted. In (iii) to (vi) above, "aryl ring", "heteroaryl ring", "heterocycloalkyl ring" and "cycloalkyl ring" are used to collectively refer to those ring moieties in the substituents to which the rings are attached together with other chemical structures. For example, "aryl ring" is used to collectively refer to aryl as well as aryl rings included in arylalkyl, aryloxy, aryloxyalkyl, arylcarbonyl, arylcarbonylalkyl, —CONH-aryl, —CONH-alkyl-aryl, —NHCO-aryl and —NHCO-alkyl-aryl.

In some embodiments, $R^5$ may be each independently selected from:

(i) H, halogen, hydroxy, —NH$_2$, =NH, —C(O)NH$_2$, nitro, cyano, amidino or carboxy or a salt thereof (for example, H, halogen, hydroxy, —NH$_2$, —C(O)NH$_2$, nitro, cyano, or carboxy or a salt thereof);

(ii) $C_1$-$C_6$ alkyl or $C_1$-$C_6$ alkoxy, which is optionally substituted with at least one substituent selected from a group consisting of halogen, hydroxy, $C_1$-$C_6$ alkyl, $C_1$-$C_6$ haloalkyl, $C_1$-$C_6$ alkoxy, $C_1$-$C_6$ haloalkoxy, —NR'R", R'C(O)—, R'S(O)$_2$—, R'S(O)$_2$NR"—, R"R'NC(O)—, and R'C(O)NR"-(for example, H, halogen, hydroxy, —NH$_2$, cyano, nitro, $C_1$-$C_6$ alkyl, $C_1$-$C_6$ alkoxy, ($C_1$-$C_6$ alkoxy)-($C_1$-$C_6$ alkyl)- or ($C_1$-$C_6$ alkoxy)-($C_1$-$C_6$ alkoxy)-);

(iii) $C_6$-$C_{10}$ aryl, ($C_6$-$C_{10}$ aryl)-($C_1$-$C_5$ alkyl)-, $C_6$-$C_{10}$ aryloxy, ($C_6$-$C_{10}$ aryloxy)-($C_1$-$C_5$ alkyl)-, $C_6$-$C_{10}$ arylcarbonyl, ($C_6$-$C_{10}$ arylcarbonyl)-($C_1$-$C_5$ alkyl)-, —CONH—($C_6$-$C_{10}$ aryl), —CONH—($C_1$-$C_5$ alkyl)-($C_6$-$C_{10}$ aryl), —NHCO—($C_6$-$C_{10}$ aryl) or —NHCO—($C_1$-$C_5$ alkyl)-($C_6$-$C_{10}$ aryl) (for example, $C_6$-$C_{10}$ aryl, ($C_6$-$C_{10}$ aryl)-($C_1$-$C_3$ alkyl)-, $C_6$-$C_{10}$ aryloxy, ($C_6$-$C_{10}$ aryloxy)-($C_1$-$C_3$ alkyl)-, $C_6$-$C_{10}$ arylcarbonyl, or ($C_6$-$C_{10}$ arylcarbonyl)-($C_1$-$C_3$ alkyl)-, wherein the aryl ring may be optionally substituted with at least one $R^{5a}$);

(iv) heteroaryl, heteroaryl-($C_1$-$C_5$ alkyl)-, heteroaryloxy, heteroaryloxy-($C_1$-$C_5$ alkyl)-, heteroarylcarbonyl, heteroaryl carbonyl-($C_1$-$C_5$ alkyl)-, —CONH-heteroaryl, —CONH—($C_1$-$C_5$ alkyl)-heteroaryl, —NHCO-heteroaryl, or —NHCO—($C_1$-$C_5$ alkyl)-heteroaryl (for example, heteroaryl, heteroaryl-($C_1$-$C_3$ alkyl)-, heteroaryloxy, heteroaryloxy-($C_1$-$C_3$ alkyl)-, heteroarylcarbonyl, or heteroarylcarbonyl-($C_1$-$C_3$ alkyl)-, wherein the heteroaryl ring is 5- to 10-membered heteroaryl containing one to three heteroatoms selected from N, O and S; or 5- or 6-membered monocyclic heteroaryl or 9- or 10-membered bicyclic heteroaryl containing one or two heteroatoms selected from N, O and S and may be optionally substituted with at least one $R^{5a}$);

(v) heterocycloalkyl, heterocycloalkyl-($C_1$-$C_5$ alkyl)-, heterocycloalkyloxy, heterocycloalkyloxy-($C_1$-$C_5$ alkyl)-, heterocycloalkylcarbonyl, heterocycloalkylcarbonyl-($C_1$-$C_5$ alkyl)-, —CONH-heterocycloalkyl, —CONH—($C_1$-$C_5$ alkyl)-heterocycloalkyl, —NHCO— heterocycloalkyl, or —NHCO—($C_1$-$C_5$ alkyl)-heterocycloalkyl (for example, heterocycloalkyl, heterocycloalkyl-($C_1$-$C_3$ alkyl)-, heterocycloalkyloxy, heterocycloalkyloxy-($C_1$-$C_3$ alkyl)-, heterocycloalkylcarbonyl, or heterocycloalkylcarbonyl-($C_1$-$C_3$ alkyl)-, wherein the heterocycloalkyl ring is 3- to 10-membered fully saturated or partially unsaturated heterocycloalkyl containing one or three heteroatoms selected from N, O and S; or 4- to 7-membered fully saturated or partially unsaturated heterocycloalkyl containing one or two heteroatoms selected from N, O and S and may be optionally substituted with at least one $R^{5a}$); or (vi) $C_3$-$C_8$ cycloalkyl, ($C_3$-$C_8$ cycloalkyl)-($C_1$-$C_5$ alkyl)-, $C_3$-$C_8$ cycloalkyloxy, ($C_3$-$C_8$ cycloalkyloxy)-($C_1$-$C_5$ alkyl)-, $C_3$-$C_8$ cycloalkylcarbonyl, ($C_3$-$C_8$ cycloalkylcarbonyl)-($C_1$-$C_5$ alkyl)-, —CONH—($C_3$-$C_8$ cycloalkyl), —CONH—($C_1$-$C_5$ alkyl)-($C_3$-$C_8$ cycloalkyl), —NHCO—($C_3$-$C_8$ cycloalkyl), or —NHCO—($C_1$-$C_5$ alkyl)-($C_3$-$C_8$ cycloalkyl) (for example, $C_4$-$C_8$ cycloalkyl, ($C_4$-$C_8$ cycloalkyl)-($C_1$-$C_3$ alkyl)-, $C_4$-$C_8$ cycloalkyloxy, ($C_4$-$C_8$ cycloalkyloxy)-($C_1$-$C_3$ alkyl)-, $C_4$-$C_8$ cycloalkylcarbonyl, or ($C_4$-$C_8$ cycloalkylcarbonyl)-($C_1$-$C_3$ alkyl)-, wherein the cycloalkyl ring may be optionally substituted with at least one $R^{5a}$).

R' and R" are each independently H or $C_1$-$C_{10}$ alkyl. In some embodiments, R' and R" may be each independently H or $C_1$-$C_6$ alkyl. For example, R' and R" may be each independently H or $C_1$-$C_3$ alkyl. Also, R' and R" may be each independently H, methyl or ethyl.

$R^{5a}$ may be selected from a group consisting of halogen, hydroxy, —NH$_2$, —NH($C_1$-$C_6$ alkyl), —N($C_1$-$C_6$ alkyl)$_2$, cyano, oxo, nitro, $C_1$-$C_6$ alkyl, $C_1$-$C_6$ alkoxy; $C_1$-$C_6$ alkyl substituted with halogen, hydroxy, $C_1$-$C_6$ alkoxy, —NH$_2$ or cyano; $C_1$-$C_6$ alkoxy substituted with halogen, hydroxy, $C_1$-$C_6$ alkyl, —NH$_2$ or cyano; and halogen-SO$_2$—, ($C_1$-$C_6$ alkyl)-SO$_2$—, —SO$_2$NH$_2$, —SO$_2$NH($C_1$-$C_6$ alkyl), and —SO$_2$N($C_1$-$C_6$ alkyl)$_2$. In some embodiments, $R^{5a}$ may be selected from a group consisting of halogen, hydroxy, oxo, $C_1$-$C_6$ alkyl, $C_1$-$C_6$ alkoxy, $C_1$-$C_6$ haloalkyl, hydroxy-($C_1$-$C_6$ alkyl)-, ($C_1$-$C_6$ alkoxy)-($C_1$-$C_6$ alkyl)-, —NH$_2$, —NH($C_1$-$C_6$ alkyl), —N($C_1$-$C_6$ alkyl)$_2$, nitro, cyano, halogen-SO$_2$—, ($C_1$-$C_6$ alkyl)-SO$_2$— and —SO$_2$NH$_2$.

In one embodiment, $R^5$ may be each independently selected from the following (i) to (vi):

(i) H, halogen, hydroxy, —NH$_2$, —C(O)NH$_2$, nitro, cyano, or carboxy or a salt thereof;

(ii) $C_1$-$C_6$ alkyl, which is optionally substituted with at least one substituent selected from a group consisting of halogen, hydroxy, $C_1$-$C_6$ haloalkyl, $C_1$-$C_6$ alkoxy, $C_1$-$C_6$ haloalkoxy, —NR'R", R'C(O)—, R'S(O)$_2$—, R'S(O)$_2$NR"—, R"R'NC(O)— and R'C(O)NR"—; $C_1$-$C_6$ alkoxy; or ($C_1$-$C_6$ alkoxy)-($C_1$-$C_6$ alkoxy)- (wherein R' and R" are each independently H or $C_1$-$C_3$ alkyl);

(iii) phenyl, phenyl-($C_1$-$C_3$ alkyl)-, phenyloxy, phenyloxy-($C_1$-$C_3$ alkyl)-, phenylcarbonyl, or phenylcarbonyl-($C_1$-$C_3$ alkyl)- (wherein the phenyl ring can be optionally substituted with at least one $R^{5a}$);

(iv) heteroaryl, heteroaryl-($C_1$-$C_3$ alkyl)-, heteroaryloxy, heteroaryloxy-($C_1$-$C_3$ alkyl)-, heteroarylcarbonyl, or heteroarylcarbonyl-($C_1$-$C_3$ alkyl)- (wherein the heteroaryl ring is selected from a group consisting of pyrrolyl, furanyl, thiophenyl, pyrazolyl, imidazolyl, isoxazolyl, oxazolyl, thiazolyl, isothiazolyl, pyridinyl, pyrimidinyl, pyrazinyl, pyridazinyl, indolyl, benzofuranyl, benzothiophenyl, benzopyrazolyl, benzimidazolyl, benzooxazolyl, benzoisoxazolyl, benzothiazolyl, benzoisothiazolyl and 1H-pyrrolo[2,3-b]pyridinyl, which can be optionally substituted with at least one $R^{5a}$);

(v) heterocycloalkyl, heterocycloalkyl-($C_1$-$C_3$ alkyl)-, heterocycloalkyloxy, heterocycloalkyloxy-($C_1$-$C_3$ alkyl)-, heterocycloalkylcarbonyl, or heterocycloalkylcarbonyl-($C_1$-$C_3$ alkyl)- (wherein the heterocycloalkyl ring is selected from a group consisting of aziridinyl, oxiranyl, oxetanyl, azetidinyl, pyrrolidinyl, tetrahydrofuranyl, tetrahydrothiophenyl, piperidinyl, tetrahydropyranyl, 4H-pyranyl, 3,6-dihydro-2H-pyranyl, 3,4-dihydro-2H-pyranyl, 1,2-dihydropyridinyl, 1,4-dihydropyridinyl, 1,2,3,6-tetrahydropyridinyl, 1,2,3,4-tetrahydropyridinyl, piperazinyl, morpholinyl, thiomorpholinyl, oxazolidinyl and 2-oxo-oxazolidinyl, which can be optionally substituted with at least one $R^{5a}$); and (vi) $C_5$-$C_7$ cycloalkyl, ($C_5$-$C_7$ cycloalkyl)-($C_1$-$C_3$ alkyl)-, $C_5$-$C_7$ cycloalkyloxy, ($C_5$-$C_7$ cycloalkyloxy)-($C_1$-$C_3$ alkyl)-, $C_5$-$C_7$ cycloalkylcarbonyl, or ($C_5$-$C_7$ cycloalkylcarbonyl)-($C_1$-$C_3$ alkyl)- (wherein the cycloalkyl ring can be optionally substituted with at least one $R^{5a}$).

In this case, $R^{5a}$ may be selected from a group consisting of halogen, hydroxy, oxo, $C_1$-$C_3$ alkyl, $C_1$-$C_3$ alkoxy, $C_1$-$C_3$ haloalkyl, hydroxy-($C_1$-$C_3$ alkyl)-, —NH$_2$, —NH($C_1$-$C_3$ alkyl), —N($C_1$-$C_3$ alkyl)$_2$, nitro, cyano, —SO$_2$F and —SO$_2$Cl.

In one embodiment, the heteroaryl ring of (iii) may be selected from a group consisting of pyridinyl, pyrazolyl, isoxazolyl, furanyl, pyrimidinyl, thiazolyl, pyrazinyl, benzimidazolyl, benzooxazolyl and 1H-pyrrolo[2,3-b]pyridinyl. In addition, the heterocycloalkyl ring of (iv) may be selected from a group consisting of pyrrolidinyl, tetrahydrofuranyl, tetrahydropyranyl, 3,6-dihydro-2H-pyranyl, morpholinyl, oxetanyl, piperidinyl and 2-oxo-oxazolidinyl.

For example, $R^5$ may be selected from a group consisting of phenyl, benzyl, 1-phenylethyl, phenoxy, pyridinylmethyl, pyridinyloxy, pyridinylcarbonylmethyl, pyrazolylmethyl, pyrrolidinylmethyl, pyrrolidinylethyl, isoxazolylmethyl, tetrahydrofuranylmethyl, tetrahydrofuranyloxy, tetrahydropyranylmethyl, 3,6-dihydro-2H-pyranylmethyl, morpholinylmethyl, oxetanylmethyl, piperidinylcarbonylmethyl, 2-oxo-oxazolidinylethyl, 2-oxo-oxazolidinylmethyl, furanylmethyl, pyrimidinylmethyl, thiazolylmethyl, pyrazinylmethyl, benzimidazolylmethyl, benzooxazolylmethyl, 1H-pyrrolo[2,3-b]pyridinylmethyl and cyclohexyl, and $R^5$ may be optionally substituted with at least one $R^{5a}$ selected from a group consisting of at least one F, Cl, OH, —CH$_3$, —OCH$_3$, cyano, oxo, —NH$_2$, NO$_2$, SO$_2$F and CF$_3$.

In some embodiments, $R^5$ may be selected from the following structures:

H, CH$_3$—, HOCH$_2$CH$_2$—, HOCH$_2$CH$_2$CH$_2$—, CF$_3$CH$_2$—, CF$_3$CH$_2$CH$_2$—,

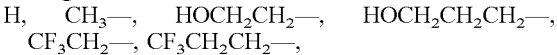

FCH$_2$CH$_2$CH$_2$-,

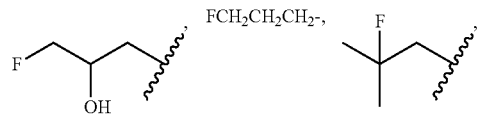

-continued
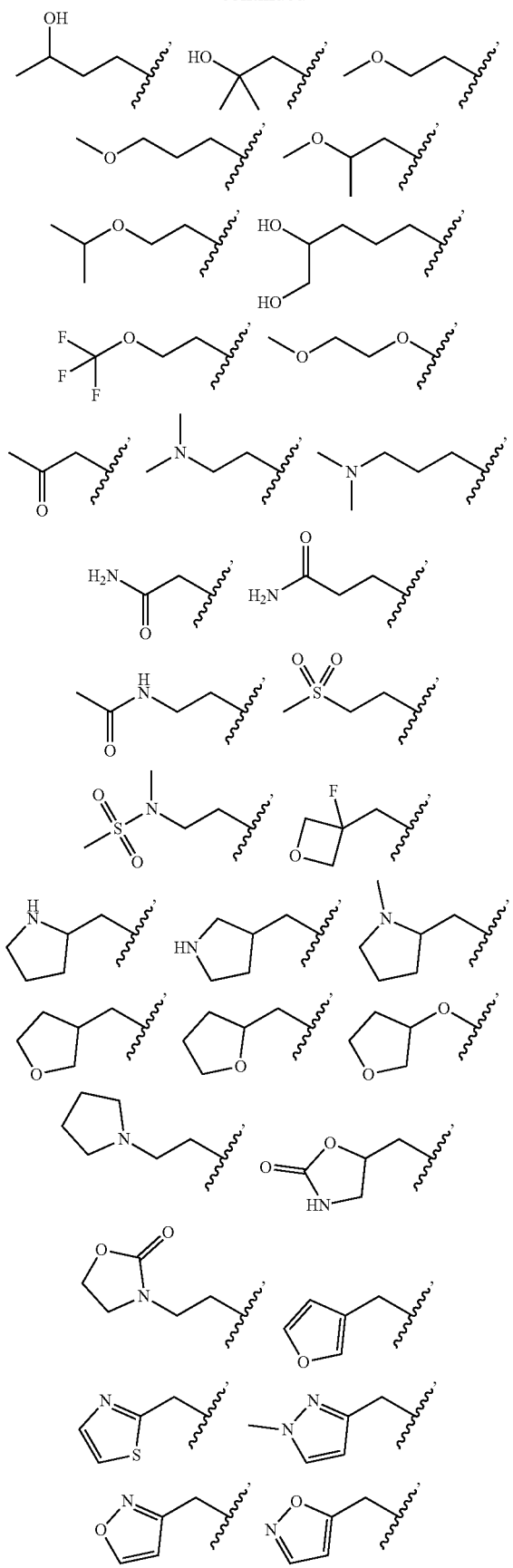
-continued
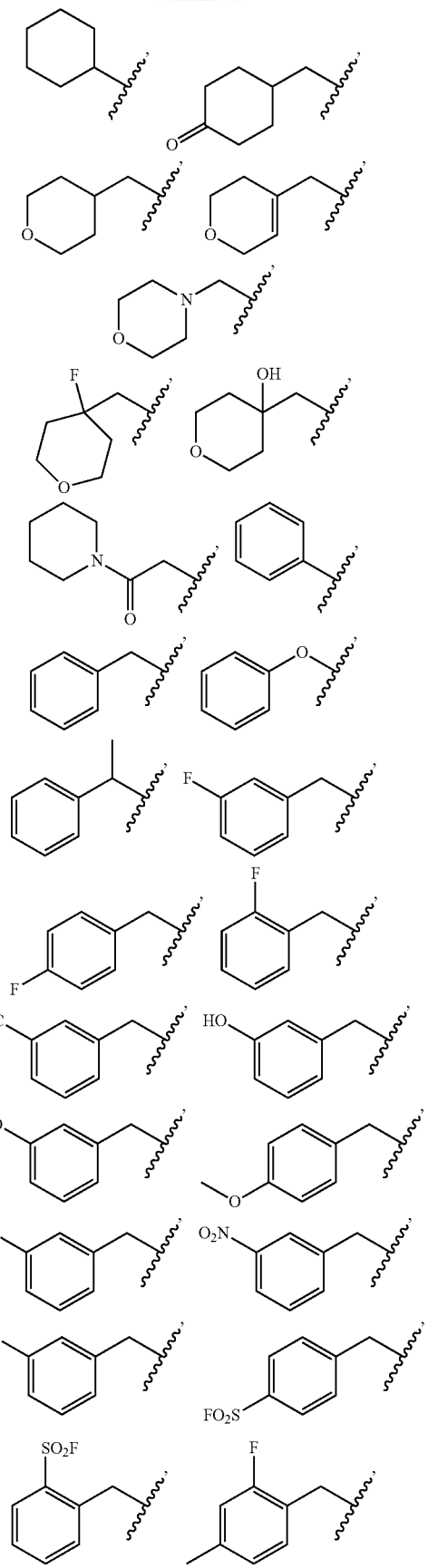

-continued

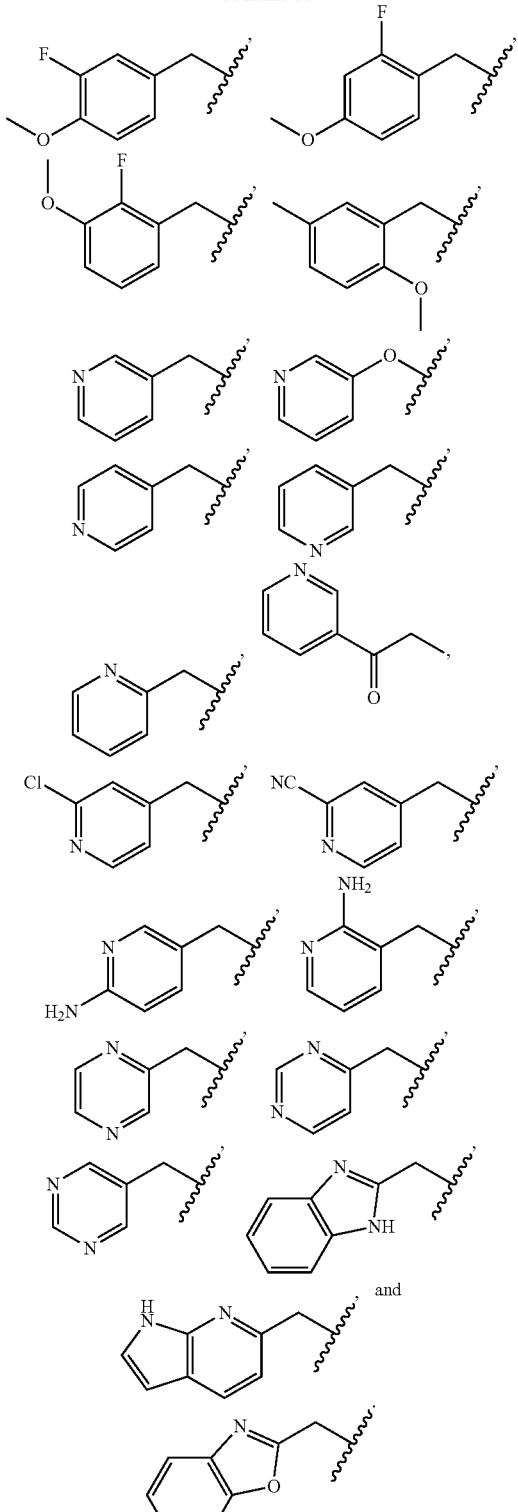

(In the above structures, ⁓ represents a binding position with the remaining residue of the compound.)

In the above fused ring structures, $R^6$ is H or $C_1$-$C_6$ alkyl. In some embodiments, $R^6$ may be H or $C_1$-$C_3$ alkyl. In some embodiments, $R^6$ may be H or methyl.

In some embodiments, the compound represented by Formula 1A may be a compound represented by the following Formula 1A-1:

[Formula 1A-1]

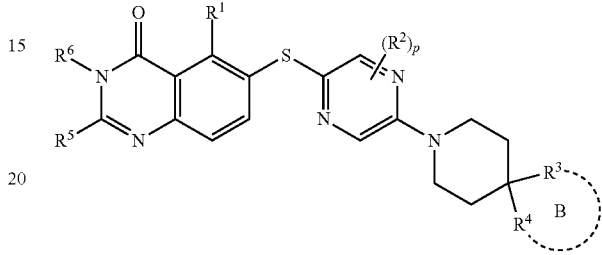

In Formula 1A-1, the definitions of $R^1$, $R^2$, $R^3$, $R^4$, $R^5$, $R^6$, Ring B and p are as described for Formula 1A above.

In some embodiments, the compound represented by Formula 1A may be selected from the following:

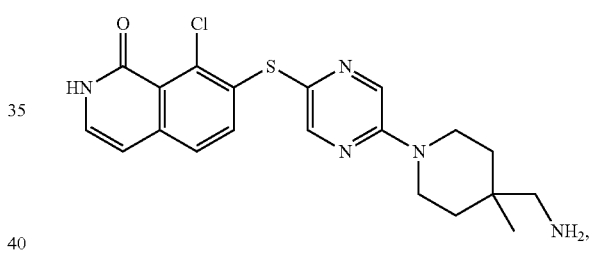

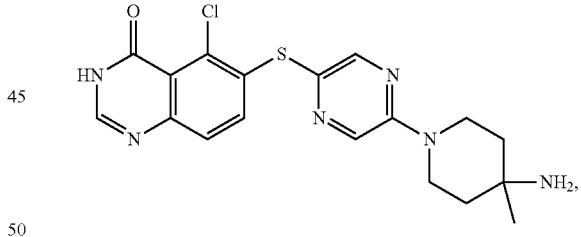

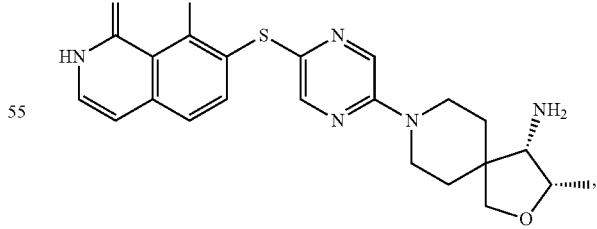

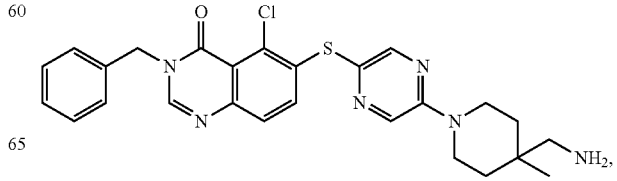

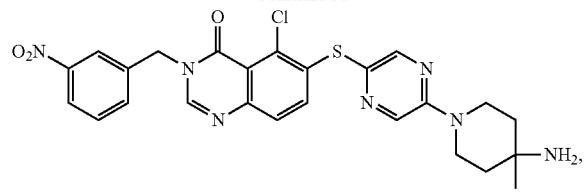
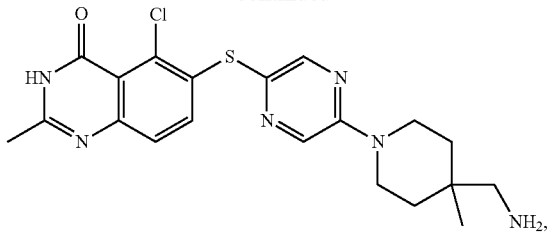
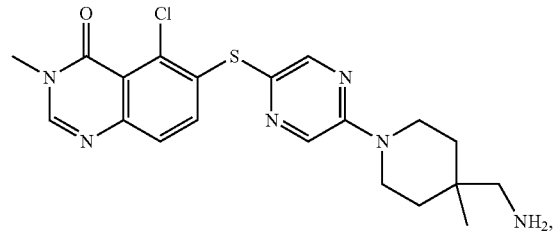
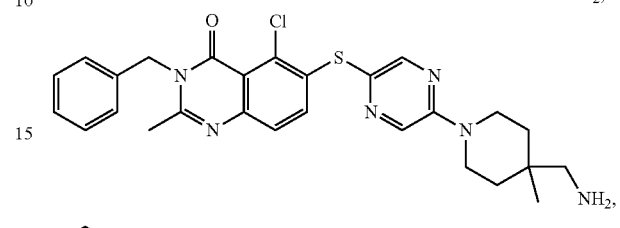
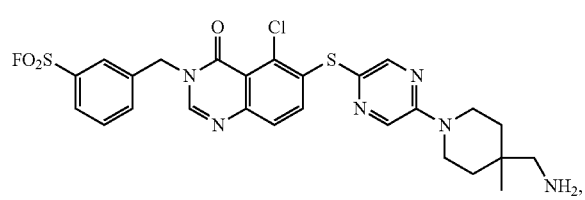
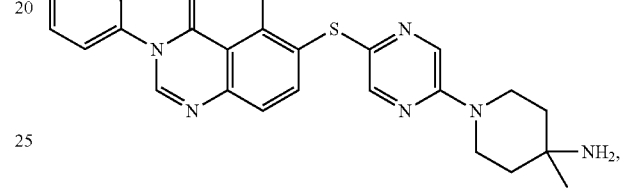
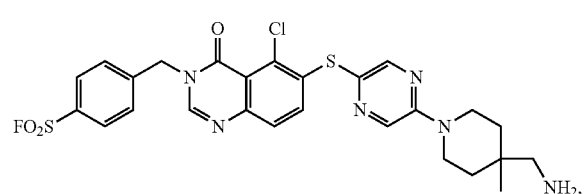
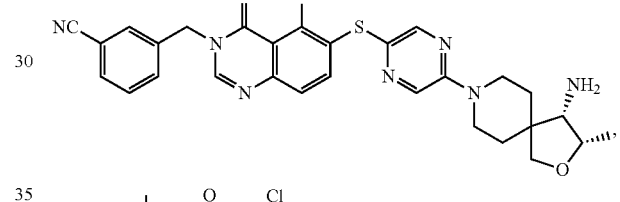
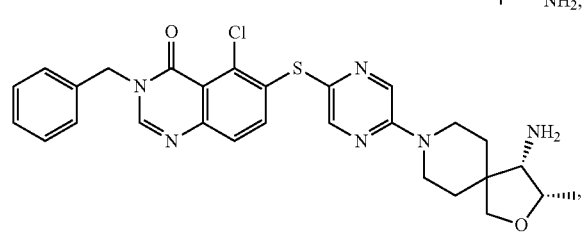
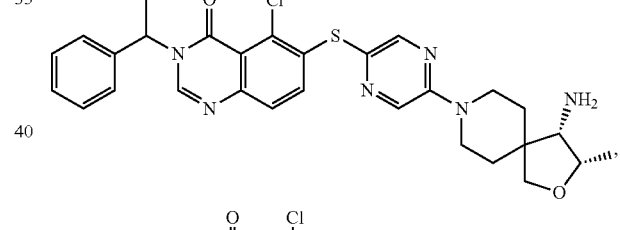
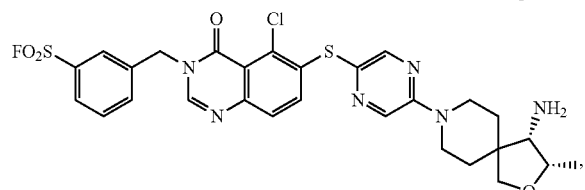
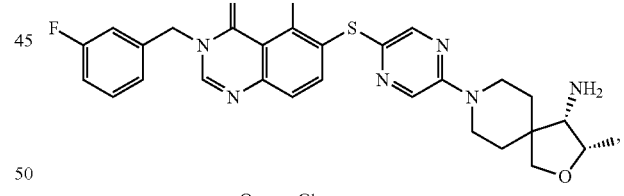
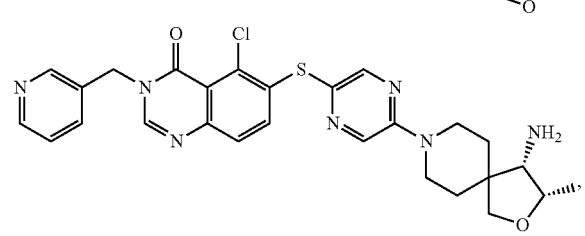
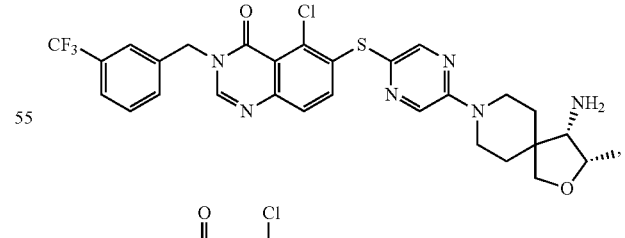
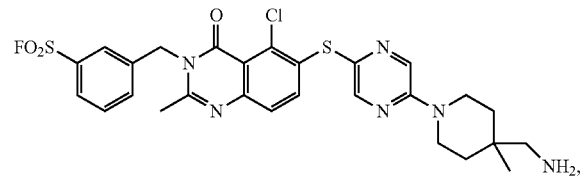
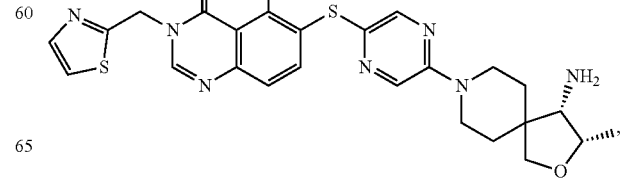

-continued
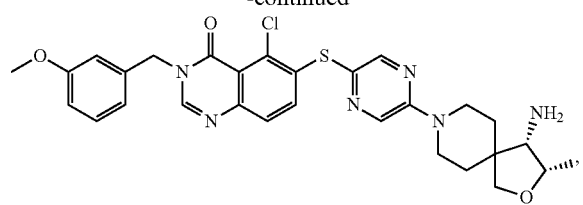
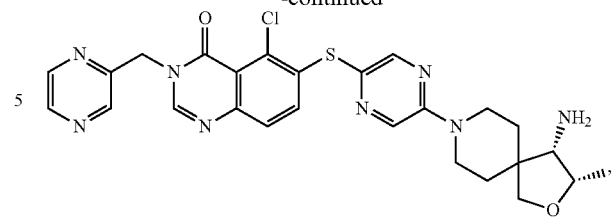
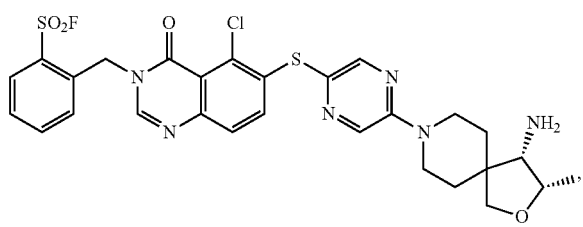
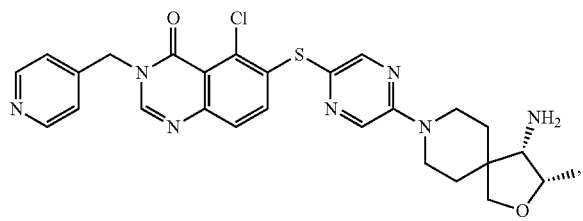
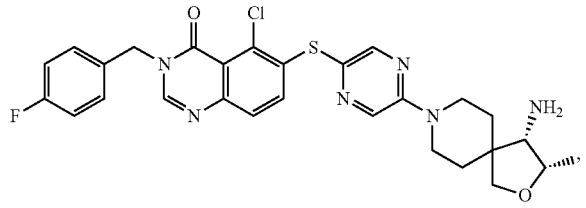
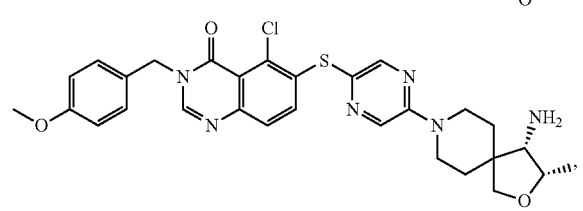
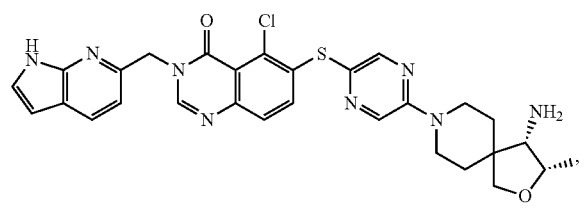
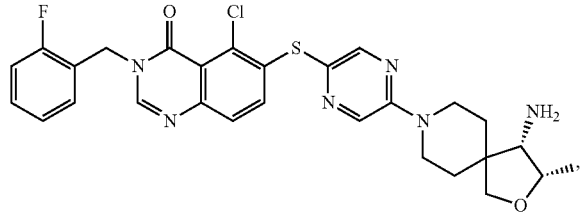
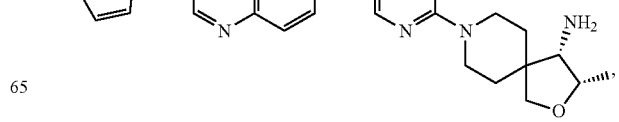

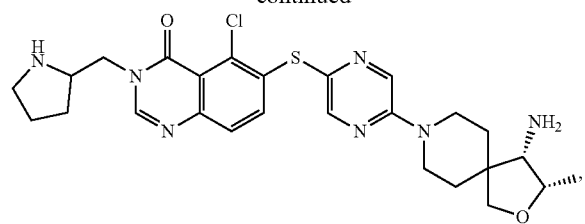
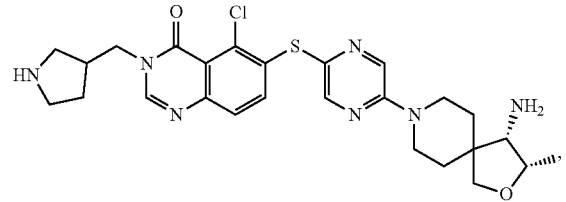
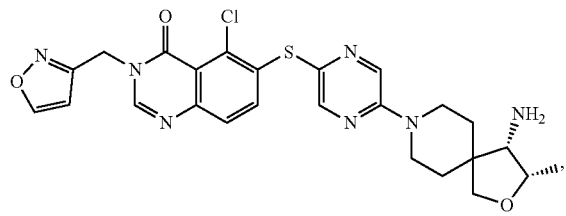
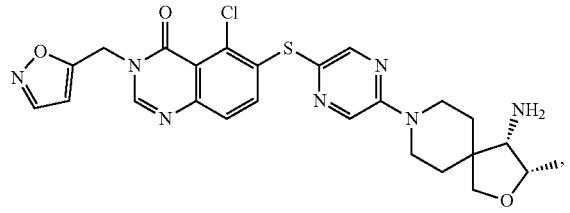
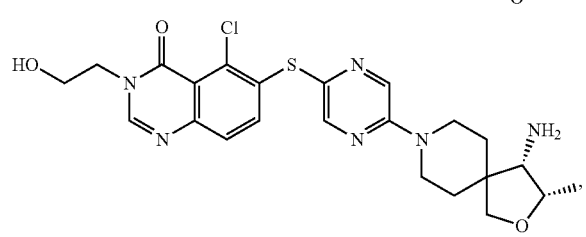
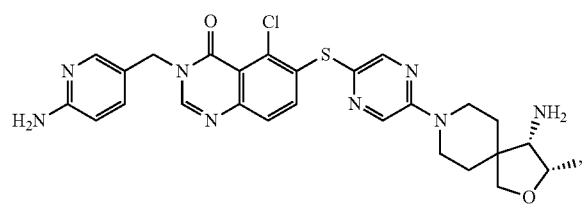
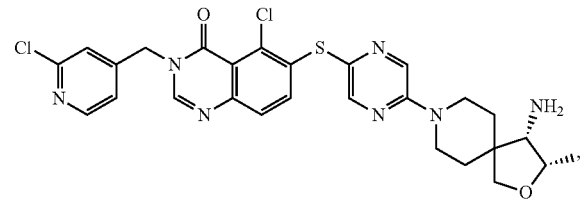
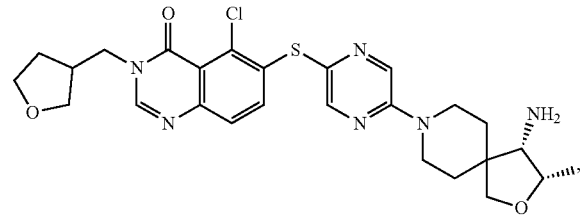
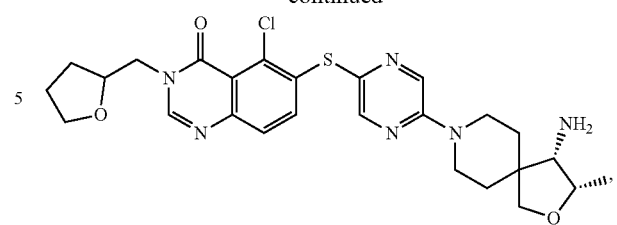
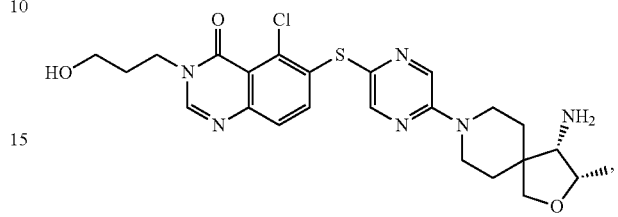

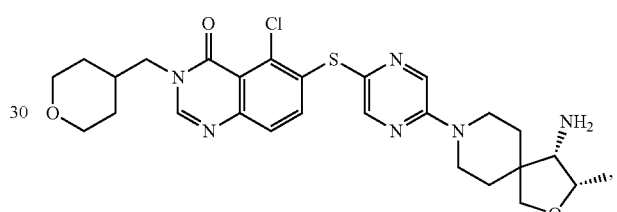
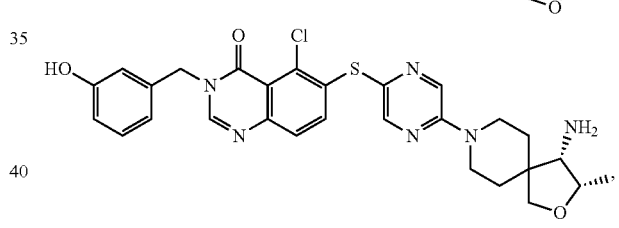
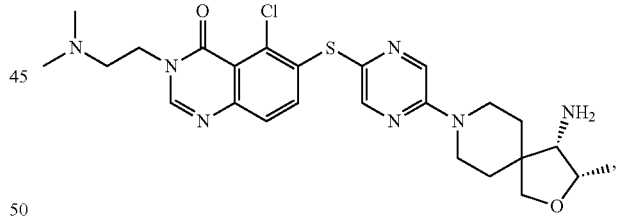
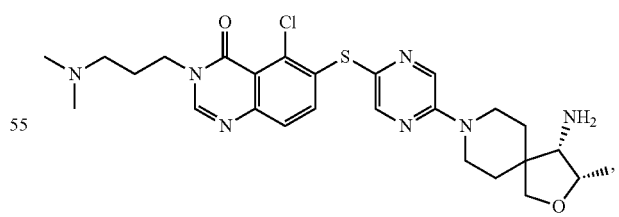
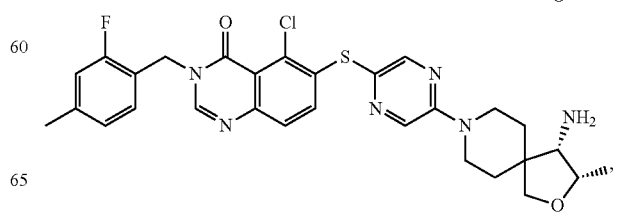

33
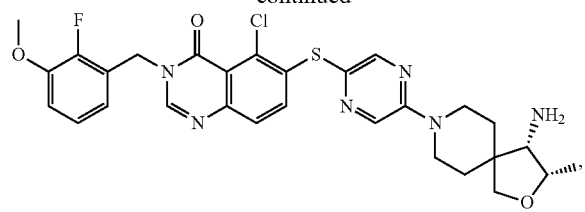
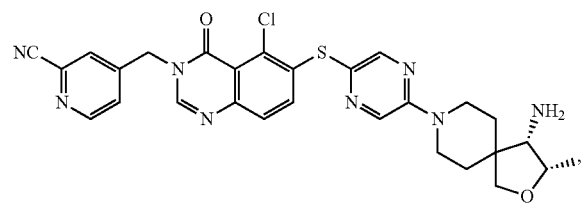
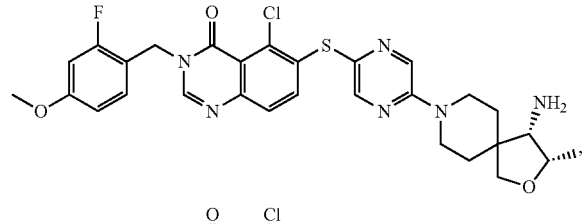
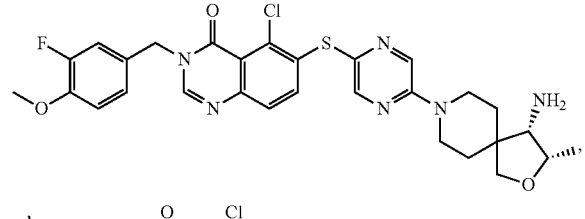
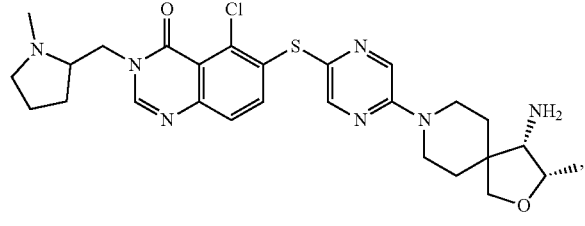
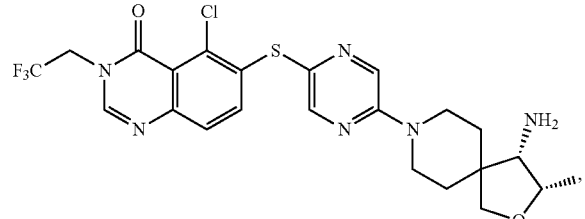
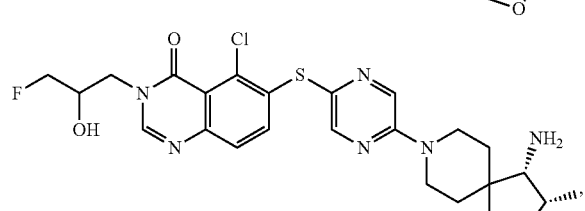
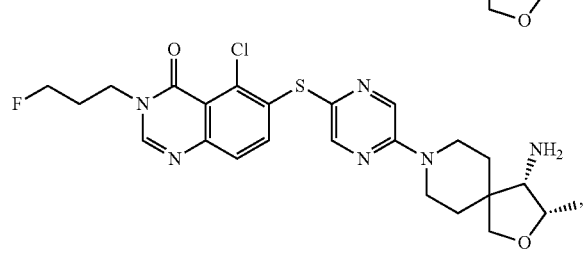
34
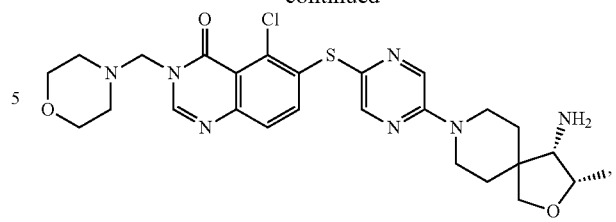
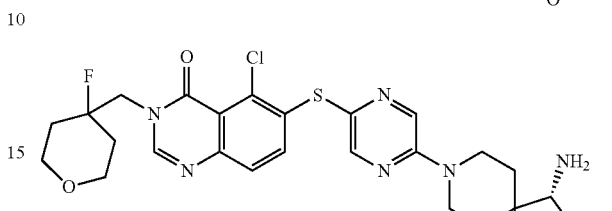
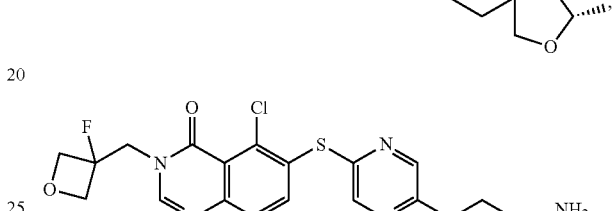
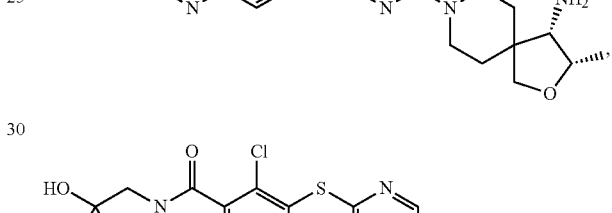
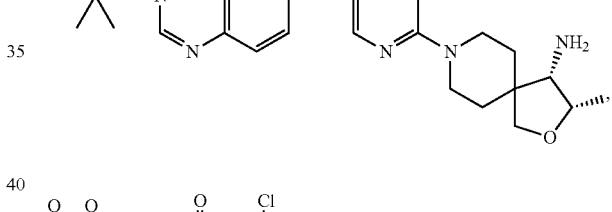
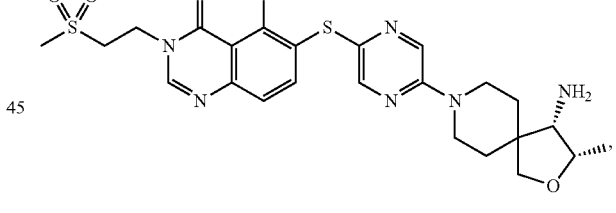
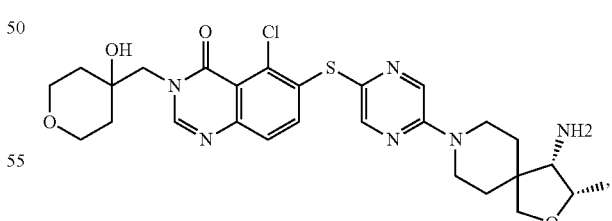
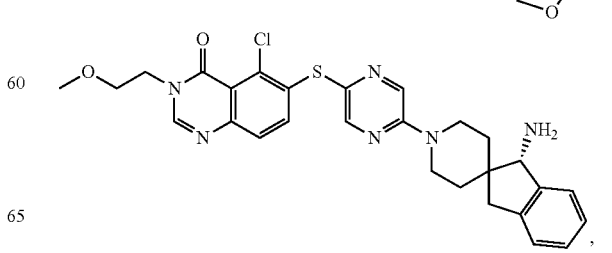

35
-continued
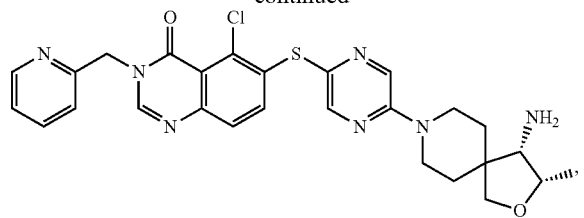
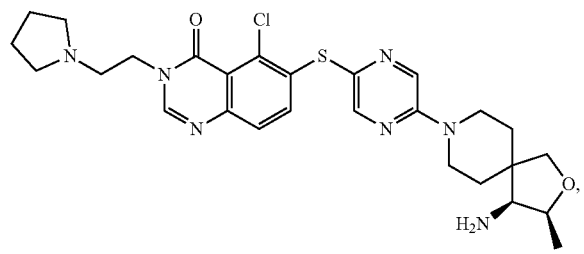
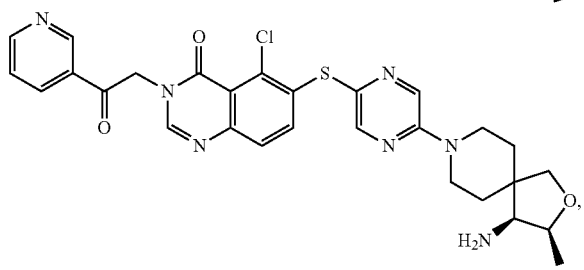
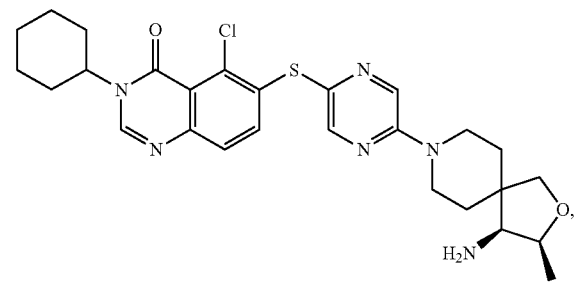
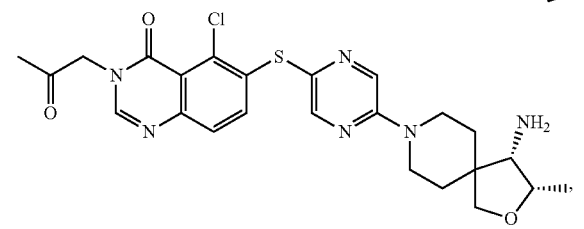
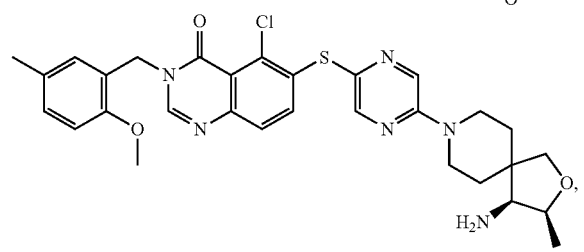
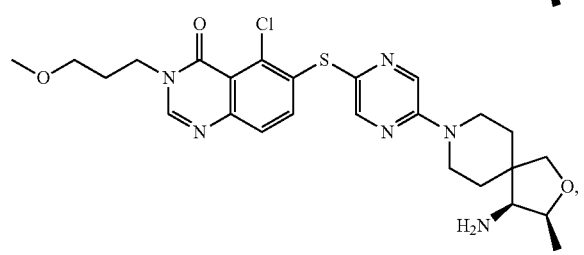
36
-continued
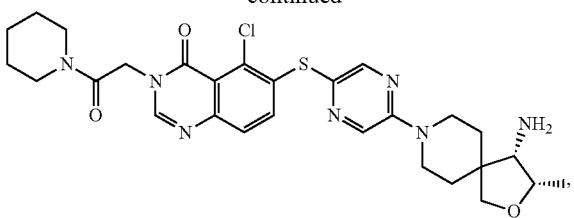
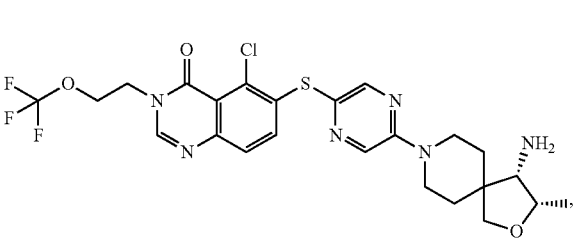
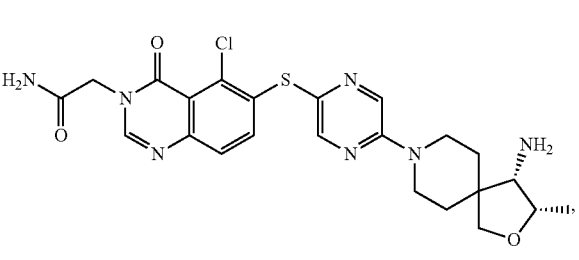
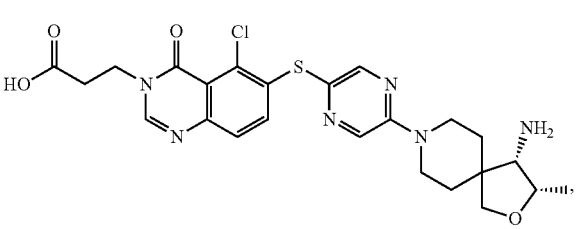
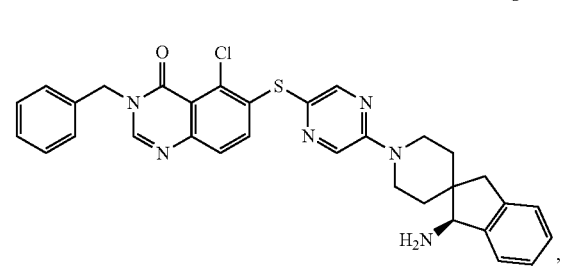
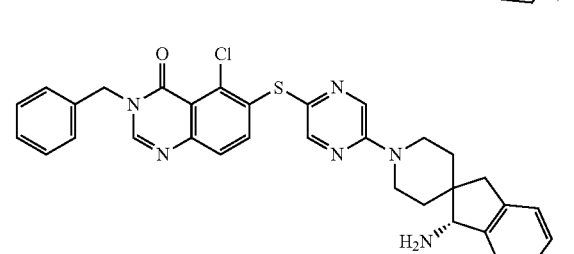
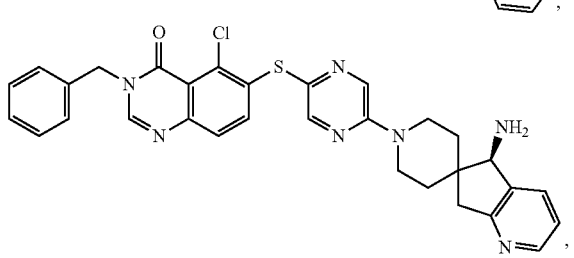

37
-continued
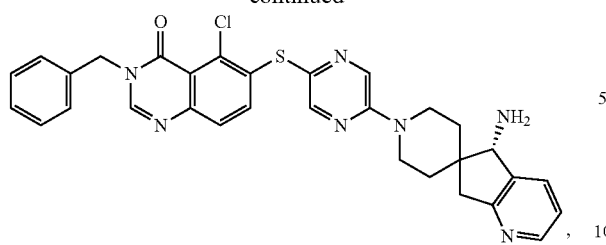,
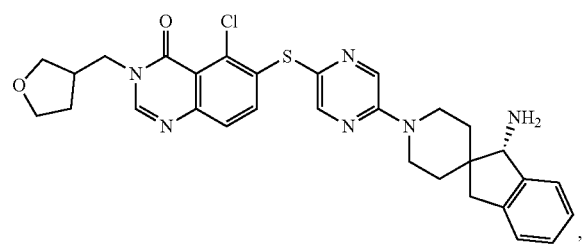,
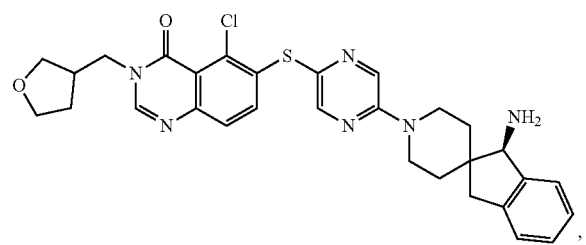,
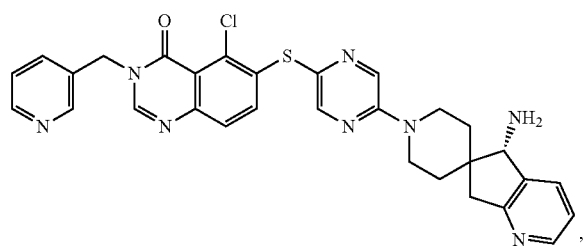,
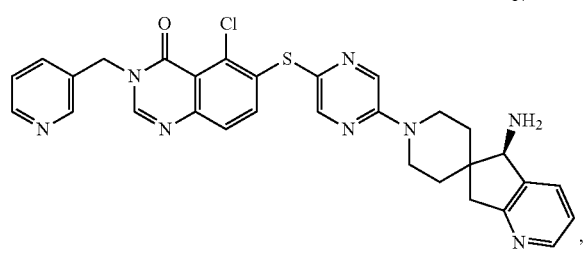,
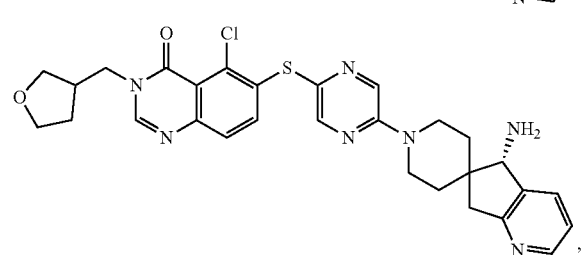,
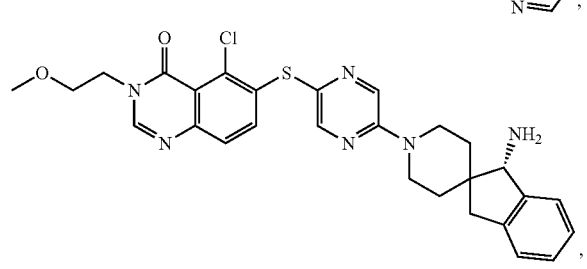,
38
-continued
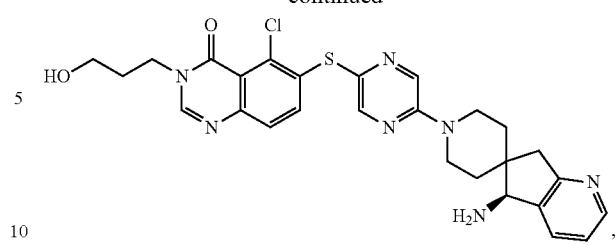,
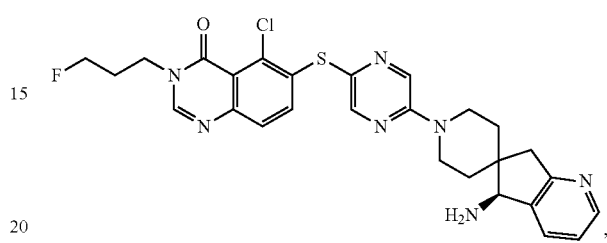,
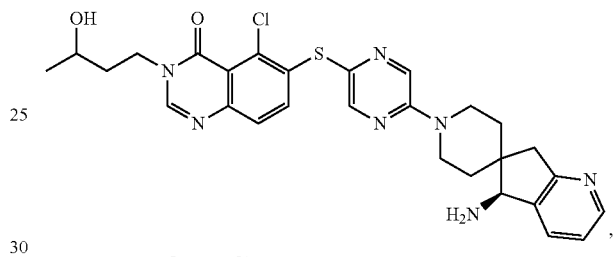,
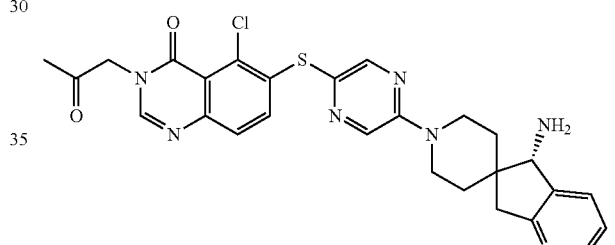,
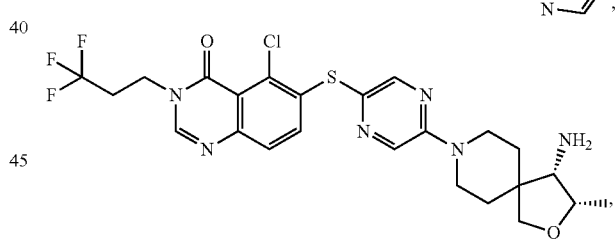,
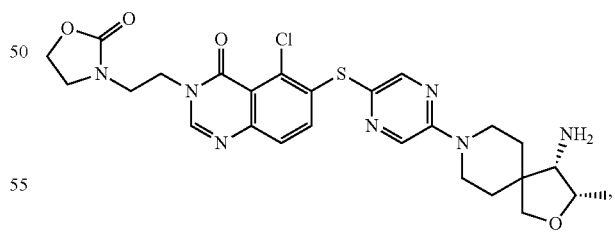,
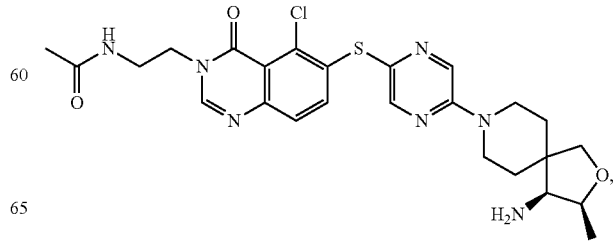,

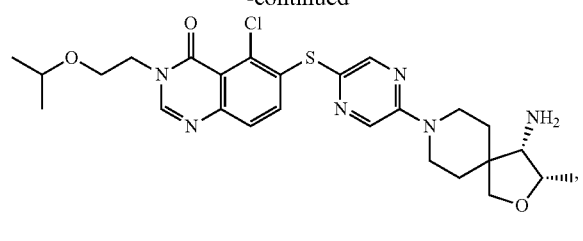
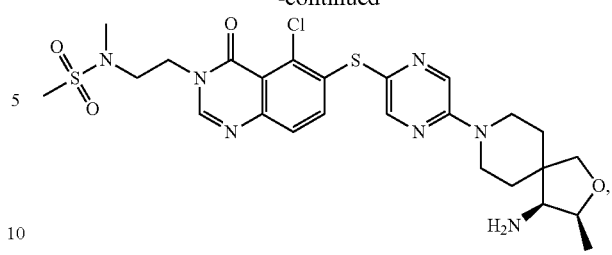
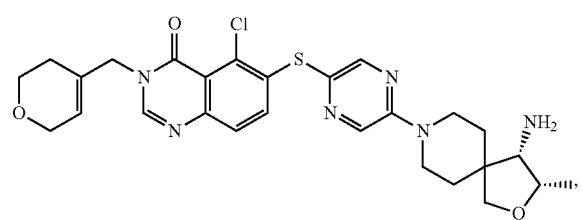
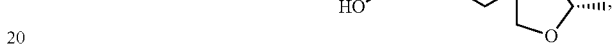
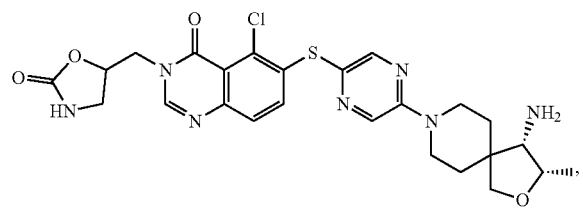
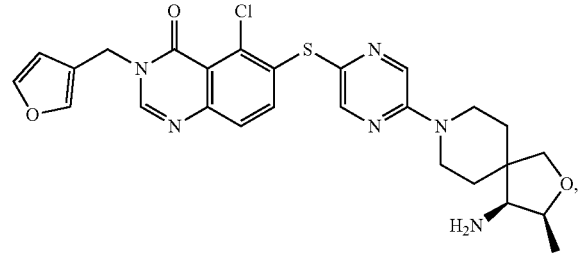
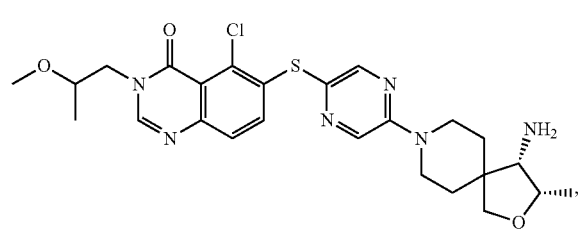
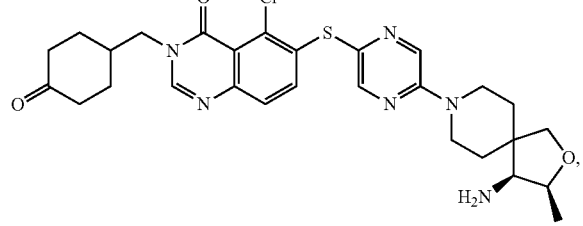
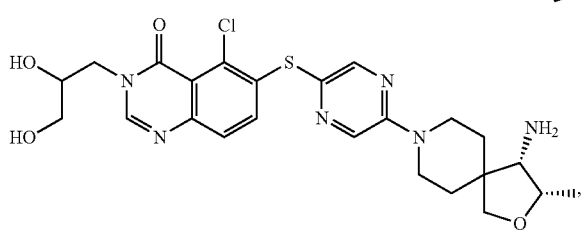
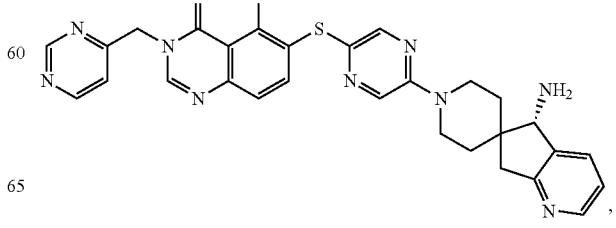

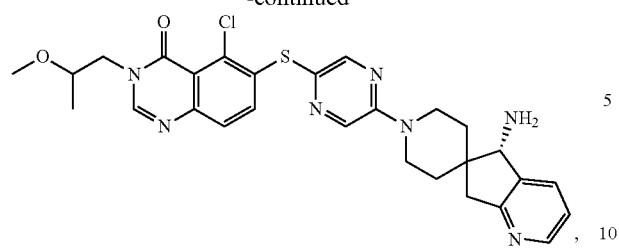
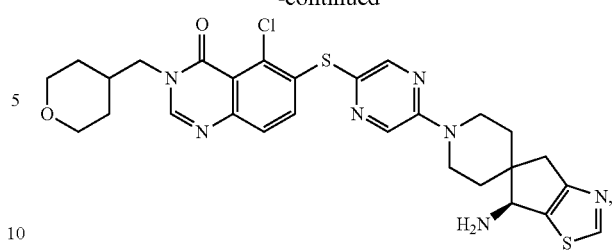
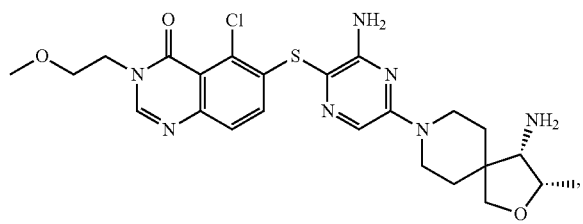
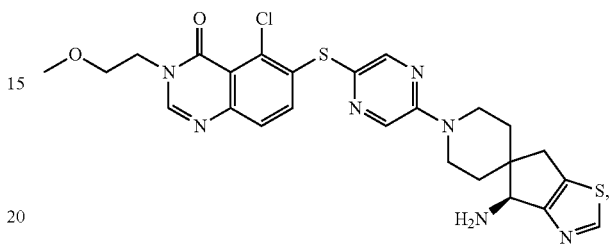
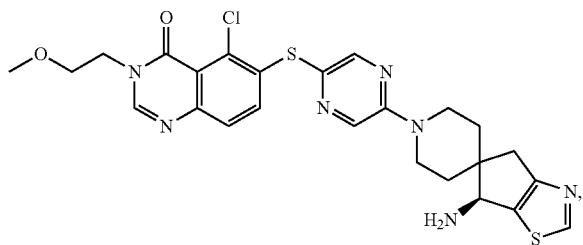
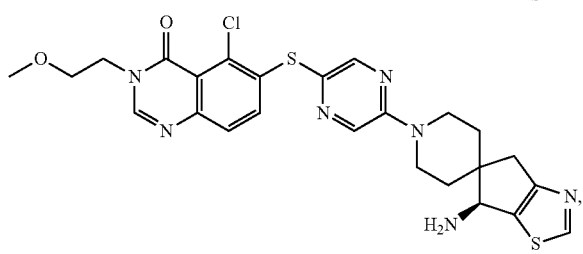
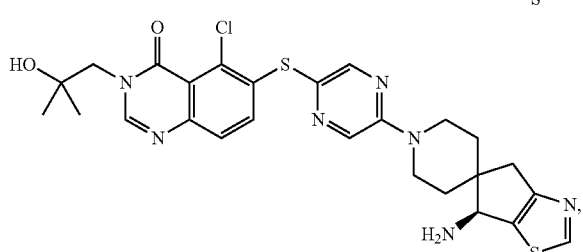
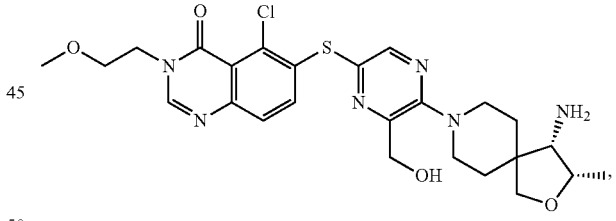
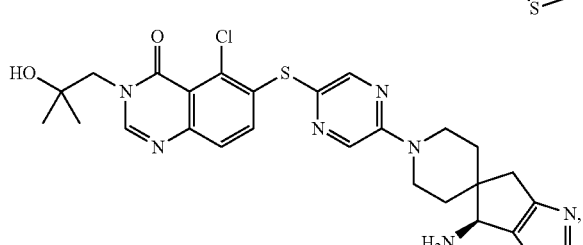
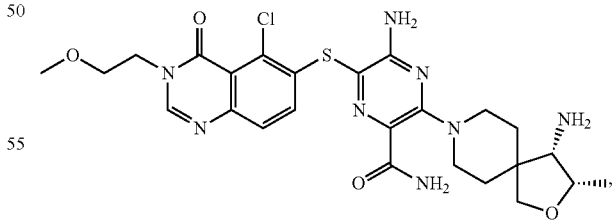
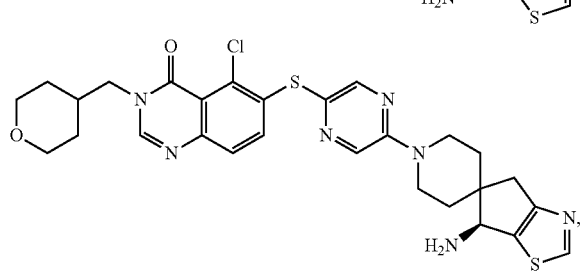
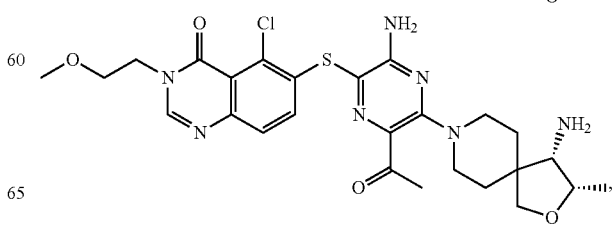

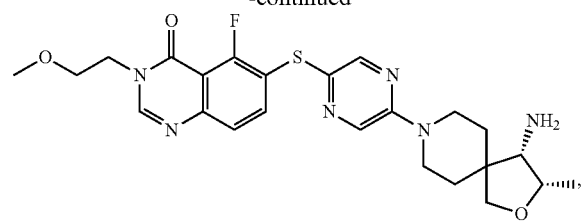
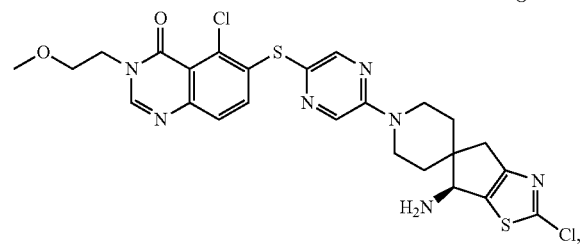
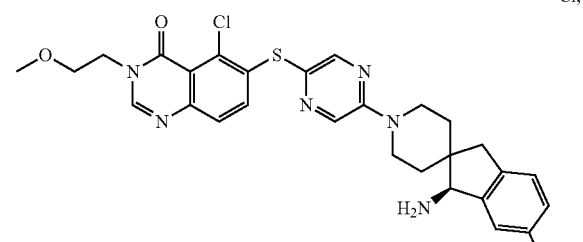
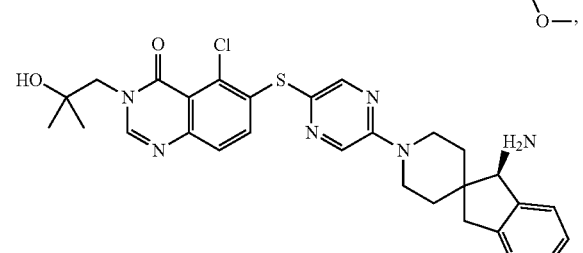
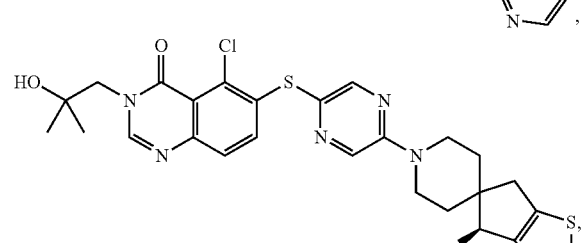
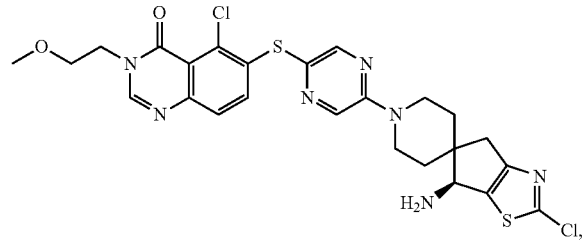
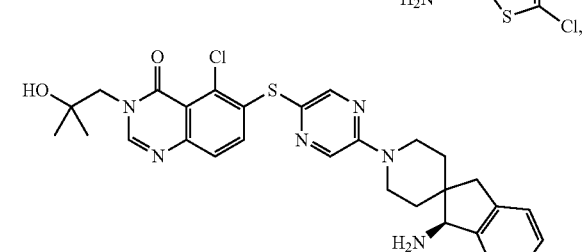
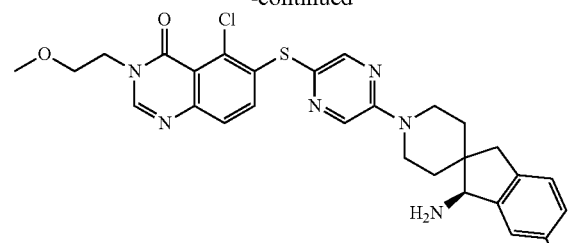
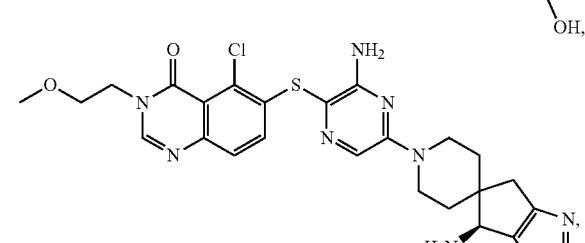
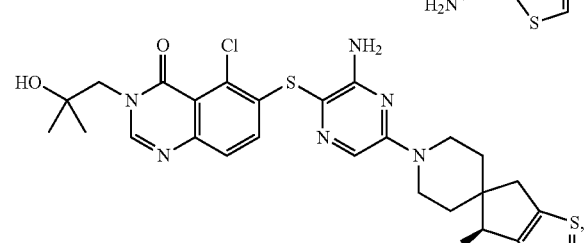
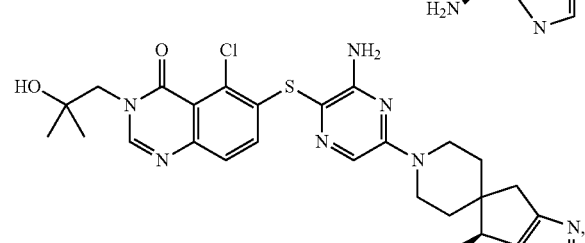
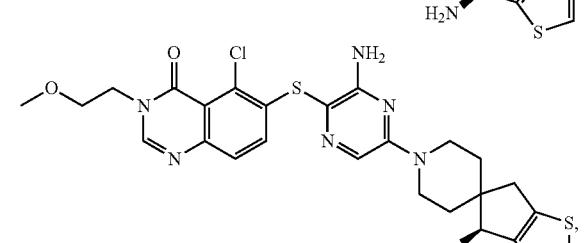
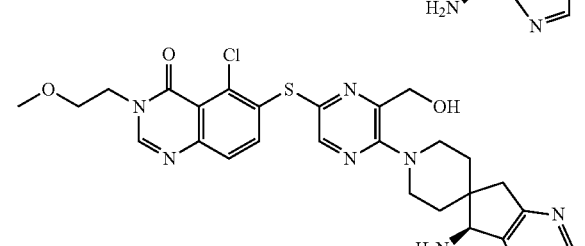
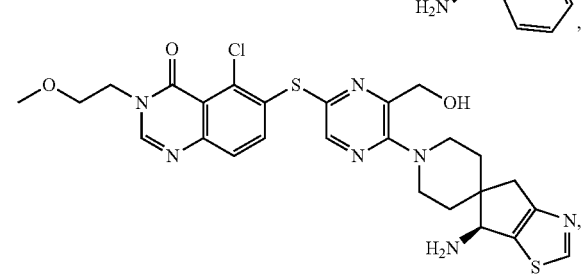

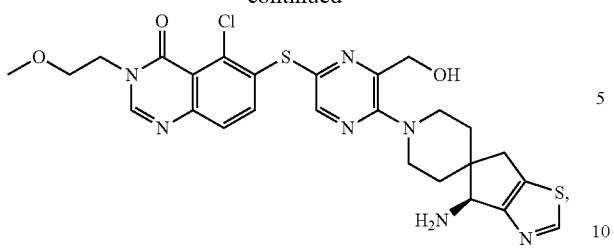
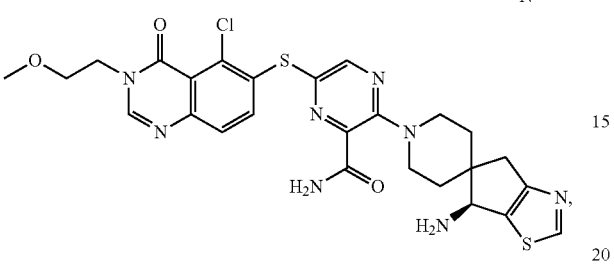
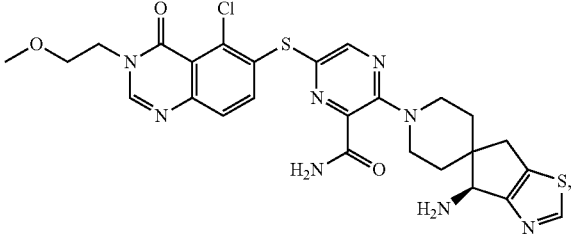
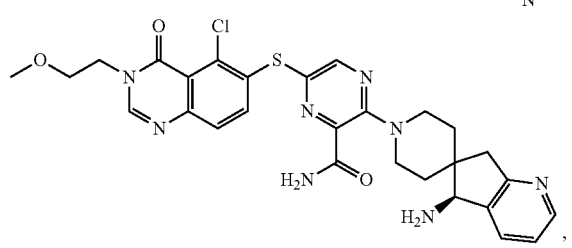
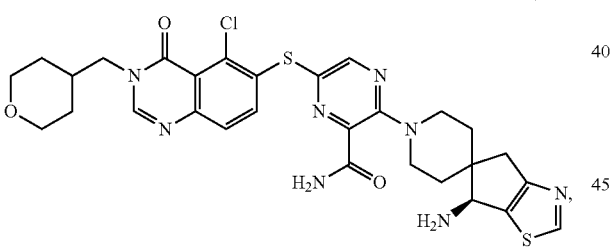
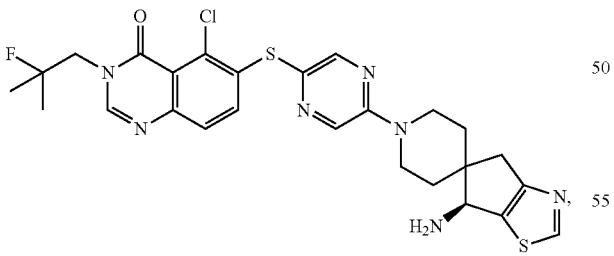
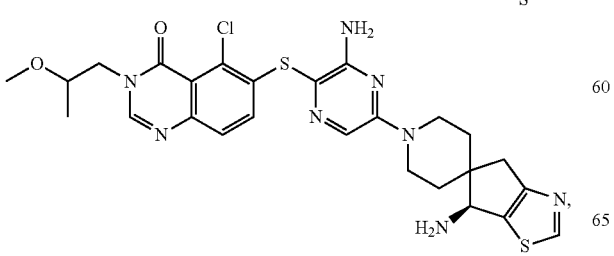
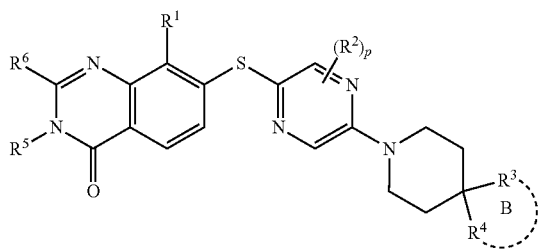
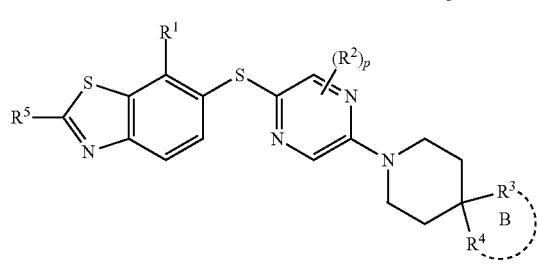
In some embodiments, the compound represented by Formula 1A may be a compound represented by any one of the following Formula 1A-2 to Formula 1A-9:
[Formula 1A-2]
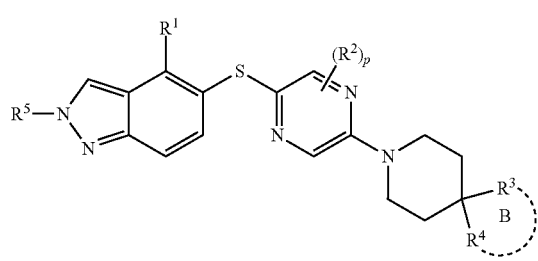
[Formula 1A-3]
[Formula 1A-4]

[Formula 1A-5]

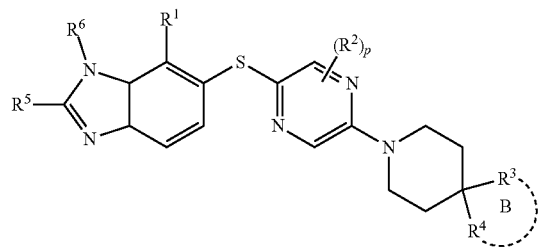

[Formula 1A-6]

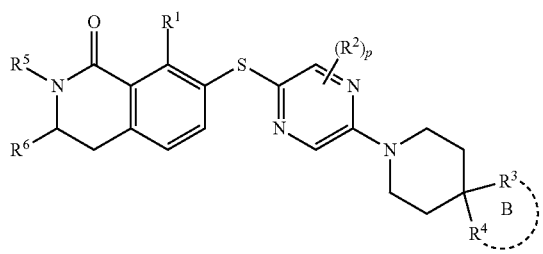

[Formula 1A-7]

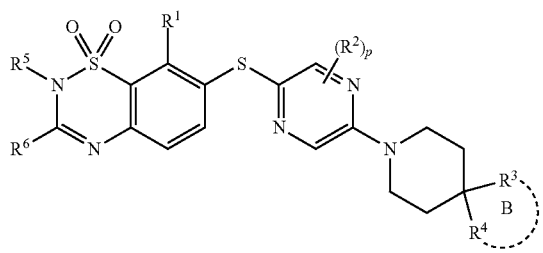

[Formula 1A-8]

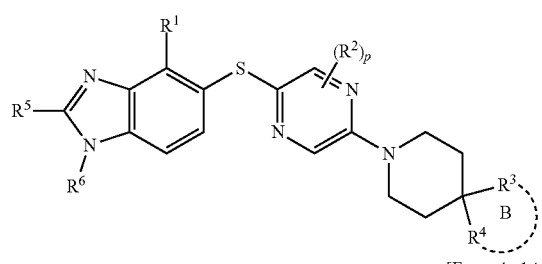

[Formula 1A-9]

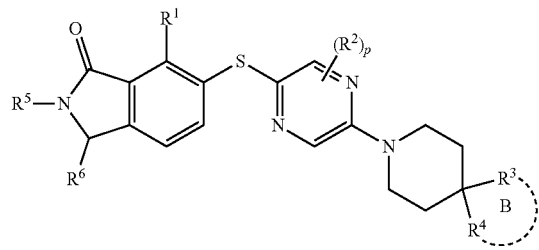

In Formula 1A-2 to Formula 1A-9, the definitions of $R^1$, $R^2$, $R^3$, $R^4$, $R^5$, $R^6$, Ring B and p are as described for Formula 1A above.

In one embodiment, the compound may be a compound of Formula 1A-4, 1A-5, 1A-8 or 1A-9.

In the compound of Formula 1A-4, 1A-5, 1A-8 or 1A-9,

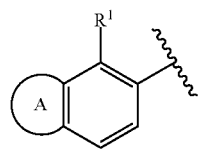

of Formula 1A is

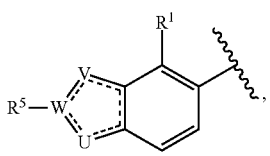

and U, V and W are defined as follows:
W is N, U is N, and V is CH, or U is $CHR^6$, and V is C(O); or
W is C, and any one of U and V is N, and the other is $NR^6$.

In one embodiment, $R^5$ of Formula 1A-4, 1A-5, 1A-8 or 1A-9 may be selected from the following (i) to (vi):

(i) H, halogen, hydroxy, $-NH_2$, $=NH$, $-C(O)NH_2$, nitro, cyano, amidino, or carboxy or a salt thereof;

(ii) $C_1$-$C_6$ alkyl, which is optionally substituted with at least one substituent selected from a group consisting of halogen, hydroxy, $C_1$-$C_6$ haloalkyl, $C_1$-$C_6$ alkoxy and $C_1$-$C_6$; $C_1$-$C_6$ alkoxy; or ($C_1$-$C_6$ alkoxy)-($C_1$-$C_6$ alkoxy)- (for example, it may be $C_1$-$C_6$ alkyl, $C_1$-$C_6$ alkoxy, or ($C_1$-$C_6$ alkoxy)-($C_1$-$C_6$ alkoxy)-, and may also be methyl, ethyl, methoxy, ethoxy, methoxyethoxy, ethoxyethoxy, and the like);

(iii) $C_6$-$C_{10}$ aryl, ($C_6$-$C_{10}$ aryl)-($C_1$-$C_3$ alkyl)- or $C_6$-$C_{10}$ aryloxy (for example, the aryl ring may be phenyl);

(iv) heteroaryl, heteroaryl-($C_1$-$C_3$ alkyl)- or heteroaryloxy (for example, the heteroaryl ring may be 5- or 6-membered monocyclic heteroaryl containing one or two N atoms, and for example, the heteroaryl ring may be pyrimidinyl or pyridinyl);

(v) heterocycloalkyl, heterocycloalkyl-($C_1$-$C_3$ alkyl)-, or heterocycloalkyloxy (for example, the heterocycloalkyl may be 4- to 7-membered fully saturated or partially unsaturated heterocycloalkyl containing one or two heteroatoms selected from N and O, and for example, the heterocycloalkyl ring may be tetrahydrofuranyl, pyrrolidinyl, tetrahydropyranyl or morpholinyl); and (vi) $C_3$-$C_8$ cycloalkyl, $C_3$-$C_8$ cycloalkyl-($C_1$-$C_3$ alkyl)- or $C_3$-$C_8$ cycloalkyloxy.

The aryl ring, heteroaryl ring, heterocycloalkyl ring and cycloalkyl ring described in (iii) to (vi) above may be each optionally substituted. For example, these rings may be optionally substituted with at least one substituent selected from halogen, hydroxy, oxo, $-NH_2$, cyano, nitro, $C_1$-$C_6$ alkyl, and $C_1$-$C_6$ alkoxy.

In one embodiment, $R^5$ of Formula 1A-4, 1A-5, 1A-8 or 1A-9 may be $C_1$-$C_6$ alkyl (for example, methyl, ethyl), benzyl, phenyl, phenoxy, tetrahydrofuranyl, tetrahydrofuranyloxy, methoxy, ethoxy, methoxyethoxy, ethoxyethoxy, pyridinyl, pyridinyloxy, pyridinylmethyl, pyrimidinyl, pyrimidinylmethyl, pyrimidinyloxy, methoxyphenyl, or methoxybenzyl.

In some embodiments, the compound represented by Formula 1A-2 to Formula 1A-9 may be selected from the following:
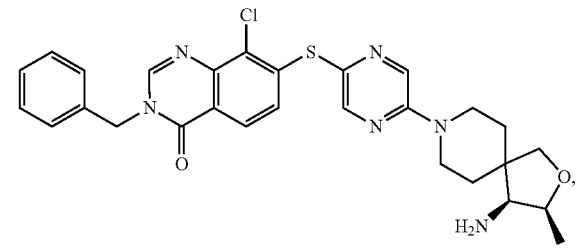
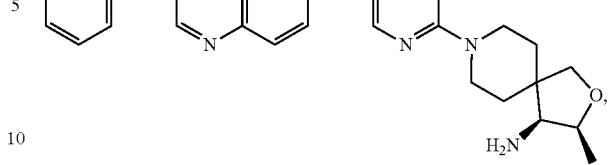
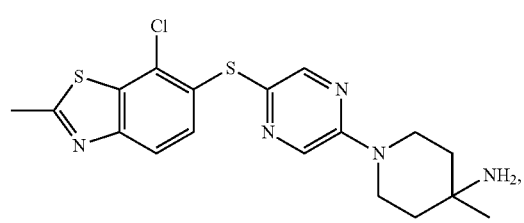
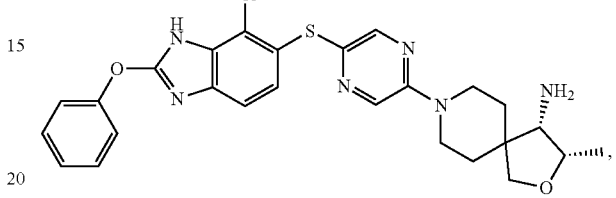
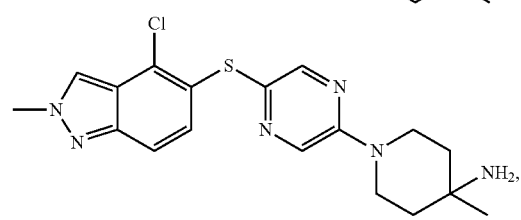
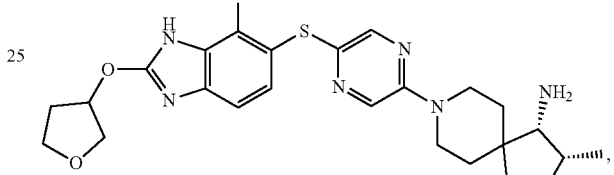
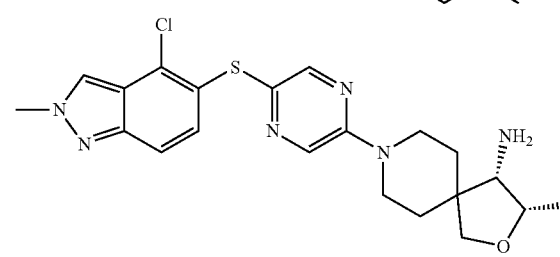
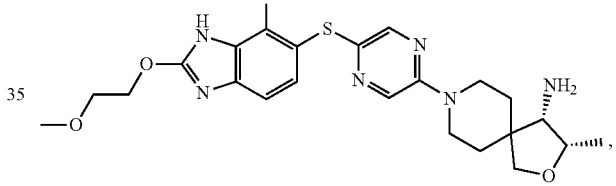
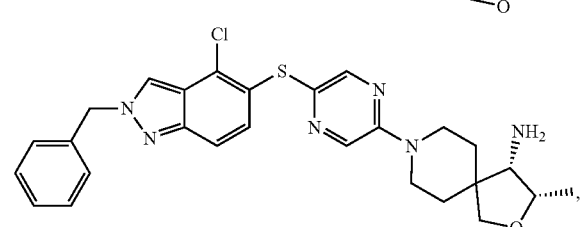
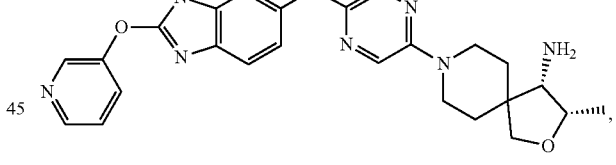
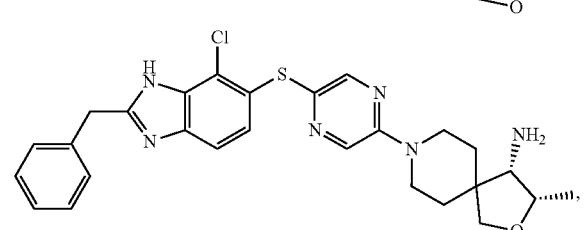
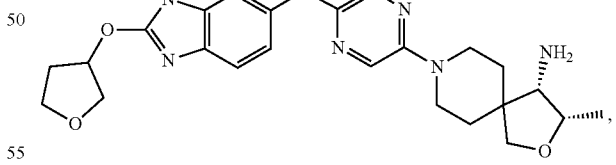
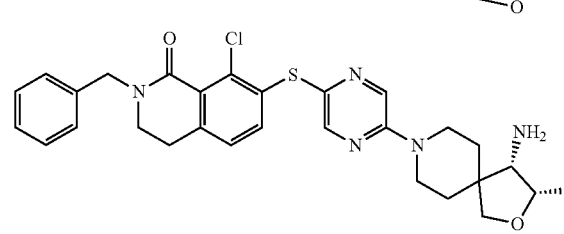
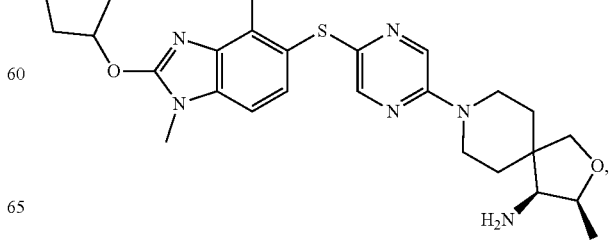

-continued

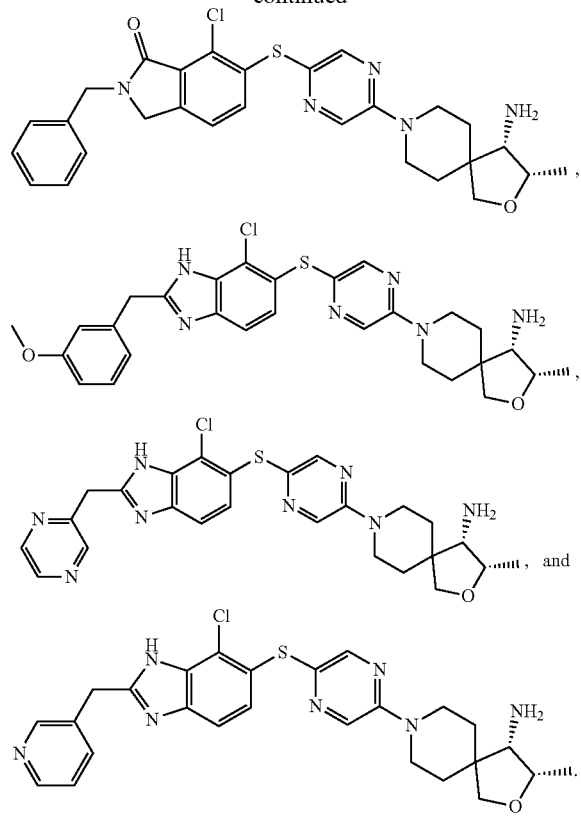

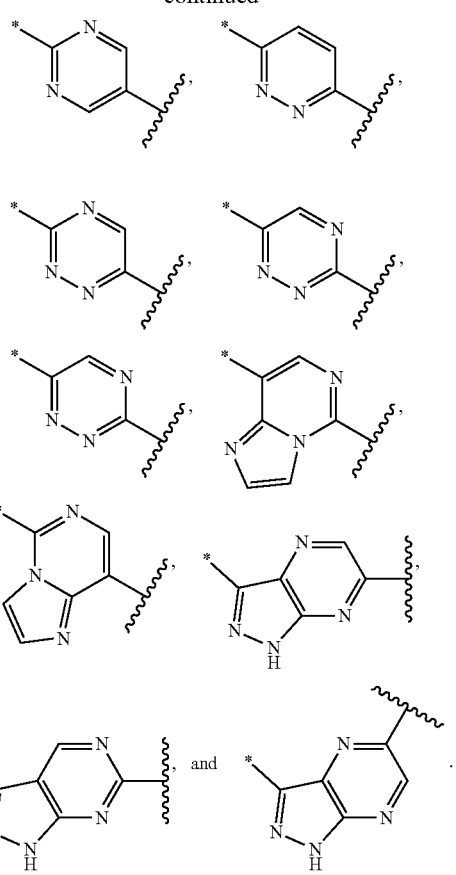

In some embodiments, the pyrazine core of the compound represented by Formula 1A may be replaced with another heteroaryl ring, for example, a 5- to 10-membered heteroaryl ring containing a nitrogen atom. The 5- to 10-membered heteroaryl ring containing a nitrogen atom may include pyridine, pyridazine, pyrimidine, triazine, imidazopyrimidine, pyrazolopyrazine or pyrazolopyrimidine.

In this case, the compound represented by Formula 1A may be represented by the following Formula 1:

[Formula 1]

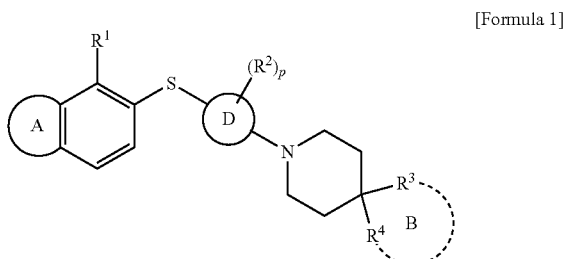

In Formula 1, ring D is selected from the following structures:

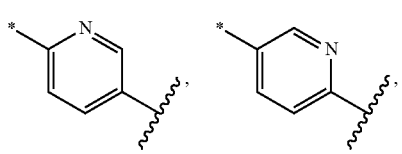

(* represents the binding position with the sulfur atom.)

The definitions of $R^1$, $R^2$, $R^3$, $R^4$, ring A, Ring B and p are as described for Formula 1A above.

Among the compounds represented by Formula 1, the compounds having, as Ring D, a structure other than the pyrazine core may be selected from, for example, the compounds represented by the following formula:

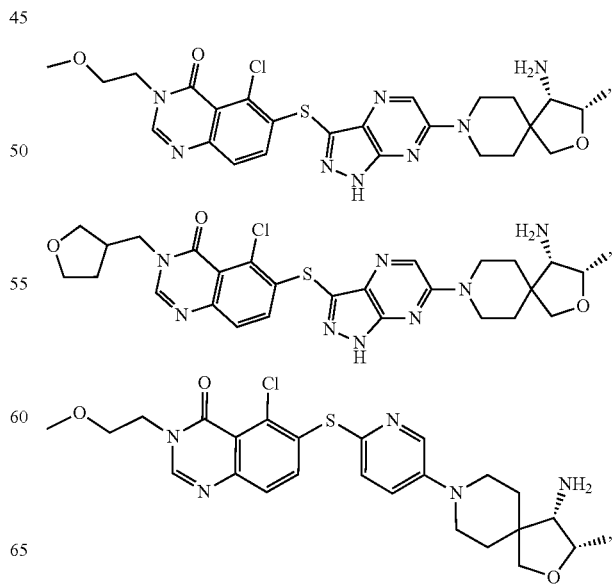

-continued

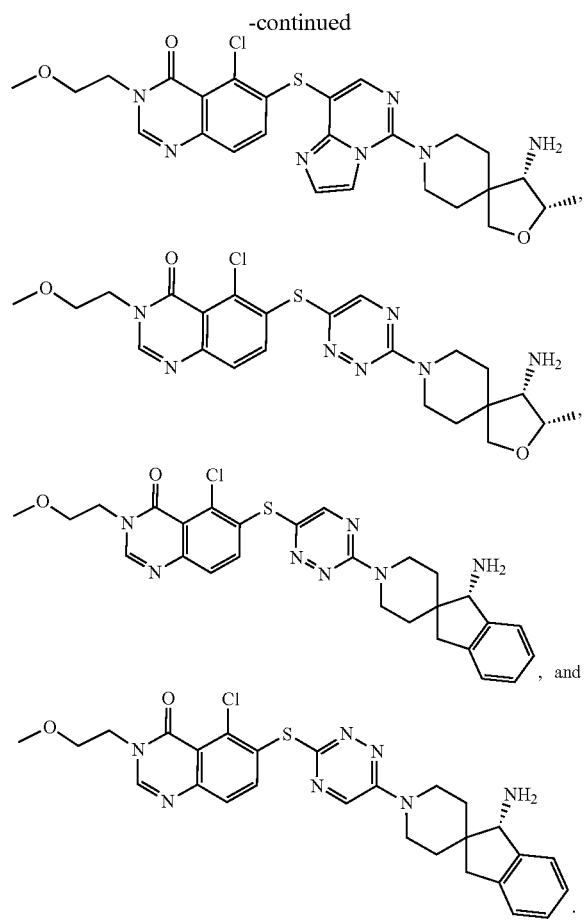

In one aspect, there is provided a compound represented by the following Formula 2, or a stereoisomer, solvate or pharmaceutically acceptable salt thereof:

[Formula 2]

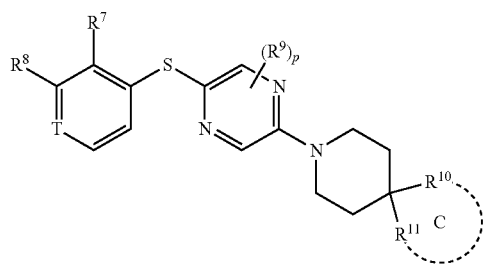

In Formula 2, T may be C or N.

In Formula 2, $R^1$ may be H, a halogen atom, or $C_1$-$C_6$ haloalkyl.

In Formula 2, $R^8$ may be —COOR$^c$, —SO$_2$R$^c$, —SO$_2$NR$^c$R$^d$, —COR$^c$, —NHCOR$^c$ or —CONHR$^c$. R$^c$ and R$^d$ may be each independently H, halogen, $C_1$-$C_6$ alkyl, —(CH$_2$)$^m$—($C_6$-$C_{10}$ aryl), —(CH$_2$)$_m$-(5- to 10-membered heteroaryl). m may be an integer of 0, 1 or 2.

The $C_6$-$C_{10}$ aryl may be phenyl. The 5- to 10-membered heteroaryl may include one or two heteroatoms selected from N, O and S. For example, the 5- to 10-membered heteroaryl may be 5-membered or 6-membered heteroaryl containing one or two N (for example, pyrrolyl, pyridinyl, pyrimidinyl, etc.).

In one embodiment, $R^8$ may be —CONN—CH$_2$-phenyl, —CONH—CH$_2$-pyridinyl, —COOCH$_3$, —SO$_2$F, —SO$_2$—NH$_2$, —SO$_2$—NH—CH$_3$, or —SO$_2$—NH—CH$_2$-phenyl.

In Formula 2, $R^9$ may be selected from a group consisting of H, halogen, hydroxy, oxo, $C_1$-$C_{20}$ alkyl, $C_1$-$C_{20}$ alkoxy, $C_2$-$C_{20}$ alkoxyalkyl, an amine group, $C_1$-$C_{20}$ alkyl substituted with an amine group, an imine group, nitro, cyano, amidino, and a carboxyl group or a salt thereof.

In Formula 2, $R^{10}$ and $R^{11}$ may be each independently H, $C_1$-$C_6$ alkyl, an amine group, or $C_1$-$C_6$ alkyl substituted with an amine group, or $R^{10}$ and $R^{11}$ may be connected to each other to form Ring C.

$R^{10}$ may be an amine group or an aminomethyl group.

$R^{11}$ may be a methyl group.

Ring C is a 3-, 4-, 5-, 6-, 7-, or 8-membered cyclic group optionally containing one oxygen atom, which may be optionally substituted with $C_1$-$C_6$ alkyl, an amine group, or $C_1$-$C_6$ alkyl substituted with an amine group. Ring C may be a substituted or unsubstituted tetrahydrofuran. The tetrahydrofuran may be substituted with one or more selected from a group consisting of $C_1$-$C_6$ alkyl, an amine group, and $C_1$-$C_6$ alkyl substituted with an amine group.

Ring C may be optionally fused with an aryl or heteroaryl ring.

In one embodiment, $R^{10}$ and $R^{11}$ may be connected to each other to form Ring C, Ring C may be cyclopentane or tetrahydrofuran, Ring C may be optionally substituted with $C_1$-$C_6$ alkyl or —NH$_2$. Also, ring C may be optionally fused with phenyl or pyridine.

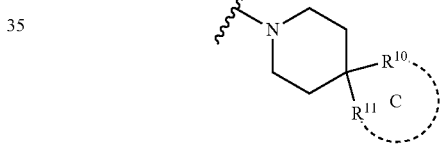

In one embodiment,

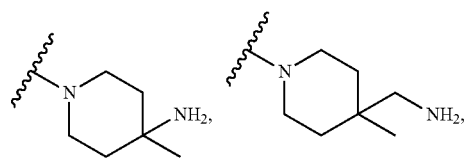

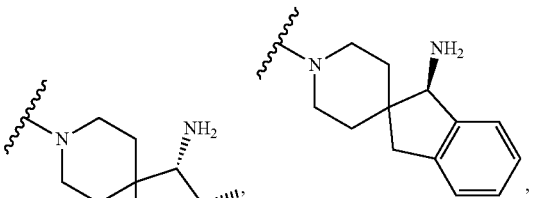

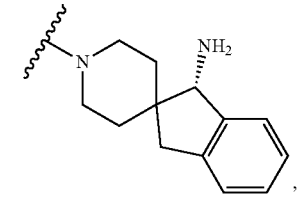

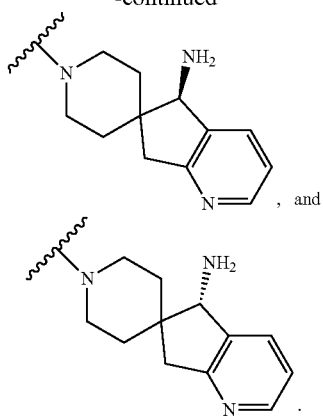, and of Formula 2 may be selected from the following:
In Formula 2, q may be an integer of 0, 1 or 2.
The compound of Formula 2 may be selected from a group consisting of the following folmulae:

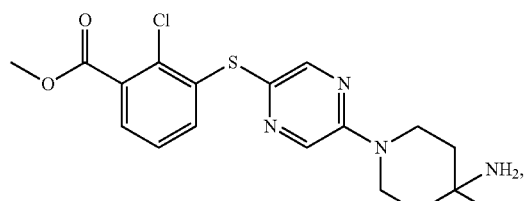

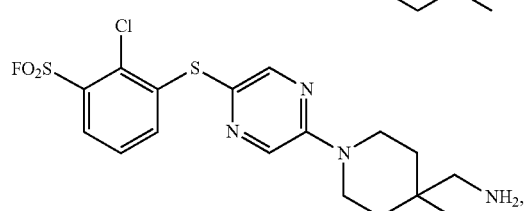

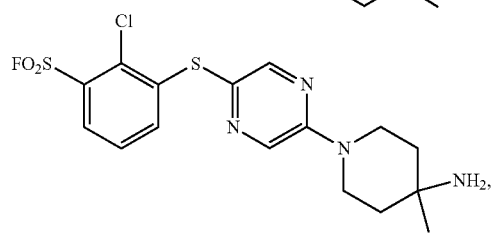

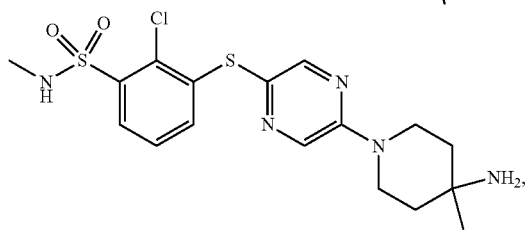

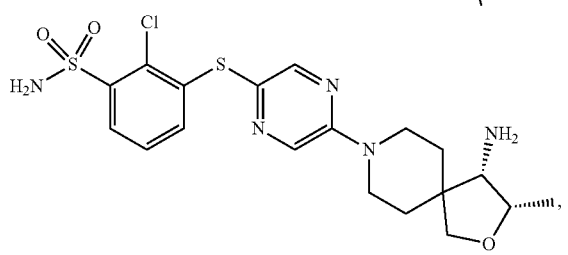

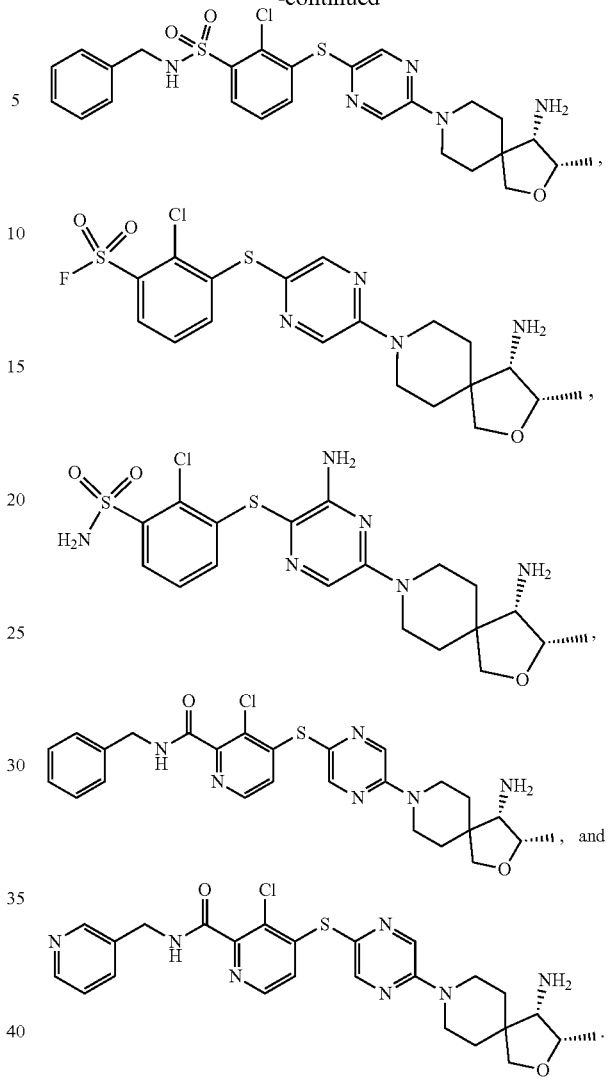

In one aspect, there is provided a compound represented by Formula 3A, or a stereoisomer, solvate or pharmaceutically acceptable salt thereof:

[Formula 3A]

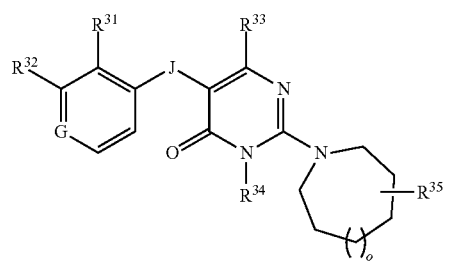

In Formula 3A, J may be absent or S.
In Formula 3A, G may be C or N.
In Formula 3A, o may be an integer of 0, 1, 2, 3, 4, or 5. o may be an integer of 0 or 1.
In Formula 3A, $R^{31}$ may be H, a halogen atom, or $C_1$-$C_6$ alkyl substituted with halogen atom. $R^{31}$ may be H or a halogen atom.

In Formula 3A, $R^{32}$ may be selected from a group consisting of H, a halogen atom, a hydroxy group, a ketone group, $C_1$-$C_{20}$ alkyl, $C_1$-$C_{20}$ alkoxy, $C_2$-$C_{20}$ alkoxyalkyl, an amine group, $C_1$-$C_{20}$ alkyl substituted with an amine group, an imine group, nitro, cyano, amidino, a carboxyl group or a salt thereof, $C_1$-$C_{20}$ heteroalkyl, $C_6$-$C_{20}$ aryl, $C_6$-$C_{20}$ arylalkyl, $C_6$-$C_{20}$ heteroaryl, $C_6$-$C_{20}$ heteroarylalkyl, $C_6$-$C_{20}$ heteroaryloxy, $C_6$-$C_{20}$ heteroaryloxyalkyl, and $C_6$-$C_{20}$ heterocycloalkyl. $R^{32}$ may be selected from a group consisting of H, a halogen atom, an amine group, —COOH, or —COO$R^e$. $R^e$ may be H, a halogen atom, or $C_1$-$C_6$ alkyl optionally substituted with a halogen atom.

In Formula 3A, $R^{31}$ and $R^{32}$ may each be halogen.

In Formula 3A, $R^{33}$ and $R^{34}$ may be each independently H, $C_1$ to $C_6$ alkyl, an amine group, or $C_1$-$C_6$ alkyl substituted with an amine group. $R^{33}$ and $R^{34}$ may be each independently H, methyl, an amine group, or $C_1$ to $C_6$ alkyl substituted with an amine group.

In Formula 3A, $R^{35}$ may represent two or more substituents. Two or more $R^{35}$ may be the same as or different from each other.

$R^{35}$ may be at least one selected from the group consisting of H, halogen, hydroxy, $C_1$-$C_{20}$ alkyl, $C_1$-$C_{20}$ alkoxy, $C_2$-$C_{20}$ alkoxyalkyl, an amine group, $C_1$-$C_{20}$ alkyl substituted with an amine group, an imine group, a nitro group, a cyano group, an amidino group, a carboxyl group or a salt thereof, $C_1$-$C_{20}$ heteroalkyl, substituted or unsubstituted $C_6$-$C_{20}$ aryl, substituted or unsubstituted $C_6$-$C_{20}$ arylalkyl, substituted or unsubstituted $C_6$-$C_{20}$ heteroaryl, substituted or unsubstituted $C_6$-$C_{20}$ heteroarylalkyl, substituted or unsubstituted $C_6$-$C_{20}$ heteroaryloxy, substituted or unsubstituted $C_6$-$C_{20}$ heteroaryloxyalkyl, and substituted or unsubstituted $C_6$-$C_{20}$ heterocycloalkyl. $R^{35}$ may be at least one selected from the group consisting of H, a halogen atom, $C_1$-$C_{20}$ alkyl, an amine group, $C_1$-$C_{20}$ alkyl substituted with an amine group, substituted or unsubstituted $C_6$-$C_{20}$ aryl, substituted or unsubstituted $C_6$-$C_{20}$ arylalkyl, substituted or unsubstituted $C_6$-$C_{20}$ heteroaryl, and substituted or unsubstituted $C_6$-$C_{20}$ heteroarylalkyl. For example, $R^{35}$ may be $C_1$-$C_6$ alkyl or $NH_2$.

In one aspect, there is provided a compound represented by the following Formula 3B, or a stereoisomer, solvate or pharmaceutically acceptable salt thereof:

[Formula 3B]

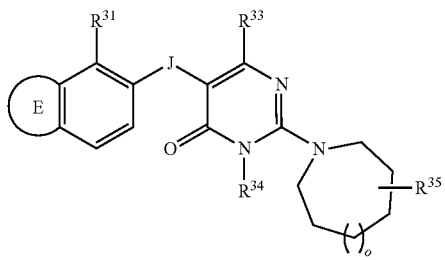

In Formula 3B, J may be absent or S.

In Formula 3B, o may be an integer of 0, 1, 2, 3, 4, or 5. o may be an integer of 0 or 1.

In Formula 3B, $R^{31}$ may be H, a halogen atom, or $C_1$-$C_6$ alkyl substituted with a halogen atom. $R^{31}$ may be H or a halogen atom.

In Formula 3B, $R^{33}$ and $R^{34}$ may be each independently H, $C_1$-$C_6$ alkyl, an amine group, or $C_1$-$C_6$ alkyl substituted with an amine group. $R^{33}$ and $R^{34}$ may be each independently H, methyl, an amine group, or $C_1$-$C_6$ alkyl substituted with an amine group.

In Formula 3B, $R^{35}$ may represent two or more substituents. Two or more $R^{35}$ may be the same as or different from each other.

$R^{35}$ may be at least one selected from the group consisting of H, a halogen atom, a hydroxy group, $C_1$-$C_{20}$ alkyl, $C_1$-$C_{20}$ alkoxy, $C_2$-$C_{20}$ alkoxyalkyl, an amine group, $C_1$-$C_{20}$ alkyl substituted with an amine group, an imine group, a nitro group, a cyano group, an amidino group, a carboxyl group or a salt thereof, $C_1$-$C_{20}$ heteroalkyl, substituted or unsubstituted $C_6$-$C_{20}$ aryl, substituted or unsubstituted $C_6$-$C_{20}$ arylalkyl, substituted or unsubstituted $C_6$-$C_{20}$ heteroaryl, substituted or unsubstituted $C_6$-$C_{20}$ heteroarylalkyl, substituted or unsubstituted $C_6$-$C_{20}$ heteroaryloxy, substituted or unsubstituted $C_6$-$C_{20}$ heteroaryloxyalkyl, and substituted or unsubstituted $C_6$-$C_{20}$ heterocycloalkyl. $R^{35}$ may be at least one selected from the group consisting of H, a halogen atom, $C_1$-$C_{20}$ alkyl, an amine group, $C_1$-$C_{20}$ alkyl substituted with an amine group, substituted or unsubstituted $C_6$-$C_{20}$ aryl, substituted or unsubstituted $C_6$-$C_{20}$ arylalkyl, substituted or unsubstituted $C_6$-$C_{20}$ heteroaryl, and substituted or unsubstituted $C_6$-$C_{20}$ heteroarylalkyl. For example, $R^{35}$ may be $C_1$-$C_6$ alkyl or $NH_2$.

In Formula 3B,

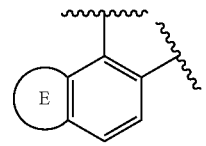 [SMILES: *c1ccccc1*]

may be

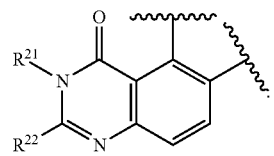

$R^{21}$ and $R^{22}$ may be each independently selected from the group consisting of H, a halogen atom, hydroxy, a ketone group, $C_1$-$C_{20}$ alkyl, $C_1$-$C_{20}$ alkoxy, $C_2$-$C_{20}$ alkoxyalkyl, an amine group, $C_1$-$C_{20}$ alkyl substituted with an amine group, an imine group, a nitro group, a cyano group, an amidino group, a carboxyl group or a salt thereof, $C_1$-$C_{20}$ heteroalkyl, $C_6$-$C_{20}$ aryl, $C_6$-$C_{20}$ arylalkyl, $C_6$-$C_{20}$ heteroaryl, $C_6$-$C_{20}$ heteroarylalkyl, $C_6$-$C_{20}$ heteroaryloxy, $C_6$-$C_{20}$ heteroaryloxyalkyl, and $C_6$-$C_{20}$ heterocycloalkyl.

$R^{21}$ and $R^{22}$ may be each independently selected from the group consisting of H, $C_1$-$C_{20}$ alkyl, an amine group, $C_1$-$C_{20}$ alkyl substituted with an amine group, $C_6$-$C_{20}$ aryl, $C_6$-$C_{20}$ arylalkyl, $C_6$-$C_{20}$ heteroaryl, and $C_6$-$C_{20}$ heteroarylalkyl.

$R^{21}$ and $R^{22}$ may be each independently H or a phenyl group.

In one aspect, there is provided a compound represented by the following Formula 3C, or a stereoisomer, solvate or pharmaceutically acceptable salt thereof:

[Formula 3C]

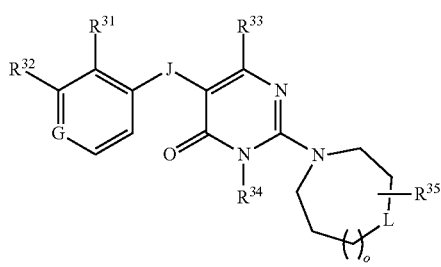

In Formula 3C, J may be absent or S.

In Formula 3C, G may be C or N.

In Formula 3C, L may be C, N, or O. When L is $CH_2$ or NH, $R^{35}$ may be substituted with the carbon atom or the nitrogen atom of L.

In Formula 3C, o may be an integer of 0, 1, 2, 3, 4, or 5. o may be an integer of 0 or 1.

In Formula 3C, $R^{31}$ may be H, a halogen atom, or $C_1$-$C_6$ alkyl substituted with a halogen atom. $R^1$ may be H or a halogen atom.

In Formula 3C, $R^{32}$ may be selected from a group consisting of H, a halogen atom, hydroxy, a ketone group, $C_1$-$C_{20}$ alkyl, $C_1$-$C_{20}$ alkoxy, $C_2$-$C_{20}$ alkoxyalkyl, an amine group, $C_1$-$C_{20}$ alkyl substituted with an amine group, an imine group, a nitro group, a cyano group, an amidino group, a carboxyl group or a salt thereof, $C_1$-$C_{20}$ heteroalkyl, $C_6$-$C_{20}$ aryl, $C_6$-$C_{20}$ arylalkyl, $C_6$-$C_{20}$ heteroaryl, $C_6$-$C_{20}$ heteroarylalkyl, $C_6$-$C_{20}$ heteroaryloxy, $C_6$-$C_{20}$ heteroaryloxyalkyl, and $C_6$-$C_{20}$ heterocycloalkyl. $R^{32}$ may be selected from a group consisting of H, a halogen atom, an amine group, —COOH, or —COOR$^f$. R f may be H, a halogen atom, or $C_1$-$C_6$ alkyl optionally substituted with a halogen atom.

In Formula 3C, $R^{31}$ and $R^{32}$ may each be halogen.

In Formula 3C, $R^{33}$ and $R^{34}$ may be each independently H, $C_1$-$C_6$ alkyl, an amine group, or $C_1$-$C_6$ alkyl substituted with an amine group. $R^{33}$ and $R^{34}$ may be each independently H, methyl, an amine group, or $C_1$-$C_6$ alkyl substituted with an amine group. For example, $R^{33}$ and $R^{34}$ are each independently H, $C_1$-$C_6$ alkyl, —$NH_2$, —$NH(C_1$-$C_6$ alkyl), —$N(C_1$-$C_6$ alkyl)$_2$, or $H_2N$—($C_1$-$C_6$ alkyl)-. In some embodiments, $R^{33}$ and $R^{34}$ may be each independently $C_1$-$C_3$ alkyl or —$NH_2$. In some embodiments, $R^{33}$ may be —$NH_2$, and $R^{34}$ may be methyl.

In Formula 3C, $R^{35}$ may represent two or more substituents. Two or more $R^{35}$ may be the same as or different from each other.

$R^{35}$ may be at least one selected from the group consisting of H, a halogen atom, hydroxy, $C_1$-$C_{20}$ alkyl, $C_1$-$C_{20}$ alkoxy, $C_2$-$C_{20}$ alkoxyalkyl, an amine group, $C_1$-$C_{20}$ alkyl substituted with an amine group, an imine group, a nitro group, a cyano group, an amidino group, a carboxyl group or a salt thereof, $C_1$-$C_{20}$ heteroalkyl, substituted or unsubstituted $C_6$-$C_{20}$ aryl, substituted or unsubstituted $C_6$-$C_{20}$ arylalkyl, substituted or unsubstituted $C_6$-$C_{20}$ heteroaryl, substituted or unsubstituted $C_6$-$C_{20}$ heteroarylalkyl, substituted or unsubstituted $C_6$-$C_{20}$ heteroaryloxy, substituted or unsubstituted $C_6$-$C_{20}$ heteroaryloxyalkyl, and substituted or unsubstituted $C_6$-$C_{20}$ heterocycloalkyl. $R^{35}$ may be at least one selected from the group consisting of H, a halogen atom, $C_1$-$C_{20}$ alkyl, an amine group, $C_1$-$C_{20}$ alkyl substituted with an amine group, substituted or unsubstituted $C_6$-$C_{20}$ aryl, substituted or unsubstituted $C_6$-$C_{20}$ arylalkyl, substituted or unsubstituted $C_6$-$C_{20}$ heteroaryl, and substituted or unsubstituted $C_6$-$C_{20}$ heteroarylalkyl. $R^{35}$ may represent two or more substituents. For example, $R^{35}$ may be $C_1$-$C_6$ alkyl substituted with at least one substituent selected from the group consisting of —$NH_2$, 5- to 10-membered heteroaryl (for example, pyridinyl), and $C_6$-$C_{10}$ aryl (for example, phenyl).

According to some embodiments,

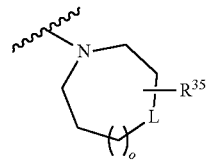

in Formula 3C may be selected from the following structures:

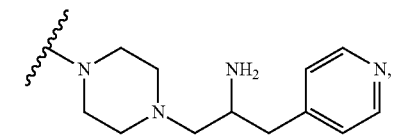

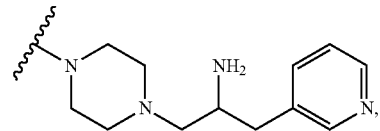

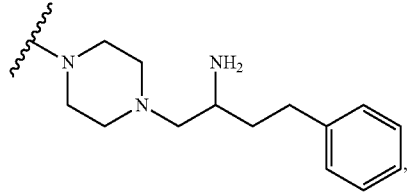

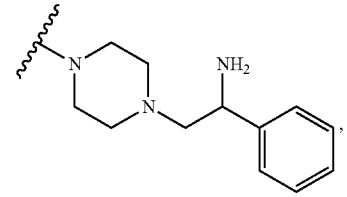

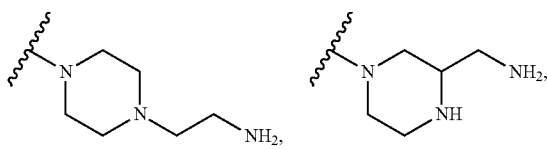

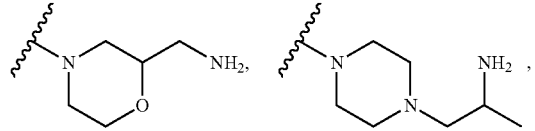

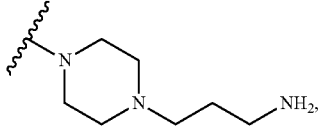

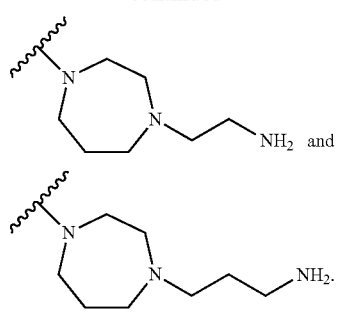

In some embodiments, in Formulae 3A to 3C, $R^{35}$ is selected from a group consisting of H, halogen, hydroxy, oxo, $C_1$-$C_{20}$ alkyl, $C_1$-$C_{20}$ alkoxy, ($C_1$-$C_{10}$ alkoxy)-($C_1$-$C_{10}$ alkyl)-, $H_2N$—($C_1$-$C_{20}$ alkyl)-, —$NH_2$, —$NH(C_1$-$C_{20}$ alkyl), —$N(C_1$-$C_{20}$ alkyl)$_2$, =NH, nitro, cyano, amidino, carboxyl or a salt thereof, heterocycloalkyl, $C_6$-$C_{20}$ aryl, ($C_6$-$C_{12}$ aryl)-($C_1$-$C_8$ alkyl)-, heteroaryl, heteroaryl-($C_1$-$C_8$ alkyl)-, heteroaryloxy, and heteroaryloxy-($C_1$-$C_8$ alkyl)-. In this case, —($C_1$-$C_8$ alkyl)- of ($C_6$-$C_{12}$ aryl)-($C_1$-$C_8$ alkyl)-, heteroaryl-($C_1$-$C_8$ alkyl)- and heteroaryloxy-($C_1$-$C_8$ alkyl)- may be optionally substituted with halogen, hydroxy, —$NH_2$, nitro or cyano.

In some embodiments, the compound represented by Formula 3A, 3B or 3C may be selected from compounds represented by the following Formulae:

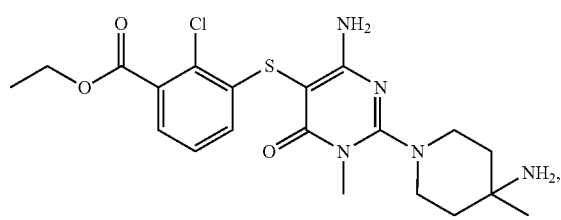

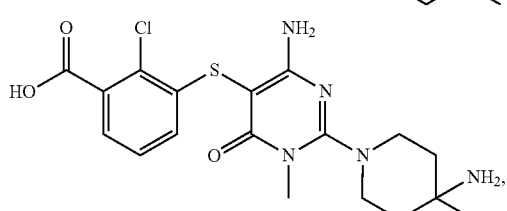

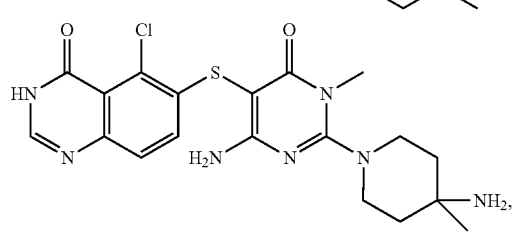

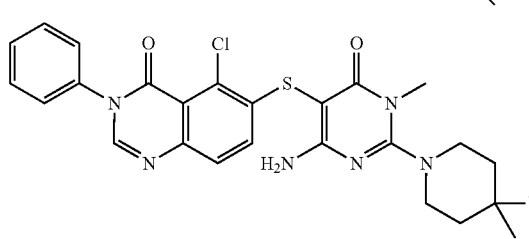

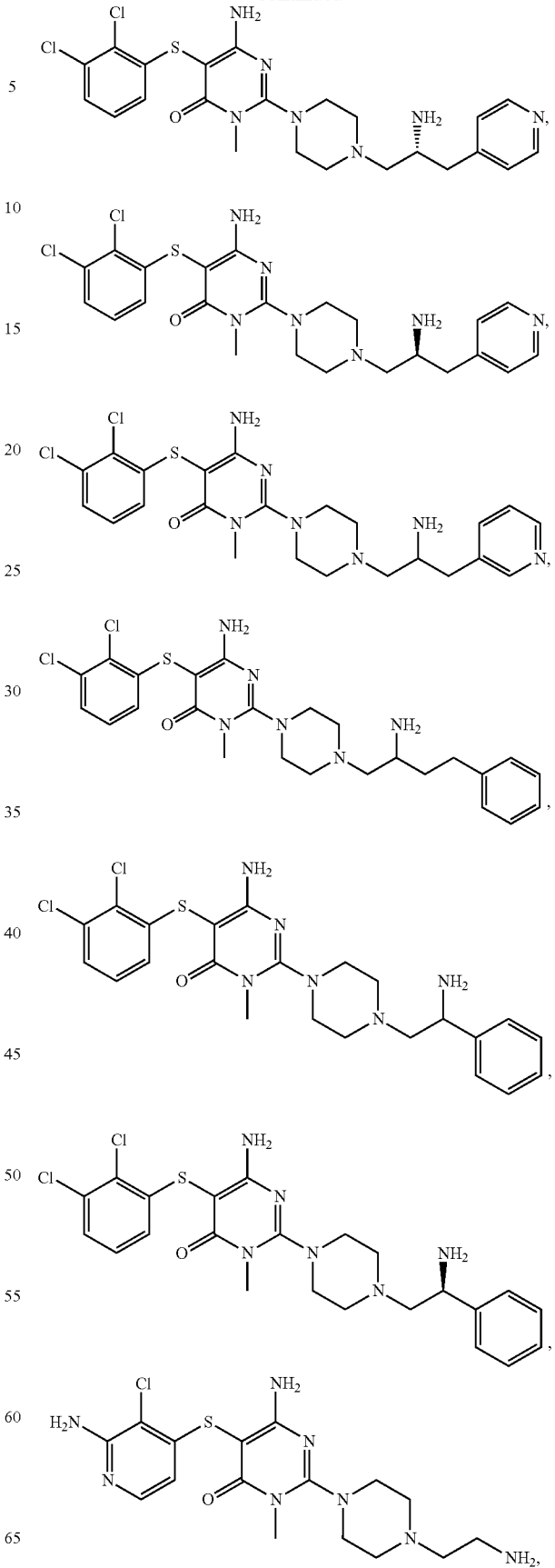

-continued

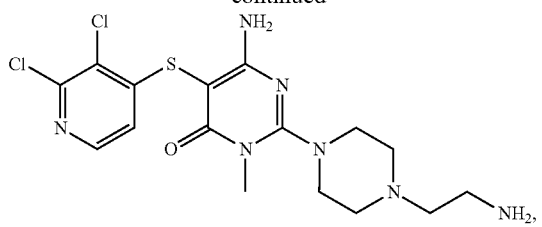

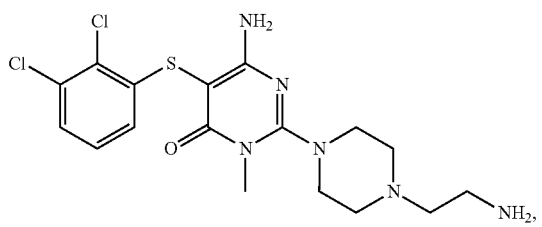

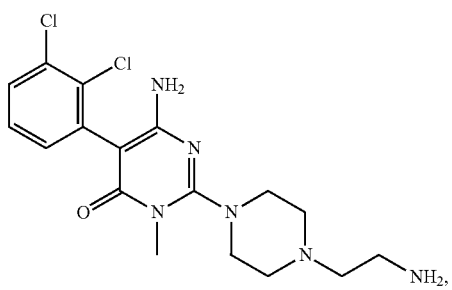

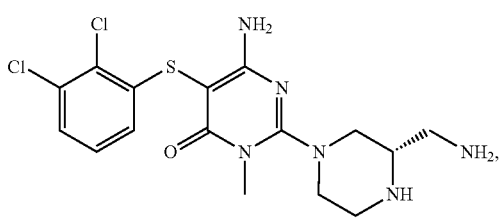

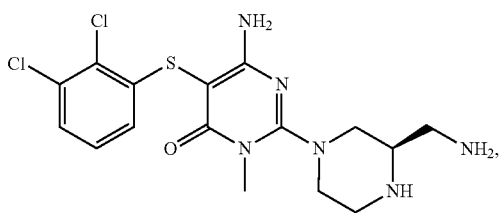

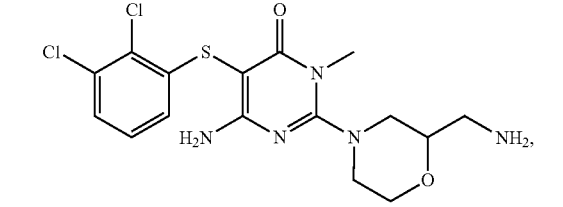

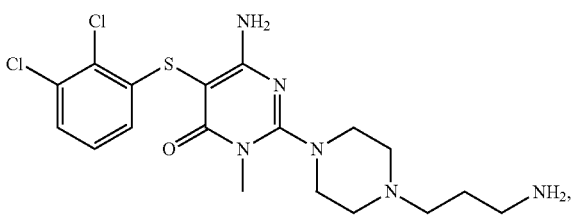

-continued

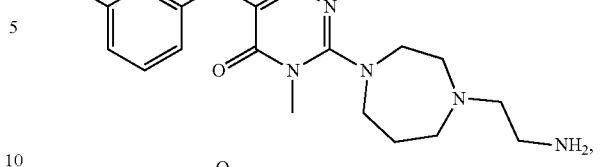

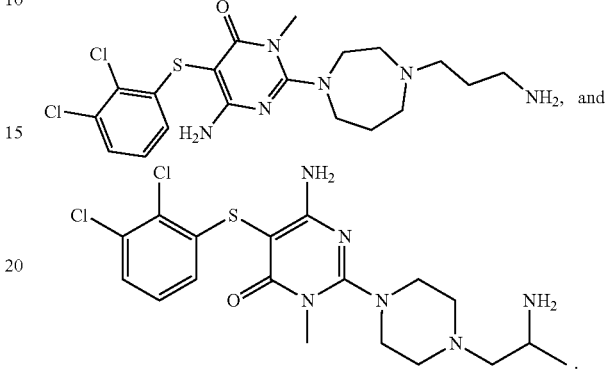

As used herein, the term "halogen" or "halogen atom" refers to an atom belonging to Group 17 of the periodic table. Halogen atoms include F, Cl, Br, I and the like.

The term "alkyl" refers to a fully saturated branched or unbranched (or straight-chain or linear) hydrocarbon. The alkyl may be a substituted or unsubstituted alkyl. The $C_1$-$C_{20}$ alkyl may be, for example, $C_1$-$C_{15}$, $C_1$-$C_{10}$, or $C_1$-$C_6$ alkyl. The $C_1$-$C_6$ alkyl may be $C_1$-$C_5$, $C_1$-$C_4$, $C_1$-$C_3$, or $C_1$-$C_2$ alkyl. The alkyl may be, for example, methyl, ethyl, n-propyl, isopropyl, n-butyl, isobutyl, sec-butyl, n-pentyl, isopentyl, neopentyl, iso-amyl, or n-hexyl.

The term "haloalkyl" refers to an alkyl substituted with at least one halogen.

The term "hydroxy" refers to an —OH functional group (hydroxyl group).

The term "oxo" refers to =O, and "substituted with oxo" means that a carbon atom has an =O substituent in the form of —C(=O)—.

The term "carbonyl" refers to —C(=O)—.

The term "alkoxy" refers to an alkyl bound to an oxygen atom. The $C_1$-$C_{20}$ alkoxy may be, for example, $C_1$-C15, $C_1$-$C_{10}$, or $C_1$-$C_6$ alkoxy. The $C_1$-$C_6$ alkoxy may be $C_1$-05, $C_1$-$C_4$, $C_1$-$C_3$, or $C_1$-$C_2$ alkoxy. The alkoxy may be methoxy, ethoxy, propoxy, butoxy, and the like.

The term "alkoxyalkyl" refers to alkoxy bound to an alkyl. The $C_2$-$C_{20}$ alkoxyalkyl may be, for example, $C_1$-$C_{15}$, $C_2$-$C_{10}$, or $C_2$-$C_6$ alkoxyalkyl. For example, $C_2$-$C_{20}$ alkoxyalkyl may be ($C_1$-$C_{10}$ alkoxy)-($C_1$-$C_{10}$ alkyl), ($C_1$-$C_6$ alkoxy)-($C_1$-$C_6$ alkyl) and the like, and the number of carbon atoms in the alkoxy group and the alkyl group may be the same or different. The alkoxy may be, for example, methoxymethyl, methoxyethyl, ethoxymethyl, ethoxyethyl, methoxypropyl, ethoxypropyl, and the like.

The term "alkoxyalkoxy" refers to alkoxy bound to alkoxy. Alkoxyalkoxy may include, for example, methoxymethoxy, methoxyethoxy, ethoxymethoxy, ethoxyethoxy, and the like.

The term "amino" refers to —$NH_2$.

The term "amine group" refers to a substituent in which one, two or all three hydrogens of ammonia are replaced with an organic functional group and includes all of primary amines, secondary amines and tertiary amines, also including an amino group.

The term "imine" refers to a functional group containing a double bond between a carbon atom and a nitrogen atom.

The term "nitro" refers to —$NO_2$.

The term "cyano" refers to —CN, which is a functional group consisting of a triple bond between a carbon atom and a nitrogen atom.

The term "amidino" refers to —C(—$NH_2$)=NH.

The term "carboxy" refers to —COOH. A salt of carboxy refers to a conjugate base of a carboxylic acid.

The term "sulfonyl" refers to a —$SO_2$— group.

The term "cycloalkyl", "cyclic ring", or "carbon ring" refers to a saturated or partially unsaturated non-aromatic monocyclic, bicyclic or tricyclic hydrocarbon group. A cyclic ring group may contain 3 to 20 carbon atoms, for example, 5 to 10, 3 to 8, or 3 to 6 carbon atoms. The monocyclic ring group can be, for example, cyclopropyl, cyclobutyl, cyclopentyl, cyclopentenyl, cyclohexyl, or cyclohexenyl, and the like. The bicyclic ring group may be, for example, bornyl, decahydronaphthyl, bicyclo[2.1.1] hexyl, bicyclo[2.2.1]heptyl, bicyclo[2.2.1]heptenyl, or bicyclo[2.2.2]octyl and the like. The tricyclic ring group may be, for example, adamantyl.

The term "aryl" also includes a group in which an aromatic ring is fused to one or more carbon rings. The $C_6$-$C_{30}$ aryl may be, for example, $C_6$-$C_{15}$, or $C_6$-$C_{10}$ aryl. Aryl may be phenyl, naphthyl, or tetrahydronaphthyl.

The term "arylalkyl" refers to an alkyl substituted with an aryl.

The term "aryloxy" refers to an aryl bound to an oxygen atom.

The term "heteroaryl" refers to a monocyclic or bicyclic aromatic compound containing one or more heteroatoms, the remaining ring atoms being carbon. The heteroaryl may include, for example, 1 to 5, 1 to 3, 1 or 2 heteroatoms, and may include 5 to 10 ring members. "Heteroaryl" may be, for example, pyrrolyl, furanyl, thiophenyl, pyrazolyl, imidazolyl, isoxazolyl, oxazolyl, thiazolyl, isothiazolyl, pyridinyl, pyrimidinyl, pyrazinyl, pyridazinyl, indolyl, benzofuranyl, benzothiophenyl, benzopyrazolyl, benzimidazolyl, benzoxazolyl, benzoisoxazolyl, benzothiazolyl, or benzoisothiazolyl, and the like.

The term "heteroarylalkyl" refers to an alkyl substituted with a heteroaryl.

The term "heteroaryloxy" refers to a heteroaryl bound to an oxygen atom.

The term "heterocycloalkyl" or "heterocyclyl" refers to a saturated or partially unsaturated cyclic hydrocarbon containing at least one heteroatom. The heterocyclyl ring group may be a single ring group, a two ring group, or a three ring group. The two ring groups may be a spiro-ring group, a bridged-ring group, and a fused-ring group. A heterocyclyl ring group may contain 3 to 20, 3 to 10, 3 to 8, 3 to 7, 5 to 7, 4 to 6, or 5 to 6 ring atoms. The heteroatom may be any one or more, for example, 1, 2 or 3 heteroatoms selected from the group consisting of N, O and S. For example, the heterocycloalkyl may be aziridinyl, oxiranyl, oxetanyl, azetidinyl, pyrrolidinyl, tetrahydrofuranyl, tetrahydrothiophenyl, piperidinyl, tetrahydropyranyl, dihydropyranyl, morpholinyl, thiomorpholinyl or oxazolidinyl, and the like.

The term "heterocycloalkylalkyl" refers to an alkyl substituted with a heterocycloalkyl.

The term "heterocycloalkyloxy" refers to a heterocycloalkyl bound to an oxygen atom.

The heteroatom may be any one or more selected from the group consisting of N, O, P, and S. The heteroatom may be 1, 2, or 3 heteroatoms selected from the group consisting of N, O and S.

The term "substituted" included in "substituted or unsubstituted" refers to replacement of hydrogen atoms and introduction of other atomic groups when a derivative is formed by substituting one or more hydrogen atoms in an organic compound with other atomic groups, and the term "substituent" refers to an atomic group as introduced. "Substituted" used herein without any limitation of a substituent may mean substitution with, for example, a halogen atom, $C_1$-$C_{20}$ alkyl substituted with a halogen atom (for example, $CCF_3$, $CHCF_2$, $CH_2F$, $CCl_3$ etc.), $C_1$-$C_{20}$ alkoxy, $C_2$-$C_{20}$ alkoxyalkyl, a hydroxy group, —$NH_2$, =NH, nitro, cyano, amidino, hydrazine, hydrazone, carboxy or a salt thereof, sulfonyl, sulfamoyl, a sulfonic acid group or a salt thereof, phosphoric acid or a salt thereof, $C_1$-$C_{20}$ alkyl, $C_2$-$C_{20}$ alkenyl, $C_2$-$C_{20}$ alkynyl, $C_6$-$C_{20}$ aryl, $C_6$-$C_{20}$ arylalkyl, $C_6$-$C_{20}$ heteroaryl, $C_7$-$C_{20}$ heteroarylalkyl, $C_6$-$C_{20}$ heteroaryloxy, $C_6$-$C_{20}$ heteroaryloxyalkyl, or $C_6$-$C_{20}$ heteroarylalkyl, and the like.

The term "isomer" included in "stereoisomer" refers to a compound that has the same molecular formula but differs in atomic connectivity or spatial arrangement of constituent atoms in the molecule. Isomers include, for example, structural isomers and stereoisomers. The stereoisomer may be a diastereomer or an enantiomer. Enantiomers refer to a pair of isomers that are non-superimposable mirror images, such as the relationship between the left and right hands, and are also called optical isomers. Enantiomers are divided into R(Rectus: clockwise) and S(Sinister: counterclockwise) when 4 or more substituents differ from each other at the chiral center carbon. Diastereomers refer to non-mirror image stereoisomers and are isomers generated by different spatial arrangement of atoms. The diastereomers may be divided into cis-trans isomers, and conformational isomers or conformers.

The term "solvate" refers to a compound solvated in an organic or inorganic solvent. The solvate is, for example, a hydrate.

The term "salt" refers to inorganic and organic acid addition salts of compounds. The pharmaceutically acceptable salt may be a salt that does not cause serious irritation to an organism administered with the compound and does not impair the biological activity and properties of the compound. The inorganic acid salt may be hydrochloride, bromate, phosphate, sulfate, or disulfate. The organic acid salt may be formate, acetate, propionate, lactate, oxalate, tartrate, malate, maleate, citrate, fumarate, besylate, camsylate, edicylate, trichloroacetate, trifluoroacetate, benzoate, gluconate, methanesulfonate, glycolate, succinate, 4-toluenesulfonate, galacturonate, embonate, glutamate, ethanesulfonate, benzenesulfonate, p-toluenesulfonate, or aspartate. The metal salt may be a calcium salt, a sodium salt, a magnesium salt, a strontium salt, or a potassium salt.

The compound of any one or more of Formulae 1, 1A, 1A-1 to 1A-9, 2, 3A, 3B and 3C may be an inhibitor for Src homology region 2 domain-containing phosphatase-2 (SHP2). Src homology region 2 domain-containing phosphatase-2(SHP2) may be a protein belonging to protein tyrosine phosphatase(PTP). The SHP2 may also be referred to as tyrosine-protein phosphatase non-receptor type 11(PTPN11), protein-tyrosine phosphatase 1D(PTP-1D), or protein-tyrosine phosphatase 2C(PTP-2C). The SHP2 may include two tandem SH2 domains at the N-terminus, together with SPP 1. The SHP2 may be a protein comprising the amino acid sequence of Uniprot No. Q06124 in humans or the amino acid sequence of Uniprot No. P35235 in mice. The SHP2 may be a wild-type SHP2 or a SHP2 mutant. The inhibitor for SHP2 may be an inhibitor that inhibits the expression or activity of SHP2.

In another aspect, there is provided a pharmaceutical composition comprising the compound according to one aspect, a stereoisomer or a solvate thereof, or a pharmaceutically acceptable salt thereof.

In another aspect, there is provided a pharmaceutical composition for preventing or treating a disease associated with the abnormal activity of Src homology region 2 domain-containing phosphatase-2 (SHP2), comprising the compound according to one aspect, a stereoisomer or a solvate thereof, or a pharmaceutically acceptable salt thereof.

The above compound, stereoisomer, solvate, pharmaceutically acceptable salt, and SHP2 are as described above.

The disease associated with the abnormal activity of SHP2 may be selected from the group consisting of cancer, cancer metastasis, cardiovascular disease, immune disorder, fibrosis, and ocular disorder.

The cancer may be selected from the group consisting of ovarian cancer, cervical cancer, endometrial cancer, uterine sarcoma, vulvar cancer, breast cancer, skin cancer, head and neck cancer, pancreatic cancer, lung cancer, large intestine cancer, colorectal cancer, gastric cancer, prostate cancer, bladder cancer, urethral cancer, liver cancer, kidney cancer, skin cancer, cerebrospinal tumor, brain cancer, thymoma, mesothelioma, bronchial cancer, nasopharyngeal cancer, laryngeal cancer, esophageal cancer, biliary tract cancer, testicular cancer, germ cell tumor, thyroid cancer, parathyroid cancer, lymphoma, myelodysplastic syndrome (MDS), myelofibrosis, acute leukemia, chronic leukemia, multiple myeloma, endocrine system cancer, and sarcoma.

The cancer metastasis refers to the spread of a tumor from a primary site to another body site, where it settles and proliferates. The cancer metastasis can cause cancer cells to spread to blood vessels, lymphatic vessels, or tissues.

The cardiovascular disease refers to a disease occurring in the heart or major arteries (for example, aorta, pulmonary arteries, carotid arteries, cerebral blood vessels, renal arteries, lower extremity arteries). The cardiovascular disease may be selected from the group consisting of hypertension, ischemic heart disease, coronary artery disease, angina pectoris, myocardial infarction, atherosclerosis (arteriosclerosis), cerebrovascular disease, stroke, arrhythmia, acute heart failure, chronic heart failure, and hypotension.

The immune disorder refers to a state in which a normal immune response is not made. The immune disorder may be selected from the group consisting of acquired immunodeficiency, autoimmune disease, systemic lupus erythematosus, scleroderma, Sjogren's syndrome, polymyositis, dermatomyositis, polymyalgia rheumatica, temporal arteritis, polyarteritis nodosa, and Behcet's syndrome.

The fibrosis refers to a symptom in which fibrous tissue is excessively increased in a part of a tissue or an organ. The fibrosis may be selected from the group consisting of hepatic fibrosis, cystic fibrosis, myelofibrosis, endocardial myocardial fibrosis, and retroperitoneal fibrosis.

The ocular disorder refers to a disorder affecting various structures of the eye. The ocular disorder may be selected from the group consisting of endophthalmitis, degenerative myopia, degenerative disorders of the eye, hypotonia of the eye, intraocular foreign body, hemophthalmos, and dislocation of the eye.

The disease associated with the abnormal activity of SHP2 may be selected from the group consisting of Noonan syndrome, Leopard syndrome, juvenile myelomonocytic leukemia (JMML), neuroblastoma, melanoma, acute myeloid leukemia, breast cancer, esophageal cancer, lung cancer, large intestine cancer, head cancer, squamous cell carcinoma of the head and neck, gastric carcinoma, anaplastic large cell lymphoma, glioblastoma, pancreatic cancer, biliary tract cancer, uterine cancer, endometrial cancer, liver cancer, and neurofibromatosis type 1.

The term "prevention" refers to any action that inhibits the occurrence of or delays the onset of a disease associated with SHP2 by administration of the pharmaceutical composition. The term "treatment" refers to any action that improves or beneficially changes the symptoms of a disease associated with SHP2 by administration of the pharmaceutical composition.

The pharmaceutical composition may include a pharmaceutically acceptable carrier. The carrier is used in the sense of including an excipient, a diluent or an adjuvant. For example, the carrier may be selected from the group consisting of lactose, dextrose, sucrose, sorbitol, mannitol, xylitol, erythritol, maltitol, starch, gum acacia, alginate, gelatin, calcium phosphate, calcium silicate, cellulose, methyl cellulose, polyvinyl pyrrolidone, water, physiological saline, buffers such as PBS, methyl hydroxybenzoate, propyl hydroxybenzoate, talc, magnesium stearate, and mineral oil. The composition may include a filler, an anti-aggregation agent, a lubricant, a wetting agent, a flavoring agent, an emulsifying agent, a preservative, or a combination thereof.

The pharmaceutical composition may be prepared in any formulation according to a conventional method. The composition may be formulated, for example, as an oral dosage form (for example, a powder, a tablet, a capsule, a syrup, a pill, or a granule) or a parenteral dosage form (for example, an injection). In addition, the composition may be prepared as a systemic formulation or as a topical formulation.

In the pharmaceutical composition, the solid preparation for oral administration may be a tablet, a pill, a powder, a granule, or a capsule. The solid preparation may further include an excipient. The excipient may be, for example, starch, calcium carbonate, sucrose, lactose, or gelatin. In addition, the solid preparation may further include a lubricant such as magnesium stearate or talc. In the pharmaceutical composition, the liquid preparation for oral administration may be a suspension, an internal solution, an emulsion, or a syrup. The liquid preparation may include water or liquid paraffin. The liquid preparation may include an excipient, for example, a wetting agent, a sweetening agent, a perfuming agent, or a preservative. In the pharmaceutical composition, the preparation for parenteral administration may be a sterile aqueous solution, a non-aqueous solution, a suspension, an emulsion, a freeze-dried preparation or a suppository. A non-aqueous solution or suspension may include a vegetable oil or an ester. The vegetable oil may be, for example, propylene glycol, polyethylene glycol, or olive oil. The ester may be, for example, ethyl oleate. The base of the suppository may be witepsol, macrogol, tween 61, cacao butter, laurin butter, or glycerogelatin.

The pharmaceutical composition comprises the compound according to one aspect, a stereoisomer, a solvate, or a pharmaceutically acceptable salt thereof as an active ingredient of the pharmaceutical composition. "Active ingredient" refers to a physiologically active substance used to achieve a pharmacological activity (for example, treatment of a disease associated with the abnormal activity of SHP2).

The pharmaceutical composition may comprise the compound according to one aspect, a stereoisomer, a solvate, or a pharmaceutically acceptable salt thereof in an effective amount. The term "effective amount" refers to an amount sufficient to exhibit the effect of preventing or treating a disease when administered to a subject in need thereof. The effective amount may be appropriately selected by one of ordinary skill in the art depending on the cell or subject to be selected. The preferred dosage of the pharmaceutical composition varies depending on the condition and body weight of the subject, the severity of the disease, the drug form, the route and duration of administration, but may be appropriately selected by one of ordinary skill in the art. The effective amount may be about 0.5 μg to about 2 g, about 1 μg to about 1 g, about 10 μg to about 500 mg, about 100 μg to about 100 mg, or about 1 mg to about 50 mg per the pharmaceutical composition. However, the compound, stereoisomer, solvate, or pharmaceutically acceptable salt thereof may be administered in an amount of, for example, about 0.0001 mg/kg to about 100 mg/kg, or about 0.001 mg/kg to about 100 mg/kg, which may be administered in divided doses 1 to 24 times a day, 1 to 7 times per 2 days to 1 week, or 1 to 24 times per 1 month to 12 months. In the pharmaceutical composition, the compound, stereoisomer, solvate, or pharmaceutically acceptable salt thereof may be included in an amount of from about 0.0001% by weight to about 10% by weight, or from about 0.001% by weight to about 1% by weight, based on the total weight of the entire composition.

The administration method may be oral or parenteral administration. The administration method may be, for example, oral, transdermal, subcutaneous, rectal, intravenous, intraarterial, intraperitoneal, intramuscular, intrasternal, topical, intranasal, intratracheal, or intradermal route. The composition may be administered systemically or locally, alone or in combination with other pharmaceutically active compounds.

In another aspect, there is provided a method for preventing or treating a disease associated with the abnormal activity of SHP2, comprising administering to a subject the compound according to one aspect, a stereoisomer or a solvate thereof, or a pharmaceutically acceptable salt thereof.

The above compound, stereoisomer, solvate, pharmaceutically acceptable salt, SHP2, disease associated with the abnormal activity of SHP2, prevention and treatment are as described above.

The subject may be a mammal, such as a human, mouse, rat, cow, horse, pig, dog, monkey, sheep, goat, ape, or cat. The subject may be a subject suffering from, or likely to suffer from, a symptom associated with a disease associated with the abnormal activity of SHP2.

The method may further comprise administering to the subject an active ingredient known to have an effect of preventing or treating a disease associated with SHP2. The known active ingredient may be administered to the subject simultaneously, separately, or sequentially with the compound according to one aspect, a stereoisomer, a solvate, or a pharmaceutically acceptable salt thereof.

The administration method may be oral or parenteral administration. The administration method may be, for example, oral, transdermal, subcutaneous, rectal, intravenous, intraarterial, intraperitoneal, intramuscular, intrasternal, topical, intranasal, intratracheal, or intradermal route. The pharmaceutical composition may be administered systemically or locally, alone or in combination with other pharmaceutically active compounds.

The preferred dosage of the pharmaceutical composition varies depending on the condition and body weight of the patient, the severity of the disease, the drug form, the route and duration of administration, but may be appropriately selected by one of ordinary skill in the art. The dosage may be, for example, in the range of about 0.001 mg/kg to about 100 mg/kg, about 0.01 mg/kg to about 10 mg/kg, or about 0.1 mg/kg to about 1 mg/kg, for an adult. The administration may be performed once a day, 2 to 24 times a day, 1 to 2 times per 3 days, 1 to 6 times a week, 1 to 10 times per 2 weeks, 1 to 15 times per 3 weeks, 1 to 3 times per 4 weeks, or 1 to 12 times a year.

In another aspect, there is provided the compound according to one aspect, a stereoisomer or a solvate thereof, or a pharmaceutically acceptable salt thereof, for use in preventing or treating a disease associated with the abnormal activity of SHP2.

The above compound, stereoisomer, solvate, pharmaceutically acceptable salt, SHP2, disease associated with the abnormal activity of SHP2, prevention, and treatment are as described above.

In another aspect, there is provided a use of the compound according to one aspect, a stereoisomer or a solvate thereof, or a pharmaceutically acceptable salt thereof, for use in the manufacture of a medicament for the prevention or treatment of a disease associated with the abnormal activity of SHP2.

The above compound, stereoisomer, solvate, pharmaceutically acceptable salt, SHP2, disease associated with the abnormal activity of SHP2, prevention, and treatment are as described above.

Effects of Invention

A disease associated with SHP2 can be effectively prevented or treated by a SHP2 inhibitor, a pharmaceutical composition for preventing or treating a disease associated with SHP2 comprising the same, a method for treating and preventing a disease using the same, and a use thereof.

Detailed Description for Carrying out the Invention

Hereinafter, the present invention will be described in more detail by way of the following examples. However, the following examples are only for illustrating the present invention, and the scope of the present invention is not limited thereto.

Preparation Example 1: Synthesis of tert-butyl (1-(5-bromopyrazin-2-yl)-4-methylpiperidin-4-yl)carbamate (Intermediate I-1)

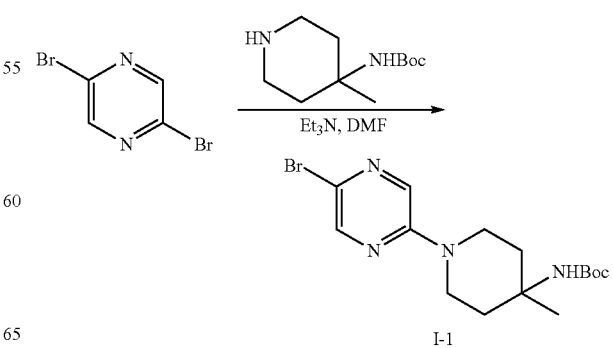

In a round bottom flask, Et₃N (5.6 mL, 42 mmol) was added dropwise to a reaction mixture of 2,5-dibromopyrazine (2 g, 8.4 mmol) and tert-butyl (4-methylpiperidin-4-yl)carbamate (1.98 g, 9.25 mmol) dissolved in DMF (dimethylformamide, 34 mL, 0.25 M), and the reaction mixture was stirred at 80° C. for 2 hours. The reaction was terminated with H₂O, and the mixture was extracted with ethyl acetate (EA). The EA layer was dried over MgSO₄, filtered and concentrated. The resulting product was separated by MPLC (Medium pressure liquid chromatography) (EA:hexane (Hx)=1:9) and concentrated to obtain Intermediate I-1 (2.43 g, 78%). ¹H NMR (400 MHz, DMSO) δ8.20 (d, J=1.2 Hz, 1H), 8.14 (d, J=1.6 Hz, 1H), 6.63 (b, 1H), 3.84-3.79 (m, 2H), 3.25-3.20 (m, 2H), 2.09 (d, J=13.2 Hz, 2H), 1.47-1.41 (m, 2H), 1.39 (s, 9H), 1.25 (s, 3H); MS m/z: 371 [M+H]⁺.

Preparation Example 2: Synthesis of tert-butyl ((1-(5-bromopyrazin-2-yl)-4-methylpiperidin-4-yl)methyl)carbamate (Intermediate I-2)

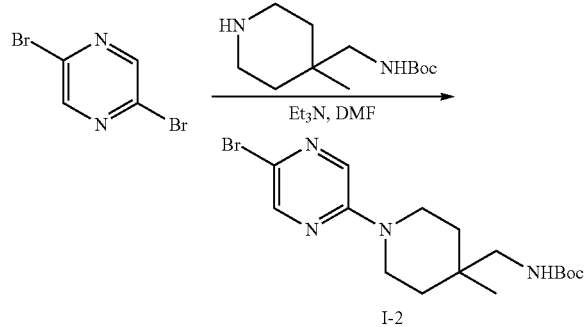

In a round bottom flask, Et₃N (5.6 mL, 39.8 mmol) was added dropwise to a reaction mixture of 2,5-dibromopyrazine (1.89 g, 7.96 mmol) and tert-butyl ((4-methylpiperidin-4-yl)methyl)carbamate (2 g, 8.76 mmol) dissolved in DMF (N,N-dimethylformamide, 32 mL, 0.25 M), and the reaction mixture was stirred at 90° C. for 2 hours. The reaction was terminated with H₂O, and the mixture was extracted with EA. The EA layer was dried over MgSO₄, filtered, concentrated and separated by MPLC(EA:Hx=1:1). The resulting compound was concentrated to obtain Intermediate I-2 (2 g, 65%). ¹H NMR (400 MHz, DMSO) δ8.19 (d, J=1.6 Hz, 1H), 8.13 (d, J=1.2 Hz, 1H), 6.91 (t, J=6.4 Hz, 1H), 3.78-3.72 (m, 2H), 3.39-3.33 (m, 2H), 2.88 (b, J=6.8 Hz, 2H), 1.45-1.40 (m, 2H), 1.38 (s, 9H), 1.29-1.23 (m, 2H), 0.90 (s, 3H); MS m/z: 385 [M+H]⁺.

Preparation Example 3: Synthesis of N-((3S,4S)-8-(5-bromopyrazin-2-yl)-3-methyl-2-oxa-8-azaspiro 14.51decan-4-yl)-2-methylpropane-2-sulfanilamide (Intermediate I-3)

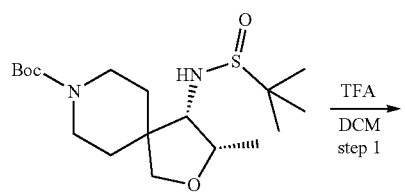

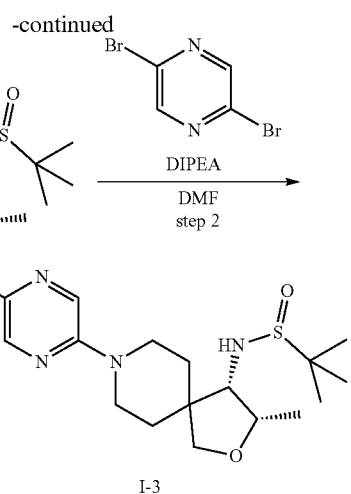

Step 1: 2-methyl-N-((3S,4S)-3-methyl-2-oxa-8-azaspiro[4.5]decan-4-yl)propane-2-sulfanilamide Tert-butyl (3 S,4S)-4-((tert-butylsulfinyl)amino)-3-methyl-2-oxa-8-azaspiro[4.5]decan-8-carboxylate (3 g, 8.0 mmol) was dissolved in dichloromethane (DCM)(200 mL, 0.04 M). The reaction mixture was slowly added dropwise with trifluoroacetic acid (TFA)(6.1 mL, 80.1 mmol) and then stirred at room temperature for 3 hours. After completion of the reaction, the reaction mixture was concentrated to obtain [2-methyl-N-((3S,4S)-3-methyl-2-oxa-8-azaspiro[4.5]decan-4-yl)propane-2-sulfanilamide].

Step 2: N-((3S,4S)-8-(5-bromopyrazin-2-yl)-3-methyl-2-oxa-8-azaspiro[4.5]decan-4-yl)-2-methylpropane-2-sulfanilamide (Intermediate I-3)

2-methyl-N-((3 S,4S)-3-methyl-2-oxa-8-azaspiro[4.5]decan-4-yl)propane-2-sulfanilamide and 2,5-dibromopyrazine (4.4 g, 16.0 mmol) were dissolved in dimethylformamide (DMF)(16 mL, 0.5 M). The reaction mixture was added with N,N-diisopropylethylamine(DIPEA) (14 mL, 80.1 mmol) and then stirred at 100° C. for 3 hours. The reaction was terminated with H₂O, and the mixture was extracted with ethylacetate(EA). The EA layer was dried over MgSO₄, filtered and then concentrated. The resulting product was separated by MPLC (EA:Hx=1:1) and concentrated to obtain Intermediate I-3 (2.4 g, 70%). ¹H NMR (400 MHz, DMSO) δ8.21 (d, J=1.6 Hz, 1H), 8.16 (d, J=1.2 Hz, 1H), 7.96 (s, 1H), 5.12 (d, J=11.2 Hz, 1H), 4.14-3.99 (m, 2H), 3.86 (d, J=8.8 Hz, 1H), 3.51 (d, J=8.8 Hz, 1H), 3.41 (dd, J=11.2, 6.0 Hz, 1H), 3.13-3.02 (m, 2H), 1.80-1.70 (m, 2H), 1.61-1.54 (m, 2H), 1.16 (s, 9H), 1.10 (d, J=6.4 Hz, 3H); MS m/z: 431 [M+H]⁺.

Preparation Example 4: Synthesis of tert-butyl ((3S,4S)-8-(5-bromopyrazin-2-yl)-3-methyl-2-oxa-8-azaspiro[4.5]decan-4-yl)carbamate (Intermediate I-4)

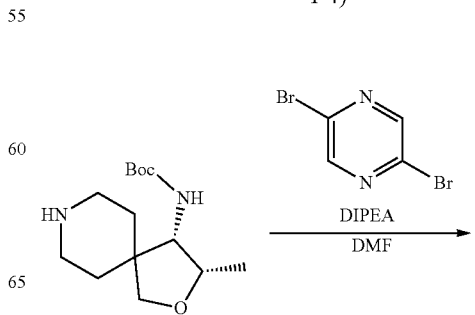

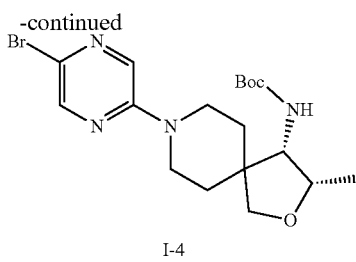

I-4

Tert-butyl 43S,4S)-3-methyl-2-oxa-8-azaspiro[4.5]decan-4-yl)carbamate (200 mg, 0.74 mmol) and 2,5-dibromopyrazine (260 mg, 1.1 mmol) were dissolved in DMF(1.5 mL, 0.5 M). The reaction mixture was added with DIPEA (0.64 mL, 3.7 mmol) and then stirred at 100° C. for 1 hour. The reaction was terminated with H₂O, and the mixture was extracted with EA. The EA layer was dried over MgSO₄, filtered and then concentrated. The resulting product was separated by MPLC (EA:Hx=1:1) and concentrated to obtain Intermediate I-4 (265 mg, 84%). ¹H NMR (400 MHz, DMSO) δ8.21 (d, J=1.6 Hz, 1H), 8.15 (d, J=1.6 Hz, 1H), 7.02 (d, J=10.4 Hz, 1H), 4.20-1.12 (m, 1H), 3.88 (dd, J=10.4, 5.2 Hz, 1H), 3.68-3.61 (m, 2H), 3.59-3.49 (m, 3H), 3.44-3.38 (m, 1H), 1.68-1.55 (m, 3H), 1.51-1.46 (m, 1H), 1.39 (s, 9H), 1.02 (d, J=6.4 Hz, 3H); MS m/z: 427 [M+H]⁺.

Preparation Example 5: Synthesis of methyl 2-chloro-3-mercaptobenzoate (Intermediate I-5)

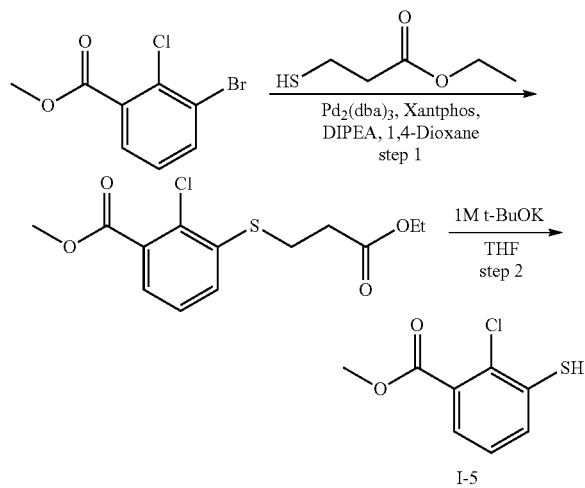

Step 1: methyl 2-chloro-3-((3-ethoxy-3-oxopropyl)thio)benzoate

In a round bottom flask, DIPEA (1.4 mL, 8.0 mmol) was added to a reaction mixture of methyl 3-bromo-2-chlorobenzoate (1 g, 4.0 mmol), ethyl-3-mercaptopropionate (0.7 mL, 5.2 mmol), Pd₂(dba)₃ (180 mg, 0.2 mmol) and XantPhos (230 mg, 0.4 mmol) dissolved in 1,4-dioxane (7 mL, 0.6 M). The reaction mixture was purged with nitrogen, and then stirred at 100° C. for 3 hours. The reaction was terminated with H₂O, and the mixture was extracted with EA. The EA layer was dried over MgSO₄, filtered and then concentrated. The resulting product was separated by MPLC (EA:Hx=1:20) and concentrated to obtain methyl 2-chloro-3-((3-ethoxy-3-oxopropyl)thio)benzoate (940 mg, 73%).

Step 2: methyl 2-chloro-3-mercaptobenzoate (Intermediate I-5)

In a round bottom flask, methyl 2-chloro-3-((3-ethoxy-3-oxopropyl)thio)benzoate (300 mg, 1.0 mmol) was dissolved in THF (tetrahydrofuran, 2 mL, 0.5 M), and then the temperature was lowered to 0. The reaction mixture was slowly added dropwise with 1 M potassium tert-butoxide solution (1.5 mL, 1 M in THF) and then stirred at room temperature for 30 minutes. After completion of the reaction, the reaction mixture was concentrated using a concentrator. The resulting product was separated by MPLC (EA:Hx=1:100) and concentrated to obtain Intermediate I-5 (110 mg, 54%). ¹H NMR (400 MHz, DMSO) δ7.75 (dd, J=7.6, 1.6 Hz, 1H), 7.50 (dd, J=7.6, 1.2 Hz, 1H), 7.32 (t, J=8.0 Hz, 1H), 6.02(bs, 1H), 3.86 (s, 3H); MS m/z: 202 [M+H]⁺.

Preparation Example 6: Synthesis of ethyl 2-chloro-3-mercaptobenzoate (Intermediate I-6)

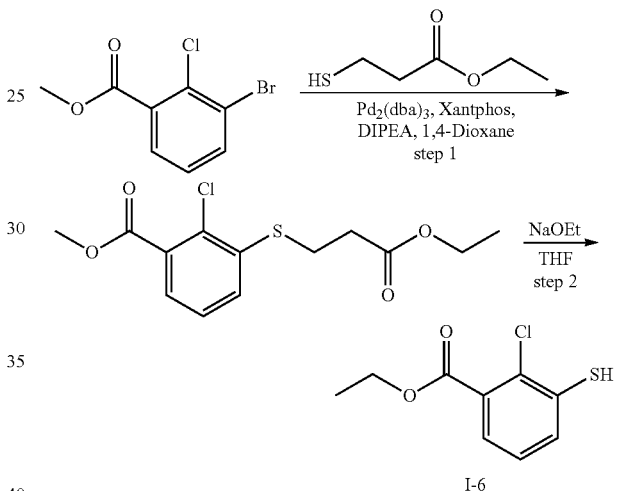

I-6

Step 1: methyl 2-chloro-3-((3-ethoxy-3-oxopropyl)thio) benzoate

In a round bottom flask, DIPEA (1.4 mL, 8.0 mmol) was added to a reaction mixture of methyl 3-bromo-2-chlorobenzoate (1 g, 4.0 mmol), ethyl-3-mercaptopropionate (0.66 mL, 5.21 mmol), Pd₂(dba)₃ (183 mg, 0.2 mmol) and XantPhos (231 mg, 0.4 mmol) dissolved in 1,4-dioxane (7 mL, 0.6 M). The reaction mixture was purged with nitrogen, and then stirred at 100° C. for 3 hours. The reaction was terminated with H₂O, and the mixture was extracted with EA. The EA layer was dried over MgSO₄, filtered and then concentrated. The resulting product was separated by MPLC EA:Hx(EA 2%) and concentrated to obtain methyl 2-chloro-3-((3-ethoxy-3-oxopropyl)thio)benzoate (2.06 g, 52%).

Step 2: ethyl 2-chloro-3-mercaptobenzoate (Intermediate I-6)

In a round bottom flask, methyl 2-chloro-3-((3-ethoxy-3-oxopropyl)thio)benzoate (200 mg, 0.66 mmol) was dissolved in THF(2.64 mL, 0.25 M), and then the temperature was lowered to 0° C. The reaction mixture was slowly added dropwise with sodium ethoxide solution (21 wt % in ethanol) (517 μL, 1.32 mmol) and then stirred at room temperature for 1 hour. After completion of the reaction, the reaction mixture was concentrated and separated by MPLC (MC: MeOH=20:1). The obtained compound was concentrated to obtain Intermediate I-6 (89 mg, 61%). ¹H NMR (400 MHz, DMSO) δ7.75 (d, J=1.6 Hz, 1H), 7.73 (d, J=1.6 Hz, 1H), 7.48 (d, J=7.6 Hz, 1H), 7.32 (t, J=7.6 Hz, 1H), 6.00 (b, 1H), 4.32 (q, J=7.2 Hz, 2H), 1.31 (t, J=7.2 Hz, 3H); MS m/z: 217 [M+H]+.

Preparation Example 7: Synthesis of 3-amino-2-chlorothiophenol (Intermediate I-7)

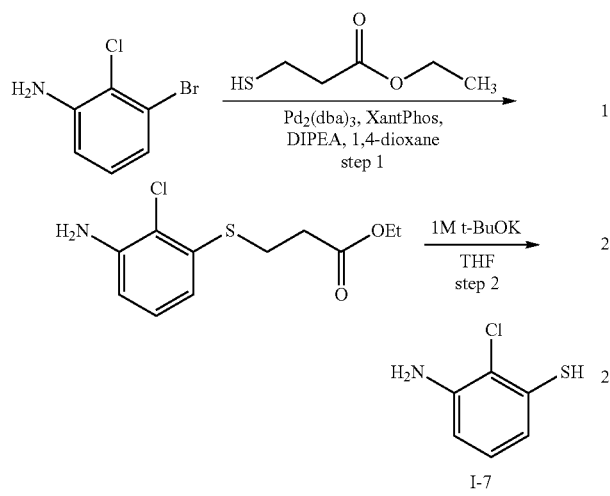

Step 1: ethyl 3-((3-amino-2-chlorophenyl)thio)propionate

In a round bottom flask, DIPEA (5.1 mL, 29.06 mmol) was added to a reaction mixture of 3-bromo-2-chloroaniline (3 g, 14.53 mmol), ethyl-3-mercaptopropionate (2.4 mL, 18.89 mmol), Pd$_2$(dba)$_3$ (665 mg, 0.73 mmol) and XantPhos (840 mg, 1.45 mmol) dissolved in 1,4-dioxane (30 mL, 0.5 M). The reaction mixture was purged with nitrogen, and then stirred at 100° C. for 12 hours. The reaction was terminated with H$_2$O, and the mixture was extracted with EA. The EA layer was dried over MgSO$_4$, filtered and then concentrated. The resulting product was separated by MPLC (EA:Hx=1:5) and concentrated to obtain ethyl 3-((3-amino-2-chlorophenyl)thio)propionate (4.0 g, 99%).

Step 2: 3-amino-2-chlorothiophenol (Intermediate I-7)

In a round bottom flask, ethyl 3-((3-amino-2-chlorophenyl)thio)propionate (4.0 g, 14.53 mmol) was dissolved in THF (73 mL, 0.2 M), and then the temperature was lowered to 0° C. The reaction mixture was slowly added dropwise with 1 M potassium tert-butoxide solution (19 mL, 1 M in THF) and then stirred at room temperature for 4 hours. The reaction was terminated with H$_2$O. The inorganic layer was adjusted to pH4 to pH5 using 1N HCl, and then extracted with EA. The EA layer was dried over MgSO$_4$, filtered and then concentrated. The resulting product was separated by MPLC (EA:Hx=1:10) and concentrated to obtain Intermediate I-7 (2.1 g, 91%). 1 H NMR (400 MHz, DMSO) δ 6.86 (t, J=8.0 Hz, 1H), 6.68 (dd, J=7.6, 1.2 Hz, 1H), 6.55 (dd, J=8.0, 1.6 Hz, 1H), 5.39 (s, 2H), 5.33 (s, 1H); MS m/z: 159 [M+H]+.

Preparation Example 8: Synthesis of 5-chloro-6-mercaptoquinazolin-4(3H)-one (Intermediate I-8)

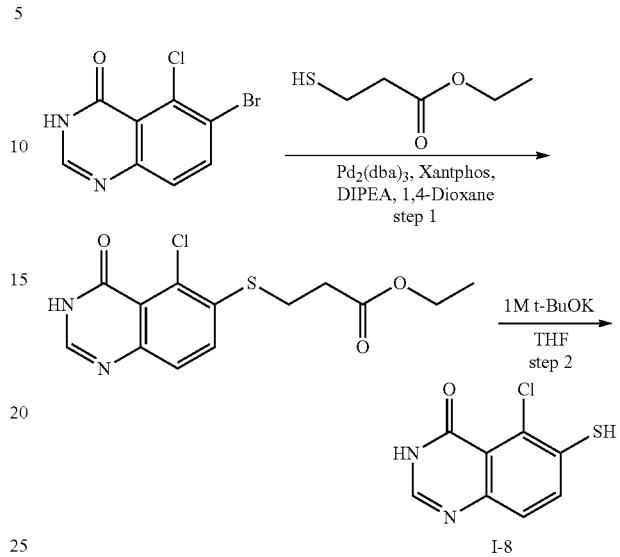

Step 1: ethyl 3-((5-chloro-4-oxo-3,4-dihydroquinazolin-6-yl)thio)propionate

DIPEA (9.2 mL, 52.9 mmol) was added dropwise to a reaction mixture of 6-bromo-5-chloroquinazolin-4(3H)-one (6.87 g, 26.47 mmol), ethyl-3-mercaptopropionate (4 mL, 34.41 mmol), Pd$_2$(dba)$_3$ (1.21 g, 1.32 mmol) and XantPhos (1.53 g, 2.65 mmol) dissolved in 1,4-dioxane (66 mL, 0.4 M). The reaction mixture was purged with nitrogen, and then stirred at 140° C. for 16 hours. The reaction was terminated with H$_2$O, and the mixture was extracted with EA. The EA layer was dried over MgSO$_4$, filtered and then concentrated to obtain ethyl 3-((5-chloro-4-oxo-3,4-dihydroquinazolin-6-yl)thio)propionate (7.03 g, 91%).

Step 2: 5-chloro-6-mercaptoquinazolin-4(3H)-one (Intermediate I-8)

Ethyl 3-((5-chloro-4-oxo-3,4-dihydroquinazolin-6-yl)thio)propionate (7.03 g, 22.5 mmol) was dissolved in THF (113 mL, 0.2 M), and then the temperature was lowered to −78° C. The reaction mixture was slowly added dropwise with potassium tert-butoxide solution (45 mL, 1 M in THF) and then stirred at room temperature for 3 hours. After completion of the reaction, the reaction mixture was concentrated and then water was added, and the pH was adjusted to 1-2 using 1N HCl, and then extracted with EA and THF. The extracted compound was concentrated to obtain Intermediate I-8 (5.17 g, 91%). $^1$H NMR (400 MHz, DMSO) δ12.31 (brs, 1H), 8.03 (d, J=3.2 Hz, 1H), 7.95 (d, J=8.4 Hz, 1H), 7.51 (d, J=8.8 Hz, 1H), 6.00 (brs, 1H); MS m/z: 212 [M+H]+.

Preparation Example 9: Synthesis of 5-chloro-6-mercapto-2-methylquinazolin-4(3H)-one (Intermediate I-9)

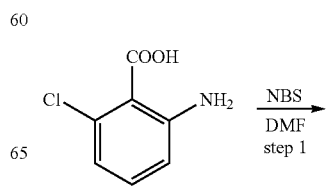

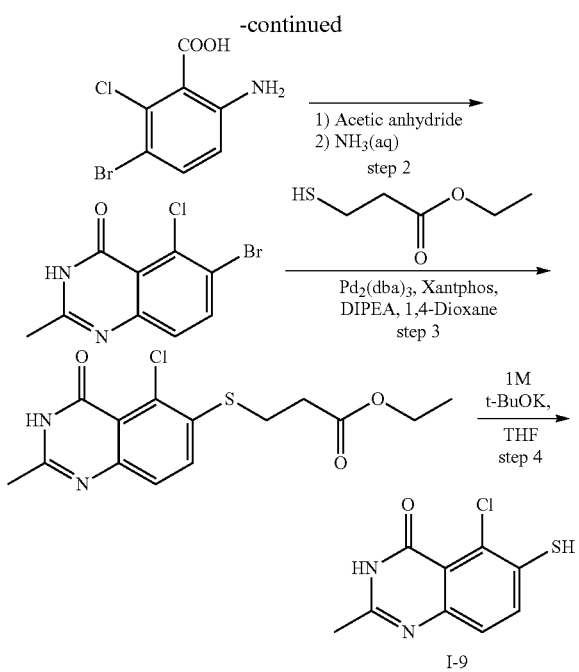

Step 1: 6-amino-3-bromo-2-chlorobenzoic acid

In a round bottom flask, 2-amino-6-chlorobenzoic acid (4 g, 23.3 mmol) was dissolved in DMF (47 mL, 0.5 M), and then the temperature was lowered to 0° C. The reaction mixture was added with NBS (N-bromo succinimide, 4.6 g, 25.6 mmol) and then stirred at room temperature for 24 hours. After completion of the reaction, water was added, and the precipitated solid was obtained by filtration. The resulting compound was dried to obtain 6-amino-3-bromo-2-chlorobenzoic acid (4.6 g, 79%).

Step 2: 6-bromo-5-chloro-2-methylquinazolin-4(3H)-one 6-amino-3-bromo-2-chlorobenzoic acid (250 mg, 1.0 mmol) and acetic anhydride (4 mL, 0.25 M) were put into a round bottom flask, and then stirred at 140° C. for 3 hours. After completion of the reaction, the reaction mixture was concentrated, and then added with $NH_3$ solution (28% in $H_2O$) (4 mL, 0.25 M) and stirred at 100° C. for 12 hours. The solid precipitated during the reaction was collected by filtration, washed with $H_2O$ and MeOH, and then dried to obtain 6-bromo-5-chloro-2-methylquinazolin-4(3H)-one (203 mg, 74%).

Step 3: ethyl 3-((5-chloro-2-methyl-4-oxo-3,4-dihydroquinazolin-6-yl)thio)propionate In a round bottom flask, DIPEA (240 μL, 1.38 mmol) was added dropwise to a reaction mixture of 6-bromo-5-chloro-2-methylquinazolin-4(3H)-one (190 mg, 0.69 mmol), ethyl-3-mercaptopropionate (97 μL, 0.76 mmol), $Pd_2(dba)_3$ (32 mg, 0.034 mmol) and XantPhos (40 mg, 0.07 mmol) dissolved in 1,4-dioxane (2.8 mL, 0.25 M). The reaction mixture was purged with nitrogen, and then stirred at 100° C. for 4 hours. The reaction was terminated with $H_2O$, and the mixture was extracted with EA. The EA layer was dried over $MgSO_4$, filtered and then concentrated. The resulting product was separated by MPLC (EA:Hx=9:1) and concentrated to obtain ethyl 3-((5-chloro-2-methyl-4-oxo-3,4-dihydroquinazolin-6-yl)thio)propionate (128 mg, 57%).

Step 4: 5-chloro-6-mercapto-2-methylquinazolin-4(3H)-one (Intermediate I-9)

In a round bottom flask, ethyl 3-((5-chloro-2-methyl-4-oxo-3,4-dihydroquinazolin-6-yl)thio)propionate (123 mg, 0.38 mmol) was dissolved in THF (1.9 mL, 0.2 M), and then the temperature was lowered to 0° C. The reaction mixture was slowly added dropwise with potassium tert-butoxide solution (0.49 mL, 1 M in THF) and then stirred for 1 hour. After completion of the reaction, the concentrated compound was filtered with EA to obtain Intermediate I-9. The obtained compound was used in the next reaction without a further purification process. MS m/z: 227 [M+H]⁺.

Preparation Example 10: Synthesis of tert-butyl (1-(5-mercaptopyrazin-2-yl)-4-methylpiperidin-4-yl) carbamate (Intermediate I-10)

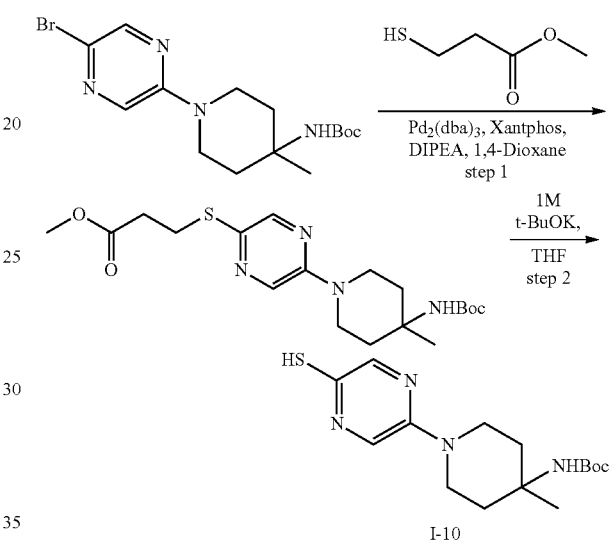

Step 1: methyl 3-((5-(4-((tert-butoxycarbonyl) amino)-4-methylpiperidin-1-yl)pyrazin-2-yl)thio) propanate In a round bottom flask, DIPEA (2.3 mL, 13.47 mmol) was added dropwise to a reaction mixture of tert-butyl (1-(5-bromopyrazin-2-yl)-4-methylpiperidin-4-yl)carbamate (2.5 g, 6.73 mmol), methyl-3-mercaptopropionate (0.82 mL, 7.41 mmol), $Pd_2(dba)_3$ (308 mg, 0.337 mmol) and XantPhos (195 mg, 0.337 mmol) dissolved in 1,4-dioxane (15 mL, 0.45 M). The reaction mixture was purged with nitrogen, and then stirred at 100° C. for 4 hours. The reaction was terminated with $H_2O$, and the mixture was extracted with EA. The EA layer was dried over $MgSO_4$, filtered and then concentrated. The resulting product was separated by MPLC (EA:Hx=9:1) and concentrated to obtain methyl 3-((5-(4-((tert-butoxy carb onyl)amino)-4-methyl piperidin-1-yl)pyrazin-2-yl)thio)propanate (2.7 g, 98%).

Step 2: tert-butyl (1-(5-mercaptopyrazin-2-yl)-4-methylpiperidin-4-yl)carbamate (Intermediate I-10)

In a round bottom flask, methyl 3-((5-(4-((tert-butoxycarbonyl)amino)-4-methylpiperidin-1-yl)pyrazin-2-yl)thio) propanate (2.7 g, 6.58 mmol) was dissolved in THF (10 mL, 0.67 M), and then the temperature was lowered to 0° C. The reaction mixture was slowly added dropwise with 1 M potassium tert-butoxide solution (5 mL, 1 M in THF) and then stirred at room temperature for 30 minutes. After completion of the reaction, the reaction mixture was concentrated using a concentrator. The resulting product was separated by MPLC and concentrated to obtain Intermediate I-10 (1.2 g, 56%). MS m/z: 325 [M+H]+.

Preparation Example 11: Synthesis of 6-bromo-7-chloro-2-methylbenzo[d]thiazole (Intermediate I-11)

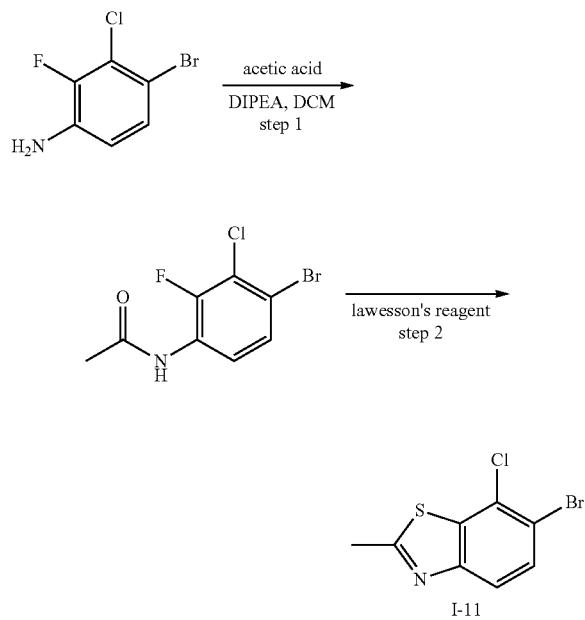

Step 1: N-(4-bromo-3-chloro-2-fluorophenyl)acetamide

At 0° C., 4-bromo-3-chloro-2-fluoroaniline (250 mg, 1.11 mmol) and diisopropylethylamine (DIPEA, 0.485 mL, 2.78 mmol) were dissolved in dichloromethane (DCM, 2 mL, 0.56 M), and then acetic anhydride (0.1 mL, 1.17 mmol) was added thereto. The reaction mixture was stirred at room temperature for 24 hours. The mixture was added with 1 M HCl and NaHCO₃ aqueous solution, and then extracted. The organic layer was dried over MgSO₄, filtered and then concentrated. The resulting product was separated by MPLC and concentrated to obtain N-(4-bromo-3-chloro-2-fluorophenyl)acetamide (200 mg, 83%).

Step 2: 6-bromo-7-chloro-2-methylbenzo[d]thiazole (Intermediate I-11)

N-(4-bromo-3-chloro-2-fluorophenyl)acetamide (200 mg, 0.75 mmol) was dissolved in xylene (3 mL, 0.25 M), and then Lawesson's reagent (300 mg, 0.45 mmol) was added thereto. The reaction mixture was stirred at 110° C. for 18 hours. The reaction mixture was added with cesium carbonate (800 mg, 1.5 mmol) and then further stirred at 110° C. for 18 hours. The organic layer was dried over MgSO₄, filtered and then concentrated. After completion of the reaction, the reaction mixture was cooled to room temperature, and then extracted by adding water and EA. The organic layer was dried over MgSO₄, filtered and then concentrated. The resulting product was separated by MPLC and concentrated to obtain Intermediate I-11 (150 mg, 76%). MS m/z: 262 [M+H]+.

Preparation Example 12: Synthesis of 4-chloro-2-methyl-2H-indazole-5-thiol (Intermediate I-12)

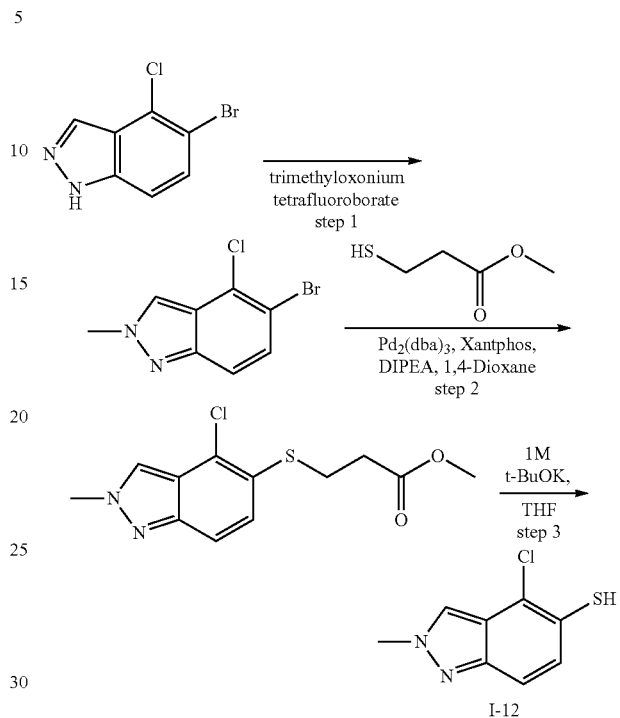

Step 1: 5-bromo-4-chloro-2-methyl-2H-indazole 5-bromo-4-chloro-1H-indazole (360 mg, 1.56 mmol) was dissolved in ethylacetate (3 mL, 0.52 M), and then solid trimethyloxonium tetrafluoroborate (250 mg, 1.70 mmol) was added at 0° C. The reaction mixture was stirred at room temperature for 4 hours. The mixture was added with aqueous NaHCO₃ solution and then extracted. The organic layer was dried over MgSO₄, filtered and then concentrated. The resulting product was separated by MPLC and concentrated to obtain 5-bromo-4-chloro-2-methyl-2H-indazole (300 mg, 79%).

Step 2: methyl 3-((4-chloro-2-methyl-2H-indazol-5-yl)thio)propanoate

In a round bottom flask, DIPEA (0.43 mL, 2.44 mmol) was added dropwise to a reaction mixture of 5-bromo-4-chloro-2-methyl-2H-indazole (250 mg, 1.56 mmol), methyl-3-mercaptopropionate (0.2 mL, 1.83 mmol), Pd₂(dba)₃ (112 mg, 0.122 mmol) and XantPhos (71 mg, 0.122 mmol) dissolved in 1,4-dioxane (5 mL, 0.31 M). The reaction mixture was purged with nitrogen, and then stirred at 100° C. for 4 hours. The reaction was terminated with H₂O, and the mixture was extracted with EA. The EA layer was dried over MgSO₄, filtered and then concentrated. The resulting product was separated by MPLC (EA:Hx=9:1) and concentrated to obtain methyl 3-((4-chloro-2-methyl-2H-indazol-5-yl)thio)propanoate (300 mg, 86%).

Step 3: 4-chloro-2-methyl-2H-indazole-5-thiol (Intermediate I-12)

In a round bottom flask, methyl 3-((4-chloro-2-methyl-2H-indazol-5-yl)thio)propanoate (300 mg, 1.22 mmol) was dissolved in THF(2 mL, 0.61 M), and then the temperature was lowered to 0. The reaction mixture was slowly added dropwise with 1 M potassium tert-butoxide solution (1 mL, 1 M in THF) and then stirred at room temperature for 30 minutes. After completion of the reaction, the reaction mixture was concentrated using a concentrator. The resulting product was separated by MPLC and concentrated to obtain Intermediate I-12 (100 mg, 47.8%). MS m/z: 199 [M+H]⁺.

Preparation Example 13: Synthesis of 5-chloro-6-mercapto-3-phenylquinazolin-4(3H)-one (Intermediate I-13)

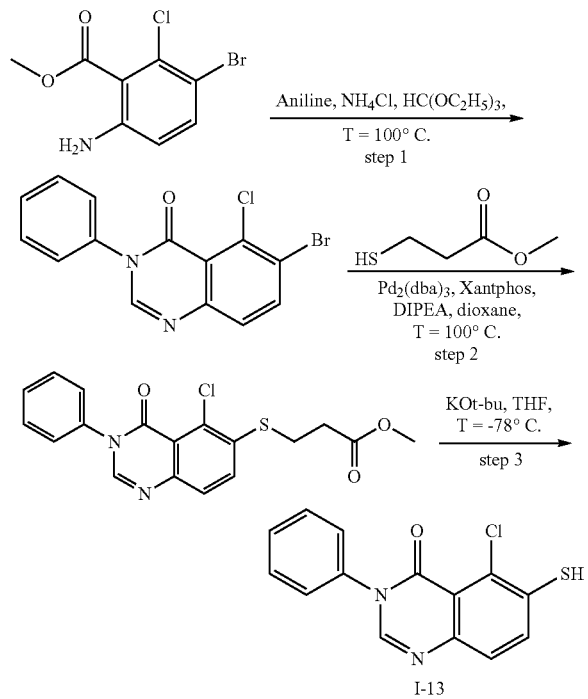

Step 1: 6-bromo-5-chloro-3-phenylquinazolin-4(3H)-one

In a round bottom flask, aniline (0.18 mL, 1.92 mmol) and NH₄Cl (43 mg, 0.80 mmol) were added dropwise to a reaction mixture of methyl 6-amino-3-bromo-2-chlorobenzoate (600 mg, 1.60 mmol) dissolved in triethyl orthoformate (0.4 mL, 2.40 mmol), and then the reaction mixture was stirred at 100° C. for 16 hours. The reaction was terminated with H₂O, and the mixture was extracted with EA. The EA layer was dried over MgSO₄, filtered and then concentrated. The resulting product was separated by MPLC (EA:Hex=1:3) and concentrated to obtain 6-bromo-5-chloro-3-phenylquinazolin-4(3H)-one (503 mg, 94%). MS m/z: 535.00 [M+H]⁺.

Step 2: methyl 3-((5-chloro-4-oxo-3-phenyl-3,4-dihydroquinazolin-6-yl)thio)propanoate In a round bottom flask, methyl 3-mercaptopropanoate (0.17 mL, 1.51 mmol), Pd₂(dba)₃ (106 mg, 0.12 mmol), XantPhos (69 mg, 0.12 mmol) and DIPEA (0.40 mL, 2.32 mmol) were added dropwise to a reaction mixture of 6-bromo-5-chloro-3-phenylquinazolin-4(3H)-one (390 mg, 1.16 mmol) dissolved in dioxane, and then the reaction mixture was stirred at 100° C. for 3 hours. The reaction was terminated with H₂O, and the mixture was extracted with EA. The EA layer was dried over MgSO₄, filtered and then concentrated. The resulting product was separated by MPLC (EA:Hex=1:3) and concentrated to obtain methyl 3-((5-chloro-4-oxo-3-phenyl-3,4-dihydroquinazolin-6-yl)thio)propanoate (116 mg, 27%). MS m/z: 375.10 [M+H]⁺.

Step 3: 5-chloro-6-mercapto-3-phenylquinazolin-4(3H)-one (Intermediate I-13)

In a round bottom flask, KOt-bu (69 mg, 0.62 mmol) was added dropwise to a reaction mixture of methyl 3-((5-chloro-4-oxo-3-phenyl-3,4-dihydroquinazolin-6-yl)thio)propanoate (116 mg, 0.31 mmol) dissolved in THF, and then the reaction mixture was stirred at −78° C. for 1 hour. The reaction was terminated with aqueous 1 M HCl solution, and the mixture was extracted with EA. The EA layer was dried over MgSO₄, filtered and then concentrated. The resulting product was separated by MPLC (EA:Hex=1:3) and concentrated to obtain Intermediate I-13 (62 mg, 69%). MS m/z: 289.00 [M+H]⁺.

Preparation Example 14: Synthesis of t-butyl N-[1-(4-amino-5-iodo-1-methyl-6-oxo-pyrimidin-2-yl)-4-methylpiperidin-4-yl]carbamate (Intermediate I-14)

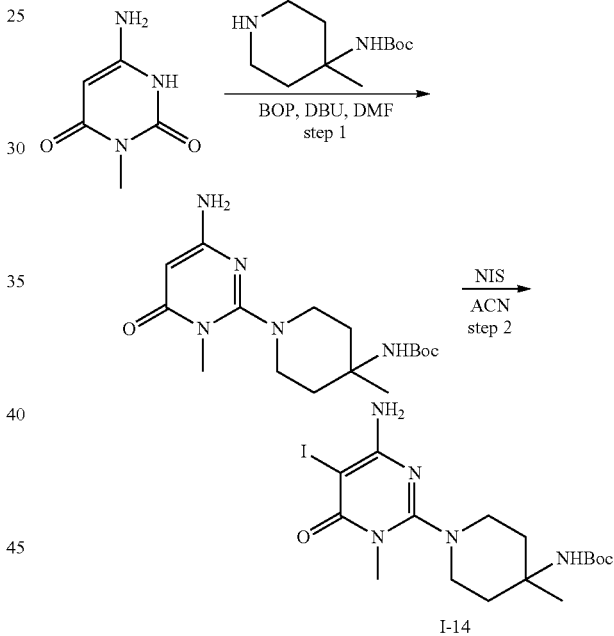

Step 1: tert-butyl (1-(4-amino-1-methyl-6-oxo-1,6-dihydropyridin-2-yl)-4-methylpiperidin-4-yl)carbamate 6-amino-3-methyl-1H-pyrimidine-2,4-dione (500 mg, 3.54 mmol), BOP (1.57 g, 3.54 mmol), and DBU (1,8-diazabicyclo[5.4.0]undec-7-ene, 539 mg, 3.54 mmol, 534.02 μL) were dissolved in DMF (10 mL, 0.35 M), and then tert-butyl (4-methylpiperidin-4-yl)carbamate (758 mg, 3.54 mmol) was added. The reaction mixture was stirred at room temperature for 16 hours. After confirming by LCMS that the reaction material had completely disappeared, the reaction mixture was added with brine (20 mL) and EtOAc (20 mL×3) and extracted. The organic layer was dried over Na₂SO₄, filtered and then concentrated. The resulting product was separated by Prep-HPLC (neutral) and concentrated to obtain tert-butyl (1-(4-amino-1-methyl-6-oxo-1,6-dihydropyridin-2-yl)-4-methylpiperidin-4-yl)carbamate (320 mg, 26.8%). MS m/z: 338 [M+H]⁺.

Step 2: tert-butyl (1-(4-amino-5-iodo-1-methyl-6-oxo-1,6-dihydropyridin-2-yl)-4-methylpiperidin-4-yl)carbamate (Intermediate I-14)

Tert-butyl (1-(4-amino-1-methyl-6-oxo-1,6-dihydropyridin-2-yl)-4-methylpiperidin-4-yl)carbamate (260 mg, 950 μmol) was dissolved in ACN (3 mL, 0.25 M), and then NIS (N-iodo succinimide, 214 mg, 950 μmol) was added thereto. The reaction mixture was stirred at room temperature for 1 hour. After a white precipitate was formed, and LCMS confirmed that the reaction material had completely disappeared, the reaction was terminated with aqueous NaHCO₃ solution, and the mixture was extracted with EA. The EA layer was dried over MgSO₄, filtered and then concentrated. The resulting product was separated by MPLC and concentrated to obtain Intermediate I-14 (360 mg, 82%). MS m/z: 464 [M+H]⁺.

Preparation Example 15: Synthesis of 2-benzyl-6-bromo-7-chloro-1H-benzo imidazole (Intermediate I-15)

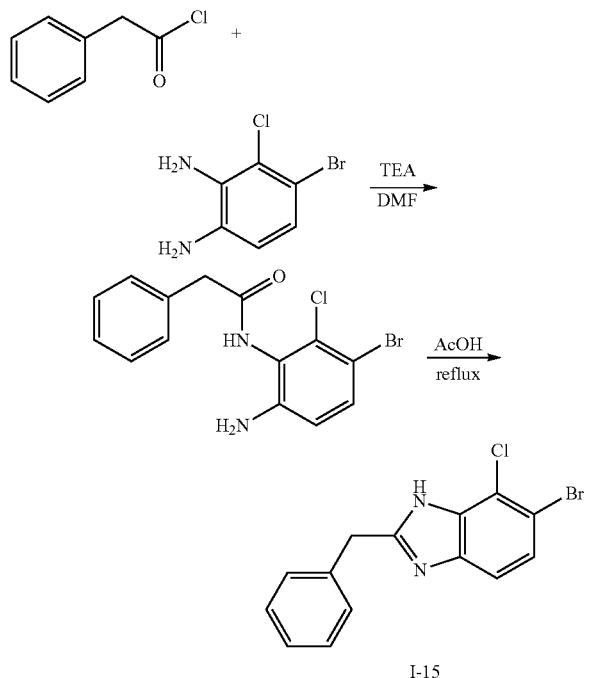

Step 1: N-(6-amino-3-bromo-2-chlorophenyl)-2-phenylacetate

In a round bottom flask, 4-bromo-3-chlorobenzene-1,2-diamine (100 mg, 0.45 mmol) was dissolved in DMF (2 mL), and then triethylamine (0.13 mL, 0.9 mmol) was added thereto. The reaction mixture was added with 2-phenylacetyl chloride (70 mg, 0.45 mmol) and then stirred at room temperature for 2 hours. The reaction was terminated with H₂O, and the mixture was extracted with EA. The EA layer was dried over MgSO₄, filtered and then concentrated. The resulting product was separated by MPLC (EA:Hex=1:3) and concentrated to obtain N-(6-amino-3-bromo-2-chlorophenyl)-2-phenylacetate (135 mg, 89%). MS m/z: 339 [M+H]⁺.

Step 2: 2-benzyl-6-bromo-7-chloro-1H-benzo[d]imidazole

Acetic acid (5 mL) was added to N-(6-amino-3-bromo-2-chlorophenyl)-2-phenylacetate (135 mg, 0.4 mmol), followed by stirring at 100° C. for 1 hour. After completion of the reaction, the mixture was added with water and extracted with DCM. The DMC layer was dried over MgSO₄, filtered and then concentrated. The resulting product was separated by MPLC and concentrated to obtain Intermediate I-15 (100 mg, 77%). MS m/z: 321 [M+H]⁺.

Preparation Example 16: Synthesis of tert-butyl ((3S,4S)-8-(5-mercaptopyrazin-2-yl)-3-methyl-2-oxa-8-azaspiro[4.5]decan-4-yl)carbamate (Intermediate I-16)

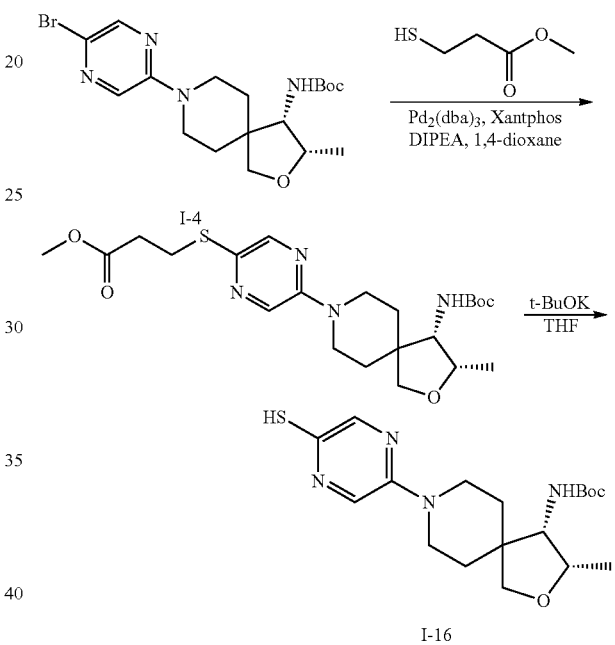

Intermediate I-16 was synthesized using Intermediate I-4 as a starting material in accordance with Preparation Example 10. MS m/z: 381 [M+H]⁺.

Preparation Example 17: Synthesis of 2-benzyl-5-bromo-4-chloro-2H-indazole (Intermediate I-17)

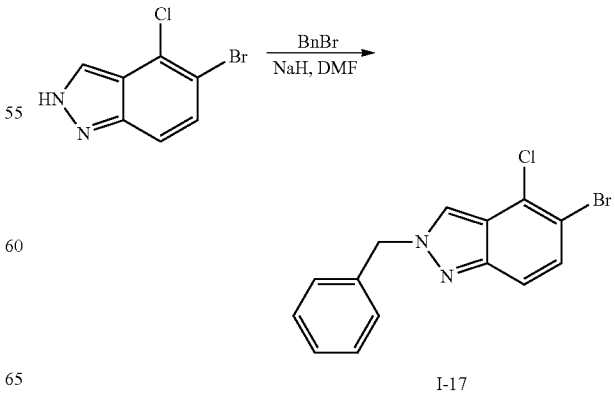

In a round bottom flask, 5-bromo-4-chloro-2H-indazole (100 mg, 0.43 mmol) was dissolved in DMF (3 mL), and then NaH (34 mg, 0.86 mmol) was added thereto. The reaction mixture was added with benzylbromide (74 mg, 0.43 mmol) and then stirred at room temperature for 2 hours. The reaction was terminated with H$_2$O, and the mixture was extracted with EA. The EA layer was dried over MgSO$_4$, filtered and then concentrated. Then, two isomers were separated by MPLC (EA:Hex=1:3) and concentrated to obtain Intermediate I-17 (50 mg, 36%). MS m/z: 321 [M+H]$^+$.

Preparation Example 18: N-benzyl-3-chloro-4-mercaptopicolinamide (Intermediate I-18)

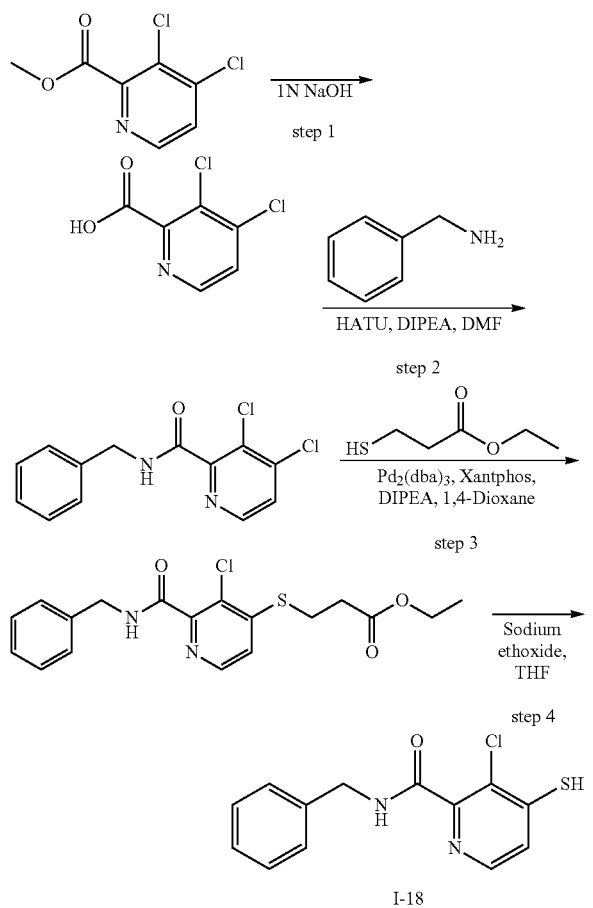

Step 1: 3,4-dichloropicolinic acid

1N NaOH solution (7.29 mL, 7.29 mmol) was added dropwise to methyl 3,4-dichloropicolinate (500 mg, 2.43 mmol), followed by stirring at 40 t for 1 hour. The reaction was terminated, and then 5M HCl solution was added dropwise to adjust the pH to 4. The precipitated solid was filtered to obtain 3,4-dichloropicolinic acid (354.6 mg, 76%). The obtained compound was used in the next reaction without a further purification process. MS m/z: 191 [M+H]$^+$.

Step 2: N-benzyl-3,4-dichloropicolinamide 3,4-dichloropicolinic acid (100 mg, 0.5 mmol) and phenylmethanamine (65 µL, 0.6 mmol) were dissolved in DMF, and DIPEA (260 µL, 1.5 mmol) was added dropwise thereto, and then HATU (1-[bis(dimethyl amino)methyl ene]-1H-1,2,3-triazolo[4,5-b]pyridinium 3-oxide hexafluorophosphate) (380 mg, 1.0 mmol) was added dropwise thereto. The reaction mixture was stirred at room temperature for 1 hour. The reaction was terminated with H$_2$O, and the mixture was extracted with EA. The EA layer was dried over MgSO$_4$, filtered and then concentrated. The resulting product was separated by MPLC (EA:Hx=1:2) and concentrated to obtain N-benzyl-3,4-dichloropicolinamide (92 mg, 66%). MS m/z: 281 [M+H]$^+$.

Step 3: ethyl 3-((2-(benzylcarbamoyl)-3-chloropyridin-4-yl)thio)propanoate

N-benzyl-3,4-dichloropicolinamide (92 mg, 0.33 mmol), ethyl-3-mercaptopropionate (63 µL, 0.495 mmol), Pd$_2$(dba)$_3$ (18 mg, 0.02 mmol) and XantPhos (19 mg, 0.033 mmol) were dissolved in 1,4-dioxane (1 mL, 0.4 M), and then DIPEA (115 µL, 0.66 mmol) was added thereto. The reaction mixture was purged with nitrogen, and then stirred at 100° C. for 18 hours. The reaction was terminated with H$_2$O, and the mixture was extracted with EA. The EA layer was dried over MgSO$_4$, filtered and then concentrated. The resulting product was separated by MPLC (EA:Hx=1:2) and concentrated to obtain ethyl 3-((2-(benzylcarbamoyl)-3-chloropyridin-4-yl)thio)propanoate (61 mg, 49%). MS m/z: 379 [M+H]$^+$.

Step 4: N-benzyl-3-chloro-4-mercaptopicolinamide

Ethyl 3-((2-(benzylcarbamoyl)-3-chloropyridin-4-yl)thio)propanoate (120 mg, 0.32 mmol) was dissolved in THF (1.6 mL, 0.2M), and then cooled to 0° C. The reaction mixture was slowly added dropwise with sodium ethoxide solution (21 wt % in ethanol) (128 µL, 0.35 mmol) and then stirred at room temperature for 1 hour. After completion of the reaction, the reaction mixture was concentrated, and methylene chloride (MC) was added to, and then the precipitated solid was filtered to obtain Intermediate I-18. The resulting compound was used in the next reaction without a further purification process. MS m/z: 279 [M+H]$^+$.

Preparation Example 19: 3-chloro-4-mercapto-N-(pyridin-3-ylmethyl)picolinamide (Intermediate I-19)

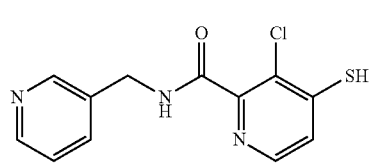

Intermediate I-19 was obtained in the same method as in Preparation Example 18, except that pyridin-3-ylmethanamine was used instead of phenylmethanamine in step 2 of Preparation Example 18. MS m/z: 280 [M+H]$^+$.

Preparation Example 20: 2-benzyl-8-chloro-7-mercapto-3,4-dihydroisoquinolin-1(2H)-one (Intermediate I-20)

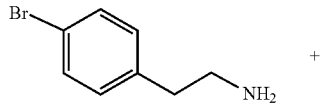

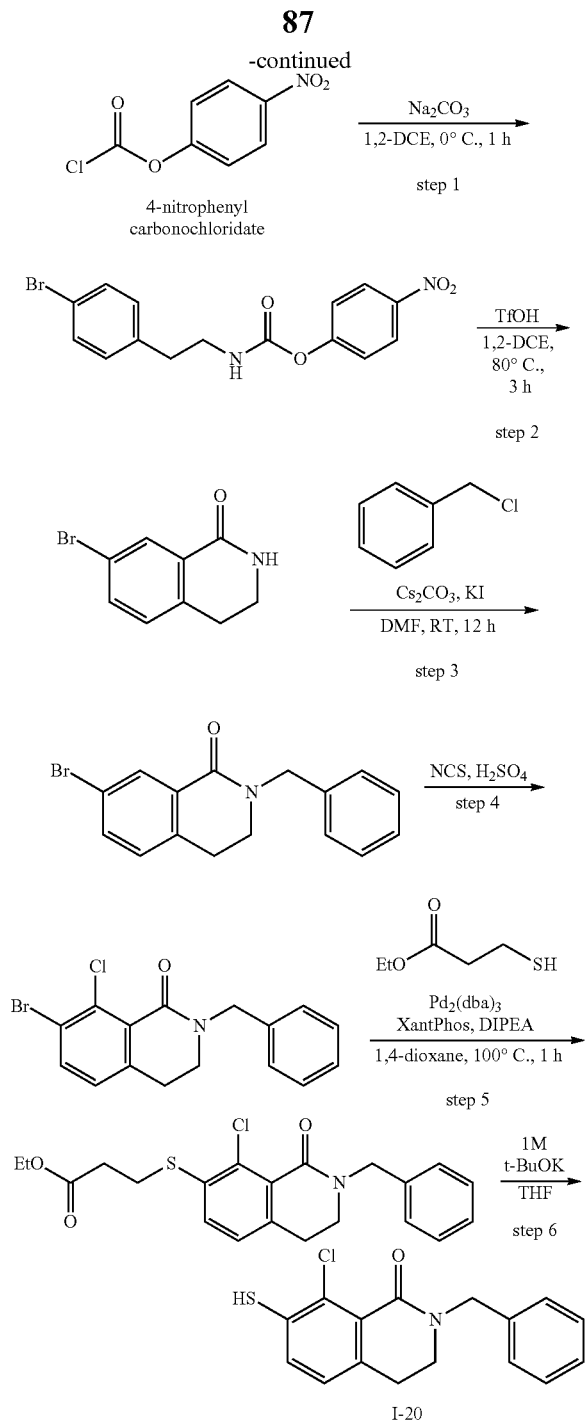

then purged with nitrogen and stirred at 0. The reaction mixture was slowly added with trifluoromethansulfonic acid (TfOH) (8.8 mL, 99.5 mmol) and then stirred at 0° C. for 10 minutes. After elevating the reaction temperature to 80° C. and stirring for 3 hours, The reaction was terminated with $H_2O$, and the mixture was extracted with EA. The EA layer was washed with 1N sodium hydroxide aqueous solution and brine. The EA layer was dried over $MgSO_4$, filtered and then concentrated. 7-bromo-3,4-dihydroisoquinolin-1(2H)-one (1150 mg, 51%) was obtained by crystallization with EA and Hx.

Step 3: 2-benzyl-7-bromo-3,4-dihydroisoquinolin-1(2H)-one 7-bromo-3,4-dihydroisoquinolin-1(2H)-one (100 mg, 0.44 mmol), benzylchloride (0.1 mL, 0.93 mmol), cesium carbonate (400 mg, 1.24 mmol) and potassium iodide (50 mg, 0.22 mmol) were dissolved in DMF (6.2 mL, 0.1M), followed by stirring at room temperature for 24 hours. The reaction was terminated with $H_2O$, and the mixture was extracted with EA. The EA layer was dried over $MgSO_4$, filtered and then concentrated. The resulting product was separated by MPLC (EA:Hx=1:10) and concentrated to obtain 2-benzyl-7-bromo-3,4-dihydroisoquinolin-1(2H)-one (110 mg, 80%).

Step 4: 2-benzyl-7-bromo-8-chloro-3,4-dihydroisoquinolin-1(2H)-one 2-benzyl-7-bromo-3,4-dihydroisoquinolin-1(2H)-one (340 mg, 1.07 mmol) was dissolved in $H_2SO_4$ (2.1 mL, 0.5M), and then stirred at 0° C. The reaction mixture was added with N-chlorosuccinimide(NCS) (160 mg, 1.18 mmol) and then stirred at room temperature for 2 hours. The reaction was terminated with $H_2O$, and the mixture was extracted with EA. The EA layer was dried over $MgSO_4$, filtered and then concentrated. The resulting product was separated by MPLC (EA:Hx=1:10) and concentrated to obtain 2-benzyl-7-bromo-8-chloro-3,4-dihydroisoquinolin-1(2H)-one (96 mg, 26%).

Step 5: ethyl 3-((2-benzyl-8-chloro-1-oxo-1,2,3,4-tetrahydroisoquinolin-7-yl)thio)propanoate 2-benzyl-7-bromo-8-chloro-3,4-dihydroisoquinolin-1(2H)-one (96 mg, 0.27 mmol), ethyl-3-mercaptopropionate (0.05 mL, 0.41 mmol), $Pd_2(dba)_3$ (25 mg, 0.03 mmol), XantPhos (16 mg, 0.03 mmol) and DIPEA (0.1 mL, 0.55 mmol) were dissolved in 1,4-dioxane (0.7 mL, 0.4M). The reaction mixture was purged with nitrogen, and then stirred at 100° C. for 1 hour. The reaction was terminated with $H_2O$, and the mixture was extracted with EA. The EA layer was dried over $MgSO_4$, filtered and then concentrated. The resulting product was separated by MPLC (EA:Hx=1:10) and concentrated to obtain ethyl 3-((2-benzyl-8-chloro-1-oxo-1,2,3,4-tetrahydroisoquinolin-7-yl)thio)propanoate (100 mg, 91%).

Step 6: 2-benzyl-8-chloro-7-mercapto-3,4-dihydroisoquinolin-1(2H)-one

Ethyl 3-((2-benzyl-8-chloro-1-oxo-1,2,3,4-tetrahydroisoquinolin-7-yl)thio)propanoate (100 mg, 0.25 mmol) was dissolved in DMF (1.3 mL, 0.2M), and then stirred at 0° C. The reaction mixture was added with 1M tert-butoxide (0.37 mL, 0.37 mmol) and then stirred at room temperature for 1 hour. The reaction was stopped, and then concentrated using a concentrator to obtain Intermediate I-20 (crude product). MS m/z: 304 [M+H]$^+$.

Step 1: 4-nitrophenyl (4-bromophenethyl)carbamate 4-bromophenethyl amine (2000 mg, 10.0 mmol) and sodium carbonate (1170 mg, 11.0 mmol) were dissolved in 1,2-dichloroethane(1,2-DCE) (100 mL, 0.1M), followed by stirring at 0° C. for 30 minutes. The reaction mixture was added with 4-nitrophenyl chloroformate (2015 mg, 10.0 mmol) and then stirred at 0° C. for 1 hour. The reaction was terminated with $H_2O$, and the mixture was extracted with EA, followed by washing with brine. The EA layer was dried over $MgSO_4$, filtered and then concentrated to obtain 4-nitrophenyl (4-bromophenethyl)carbamate (3630 mg, 99%).

Step 2: 7-bromo-3,4-dihydroisoquinolin-1(2H)-one 4-nitrophenyl (4-bromophenethyl)carbamate (3630 mg, 9.95 mmol) was dissolved in 1,2-DCE (100 mL, 0.1M), and Preparation Example 21: N—((S)-1'-(5-bromopyrazin-2-yl)-1,3-dihydrospiro[indene-2,4'-piperidin]-1-yl)-2-methylpropane-2-sulfinamide (Intermediate I-21)

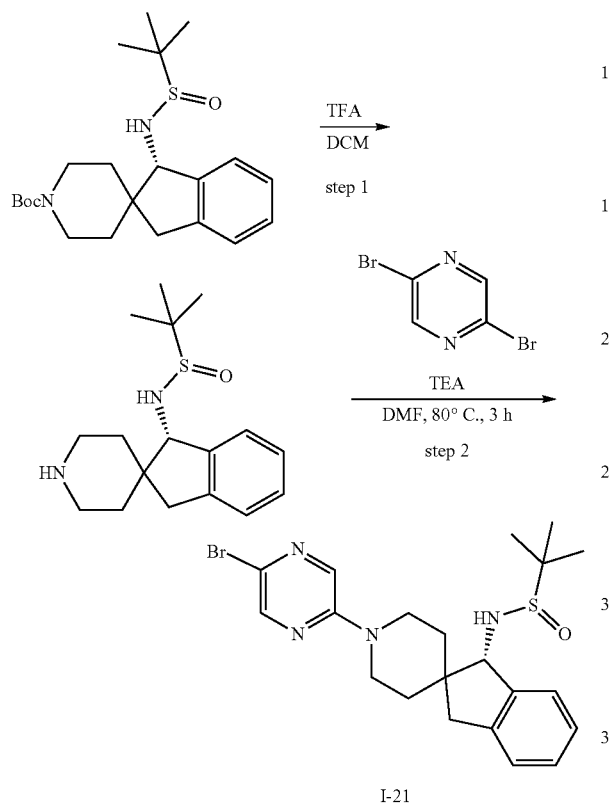

Step 1: N—((S)-1,3-dihydrospiro[indene-2,4'-piperidin]-1-yl)-2-methylpropane-2-sulfinamide Tert-butyl (1 S)-1-((tert-butyl sulfinyl)amino)-1,3-dihydrospiro[indene-2,4'-piperidine]-1'-carboxylate (0.5 g, 1.23 mmol) was dissolved in DCM (6.9 ml, 0.18 M). The reaction mixture was slowly added dropwise with TFA (1.3 ml, 0.095 M) and then stirred at room temperature for 3 hours. After completion of the reaction, the reaction mixture was concentrated to obtain N—((S)-1,3-dihydrospiro[indene-2,4'-piperidin]-1-yl)-2-methylpropane-2-sulfinamide.

Step 2: N—((S)-1'(5-bromopyrazin-2-yl)-1,3-dihydrospiro[indene-2,4'-piperidin]-1-yl)-2-methylpropane-2-sulfinamide N—((S)-1,3-dihydrospiro[indene-2,4'-piperidin]-1-yl)-2-methylpropane-2-sulfinamide and 2,5-dibromopyrazine (0.51 g, 1.84 mmol) were dissolved in DMF (8.2 ml, 0.15 M). The reaction mixture was added with triethylamine (TEA) (0.83 mL, 5.90 mmol) and then stirred at 80° C. for 3 hours. The reaction was terminated with H₂O, and the mixture was extracted with EA. The EA layer was dried over MgSO₄, filtered and then concentrated. The resulting product was separated by MPLC (EA:Hx=1:3) and concentrated to obtain Intermediate I-21 (150 mg, 26%).

Preparation Example 22: 6-bromo-5-chloro-3H-quinazolin-4-one (Intermediate I-22)

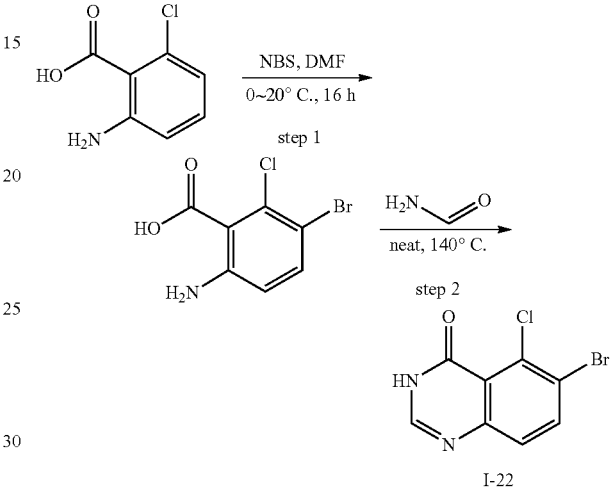

Step 1: 6-amino-3-bromo-2-chloro-benzoic acid

To a solution of 2-amino-6-chloro-benzoic acid (10.0 g, 58.2 mmol) in DMF(100 mL) was added NB S (12.4 g, 69.9 mmol) in 4 portions at 0-10° C. The reaction mixture was stirred at 0-25° C. for 16 hours. The mixture was diluted with water (20 mL) and extracted with EtOAc(3×20 mL). The organic layer was washed with brine (2×50 mL), and then dried over anhydrous sodium sulfate and filtered. The filtrate was concentrated under vacuum to obtain 6-amino-3-bromo-2-chloro-benzoic acid (14.0 g, 95% yield) as a brown oil. ¹H NMR (400 MHz, DMSO-d₆) δ=7.40 (d, J=8.8 Hz, 1H), 6.65 (d, J=8.8 Hz, 1H).

Step 2: 6-bromo-5-chloro-3H-quinazolin-4-one A mixture of 6-amino-3-bromo-2-chloro-benzoic acid (10.0 g, 27.9 mmol) in formamide (18.2 g, 405 mmol) was stirred at 140° C. for 5 hours. The reaction mixture was diluted with NH₄Cl (20 mL) and filtered. The filter cake was dried under vacuum to obtain Intermediate I-22 (4.00 g, 55% yield) as a brown solid. ¹H NMR (400 MHz, DMSO-d₆) δ=8.13 (s, 1H), 8.11 (d, J=8.8 Hz, 1H), 7.54 (d, J=8.8 Hz, 1H).

Preparation Example 23: 3-benzyl-6-((5-bromopyrazin-2-yl)thio)-5-chloroquinazolin-4(3H)-one (Intermediate I-23)

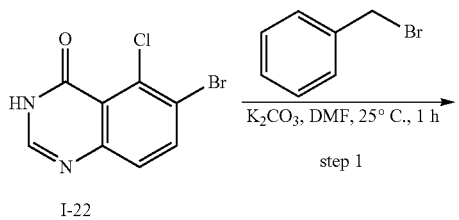

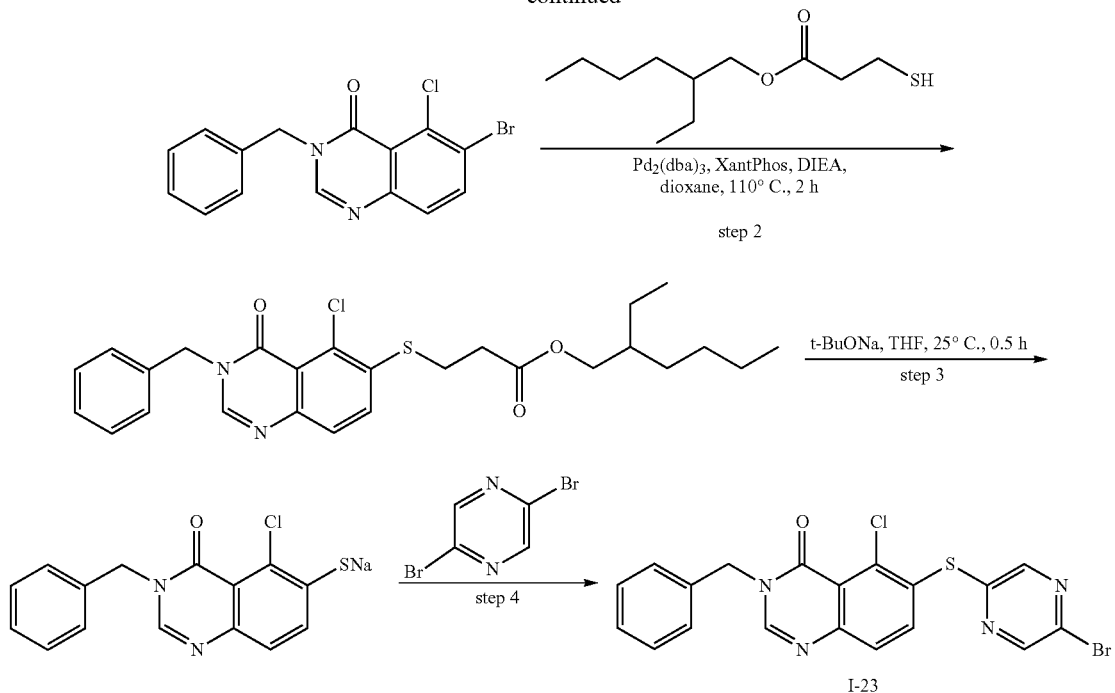

step 2 step 3 step 4

I-23

Step 1: 3-benzyl-6-bromo-5-chloro-quinazolin-4-one

A mixture of Intermediate I-22 (4.00 g, 12.3 mmol), bromomethylbenzene (2.53 g, 14.8 mmol), and $K_2CO_3$ (3.41 g, 24.6 mmol) in DMF (40 mL) was stirred at 25° C. for 16 hours. The reaction mixture was diluted with water (30 mL) and extracted with EtOAc (10 mL). The combined organic layers were washed with brine(2×20 mL), dried over $Na_2SO_4$, and then filtered and concentrated under vacuum to obtain a residue. The residue was purified by silica gel chromatography (PE:EtOAc=2:1) to obtain 3-benzyl-6-bromo-5-chloro-quinazolin-4-one(2.00 g, 46% yield) as a brown solid. $^1H$ NMR (400 MHz, DMSO-$d_6$) δ=8.68 (s, 1H), 8.14 (d, J=8.8 Hz, 1H), 7.58 (d, J=8.8 Hz, 1H), 7.41-7.29 (m, 5H), 5.17 (s, 2H).

Step 2: 2-ethylhexyl 34(3-benzyl-5-chloro-4-oxo-3,4-dihydroquinazolin-6-yl)thio)propanoate A mixture of 3-benzyl-6-bromo-5-chloro-quinazolin-4-one (1.60 g, 4.58 mmol), 2-ethylhexyl 3-sulfanylpropanoate (999 mg, 4.58 mmol), $Pd_2(dba)_3$ (41 mg, 457 μmol), XantPhos (529 mg, 915 μmol) and DIEA (1.77 g, 13.7 mmol) in dioxane (10 mL) was stirred under $N_2$ at 110° C. for 16 hours. The reaction mixture was filtered, and the filtrate was concentrated under vacuum to obtain a residue. The residue was purified by silica gel chromatography (PE:EtOAc=3:1) to obtain 2-ethylhexyl 3-((3-benzyl-5-chloro-4-oxo-3,4-dihydroquinazolin-6-yl)thio)propanoate (2.00 g, 89% yield) as a yellow oil.

Step 3: Sodium 3-benzyl-5-chloro-4-oxo-3,4-dihydroquinazolin-6-thiolate

To a solution of 2-ethylhexyl 3-((3-benzyl-5-chloro-4-oxo-3,4-dihydroquinazolin-6-yl)thio)propanoate (500 mg, 1.03 mmol) in THF (5 mL) was added t-BuONa (147 mg, 1.54 mmol) at 25° C. The reaction mixture was stirred at 25° C. for 1 hour. After completion of the reaction, the reaction mixture was added with PE and then filtered. The filter cake was dried under vacuum to obtain sodium 3-benzyl-5-chloro-4-oxo-3,4-dihydroquinazolin-6-thiolate (230 mg, 68% yield) as a red solid. $^1H$ NMR (400 MHz, $D_2O$) δ=8.28 (s, 1H), 7.98 (d, J=8.8 Hz, 1H), 7.38-7.32 (m, 5H), 7.28 (d, J=8.8 Hz, 1H), 5.17 (s, 2H).

Step 4: 3-benzyl-64(5-bromopyrazin-2-yl)thio)-5-chloroquinazolin-4(3H)-one

To a solution of 2,5-dibromopyrazine (1.00 g, 4.20 mmol) and $K_2CO_3$(195 mg, 1.42 mmol) in DMF (10 mL) was added sodium 3-benzyl-5-chloro-4-oxo-3,4-dihydroquinazolin-6-thiolate (230 mg, 708 μmol) in DMF (10 mL) at 0° C. The reaction mixture was stirred at 0-25° C. for 16 hours. The reaction mixture was diluted with water (30 mL), and the mixture was extracted with EtOAc (2×20 mL). The combined organic layers were washed with brine (20 mL), dried over $Na_2SO_4$, and then filtered and concentrated under vacuum to obtain a residue. The residue was purified by silica gel chromatography (PE:EtOAc=2:1) to obtain Intermediate I-23 (110 mg, 33% yield) as a yellow oil. $^1H$ NMR (400 MHz, $CDCl_3$) δ=8.36 (d, J=1.6 Hz, 1H), 8.12 (d, J=1.6 Hz, 1H), 8.09 (s, 1H), 7.83 (d, J=8.8 Hz, 1H), 7.56 (d, J=8.8 Hz, 1H), 7.33-7.25 (m, 5H), 5.10 (s, 2H).

Preparation Example 24: (R)-2-methyl-N-[(1R)-spiro[indane-2,4'-piperidin]-1-yl]propane-2-sulfinamide (Intermediate I-24)

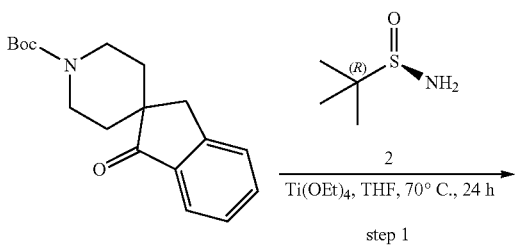

step 1

Step 1: tert-butyl 1-[(R)-tert-butylsulfinyl]iminospiro[indene-2,4'-piperidine]-1'-carboxylate A mixture of tert-butyl 1-oxospiro[indane-2,4'-piperidine]-1'-carboxylate (1.00 g, 3.32 mmol), (R)-2-methylpropane-2-sulfinamide (402 mg, 3.32 mmol) and Ti(OEt)$_4$ (2.27 g, 9.95 mmol) in THF (5 mL) was stirred at 70° C. for 36 hours. The reaction mixture was poured into water (10 mL) at 0° C. and then filtered. The filtrate was diluted with water (10 mL), and the mixture was extracted with EtOAc (2×20 mL). The combined organic layers were washed with brine (20 mL), and dried over Na$_2$SO$_4$, and then filtered and concentrated under vacuum to obtain a residue. The residue was purified by silica gel chromatography (PE:EtOAc=3:1) to obtain tert-butyl 1-[(R)-tert-butylsulfinyl]iminospiro[indene-2,4'-piperidine]-1'-carboxylate (900 mg, 67% yield) as a yellow solid. $^1$H NMR (400 MHz, CDCl$_3$) δ=8.41 (d, J=6.4 Hz, 1H), 7.55-7.48 (m, 1H), 7.43-7.35 (m, 2H), 4.18-4.08 (m, 2H), 3.06 (s, 2H), 3.00-2.86 (m, 2H), 2.04-1.90 (m, 2H), 1.48 (s, 9H), 1.42 (d, J=14.4 Hz, 1H), 1.32 (s, 9H), 1.28-1.24 (m, 1H).

Step 2: tert-butyl (1R)-1-[[(R)-tert-butylsulfinyl]amino]spiro[indene-2,4'-piperidine]-1'-carboxylate To a solution of tert-butyl 1-[(R)-tert-butylsulfinyl]iminospiro[indene-2,4'-piperidine]-1'-carboxylate (800 mg, 1.98 mmol) in THF (10 mL) was added LiBH$_4$(129 mg, 5.93 mmol) under N$_2$ at –78° C. The reaction mixture was stirred at –78~25° C. for 16 hours. The reaction mixture was quenched by addition of NH$_4$Cl (10 mL) at 0° C., and then diluted with water (10 mL), and the mixture was extracted with EtOAc (2×20 mL). The combined organic layers were washed with brine (2×20 mL), dried over Na$_2$SO$_4$, and then filtered and concentrated under vacuum to obtain a residue. The residue was purified by Prep-HPLC (Column: Welch Ultimate XB—CN 250*70*10 um; mobile phase: [hexane-EtOH(0.1% NH$_3$·H$_2$O)]; B %: 1%-35%, 15 minutes) to obtain tert-butyl (1S)-1-[[(R)-tert-butylsulfinyl]amino]spiro[indane-2,4'-piperidine]-1'-carboxylate (540 mg, 67% yield) and tert-butyl (1R)-1-[[(R)-tert-butylsulfinyl]amino]spiro[indene-2,4'-piperidine]-1'-carboxylate (130 mg, 16% yield) as a white solid, respectively.

Tert-butyl (1 S)-1-[[(R)-tert-butyl sulfinyl]amino]spiro[indene-2,4'-piperidine]-1'-carboxylate: $^1$H NMR (400 MHz, CDCl$_3$) δ=7.23 (d, J=6.4 Hz, 1H), 7.18-7.12 (m, 3H), 4.43 (d, J=9.2 Hz, 1H), 4.02-3.87 (m, 2H), 3.57-3.38 (m, 1H), 3.11-2.74 (m, 4H), 2.69-2.58 (m, 1H), 2.09-1.96 (m, 1H), 1.47-1.42 (m, 2H), 1.39 (s, 9H), 1.22 (s, 9H).

Tert-butyl (1R)-1-[[(R)-tert-butylsulfinyl]amino]spiro[indene-2,4'-piperidine]-1'-carboxylate: $^1$H NMR (400 MHz, CDCl$_3$) δ=7.63-7.60 (m, 1H), 7.24-7.18 (m, 3H), 4.47 (d, J=8.0 Hz, 1H), 4.02-3.92 (m, 2H), 3.31-3.28 (m, 1H), 3.08-3.04 (m, 1H), 2.98-2.92 (m, 2H), 2.70-2.66 (m, 1H), 1.74-1.70 (m, 2H), 1.58-1.54 (m, 2H), 1.47 (s, 9H), 1.29 (s, 9H).

Step 3: (R)-2-methyl-N-[(1R)-spiro[indene-2,4'-piperidin]-1-yl]propane-2-sulfinamide A mixture of tert-butyl (1R)-1-[[(R)-tert-butylsulfinyl]amino]spiro[indane-2,4'-piperidine]-1'-carboxylate (130 mg, 319 μmol) and TFA (1.30 mL) in DCM (5 mL) was stirred at 0° C. for 1 hour. The reaction mixture was diluted with saturated aqueous NaHCO$_3$ (10 mL), and the mixture was extracted with EtOAc (2×10 mL). The combined organic layers were washed with brine (2×10 mL), dried over Na$_2$SO$_4$, and then filtered and concentrated under vacuum to obtain Intermediate I-24 (90 mg, 91% yield) as a colorless oil. $^1$H NMR (400 MHz, CDCl$_3$) δ=7.66-7.64 (m, 1H), 7.26-7.18 (m, 3H), 4.48 (d, J=9.2 Hz, 1H), 4.11-3.98 (m, 2H), 3.32 (d, J=9.2 Hz, 1H), 3.18-3.02 (m, 3H), 2.97-2.81 (m, 2H), 2.70 (d, J=15.2 Hz, 1H), 1.65 (d, J=15.2 Hz, 2H), 1.31 (s, 9H).

Preparation Example 25: (R)-2-methyl-N-[(5S)-spiro[5,7-dihydrocyclopenta[b]pyridine-6,4'-piperidin]-5-yl]propane-2-sulfinamide (Intermediate I-25) and (R)-2-methyl-N-[(5R)-spiro[5,7-dihydrocyclopenta[b]pyridine-6,4'-piperidin]-5-yl]propane-2-sulfinamide (Intermediate I-26)

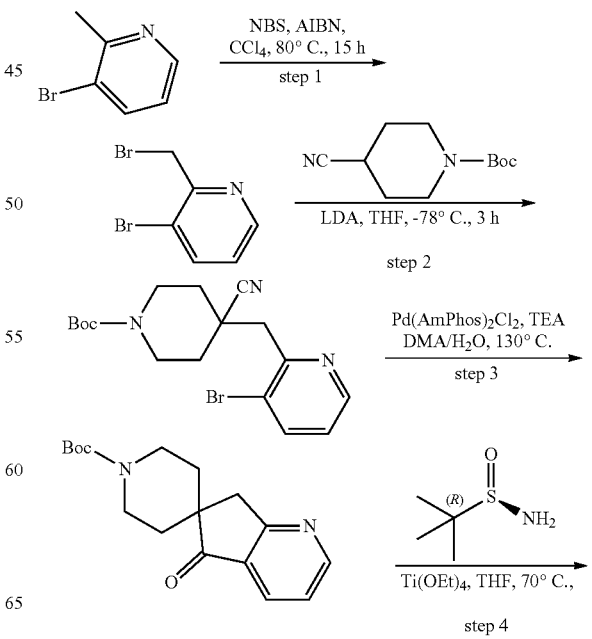

-continued

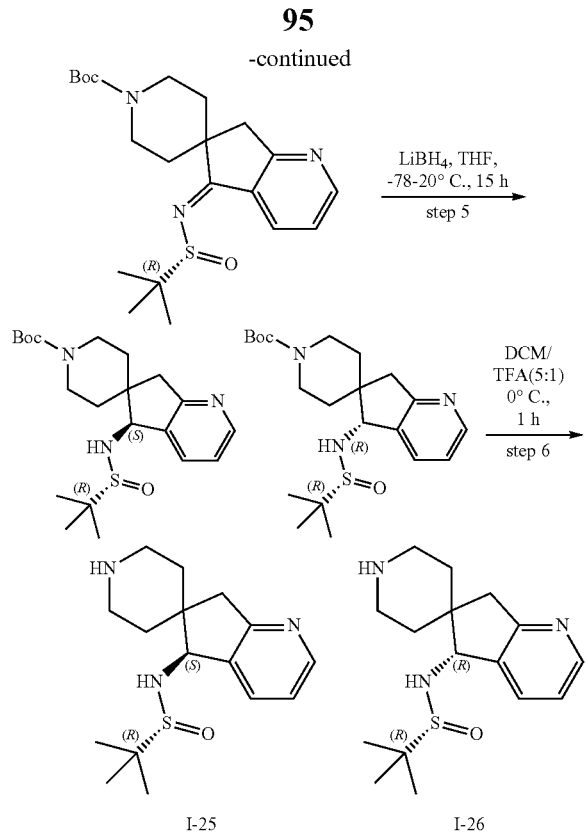

I-25    I-26

Step 1: 3-bromo-2-(bromomethyl)pyridine

To a solution of 3-bromo-2-methyl-pyridine (20.0 g, 116 mmol) in CCl$_4$ (200 mL), N-bromosuccinimide(NBS) (22.8 g, 128 mmol) and azobisisobutyronitrile(AIBN) (1.91 g, 11.6 mmol) were added, and the mixture was stirred at 80° C. for 12 hours. The reaction mixture was filtered and concentrated under reduced pressure to obtain a residue. The residue was purified by MPLC (PE/EA=30:1) to obtain 3-bromo-2-(bromomethyl)pyridine (12.5 g, 42% yield) as a brown solid. 1 1-1 NMR (400 MHz, DMSO-d$_6$) δ=8.60-8.53 (m, 1H), 8.16-8.08 (m, 1H), 7.38-7.26 (m, 1H), 4.80-4.70 (m, 2H); MS (EI) m/z: 251.8 [M+H]$^+$.

Step 2: tert-butyl 4-[(3-bromo-2-pyridyl)methyl]-4-cyano-piperidine-1-carboxylate To a solution of tert-butyl 4-cyanopiperidine-1-carboxylate (10.1 g, 47.8 mmol) in THF (100 mL) was added lithium diisopropylamide(LDA) (2M, 23.9 mL), followed by stirring at −78° C. for 0.5 hours. Then, the reaction mixture was slowly added with 3-bromo-2-(bromomethyl)pyridine (10.0 g, 39.9 mmol) in THF (100 mL) and then stirred at −78° C. for 2.5 hours. The reaction mixture was quenched by addition of aqueous ammonium chloride (100 mL) at 0° C., diluted with water (100 mL), and extracted with EA (3×200 mL). The combined organic layers were washed with brine (3×100 mL), dried over anhydrous sodium sulfate, and then filtered and concentrated under reduced pressure to obtain a residue. The residue was purified by reverse phase flash column chromatography (0.1% FA) to obtain tert-butyl 4-[(3-bromo-2-pyridyl)methyl]-4-cyano-piperidine-1-carboxylate (13.5 g, 89% yield) as a brown solid. $^1$H NMR (400 MHz, DMSO-d$_6$) δ=8.60-8.53 (m, 1H), 8.14-8.07 (m, 1H), 7.32-7.24 (m, 1H), 4.01-3.90 (m, 2H), 3.25 (s, 2H), 3.01-2.78 (m, 2H), 2.12-2.03 (m, 2H), 1.73-1.56 (m, 2H), 1.44-1.35 (m, 9H); MS(O) m/z: 402.0 [M+23]$^+$.

Step 3: tert-butyl 5-oxospiro[7H-cyclopenta[b]pyridine-6,4'-piperidine]-1'-carboxylate A mixture of tert-butyl 4-[(3-bromo-2-pyridyl)methyl]-4-cyano-piperidine-1-carboxylate (5.90 g, 15.5 mmol), 4-di-tert-butylphosphanyl-N,N-dimethyl-aniline; dichloropalladium (Pd(AmPhos)Cl$_2$) (1.10 g, 1.55 mmol), TEA (6.28 g, 62.1 mmol) in dimethylacetamide(DMA) (120 mL) and H$_2$O (12 mL) was degassed and then purged 3 times with N$_2$. The mixture was stirred under N$_2$ atmosphere at 130° C. for 12 hours. The reaction mixture was quenched by addition of aqueous ammonium chloride (50 mL) at 25° C., and then diluted with water (50 mL), and extracted with EA (3×100 mL). The combined organic layers were washed with brine (3×50 mL), dried over anhydrous sodium sulfate, and then filtered and concentrated under reduced pressure to obtain a residue. The residue was purified by silica gel chromatography (PE/EA=3:1) to obtain tert-butyl 5-oxospiro[7H-cyclopenta[b]pyridine-6,4'-piperidine]-1'-carboxylate (3.2 g, 68% yield) as a brown solid. $^1$H NMR (400 MHz, CDCl$_3$) δ=8.89-8.79 (m, 1H), 8.09-8.00 (m, 1H), 7.40-7.32 (m, 1H), 4.22-4.05 (m, 2H), 3.10 (s, 2H), 3.12-3.02 (m, 2H), 2.01-1.90 (m, 2H), 1.51-1.44 (m, 11H); MS(O) m/z: 303.4 [M+H]$^+$.

Step 4: tert-butyl (5Z)-5-[(R)-tert-butylsulfinyl]iminospiro[7H-cyclopenta[b]pyridine-6,4'-piperidine]-1'-carboxylate To a solution of tert-butyl 5-oxospiro[7H-cyclopenta[b]pyridine-6,4'-piperidine]-1'-carboxylate (3.00 g, 9.92 mmol) in THF (30 mL), Ti(OEt)$_4$ (34.0 g, 149 mmol) and (R)-2-methylpropane-2-sulfinamide (4.81 g, 39.7 mmol) were added. The mixture was stirred at 70° C. for 12 hours. The reaction mixture was diluted with EA (300 mL) and quenched with water (50 mL), and then filtered and extracted with EA (3×100 mL). The combined organic layers were washed with brine (3×50 mL), dried over anhydrous sodium sulfate, and then filtered and concentrated under reduced pressure to obtain a residue. The residue was purified by reverse phase flash column chromatography (0.1% ammonium hydroxide) to obtain tert-butyl (5Z)-5-[(R)-tert-butylsulfinyl]iminospiro[7H-cyclopenta[b]pyridine-6,4'-piperidine]-1'-carboxylate (3.35 g, 83% yield) as a yellow solid. $^1$ H NMR (400 MHz, DMSO-d$_6$) δ 8.79-8.74 (m, 1H), 8.69-8.61 (m, 1H), 7.50-7.44 (m, 1H), 4.00-3.93 (m, 2H), 3.00 (s, 2H), 3.02-2.89 (m, 2H), 1.81-1.68 (m, 2H), 1.58-1.50 (m, 2H), 1.44-1.42 (m, 9H), 1.27-1.22 (m, 9H); MS (EI) m/z: 406.2 [M+H]$^+$.

Step 5: tert-butyl (5S)-5-[[(R)-tert-butylsulfinyl]amino]spiro[5,7-dihydrocyclopenta[b]pyridine-6,4'-piperidine]-1'-carboxylate and tert-butyl (5R)-5-[[(R)-tert-butylsulfinyl]amino]spiro[5,7-dihydrocyclopenta[b]pyridine-6,4'-piperidine]-1'-carboxylate To a solution of tert-butyl (5Z)-5-[(R)-tert-butylsulfinyl]iminospiro[7H-cyclopenta[b]pyridine-6,4'-piperidine]-1'-carboxylate (2.00 g, 4.93 mmol) in THF (20 mL) was added LiBH$_4$ (537 mg, 24.7 mmol), and the mixture was stirred at −70° C. for 2 hours. The reaction mixture was quenched by addition of aqueous ammonium chloride(20 mL) at 0° C., and then diluted with water (30 mL) and extracted with EA (3×50 mL). The combined organic layers were washed with brine (3×20 mL), dried over anhydrous sodium sulfate, and then filtered and concentrated under reduced pressure to obtain a residue. The residue was purified by Prep-HPLC Column: Welch Ultimate XB—CN 250*50*10 um, mobile phase: [hexane-EtOH(0.1% NH$_3$·H$_2$O)], B %: 10%-50%, 15 minutes to obtain the following compounds as a yellow solid, respectively.

Tert-butyl (5S)-5-[[(R)-tert-butylsulfinyl]amino]spiro[5,7-dihydrocyclopenta[b]pyridine-6,4'-piperidine]-1'-carboxylate(630 mg, 31% yield): $^1$H NMR (400 MHz, CDCl$_3$) δ=8.56-8.51 (m, 1H), 8.33-8.26 (m, 1H), 7.38-7.32 (m, 1H), 4.56-4.51 (m, 1H), 4.07-3.96 (m, 2H), 3.60-3.51 (m, 1H), 3.36-3.27 (m, 1H), 2.98 (s, 2H), 1.83-1.71 (m, 1H), 1.50-1.47 (m, 11H), 1.34-1.26 (m, 11H); MS (EI) m/z: 408.3 [M+H]$^+$.

Tert-butyl (5R)-5-[[(R)-tert-butyl sulfinyl]amino]spiro[5,7-dihydrocyclopenta[b]pyridine-6,4'-piperidine]-1'-carboxylate(150 mg, 7% yield): $^1$H NMR (400 MHz, CDCl$_3$) δ=8.59-8.52 (m, 1H), 7.94-7.86 (m, 1H), 7.39-7.31 (m, 1H), 4.60-4.55 (m, 1H), 4.09-3.97 (m, 2H), 3.74-3.64 (m, 1H), 3.54-3.39 (m, 1H), 3.05-2.94 (m, 2H), 1.55-1.49 (m, 2H), 1.47-1.46 (m, 10H), 1.30-1.25 (m, 11H).

Step 6: (R)-2-methyl-N-[(5S)-spiro[5,7-dihydrocyclopenta[b]pyridine-6,4'-piperidin]-5-yl]propane-2-sulfinamide and (R)-2-methyl-N-[(5R)-spiro[5,7-dihydrocyclopenta[b]pyridine-6,4'-piperidin]-5-yl]propane-2-sulfinamide To a solution of tert-butyl (5S)-5-[[(R)-tert-butylsulfinyl]amino]spiro[5,7-dihydrocyclopenta[b]pyridine-6,4'-piperidine]-1'-carboxylate (200 mg, 491 μmol) in DCM (5 mL) was added TFA (1.68 g, 14.7 mmol), and the mixture was stirred at 0° C. for 1 hour. The reaction mixture was poured into aqueous K$_2$CO$_3$ (20 mL) at 25° C., and then diluted with water (30 mL) and extracted with DCM (3×50 mL). The combined organic layers were washed with brine (3×20 mL), dried over anhydrous sodium sulfate, and then filtered and concentrated under reduced pressure to obtain Intermediate I-25 (140 mg, 92% yield) as a yellow solid. $^1$H NMR (400 MHz, CDCl$_3$)=8.49-8.42 (m, 1H), 8.12-8.04 (m, 1H), 7.25-7.19 (m, 1H), 4.55-4.50 (m, 1H), 3.38-3.32 (m, 2H), 3.26-3.06 (m, 1H), 2.85-2.81 (m, 2H), 2.30-2.14 (m, 2H), 1.99-1.82 (m, 2H), 1.37-1.31 (m, 11H); MS (EI) m/z: 308.4 [M+H]$^+$.

Meanwhile, Intermediate I-26 (100 mg, 90% yield) was obtained as a yellow solid in the same method as in the preparation of Intermediate I-25, using tert-butyl (5R)-5-[[(R)-tert-butylsulfinyl]amino]spiro[5,7-dihydrocyclopenta[b]pyridine-6,4'-piperidine]-1'-carboxylate. 1 H NMR (400 MHz, CDCl$_3$)=8.46-8.41 (m, 1H), 7.61-7.59 (m, 1H), 7.16-7.12 (m, 1H), 4.55-4.52 (m, 1H), 4.08-4.01 (m, 1H), 3.23-3.11 (m, 2H), 2.91-2.81 (m, 3H), 2.26-2.20 (m, 1H), 1.81-1.75 (m, 1H), 1.67-1.63 (m, 1H), 1.33-1.31 (m, 11H), MS (EI) m/z: 308.4 [M+H]$^+$.

Preparation Example 26: 6-((5-bromopyrazin-2-yl)thio)-5-chloro-3-((tetrahydrofuran-3-yl)methyl)quinazolin-4(3H)-one (Intermediate I-27)

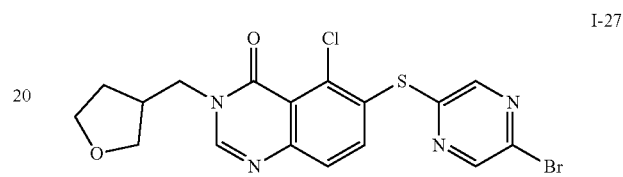

Intermediate I-27 was obtained as a yellow solid in the same method as in Preparation Example 23, except that 3-(bromomethyl)tetrahydrofuran was used instead of bromomethylbenzene in step 1 of Preparation Example 23. $^1$H NMR (400 MHz, CDCl$_3$) δ=8.37 (s, 1H), 8.16 (s, 1H), 8.13 (s, 1H), 8.00 (s, 1H), 7.85 (d, J=8.8 Hz, 1H), 7.58 (d, J=8.8 Hz, 1H), 3.97-3.90 (m, 2H), 3.73-3.70 (m, 2H), 3.58-3.54 (m, 1H), 2.89-2.77 (m, 1H), 2.10-2.00 (m, 1H), 1.67-1.59 (m, 1H).

Preparation Example 27: 5-chloro-6-((5-iodopyrazin-2-yl)thio)-3-(pyridin-3-ylmethyl)quinazolin-4(3H)-one (Intermediate I-28)

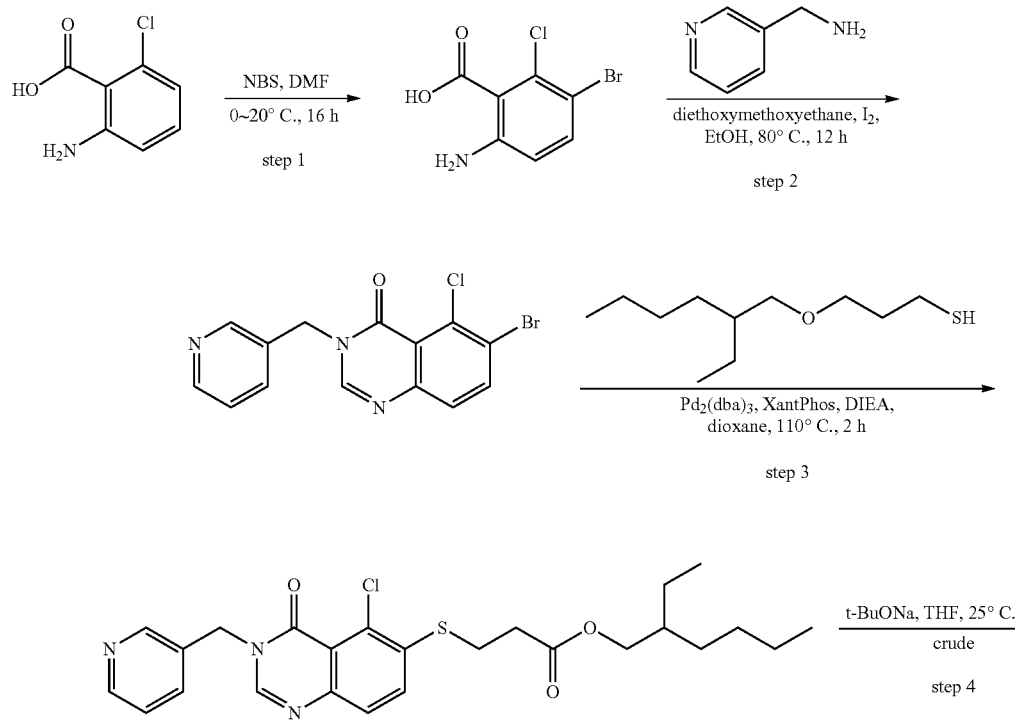

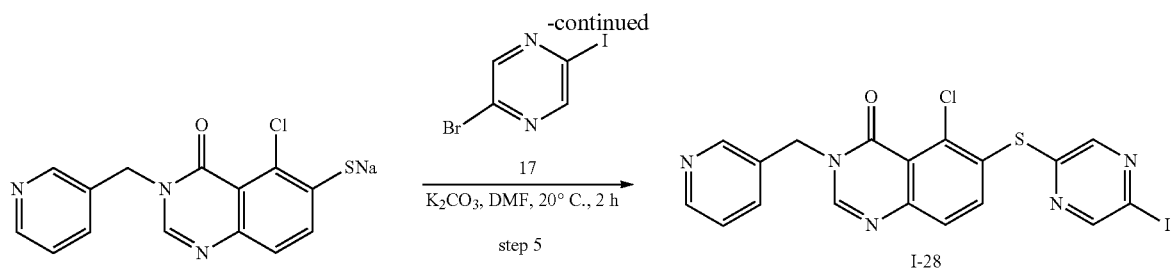

step 5

Step 1: 6-amino-3-bromo-2-chloro-benzoic acid

To a solution of 2-amino-6-chloro-benzoic acid (5 g, 29.1 mmol) in DMF (50 mL) was added NBS (5.71 g, 32.1 mmol), and the mixture was stirred at 0° C. for 2 hours. The reaction mixture was quenched with water (100 mL) and extracted with EA (100 mL×3). The combined organic layers were washed with brine (50 mL×3), dried over anhydrous sodium sulfate, and then filtered and concentrated under reduced pressure to obtain 6-amino-3-bromo-2-chloro-benzoic acid (7 g, 96% yield) as a yellow solid. $^1$H NMR (400 MHz, DMSO-$d_6$) δ=7.40 (d, J=8.8 Hz, 1H), 6.65 (d, J=8.8 Hz, 1H), 3.47 (br s, 2H); MS (EI) m/z: 249.8 [M+H]$^+$.

Step 2: 6-bromo-5-chloro-3-(pyridin-3-ylmethyl)quinazolin-4(3H)-one

To a solution of 6-amino-3-bromo-2-chloro-benzoic acid (3 g, 12.0 mmol) in EtOH (60 mL), I2 (304 mg, 1.20 mmol), diethoxymethoxyethane (2.66 g, 18.0 mmol) and 3-pyridylmethanamine (1.94 g, 18.0 mmol) were added, and the mixture was stirred at 80° C. for 12 hours. The reaction mixture was quenched by addition of aqueous ammonium chloride(50 mL) at 25° C., and then diluted with water (50 mL) and extracted with EA (100 mL×3). The combined organic layers were washed with brine (50 mL×3), dried over anhydrous sodium sulfate, and then filtered and concentrated under reduced pressure to obtain a residue. The residue was triturated with MeOH (30 mL) to obtain 6-bromo-5-chloro-3-(pyridin-3-ylmethyl)quinazolin-4(3H)-one (1.5 g, 36% yield) as a brown solid. $^1$H NMR (400 MHz, CDCl$_3$) δ=8.69 (d, J=1.6 Hz, 1H), 8.60 (dd, J=1.2, 4.6 Hz, 1H), 8.17 (s, 1H), 7.96 (d, J=8.8 Hz, 1H), 7.77 (d, J=8.0 Hz, 1H), 7.50 (d, J=8.8 Hz, 1H), 7.31 (dd, J=4.8, 8.0 Hz, 1H), 5.17 (s, 2H); MS (EI) m/z: 351.9 [M+E-1]$^+$.

Step 3 to Step 5: 5-chloro-64(5-iodopyrazin-2-yl)thio)-3-(pyridin-3-ylmethyl)quinazolin-4(3H)-one Intermediate I-28 was obtained as a yellow solid in the same method as in steps 2 to 4 of Preparation Example 23, using 5-chloro-6-((5-iodopyrazin-2-yl)thio)-3-(pyridin-3-ylmethyl)quinazolin-4(3H)-one as a starting material. $^1$H NMR (400 MHz, CDCl$_3$) δ=8.72 (s, 1H), 8.61 (s, 1H), 8.44 (s, 1H), 8.22 (s, 2H), 7.92 (d, J=8.4 Hz, 1H), 7.81 (d, J=7.6 Hz, 1H), 7.65 (d, J=8.6 Hz, 1H), 7.35 (dd, J=5.2, 7.6 Hz, 1H), 5.19 (s, 2H); MS (EI) m/z: 508.0 [M+H]$^+$.

Preparation Example 28: 6-((5-bromopyrazin-2-yl)thio)-5-chloro-3-(2-methoxyethyl)quinazolin-4(3H)-one (Intermediate I-29)

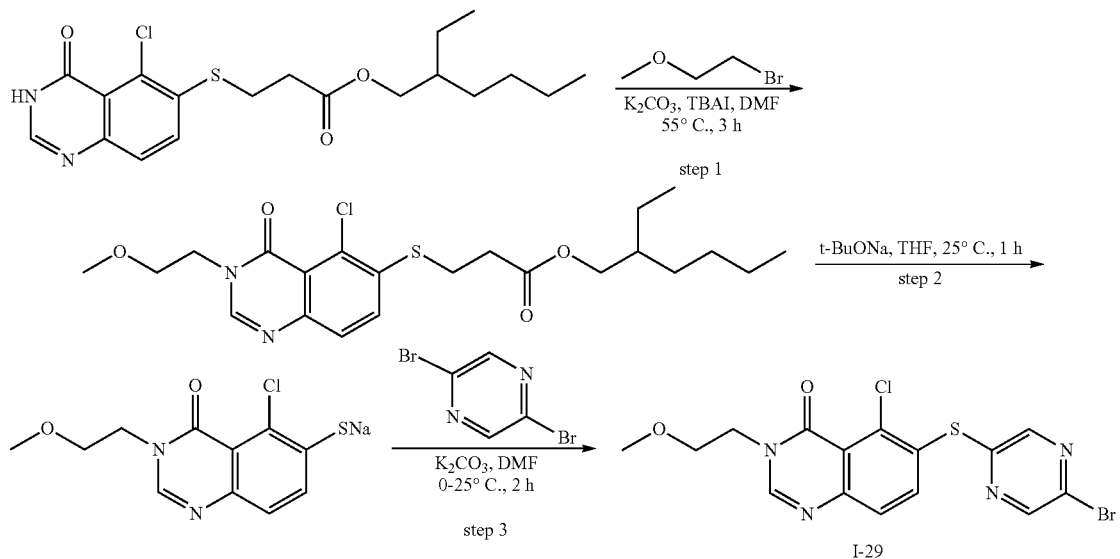

Step 1: 2-ethylhexyl 3-((5-chloro-3-(2-methoxyethyl)-4-oxo-3,4-dihydroquinazolin-6-yl)thio)propanoate To a solution of ethyl 3-((5-chloro-4-oxo-3,4-dihydroquinazolin-6-yl)thio)propanoate (10 g, 25.2 mmol) in DMF (100 mL), 1-bromo-2-methoxy-ethane (4.2 g, 30.2 mmol), K$_2$CO$_3$ (6.96 g, 50.4 mmol) and TBAI (931 mg, 2.52 mmol) were added, and the mixture was stirred at 55° C. for 3 hours. The reaction mixture was quenched with aqueous ammonium chloride solution (50 mL), diluted with water (50 mL), and then extracted with EA (100 mL×3). The combined organic layers were washed with brine (50 mL×3), dried over anhydrous sodium sulfate, and then filtered and concentrated under reduced pressure. The residue was purified by column chromatography (0.1% formic acid) to obtain 2-ethylhexyl 3-(5-chloro-3-(2-methoxyethyl)-4-oxo-3,4-dihydroquinazolin-6-yl)thio)propanoate (6.8 g, 59% yield) as a yellow solid. $^1$H NMR (400 MHz, CDCl$_3$) δ=8.04 (s, 1H), 7.67-7.59 (m, 2H), 4.15 (t, J=4.8 Hz, 2H), 4.05 (dd, J=2.0, 5.8 Hz, 2H), 3.71-3.65 (m, 2H), 3.33 (s, 3H), 3.30-3.25 (m, 2H), 2.71 (t, J=7.6 Hz, 2H), 1.62-1.54 (m, 1H), 1.40-1.34 (m, 2H), 1.31-1.26 (m, 6H), 0.91-0.85 (m, 6H); MS (EI) m/z: 455.3 [M+H]$^+$.

Step 2 and Step 3: 6-((5-bromopyrazin-2-yl)thio)-5-chloro-3-(2-methoxyethyl)quinazolin-4(3H)-one Intermediate I-29 (1.4 g, 22%) was obtained as a yellow solid in the same method as in step 3 and 4 of Preparation Example 23, using 2-ethylhexyl 3-(5-chloro-3-(2-methoxyethyl)-4-oxo-3,4-dihydroquinazolin-6-yl)thio)propanoate as a starting material. $^1$H NMR (400 MHz, CDCl$_3$) δ=8.44 (s, 1H), 8.19 (s, 1H), 8.13 (s, 1H), 7.92 (d, J=8.4 Hz, 1H), 7.65 (d, J=8.4 Hz, 1H), 4.17 (t, J=4.8 Hz, 2H), 3.73-3.66 (m, 2H), 3.35 (s, 3H); MS (EI) m/z: 429.1 [M+H]$^+$.

Preparation Example 29: 3-[3-[tert-butyl(dimethyl)silyl]oxypropyl]-5-chloro-6-(5-iodopyrazin-2-yl)thio-quinazolin-4(3H)-one (Intermediate I-30)

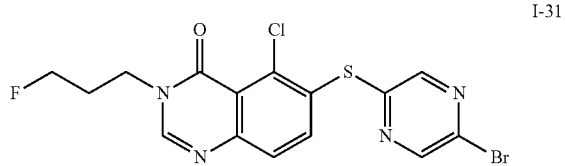 [SMILES: O=c1c2c(Cl)c(Sc3cnc(Br)cn3)ccc2ncn1CCCF]

Intermediate I-30 (470 mg, 32%) was prepared in the same method as in Preparation Example 28, except that (3-bromopropoxy)(tert-butyl)dimethylsilane was used instead of 1-bromo-2-methoxyethane in step 1 of Preparation Example 28. $^1$H NMR (400 MHz, CDCl$_3$) δ=8.60-8.42 (m, 1H), 8.23-8.17 (m, 1H), 8.13 (s, 1H), 7.91 (d, J=8.4 Hz, 1H), 7.68-7.61 (m, 1H), 4.13 (t, J=6.4 Hz, 2H), 3.67 (t, J=5.6 Hz, 2H), 2.06-1.97 (m, 2H), 0.92 (s, 9H), 0.08 (s, 6H).

Preparation Example 30: 6-(5-bromopyrazin-2-yl)thio-5-chloro-3-(3-fluoropropyl)qiuinazolin-4(3H)-one (Intermediate I-31)

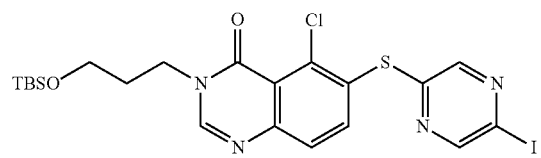

Intermediate I-31 (320 mg, 20%) was prepared in the same method as in Preparation Example 28, except that 1-bromo-3-fluoropropane was used instead of 1-bromo-2-methoxyethane in step 1 of Preparation Example 28. $^1$H NMR (400 MHz, CDCl$_3$) δ=8.45 (d, J=1.2 Hz, 1H), 8.20 (d, J=1.2 Hz, 1H), 8.11 (s, 1H), 7.93 (d, J=8.8 Hz, 1H), 7.66 (d, J=8.8 Hz, 1H), 4.62 (t, J=5.6 Hz, 1H), 4.50 (t, J=5.6 Hz, 1H), 4.16 (t, J=6.8 Hz, 2H), 2.32-2.26 (m, 1H), 2.23-2.18 (m, 1H); MS(O) m/z: 431.1 [M+H]$^+$.

Preparation Example 31: 6-(5-bromopyrazin-2-yl)thio-3-[3-[tert-butyl(dimethyl)silyloxybutyl]-5-chloro-quinazolin-4(3H)-one (Intermediate I-32)

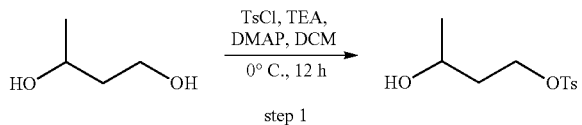

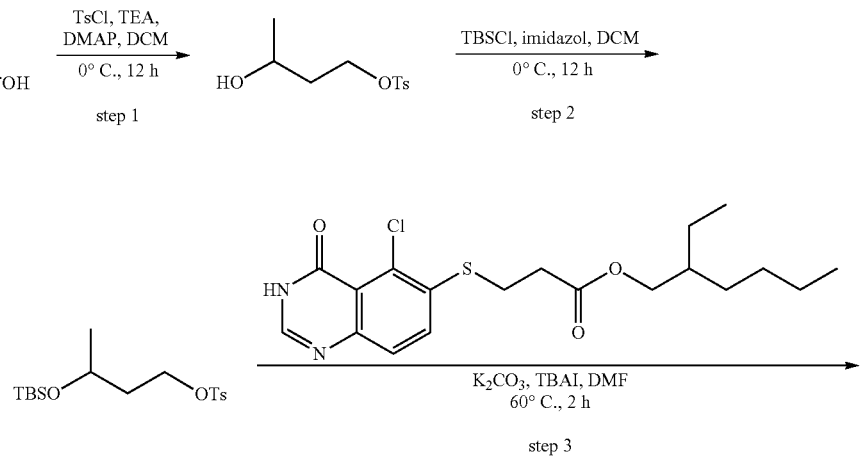

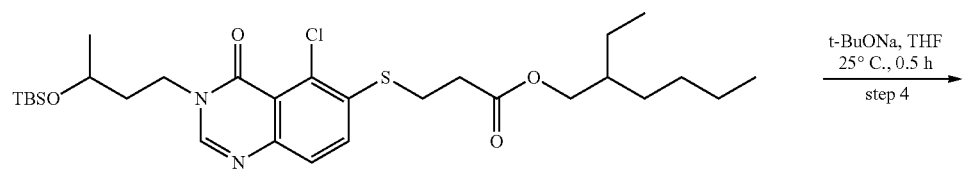

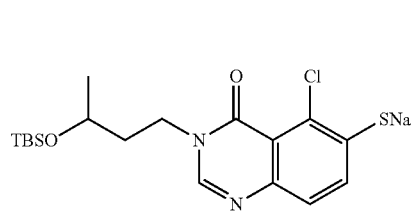 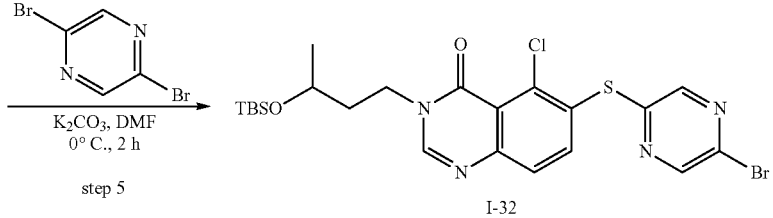

Step 1: 3-hydroxybutyl-4-methylbenzenesulfonate

To a solution of butane-1,3-diol (2.0 g, 22.2 mmol) and TEA (6.74 g, 66.6 mmol) in DMF (30 mL), TosCl (5.08 g, 26.6 mmol) and DMAP (271 mg, 2.22 mmol) were added, and the mixture was stirred at 0° C. for 12 hours. The reaction mixture was quenched with aqueous ammonium chloride solution (50 mL), diluted with water (50 mL), and then extracted with DCM (100 mL×3). The combined organic layers were washed with brine (50 mL×3), dried over anhydrous sodium sulfate, and then filtered and concentrated under reduced pressure to obtain 6-amino-3-bromo-2-chloro-benzoic acid (7 g, 96% yield) as a yellow solid. The residue was purified by column chromatography (PE/EA=3/1) to obtain 3-hydroxybutyl-4-methylbenzenesulfonate (4.2 g, 77% yield). $^1$H NMR (400 MHz, CDCl$_3$) δ=7.80 (d, J=8.0 Hz, 2H), 7.35 (d, J=8.0 Hz, 2H), 4.28-4.21 (m, 1H), 4.16-4.08 (m, 1H), 3.97-3.91 (m, 1H), 2.45 (s, 3H), 1.88-1.78 (m, 1H), 1.74-1.72 (m, 1H), 1.72-1.65 (m, 1H), 1.19 (d, J=6.0 Hz, 3H).

Step 2: 3-[tert-butyl)dimethyl)silyl]oxybutyl 4-methylbenzenesulfonate

To a solution of 3-hydroxybutyl-4-methylbenzenesulfonate (4.0 g, 16.4 mmol) in DCM (40 mL), imidazole (2.79 g, 40.9 mmol) and DMAP (200 mg, 1.64 mmol) were added, and TBSCl (2.96 g, 19.7 mmol) was slowly added dropwise. The mixture was stirred at 0° C. for 12 hours. The reaction mixture was quenched with aqueous ammonium chloride solution (50 mL), diluted with water (100 ml), and then extracted with DCM (100 mL×3). The combined organic layers were washed with brine (50 mL×3), dried over anhydrous sodium sulfate, and then filtered and concentrated under reduced pressure to obtain 6-amino-3-bromo-2-chloro-benzoic acid (7 g, 96% yield) as a yellow solid. The residue was purified by column chromatography (PE/EA=15/1) to obtain 3-[tert-butyl(dimethyl)silyl]oxybutyl 4-methylbenzenesulfonate (5.3 g, 90% yield). 1 H NMR (400 MHz, CDCl$_3$) δ=7.80 (d, J=8.0 Hz, 2H), 7.35 (d, J=8.0 Hz, 2H), 4.14-4.08 (m, 2H), 3.95-3.87 (m, 1H), 2.46 (s, 3H), 1.82-1.65 (m, 2H), 1.11 (d, J=6.0 Hz, 3H), 0.82 (s, 9H), 0.00 (d, J=17.6 Hz, 6H).

Steps 3 to 5: 6-(5-bromopyrazin-2-yl)thio-3-[3-[tert-butyl)dimethyl)silyl]oxybutyl]-5-chloro-quinazolin-4(3H)-one Intermediate I-32 (320 mg, 19%) was prepared in the same method as in Preparation Example 28, using 3-[Cert-butyl(dimethyl)silyl]oxybutyl 4-methylbenzenesulfonate obtained in step 2 above as a starting material. $^1$H NMR (400 MHz, CDCl$_3$) δ=8.44 (d, J=1.2 Hz, 1H), 8.19 (d, J=1.2 Hz, 1H), 8.09 (s, 1H), 7.91 (d, J=8.8 Hz, 1H), 7.64 (d, J=8.8 Hz, 1H), 4.10-4.06 (m, 2H), 4.02-3.96 (m, 1H), 2.03-1.95 (m, 1H), 1.90-1.81 (m, 1H), 1.22 (d, J=6.4 Hz, 3H), 0.93 (s, 9H), 0.10 (s, 6H); MS (EI) m/z: 557.1 [M+H]$^+$.

Preparation Example 32: Sodium 5-((3S,4S)-4-(tert-butoxycarbonyl)amino)-3-methyl-2-oxa-8-azaspiro[4.5]decan-8-yl]pyrazine-2-thiolate (Intermediate I-33)

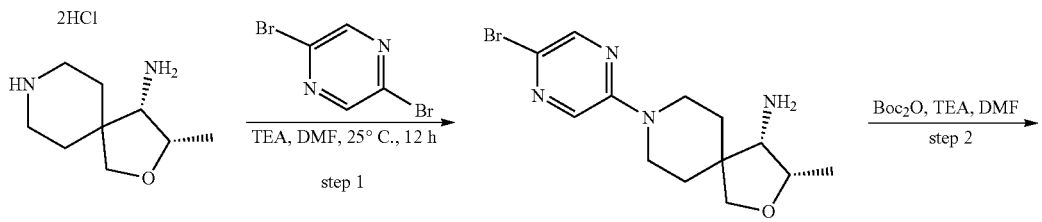

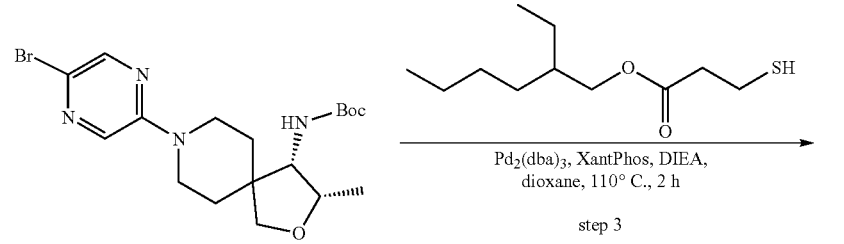

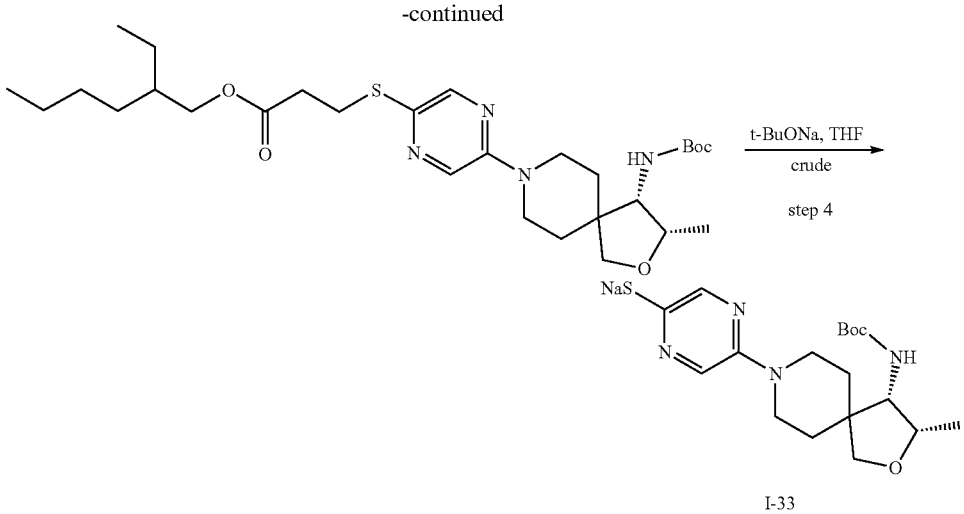

I-33

Step 1: (3S,4S)-8-(5-bromopyrazin-2-yl)-3-methyl-2-oxa-8-azaspiro[4.5]decan-4-amine To a solution of (3S,4S)-3-methyl-2-oxa-8-azaspiro[4.5]decan-4-amine (5.00 g, 20.6 mmol, 2HCl) in DMF (50 mL), TEA (6.24 g, 61.7 mmol) and 2,5-dibromopyrazine (4.89 g, 20.6 mmol) were added, and the mixture was stirred at 25° C. for 12 hours. The reaction mixture was quenched by addition of aqueous ammonium chloride (100 mL) at 25° C., and then diluted with water (100 mL) and extracted with EA (3×200 mL). The combined organic layers were washed with brine (3×100 mL), dried over anhydrous sodium sulfate, and then filtered and concentrated under reduced pressure to obtain (3 S,4S)-8-(5-bromopyrazin-2-yl)-3-methyl-2-oxa-8-azaspiro[4.5]decan-4-amine (6.7 g, crude product) as a yellow oil, which was used directly in the next step. MS (EI) m/z: 329.1 [M+H]$^+$.

Step 2: tert-butyl N-[(3S,4S)-8-(5-bromopyrazin-2-yl)-3-methyl-2-oxa-8-azaspiro[4.5]decan-4-yl]carbamate To a solution of (3S,4S)-8-(5-bromopyrazin-2-yl)-3-methyl-2-oxa-8-azaspiro[4.5]decan-4-amine (6.7 g, 20.5 mmol) in DMF (50 mL), Boc$_2$O (6.70 g, 30.7 mmol) and TEA (3.11 g, 30.7 mmol) were added, and the mixture was stirred at 25° C. for 2 hours. The reaction mixture was quenched by addition of aqueous ammonium chloride(100 mL) at 25, and then diluted with water (100 mL) and extracted with EA (3×200 mL). The combined organic layers were washed with brine (3×100 mL), dried over anhydrous sodium sulfate, and then filtered and concentrated under reduced pressure to obtain a residue. The residue was purified by column chromatography(PE/EA=5:1) to obtain tert-butyl N-[(3S,4S)-8-(5-bromopyrazin-2-yl)-3-methyl-2-oxa-8-azaspiro[4.5]decan-4-yl]carbamate (5.5 g, 63% yield) as a yellow solid. MS (EI) m/z: 429.1 [M+H]$^+$.

Step 3: 2-ethylhexyl 34(54(3S,4S)-4-((tert-butoxycarbonyl)amino)-3-methyl-2-oxa-8-azaspiro[4.5]decan-8-yl)pyrazin-2-yl)thio)propanoate A mixture of tert-butyl N-[(3S,4S)-8-(5-bromopyrazin-2-yl)-3-methyl-2-oxa-8-azaspiro[4.5]decan-4-yl]carbamate (5.50 g, 12.9 mmol), 2-ethylhexyl 3-sulfanylpropanoate (4.22 g, 19.3 mmol), Pd$_2$(dba)$_3$ (1.18 g, 1.29 mmol), XantPhos (1.49 g, 2.57 mmol) and DIEA (4.96 g, 38.6 mmol) in dioxane (80 mL) was degassed and purged 3 times with N$_2$, and then the reaction mixture was stirred under N$_2$ atmosphere at 110° C. for 12 hours. The reaction mixture was filtered and concentrated under reduced pressure to obtain a residue. The residue was purified by column chromatography (PE/EA=3:1) to obtain 2-ethylhexyl 3-[5-[(3S,4S)-4-(tert-butoxycarbonylamino)-3-methyl-2-oxa-8-azaspiro[4.5]decan-8-yl]pyrazin-2-yl]sulfanylpropanoate (5.00 g, 69% yield) as a yellow oil. $^1$H NMR (400 MHz, CDCl$_3$) δ=8.08 (s, 1H), 8.06 (s, 1H), 4.63 (d, J=10.8 Hz, 1H), 4.23-4.13 (m, 1H), 4.01 (dd, J=5.8, 2.6 Hz, 2H), 3.82-3.59 (m, 4H), 3.57-3.46 (m, 1H), 3.44-3.33 (m, 1H), 3.28 (t, J=7.2 Hz, 2H), 2.69 (t, J=7.2 Hz, 2H), 1.92-1.71 (m, 4H), 1.62-1.52 (m, 2H), 1.45 (s, 9H), 1.41-1.32 (m, 3H), 1.30-1.27 (m, 6H), 1.21 (d, J=6.4 Hz, 2H), 0.93-0.86 (m, 6H); MS (EI) m/z: 565.4 [M+H]$^+$.

Step 4: Sodium 5-((3S,4S)-4-(tert-butoxycarbonyl)amino)-3-methyl-2-oxa-8-azaspiro[4.5]decan-8-yl]pyrazine-2-thiolate To a solution of 2-ethylhexyl 3-[5-[(3S,4S)-4-(tert-butoxycarbonylamino)-3-methyl-2-oxa-8-azaspiro[4.5]decan-8-yl]pyrazin-2-yl]sulfanylpropanoate (270 mg, 478 μmol) in THF (5 mL) was added t-BuONa (68.9 mg, 717 μmol), and the mixture was stirred at 25° C. for 0.5 hours. The residue was triturated with PE (10 mL) to obtain Intermediate I-33 (150 mg, crude product) as a yellow solid, which was used directly in the next step. MS (EI) m/z: 381.1 [M+H]$^+$.

Preparation Example 33: 2-benzyl-8-chloro-7-iodo-2H-benzo[e][1,2,4]thiazine 1,1-dioxide (Intermediate I-34)

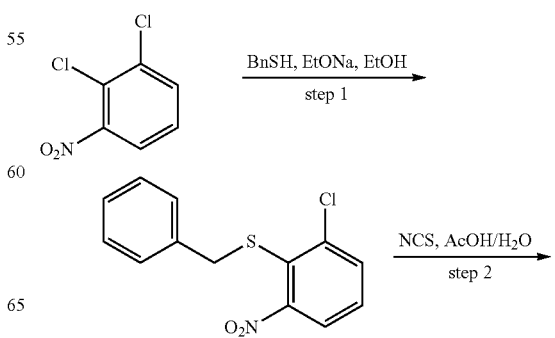

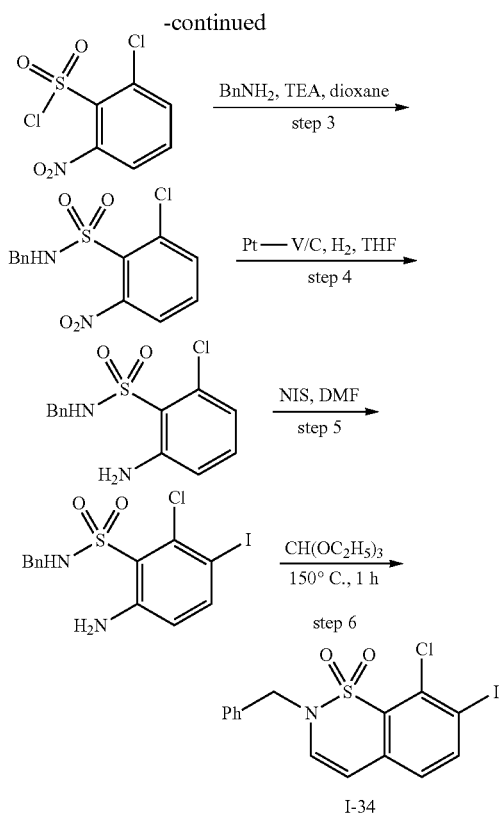

Step 1: benzyl (2-chloro-6-nitrophenyl)sulfane

To a solution of phenylmethanthiol(BnSH) (3.23 g, 26.0 mmol) in EtOH (50 mL) was added EtONa (1.95 g, 28.7 mmol). Subsequently, the mixture was added with 1,2-dichloro-3-nitro-benzene (5.0 g, 26.0 mmol) and then stirred at 80° C. for 1 hour. The reaction mixture was quenched by addition of aqueous ammonium chloride (20 mL) at 25, and then diluted with water (30 mL) and extracted with EA (3×50 mL). The combined organic layers were washed with brine (3×20 mL), dried over anhydrous sodium sulfate, and then filtered and concentrated under reduced pressure to obtain a residue. The residue was purified by column chromatography (PE/EA=10:1) to obtain benzyl (2-chloro-6-nitrophenyl)sulfane (5.7 g, 78% yield) as a yellow solid. $^1$H NMR (400 MHz, DMSO-$d_6$) δ=7.86 (dd, J=8.0, 1.2 Hz, 1H), 7.76 (dd, J=8.0, 1.2 Hz, 1H), 7.60-7.56 (m, 1H), 7.25-7.19 (m, 3H), 7.12-7.07 (m, 2H), 4.15 (s, 2H).

Step 2: 2-chloro-6-nitrobenzenesulfonyl chloride

To a solution of 2-benzylsulfanyl-1-chloro-3-nitrobenzene (3.70 g, 13.2 mmol) in AcOH(40 mL) and $H_2O$(13 mL) was added NCS (7.06 g, 52.9 mmol). The mixture was stirred at ° C. for 3 hours. The reaction mixture was diluted with water (100 mL) and extracted with EA (3×100 mL). The combined organic layers were dried over anhydrous sodium sulfate, and then filtered and concentrated under reduced pressure to obtain a residue. The residue was purified by column chromatography (PE/EA=5:1) to obtain 2-chloro-6-nitrobenzenesulfonyl chloride (2.70 g, 79% yield) as a yellow solid. $^1$H NMR (400 MHz, DMSO-$d_6$) δ=7.65-7.60 (m, 1H), 7.50-7.46 (m, 2H).

Step 3: N-benzyl-2-chloro-6-nitrobenzenesulfonamide

To a solution of 2-chloro-6-nitrobenzenesulfonyl chloride (2.80 g, 10.9 mmol) in dioxane(30 mL), TEA (1.66 g, 16.4 mmol) and phenylmethanamine(BnNH$_2$) (1.76 g, 16.40 mmol) were added, and the mixture was stirred at 0° C. for 12 hours. The reaction mixture was quenched by addition of aqueous ammonium chloride (50 mL) at 25, and then diluted with water (50 mL) and extracted with EA (3×100 mL). The combined organic layers were washed with brine (3×50 mL), dried over anhydrous sodium sulfate, and then filtered and concentrated under reduced pressure to obtain a residue. The residue was purified by column chromatography (PE/EA=5:1) to obtain N-benzyl-2-chloro-6-nitrobenzenesulfonamide (2.5 g, 70% yield) as a yellow solid. 1 H NMR (400 MHz, DMSO-$d_6$) δ=9.09 (br s, 1H), 7.81-7.76 (m, 1H), 7.75-7.69 (m, 2H), 7.24-7.11 (m, 5H), 4.14 (s, 2H).

Step 4: 2-amino-N-benzyl-6-chlorobenzenesulfonamide

To a solution of N-benzyl-2-chloro-6-nitrobenzenesulfonamide (2.00 g, 6.12 mmol) in THF (30 mL) was added Pt—V/C (239 mg, 1.22 mmol), and the mixture was stirred at 25° C. for 2 hours under $H_2$ atmosphere (15 psi). The reaction mixture was filtered and concentrated under reduced pressure to obtain 2-amino-N-benzyl-6-chlorobenzenesulfonamide (1.8 g, 99% yield) as a yellow solid. $^1$H NMR (400 MHz, DMSO-$d_6$) δ=8.20 (t, J=6.4 Hz, 1H), 7.30-7.16 (m, 5H), 7.10 (t, J=8.0 Hz, 1H), 6.73 (dd, J=8.4, 0.8 Hz, 1H), 6.59 (dd, J=7.6, 0.8 Hz, 1H), 6.55 (s, 2H), 4.03 (d, J=6.4 Hz, 2H); MS (EI) m/z: 297.0 [M+H]$^+$.

Step 5: 6-amino-N-benzyl-2-chloro-3-iodobenzenesulfonamide

To a solution of 2-amino-N-benzyl-6-chloro-benzenesulfonamide (2.00 g, 6.74 mmol) in DMF (20 mL) was added N-iodosuccinimide(NIS) (1.67 g, 7.41 mmol), and the mixture was stirred at 80° C. for 2 hours. The reaction mixture was quenched by addition of aqueous ammonium chloride (20 mL) at 25, and then diluted with water (50 mL) and extracted with EA (3×50 mL). The combined organic layers were washed with brine (3×20 mL), dried over anhydrous sodium sulfate, and then filtered and concentrated under reduced pressure to obtain a residue. The residue was purified by column chromatography (PE/EA=3:1) to obtain 6-amino-N-benzyl-2-chloro-3-iodobenzenesulfonamide (2.4 g, 84% yield) as a yellow solid. $^1$H NMR (400 MHz, DMSO-$d_6$) δ =8.34 (t, J=6.4 Hz, 1H), 7.56 (d, J=9.0 Hz, 1H), 7.26-7.14 (m, 5H), 6.70 (br s, 2H), 6.55 (d, J=9.0 Hz, 1H), 4.02 (d, J=6.4 Hz, 2H); MS (EI) m/z: 422.9 [M+H]$^+$.

Step 6: 2-benzyl-8-chloro-7-iodo-2H-benzo[e][1,2,4]thiazine 1,1-dioxide

To a solution of 6-amino-N-benzyl-2-chloro-3-iodobenzenesulfonamide (2.3 g, 5.44 mmol) in diethoxymethoxyethane (24.1 g, 163 mmol) was added triethyl orthoformate, and the mixture was stirred at 150° C. for 1 hour. The reaction mixture was filtered and concentrated under reduced pressure to obtain a residue. The residue was triturated with MeOH (30 mL) to obtain Intermediate I-34 (2.1 g, 89% yield) as an off-white solid.

Preparation Example 34: 6-bromo-2,7-dichloro-1-((2-trimethylsilyl)ethoxy)methyl)-1H-benzo[d]imidazole (Intermediate I-35)

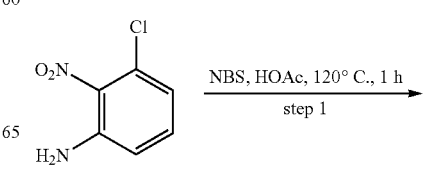

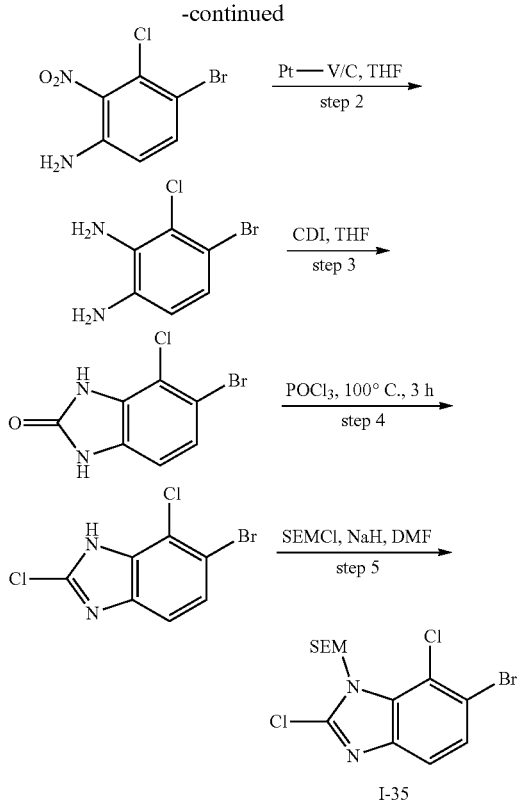

Step 1: 4-bromo-3-chloro-2-nitroaniline

To a solution of 3-chloro-2-nitroaniline (5.0 g, 29.0 mmol) in HOAc (250 mL) was added NBS (5.16 g, 29.0 mmol), and the mixture was stirred at 120° C. for 1 hour. The reaction mixture was quenched with water (100 mL) and extracted with EA (3×100 mL). The combined organic layers were washed with brine (3×100 mL), dried over anhydrous sodium sulfate, and then filtered and concentrated under reduced pressure to obtain a residue. The residue was purified by column chromatography (PE/EA=10/1) to obtain 4-bromo-3-chloro-2-nitroaniline (5.35 g, 73% yield) as a brown solid. 1 I-1 NMR (400 MHz, DMSO-$d_6$) δ=7.56 (d, J=9.2 Hz, 1H), 6.83 (d, J=9.2 Hz, 1H), 6.42 (s, 2H).

Step 2: 4-bromo-3-chlorobenzene-1,2-diamine

To a solution of 4-bromo-3-chloro-2-nitroaniline (3.8 g, 15.1 mmol) in THF (40 mL) was added Pt—V/C (983 mg, 151 μmol, 3% purity), and the mixture was stirred at 25° C. for 1 hour under $H_2$ atmosphere (15 psi). The reaction mixture was filtered and concentrated under reduced pressure to obtain 4-bromo-3-chloro-benzene-1,2-diamine (3.1 g, 90% yield) as a brown solid. $^1$H NMR (400 MHz, DMSO-$d_6$) δ=6.70 (d, J=8.4 Hz, 1H), 6.42 (d, J=8.4 Hz, 1H), 4.97 (br s, 4H).

Step 3: 5-bromo-4-chloro-1,3-dihydrobenzimidazol-2-one

To a solution of 4-bromo-3-chloro-benzene-1,2-diamine (470 mg, 2.12 mmol) in DMF (25 mL) was added 1,1'-carbodiimide(CDI) (413 mg, 2.55 mmol), and the mixture was stirred at 25° C. for 2 hours. The reaction mixture was poured into water (40 mL), thereby obtaining an off-white precipitate. The solid was collected and washed with EA (40 mL), and then dried under vacuum to obtain 5-bromo-4-chloro-1,3-dihydrobenzimidazol-2-one (370 mg, 71% yield) as an off-white solid. 1 I-1 NMR (400 MHz, DMSO-$d_6$) δ=11.36 (s, 1H), 11.05 (s, 1H), 7.28 (d, J=8.0 Hz, 1H), 6.85 (d, J=8.0 Hz, 1H).

Step 4: 6-bromo-2,7-dichloro-1H-benzimidazole

A solution of 5-bromo-4-chloro-1,3-dihydrobenzimidazol-2-one (350 mg, 1.41 mmol) in $POCl_3$ (2 mL) was stirred at 100° C. for 3 hours. The reaction mixture was concentrated under reduced pressure to obtain a residue. The residue was quenched by addition of aqueous $NaHCO_3$(20 mL) at 25° C., and then diluted with water (30 mL) and extracted with EA (3×50 mL). The combined organic layers were washed with brine (3×20 mL), dried over anhydrous sodium sulfate, and then filtered and concentrated under reduced pressure to obtain 6-bromo-2,7-dichloro-1H-benzimidazole (340 mg, 90% yield) as a yellow solid. $^1$H NMR (400 MHz, DMSO-$d_6$) δ=7.55 (d, J=8.4 Hz, 1H), 7.43 (d, J=8.4 Hz, 1H); MS (EI) m/z: 267.0 [M+H]$^+$.

Step 5: 6-bromo-2,7-dichloro-1-((2-trimethylsilyl)ethoxy)methyl)-1H-benzo[d]imidazole To a solution of 6-bromo-2,7-dichloro-1H-benzimidazole (290 mg, 1.09 mmol) in DMF (5 mL) was added NaH (48.0 mg, 1.20 mmol), and the mixture was stirred at 0° C. for 0.5 hours. Subsequently, the mixture was slowly added with 2-(trimethylsilyl)ethoxymethyl chloride(SEM-Cl) (273 mg, 1.64 mmol) in THF (5 mL) and then stirred at 0° C. for 1.5 hours. The reaction mixture was quenched by addition of aqueous ammonium chloride (20 mL) at 25, and then diluted with water (30 mL) and extracted with EA (3×50 mL). The combined organic layers were washed with brine (3×20 mL), dried over anhydrous sodium sulfate, and then filtered and concentrated under reduced pressure to obtain a residue. The residue was purified by column chromatography (PE/EA=30/1) to obtain Intermediate I-35 (400 mg, 93% yield) as a yellow solid. $^1$H NMR (400 MHz, $CDCl_3$) δ=7.61 (d, J=8.4 Hz, 1H), 7.28 (d, J=8.4 Hz, 1H), 3.66-3.63 (m, 2H), 3.60-3.53 (m, 2H), 0.94-0.88 (m, 2H), 0.04 (s, 9H); MS (EI) m/z: 397.1 [M+H]$^+$.

Preparation Example 35: 6-bromo-7-chloro-1-methyl-2-tetrahydrofuran-3-yloxy-benzimidazole (Intermediate I-36) and 5-bromo-4-chloro-1-methyl-2-tetrahydrofuran-3-yloxy-benzimidazole (Intermediate I-37)

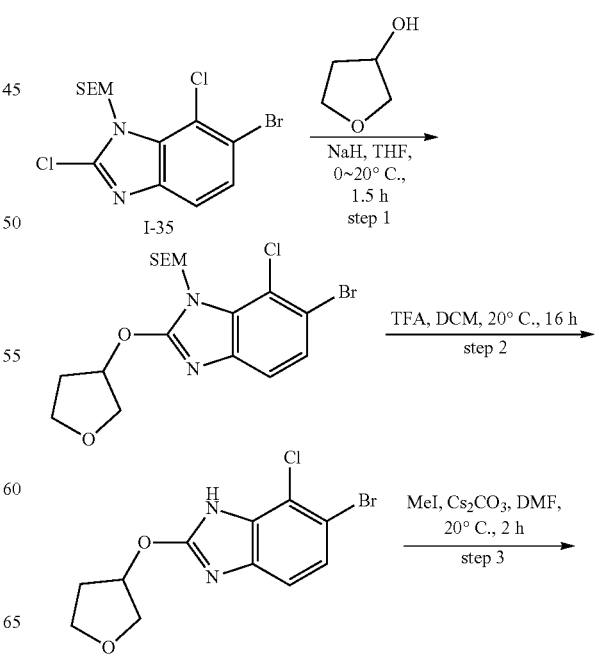

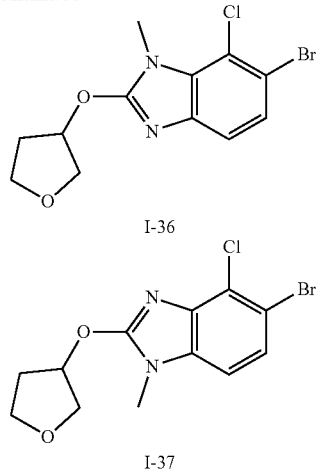

I-36

I-37

Step 1: 2-[(6-bromo-7-chloro-2-tetrahydrofuran-3-yloxy-benzimidazol-1-yl)methoxy]ethyl-trimethyl-silane To a mixture of tetrahydrofuran-3-ol (166 mg, 1.89 mmol) in THF (5 mL) was added NaH (75.5 mg, 1.89 mmol, 60% purity) at 0° C. The mixture was stirred under nitrogen atmosphere at 0° C. for 0.5 hours. Then, a solution of Intermediate I-35 (500 mg, 1.26 mmol) in THF (2 mL) was added at 0° C. The mixture was stirred under nitrogen atmosphere at 20° C. for 1 hour. The reaction mixture was quenched with water (10 mL) at 0° C., and then diluted with water (20 mL) and extracted with EA (3×20 mL). The organic layer was washed with brine (2×30 mL). The organic layer was dried over anhydrous sodium sulfate and filtered. The filtrate was concentrated under vacuum. The crude product was purified by reverse phase flash column chromatography (0.1% FA codition) to obtain 2-[(6-bromo-7-chloro-2-tetrahydrofuran-3-yloxy-benzimidazol-1-yl)methoxy]ethyl-trimethyl-silane (230 mg, 41% yield) as a yellow oil. $^1$H NMR (400 MHz, CDCl$_3$) δ=7.41 (d, J=8.4 Hz, 1H), 7.11 (d, J=8.4 Hz, 1H), 5.91-5.83 (m, 1H), 5.35 (s, 2H), 4.14-4.06 (m, 2H), 4.05-3.99 (m, 1H), 3.98-3.91 (m, 1H), 3.54-3.49 (m, 2H), 2.44-2.33 (m, 1H), 2.31-2.22 (m, 1H), 0.90 (d, J=8.4 Hz, 2H), −0.03 (d, J=1.2 Hz, 9H).

Step 2: 6-bromo-7-chloro-2-tetrahydrofuran-3-yloxy-1H-benzimidazole

To a mixture of 2-[(6-bromo-7-chloro-2-tetrahydrofuran-3-yloxy-benzimidazol-1-yl)methoxy]ethyl-trimethyl-silane (230 mg, 513 μmol) in DCM (2 mL) was added TFA (3.08 g, 27.0 mmol, 2 mL). The reaction mixture was stirred at 20° C. for 16 hours. The reaction mixture was concentrated under vacuum. The residue was diluted with water (10 mL) and basified with saturated aqueous K$_2$CO$_3$ solution until the pH became 7. The mixture was extracted with EA (3×10 mL). The organic layer was washed with brine (2×50 mL). The organic layer was dried over anhydrous sodium sulfate and filtered. The filtrate was concentrated under vacuum to obtain 6-bromo-7-chloro-2-tetrahydrofuran-3-yloxy-1H-benzimidazole (160 mg, 98% yield) as a yellow oil. MS (EI) m/z: 318.9 [M+H]$^+$.

Step 3: 6-bromo-7-chloro-1-methyl-2-tetrahydrofuran-3-yloxy-benzimidazole and 5-bromo-4-chloro-1-methyl-2-tetrahydrofuran-3-yloxy-benzimidazole To a mixture of 6-bromo-7-chloro-2-tetrahydrofuran-3-yloxy-1H-benzimidazole (160 mg, 503 μmol) and Cs$_2$CO$_3$ (492 mg, 1.51 mmol) in DMF (5 mL) was added MeI (107 mg, 755 μmol). The reaction mixture was stirred at 20° C. for 2 hours, diluted with water (20 mL) and extracted with EA (3×20 mL). The organic layer was washed with brine (2×50 mL). The organic layer was dried over anhydrous sodium sulfate and filtered. The filtrate was concentrated under vacuum. The residue was purified by Prep-HPLC (Column: Phenomenex luna C18 150*25 mm* 10 um; mobile phase: [water(FA)-I]; B %: 44%-64%, 2 minutes) to obtain Intermediate I-36 and Intermediate I-37 as a yellow solid, respectively.

6-bromo-7-chloro-1-methyl-2-tetrahydrofuran-3-yloxy-benzimidazole (53 mg, 31% yield): $^1$H NMR (400 MHz, CDCl$_3$) δ=7.40 (d, J=8.4 Hz, 1H), 7.28 (d, J=8.4 Hz, 1H), 5.71-5.63 (m, 1H), 4.15-4.09 (m, 1H), 4.09-4.02 (m, 2H), 3.98-3.91 (m, 1H), 3.87 (s, 3H), 2.43-2.34 (m, 1H), 2.33-2.24 (m, 1H).

5-bromo-4-chloro-1-methyl-2-tetrahydrofuran-3-yl oxy-benzimidazole(40 mg, 24% yield): $^1$H NMR (400 MHz, CDCl$_3$) δ=7.39 (d, J=8.4 Hz, 1H), 6.95 (d, J=8.4 Hz, 1H), 5.87-5.82 (m, 1H), 4.15-4.10 (m, 1H), 4.09-4.02 (m, 2H), 3.97-3.91 (m, 1H), 3.55 (s, 3H), 2.46-2.34 (m, 1H), 2.33-2.22 (m, 1H).

Preparation Example 36: tert-butyl ((3S,4S)-8-(5-bromo-3-(hydroxymethyl)-6-methylpyrazin-2-yl)-3-methyl-2-oxa-8-azaspiro[4.5]decan-4-yl)carbamate (Intermediate I-38)

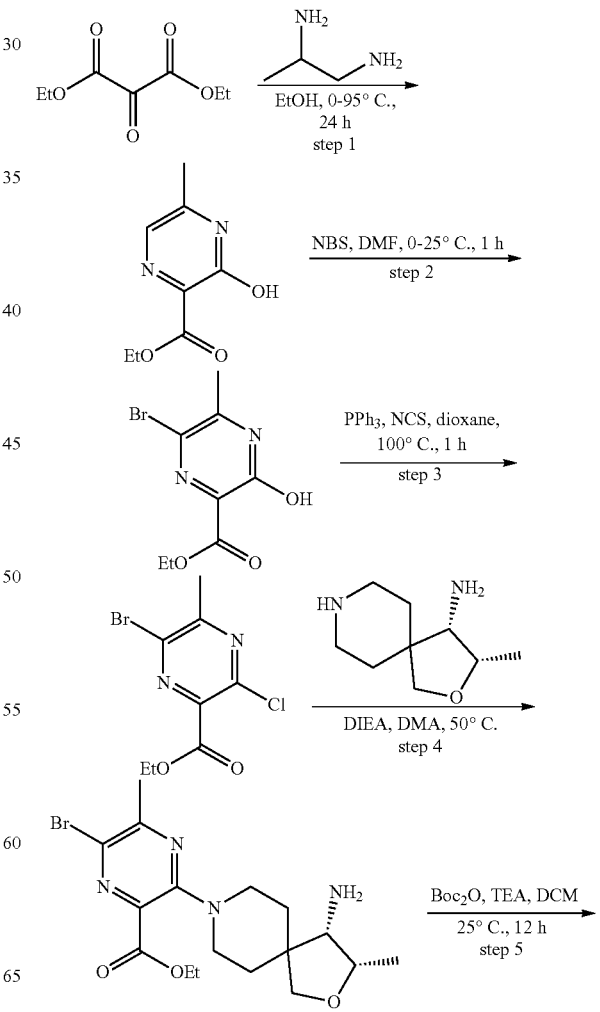

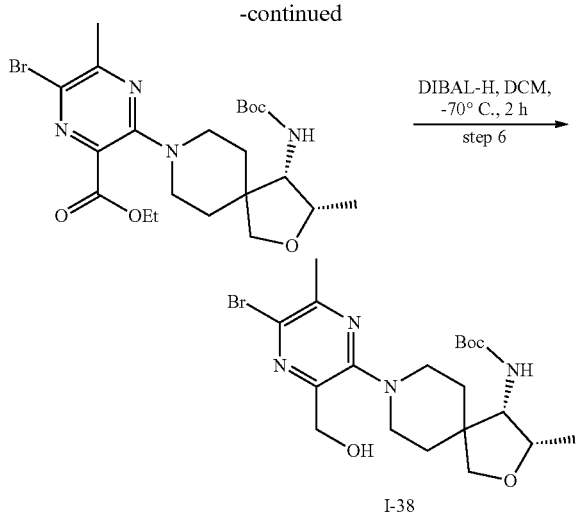

Step 1: ethyl 3-hydroxy-5-methyl-pyrazine-2-carboxylate

To a stirred mixture of propane-1,2-diamine (25.5 g, 344 mmol) in EtOH (300 mL) was added diethyl 2-oxopropanedioate (59.9 g, 344 mmol) dropwise at 0° C., the mixture was warmed to 25° C. The reaction mixture was stirred at 25° C. for 2 hours, and then the reaction mixture was stirred at 95° C. for 18 hours. The reaction mixture was concentrated under reduced pressure to obtain a residue. The residue was triturated with EA (100 mL) to obtain ethyl 3-hydroxy-5-methyl-pyrazine-2-carboxylate (10 g, 16% yield) as a red solid. $^1$H NMR (400 MHz, CDCl$_3$) δ=11.46 (br s, 1H), 8.16 (s, 1H), 4.55 (q, J=7.2 Hz, 2H), 2.58 (s, 3H), 1.49 (t, J=7.2 Hz, 3H).

Step 2: ethyl 6-bromo-3-hydroxy-5-methyl-pyrazine-2-carboxylate

To a solution of ethyl 3-hydroxy-5-methyl-pyrazine-2-carboxylate (2.85 g, 15.6 mmol) in DMF (60 mL) was added NBS (2.92 g, 16.4 mmol), and the mixture was stirred at 0° C. for 1 hour. The reaction mixture was quenched by addition of aqueous ammonium chloride (50 mL) at 25, and then diluted with water (50 mL) and extracted with EA (100 mL×3). The combined organic layers were washed with brine (50 mL×3), dried over anhydrous sodium sulfate, and then filtered and concentrated under reduced pressure to obtain a residue. The residue was purified by column chromatography (PE/EA=10/1 to 5:1) to obtain ethyl 6-bromo-3-hydroxy-5-methyl-pyrazine-2-carboxylate (2.65 g, 65% yield) as a yellow solid. $^1$H NMR (400 MHz, DMSO-d$_6$) δ=12.56 (br s, 1H), 4.35 (q, J=7.2 Hz, 2H), 3.37 (s, 3H), 1.34 (t, J=7.2 Hz, 3H); MS (EI) m/z: 261.3 [M+H]$^+$.

Step 3: ethyl 6-bromo-3-chloro-5-methyl-pyrazine-2-carboxylate

To PPh$_3$ (3.01 g, 11.5 mmol) in dioxane (30 mL) was added NCS (1.56 g, 11.68 mmol), and the resulting mixture was warmed to 25° C. and stirred for 30 minutes, and then ethyl 6-bromo-3-hydroxy-5-methyl-pyrazine-2-carboxylate (1 g, 3.83 mmol) was added at once, and the resulting mixture was warmed to 100° C. and stirred for 1 hour. The reaction mixture was then cooled to room temperature and added with TEA (3.88 g, 38.3 mmol). The reaction mixture was filtered and concentrated under reduced pressure to obtain a residue. The residue was purified by column chromatography(PE/EA=15/1 to 10:1) to obtain ethyl 6-bromo-3-chloro-5-methyl-pyrazine-2-carboxylate (0.3 g, 28% yield) as a yellow oil. $^1$H NMR (400 MHz, CDCl$_3$) δ=4.53-4.44 (m, 2H), 2.71 (s, 3H), 1.44 (t, J=7.2 Hz, 3H).

Step 4: ethyl 3-1(3S,4S)-4-amino-3-methyl-2-oxa-8-azaspiro[4.5]decan-8-yl]-6-bromo-5-methyl-pyrazine-2-carboxylate To a solution of ethyl 6-bromo-3-chloro-5-methyl-pyrazine-2-carboxylate (0.3 g, 1.07 mmol) in DMA (4 mL), DIEA (694 mg, 5.37 mmol) and (3S,4S)-3-methyl-2-oxa-8-azaspiro[4.5]decan-4-amine (287 mg, 1.18 mmol, 2HCl) were added, and the mixture was stirred at 60° C. for 12 hours. The reaction mixture was quenched by addition of aqueous ammonium chloride (20 mL) at 25° C., and then diluted with water (30 mL) and extracted with EA (50 mL×3). The combined organic layers were washed with brine (20 mL×3), dried over anhydrous sodium sulfate, and then filtered and concentrated under reduced pressure to obtain a residue. The residue was purified by reverse phase flash column chromatography (0.1% FA) to obtain ethyl 3-[(3 S,4S)-4-amino-3-methyl-2-oxa-8-azaspiro[4.5]decan-8-yl]-6-bromo-5-methyl-pyrazine-2-carboxylate (350 mg, crude product) as a yellow oil. MS (EI) m/z: 415.3 [M+H]$^+$.

Step 5: ethyl 6-bromo-3-[(3S,4S)-4-(tert-butoxycarbonylamino)-3-methyl-2-oxa-8-azaspiro[4.5]decan-8-yl]-5-methyl-pyrazine-2-carboxylate To a solution of ethyl 3-[(3S,4S)-4-amino-3-methyl-2-oxa-8-azaspiro[4.5]decan-8-yl]-6-bromo-5-methyl-pyrazine-2-carboxylate (250 mg, 605 μmol) in DCM (10 mL), Boc$_2$O (198 mg, 907 μmol) and TEA (184 mg, 1.81 mmol) were added. The mixture was stirred at 25° C. for 12 hours. The reaction mixture was filtered, and the filtrate was concentrated under reduced pressure to obtain a residue. The residue was purified by reverse phase flash column chromatography (0.1% FA) to obtain ethyl 6-bromo-3-[(3S,4S)-4-(tert-butoxycarbonylamino)-3-methyl-2-oxa-8-azaspiro [4.5]decan-8-yl]-5-methyl-pyrazine-2-carboxylate (250 mg, 80% yield) as a yellow solid. MS (EI) m/z: 513.2 [M+H]$^+$.

Step 6: tert-butyl N-[(3S,4S)-8-[5-bromo-3-(hydroxymethyl)-6-methyl-pyrazin-2-yl]-3-methyl-2-oxa-8-azaspiro [4.5]decan-4-yl]carbamate To a solution of ethyl 6-bromo-3-[(3S,4S)-4-(tert-butoxycarbonylamino)-3-methyl-2-oxa-8-azaspiro[4.5]decan-8-yl]-5-methyl-pyrazine-2-carboxylate (150 mg, 292 μmol) in DCM (5 mL) was added diisobutylaluminum hydride (DIBAL-H) (1 M in toluene, 1.17 mL), and the mixture was stirred at −70° C. for 2 hours. The reaction mixture was quenched by addition of 2 mL of MeOH at −70° C. and then diluted with DCM (50 mL). The mixture was filtered and the filtrate was concentrated under reduced pressure to obtain a residue. The residue was purified by Pre-TLC (PE/EA=1:1) to obtain Intermediate I-38 (120 mg, 87% yield) as a yellow solid. MS (EI) m/z: 471.3 [M+H]$^+$.

Preparation Example 37: (R)-N-((S)-1'(5-((5-chloro-4-oxo-3,4-dihydroquinazolin-6-yl)thio)pyrazin-2-yl)-5,7-dihydrospiro[cyclopenta[b]pyridine-6,4'-piperidin]-5-yl)-2-methylpropane-2-sulfinamide (Intermediate I-39)

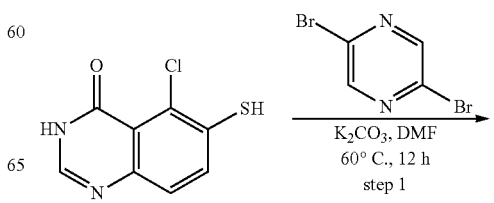

115

-continued

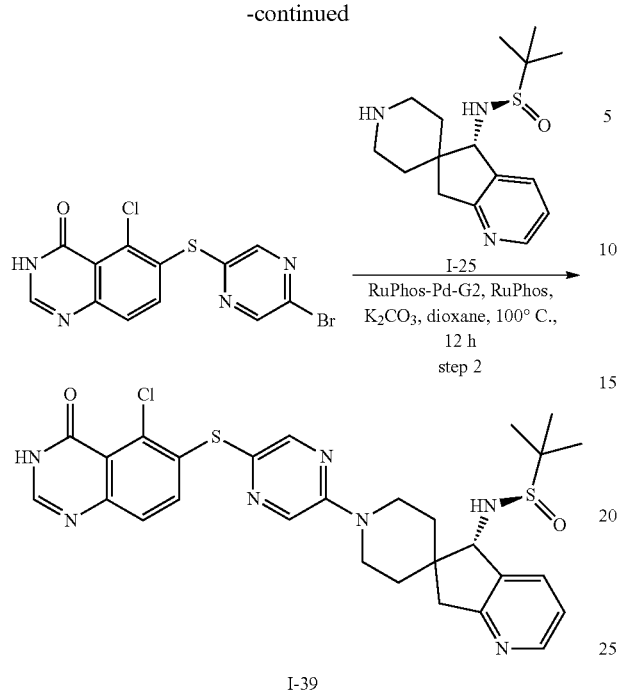

I-39

Step 1: 6-(5-bromopyrazin-2-yl)sulfanyl-5-chloro-3H-quinazolin-4-one

To a solution of 5-chloro-6-mercaptoquinazolin-4(3H)-one (880 mg, 3.75 mmol) in DMF (20 mL), $K_2CO_3$ (1.56 g, 11.3 mmol) and 2,5-dibromopyrazine (3.57 g, 15.00 mmol) were added, and the mixture was stirred at 0° C. for 2 hours. The reaction mixture was quenched by addition of aqueous ammonium chloride (50 mL) at 25, and then diluted with water (50 mL) and extracted with EA (100 mL×3). The combined organic layers were washed with brine (50 mL×3), dried over anhydrous sodium sulfate, and then filtered and concentrated under reduced pressure to obtain a residue. The residue was purified by column chromatography (PE/EA=1/1 to 0:1) to obtain 6-(5-bromopyrazin-2-yl)sulfanyl-5-chloro-3H-quinazolin-4-one(500 mg, 36% yield) as a yellow solid. $^1$H NMR (400 MHz, DMSO-d$_6$) δ=12.50 (br s, 1H), 8.71 (d, J=1.0 Hz, 1H), 8.46-8.43 (m, 1H), 8.15 (s, 1H), 7.98 (d, J=8.8 Hz, 1H), 7.61 (d, J=8.8 Hz, 1H); MS (EI) m/z: 371.1 [M+H]$^+$.

Step 2: (R)-N-((S)-1'-(54(5-chloro-4-oxo-3,4-dihydroquinazolin-6-yl)thio)pyrazin-2-yl)-5,7-dihydrospiro[cyclopenta[b]pyridine-6,4'-piperidin]-5-yl)-2-m ethylpropane-2-sulfinamide A mixture of 6-(5-bromopyrazin-2-yl)sulfanyl-5-chloro-3H-quinazolin-4-one (150 mg, 406 μmol), Intermediate I-25 (150 mg, 487 μmol), [2-(2-aminophenyl)phenyl]-chloro-palladium; dicyclohexyl-[2-(2,6-diisopropoxyphenyl)phenyl]phosphane (RuPhos-Pd-G2) (31.5 mg, 40.6 μmol), 2-dicyclohexylphosphino-2',6'-diisopropoxybiphenyl(RuPhos) (37.8 mg, 81.2 μmol) and $K_2CO_3$ (168 mg, 1.22 mmol) in dioxane (5 mL) was degassed and purged 3 times with $N_2$, and then the mixture was stirred under $N_2$ atmosphere at 100° C. for 12 hours. The reaction mixture was quenched by addition of MeOH (2 mL) at −70° C., diluted with DCM (50 mL), and then filtered and concentrated under reduced pressure to obtain a residue. The residue was purified by reverse phase flash column chromatography (0.1% FA) to obtain Intermediate I-39 (80 mg, 33% yield) as a yellow solid. MS (EI) m/z: 596.1 [M+H]$^+$.

116

Preparation Example 38: 3-benzyl-7-bromo-8-chloro-quinazolin-4-one (Intermediate I-40)

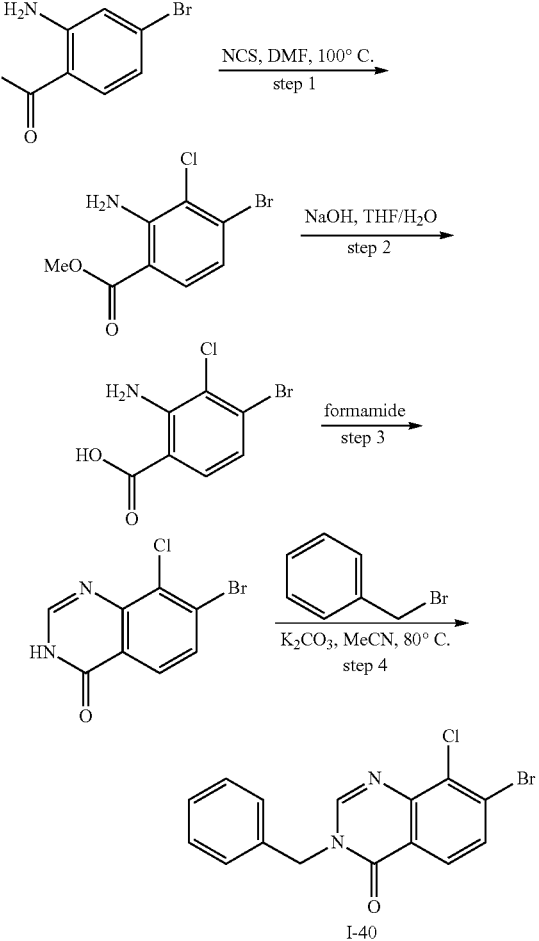

I-40

Step 1: methyl 2-amino-4-bromo-3-chloro-benzoate

To a solution of methyl 2-amino-4-bromo-benzoate (20.0 g, 86.9 mmol) in DMF (200 mL) was added NCS (12.7 g, 95.6 mmol). The mixture was stirred at 100° C. for 4 hours. The reaction mixture was diluted with water (300 mL) and extracted with EtOAc (3×200 mL). The combined organic layers were washed with brine (3×150 mL), dried over $Na_2SO_4$, and then filtered and concentrated under reduced pressure to obtain a residue. The residue was purified by silica gel chromatography (PE:EA=1:0), and then crude product was purified by reverse phase flash column chromatography (0.1% FA condition) to obtain methyl 2-amino-4-bromo-3-chloro-benzoate (4 g, 17% yield) as a yellow solid. $^1$H NMR (400 MHz, CDCl$_3$) δ=7.67 (d, J=8.8 Hz, 1H), 6.92 (d, J=8.8 Hz, 1H), 6.49 (br s, 2H), 3.89 (s, 3H).

Step 2: 2-amino-4-bromo-3-chloro-benzoic acid

To a solution of methyl 2-amino-4-bromo-3-chloro-benzoate (2.00 g, 7.56 mmol) in THF (18 mL) and water (6 mL) was added NaOH (1.51 g, 37.8 mmol). The mixture was stirred at 40° C. for 12 hours. The residue was adjusted to pH 6 with 1M HCl to obtain a white solid precipitate. The solid was collected and then dried under vacuum to obtain 2-amino-4-bromo-3-chloro-benzoic acid (1.80 g, 95% yield) as a white solid. $^1$H NMR (400 MHz, DMSO-d$_6$) δ=13.16 (br s, 1H), 7.64 (d, J=8.8 Hz, 1H), 7.09 (br s, 2H), 6.94 (d, J=8.8 Hz, 1H).

Step 3: 7-bromo-8-chloro-3H-quinazolin-4-one

A solution of 2-amino-4-bromo-3-chloro-benzoic acid (1.00 g, 3.99 mmol) in formamide (6.78 g, 150 mmol, 6 mL) was stirred at 140° C. for 16 hours. The reaction mixture was filtered and the filtrate was washed with EA (20 mL). The filter cake was dried under vacuum to obtain 7-bromo-8-chloro-3H-quinazolin-4-one (900 mg, crude product) as a yellow solid. $^1$H NMR (400 MHz, DMSO-$d_6$) δ=8.24 (s, 1H), 7.97 (d, J=8.8 Hz, 1H), 7.84 (d, J=8.8 Hz, 1H).

Step 4: 3-benzyl-7-bromo-8-chloro-quinazolin-4-one

A mixture of 7-bromo-8-chloro-3H-quinazolin-4-one (300 mg, 1.16 mmol), benzyl bromide (395 mg, 2.31 mmol) and $K_2CO_3$ (479 mg, 3.47 mmol) in acetonitrile (MeCN) (2 mL) was stirred at 80° C. for 24 hours. The reaction mixture was filtered and the filtrate was purified by reverse phase flash column chromatography (0.1% FA) to obtain Intermediate I-40 (60 mg, 14% yield) as a yellow solid. $^1$H NMR (400 MHz, DMSO-$d_6$) δ=8.74 (s, 1H), 7.90 (d, J=8.8 Hz, 1H), 7.88 (d, J=8.8 Hz, 1H), 7.28-7.38 (m, 5H), 5.19 (s, 2H).

Preparation Example 39:
2-benzyl-7-chloro-6-iodoisoindolin-1-one
(Intermediate I-41)

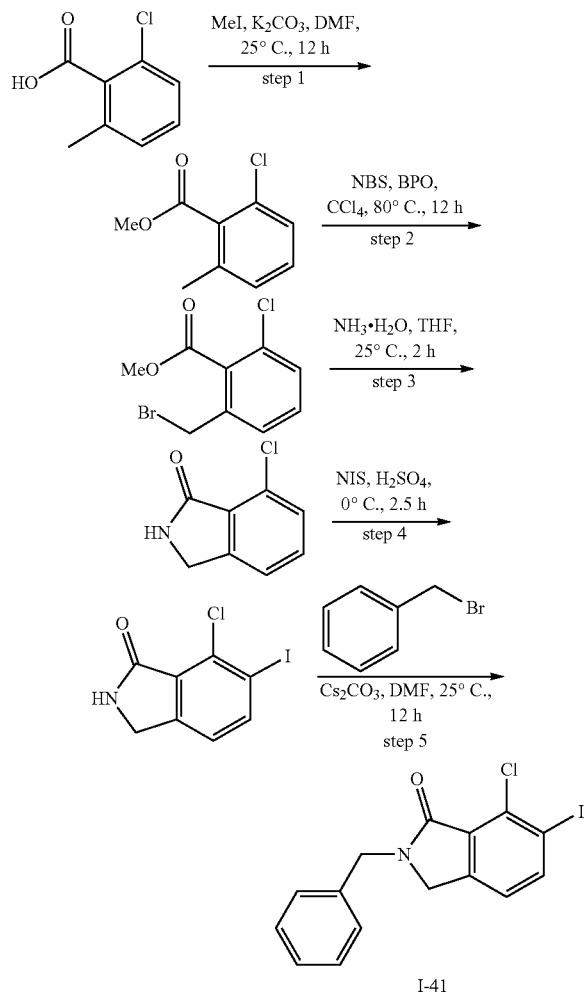

I-41

Step 1: methyl 2-chloro-6-methylbenzoate

To a solution of 2-chloro-6-methyl-benzoic acid (10.0 g, 58.6 mmol) in DMF (100 mL), MeI (24.9 g, 175 mmol) and $K_2CO_3$ (12.1 g, 87.9 mmol) were added, and the mixture was stirred at 25° C. for 12 hours. The reaction mixture was quenched by addition of aqueous ammonium chloride (100 mL) at 25° C., and then diluted with water (100 mL) and extracted with EA (3×200 mL). The combined organic layers were washed with brine (3×100 mL), dried over anhydrous sodium sulfate, and then filtered and concentrated under reduced pressure to obtain methyl 2-chloro-6-methyl-benzoate (10.5 g, 97% yield) as a yellow oil. $^1$H NMR (400 MHz, CDCl$_3$) δ=7.25-7.21 (m, 2H), 7.13-7.10 (m, 1H), 3.99 (s, 3H), 2.36 (s, 3H); MS (EI) m/z: 185.0 [M+H]$^+$.

Step 2: methyl 2-(bromomethyl)-6-chloro-benzoate

To a solution of methyl 2-chloro-6-methyl-benzoate (7.90 g, 42.8 mmol) in CCl$_4$ (70 mL), NBS (8.38 g, 47.1 mmol) and benzoyl peroxide(BPO) (207 mg, 856 μmol) were added, and the mixture was stirred at 80° C. for 12 hours. The reaction mixture was filtered and the filtrate was concentrated under reduced pressure to obtain methyl 2-(bromomethyl)-6-chloro-benzoate (10 g, crude product) as a yellow oil. MS (EI) m/z: 263.0 [M+H]$^+$.

Step 3: 7-chloroisoindolin-1-one

To a solution of methyl 2-(bromomethyl)-6-chloro-benzoate (10.0 g, 38.0 mmol) in THF (50 mL) was added NH$_3$·H$_2$O (53.2 g, 379 mmol, 30% purity), and the mixture was stirred at 25° C. for 2 hours. The reaction mixture was quenched by addition of aqueous ammonium chloride (50 mL) at 25° C., and then diluted with water (100 mL) and extracted with EA (3×150 mL). The combined organic layers were washed with brine (3×100 mL), dried over anhydrous sodium sulfate, and then filtered and concentrated under reduced pressure to obtain a residue. The residue was purified by column chromatography (PE/EA=0/1) to obtain 7-chloroisoindolin-1-one (2.8 g, 44% yield) as a yellow solid. $^1$H NMR (400 MHz, DMSO-$d_6$) δ=8.69 (br s, 1H), 7.60-7.52 (m, 2H), 7.46 (d, J=7.2 Hz, 1H), 4.35 (s, 2H).

Step 4: 7-chloro-6-iodo-isoindolin-1-one

To a solution of 7-chloroisoindolin-1-one (12 g, 71.6 mmol) in H$_2$SO$_4$(120 mL) was added NIS (20.9 g, 93.0 mmol), and the mixture was stirred at 0° C. for 2.5 hours. The reaction mixture was poured into ice water, and then diluted with water (200 mL) and extracted with EA (3×300 mL). The combined organic layers were washed with brine (3×150 mL), dried over anhydrous sodium sulfate, and then filtered and concentrated under reduced pressure to obtain a residue. The residue was purified by column chromatography (PE/EA=1:1) to obtain 7-chloro-6-iodo-isoindolin-1-one (3 g, 14% yield) as a yellow solid. $^1$H NMR (400 MHz, DMSO-$d_6$) δ=8.75 (br s, 1H), 8.15 (d, J=8.4 Hz, 1H), 7.32 (d, J=8.4 Hz, 1H), 4.27 (s, 2H); MS (EI) m/z: 293.8 [M+H]$^+$.

Step 5: 2-benzyl-7-chloro-6-iodoisoindolin-1-one

To a solution of 7-chloro-6-iodo-isoindolin-1-one (500 mg, 1.70 mmol), bromomethylbenzene (437 mg, 2.56 mmol) in DMF (10 mL) was added Cs$_2$CO$_3$ (1.11 g, 3.41 mmol), and the mixture was stirred at 25° C. for 12 hours. The reaction mixture was quenched by addition of aqueous ammonium chloride (20 mL) at 25° C., and then diluted with water (30 mL) and extracted with EA (3×50 mL). The combined organic layers were washed with brine (3×20 mL), dried over anhydrous sodium sulfate, and then filtered and concentrated under reduced pressure to obtain a residue. The residue was purified by Prep-HPLC (Column: Phenomenex luna C18 150*40 mm*15 um; mobile phase: [water (FA)-ACN]; B %: 50%-80%, 10 minutes) to obtain Intermediate I-41 (80 mg, 20% yield) as a white solid. $^1$H NMR (400 MHz, CDCl$_3$) δ=8.00 (d, J=8.0 Hz, 1H), 7.37-7.27 (m, 5H), 7.02 (d, J=8.0 Hz, 1H), 4.79 (s, 2H), 4.17 (s, 2H).

Preparation Example 40: 6-(3-amino-5-chloro-pyrazin-2-yl)sulfanyl-5-chloro-3-(2-methoxyethyl)quinazolin-4-one (Intermediate I-42)

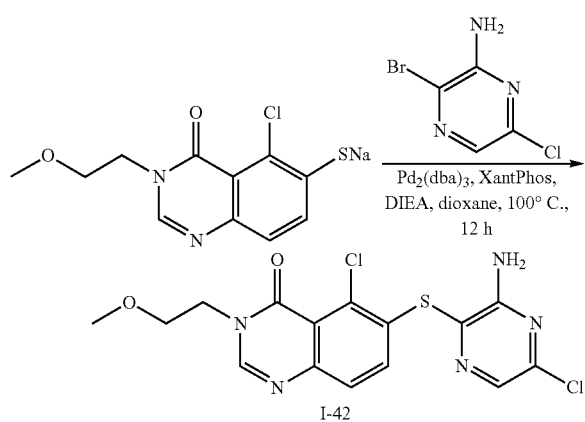

A mixture of [5-chloro-3-(2-methoxyethyl)-4-oxo-quinazolin-6-yl]sulfanyl sodium (630 mg, 2.15 mmol) obtained in step 2 of Preparation Example 28, 3-bromo-6-chloro-pyrazine-2-amine (538 mg, 2.58 mmol), Pd$_2$(dba)$_3$ (197 mg, 215 XantPhos (249 mg, 431 umo) and DIEA (835 mg, 6.46 mmol) in dioxane (20 mL) was degassed, and purged 3 times with N$_2$, and then the mixture was stirred under N$_2$ atmosphere at 100° C. for 12 hours. The reaction mixture was filtered, and the filtrate was concentrated under reduced pressure to obtain a residue. The residue was purified by reverse phase flash column chromatography (0.1% FA) to obtain Intermediate I-42 (120 mg, 14% yield) as a yellow solid. $^1$H NMR (400 MHz, CDCl$_3$) δ=8.08 (s, 1H), 7.92 (s, 1H), 7.57-7.53 (m, 1H), 7.49-7.45 (m, 1H), 5.16 (br s, 2H), 4.16 (t, J=4.8 Hz, 2H), 3.68 (t, J=4.8 Hz, 2H), 3.33 (s, 3H); MS (EI) m/z: 398.0 [M+H]$^+$.

Preparation Example 41: 6-bromo-7-chloro-2-(3-methoxybenzyl)-1H-benzo[d]imidazole (Intermediate I-43)

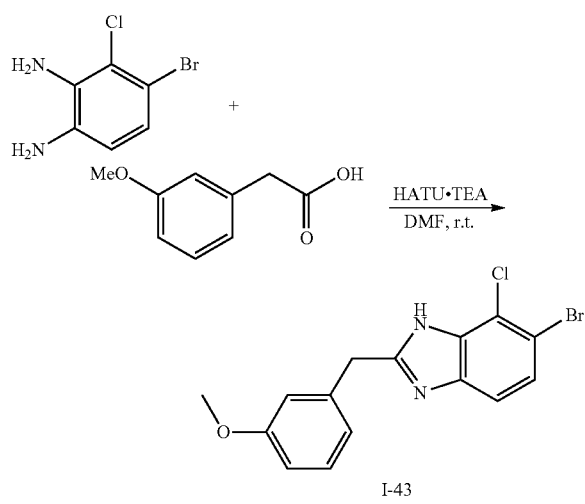

4-bromo-3-chlorobenzene-1,2-diamine (150 mg, 0.677 mmol) was dissolved in DMF (8.2 mL, 0.15 M), and 2-(3-methoxyphenyl)acetic acid (113 mg, 0.677 mmol), HATU (515 mg, 1.354 mmol) and TEA (0.19 mL, 1.354 mmol) were added thereto, and then stirred at room temperature for 8 hours. The reaction was terminated with H$_2$O and extracted with EA. The EA layer was dried over MgSO$_4$, filtered and then concentrated. The resulting product was separated by MPLC (EA:Hx=1:3) and concentrated to obtain Intermediate I-43 (150 mg, yield 60%). MS (EI) m/z: 351.6 [M+H]$^+$.

Preparation Example 42: (S)-2-methyl-N-[(1R)-spiro[indane-2,4'-piperidin]-1-yl]propane-2-sulfinamide (Intermediate I-44)

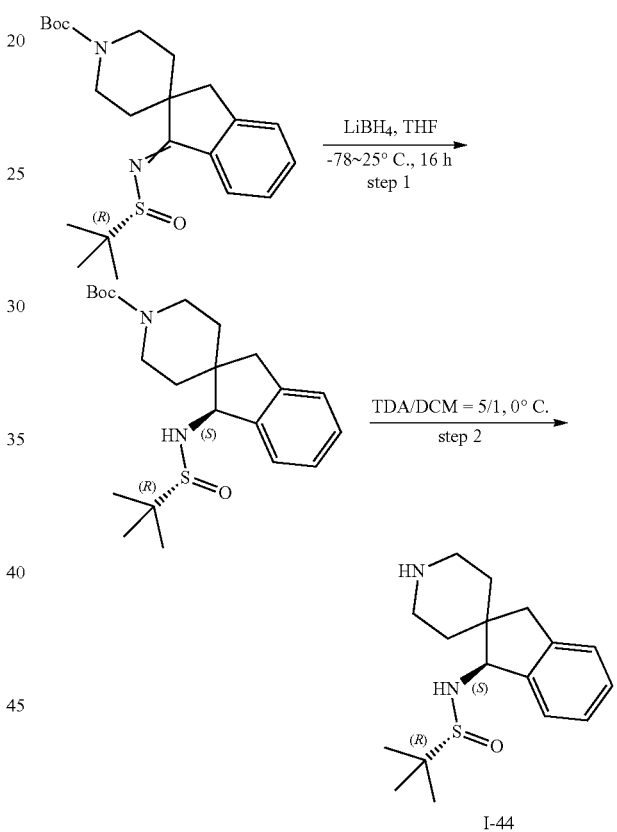

Step 1: tert-butyl (S)-1-(((R)-tert-butylsulfinyl)amino)-1,3-dihydrospiro[indene-2,4'-piperidine]-1'-carboxylate To a solution of tert-butyl 1-[(R)-tert-butylsulfinyl]iminospiro[indene-2,4'-piperidine]-1'-carboxylate (800 mg, 1.98 mmol) in THF (10 mL) was added LiBH$_4$ (129 mg, 5.93 mmol) under N$_2$ at −78° C. The reaction mixture was stirred at −78~25° C. for 16 hours. The reaction mixture was quenched by addition of NH$_4$Cl (10 mL) at 0° C., and then diluted with water (10 mL) and extracted with EtOAc (2×20 mL). The combined organic layers were washed with brine (2×20 mL), dried over Na$_2$SO$_4$, and then filtered and concentrated under vacuum to obtain a residue. The residue was purified by Prep-HPLC (Column: Welch Ultimate XB—CN 250*70*10 μm; mobile phase: [hexane-EtOH(0.1% NH$_3$·H$_2$O)]; B %: 1%-35%, 15 minutes) to obtain tert-butyl (1S)-1-[[(R)-tert-butylsulfinyl]amino]spiro[indane-2,4'-piperidine]-1'-carboxylate (540 mg, 67% yield) and tert-butyl (1R)-1-[[(R)-tert-butyl sulfinyl]amino]spiro[indene-2,4'-piperidine]-1'-carboxylate (130 mg, 16% yield) as a white solid, respectively.

Tert-butyl (1 S)-1-[[(R)-tert-butyl sulfinyl]amino]spiro [indene-2,4'-piperidine]-1'-carboxylate: ¹H NMR (400 MHz, CDCl₃) δ=7.23 (d, J=6.4 Hz, 1H), 7.18-7.12 (m, 3H), 4.43 (d, J=9.2 Hz, 1H), 4.02-3.87 (m, 2H), 3.57-3.38 (m, 1H), 3.11-2.74 (m, 4H), 2.69-2.58 (m, 1H), 2.09-1.96 (m, 1H), 1.47-1.42 (m, 2H), 1.39 (s, 9H), 1.22 (s, 9H).

Step 3: (R)-N-((S)-1,3-dihydrospiro[indene-2,4'-piperidin]-1-yl)-2-methylpropane-2-sulfinamide A mixture of tert-butyl (1 S)-1-[[(R)-tert-butyl sulfinyl] amino]spiro[indene-2,4'-piperidine]-1'-carboxylate (100 mg, 245 μmol) and TFA (1.30 mL) in DCM (5 mL) was stirred at 0° C. for 1 hour. The reaction mixture was diluted with saturated aqueous NaHCO₃ (10 mL) and extracted with EtOAc (2×10 mL). The combined organic layers were washed with brine (2×10 mL), dried over Na₂SO₄, and then filtered and concentrated under vacuum to obtain Intermediate I-44 (70 mg, 92% yield) as a colorless oil.

¹H NMR (400 MHz, CDCl₃) δ=7.29 (s, 1H), 7.26-7.19 (m, 3H), 4.49 (d, J=10.4 Hz, 1H), 4.01 (br s, 1H), 3.63 (d, J=10.4 Hz, 1H), 3.20-3.02 (m, 3H), 2.94-2.66 (m, 3H), 2.23-2.21 (m, 1H), 1.72-1.66 (m, 1H), 1.60-1.57 (m, 1H), 1.33 (s, 9H), 1.19 (d, J=1.6 Hz, 1H).

Preparation Example 43: 6-bromo-7-chloro-2-(pyrazin-2-ylmethyl)-1H-benzo[d]imidazole (Intermediate I-45)

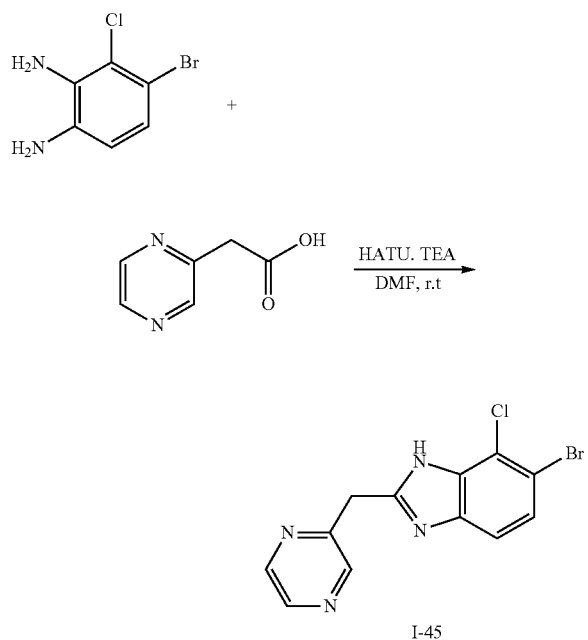

Intermediate I-45 (100 mg, 20%) was prepared in the same method as in Preparation Example 41, except that 2-(pyrazin-2-yl)acetic acid was used instead of 2-(3-methoxyphenyl)acetic acid in Preparation Example 41. MS (EI) m/z: 323.5 [M+H]⁺.

Preparation Example 44: 6-bromo-7-chloro-2-(pyridin-3-ylmethyl)-1H-benzo[d]imidazole (Intermediate I-46)

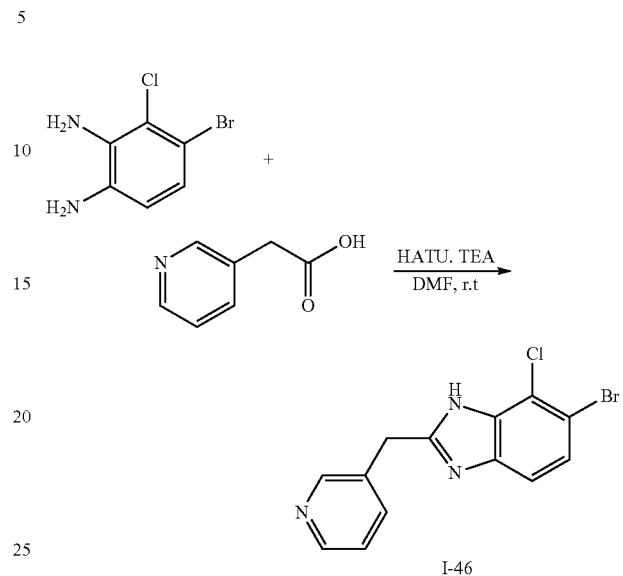

Intermediate I-46 (100 mg, 20%) was prepared in the same method as in Preparation Example 41, except that 2-(pyridin-3-yl)acetic acid was used instead of 2-(3-methoxyphenyl)acetic acid in Preparation Example 41. MS (EI) m/z: 322.5 [M+H]⁺.

Preparation Example 45: tert-butyl 2-chloro-6-oxo-spiro[4H-cyclopenta[d]thiazole-5,4'-piperidine]-1'-carboxylate (Intermediate I-47)

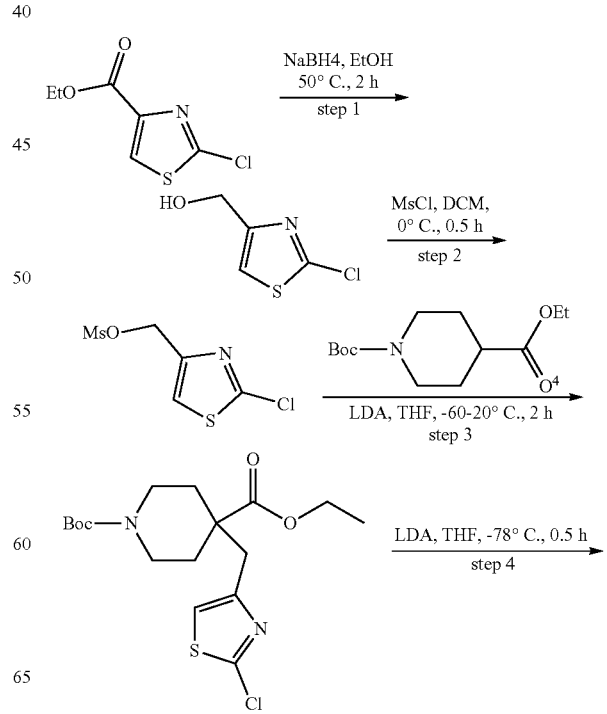

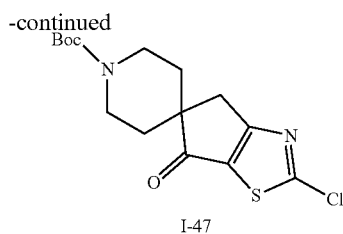

I-47

Step 1: (2-chlorothiazol-4-yl)methanol

To a solution of ethyl 2-chlorothiazole-4-carboxylate (30 g, 157 mmol) in EtOH (300 mL) was added NaBH₄ (41.5 g, 1.10 mol), and the mixture was stirred at 50° C. for 2 hours. The reaction mixture was quenched with aqueous ammonium chloride solution (100 mL) at 0° C., diluted in water (100 ml), and then extracted with EA (200 mL×3). The combined organic layers were washed with brine (200 mL×3), dried over anhydrous sodium sulfate, and then filtered and concentrated under reduced pressure. The residue was purified by column chromatography to obtain (2-chlorothiazol-4-yl)methanol (22 g, 94% yield) as a colorless oil. ¹H NMR (400 MHz, CDCl₃) δ=7.12 (s, 1H), 4.73-4.70 (m, 2H), 2.52-2.34 (m, 1H); MS (EI) m/z: 150.5 [M+H]⁺.

Step 2: (2-chlorothiazol-4-yl)methylmethansulfonate

To a solution of ethyl 2-chlorothiazole-4-carboxylate(30 g, 157 mmol) in DCM (300 mL), TEA (27.1 g, 267 mmol) and MSCl (21.4 g, 187 mmol) were added at 0° C., and the mixture was stirred at 0° C. for 0.5 hours. The reaction mixture was quenched with aqueous NaHCO₃ solution (100 mL) at 25° C., diluted in water (100 ml), and then extracted with DCM (200 mL×3). The combined organic layers were washed with brine (100 mL×3), dried over anhydrous sodium sulfate, and then filtered and concentrated under reduced pressure to obtain (2-chlorothiazol-4-yl)methylmethansulfonate (28 g, crude product) as a yellow oil. ¹H NMR (400 MHz, CDCl₃) δ=7.29 (s, 1H), 5.19 (s, 2H), 3.01 (s, 3H)

Step 3: O1-tert-butyl O4-ethyl 4-[(2-chlorothiazol-4-yl)methyl]piperidine-1,4-dicarboxylate A solution of ethyl 2-chlorothiazole-4-carboxylate (30 g, 157 mmol) in THF (30 mL) was stirred at −60° C. under nitrogen, and then LDA (2 M, 81.6 mL) was added thereto dropwise. The reaction mixture was stirred at −60° C. for 0.5 hours and added dropwise with (2-chlorothiazol-4-yl)methylmethansulfonate (26.5 g, 117 mmol) in THF (15 ml). The reaction mixture was stirred at −60° C. for 0.5 hours, and then the temperature was slowly increased to room temperature and stirred for 2 hours. The reaction mixture was quenched with aqueous ammonium chloride solution (100 mL), diluted in water (200 ml), and then extracted with EA (300 mL×3). The combined organic layers were washed with brine (150 mL×3), dried over anhydrous sodium sulfate, and then filtered and concentrated under reduced pressure. The residue was purified by column chromatography (0.1% FA) to obtain O1-tert-butyl O4-ethyl 4-[(2-chlorothiazol-4-yl)methyl]piperidine-1,4-dicarboxylate(14 g, 31% yield) as a yellow oil. ¹H NMR (400 MHz, CDCl₃) δ=6.80 (s, 1H), 4.15 (q, J=7.2 Hz, 2H), 3.89 (s, 2H), 2.94-2.84 (m, 4H), 2.11 (d, J=13.2 Hz, 2H), 1.52-1.47 (m, 2H), 1.45 (s, 9H), 1.24 (t, J=7.2 Hz, 3H).

Step 4: tert-butyl 2-chloro-6-oxo-spiro[4H-cyclopenta[d]thiazole-5,4'-piperidine]-1'-carboxylate To a solution of O1-tert-butyl O4-ethyl 4-[(2-chlorothiazol-4-yl)methyl]piperidine-1,4-dicarboxylate (13.8 g, 35.5 mmol) in THF (300 mL) was added dropwise LDA (2 M, 44.4 mL), and the reaction mixture was stirred at 70° C. for 0.5 hours. The reaction mixture was quenched with aqueous ammonium chloride solution (100 mL) at 0° C., diluted in water (100 ml), and then extracted with EA(200 mL×3). The combined organic layers were washed with brine (200 mL×3), dried over anhydrous sodium sulfate, and then filtered and concentrated under reduced pressure. The residue was purified by column chromatography to obtain Intermediate I-47 (6.1 g, 50% yield) as a yellow oil. ¹H NMR (400 MHz, CDCl₃) δ=4.16 (br s, 2H), 3.09-3.02 (s, 2H), 3.01-2.90 (m, 2H), 2.02-1.92 (m, 2H), 1.52-1.48 (m, 11H).

Preparation Example 46: (R)-2-methyl-N-[(6S)-spiro[4,6-dihydrocyclopenta[d]thiazole-5,4'-piperidin]-6-yl]propane-2-sulfinamide (Intermediate I-48)

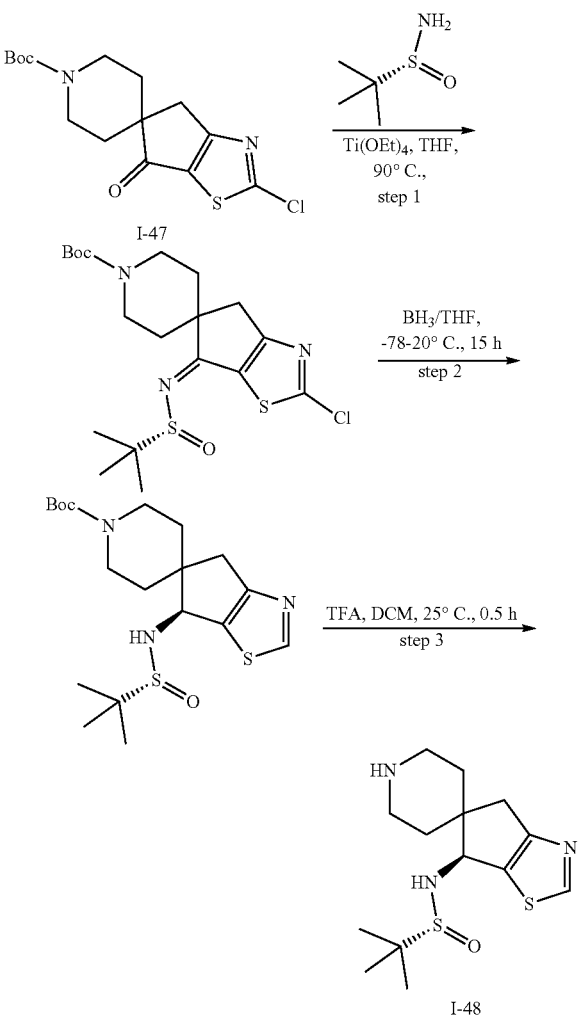

I-48

Step 1: tert-butyl (6Z)-6-[(R)-tert-butylsulfinyl]imino-2-chloro-spiro[4H-cyclopenta[d]thiazole-5,4'-piperidine]-1'-carboxylate To a solution of Intermediate I-47 (3.0 g, 8.75 mmol) and (R)-2-methylpropane-2-sulfinamide (4.24 g, 35.0 mmol) in THF (30 mL) was added dropwise Ti(OEt)₄ (29.9 g, 131 mmol), and the reaction mixture was stirred at 90° C. for 12 hours. The reaction mixture was added with EA (300 mL), diluted in water (50 ml), and then extracted with EA (100 mL×3). The combined organic layers were washed with brine (100 mL×3), dried over anhydrous sodium sulfate, and then filtered and concentrated under reduced pressure. The residue was purified by column chromatography to obtain tert-butyl (6Z)-6-[(R)-tert-butylsulfinyl]imino-2-chloro-spiro[4H-cyclopenta[d]thiazole-5,4'-piperidine]-1'-carboxylate (3.5 g, 90% yield) as a yellow solid. 1 H NMR (400 MHz, CDCl$_3$) δ=4.28-4.14 (m, 2H), 2.96-2.84 (m, 4H), 2.05-1.91 (m, 2H), 1.61-1.55 (m, 2H), 1.49 (s, 9H), 1.28 (s, 9H); MS (EI) m/z: 446.0 [M+H]$^+$.

Step 2: tert-butyl (6S)-6-[[(R)-tert-butylsulfinyl]amino]spiro[4,6-dihydrocyclopenta[d]thiazole-5,4'-piperidine]-1'-carboxylate To a solution of tert-butyl (6Z)-6-[(R)-tert-butyl sulfinyl] imino-2-chloro-spiro[4H-cyclopenta[d]thiazole-5,4'-piperidine]-1'-carboxylate (3.5 g, 7.85 mmol) in THF (30 mL) was added BH$_3$. THF (1 M, 31.4 mL), and the reaction mixture was stirred at −70° C. for 2 hours. The reaction mixture was quenched with MeOH (10 mL) at 0° C., diluted in water (100 ml), and then extracted with EA(100 mL×3). The combined organic layers were washed with brine (50 mL×3), dried over anhydrous sodium sulfate, and then filtered and concentrated under reduced pressure. The residue was purified by column chromatography to obtain tert-butyl (65)-6-[[(R)-tert-butyl sulfinyl]amino]spiro[4,6-dihydrocyclopenta[d]thiazole-5,4'-piperidine]-1'-carboxylate (660 mg, 20%) as a yellow solid. $^1$H NMR (400 MHz, CDCl$_3$) δ=8.78 (s, 1H), 4.57 (d, J=8.6 Hz, 1H), 4.13-3.95 (m, 2H), 3.65-3.52 (m, 1H), 3.06-2.98 (m, 1H), 2.95-2.85 (m, 2H), 1.91-1.78 (m, 2H), 1.64 (d, J=14.0 Hz, 2H), 1.47 (s, 9H), 1.24-1.21 (s, 9H).

Step 3: (R)-2-methyl-N-[(6S)-spiro[4,6-dihydrocyclopenta[d]thiazole-5,4'-piperidin]-6-yl]propane-2-sulfinamide To a solution of tert-butyl (6S)-6-[[(R)-tert-butylsulfinyl]amino]spiro[4,6-dihydrocyclopenta[d]thiazole-5,4'-piperidine]-1'-carboxylate (200 mg, 484 μmol) in DCM (6 mL) was added TFA (2.76 g, 24.2 mmol), and the reaction mixture was stirred at 25° C. for 0.5 hours. The reaction mixture was quenched with saturated aqueous K$_2$CO$_3$ solution (20 mL) at 25° C., diluted in water (30 ml), and then extracted with DCM (50 mL×3). The combined organic layers were washed with brine (20 mL×3), dried over anhydrous sodium sulfate, and then filtered and concentrated under reduced pressure to obtain Intermediate I-48 (140 mg, crude product) as a yellow solid. $^1$H NMR (400 MHz, CDCl$_3$) δ=8.77 (s, 1H), 4.58 (d, J=8.8 Hz, 1H), 3.67 (d, J=8.8 Hz, 1H), 3.16-3.05 (m, 2H), 2.90-2.84 (m, 2H), 2.60-2.36 (m, 2H), 1.93-1.85 (m, 2H), 1.69-1.61 (m, 1H), 1.59-1.53 (m, 1H), 1.24 (s, 9H).

Preparation Example 47: (S)-2-methyl-N-[(6R)-spiro[4,6-dihydrocyclopenta[d]thiazole-5,4'-piperidin]-6-yl]propane-2-sulfinamide (Intermediate I-49)

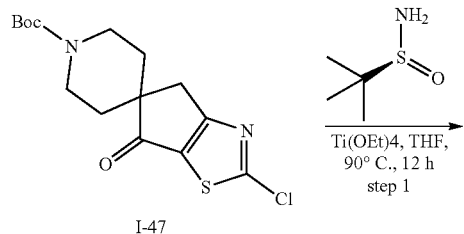

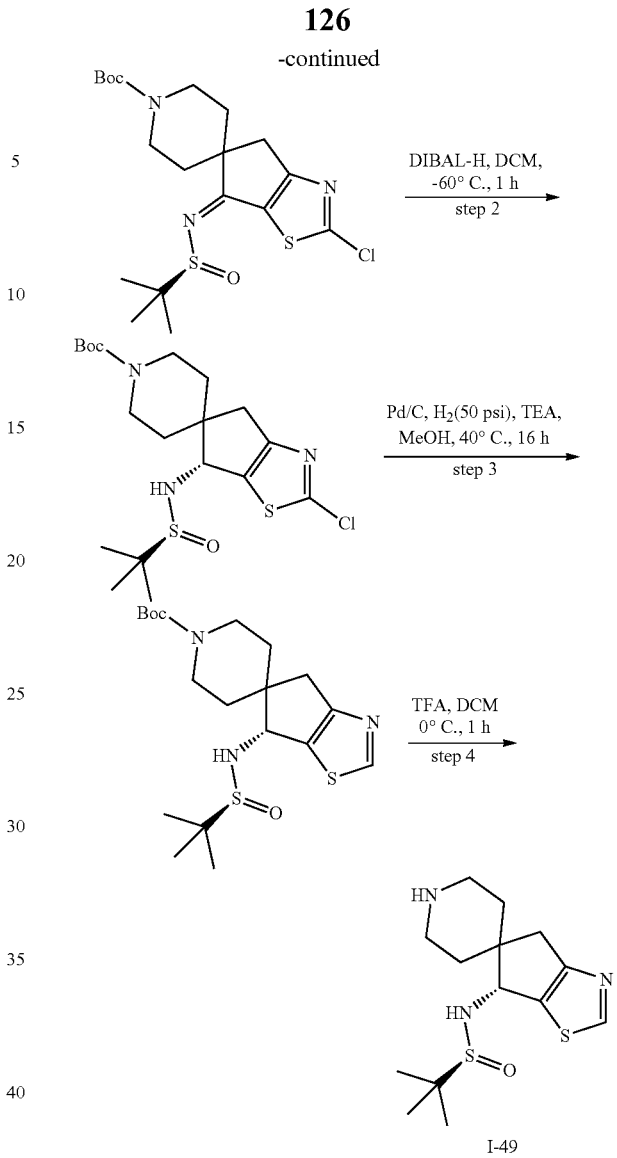

Step 1: tert-butyl (6Z)-6-[(S)-tert-butylsulfinyl]imino-2-chloro-spiro[4H-cyclopenta[d]thiazole-5,4'-piperidine]-1'-carboxylate To a solution of Intermediate I-47 (3.0 g, 8.75 mmol) in THF (30 mL), Ti(OEt)$_4$ (29.9 g, 131 mmol) and (S)-2-methylpropane-2-sulfinamide (4.24 g, 35.0 mmol) were added, and the reaction mixture was stirred at 90° C. for 12 hours. The reaction mixture was quenched with water (30 ml) and extracted with EA (300 mL). After filtration, the filtrate was concentrated under reduced pressure, added with EA (100 mL), washed with brine (20 mL×3), dried over anhydrous sodium sulfate, and then filtered and then concentrated under reduced pressure. The residue was purified by column chromatography to obtain tert-butyl (6Z)-6-[(S)-tert-butylsulfinyl]imino-2-chloro-spiro[4H-cyclopenta[d]thiazole-5,4'-piperidine]-1'-carboxylate (3.7 g, 94% yield) as a yellow solid. $^1$H NMR (400 MHz, CDCl$_3$) δ=4.28-4.15 (m, 2H), 2.97-2.86 (m, 4H), 2.06-1.98 (m, 1H), 1.97-1.91 (m, 1H), 1.58-1.52 (m, 2H), 1.49 (s, 9H), 1.28 (s, 9H).

Step 2: tert-butyl (6R)-6-[[(S)-tert-butylsulfinyl]amino]-2-chloro-spiro[4,6-dihydrocyclopenta[d]thiazole-5,4'-piperidine]-1'-carboxylate To a solution of tert-butyl (6Z)-6-[(S)-tert-butylsulfinyl] imino-2-chloro-spiro[4H-cyclopenta[d]thiazole-5,4'-piperidine]-1'-carboxylate (2.0 g, 4.48 mmol) in DCM (20 mL) was added DIBAL-H (1 M, 13.4 mL), and the reaction mixture was stirred at −60° C. for 1 hour. The reaction mixture was quenched with methanol (0.5 ml) at −60° C. and filtered. The filtrate was concentrated under reduced pressure and purified by column chromatography to obtain tert-butyl (6R)-6-[[(S)-tert-butyl sulfinyl]amino]-2-chloro-spiro[4, 6-dihydrocyclopenta[d]thiazole-5,4'-piperidine]-1'-carboxylate(1.6 g, 78% yield) as a pale yellow solid. $^1$H NMR (400 MHz, CDCl$_3$) δ=4.53 (d, J=8.4 Hz, 1H), 4.10-3.94 (m, 2H), 3.55 (d, J=8.4 Hz, 1H), 3.07-2.77 (m, 4H), 1.90-1.75 (m, 2H), 1.63 (d, J=8.0 Hz, 1H), 1.57 (br s, 1H), 1.47 (s, 9H), 1.23 (s, 9H); MS (EI) m/z: 448.2 [M+H]$^+$.

Step 3: tert-butyl (6R)-6-[[(S)-tert-butylsulfanyl]amino] spiro[4,6-dihydrocyclopenta[d]thiazole-5,4'-piperidine]-1'-carboxylate To a solution of tert-butyl (6R)-6-[[(S)-tert-butylsulfinyl] amino]-2-chloro-spiro[4,6-dihydrocyclopenta[d]thiazole-5, 4'-piperidine]-1'-carboxylate (1.0 g, 2.23 mmol) in methanol (10 mL) was added TEA (677 mg, 6.70 mmol), followed by purging 3 times with N$_2$. Pd/C (100 mg, 10% purity) was added to the reaction mixture, and H$_2$ gas was injected thereinto. The reaction mixture was stirred at 40° C. for 16 hours. After filtration, the filtrate was concentrated under reduced pressure, and then the residue was purified by column chromatography to obtain tert-butyl (6R)-6-[[(S)-tert-butylsulfanyl]amino]spiro[4,6-dihydrocyclopenta[d] thiazole-5,4'-piperidine]-1'-carboxylate (880 mg, 93% yield) as a white solid. $^1$H NMR (400 MHz, CDCl$_3$) δ=8.79 (s, 1H), 4.58 (d, J=8.8 Hz, 1H), 4.09-3.90 (m, 2H), 3.68-3.53 (m, 1H), 3.08-2.81 (m, 4H), 1.93-1.76 (m, 2H), 1.68-1.57 (m, 2H), 1.47 (s, 9H), 1.23 (s, 9H); MS (EI) m/z: 414.2 [M+H]$^+$.

Step 4: (S)-2-methyl-N-[(6R)-spiro[4,6-dihydrocyclopenta[d]thiazole-5,4'-piperidin]-6-yl]propane-2-sulfinamide To a solution of tert-butyl (6R)-6-[[(5)-tert-butylsulfanyl] amino]spiro[4,6-dihydrocyclopenta[d]thiazole-5,4'-piperidine]-1'-carboxylate (400 mg, 967 μmol) in DCM (9 mL) was added TFA (3 mL), followed by stirring at 0° C. for 1 hour. The reaction mixture was concentrated under reduced pressure, adjusted to pH 9 with sat. K$_2$CO$_3$, and then extracted with DCM/i-PrOH=3/1 (3×5 mL). The organic layer was dried over anhydrous sodium sulfate, filtered, and then concentrated under reduced pressure to obtain Intermediate I-49 (310 mg, crude product) as a light yellow oil. MS (EI) m/z: 314.2 [M+H]$^+$.

Preparation Example 48: 6-(5-bromopyrazin-2-yl) sulfanyl-5-chloro-3H-quinazolin-4-one (Intermediate I-50)

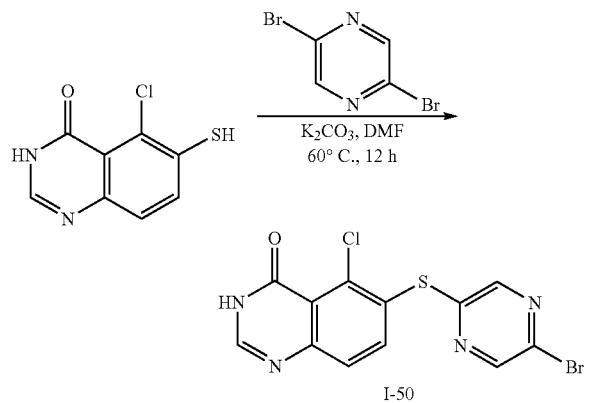

To a solution of 5-chloro-6-mercaptoquinazolin-4(3H)-one (880 mg, 3.75 mmol) in DMF (20 mL), K$_2$CO$_3$ (1.56 g, 11.3 mmol) and 2,5-dibromopyrazine (3.57 g, 15.00 mmol) were added, and the mixture was stirred at 0° C. for 2 hours. The reaction mixture was quenched by addition of aqueous ammonium chloride (50 mL) at 25° C., diluted with water (50 mL), and extracted with EA (100 mL×3). The combined organic layers were washed with brine (50 mL×3), dried over anhydrous sodium sulfate, and then filtered and concentrated under reduced pressure to obtain a residue. The residue was purified by column chromatography (PE/EA=1/1 to 0:1) to obtain Intermediate I-50 (500 mg, 36% yield) as a yellow solid. $^1$H NMR (400 MHz, DMSO-d$_6$) δ=12.50 (br s, 1H), 8.71 (d, J=1.0 Hz, 1H), 8.46-8.43 (m, 1H), 8.15 (s, 1H), 7.98 (d, J=8.8 Hz, 1H), 7.61 (d, J=8.8 Hz, 1H); MS (EI) m/z: 371.1 [M+H]$^+$.

Preparation Example 49: (S)-N-[(6R)-1'-[5-[(5-chloro-4-oxo-3H-quinazolin-6-yl)sulfanyl]pyrazin-2-yl]spiro[4,6-dihydrocyclopenta[d]thiazole-5,4'-piperidin]-6-yl]-2-methyl-propane-2-sulfinamide (Intermediate I-51)

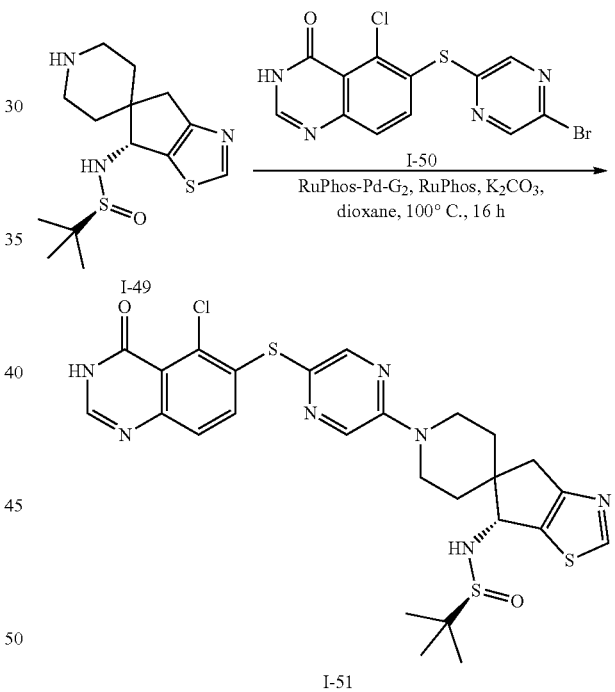

To a solution of Intermediate I-50 (402 mg, 1.09 mmol) in dioxane (5 mL), Intermediate I-49 (310 mg, 989 μmol), RuPhos (92.3 mg, 198 μmol), RuPhos-Pd-G2 (76.8 mg, 98.9 μmol) and K$_2$CO$_3$ (410 mg, 2.97 mmol) were added, and the mixture was stirred at 100° C. for 16 hours. The reaction mixture was concentrated under reduced pressure, and the residue was purified by column chromatography to obtain Intermediate I-51 (180 mg, 28% yield) as a yellow solid. $^1$H NMR (400 MHz, CDCl$_3$) δ=8.83 (s, 1H), 8.28 (s, 1H), 8.24 (s, 1H), 7.96 (s, 1H), 7.50 (d, J=8.8 Hz, 1H), 7.30 (s, 1H), 4.67 (d, J=8.4 Hz, 1H), 4.49-4.22 (m, 2H), 3.89 (d, J=9.6 Hz, 1H), 3.31-3.25 (m, 1H), 3.23-3.13 (m, 2H), 3.11-2.93 (m, 2H), 1.84 (s, 2H), 1.78 (d, J=4.4 Hz, 1H), 1.75 (d, J=4.0 Hz, 1H), 1.26 (s, 9H); MS (EI) m/z: 602.3 [M+H]$^+$.

Preparation Example 50: (R)-N-[(6S)-1'-[5-[(5-chloro-4chloro-3H-quinazolin-6-yl)sulfanyl]pyrazin-2-yl]spiro]4,6-dihydrocyclopenta[d]thiazole-5,4'-piperidin]-6-yl]-2-methyl-propane-2-sulfinamide (Intermediate I-52)

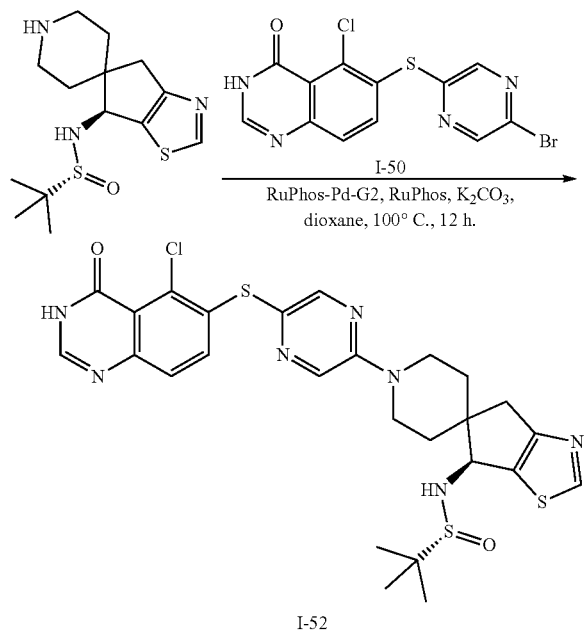

Intermediate I-52 (300 mg, 53%) was prepared in the same method as in Preparation Example 49, except that Intermediate I-48 was used instead of Intermediate I-49 in Preparation Example 49. $^1$H NMR (400 MHz, CDCl$_3$) δ=10.74-10.64 (m, 1H), 8.82 (s, 1H), 8.26 (s, 1H), 8.23 (s, 1H), 7.98-7.92 (m, 1H), 7.48 (d, J=8.8 Hz, 1H), 7.29 (s, 1H), 4.68 (d, J=8.8 Hz, 1H), 4.41 (d, J=13.2 Hz, 1H), 4.35-4.26 (m, 1H), 3.29-3.16 (m, 2H), 3.11-3.02 (m, 1H), 2.99-2.93 (m, 1H), 2.18-1.99 (m, 2H), 1.87-1.75 (m, 2H), 1.27 (s, 9H).

Preparation Example 51: tert-butyl 2-chloro-4-oxo-spiro[6H-cyclopenta[d]thiazole-5,4'-piperidine]-1'-carboxylate (Intermediate I-53)

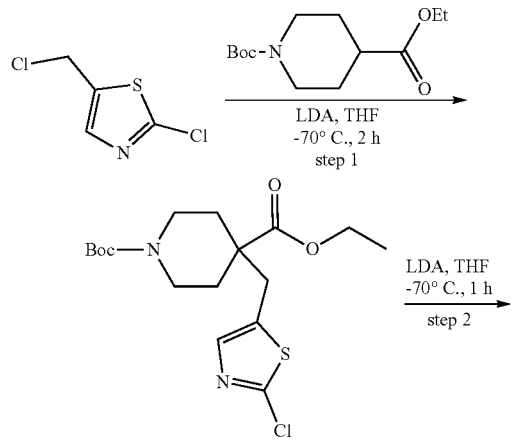

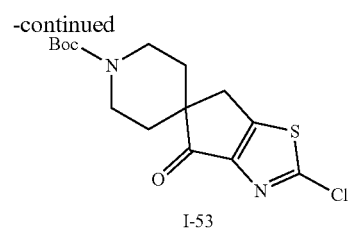

Step 1: O4-ethyl 4-[(2-chlorothiazole-5-yl)methyl]piperidine-1,4-dicarboxylate

To a solution of O1-tert-butyl 04-ethyl piperidine-1,4-dicarboxylate (30.3 g, 118 mmol) in THF (200 mL) was added LDA (2 M, 64.3 mL) at −70° C., and the mixture was stirred at −70° C. for 1 hour. The reaction mixture was added dropwise with 2-chloro-5-(chloromethyl)thiazole (18 g, 107 mmol) in THF (40 mL) and stirred at −70° C. for 1 hour. The reaction mixture was quenched with aqueous ammonium chloride solution and extracted with EA (3×200 mL). The combined organic layers were washed with brine (200 mL×2), dried over anhydrous sodium sulfate, and then filtered and concentrated under reduced pressure. The residue was purified by column chromatography to obtain 04-ethyl 4-[(2-chlorothiazole-5-yl)methyl]piperidine-1,4-dicarboxylate (25 g, 60% yield) as a yellow oil. $^1$H NMR (400 MHz, CDCl$_3$) δ=7.22 (s, 1H), 4.18 (q, J=7.2 Hz, 2H), 3.97-3.77 (m, 2H), 3.00 (s, 2H), 2.95 (s, 2H), 2.11 (d, J=13.2 Hz, 2H), 1.46 (s, 9H), 1.41 (d, J=4.4 Hz, 2H), 1.26 (t, J=7.2 Hz, 3H).

Step 2: tert-butyl 2-chloro-4-oxo-spiro[6H-cyclopenta[d]thiazole-5,4'-piperidine]-1'-carboxylate To a solution of 04-ethyl 4-[(2-chlorothiazole-5-yl)methyl]piperidine-1,4-dicarboxylate (15 g, 38.6 mmol) in THF (350 mL) was added LDA (2 M, 30.9 mL) at −70° C., and the mixture was stirred at −70° C. for 1 hour. The reaction mixture was quenched with aqueous ammonium chloride solution (500 mL) at 0° C. and extracted with EA (3×100 mL). The combined organic layers were washed with brine (200 mL×2), dried over anhydrous sodium sulfate, and then filtered and concentrated under reduced pressure. The residue was purified by column chromatography to obtain Intermediate I-53 (4.0 g, 30% yield) as a yellow solid. $^1$H NMR (400 MHz, CDCl$_3$) δ=4.26-4.03 (m, 2H), 3.11 (s, 2H), 2.99 (t, J=12.0 Hz, 2H), 2.03-1.92 (m, 2H), 1.55-1.51 (m, 1H), 1.48 (s, 9H), 1.47-1.44 (m, 1H).

Preparation Example 52: (S)-2-methyl-N-[(4R)-spiro[4,6-dihydrocyclopenta[d]thiazole-5,4'-piperidin]-4-yl]propane-2-sulfinamide (Intermediate I-54)

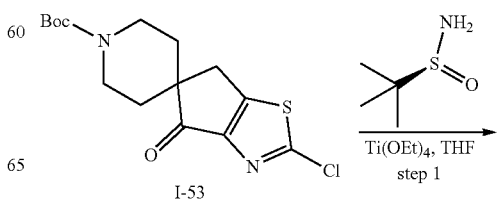

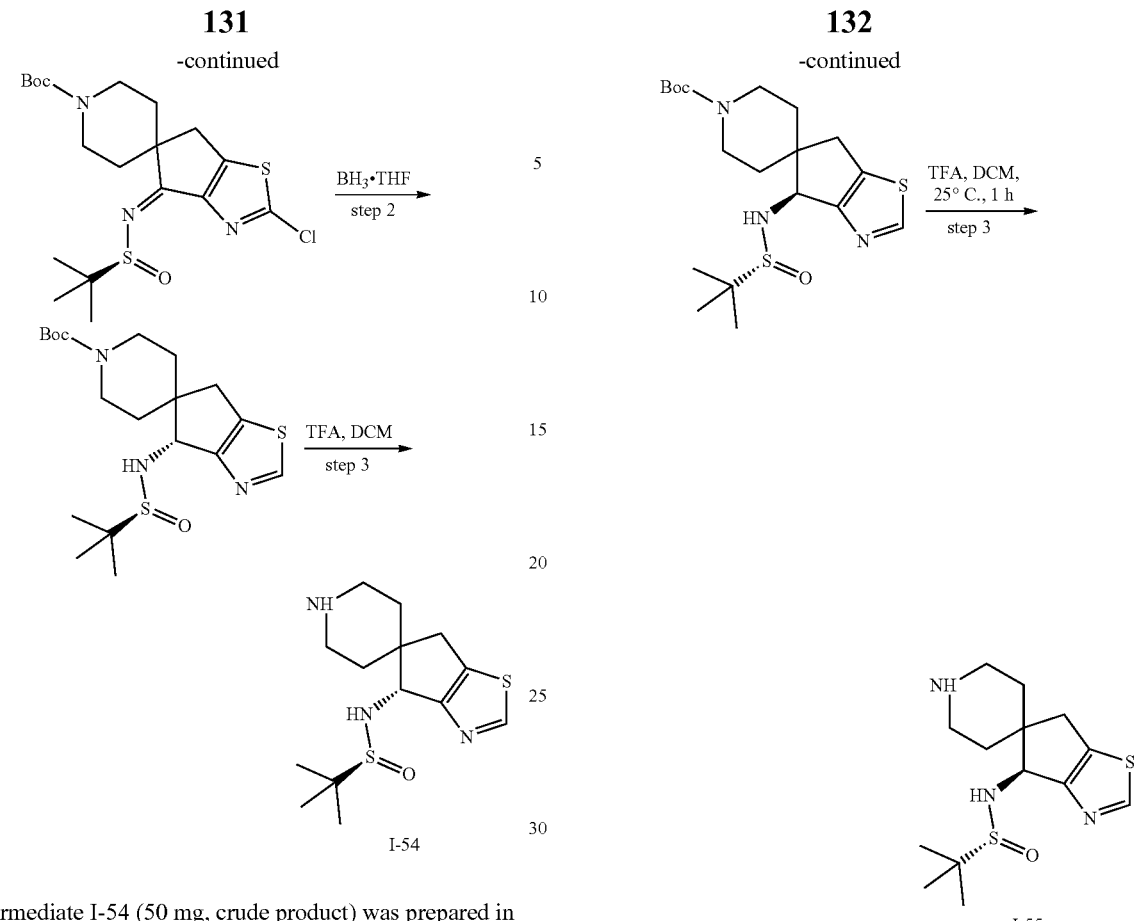

Intermediate I-54 (50 mg, crude product) was prepared in the same method as in Preparation Example 46, except that Intermediate I-53 was used instead of Intermediate I-47, and (S)-2-methylpropane-2-sulfinamide was used instead of (R)-2-methylpropane-2-sulfinamide in Preparation Example 46. $^1$H NMR (400 MHz, CDCl$_3$) δ=9.91-9.65 (m, 1H), 8.76-8.52 (m, 1H), 4.59 (s, 1H), 3.53-3.37 (m, 2H), 3.33-3.16 (m, 2H), 3.10-3.01 (m, 1H), 2.93-2.85 (m, 1H), 2.37-2.14 (m, 2H), 2.00-1.81 (m, 2H), 1.28 (s, 9H).

Preparation Example 53: (R)-2-methyl-N-(4S)-spiro[4,6-dihydrocyclopenta[d]thiazole-5,4'-piperidin]-4-yl]propane-2-sulfinamide (Intermediate I-55)

Intermediate I-55 (260 mg) was prepared in the same method as in Preparation Example 52, except that (R)-2-methylpropane-2-sulfinamide was used instead of (S)-2-methylpropane-2-sulfinamide in Preparation Example 52. $^1$H NMR (400 MHz, CDCl$_3$) δ=8.74 (s, 1H), 4.49 (d, J=9.2 Hz, 1H), 3.84 (d, J=8.8 Hz, 1H), 3.20-3.11 (m, 2H), 3.01-2.96 (m, 1H), 2.94-2.88 (m, 2H), 2.85-2.80 (m, 1H), 2.04-1.90 (m, 2H), 1.71 (d, J=13.2 Hz, 1H), 1.57 (d, J=14.0 Hz, 1H), 1.28 (s, 9H).

Preparation Example 54: (S)-N-[(4R)-1'-[5-[(5-chloro-4chloro-3H-quinazolin-6-yl)sulfanyl]pyrazin-2-yl]spiro[4,6-dihydrocyclopenta[d]thiazole-5,4'-piperidin]-4-yl]-2-methyl-propane-2-sulfinamide (Intermediate I-56)

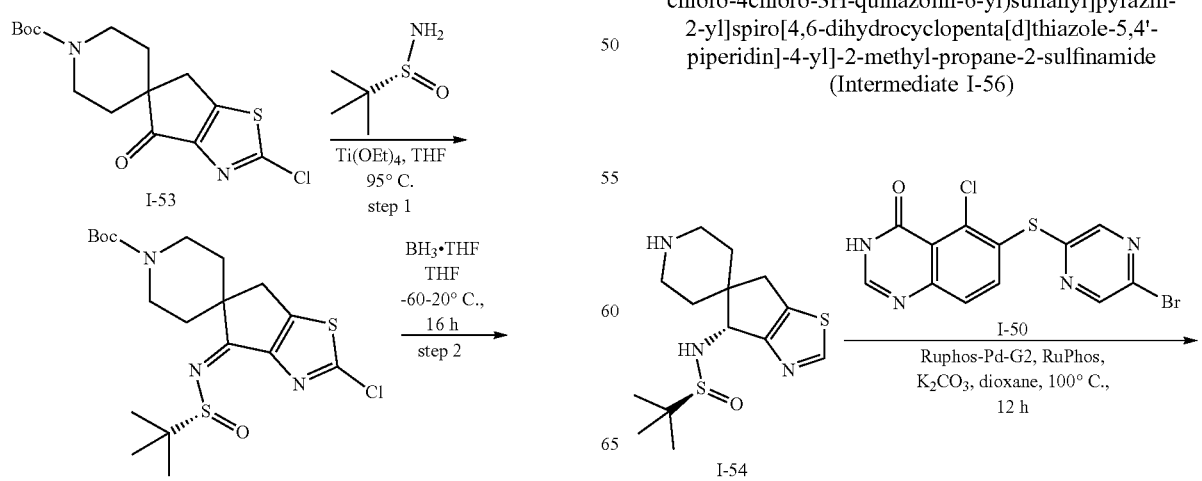

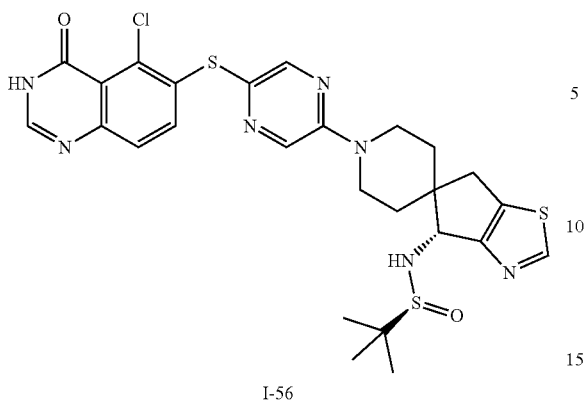

I-56

Intermediate I-56 (240 mg, 34%) was prepared in the same method as in Preparation Example 49, except that Intermediate I-54 was used instead of Intermediate I-49 in Preparation Example 49. $^1$H NMR (400 MHz, DMSO-$d_6$) δ=12.48-12.11 (m, 1H), 8.98 (s, 1H), 8.51 (d, J=1.2 Hz, 1H), 8.31 (d, J=1.2 Hz, 1H), 8.04 (s, 1H), 7.50 (d, J=8.8 Hz, 1H), 7.19 (d, J=8.8 Hz, 1H), 5.78 (d, J=10.4 Hz, 1H), 4.35-4.20 (m, 3H), 3.29-3.15 (m, 2H), 3.04-2.94 (m, 1H), 2.92-2.85 (m, 1H), 1.97-1.90 (m, 1H), 1.85-1.76 (m, 1H), 1.74-1.66 (m, 2H), 1.16 (s, 9H).

Preparation Example 55: tert-butyl N-[(3S,4S)-8-[5-bromo-3-(hydroxymethyl)pyrazin-2-yl]-3-methyl-2-oxa-8-azaspiro[4.5]decan-4-yl]carbamate (Intermediate I-57)

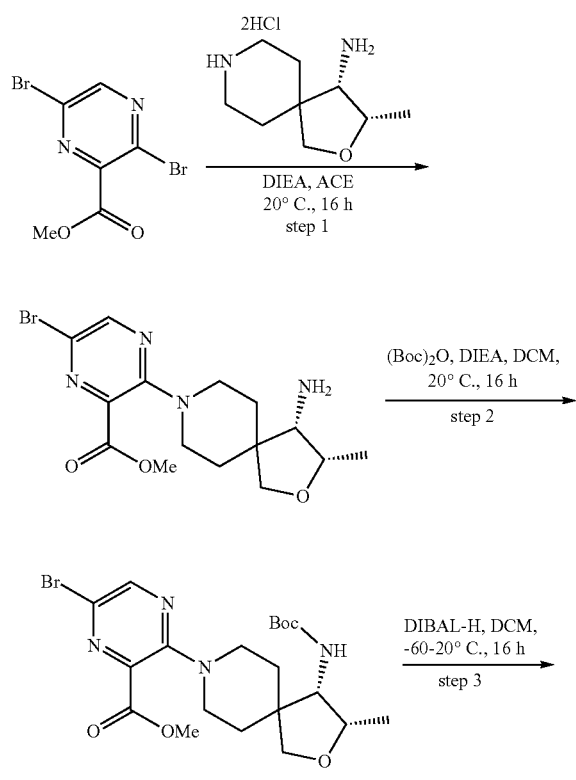

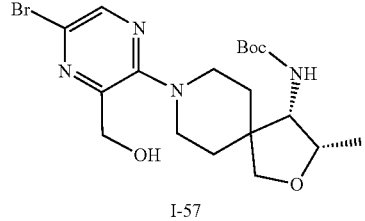

I-57

Step 1: methyl 3-[(3S,4S)-4-amino-3-methyl-2-oxa-8-azaspiro[4.5]decan-8-yl]-6-bromo-pyrazine-2-carboxylate To a solution of methyl 3,6-dibromopyrazine-2-carboxylate (500 mg, 1.69 mmol) in ACN (10 mL), DIPEA (1.09 g, 8.45 mmol) and (3S,4S)-3-methyl-2-oxa-8-azaspiro[4.5]decan-4-amine (384 mg, 1.86 mmol, HCl) were added, and the mixture was stirred at 20° C. for 16 hours. The reaction mixture was concentrated under reduced pressure to obtain methyl 3-[(3S,4S)-4-amino-3-methyl-2-oxa-8-azaspiro[4.5]decan-8-yl]-6-bromo-pyrazine-2-carboxylate (650 mg, crude product) as a brown oil. MS (EI) m/z: 387.0 [M+H]$^+$.

Step 2: methyl 6-bromo-3-[(3S,4S)-4-(tert-butoxycarbonylamino)-3-methyl-2-oxa-8-azaspiro[4.5]decan-8-yl]pyrazine-2-carboxylate To a solution of methyl 3-[(3S,4S)-4-amino-3-methyl-2-oxa-8-azaspiro[4.5]decan-8-yl]-6-bromo-pyrazine-2-carboxylate (650 mg, 1.69 mmol) in CM (10 mL), DIPEA (436 mg, 3.37 mmol) and (Boc)$_2$O (552 mg, 2.53 mmol) were added, and the mixture was stirred at 20° C. for 16 hours. The reaction mixture was diluted with water (20 mL) and extracted with EA (3×10 mL). The combined organic layers were dried over anhydrous sodium sulfate, and then filtered and concentrated under reduced pressure. The residue was purified by column chromatography to obtain methyl 6-bromo-3-[(3S,4S)-4-(tert-butoxycarbonylamino)-3-methyl-2-oxa-8-azaspiro[4.5]decan-8-yl]pyrazine-2-carboxylate (710 mg, 83% yield) as a yellow solid. $^1$H NMR (400 MHz, CDCl$_3$) δ=8.12 (s, 1H), 4.55-4.47 (m, 1H), 4.14-4.04 (m, 1H), 3.96-3.81 (m, 4H), 3.64-3.57 (m, 2H), 3.57-3.44 (m, 2H), 3.38-3.29 (m, 1H), 3.27-3.13 (m, 1H), 1.78-1.73 (m, 1H), 1.72-1.63 (m, 2H), 1.57-1.52 (m, 1H), 1.38 (s, 9H), 1.12 (d, J=6.4 Hz, 3H); MS (EI) m/z: 487.0 [M+H]$^+$.

Step 3: tert-butyl N-[(3S,4S)-8-[5-bromo-3-(hydroxymethyl)pyrazin-2-yl]-3-methyl-2-oxa-8-azaspiro[4.5]decan-4-yl]carbamate To a solution of methyl 6-bromo-3-[(3S,4S)-4-(tert-butoxycarbonylamino)-3-methyl-2-oxa-8-azaspiro[4.5]decan-8-yl]pyrazine-2-carboxylate (300 mg, 618 μmol) in DCM (10 mL) was added DIBAL-H (1 M, 1.85 mL) at −60° C., and the mixture was stirred at 20° C. for 16 hours. The reaction mixture was quenched with methanol (0.5 mL) at −60° C. and filtered. The filtrate was concentrated under reduced pressure, and then the residue was purified by column chromatography to obtain Intermediate I-57 (90 mg, 31%) as a white solid. $^1$H NMR (400 MHz, CDCl$_3$) δ=8.20 (s, 1H), 4.65 (s, 2H), 4.60 (d, J=10.4 Hz, 1H), 4.22-4.15 (m, 1H), 3.98 (dd, J=4.4, 10.8 Hz, 1H), 3.70-3.65 (m, 2H), 3.40-3.27 (m, 2H), 3.15-3.09 (m, 1H), 3.03-2.97 (m, 1H), 1.96-1.83 (m, 2H), 1.81 (d, J=3.2 Hz, 1H), 1.68-1.62 (m, 1H), 1.46 (s, 9H), 1.20 (d, J=6.4 Hz, 3H); MS (EI) m/z: 459.0 [M+H]$^+$.

Preparation Example 56: tert-butyl N-[(3S,4S)-8-(6-amino-5-bromo-3-carbamoyl-pyrazin-2-yl)-3-methyl-2-oxa-8-azaspiro[4.5]decan-4-yl]carbamate (Intermediate I-58)

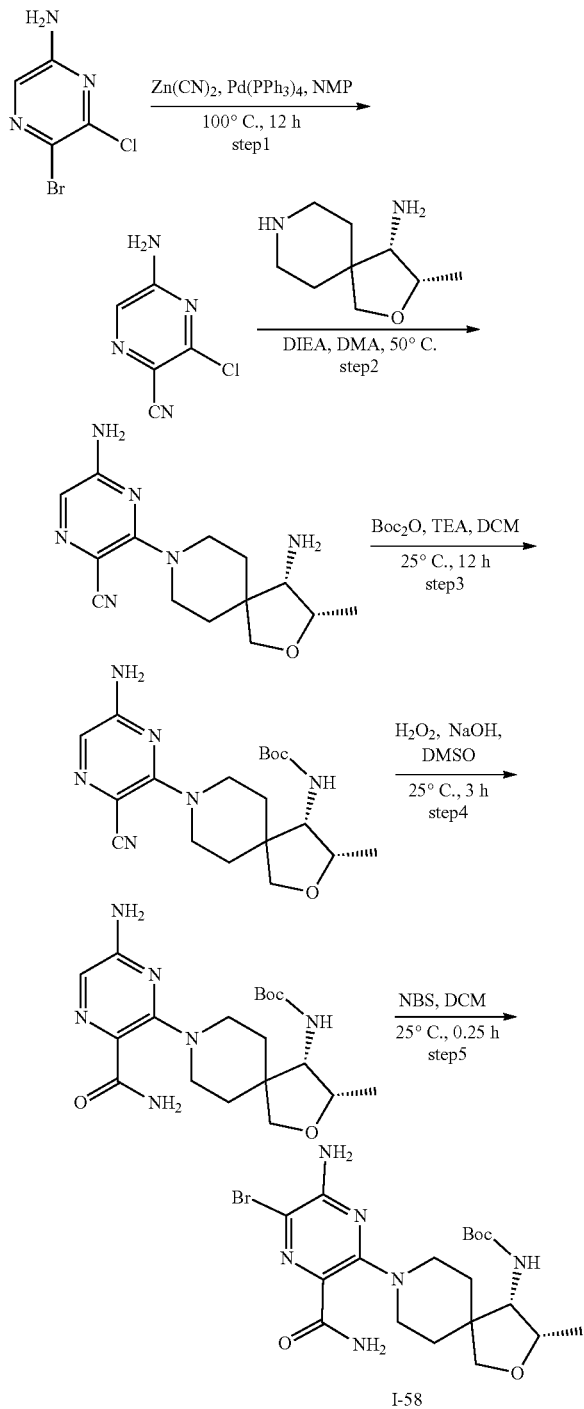

Step 1: 5-amino-3-chloro-pyrazine-2-carbonitrile

To a solution of 5-bromo-6-chloro-pyrazine-2-amine (10 g, 48.0 mmol) in NMP (100 mL) was added Pd(PPh$_3$)$_4$ (2.77 g, 2.40 mmol), and the mixture was stirred at 100° C. for 12 hours. The reaction mixture was quenched with aqueous ammonium chloride solution (100 mL) at room temperature, diluted with water (100 mL), and then extracted with EA (3×200 mL). The combined organic layers were washed with brine (3×100 mL), dried over Na$_2$SO$_4$, and then filtered and concentrated under vacuum. The residue was purified by column chromatography to obtain 5-amino-3-chloro-pyrazine-2-carbonitrile (2.6 g, 35%) as a yellow solid. $^1$H NMR (400 MHz, DMSO-d$_6$) δ=8.11 (s, 2H), 7.87 (s, 1H).

Step 2: 5-amino-3-[(3S,4S)-4-amino-3-methyl-2-oxa-8-azaspiro[4.5]decan-8-yl]pyrazine-2-carbonitrile To a solution of 5-amino-3-chloro-pyrazine-2-carbonitrile (1.0 g, 6.47 mmol) in DMF (10 mL), (3 S,4S)-3-methyl-oxa-8-azaspiro[4.5]decan-4-amine (1.21 g, 7.12 mmol, 2 HCl) and DIEA (4.18 g, 32.4 mmol) were added, and the mixture was stirred at 80° C. for 12 hours. The reaction mixture was quenched with aqueous ammonium chloride solution (20 mL) at room temperature, diluted with water (30 mL), and then extracted with DCM (3×50 mL). The combined organic layers were washed with brine (3×20 mL), dried over Na$_2$SO$_4$, and then filtered and concentrated under vacuum to obtain 5-amino-3-[(3S,4S)-4-amino-3-methyl-2-oxa-8-azaspiro[4.5]decan-8-yl]pyrazine-2-carbonitrile (1.8 g, crude product) as a yellow solid. MS (EI) m/z: 289.4 [M+H]$^+$.

Step 3: tert-butyl N-[(3S,4S)-8-(6-amino-3-cyano-pyrazin-2-yl)-3-methyl-2-oxa-8-azaspiro[4.5]decan-4-yl]carbamate To a solution of 5-amino-3-[(3S,4S)-4-amino-3-methyl-2-oxa-8-azaspiro[4.5]decan-8-yl]pyrazine-2-carbonitrile (1.8 g, 6.24 mmol) in DMF (15 mL), Boc$_2$O (2.04 g, 9.36 mmol) and TEA (1.90 g, 18.7 mmol) were added, and the mixture was stirred at 25° C. for 2 hours. The reaction mixture was quenched with aqueous ammonium chloride solution (20 mL) at room temperature, diluted with water (30 mL), and then extracted with EA (3×50 mL). The combined organic layers were washed with brine (3×20 mL), dried over Na$_2$SO$_4$, and then filtered and concentrated under vacuum. The residue was purified by column chromatography to obtain tert-butyl N-[(3 S,4S)-8-(6-amino-3-cyano-pyrazin-2-yl)-3-methyl-2-oxa-8-azaspiro[4.5]decan-4-yl]carbamate (1.3 g, 54%) as a yellow solid. $^1$H NMR (400 MHz, CDCl$_3$) δ=7.39 (s, 1H), 4.86-4.81 (m, 2H), 4.62 (d, J=10.8 Hz, 1H), 4.20-4.15 (m, 1H), 3.98 (dd, J=4.4, 10.8 Hz, 1H), 3.93-3.82 (m, 2H), 3.71-3.63 (m, 3H), 3.62-3.54 (m, 1H), 1.90-1.72 (m, 3H), 1.65-1.60 (m, 1H), 1.46 (s, 9H), 1.20 (d, J=6.4 Hz, 3H).

Step 4: tert-butyl N-[(3S,4S)-8-(6-amino-3-carbamoyl-pyrazin-2-yl)-3-methyl-2-oxa-8-azaspiro[4.5]decan-4-yl]carbamate To a solution of tert-butyl N-[(3S,4S)-8-(6-amino-3-cyano-pyrazin-2-yl)-3-methyl-2-oxa-8-azaspiro[4.5]decan-4-yl]carbamate (300 mg, 772 μmol) in DMSO (6 mL), NaOH (92.7 mg, 2.32 mmol) and H$_2$O$_2$ (4.38 g, 38.6 mmol) were added, and the mixture was stirred at 20° C. for 2 hours. The reaction mixture was quenched with aqueous sodium thiosulfate solution (5 mL) at room temperature, diluted with water (30 mL), and then extracted with EA (3×50 mL). The combined organic layers were washed with brine (3×20 mL), dried over Na$_2$SO$_4$, and then filtered and concentrated under vacuum. The residue was purified by column chromatography to obtain tert-butyl N-[(3 S,4S)-8-(6-amino-3-carbamoyl-pyrazin-2-yl)-3-methyl-2-oxa-8-azaspiro[4.5]decan-4-yl]carbamate (160 mg, 51% yield) as a yellow solid. $^1$H NMR (400 MHz, CDCl$_3$) δ=7.39 (s, 1H), 7.32 (s, 1H), 5.42-5.33 (m, 1H), 4.71-4.65 (m, 2H), 4.61 (d, J=10.4 Hz, 1H), 4.18-4.13 (m, 1H), 3.95 (dd, J=4.4, 10.8 Hz, 1H), 3.71-3.66 (m, 1H), 3.65-3.59 (m, 1H), 3.58-3.49 (m, 1H), 3.37-3.30 (m, 1H), 3.29-3.21 (m, 1H), 1.89-1.83 (m, 1H), 1.81-1.72 (m, 2H), 1.68-1.62 (m, 1H), 1.44 (s, 9H), 1.18 (d, J=6.4 Hz, 3H); MS (EI) m/z: 407.4 [M+H]⁺.

Step 5: tert-butyl N-[(3S,4S)-8-(6-amino-5-bromo-3-carbamoyl-pyrazin-2-yl)-3-methyl-2-oxa-8-azaspiro[4.5]decan-4-yl]carbamate To a solution of tert-butyl N-[(3S,4S)-8-(6-amino-3-carbamoyl-pyrazin-2-yl)-3-methyl-2-oxa-8-azaspiro[4.5]decan-4-yl]carbamate (160 mg, 394 µmol) in DCM (2 mL) was added NBS (77.1 mg, 433 µmol), and the mixture was stirred at 0° C. for 0.25 hours. The reaction mixture was quenched with aqueous ammonium chloride solution (10 mL) at room temperature, diluted with water (20 mL), and then extracted with DCM (3×30 mL). The combined organic layers were washed with brine (3×20 mL), dried over Na₂SO₄, and then filtered and concentrated under vacuum. The residue was purified by column chromatography to obtain Intermediate I-58 (160 mg, 84% yield) as a yellow solid. ¹H NMR (400 MHz, CDCl₃) δ=7.17 (s, 1H), 5.29-5.23 (m, 1H), 5.10 (s, 2H), 4.61 (d, J=10.4 Hz, 1H), 4.19-4.12 (m, 1H), 3.95 (dd, J=4.4, 10.4 Hz, 1H), 3.68 (d, J=7.6 Hz, 1H), 3.63-3.58 (m, 1H), 3.59-3.51 (m, 1H), 3.37-3.32 (m, 1H), 3.30-3.23 (m, 1H), 1.89-1.83 (m, 1H), 1.77 (d, J=5.4 Hz, 1H), 1.67-1.58 (m, 2H), 1.44 (s, 9H), 1.21-1.16 (m, 3H); MS (EI) m/z: 487.3 [M+H]⁺.

Preparation Example 57: 6-bromo-5-fluoro-3-(2-methoxyethyl)quinazolin-4-one (Intermediate I-59)

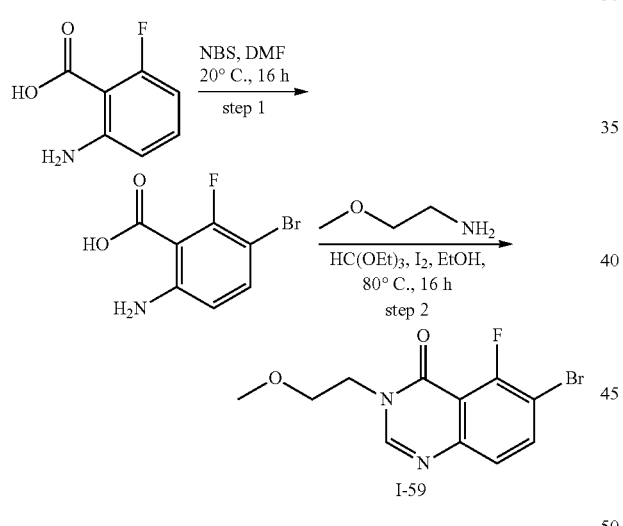

Step 1: 6-amino-3-bromo-2-fluoro-benzoic acid

To a solution of 2-amino-6-fluorobenzoic acid (20.0 g, 129 mmol) in DMF (200 mL) was added NBS (24.1 g, 135 mmol), and the mixture was stirred at 20° C. for 16 hours. The reaction mixture was diluted with water (200 mL) and then extracted with EA (3×100 mL). The combined organic layers were washed with brine (100 mL), dried over Na₂SO₄, and then filtered and concentrated under vacuum to obtain 6-amino-3-bromo-2-fluoro-benzoic acid (24.3 g, 73.3% yield) as a light color solid. ¹H NMR (400 MHz, DMSO-d₆) δ=7.39 (dd, J=7.6, 8.8 Hz, 1H), 6.56 (dd, J=1.2, 8.8 Hz, 1H); MS (EI) m/z: 234.0 [M+H]⁺.

Step 2: 6-bromo-5-fluoro-3-(2-methoxyethyl)quinazolin-4-one

To a solution of 6-amino-3-bromo-2-fluoro-benzoic acid (2.0 g, 8.55 mmol) in ethanol (20 mL), I₂ (217 mg, 855 µmol), diethoxymethoxyethane (1.90 g, 12.8 mmol) and 2-methoxyethaneamine (963 mg, 12.8 mmol) were added, and the mixture was stirred at 80° C. for 16 hours. The reaction mixture was diluted with water (20 mL), and then extracted with EA (3×15 mL). The combined organic layers were dried over Na₂SO₄, and then filtered and concentrated under vacuum. EtOAc (10 mL) was added to the residue to obtain Intermediate I-59 (970 mg, 37% yield) as a white solid. ¹H NMR (400 MHz, CDCl₃) δ=8.08 (s, 1H), 7.87 (dd, J=6.8, 8.8 Hz, 1H), 7.42 (dd, J=1.2, 8.8 Hz, 1H), 4.19-4.14 (m, 2H), 3.70-3.66 (m, 2H), 3.33 (s, 3H).

Preparation Example 58: (S)—N—((R)-2-chloro-4,6-dihydrospiro[cyclopenta[d]thiazole-5,4'-piperidin]-6-yl)-2-methylpropane-2-sulfinamide (Intermediate I-60)

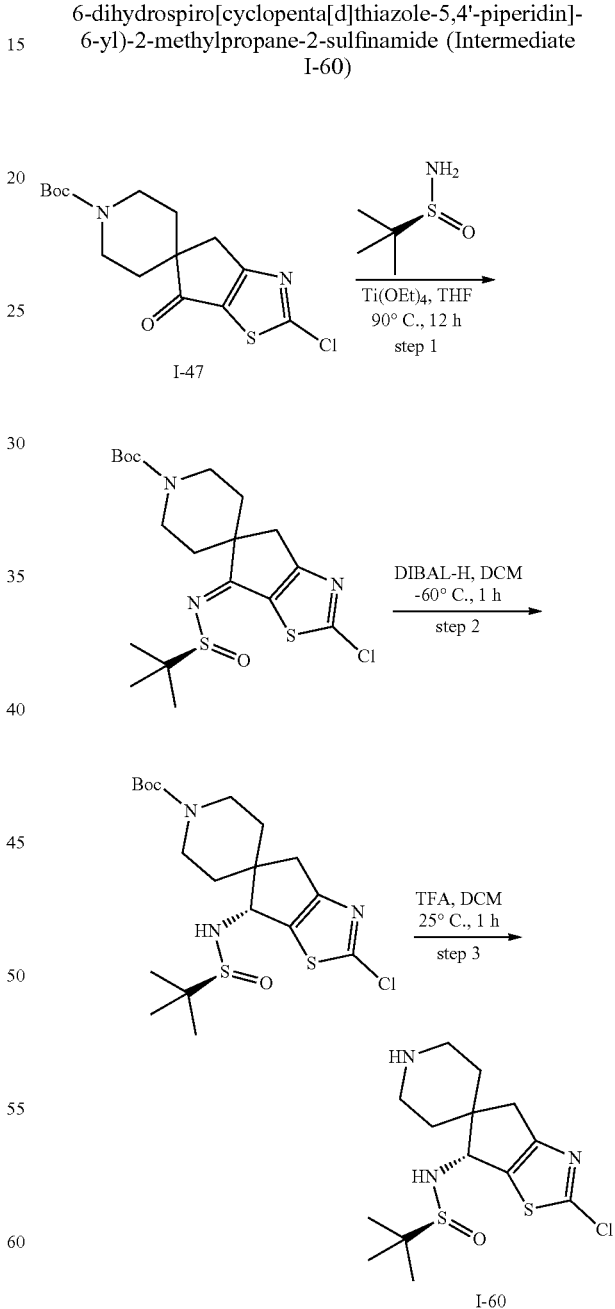

Intermediate I-60 (300 mg, 53%) was prepared in accordance with the same procedure as Preparation Example 47, excluding step 3 therefrom. MS (EI) m/z: 348.1 [M+H]⁺.

Preparation Example 59: (R)—N—((S)-5-methoxy-1,3-dihydrospiro[indene-2,4'-piperidin]-3-yl]-2-methylpropane-2-sulfinamide (Intermediate I-61)

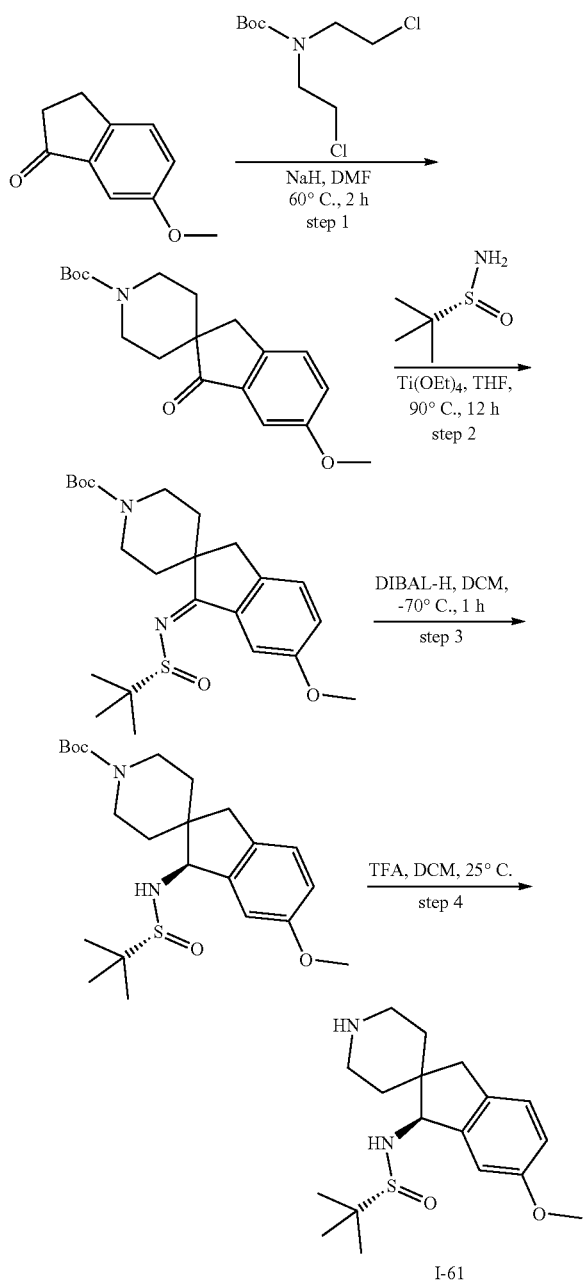

Step 1: tert-butyl 6-methoxy-1-oxo-1,3-dihydrospiro[indene-2,4'-piperidine]-1'-carboxylate To a solution of 6-methoxy-2,3-dihydro-1H-inden-1-one (5.0 g, 30.8 mmol) in DMF (30 mL) was added NaH (3.70 g, 92.5 mmol, 60% purity), and the mixture was stirred at 60° C. for 0.5 hours. The reaction mixture was slowly added dropwise with tert-butyl N,N-bis(2-chloroethyl)carbamate (8.21 g, 33.9 mmol) and then stirred at 60° C. for 1.5 hours. The reaction mixture was quenched by addition of aqueous ammonium chloride (100 mL) at 25, diluted with water (100 mL), and extracted with EA (3×200 mL). The combined organic layers were washed with brine (3×100 mL), dried over anhydrous sodium sulfate, and then filtered and concentrated under reduced pressure. The residue was separated by column chromatography to obtain tert-butyl 6-methoxy-1-oxo-1,3-dihydrospiro[indene-2,4'-piperidine]-1'-carboxylate (640 mg, 6% yield) as a yellow solid. $^1$H NMR (400 MHz, CDCl$_3$) δ=7.37-7.34 (m, 1H), 7.21 (s, 2H), 4.21-4.07 (m, 2H), 3.84 (s, 3H), 3.09-2.95 (m, 4H), 1.95-1.87 (m, 2H), 1.49 (s, 9H), 1.39 (d, J=13.2 Hz, 2H).

Step 2: tert-butyl (R,Z)-1-((tert-butylsulfinyl)imino-6-methoxy-1,3-dihydrospiro[indene-2,4'-piperidine]-1'-carboxylate To a solution of tert-butyl 6-methoxy-1-oxo-1,3-dihydrospiro[indene-2,4'-piperidine]-1'-carboxylate (630 mg, 1.90 mmol) in THF (6 mL), Ti(OEt)$_4$ (6.50 g, 28.5 mmol) and (R)-2-methylpropane-2-sulfinamide (922 mg, 7.60 mmol) were added, and the mixture was stirred at 90° C. for 12 hours. The reaction mixture was diluted with EA (100 mL), quenched with water (20 mL), and then filtered and concentrated under reduced pressure. The mixture was extracted with EA (3×50 mL), and the combined organic layers were washed with brine (3×20 mL), dried over anhydrous sodium sulfate, and then filtered and concentrated under reduced pressure. The residue was separated by column chromatography to obtain tert-butyl (R,Z)-1-((tert-butylsulfinyl)imino-6-methoxy-1,3-dihydrospiro[indene-2,4'-piperidine]-1'-carboxylate (800 mg, 97%) as a yellow solid. $^1$H NMR (400 MHz, CDCl$_3$) δ=8.08-7.97 (m, 1H), 7.30-7.24 (m, 1H), 7.14-7.10 (m, 1H), 4.20-4.08 (m, 2H), 3.87 (s, 3H), 3.01-2.98 (m, 2H), 2.97-2.88 (m, 2H), 1.54-1.50 (m, 2H), 1.49 (s, 9H), 1.46-1.40 (m, 2H), 1.34 (s, 9H).

Step 3: tert-butyl (S)-1-4(R)-tert-butylsulfinyl)amino)-6-methoxy-1,3-dihydrospiro[indene-2,4'-piperidine]-1'-carboxylate To a solution of tert-butyl (R,Z)-1-((tert-butylsulfinyl) imino-6-methoxy-1,3-dihydrospiro[indene-2,4'-piperidine]-1'-carboxylate (800 mg, 1.84 mmol) in DCM (10 mL) was added DIBAL-H (1 M, 5.52 mL), and the mixture was stirred at −70° C. for 1 hour. The reaction mixture was quenched with methanol (2 mL), diluted with DCM (100 mL) and then filtered, and the filtrate was concentrated under reduced pressure. The residue was separated by column chromatography to obtain tert-butyl (S)-1-(((R)-tert-butylsulfinyl)amino)-6-methoxy-1,3-dihydrospiro[indene-2,4'-piperidine]-1'-carboxylate (520 mg, 65%) as a yellow solid. $^1$H NMR (400 MHz, CDCl$_3$) δ=7.11 (d, J=8.0 Hz, 1H), 6.85 (s, 1H), 6.79 (dd, J=2.0, 8.0 Hz, 1H), 4.46 (d, J=9.6 Hz, 1H), 4.02 (d, J=13.2 Hz, 1H), 3.79 (s, 3H), 3.62-3.46 (m, 1H), 3.05-2.96 (m, 1H), 2.90 (dt, J=2.8, 12.8 Hz, 2H), 2.68-2.57 (m, 1H), 1.81-1.54 (m, 2H), 1.54-1.49 (m, 1H), 1.49-1.47 (m, 1H), 1.46 (s, 9H), 1.30 (s, 9H).

Step 4: (R)-N4(S)-5-methoxy-1,3-dihydrospiro[indene-2,4'-piperidin]-3-yl]-2-methylpropane-2-sulfinamide To a solution of tert-butyl (S)-1-(((R)-tert-butylsulfinyl) amino)-6-methoxy-1,3-dihydrospiro[indene-2,4'-piperidine]-1'-carboxylate (520 mg, 1.19 mmol) in DCM (6 mL) was added TFA (2.72 g, 23.8 mmol), and the mixture was stirred at 20° C. for 1 hour. The reaction mixture was concentrated under reduced pressure, and the residue was quenched with calcium carbonate aqueous solution (20 mL), diluted with water (30 mL) and then extracted with DCM (3×50 mL). The mixture was washed with brine (3×20 mL), dried over anhydrous sodium sulfate, and then filtered and concentrated under reduced pressure. The residue was separated by column chromatography to obtain Intermediate I-61 (390 mg, crude product) as a yellow solid. $^1$H NMR (400 MHz, CDCl$_3$) δ=7.11 (d, J=8.0 Hz, 1H), 6.82 (d, J=2.0 Hz, 1H), 6.78 (dd, J=2.4, 8.0 Hz, 1H), 4.43 (d, J=10.4 Hz, 1H), 3.79 (s, 3H), 3.63 (d, J=10.4 Hz, 1H), 3.11-3.02 (m, 3H), 2.87 (dd, J=2.0, 12.4 Hz, 1H), 2.79-2.74 (m, 1H), 2.63 (d, J=15.2 Hz, 1H), 2.15 (dt, J=4.4, 12.8 Hz, 1H), 1.69-1.61 (m, 1H), 1.56 (dd, J=2.4, 13.2 Hz, 1H), 1.31 (s, 9H).

Preparation Example 60: (S)-N-[(4R)-1'-[5-[(5-chloro-4chloro-3H-quinazolin-6-yl)sulfanyl]pyrazin-2-yl]spiro[4,6-dihydrocyclopenta[d]thiazole-5,4'-piperidin]-4-yl]-2-methyl-propane-2-sulfinamide (Intermediate I-62)

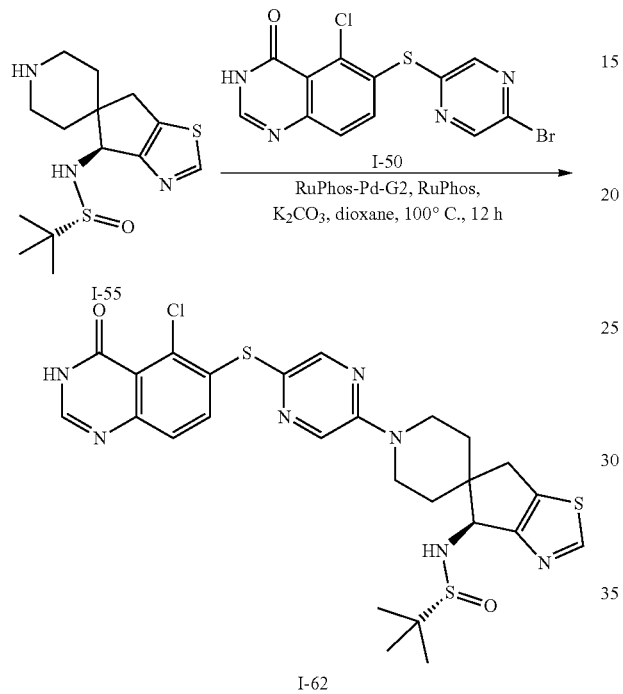

Intermediate I-62 (300 mg, 41% yield) was prepared in the same method as in Preparation Example 49, except that Intermediate I-55 was used instead of Intermediate I-49 in Preparation Example 49. $^1$H NMR (400 MHz, CDCl$_3$) δ=8.76 (s, 1H), 8.26 (d, J=1.2 Hz, 1H), 8.23 (s, 1H), 7.97-7.94 (m, 1H), 7.48 (d, J=8.8 Hz, 1H), 7.27-7.23 (m, 1H), 4.58 (d, J=9.2 Hz, 1H), 4.35-4.28 (m, 1H), 4.23 (d, J=13.6 Hz, 1H), 4.01-3.96 (m, 1H), 3.50 (s, 2H), 3.31 (dd, J=2.0, 13.6 Hz, 2H), 1.87-1.81 (m, 2H), 1.77-1.73 (m, 2H), 1.30 (s, 9H); MS (EI) m/z: 602.1 [M+H]$^+$.

Preparation Example 61: (R)-N-[(6S)-2-chlorospiro[4,6-dihydrocyclopenta[d]thiazole-5,4'-piperidin]-6-yl]-2-methyl-propane-2-sulfinamide (Intermediate I-63)

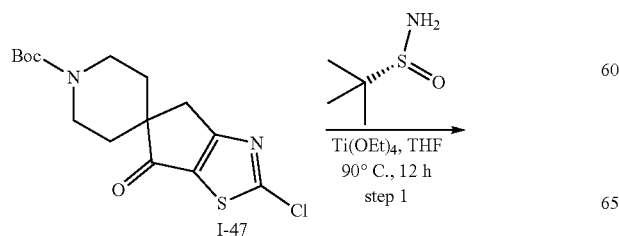

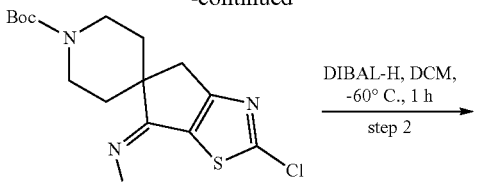

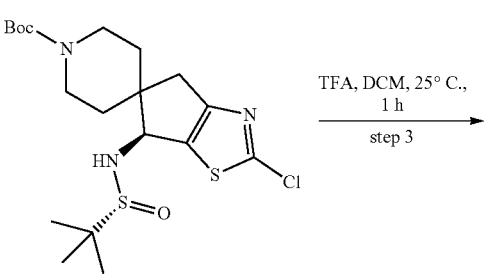

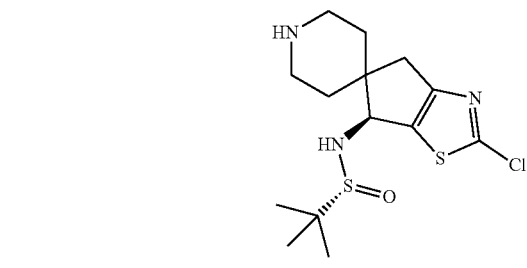

Intermediate I-63 (100 mg, crude product) was prepared in the same procedure as in Preparation Example 58, except that (R)-2-methylpropane-2-sulfinamide was used instead of (S)-2-methylpropane-2-sulfinamide. MS (EI) m/z: 348.3 [M+H]$^+$.

Preparation Example 62: (R)-N-((S)-5-hydroxy-1,3-dihydrospiro[indene-2,4'-piperidin]-3-yl)-2-methyl-propane-2-sulfinamide (Intermediate I-64)

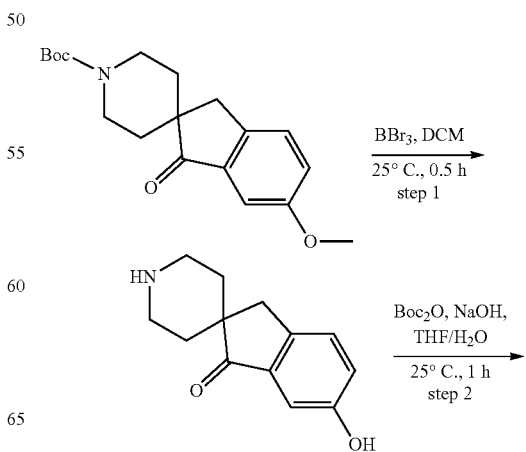

-continued

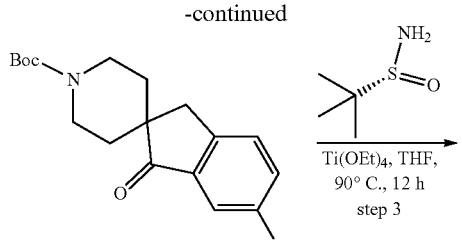

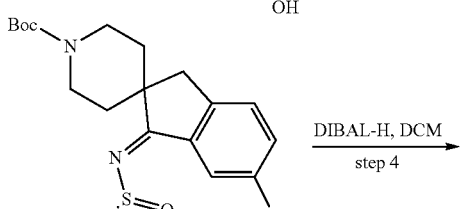

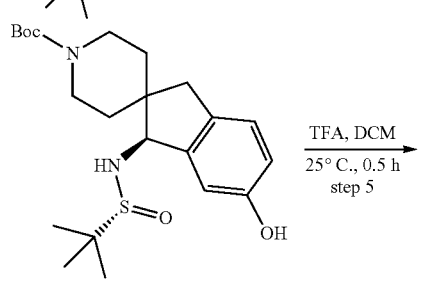

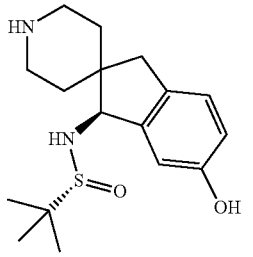

I-64

Step 1: 6-hydroxyspiro[indene-2,4'-piperidin]-1(3H)-one

To a solution of tert-butyl 6-methoxy-1-oxo-1,3-dihydrospiro[indene-2,4'-piperidine]-1'-carboxylate (1.5 g, 4.53 mmol) in DCM (15 mL) was added BBr₃ (11.3 g, 45.3 mmol), and the mixture was stirred at 0° C. for 1 hour. The reaction mixture was quenched by addition of water (50 mL) at 0° C. and then extracted with DCM(50 mL×3). The combined organic layers were washed with brine (20 mL×3), dried over anhydrous sodium sulfate, and then filtered and concentrated under reduced pressure to obtain 6-hydroxyspiro[indene-2,4'-piperidin]-1(3H)-one (980 mg, crude product) as a yellow solid. MS (EI) m/z: 217.3 [M+H]⁺.

Step 2: tert-butyl 6-hydroxy-1-oxo-1,3-dihydrospiro[indene-2,4'-piperidine]-1'-carboxylate To a solution of 6-hydroxyspiro[indene-2,4'-piperidin]-1(3H)-one (980 mg, 4.51 mmol) in THF (10 mL) and water (10 mL), Boc₂O (1.97 g, 9.02 mmol) and NaOH (902 mg, 22.6 mmol) were added, and the mixture was stirred at 25° C. for 1 hour. The reaction mixture was quenched by addition of aqueous ammonium chloride solution (20 mL) at 25° C., diluted with water (30 mL) and extracted with EA (50 mL×3). The combined organic layers were washed with brine (20 mL×3), dried over anhydrous sodium sulfate, and then filtered and concentrated under reduced pressure. The residue was separated by column chromatography to obtain tert-butyl 6-hydroxy-1-oxo-1,3-dihydrospiro[indene-2,4'-piperidine]-1'-carboxylate (1.3 g, 91% yield) as a yellow solid. MS (EI) m/z: 340.3 [M+Na]⁺.

Step 3 to Step 5: (R)-N-((S)-5-hydroxy-1,3-dihydrospiro[indene-2,4'-piperidin]-3-yl)-2-methylpropane-2-sulfinamide Intermediate I-64 (90 mg, 66% yield) was prepared by using (R)-2-methylpropane-2-sulfinamide instead of (S)-2-methylpropane-2-sulfinamide in step 1 of Preparation Example 47, and performing step 2 and step 4 thereof with the resulting intermediate. MS (EI) m/z: 323.4 [M+H]⁺.

Preparation Example 63: 6-((3-amino-5-chloropyrazin-2-yl)thio)-5-chloroquinazolin-4(3H)-one (Intermediate I-65)

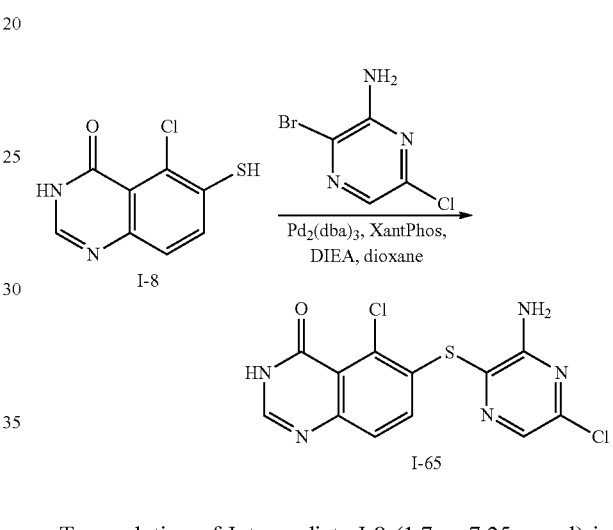

To a solution of Intermediate I-8 (1.7 g, 7.25 mmol) in dioxane(50 mL), 3-bromo-6-chloro-pyrazine-2-amine (1.66 g, 7.97 mmol), Pd₂(dba)₃ (664 mg, 725 XantPhos (838 mg, 1.45 mmol) and DIEA (2.81 g, 21.7 mmol) were added, and the mixture was stirred at 100° C. for 12 hours. The reaction mixture was quenched by addition of aqueous ammonium chloride solution (50 mL) at 25° C., followed by filtering the resulting solid. The solid was washed with EA (50 mL) and methanol (30 mL), and then concentrated under reduced pressure to obtain Intermediate I-65 (0.7 g, 28% yield) as a black solid. ¹H NMR (400 MHz, DMSO-d₆) δ=8.09 (s, 1H), 7.74 (s, 1H), 7.57-7.52 (m, 2H), 7.11 (s, 1H), 3.30 (s, 2H).

Preparation Example 64: 6-bromo-3-((S)-6-(((R)-tert-butylsulfinyl)amino)-4,6-dihydrospiro[cyclopenta[d]thiazole-5,4'-piperidin]-1'-yl)pyrazine-2-carboxamide (Intermediate I-66)

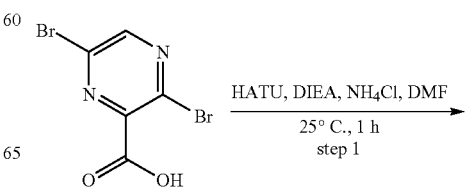

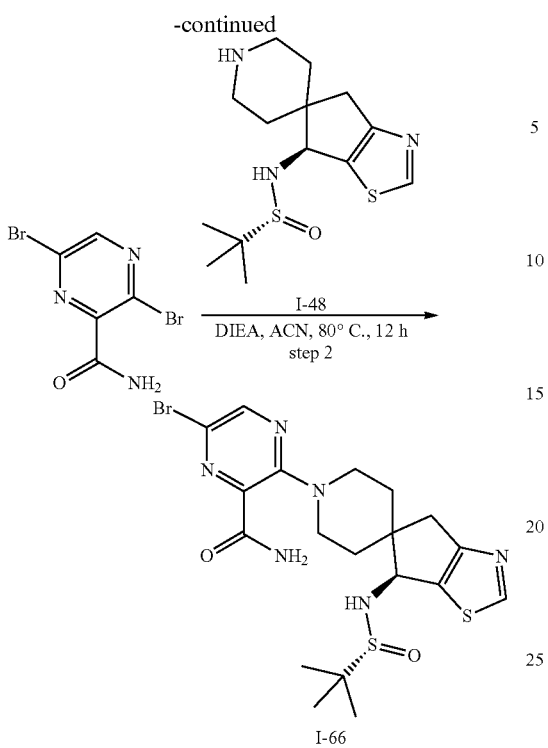

Step 1: 3,6-dibromopyrazine-2-carboxamide

To a solution of 3,6-dibromopyrazine-2-carboxylic acid (1.0 g, 3.55 mmol) in DMF (10 mL), NH$_4$Cl (570 mg, 10.6 mmol), HATU (1.62 g, 4.26 mmol) and DIEA (2.29 g, 17.7 mmol) were added, and the mixture was stirred at 25° C. for 1 hour. The reaction mixture was quenched by addition of aqueous ammonium chloride solution (20 mL) at 25° C., and then added with water (30 mL) and extracted with EA (50 mL×3). The combined organic layers were washed with brine (20 mL×3), dried over anhydrous sodium sulfate, and then filtered and concentrated under reduced pressure. The residue was purified by column chromatography to obtain 3,6-dibromopyrazine-2-carboxamide (310 mg, 31% yield) as a yellow solid. $^1$H NMR (400 MHz, DMSO-d$_6$) δ=8.51 (s, 1H), 8.44 (s, 1H), 8.19 (s, 1H)

Step 2: 6-bromo-34(S)-6-4(R)-tert-butylsulfinyl)amino)-4,6-dihydrospiro[cyclopenta[d]thiazole-5,4'-piperidin]-1'-yl)pyrazine-2-carboxamide To a solution of 3,6-dibromopyrazine-2-carboxamide (100 mg, 0.36 mmol) in ACN (3 mL), DIEA (230 mg, 1.78 mmol) and Intermediate I-48 (112 mg, 0.36 mmol) were added, and the mixture was stirred at 80° C. for 12 hours. The reaction mixture was filtered, and the filtrate was concentrated under reduced pressure. The residue was separated by column chromatography to obtain Intermediate I-66 (130 mg, 71% yield) as a yellow solid. $^1$H NMR (400 MHz, CDCl$_3$) δ =8.80 (s, 1H), 8.20 (s, 1H), 7.30 (s, 1H), 5.95-5.88 (m, 1H), 4.60 (d, J=8.8 Hz, 1H), 3.97 (t, J=13.2 Hz, 2H), 3.87 (d, J=8.8 Hz, 1H), 3.36-3.24 (m, 2H), 3.03-2.93 (m, 2H), 2.02 (dd, J=3.6, 13.2 Hz, 2H), 1.77-1.68 (m, 2H), 1.22 (s, 9H).

Preparation Example 65: 6-bromo-3-((S)-4-(((R)-tert-butylsulfinyl)amino)-4,6-dihydrospiro 1cyclopenta thiazole-5,4'-piperidin]-1'-yl)pyrazine-2-carboxamide (Intermediate I-67)

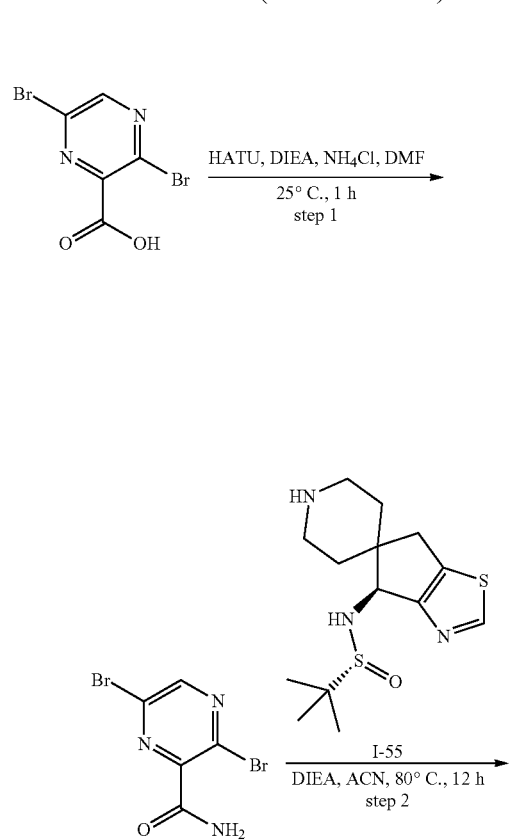

Intermediate I-67 (80 mg, 55% yield) was synthesized in the same method as in Preparation Example 64, except that Intermediate I-55 was used instead of Intermediate I-48 in step 2 of Preparation Example 64. $^1$H NMR (400 MHz, CDCl$_3$) δ=8.73 (s, 1H), 8.20 (s, 1H), 7.28 (s, 1H), 5.73 (s, 1H), 4.50 (d, J=9.2 Hz, 1H), 3.98-3.85 (m, 2H), 3.72 (d, J=9.2 Hz, 1H), 3.42-3.32 (m, 2H), 3.06-3.00 (m, 1H), 2.95-2.89 (m, 1H), 2.17-2.07 (m, 1H), 2.05-2.00 (m, 1H), 1.72 (d, J=2.4 Hz, 2H), 1.25 (s, 9H).

147

Preparation Example 66: 6-bromo-3-((S)-4-(((R)-tert-butylsulfinyl)amino)-4,6-dihydrospiro[cyclopenta[d]thiazole-5,4'-piperidin]-1'-yl)pyrazine-2-carboxamide (Intermediate I-68)

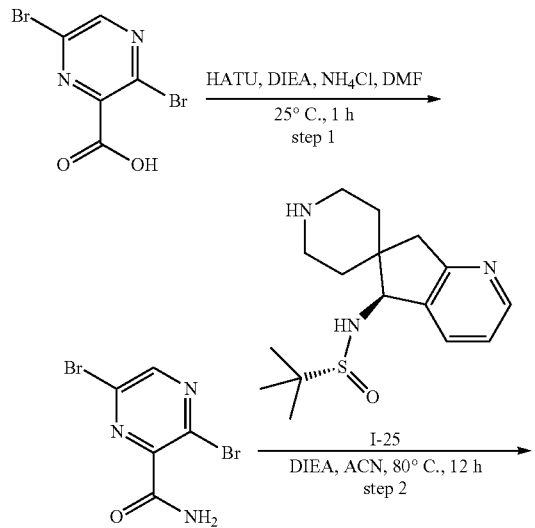

148

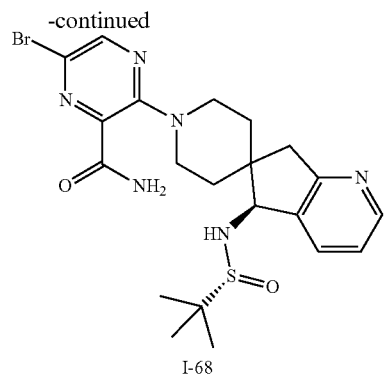

I-68

Intermediate I-68 (70 mg, 78% yield) was synthesized in the same method as in Preparation Example 64, except that Intermediate I-25 was used instead of Intermediate I-48 in step 2 of Preparation Example 64. $^1$H NMR (400 MHz, CDCl$_3$) δ=8.44 (d, J=4.4 Hz, 1H), 8.21 (s, 1H), 7.98 (d, J=7.6 Hz, 1H), 7.31-7.27 (m, 2H), 7.16 (dd, J=4.4, 7.6 Hz, 1H), 5.57-5.49 (m, 1H), 4.54 (d, J=10.0 Hz, 1H), 3.95-3.87 (m, 2H), 3.36-3.27 (m, 2H), 3.26-3.20 (m, 2H), 1.97 (d, J=4.0 Hz, 1H), 1.84 (d, J=4.0 Hz, 2H), 1.70-1.64 (m, 1H), 1.65-1.64 (m, 1H), 1.28 (s, 9H).

Preparation Example 67: Sodium 5-chloro-4-oxo-3-((tetrahydro-2H-pyran-4-yl)methyl)-3,4-dihydroquinazolin-6-thiolate (Intermediate I-69)

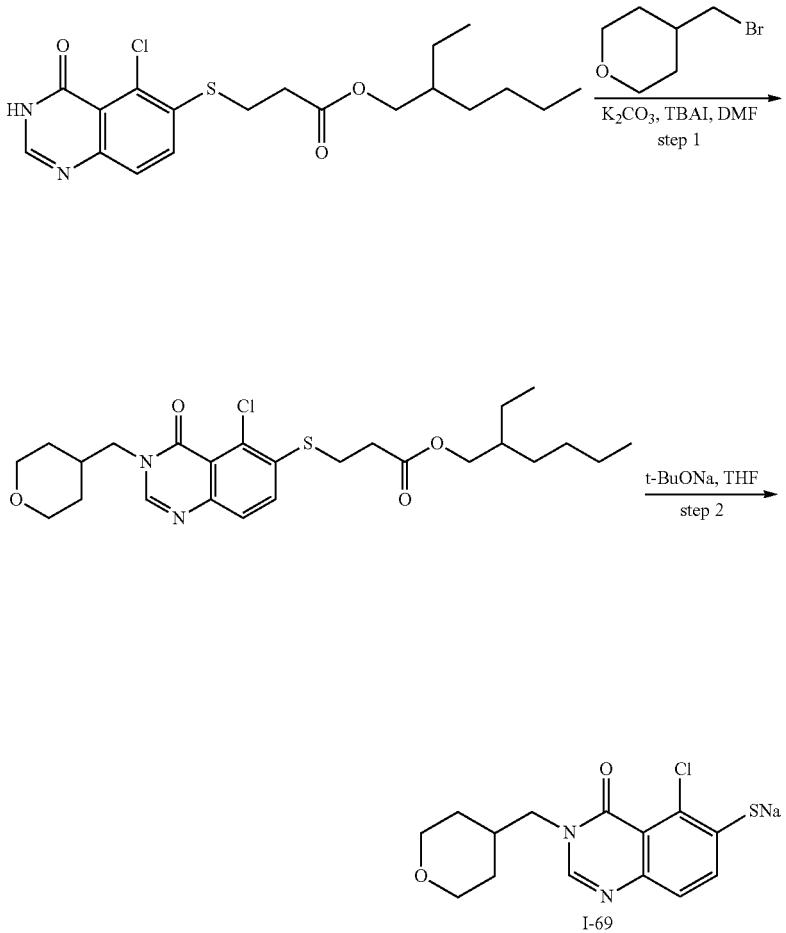

Intermediate I-69 (85 mg, crude product) was synthesized in the same method as in steps 1 and 2 of Preparation Example 28, except that 4-(bromomethyl)tetrahydro-2H-pyran was used instead of 1-bromo-2-methoxyethane in step 1 of Preparation Example 28. MS (EI) m/z: 310.9 [M+H]⁺.

Preparation Example 68: 6-((5-bromopyrazin-2-yl)thio)-5-chloro-3-(2-fluoro-2-methylpropyl)quinazolin-4(3H)-one (Intermediate I-70)

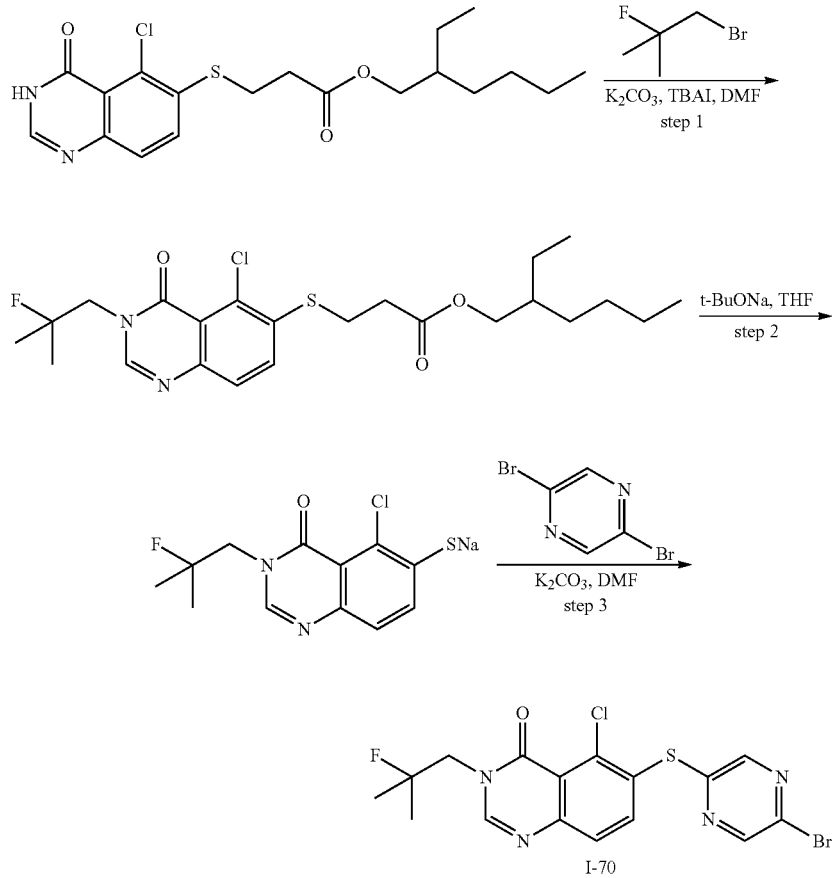

Intermediate I-70 (150 mg, 65% yield) was synthesized in the same method as in Preparation Example 28, except that 1-bromo-2-fluoro-2-methylpropane was used instead of 1-bromo-2-methoxyethane in step 1 of Preparation Example 28. ¹H NMR (400 MHz, CDCl₃) δ =9.08 (d, J=0.8 Hz, 1H), 8.69 (d, J=0.8 Hz, 1H), 8.49 (s, 1H), 7.80 (d, J=8.8 Hz, 1H), 7.65 (d, J=8.8 Hz, 1H), 3.27 (d, J=17.2 Hz, 2H), 1.58 (s, 3H), 1.53 (s, 3H).

Preparation Example 69: 6-((3-amino-5-chloropyrazin-2-yl)thio)-5-chloro-3-(2-methoxypropyl)quinazolin-4(3H)-one (Intermediate I-71)

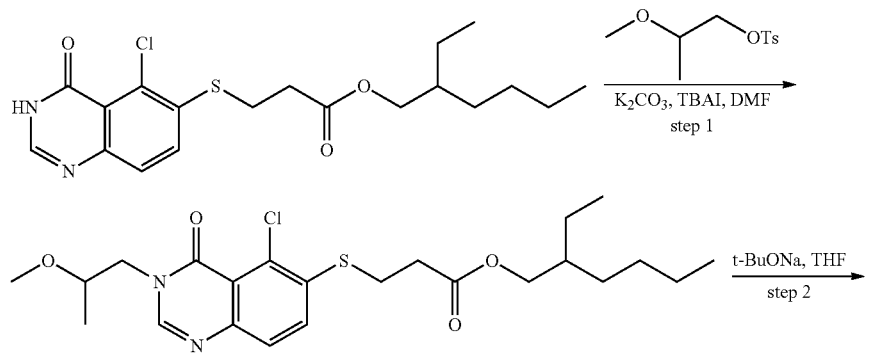

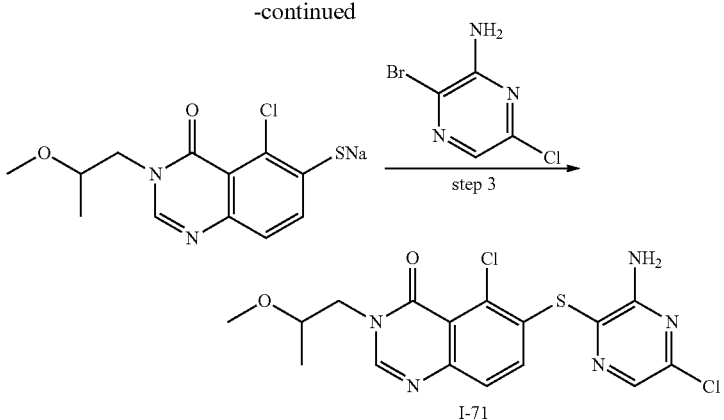

Intermediate I-71 (150 mg, 65% yield) was synthesized in the same method as in Preparation Example 28, except that 2-methoxypropyl 4-methylbenzenesulfonate was used instead of 1-bromo-2-methoxyethane in step 1 of Preparation Example 28. MS (EI) m/z: 411.9 [M+H]$^+$.

Preparation Example 70: Synthesis of N-((R)-8-(5-bromopyrazin-2-yl)-8-azaspiro[4.5]decan-1-yl)-2-methylpropane-2-sulfinamide (Intermediate I-72)

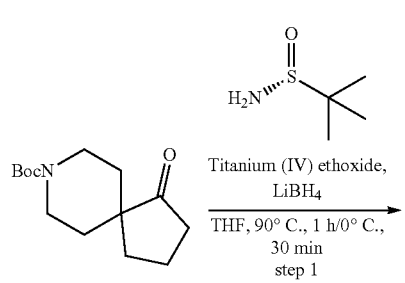

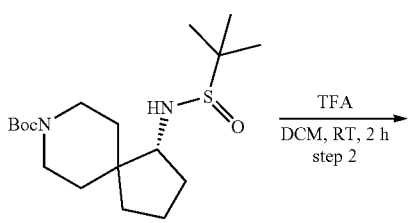

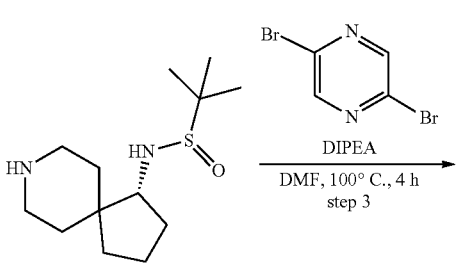

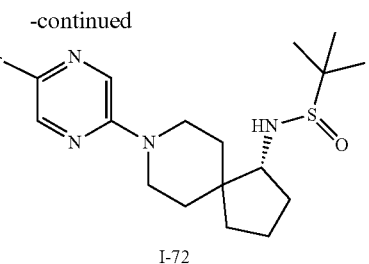

Step 1: tert-butyl (1R)-1-((tert-butylsulfinyl)amino)-8-azaspiro[4.5]decan-8-carboxylate Tert-butyl 1-oxo-8-azaspiro[4.5]decan-8-carboxylate (2 g, 7.89 mmol), titanium(IV) ethoxide (6.63 mL, 31.6 mmol), (R)-2-methylpropane-2-sulfinamide (1.91 g, 15.78 mmol) were dissolved in THF (36 mL, 0.22 M) and stirred at 90° C. for 1 hour. The temperature was lowered to 0° C., and the mixture was added with LiBH$_4$ (21 mg, 9.7 mmol) and stirred for 30 minutes. The reaction was terminated with MeOH, and the mixture was concentrated. The resulting product was diluted with brine and then extracted with EA. The precipitated white solid was filtered to obtain tert-butyl (1R)-1-((tert-butylsulfinyl)amino)-8-azaspiro[4.5]decan-8-carboxylate (912.7 mg, 32%) in the flask. MS m/z: 373.5 [M+H]$^+$.

Step 2: 2-methyl-N-OR)-8-azaspiro[4.5]decan-1-yl)propane-2-sulfinamide

Tert-butyl (1R)-1-((tert-butylsulfinyl)amino)-8-azaspiro[4.5]decan-8-carboxylate (913 mg, 2.55 mmol) was dissolved in DCM (51 mL, 0.05 M). The reaction mixture was slowly added dropwise with trifluoroacetic acid (2.9 mL, 38.3 mmol) and then stirred at room temperature for 2 hours. After completion of the reaction, the resulting product was concentrated to obtain 2-methyl-N-((R)-8-azaspiro[4.5]decan-1-yl)propane-2-sulfinamide. MS m/z: 273.5 [M+H]$^+$.

Step 3: N-((R)-8-(5-bromopyrazin-2-yl)-8-azaspiro[4.5]decan-1-yl)-2-methylpropane-2-sulfinamide 2-methyl-N-((R)-8-azaspiro[4.5]decan-1-yl)propane-2-sulfinamide (crude product, 2.55 mmol) and 2,5-dibromopyrazine (1.4 g, 5.1 mmol) were dissolved in DMF (5.1 mL, 0.5M). The mixture was added with DIPEA (6.6 mL, 38.25 mmol) and then stirred at 100° C. for 3 hours. The reaction was terminated with H$_2$O, and the mixture was extracted with EA. The EA layer was dried over MgSO$_4$, filtered and then concentrated. The resulting product was separated by MPLC (EA:Hx=1:1) and then concentrated to obtain Intermediate I-72 (382 mg, 36%). MS m/z: 430.5 [M+H]$^+$.

Preparation Example 71: potassium 5-chloro-3-(2-methoxyethyl)-4-oxo-3,4-dihydroquinazolin-6-thiolate (Intermediate I-73)

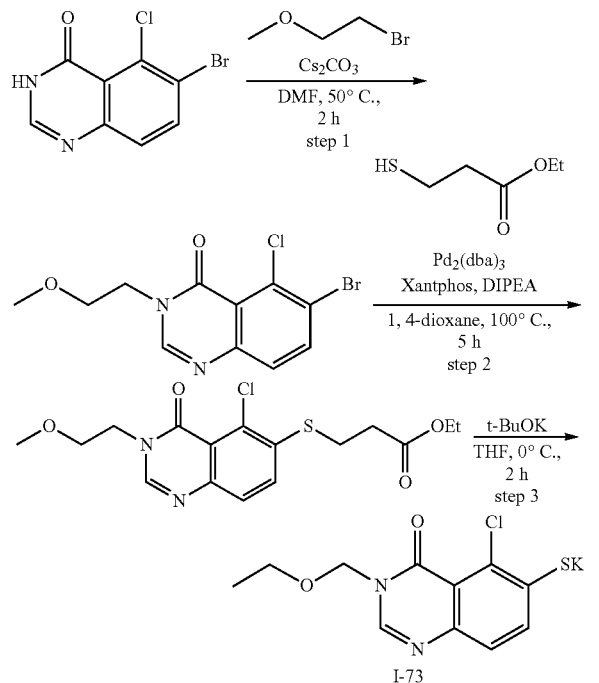

I-73

Step 1: 6-bromo-5-chloro-3-(2-methoxyethyl)quinazolin-4(3H)-one

In a round bottom flask, 6-bromo-5-chloroquinazolin-4(3H)-one (58.7 g, 226.1 mmol), 1-bromo-2-methoxyethane (32 mL, 339.2 mmol) and cesium carbonate (147 g, 452.3 mmol) were dissolved in DMF (565 mL, 0.4 M), and then stirred at 50° C. for 2 hours. The reaction was terminated with aqueous NaHCO$_3$ solution, and the mixture was extracted with EA. The EA layer was dried over MgSO$_4$, filtered and concentrated. EA and Hx were added to precipitate a solid, and then the solid was filtered to obtain 6-bromo-5-chloro-3-(2-methoxyethyl)quinazolin-4(3H)-one (53.5 g, 74.5%). MS m/z: 318.5 [M+H]$^+$.

Step 2: ethyl 3-((5-chloro-3-(2-methoxyethyl)-4-oxo-3,4-dihydroquinazolin-6-yl)thio)propanoate In a round bottom flask, 6-bromo-5-chloro-3-(2-methoxyethyl)quinazolin-4(3H)-one (26.7 g, 84.2 mmol), ethyl-3-mercaptopropionate (20.4 mL, 160 mmol), Pd$_2$(dba)$_3$ (3.7 g, 4.0 mmol) and XantPhos (4.6 g, 8.0 mmol) were dissolved in 1,4-dioxane (267 mL, 0.3 M), and then DIPEA (28 mL, 160.4 mmol) was added dropwise thereto. The reaction mixture was purged with nitrogen, and then stirred at 120° C. for 5 hours. After being filtered through celite, the mixture was added with H$_2$O and extracted with EA. The EA layer was dried over MgSO$_4$, filtered and then concentrated. EA and Hx were added, and then the precipitated solid was filtered to obtain ethyl 3-((5-chloro-3-(2-m ethoxy ethyl)-4-oxo-3,4-dihydroquinazolin-6-yl)thio)propanoate (58.7 g, 99%). MS m/z: 371.5 [M+H]$^+$.

Step 3: potassium 5-chloro-3-(2-methoxyethyl)-4-oxo-3,4-dihydroquinazolin-6-thiolate In a round bottom flask, ethyl 3-((5-chloro-3-(2-m ethoxy ethyl)-4-oxo-3,4-dihydroquinazolin-6-yl)thio)propanoate (29.4 g, 79.2 mmol) was dissolved in THF (400 mL, 0.2 M), and then the temperature was lowered to 0° C. The reaction mixture was slowly added dropwise with potassium tert-butoxide (9.7 g, 87.1 mmol) and stirred at 0° C. for 30 hours. After completion of the reaction, the reaction mixture was concentrated to obtain Intermediate I-73 (45.7 g, 93%). MS m/z: 270.5 [M+H]$^+$.

Preparation Example 72: Synthesis of N—((S)-1'-(6-chloro-1,2,4-triazin-3-yl)-1,3-dihydrospiro[indene-2,4'-piperidin]-1-yl)-2-methylpropane-2-sulfinamide (Intermediate I-74) and N—((S)-1'-(3-chloro-1,2,4-triazin-6-yl)-1,3-dihydrospiro(indene-2,4'-piperidin]-1-yl)-2-methylpropane-2-sulfinamide (Intermediate I-75)

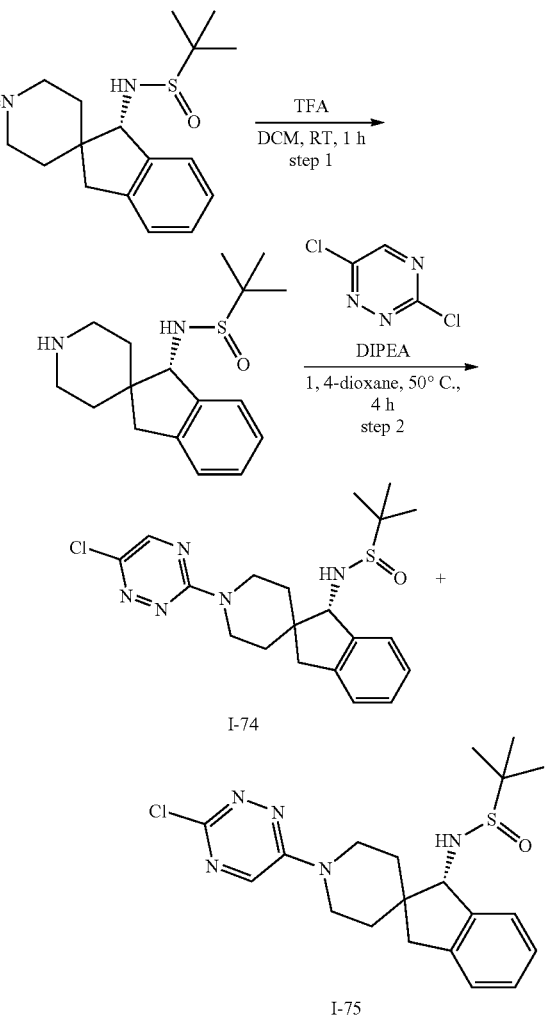

Step 1: N—((S)-1,3-dihydrospiro[indene-2,4'-piperidin]-1-yl)-2-methylpropane-2-sulfinamide Tert-butyl (1 S)-1-((tert-butyl sulfinyl)amino)-1,3-dihydrospiro[indene-2,4'-piperidine]-1'-carboxylate (201 mg, 0.49 mmol) was dissolved in DCM (1.63 mL, 0.3 M). The reaction mixture was slowly added dropwise with trifluoroacetic acid (TFA) (0.38 mL, 4.94 mmol) and then stirred at room temperature for 2 hours. After completion of the reaction, the resulting product was concentrated to obtain N—((S)-1,3-dihydrospiro[indene-2,4'-piperidin]-1-yl)-2-methylpropane-2-sulfinamide. MS m/z: 307.5 [M+H]$^+$.

Step 2: N—((S)-1'-(6-chloro-1,2,4-triazin-3-yl)-1,3-dihydrospiro[indene-2,4'-piperidin]-1-yl)-2-methylpropane-2-sulfinamide (Intermediate I-74) and N—((S)-1'-(3-chloro-1,2,4-triazin-6-yl)-1,3-dihydrospiro[indene-2,4'-piperidin]-1-yl)-2-methylpropane-2-sulfinamide (Intermediate I-75)

N—((S)-1,3-dihydrospiro[indene-2,4'-piperidin]-1-yl)-2-methylpropane-2-sulfinamide (crude product, 0.49 mmol) as concentrated and 3,6-dichloro-1,2,4-triazine (73 mg, 0.49 mmol) were dissolved in 1,4-dioxane (2.45 mL, 0.2 M). The mixture was added with DIPEA (0.85 mL, 4.9 mmol) and then stirred at 50° C. for 4 hours. The reaction was terminated with $H_2O$, and the mixture was extracted with EA. The EA layer was dried over $MgSO_4$, filtered and then concentrated. The resulting product was purified by MPLC (EA: Hx=1:1) and then concentrated to obtain Intermediate I-74 (65.6 mg, 32%) and Intermediate I-75 (55.7 mg, 27%). MS m/z: 420.5 [M+H]$^+$.

Preparation Example 73: Synthesis of 6-amino-5-((2,3-dichlorophenyl)thio)-3-methyl-2-(piperazin-1-yl)pyrimidin-4(3H)-one (Intermediate I-76)

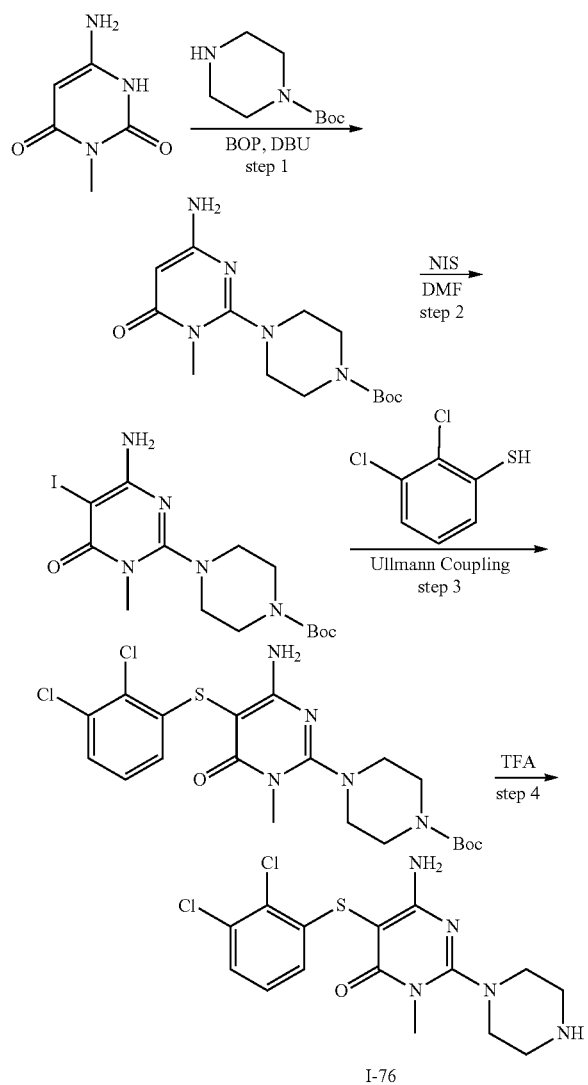

Step 1: t-butyl 4-(4-amino-1-methyl-6-oxo-pyrimidin-2-yl)piperazine-1-carboxylate 6-amino-3-methyl-1H-pyrimidine-2,4-dione (2 g, 14.17 mmol), BOP (benzotriazol-1-yloxytris(dimethylamino)phosphonium hexafluorophosphate, 6.27 g, 14.17 mmol), DBU (1,8-diazabicyclo[5.4.0]undec-7-ene, 2.16 g, 14.17 mmol, 2.14 mL) were dissolved in DMF (30.0 mL, 0.47 M), and then tert-butyl piperazine-1-carboxylate (2.90 g, 15.59 mmol) was added thereto. The reaction mixture was stirred at room temperature for 16 hours. After confirming by LCMS that the reaction material had completely disappeared, the reaction mixture was added with brine (20.0 mL) and EtOAc (20.0 mL×3) and extracted. The organic layer was dried over $Na_2SO_4$, filtered and then concentrated. The resulting product was separated by Prep-HPLC (neutral) and concentrated to obtain t-butyl 4-(4-amino-1-methyl-6-oxo-pyrimidin-2-yl)piperazine-1-carboxylate (1.8 g, 40.7%). $^1$H NMR (400 MHz, CHLOROFORM-d) δ=5.23 (s, 1H), 4.50 (s, 2H), 3.62-3.52 (m, 4H), 3.42 (s, 3H), 3.18-3.09 (m, 4H), 1.49 (s, 9H); MS m/z: 310.3 [M+H]$^+$.

Step 2: t-butyl 4-(4-amino-5-iodo-1-methyl-6-oxo-1,6-dihydropyrimidin-2-yl)piperazine-1-carboxylate Tert-butyl 4-(4-amino-1-methyl-6-oxo-pyrimidin-2-yl)piperazine-1-carboxylate (1.6 g, 5.17 mmol) was dissolved in DMF (10 mL, 0.52 M), and then NIS (N-iodosuccinimide, 1.16 g, 5.17 mmol) was added thereto. The reaction mixture was stirred at room temperature for 1 hour. After a white precipitate was formed, and LCMS confirmed that the reaction materials had completely disappeared, the reaction was terminated by addition of aqueous $Na_2SO_3$ (5 mL). After filtration, the filter cake was washed with MBTE (methyl tertiary-butyl ether, 200 mL). The filter cake was dried to obtain t-butyl 4-(4-amino-5-iodo-1-methyl-6-oxo-1,6-dihydropyrimidin-2-yl)piperazine-1-carboxylate (1.8 g, 75.6%) as a white solid. $^1$H NMR (400 MHz, DMSO-d$_6$) δ =3.44 (br s, 4H), 3.32 (s, 3H), 3.13-3.02 (m, 4H), 1.42 (s, 9H); MS m/z: 435.9 [M+H]$^+$.

Step 3: tert-butyl 4-(4-amino-5-((2,3-dichlorophenyl)thio)-1-methyl-6-oxo-1,6-dihydropyrimidin-2-yl)piperazine-1-carboxylate 2,3-dichlorobenzenethiol (395 mg, 2.21 mmol), t-butyl 4-(4-amino-5-iodo-1-methyl-6-oxo-1,6-dihydropyrimidin-2-yl)piperazine-1-carboxylate (800 mg, 1.84 mmol), (1R,2R)-N1,N2-dimethylcyclohexane-1,2-diamine (26.14 mg, 183.80 µmol) and $K_3PO_4$ (780.28 mg, 3.68 mmol) were dissolved in dioxane (15 mL), and then CuI (35.00 mg, 183.80 µmol) was added thereto. The reaction mixture was stirred at 90° C. for 16 hours. The reaction mixture was added with aqueous $NaHCO_3$ solution and EtOAc and extracted. The organic layer was dried over $MgSO_4$, filtered and then concentrated. The resulting product was separated by MPLC and concentrated to obtain tert-butyl 4-(4-amino-5-((2,3-di chlorophenyl)thio)-1-methyl-6-oxo-1,6-dihydropyrimidin-2-yl)piperazine-1-carboxylate (640.0 mg, 71%). MS m/z: 486 [M+H]$^+$.

Step 4: 6-amino-5-((2,3-dichlorophenyl)thio)-3-methyl-2-(piperazin-1-yl)pyrimidin-4(3H)-one Tert-butyl 4-(4-amino-5-((2,3-di chlorophenyl)thio)-1-methyl-6-oxo-1,6-dihydropyrimidin-2-yl)piperazine-1-carboxylate (640 mg, 1.32 mmol) was dissolved in DCM (dichloromethane, 3 mL, 0.4 M), and then the reaction mixture was added with TFA (1 mL) and stirred at 25° C. for 30 minutes. The reaction solution was concentrated, and then separated by MPLC to obtain Intermediate I-76 (400 mg, 79%). MS m/z: 386 [M+H]$^+$.

Preparation Example 74: Synthesis of 6-amino-5-((2,3-dichlorophenyl)thio)-3-methyl-2-(1,4-diazepan-1-yl)pyrimidin-4(3H)-one (Intermediate I-77)

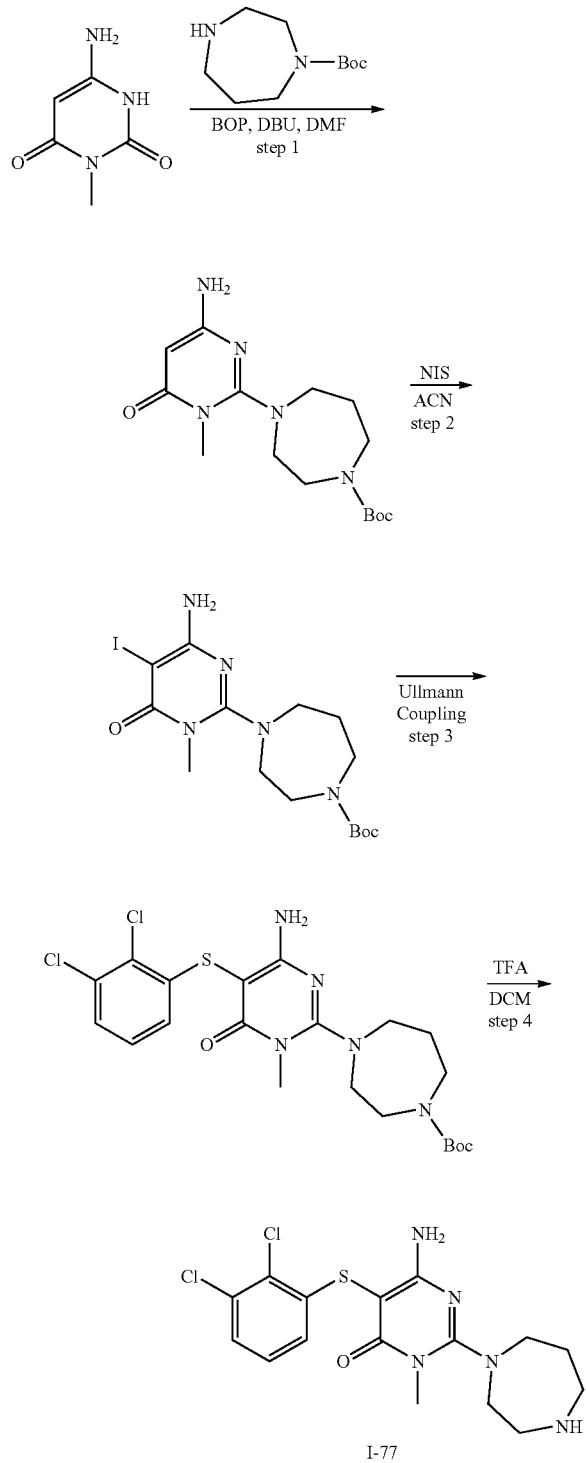

Intermediate I-77 was synthesized in the same method as in Preparation Example 73, except that tert-butyl 1,4-diazepane-1-carboxylate was used instead of tert-butyl piperazine-1-carboxylate. MS m/z: 400 [M+H]⁺.

Preparation Example 75: Synthesis of t-butyl N-[2-[4-(4-amino-5-iodo-1-methyl-6-oxo-pyrimidin-2-yl)-piperazin-1-yl]ethyl]carbamate (Intermediate I-78)

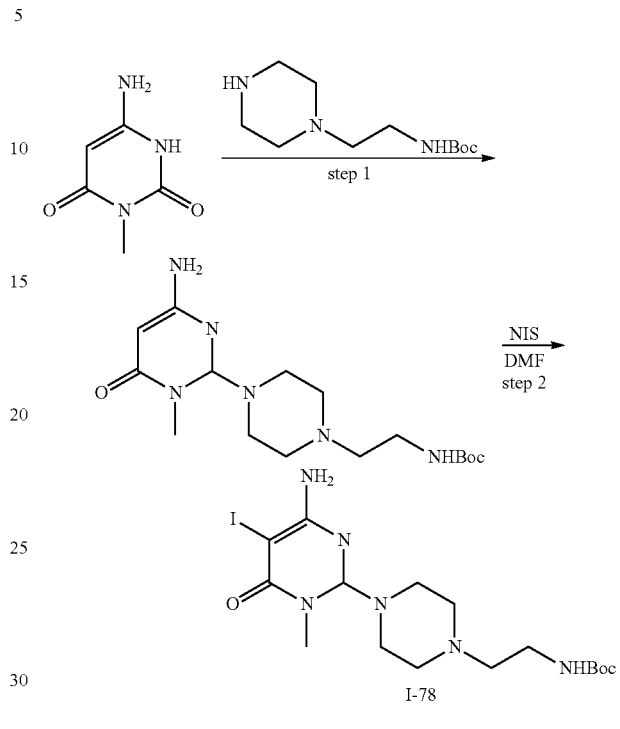

Step 1: t-butyl N-[2-[4-(4-amino-1-methyl-6-oxo-pyrimidin-2-yl)-piperazin-1-yl]ethyl]carbamate 6-amino-3-methyl-1H-pyrimidine-2,4-dione (500 mg, 3.54 mmol), BOP (1.57 g, 3.54 mmol), DBU (539 mg, 3.54 mmol, 534.02 µL) were dissolved in DMF (10 mL, 0.35 M), and then tert-butyl piperazine-1-carboxylate (812 mg, 3.54 mmol) was added thereto. The reaction mixture was stirred at room temperature for 16 hours. After confirming by LCMS that the reaction materials had completely disappeared, the reaction mixture was added with brine (20 mL) and EtOAc (20 mL×3) and extracted. The organic layer was dried over $Na_2SO_4$, filtered and then concentrated. The resulting product was separated by Prep-HPLC (neutral) and concentrated to obtain t-butyl N4244-(4-amino-1-methyl-6-oxo-pyrimidin-2-yl)-piperazin-1-yl]ethyl]carbamate (320 mg, 23.6%). $^1$H NMR (400 MHz, CHLOROFORM-d) δ=5.22 (s, 1H), 5.04-4.92 (m, 1H), 4.45 (br d, J=6.3 Hz, 1H), 3.41 (s, 3H), 3.28 (br d, J=4.8 Hz, 2H), 3.23-3.17 (m, 4H), 2.63-2.56 (m, 4H), 2.54 (t, J=6.0 Hz, 2H), 1.48 (s, 9H); MS m/z: 353.4 [M+H]⁺.

Step 2: t-butyl N-[2-[4-(4-amino-5-iodo-1-methyl-6-oxo-pyrimidin-2-yl)-piperazin-1-yl]ethyl]carbamate Tert-butyl N4244-(4-amino-1-methyl-6-oxo-pyrimidin-2-yl)-piperazin-1-yl]ethyl]carbamate (260 mg, 737 µmol) was dissolved in DMF (3 mL, 0.25 M), and then NIS (166 mg, 737 µmol) was added thereto. The reaction mixture was stirred at room temperature for 1 hour. After a white precipitate was formed, and LCMS confirmed that the reaction materials had completely disappeared, the reaction was terminated with aqueous $NaHCO_3$ solution, and the mixture was extracted with EA. The EA layer was dried over $MgSO_4$, filtered and then concentrated. The resulting product was separated by MPLC and concentrated to obtain Intermediate I-78 (360 mg, 97%). $^1$H NMR (400 MHz, CHLOROFORM-d) δ=5.03 (s, 2H), 4.98 (br s, 1H), 3.47 (s, 3H), 3.29 (br d, J=5.1 Hz, 2H), 3.25-3.18 (m, 4H), 2.61 (br s, 4H), 2.55 (br t, J=5.9 Hz, 2H), 1.48 (s, 9H); MS m/z: 479.3 [M+H]⁺.

Preparation Example 76: Synthesis of tert-butyl (1-(4-amino-5-iodo-1-methyl-6-oxo-1,6-dihydropyrimidin-2-yl)-4-methylpiperidin-4-yl)carbamate (Intermediate I-79)

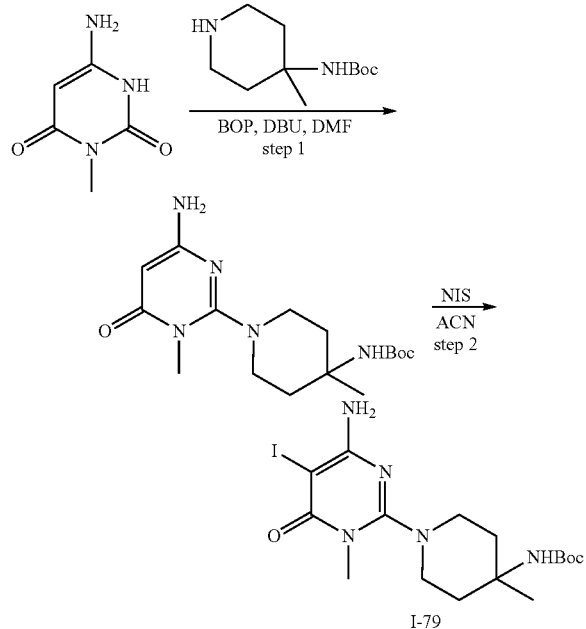

Step 1: tert-butyl (1-(4-amino-1-methyl-6-oxo-1,6-dihydropyrimidin-2-yl)-4-methylpiperidin-4-yl)carbamate In a round bottom flask, 6-amino-3-methylpyrimidine-2,4 (1H, 3H)-dione (300 mg, 2.13 mmol) and BOP (benzotriazol-1-yloxytris(dimethylamino)phosphonium hexafluorophosphate, 942 mg, 2.13 mmol), DBU (1,8-diazabicyclo[5.4.0]undec-7-ene, 324 mg, 2.13 mmol, 0.32 mL) were dissolved in DMF, and then 1-(tert-butyl) 2-methyl (S)-piperazine-1,2-dicarboxylate (502.1 mg, 2.34 mmol) was added dropwise thereto. The reaction mixture was stirred at room temperature for 16 hours. The reaction was terminated with H₂O, and the mixture was extracted with EA. The EA layer was dried over MgSO₄, filtered and concentrated. The resulting product was separated by MPLC (MeOH:DCM=1:10) and concentrated to obtain tert-butyl (1-(4-amino-1-methyl-6-oxo-1,6-dihydropyrimidin-2-yl)-4-methylpiperidin-4-yl)carbamate (760 mg, 97%). MS m/z: 368.20 [M+H]⁺.

Step 2: tert-butyl (1-(4-amino-5-iodo-1-methyl-6-oxo-1,6-dihydropyrimidin-2-yl)-4-methylpiperidin-4-yl)carbamate In a round bottom flask, NIS (567 mg, 2.52 mmol) was added dropwise to a reaction mixture of 1-(tert-butyl) 2-methyl (S)-4-(4-amino-1-methyl-6-oxo-1,6-dihydropyrimidin-2-yl)piperazine-1,2-dicarboxylate (772 mg, 2.52 mmol) dissolved in ACN. The reaction mixture was stirred at room temperature for 2 hours. The reaction was terminated with H₂O, and the mixture was extracted with EA. The EA layer was dried over MgSO₄, filtered and concentrated. The resulting product was separated by MPLC (MeOH: DCM=1:10) and concentrated to obtain Intermediate I-79 (981 mg, 94%). MS m/z: 494.10 [M+H]⁺.

Example 1: Synthesis of methyl 3-((5-(4-amino-4-methylpiperidin-1-yl)pyrazin-2-yl)thio)-2-chlorobenzoate

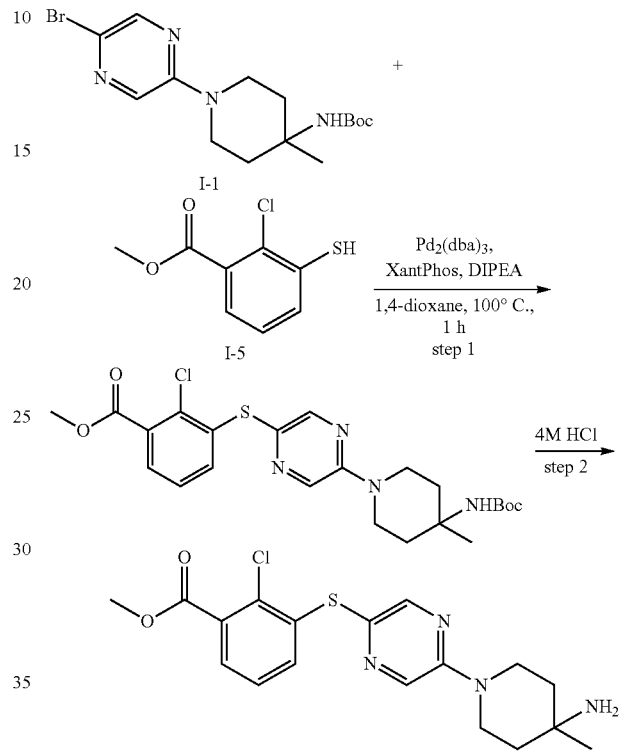

Step 1: methyl 3-((5-(4-((tert-butoxycarbonyl)amino)-4-methylpiperidin-1-yl)pyrazin-2-yl)thio)-2-chlorobenzoate In a round bottom flask, Intermediate I-1 (220 mg, 0.59 mmol), Intermediate I-5 (110 mg, 0.53 mmol), Pd₂(dba)₃ (50 mg, 0.053 mmol) and XantPhos (30 mg, 0.053 mmol) were dissolved in 1,4-dioxane (2.2 mL, 0.25 M), and then DIPEA (0.19 mL, 1.07 mmol) was added thereto. The reaction mixture was purged with nitrogen and stirred at 100° C. for 1 hour. The resulting product was washed with EA and filtered through celite, and the filtrate was concentrated. The resulting product was separated by MPLC (EA:Hx=1:5) and then concentrated to obtain methyl 3-((5-(4-((tert-butoxycarbonyl)amino)-4-methylpiperidin-1-yl)pyrazin-2-yl)thio)-2-chlorobenzoate (230 mg, 87%). MS m/z: 494.1 [M+H]⁺.

Step 2: methyl 3-((5-(4-amino-4-methylpiperidin-1-yl)pyrazin-2-yl)thio)-2-chlorobenzoate In a round bottom flask, methyl 3-((5-(4-((tert-butoxycarbonyl)amino)-4-methylpiperidin-1-yl)pyrazin-2-yl)thio)-2-chlorobenzoate (22 mg, 0.045 mmol) was dissolved in DCM (0.15 mL, 0.3 M). 4 M HCl in dioxane (0.15 mL) was slowly added dropwise to the reaction mixture, followed by stirring at room temperature for 1 hour. The reaction was terminated with aqueous NaHCO₃ solution, and the mixture was extracted with EA. The EA layer was dried over MgSO₄, filtered and then concentrated. The resulting product was separated by MPLC (MeOH:MC=1:10) and concentrated to obtain the compound of Example 1 (8 mg, 43%). ¹H NMR (400 MHz, CDCl₃) δ 8.23 (d, J=1.6 Hz, 1H), 8.19 (d, J=1.2 Hz, 1H), 7.55 (dd, J=6.4, 2.0 Hz, 1H), 7.15 (t, J=8.0 Hz, 1H), 7.08 (dd, J=8.0, 2.0 Hz, 1H), 3.93 (s, 3H), 3.83-3.75 (m, 2H), 3.67-3.61 (m, 2H), 1.77-1.66 (m, 4H), 1.32 (s, 3H); MS m/z: 393 [M+H]⁺.

Example 2: Synthesis of ethyl 3-((4-amino-2-(4-amino-4-methylpiperidin-1-yl)-1-methyl-6-oxo-1,6-dihydropyrimidin-5-yl)thio)-2-chlorobenzoate

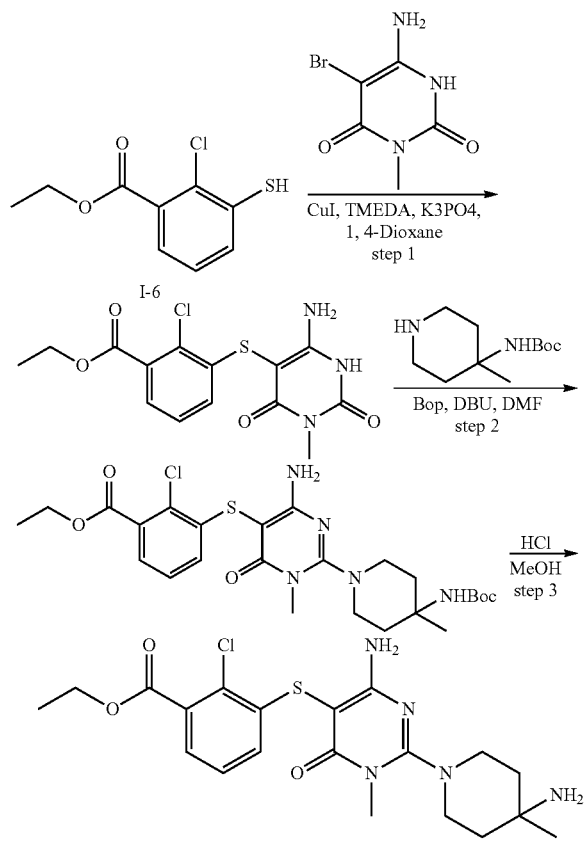

Step 1: ethyl 3-((6-amino-3-methyl-2,4-dioxo-1,2,3,4-tetrahydropyrimidin-5-yl)thio)-2-chlorobenzoate In a round bottom flask, Intermediate I-6 (89 mg, 0.4 mmol), 6-amino-5-bromo-3-methylpyrimidine-2,4(1H,3H)-dione (75 mg, 0.34 mmol), CuI (13 mg, 0.068 mmol), TMEDA (tetramethylethylenediamine, 20 μL, 0.136 mmol) and K₃(PO)₄ (217 mg, 1.02 mmol) were dissolved in 1,4-dioxane (0.8 mL, 0.5 M), followed by stirring at 100° C. for 1 hour. The reaction was terminated with H₂O, and the mixture was extracted with EA. The EA layer was dried over MgSO₄, filtered and concentrated. The resulting product was separated by MPLC (MC:MeOH=20:1) and concentrated to obtain ethyl 3-((6-amino-3-methyl-2,4-dioxo-1,2,3,4-tetrahydropyrimidin-5-yl)thio)-2-chlorobenzoate (38 mg, 32%). MS m/z: 356.5 [M+H]⁺.

Step 2: ethyl 3-((4-amino-2-(4-((tert-butoxycarbonyl)amino)-4-methylpiperidin-1-yl)-1-methyl-6-oxo-1,6-dihydropyrimidin-5-yl)thio)-2-chlorobenzoate In a round bottom flask, ethyl 3-((6-amino-3-methyl-2,4-dioxo-1,2,3,4-tetrahydropyrimidin-5-yl)thio)-2-chlorobenzoate (38 mg, 0.11 mmol), tert-butyl (4-methylpiperidin-4-yl)carbamate (34 mg, 0.16 mmol), BOP (232 mg, 0.33 mmol) and DBU (84 mg, 0.55 mmol) were dissolved in DMF (0.1 mL, 0.1 M), followed by stirring at room temperature for 1 hour. The reaction was terminated with H₂O, and the mixture was extracted with EA. The EA layer was dried over MgSO₄, filtered and concentrated. The resulting product was separated by MPLC (EA:Hx=4:1) and concentrated to obtain ethyl 3-((4-amino-2-(4-((tert-butoxycarbonyl)amino)-4-methylpiperidin-1-yl)-1-methyl-6-oxo-1,6-dihydropyrimidin-5-yl)thio)-2-chlorobenzoate (31 mg, 54%). MS m/z: 553.1 [M+H]⁺.

Step 3: ethyl 3-((4-amino-2-(4-amino-4-methylpiperidin-1-yl)-1-methyl-6-oxo-1,6-dihydropyrimidin-5-yl)thio)-2-chlorobenzoate In a round bottom flask, ethyl 3-((4-amino-2-(4-((tert-butoxycarbonyl)amino)-4-methylpiperidin-1-yl)-1-methyl-6-oxo-1,6-dihydropyrimidin-5-yl)thio)-2-chlorobenzoate (31 mg, 0.06 mmol) was dissolved in methanol (1.2 mL, 0.05 M). The reaction mixture was added with 4 M HCl in dioxane (1.5 mL) and stirred at room temperature for 30 minutes. After completion of the reaction, the reaction mixture was concentrated using a concentrator. The resulting product was separated by MPLC (MC:MeOH=20:1) and concentrated to obtain the compound of Example 2 (10.4 mg, 38%). ¹H NMR (400 MHz, DMSO) δ7.41 (dd, J=6.4, 1.2 Hz, 1H), 7.28 (t, J=8 Hz, 1H), 6.89 (dd, J=6.4, 1.6 Hz, 1H), 6.77-6.57 (m, 2H), 4.34(q, J=7.2 Hz, 2H), 3.41-3.36 (m, 2H), 3.27 (s, 3H), 3.24-3.21 (m, 2H), 1.64 (m, 4H), 1.34-1.30 (m, 3H), 1.24-1.22 (m, 3H); MS m/z: 452 [M+H]⁺.

Example 3: Synthesis of 6-((5-(4-(aminomethyl)-4-methylpiperidin-1-yl)pyrazin-2-yl)thio)-5-chloroquinazolin-4(3H)-one

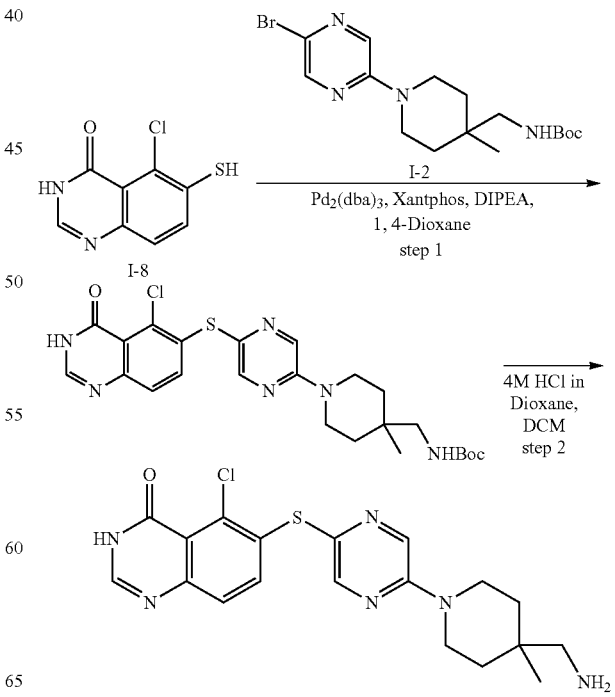

Step 1: tert-butyl((1-(5-((5-chloro-4-oxo-3,4-dihydroquinazolin-6-yl)thio)pyrazin-2-yl)-4-methylpiperidin-4-yl)methyl)carbamate In a round bottom flask, Intermediate I-8 (150 mg, 0.6 mmol), Intermediate I-2 (154 mg, 0.4 mmol), Pd$_2$(dba)$_3$ (36 mg, 0.04 mmol) and XantPhos (46 mg, 0.08 mmol) were dissolved in 1,4-dioxane (1 mL, 0.4 M), and then DIPEA (139 µL, 0.8 mmol) was added thereto. The reaction mixture was purged with nitrogen, and then stirred at 100° C. for 4 hours. The reaction was terminated with H$_2$O, and the mixture was extracted with EA. The EA layer was dried over MgSO$_4$, filtered and then concentrated. The resulting product was separated by MPLC (MC:MeOH=9:1) and concentrated to obtain tert-butyl ((1-(5-((5-chloro-4-oxo-3,4-dihydroquinazolin-6-yl)thio)pyrazin-2-yl)-4-methylpiperidin-4-yl)methyl)carbamate (5 mg, 3%). MS m/z: 518.1 [M+H]$^+$.

Step 2: 6-((5-(4-(aminomethyl)-4-methylpiperidin-1-yl)pyrazin-2-yl)thio)-5-chloroquinazolin-4(3H)-one Tert-butyl ((1-(5-((5-chloro-4-oxo-3,4-dihydroquinazolin-6-yl)thio)pyrazin-2-yl)-4-methylpiperidin-4-yl)methyl)carbamate (5 mg, 0.01 mmol) was put into a round bottom flask and dissolved in DCM (0.25 mL). The reaction mixture was slowly added dropwise with 4 M HCl in dioxane (0.25 mL) and then stirred at room temperature for 30 minutes. After completion of the reaction, the resulting product was concentrated and added with EA dropwise. The precipitated solid was filtered with EA to obtain the compound of Example 3 (3 mg, 66%) in the form of a salt. $^1$H NMR (400 MHz, DMSO) δ12.51-12.39 (m, 1H), 8.48 (d, J=1.6 Hz, 1H), 8.31 (d, J=1.2 Hz, 1H), 8.07 (s, 1H), 7.90-7.83 (m, 3H), 7.52 (d, J=8.8 Hz, 1H), 7.21 (d, J=8.8 Hz, 1H), 3.97-3.93 (m, 2H), 2.81-2.80 (m, 2H), 1.59-1.44 (m, 4H), 1.10 (s, 3H); MS m/z: 417 [M+H]$^+$.

Example 4: Synthesis of 6-((5-(4-amino-4-methylpiperidin-1-yl)pyrazin-2-yl)thio)-5-chloroquinazolin-4(3H)-one

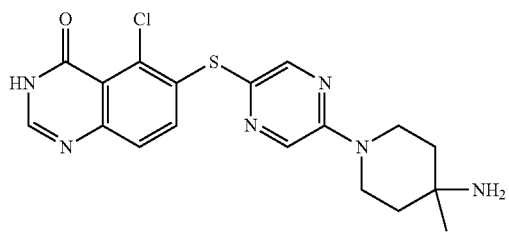 [SMILES: CC1(N)CCN(c2cnc(Sc3ccc4nc[nH]c(=O)c4c3Cl)cn2)CC1]

The compound of Example 4 was synthesized in the same method as in Example 3 above, except that Intermediate I-1 was used instead of Intermediate I-2. $^1$H NMR (400 MHz, DMSO) δ8.50 (d, J=1.2 Hz, 1H), 8.34 (d, J=1.2 Hz, 1H), 8.09 (s, 1H), 7.52 (d, J=8.8 Hz, 1H), 7.24 (d, J=8.8 Hz, 1H), 4.10-4.01 (m, 2H), 3.46-3.41 (m, 2H), 1.84-1.77 (m, 4H), 1.40 (s, 3H); MS m/z: 403 [M+H]$^+$.

Example 5: Synthesis of 6-((5-((3S,4S)-4-amino-3-methyl-2-oxa-8-azaspiro[4.5]decan-8-yl)pyrazin-2-yl)thio)-5-chloroquinazolin-4(3H)-one

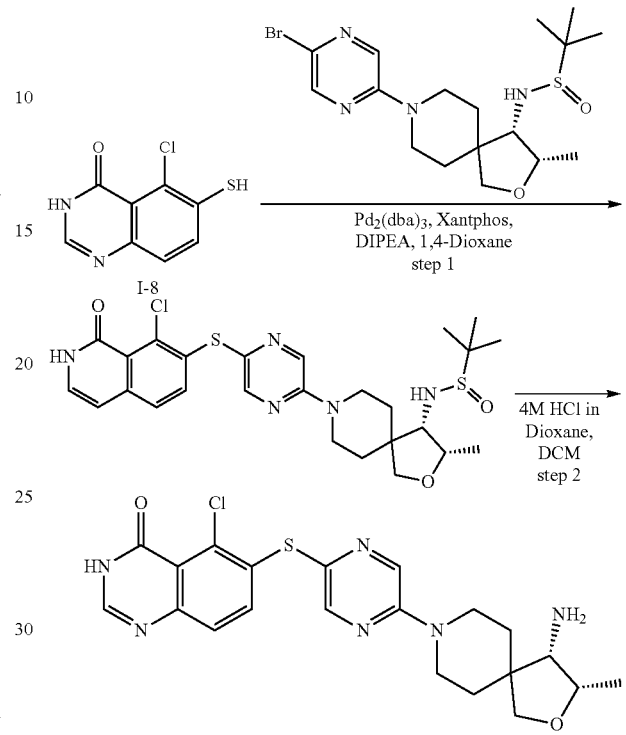

Step 1: N-((3S,4S)-8-(5-((5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfanilamide In a round bottom flask, Intermediate I-8 (108 mg, 0.43 mmol), Intermediate I-3 (170 mg, 0.39 mmol), Pd$_2$(dba)$_3$ (36 mg, 0.04 mmol) and XantPhos (46 mg, 0.08 mmol) were dissolved in 1,4-dioxane (1 mL, 0.4 M), and then DIPEA (136 µL, 0.8 mmol) was added thereto. The reaction mixture was purged with nitrogen, and then stirred at 100° C. for 4 hours. The reaction was terminated with H$_2$O, and the mixture was extracted with EA. The EA layer was dried over MgSO$_4$, filtered and then concentrated. The resulting product was separated by MPLC (MC:MeOH=9:1) and concentrated to obtain N-((3S,4S)-8-(5-((5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfanilamide (10.3 mg, 5%). MS m/z: 560.1 [M+H]$^+$.

Step 2: 6-054(3S,4S)-4-amino-3-methyl-2-oxa-8-azaspiro[4.5]decan-8-yl)pyrazin-2-yl)thio)-5-chloroquinazolin-4(3H)-one N-((3 S,4S)-8-(5-((5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfanilamide (10.3 mg, 0.017 mmol) was put into a round bottom flask and dissolved in DCM (0.25 mL). The reaction mixture was slowly added dropwise with 4 M HCl in dioxane (63 µL) and then stirred at room temperature for 30 minutes. After completion of the reaction, the resulting product was concentrated and added with EA dropwise. The precipitated solid was filtered with EA to obtain the compound of Example 5 (4 mg, 47%). $^1$H NMR (400 MHz, DMSO) δ12.61-12.54 (m, 1H), 8.52 (d, J=1.6 Hz, 1H), 8.33 (d, J=1.6 Hz, 1H), 8.10 (s, 2H), 8.09(b, 2H), 7.52 (d, J=8.8 Hz, 1H), 7.24 (d, J=8.8 Hz, 1H), 4.30-4.19 (m, 3H), 3.93 (d, J=9.2 Hz, 1H), 3.70 (d, J=9.2 Hz, 1H), 3.40 (t, J=5.6 Hz, 1H), 3.20-3.13 (m, 2H), 1.84-1.71 (m, 3H), 1.62-1.59 (m, 1H), 1.24 (d, J=6.4 Hz, 3H); MS m/z: 459 [M+H]$^+$.

Example 6: Synthesis of 3-((5-(4-(aminomethyl)-4-methylpiperidin-1-yl)pyrazin-2-yl)thio)-2-chlorobenzenesulfonyl fluoride

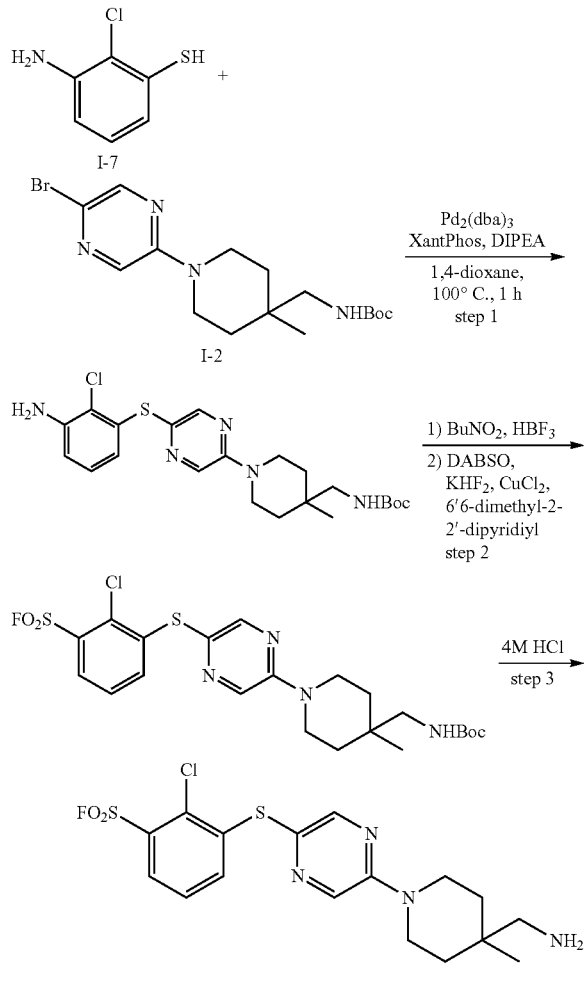

Step 1: tert-butyl ((1-(5-((3-amino-2-chlorophenyl)thio)pyrazin-2-yl)-4-methylpiperidin-4-yl)methyl)carbamate In a round bottom flask, Intermediate I-2 (200 mg, 0.52 mmol), Intermediate I-7 (100 mg, 0.62 mmol), Pd$_2$(dba)$_3$ (48 mg, 0.052 mmol) and XantPhos (30 mg, 0.052 mmol) were dissolved in 1,4-dioxane (2.1 mL, 0.25 M), and then DIPEA (0.18 mL, 1.04 mmol) was added thereto. The reaction mixture was purged with nitrogen, and then stirred at 100° C. for 1 hour. The reaction was terminated with H$_2$O, and the mixture was extracted with EA. The EA layer was dried over MgSO$_4$, filtered and then concentrated. The resulting product was separated by MPLC (EA:Hx=1:5) and concentrated to obtain tert-butyl((1-(5-((3-amino-2-chlorophenyl)thio)pyrazin-2-yl)-4-methylpiperidin-4-yl)methyl)carbamate (187 mg, 78%). MS m/z: 465.1 [M+H]$^+$.

Step 2: tert-butyl ((1-(5-((2-chloro-3-(fluorosulfonyl)phenyl)thio)pyrazin-2-yl)-4-methylpiperidin-4-yl)methyl)carbamate In a round bottom flask, tert-butyl ((1-(5-((3-amino-2-chlorophenyl)thio)pyrazin-2-yl)-4-methylpiperidin-4-yl)methyl)carbamate (210 mg, 0.45 mmol) was dissolved in ethanol (0.5 mL, 1.0 M), and then purged with nitrogen. The reaction mixture was added with 48 wt % of tetrafluoroboric acid (HBF$_3$, 0.11 mL, 0.91 mmol) and then the temperature was lowered to 0° C. Tert-butylnitrile (0.15 mL, 1.14 mmol) was added, followed by stirring at room temperature for 30 minutes. The resulting product was concentrated using a concentrator. 1,4-diazabicyclo[2,2,2]octane (1,4-diazabicyclo[2.2.2]octane bis(sulfur dioxide) adduct: DABSO, 110 mg, 0.045 mmol), potassium bifluoride (177 mg, 2.27 mmol), copper chloride (12 mg, 20 mol %) and 6,6'-dimethyl-2,2'-pyridyl (17 mg, 20 mol %) were added to a round bottom flask containing the reaction mixture, and then dissolved in acetonitrile (2.3 mL, 0.2 M). The reaction mixture was purged with nitrogen and stirred at room temperature for 3 hours. The reaction was terminated with aqueous NaHCO$_3$ solution, and the mixture was extracted with EA. The EA layer was dried over MgSO$_4$, filtered and then concentrated. The resulting product was separated by MPLC (EA:Hx=1:5) and concentrated to obtain tert-butyl ((1-(5-((2-chloro-3-(fluorosulfonyl)phenyl)thio)pyrazin-2-yl)-4-methylpiperidin-4-yl)methyl)carbamate (13 mg, 7%). MS m/z: 532.1 [M+H]$^+$.

Step 3: 34(5-(4-(aminomethyl)-4-methylpiperidin-1-yl)pyrazin-2-yl)thio)-2-chlorobenzenesulfonyl fluoride In a round bottom flask, tert-butyl ((1-(5-((2-chloro-3-(fluorosulfonyl)phenyl)thio)pyrazin-2-yl)-4-methylpiperidin-4-yl)methyl)carbamate (13 mg, 0.024 mmol) was dissolved in methanol (0.5 mL, 0.05 M). The reaction mixture was added with 4 M HCl solution (0.7 mL, 4 M in dioxane) and then stirred at room temperature for 30 minutes. After completion of the reaction, the reaction mixture was concentrated using a concentrator. The resulting product was washed with EA, and then filtered to obtain the compound of Example 6 (12 mg, 99%). $^1$H NMR (400 MHz, DMSO) δ 8.45 (d, J=1.6 Hz, 1H), 8.24 (d, J=1.2 Hz, 1H), 7.74-7.71 (m, 4H), 7.17 (t, J=8.0 Hz, 1H), 6.87 (dd, J=7.6, 1.6 Hz, 1H), 3.95-3.92 (m, 2H), 3.46-3.41 (m, 2H), 2.80-2.79 (m, 2H), 1.58-1.52 (m, 2H), 1.49-1.43 (m, 2H), 1.09 (s, 3H); MS m/z: 431 [M+H]$^+$.

Example 7: Synthesis of 3-((5-(4-amino-4-methylpiperidin-1-yl)pyrazin-2-yl)thio)-2-chlorobenzenesulfonyl fluoride

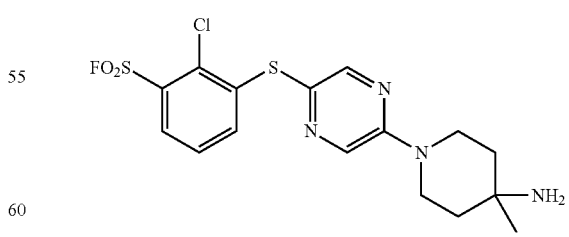

The compound of Example 7 was synthesized in the same method as in Example 6 above, except that Intermediate I-1 was used instead of Intermediate I-2. $^1$H NMR (400 MHz, DMSO) δ8.49 (d, J=1.2 Hz, 1H), 8.36 (d, J=1.2 Hz, 1H), 8.06 (dd, J=8.0 Hz, 1.2 Hz, 1H), 7.58 ((t, J=8.0 Hz, 1H), 7.40

(dd, J=8.0 Hz, 1.2 Hz, 1H), 3.92-3.88 (m, 2H), 3.63-3.60 (m, 2H), 1.65-1.62 (m, 4H), 1.27 (s, 3H); MS m/z: 417 [M+H]⁺.

Example 8: Synthesis of 3-((5-(4-amino-4-methylpiperidin-1-yl)pyrazin-2-yl)thio)-2-chloro-N-methylbenzenesulfonamide

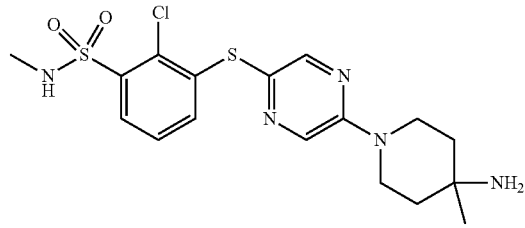 [SMILES: CNS(=O)(=O)c1cccc(Sc2cnc(N3CCC(C)(N)CC3)cn2)c1Cl]

The compound of Example 8 was synthesized in the same method as in Example 6 above, except that Intermediate I-1 was used instead of Intermediate I-2, and KCl was used instead of KHF₂, and then methylamine (10 equivalents) and DIPEA (3 equivalents) were added. ¹H NMR (400 MHz, DMSO) δ8.45 (d, J=1.6 Hz, 1H), 8.29 (d, J=1.6 Hz, 1H), 7.75 (dd, J=8.0 Hz, 1.6 Hz, 1H), 7.41 (t, J=8.0 Hz, 1H), 7.08 (dt, J=8.0 Hz, 1.2 Hz, 1H), 3.91-3.80 (m, 2H), 3.63-3.55 (m, 2H), 2.49 (s, 3H), 1.47-1.42 (m, 4H), 1.10 (s, 3H); MS m/z: 428 [M+H]⁺.

Example 9: Synthesis of 3-((5-((3S,4S)-4-amino-3-methyl-2-oxa-8-azaspiro[4.5]decan-8-yl)pyrazin-2-yl)thio)-2-chlorobenzenesulfonamide

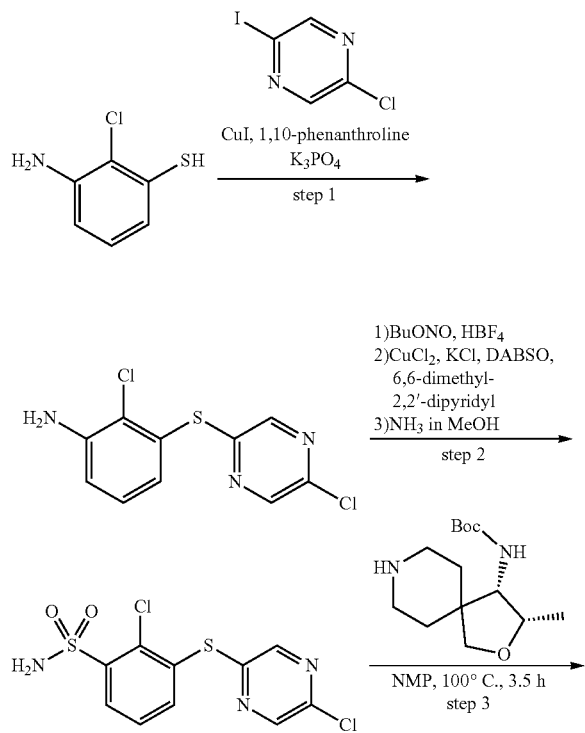

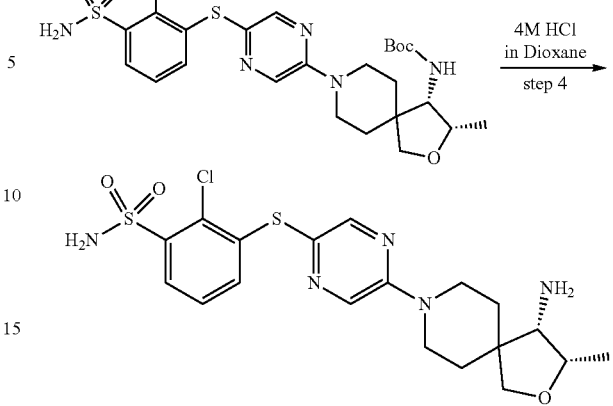

Step 1: 2-chloro-3-((5-chloropyrazin-2-yl)thio)aniline 2-chloro-5-iodopyrazine (116 mg, 0.48 mmol), 3-amino-2-chlorobenzenethiol (100 mg, 0.62 mmol), K₃PO₄ (266 mg, 1.25 mmol), CuI (18 mg, 0.09 mmol), 1,10-phenanthroline (38 mg, 0.19 mmol) and 1,4-dioxane (1.6 mL, 0.3 M) were put into a round bottom flask, and purged with nitrogen and then stirred at 80° C. for 1.5 hours. The reaction mixture was filtered, and the filtrate was concentrated and then separated by MPLC (EA:Hx=1:2). The resulting product was concentrated to obtain 2-chloro-3-((5-chloropyrazin-2-yl)thio)aniline (75 mg, 57%). MS m/z: 273.1 [M+H]⁺.

Step 2: 2-chloro-3-((5-chloropyrazin-2-yl)thio)benzenesulfonamide

In a round bottom flask, 2-chloro-3-((5-chloropyrazin-2-yl)thio)aniline (75 mg, 0.27 mmol) was dissolved in ethanol (0.2 mL, 1.5 M), and then purged with nitrogen. The reaction mixture was added with 48 wt % of tetrafluoroboric acid (0.07 mL) and then the temperature was lowered to 0° C. Tert-butylnitrile (0.08 mL, 0.6 mmol) was added, followed by stirring at room temperature for 30 minutes. The resulting product was concentrated using a concentrator. 1,4-diazabicyclo[2,2,2]octane (73 mg, 0.304 mmol), potassium chloride (144 mg, 1.93 mmol), copper chloride (7.4 mg, 20 mol %) and 6,6'-dimethyl-2,2'-pyridyl (10 mg, 20 mol %) were added to a round bottom flask containing the reaction mixture and dissolved in acetonitrile (1.3 mL, 0.2 M). The reaction mixture was purged with nitrogen, and then stirred at room temperature for 30 minutes. The reaction mixture was added with ammonia solution (0.8 mL, 7 M in MeOH) and then stirred at room temperature for 30 minutes. The reaction was terminated with aqueous NaHCO₃ solution, and the mixture was extracted with EA. The EA layer was dried over MgSO₄, filtered and then concentrated. The resulting product was separated by MPLC (EA:Hx=1:2) and concentrated to obtain 2-chloro-3-((5-chloropyrazin-2-yl)thio)benzenesulfonamide (10 mg, 11%). MS m/z: 337.1 [M+H]⁺.

Step 3: tert-butyl((3S,4S)-8-(54(2-chloro-3-sulfamoylphenyl)thio)pyrazin-2-yl)-3-methyl-2-oxa-8-azaspiro[4.5]decan-4-yl)carbamate NMP (N-methyl-2-pyrrolidone, 0.1 mL, 0.3 M) was added to 2-chloro-3-((5-chloropyrazin-2-yl)thio)benzenesulfonamide (10 mg, 0.03 mmol), tert-butyl ((3S,4S)-3-methyl-2-oxa-8-azaspiro[4.5]decan-4-yl)carbamate (9 mg, 0.03 mmol), and DIPEA (30 µL, 0.18 mmol), followed by stirring at 100° C. for 3 hours. The reaction was terminated with aqueous solution, and the mixture was extracted with EA. The EA layer was dried over MgSO₄, filtered and then concentrated. The resulting product was separated by MPLC (EA:Hx=1:1) and concentrated to obtain tert-butyl((3 S,4S)-8-(5-((2-chloro-3-sulfamoylphenyl)thio)pyrazin-2-yl)-3-methyl-2-oxa-8-azaspiro[4.5]decan-4-yl)carbamate (10 mg, 59%). MS m/z: 571.1 [M+H]⁺.

Step 4: 34(54(3S,4S)-4-amino-3-methyl-2-oxa-8-azaspiro[4.5]decan-8-yl)pyrazin-2-yl)thio)-2-chlorobenzenesulfonamide Tert-butyl ((3 S,4S)-8-(5-((2-chloro-3-sulfamoylphenyl)thio)pyrazin-2-yl)-3-methyl-2-oxa-8-azaspiro[4.5]decan-4-yl)carbamate (10 mg, 0.018 mmol) was dissolved in methanol (0.3 mL, 0.05 M). The reaction mixture was added with 4 M HCl solution (0.3 mL, 4 M in dioxane) and then stirred at room temperature for 30 minutes. EA was added slowly to precipitate a solid, which was filtered to obtain the compound of Example 9 (5 mg, 55%). ¹H NMR (400 MHz, DMSO) δ 8.51 (d, J=1.2 Hz, 1H), 8.32 (d, J=1.2 Hz, 1H), 7.81 (dd, J=8.0 Hz, 1.6 Hz, 1H), 7.71 (s, 2H), 7.40 (t, J=8.0 Hz, 1H), 7.10 (dd, J=8.0 Hz, 1.2 Hz, 1H), 4.31-4.18 (m, 3H), 3.70-3.68 (m, 1H), 3.45-3.39 (m, 1H), 3.20-3.12 (m, 2H), 1.84-1.70 (m, 3H), 1.62-1.58 (m, 1H), 1.23 (d, J=6.4 Hz, 3H); MS m/z: 470 [M+H]⁺.

Example 10: Synthesis of 3-((5-((3S,4S)-4-amino-3-methyl-2-oxa-8-azaspiro[4.5]decan-8-yl)pyrazin-2-yl)thio)-N-benzyl-2-chlorobenzenesulfonamide

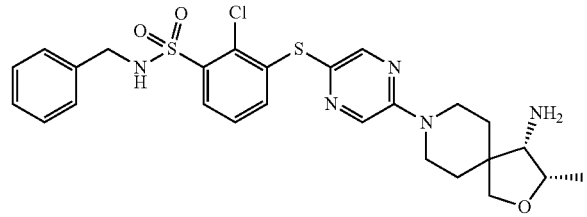 [SMILES: C[C@@H]1OCC2(CCN(c3cnc(Sc4cccc(S(=O)(=O)NCc5ccccc5)c4Cl)cn3)CC2)[C@@H]1N]

The compound of Example 10 was synthesized in the same method as in Example 9, except that benzylamine was used instead of ammonia. ¹H NMR (400 MHz, DMSO) δ8.55 (t, J=6.0 Hz, 1H), 8.51 (d, J=1.2 Hz, 1H), 8.30 (d, J=1.2 Hz, 1H), 7.74 (dd, J=7.6 Hz, 1.6 Hz, 1H), 7.34 (t, J=8.0 Hz, 1H), 7.26-7.18 (m, 5H), 7.07 (dd, J=8.0 Hz, 1.6 Hz, 1H), 4.30-4.18 (m, 3H), 4.11 (d, J=6.0 Hz, 2H), 3.91 (d, J=9.2 Hz, 1H), 3.42-3.41 (m, 1H), 3.21-3.13 (m, 2H), 1.82-1.74 (m, 3H), 1.62-1.58 (m, 2H), 1.23 (d, J=6.4 Hz, 3H); MS m/z: 460 [M+H]⁺.

Example 11: Synthesis of 3-((5-((3S,4S)-4-amino-3-methyl-2-oxa-8-azaspiro[4.5]decan-8-yl)pyrazin-2-yl)thio)-2-chlorobenzenesulfonyl fluoride

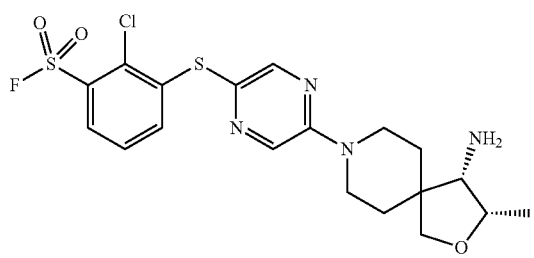 [SMILES: C[C@@H]1OCC2(CCN(c3cnc(Sc4cccc(S(=O)(=O)F)c4Cl)cn3)CC2)[C@@H]1N]

The compound of Example 11 was synthesized in the same method as in Example 9, except that KHF₂ was used instead of ammonia. ¹H NMR (400 MHz, CDCl₃) δ8.3-8.2 (m, 2H), 7.92 (s, 1H), 7.40-7.35 (m, 2H), 4.38 (m, 3H), 4.05-3.97 (m, 1H), 3.85-3.80 (m, 1H), 3.30-3.10 (m, 2H), 2.12-1.94 (m, 2H), 1.85-1.78 (m, 2H), 1.40 (d, J=4.4 Hz, 3H); MS m/z: 473 [M+H]⁺.

Example 12: Synthesis of 3-((3-amino-5-((3S,4S)-4-amino-3-methyl-2-oxa-8-azaspiro[4.5]decan-8-yl)pyrazin-2-yl)thio)-2-chlorobenzenesulfonamide

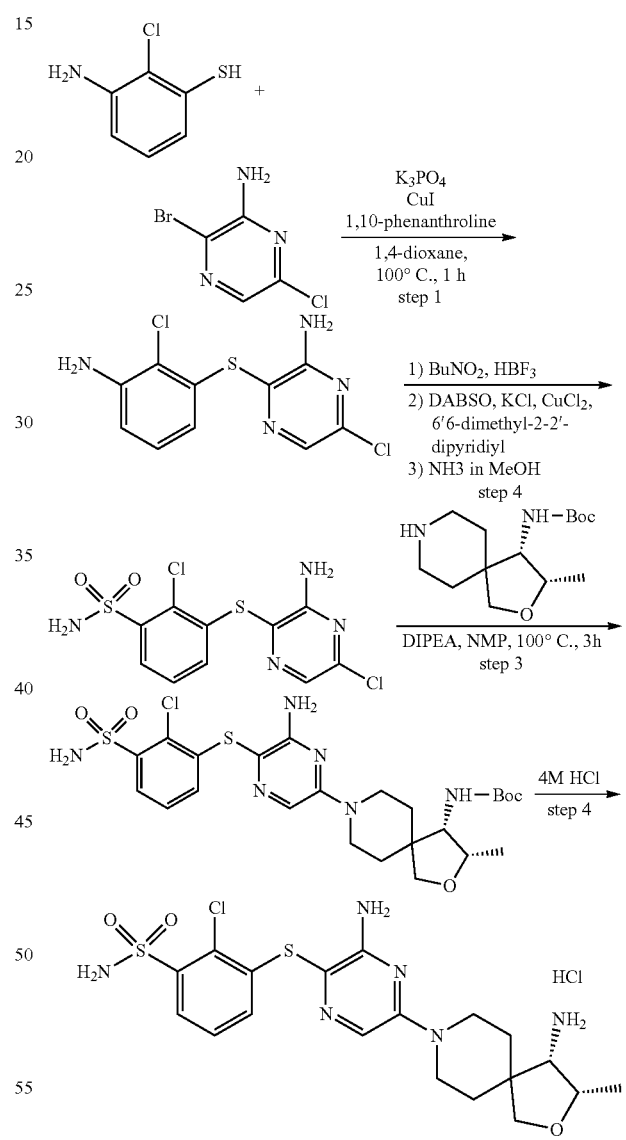

Step 1: 3-((3-amino-2-chlorophenyl)thio)-6-chloropyrazine-2-amine 3-bromo-6-chloropyrazine-2-amine (501 mg, 2.409 mmol), 3-amino-2-chlorobenzenethiol (500 mg, 3.132 mmol), K₃PO₄ (1.3 g, 6.24 mmol), CuI (92 mg, 0.482 mmol), 1,10-phenanthroline (190 mg, 0.96 mmol) and 1,4-dioxane (8.0 mL, 0.3 M) were put into a round bottom flask, and purged with nitrogen and then stirred at 80° C. for 6 hours. The reaction mixture was filtered, and the filtrate was concentrated and then separated by MPLC (EA:Hx=1:2).

The resulting product was concentrated to obtain 3-((3-amino-2-chlorophenyl)thio)-6-chloropyrazine-2-amine (155 mg, 22%). MS m/z: 288.1 [M+H]+.

Step 2: 3-((3-amino-5-chloropyrazin-2-yl)thio)-2-chlorobenzenesulfonamide

In a round bottom flask, 3-((3-amino-2-chlorophenyl)thio)-6-chloropyrazine-2-amine (90 mg, 0.31 mmol) was dissolved in ethanol (0.2 mL, 1.5 M), and then purged with nitrogen. The reaction mixture was added with 48 wt % of tetrafluoroboric acid (0.06 mL) and then the temperature was lowered to 0° C. Tert-butyl nitrile (0.07 mL, 0.6 mmol) was added, followed by stirring at room temperature for 30 minutes. The resulting product was concentrated using a concentrator. 1,4-diazabicyclo[2,2,2]octane (75 mg, 0.344 mmol), potassium chloride (163 mg, 2.19 mmol), copper chloride (8.4 mg, 20 mol %) and 6,6'-dimethyl-2,2'-pyridyl (11 mg, 20 mol %) were put into a round bottom flask containing the reaction mixture, and then dissolved in acetonitrile (1.5 mL, 0.2 M). The reaction mixture was purged with nitrogen and stirred at room temperature for 30 minutes. The reaction mixture was added with ammonia solution (0.8 mL, 7 M in MeOH) and then stirred at room temperature for 30 minutes. The reaction was terminated with aqueous NaHCO₃ solution, and the mixture was extracted with EA. The EA layer was dried over MgSO₄, filtered and then concentrated. The resulting product was separated by MPLC (EA:Hx=1: 2) and concentrated to obtain 3-((3-amino-5-chloropyrazin-2-yl)thio)-2-chlorobenzenesulfonamide (16 mg, 15%). MS m/z: 352.1 [M+H]+.

Step 3: tert-butyl ((3S,4S)-8-(6-amino-5-((2-chloro-3-sulfamoylphenyl)thio)pyrazin-2-yl)-3-methyl-2-oxa-8-azaspiro[4.5]decan-4-yl)carbamate NMP (0.1 mL, 0.3 M) was added to 3-((3-amino-5-chloropyrazin-2-yl)thio)-2-chlorobenzenesulfonamide (15 mg, 0.043 mmol), tert-butyl((3S,4S)-3-methyl-2-oxa-8-azaspiro[4.5]decan-4-yl)carbamate (12 mg, 0.043 mmol), and DIPEA (15 mg, 0.086 mmol), followed by stirring at 100° C. for 3 hours. The reaction was terminated with aqueous solution, and the mixture was extracted with EA. The EA layer was dried over MgSO₄, filtered and then concentrated. The resulting product was separated by MPLC (EA:Hx=1:1) and concentrated to obtain tert-butyl ((3 S,4S)-8-(6-amino-5-((2-chloro-3-sulfamoylphenyl)thio)pyrazin-2-yl)-3-methyl-2-oxa-8-azaspiro[4.5]decan-4-yl)carbamate (10 mg, 40%). MS m/z: 586.1 [M+H]+.

Step 4: 3-((3-amino-5-((3S,4S)-4-amino-3-methyl-2-oxa-8-azaspiro[4.5]decan-8-yl)pyrazin-2-yl)thio)-2-chlorobenzenesulfonamide Tert-butyl ((3 S,4S)-8-(6-amino-5-((2-chloro-3-sulfamoylphenyl)thio)pyrazin-2-yl)-3-methyl-2-oxa-8-azaspiro[4.5]decan-4-yl)carbamate (10 mg, 0.017 mmol) was dissolved in methanol (0.1 mL, 0.1 M). The reaction mixture was added with 4 M HCl solution (0.7 mL, 4 M in dioxane) and then stirred at room temperature for 30 minutes. EA was added slowly to precipitate a solid, which was filtered to obtain the compound of Example 12 (5 mg, 56%). 1 H NMR (400 MHz, DMSO) δ7.74 (dd, J=8.0 Hz, 1.2 Hz, 1H), 7.69 (s, 1H), 7.68 (s, 1H), 7.36 (t, J=8.0 Hz, 1H), 6.81 (dd, J=8.0 Hz, 1.2 Hz, 1H), 6.26 (brs, 2H), 4.21-4.11 (m, 3H), 3.92-3.87 (m, 1H), 3.42-3.38 (m, 1H), 3.10-3.0 (m, 2H), 1.78-1.50 (m, 2H), 1.23 (d, J=6.8 Hz, 3H); MS m/z: 485 [M+H]+.

Example 13: Synthesis of 6-((5-(4-(aminomethyl)-4-methylpiperidin-1-yl)pyrazin-2-yl)thio)-3-benzyl-5-chloroquinazolin-4(3H)-one

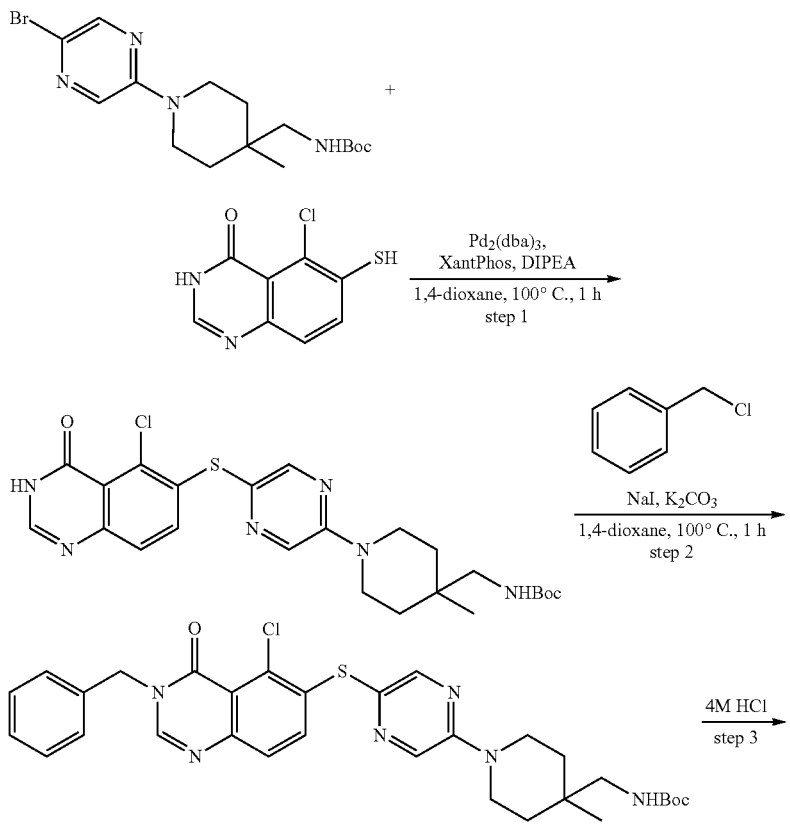

-continued

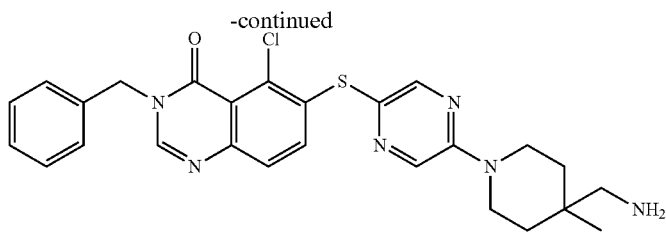

Step 1: tert-butyl ((1-(5-((5-chloro-4-oxo-3,4-dihydroquinazolin-6-yl)thio)pyrazin-2-yl)-4-methylpiperidin-4-yl)methyl)carbamate In a round bottom flask, Intermediate I-2 (275 mg, 0.71 mmol), Intermediate I-8 (215 mg, 0.86 mmol), Pd$_2$(dba)$_3$ (64 mg, 0.07 mmol) and XantPhos (40 mg, 0.07 mmol) were dissolved in 1,4-dioxane (3.0 mL, 0.25 M), and then DIPEA (0.25 mL, 1.4 mmol) was added thereto. The reaction mixture was purged with nitrogen and stirred at 100° C. for 1 hour. The reaction was terminated with H$_2$O, and the mixture was extracted with EA. The EA layer was dried over MgSO$_4$, filtered and then concentrated. The resulting product was separated by MPLC (EA:Hx=1:1) and concentrated to obtain tert-butyl ((1-(5-((5-chloro-4-oxo-3,4-dihydroquinazolin-6-yl)thio)pyrazin-2-yl)-4-methylpiperidin-4-yl)methyl)carbamate (144 mg, 40%). MS m/z: 518.1 [M+H]$^+$.

Step 2: tert-butyl ((1-(5-((3-benzyl-5-chloro-4-oxo-3,4-dihydroquinazolin-6-yl)thio)pyrazin-2-yl)-4-methylpiperidin-4-yl)methyl)carbamate In a round bottom flask, tert-butyl ((1-(5-((5-chloro-4-oxo-3,4-dihydroquinazolin-6-yl)thio)pyrazin-2-yl)-4-methylpiperidin-4-yl)methyl)carbamate (30 mg, 0.05 mmol), benzylchloride (6 µL, 0.05 mmol), sodium iodide (7 mg, 0.05 mmol), and potassium carbonate (34 mg, 0.25 mmol) were dissolved in acetone (0.5 mL, 0.1 M). The reaction mixture was stirred at 100° C. for 1 hour. The reaction was terminated with H$_2$O, and the mixture was extracted with EA. The EA layer was dried over MgSO$_4$, filtered and then concentrated. The resulting product was separated by MPLC (EA:Hx=1:1) and concentrated to obtain tert-butyl((1-(5-((3-benzyl-5-chloro-4-oxo-3,4-dihydroquinazolin-6-yl)thio)pyrazin-2-yl)-4-methylpiperidin-4-yl)methyl)carbamate (21 mg, 60%). MS m/z: 608.1 [M+H]$^+$.

Step 3: 6-((5-(4-(aminomethyl)-4-methylpiperidin-1-yl)pyrazin-2-yl)thio)-3-benzyl-5-chloroquinazolin-4(3H)-one In a round bottom flask, tert-butyl ((1-(5-((3-benzyl-5-chloro-4-oxo-3,4-dihydroquinazolin-6-yl)thio)pyrazin-2-yl)-4-methylpiperidin-4-yl)methyl)carbamate (21 mg, 0.03 mmol) was dissolved in methanol (0.6 mL, 0.05 M). The reaction mixture was added with 4 M hydrochloric acid (0.8 mL, 4 M in dioxane) and stirred at room temperature for 30 minutes. After completion of the reaction, the reaction mixture was concentrated using a concentrator. The reaction mixture was washed with EA, and the solid was collected by filtration to obtain the compound of Example 13 (16 mg, 99%). $^1$H NMR (400 MHz, DMSO) δ8.61 (s, 1H), 8.47 (d, J=1.6 Hz, 1H), 8.30 (d, J=1.2 Hz, 1H), 7.93(bs, 3H), 7.55 (d, J=8.8 Hz, 1H), 7.39-7.29 (m, 5H), 7.24 (d, J=8.8 Hz, 1H), 5.17 (s, 2H), 3.96-3.91 (m, 2H), 3.50-3.43 (m, 2H), 2.80-2.79 (m, 2H), 1.60-1.53 (m, 2H), 1.48-1.45 (m, 2H), 1.10 (s, 3H); MS m/z: 507 [M+H]$^+$.

Example 14: Synthesis of 6-((5-(4-amino-4-methylpiperidin-1-yl)pyrazin-2-yl)thio)-5-chloro-3-(3-nitrobenzyl)quinazolin-4(3H)-one

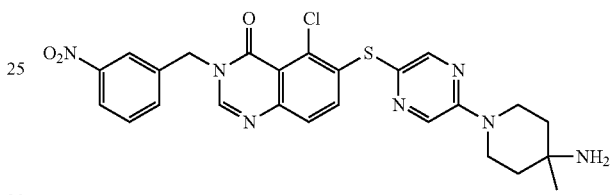

The compound of Example 14 was synthesized in the same method as in Example 13, except that Intermediate I-1 was used instead of Intermediate I-2, and 3-nitrobenzylbromide was used instead of benzylchloride. $^1$H NMR (400 MHz, CDCl$_3$) δ8.26 (d, J=1.2 Hz, 1H), 8.21-8.18 (m, 2H), 8.11 (s, 1H), 7.75 (d, J=8.0 Hz, 1H), 7.56 (t, J=8.0 Hz, 1H), 7.47 (d, J=8.8 Hz, 1H), 7.30 (d, J=8.8 Hz, 1H), 7.21 (s, 1H), 5.23 (s, 2H), 3.81-3.65 (m, 4H), 1.67-1.62 (m, 4H), 1.25 (s, 3H); MS m/z: 538 [M+H]$^+$.

Example 15: Synthesis of 6-((5-(4-(aminomethyl)-4-methylpiperidin-1-yl)pyrazin-2-yl)thio)-5-chloro-3-methylquinazolin-4(3H)-one

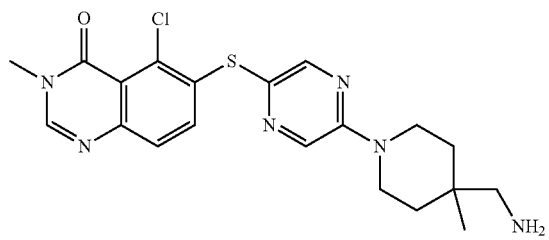 [SMILES: Cn1cnc2ccc(Sc3cnc(N4CCC(C)(CN)CC4)cn3)c(Cl)c2c1=O]

The compound of Example 15 was synthesized in the same method as in Example 13, except that MeI was used instead of benzylchloride. $^1$H NMR (400 MHz, DMSO) δ8.49 (s, 1H), 8.29 (s, 1H), 8.32 (d, J=1.2 Hz, 1H), 7.86(bs, 3H), 7.52 (d, J=8.8 Hz, 1H), 7.20 (d, J=8.8 Hz, 1H), 4.01-3.93 (m, 2H), 3.58-3.44 (m, 5H), 2.81-2.80 (m, 2H), 1.60-1.53 (m, 2H), 1.48-1.45 (m, 4H), 1.10 (s, 3H); MS m/z: 531 [M+H]$^+$.

Example 16: Synthesis of 3-((6-((5-(4-(aminomethyl)-4-methylpiperidin-1-yl)pyrazin-2-yl)thio)-5-chloro-4-oxoquinazolin-3(4H)-yl)methyl)benzenesulfonyl fluoride

Example 17: Synthesis of 4-((6-((5-(4-(aminomethyl)-4-methylpiperidin-1-yl)pyrazin-2-yl)thio)-5-chloro-4-oxoquinazolin-3(4H)-yl)methyl)benzenesulfonyl fluoride

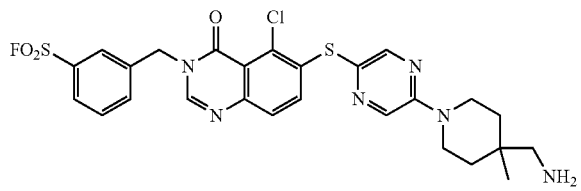

The compound of Example 16 was synthesized in the same method as in Example 13, except that 3-(bromomethyl)benzenesulfonyl fluoride was used instead of benzylchloride. ¹H NMR (400 MHz, DMSO) δ8.68 (s, 1H), 8.48 (d, J=1.2 Hz, 1H), 8.31 (d, J=1.2 Hz, 1H), 8.23 (s, 1H), 8.11-8.08 (m, 1H), 7.96 (d, J=8.0 Hz, 1H), 7.84(bs, 3H), 7.79 (t, J=8.0 Hz, 1H), 7.56 (d, J=8.4 Hz, 1H), 7.24 (d, J=8.8 Hz, 1H), 5.30 (s, 2H), 3.96-3.93 (m, 2H), 3.49-3.44 (m, 2H), 2.81-2.79 (m, 2H), 1.59-1.52 (m, 2H), 1.48-1.44 (m, 2H), 1.09 (s, 3H); MS m/z: 589 [M+H]⁺.

The compound of Example 17 was synthesized in the same method as in Example 13, except that 4-(bromomethyl)benzenesulfonyl fluoride was used instead of benzylchloride. ¹H NMR (400 MHz, DMSO) δ8.64 (s, 1H), 8.48 (d, J=1.2 Hz, 1H), 8.31 (d, J=1.2 Hz, 1H), 8.13 (d, J=8.4 Hz, 2H), 7.90(bs, 3H), 7.75 (d, J=8.4 Hz, 2H), 7.58 (d, J=8.8 Hz, 1H), 7.26 (d, J=8.8 Hz, 1H), 5.33 (s, 2H), 4.06-3.93 (m, 4H), 3.50-3.44 (m, 2H), 2.81-2.79 (m, 2H), 1.60-1.53 (m, 2H), 1.48-1.44 (m, 2H), 1.10 (s, 3H); MS m/z: 589 [M+H]⁺.

Example 18: Synthesis of 6-((5-((3S,4S)-4-amino-3-methyl-2-oxa-8-azaspiro[4.5]decan-8-yl)pyrazin-2-yl)thio)-3-benzyl-5-chloroquinazolin-4(3H)-one

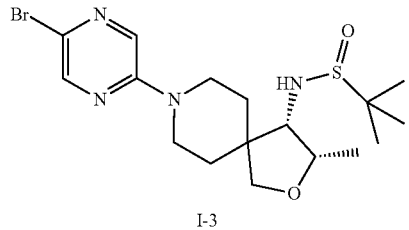

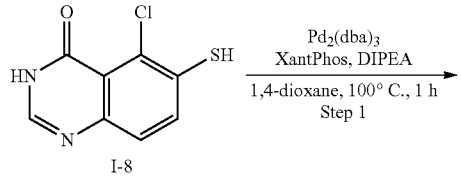

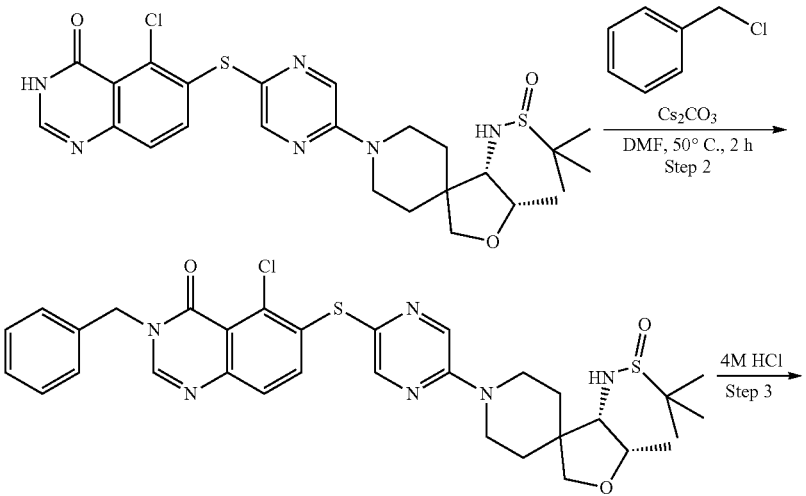

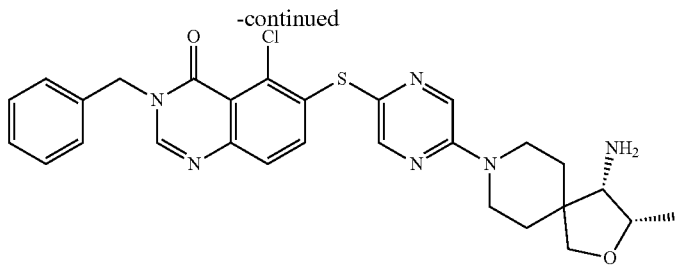

Step 1: N4(3S,4S)-8-(54(5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfanilamide In a round bottom flask, Intermediate I-3 (345 mg, 0.8 mmol), Intermediate I-8 (300 mg, 1.2 mmol), Pd$_2$(dba)$_3$ (73 mg, 0.08 mmol) and XantPhos (46 mg, 0.08 mmol) were dissolved in 1,4-dioxane (3.2 mL, 0.25 M), and then DIPEA (0.28 mL, 1.6 mmol) was added thereto. The reaction mixture was purged with nitrogen, and then stirred at 100° C. for 1 hour. The reaction was terminated with H$_2$O, and the mixture was extracted with EA. The EA layer was dried over MgSO$_4$, filtered and then concentrated. The resulting product was separated by MPLC (MeOH:MC=1:50) and concentrated to obtain N-((3S,4S)-8-(5-((5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfanilamide (190 mg, 42%). MS m/z: 564.1 [M+H]$^+$.

Step 2: N4(3S,4S)-8-(54(3-benzyl-5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfanilamide In a round bottom flask, N-((3S,4S)-8-(5-((5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfanilamide (50 mg, 0.09 mmol), benzylchloride (13 μL, 0.12 mmol) and cesium carbonate (44 mg, 0.13 mmol) were dissolved in DMF (0.9 mL, 0.1 M). The reaction mixture was stirred at 50° C. for 2 hours. The reaction was terminated with aqueous NaHCO$_3$ solution, and the mixture was extracted with EA. The EA layer was dried over MgSO$_4$, filtered and then concentrated. The resulting product was separated by MPLC (MeOH:MC=1:50) and concentrated to obtain N-((3S,S5)-8-(5-((3-benzyl-5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfanilamide (37 mg, 62%). MS m/z: 654.1 [M+H]$^+$.

Step 3: 64(54(3S,4S)-4-amino-3-methyl-2-oxa-8-azaspiro[4.5]decan-8-yl)pyrazin-2-yl)thio)-3-benzyl-5-chloroquinazolin-4(3H)-one In a round bottom flask, N-((3 S,4S)-8-(5-((3-benzyl-5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfanilamide (37 mg, 0.056 mmol) was dissolved in DCM (0.6 mL, 0.1 M). The reaction mixture was added with 4 M hydrochloric acid (0.14 mL, 4 M in dioxane) and then stirred at 40° C. for 30 minutes. After completion of the reaction, the reaction mixture was concentrated using a concentrator. The reaction mixture was washed with EA, and then the solid was collected by filtration to obtain the compound of Example 18 (35 mg, 99%). $^1$H NMR (400 MHz, DMSO) δ8.61 (s, 1H), 8.51 (s, 1H), 8.33 (s, 1H), 8.07(bs, 3H), 7.55 (d, J=8.8 Hz, 1H), 7.38-7.31 (m, 5H), 7.52 (d, J=8.8 Hz, 1H), 5.17 (s, 2H), 4.30-4.19 (m, 3H), 3.92 (d, J=9.2 Hz, 1H), 3.70 (d, J=9.2 Hz, 1H), 3.42-3.41 (m, 1H), 3.20-3.12 (m, 2H), 1.82-1.71 (m, 3H), 1.62-1.58 (m, 1H), 1.23 (d, J=6.4 Hz, 3H); MS m/z: 549 [M+H]$^+$.

Example 19: Synthesis of 3-((6-((5-(((3S,4S)-4-amino-3-methyl-2-oxa-8-azospiro[4.5]decan-8-yl)pyrazin-2-yl)thio)-5-chloro-4-oxoquinazolin-3(4H)-yl)methyl)benzenesulfonyl fluoride

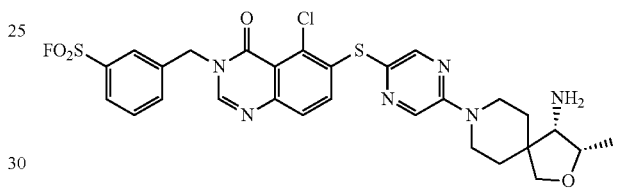

The compound of Example 19 was synthesized in the same method as in Example 18, except that 3-(bromomethyl)benzenesulfonyl fluoride was used instead of benzyl chloride. $^1$H NMR (400 MHz, DMSO) δ8.68 (s, 1H), 8.511 (d, J=1.2 Hz, 1H), 8.32 (d, J=1.2 Hz, 1H), 8.23 (s, 1H), 8.11-8.09 (m, 4H), 7.96 (d, J=8.0 Hz, 1H), 7.79 (t, J=8.0 Hz, 1H), 7.56 (d, J=8.8 Hz, 1H), 7.26 (d, J=8.8 Hz, 1H), 5.30 (s, 2H), 4.30-4.19 (m, 2H), 3.93 (d, J=8.8 Hz, 1H), 3.70 (d, J=9.2 Hz, 1H), 3.20-3.12 (m, 2H), 1.98-1.92 (m, 2H), 1.80-1.74 (m, 3H), 1.62-1.59 (m, 1H), 1.24 (d, J=6.4 Hz, 3H); MS m/z: 631 [M+H]$^+$.

Example 20: Synthesis of 6-((5-(((3S,4S)-4-amino-3-methyl-2-oxa-8-azospiro[4.5]decan-8-yl)pyrazin-2-yl)thio)-5-chloro-3-(pyridin-3-ylmethyl)quinazolin-4H-one

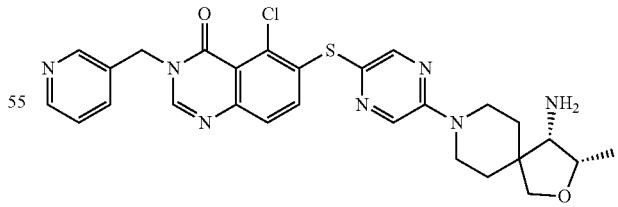

The compound of Example 20 was synthesized in the same method as in Example 18, except that 3-(bromomethyl)pyridine was used instead of benzyl chloride. $^1$H NMR (400 MHz, DMSO) δ8.93 (s, 1H), 8.77-8.75 (m, 1H), 8.66 (s, 1H), 8.51 (d, J=1.2 Hz, 1H), 8.38-8.36 (m, 1H), 8.32 (d, J=1.2 Hz, 1H), 8.11 (s, 3H), 7.86-7.83 (m, 1H), 7.56 (d, J=8.4 Hz, 1H), 7.26 (d, J=8.4 Hz, 1H), 5.29 (s, 2H), 4.30-4.19 (m, 3H), 3.93 (d, J=8.8 Hz, 1H), 3.70 (d, J=8.8 Hz, 1H), 3.20-3.13 (m, 3H), 1.83-1.71 (m, 3H), 1.62-1.59 (m, 1H), 1.24 (d, J=6.4 Hz, 3H); MS m/z: 550 [M+H]⁺.

Example 21: Synthesis of 3-((6-((5-(4-(aminomethyl)-4-methylpiperidin-1-yl)pyrazin-2-yl)thio)-5-chloro-2methyl-4-oxoquinazolin-3(4H)-yl)methyl)benzenesulfonyl fluoride

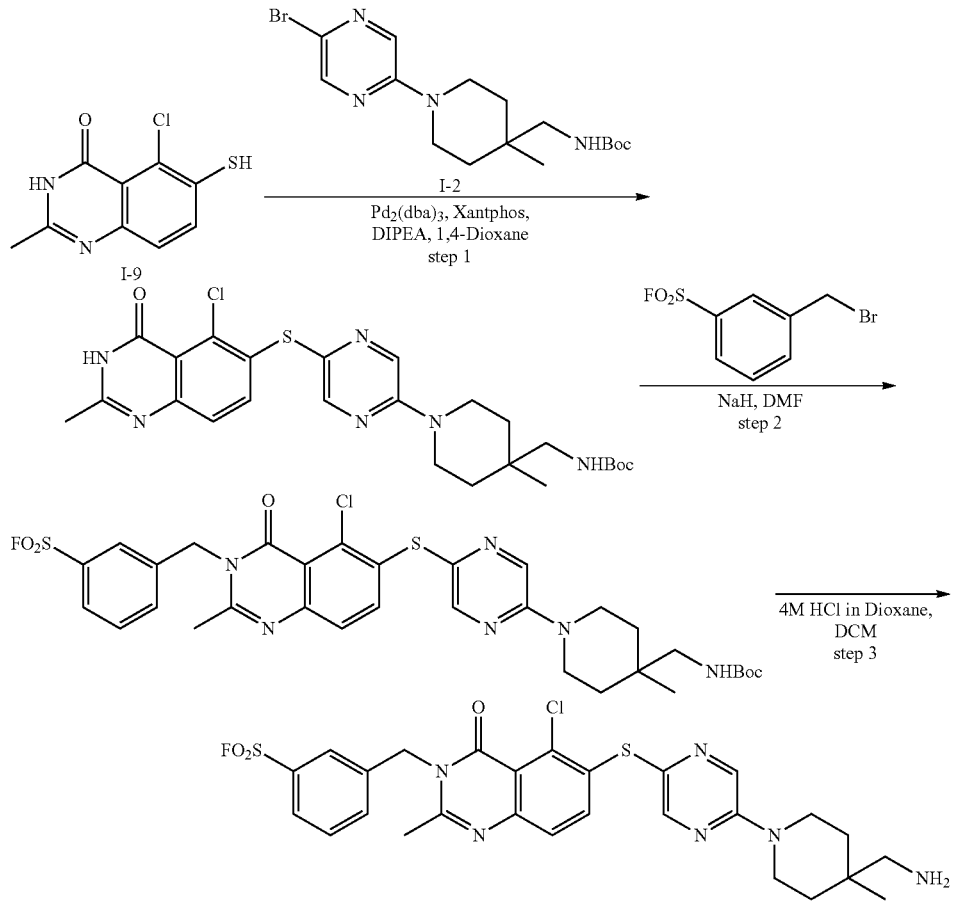

Step 1: tert-butyl ((1-(54(5-chloro-2-methyl-4-oxo-3,4-dihydroquinazolin-6-yl)thio)pyrazin-2-yl)-4-methylpiperidin-4-yl)methyl)carbamate In a round bottom flask, Intermediate I-2 (132 mg, 0.34 mmol), Intermediate I-9 (131 mg, 0.58 mmol), Pd₂(dba)₃ (16 mg, 0.017 mmol) and XantPhos (20 mg, 0.034 mmol) were dissolved in 1,4-dioxane (1 mL, 0.3 M), and then DIPEA (120 μL, 0.68 mmol) was added thereto. The reaction mixture was purged with nitrogen and stirred at 100° C. for 4 hours. The reaction was terminated with H₂O, and the mixture was extracted with EA. The EA layer was dried over MgSO₄, filtered and then concentrated. The resulting product was separated by MPLC (MC:MeOH=9:1) and concentrated to obtain tert-butyl ((1-(5-((5-chloro-2-methyl-4-oxo-3,4-dihydroquinazolin-6-yl)thio)pyrazin-2-yl)-4-methylpiperidin-4-yl)methyl)carbamate (67 mg, 37%). MS m/z: 532.1 [M+H]⁺.

Step 2: tert-butyl ((1-(54(5-chloro-3-(3-(fluorosulfonyl)benzyl)-2-methyl-4-oxo-3,4-dihydroquinazolin-6-yl)thio)pyrazin-2-yl)-4-methylpiperidin-4-yl)methyl)carbamate In a round bottom flask, tert-butyl ((1-(5-((5-chloro-2-methyl-4-oxo-3,4-dihydroquinazolin-6-yl)thio)pyrazin-2-yl)-4-methylpiperidin-4-yl)methyl)carbamate (15 mg, 0.03 mmol) was dissolved in DMF (0.5 mL), and then NaH (1.4 mg, 0.06 mmol) was added thereto at 0° C. The reaction mixture was stirred at 0° C. for 1 hour and added with 3-(bromomethyl)benzenesulfonyl fluoride (7.9 mg, 0.031 mmol). The reaction mixture was stirred at room temperature for 12 hours, the reaction was terminated with H₂O, and the mixture was extracted with EA. The EA layer was dried over MgSO₄, filtered and then concentrated. The resulting product was separated by MPLC (EA:Hx=4:1) and concentrated to obtain tert-butyl((1-(5-((5-chloro-3-(3-(fluorosulfonyl)benzyl)-2-methyl-4-oxo-3,4-dihydroquinazolin-6-yl)thio)pyrazin-2-yl)-4-methylpiperidin-4-yl)methyl)carbamate (8.2 mg, 39%). MS m/z: 704.1 [M+H]⁺.

Step 3: 34(64(5-(4-(aminomethyl)-4-methylpiperidin-1-yl)pyrazin-2-yl)thio)-5-chloro-2-methyl-4-oxoquinazolin-3(4H)-yl)methyl)benzenesulfonyl fluoride Tert-butyl ((1-(5-((5-chloro-3-(3-(fluoro sulfonyl)benzyl)-2-methyl-4-oxo-3,4-dihydroquinazolin-6-yl)thio)pyrazin-2-yl)-4-methylpiperidin-4-yl)methyl)carbamate (8.2 mg, 0.012 mmol) was put into a round bottom flask and dissolved in DCM (0.25 mL). The reaction mixture was slowly added dropwise with 4 M HCl in dioxane (0.25 mL) and then stirred at room temperature for 30 minutes. After completion of the reaction, the resulting product was concentrated, and then EA was added thereto dropwise. The precipitated solid was filtered with EA to obtain the compound of Example 21 (3.5 mg, 48%). ¹H NMR (400 MHz, DMSO) δ8.55 (s, 1H), 8.37 (d, J=1.2 Hz, 1H), 8.1 (s, 1H), 8.15-8.14 (m, 1H), 7.90(b, 3H), 7.82 (d, J=4.4 Hz, 2H), 7.56 (d, J=8.8 Hz, 1H), 7.30 (d, J=8.8 Hz, 1H), 5.52 (s, 2H), 4.02-3.99 (m, 2H), 3.55-3.50 (m, 2H), 2.87-2.86 (m, 2H), 2.55 (s, 3H), 1.64-1.51 (m, 4H), 1.16 (s, 3H); MS m/z: 603 [M+H]⁺.

Example 22: Synthesis of 6-((5-(4-(aminomethyl)-4-methylpiperidin-1-yl)pyrazin-2-yl)thio)-5-chloro-2-methylquinazolin-4(3H)-one

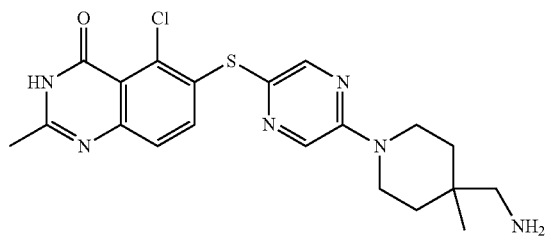 [SMILES: Cc1nc2ccc(Sc3cnc(N4CCC(C)(CN)CC4)cn3)c(Cl)c2c(=O)[nH]1]

The compound of Example 22 was synthesized in the same method as in Example 21, by performing Boc-deprotection on tert-butyl ((1-(5-((5-chloro-3-(3-(fluorosulfonyl)benzyl)-2-methyl-4-oxo-3,4-dihydroquinazolin-6-yl)thio)pyrazin-2-yl)-4-methylpiperidin-4-yl)methyl)carbamate obtained in Step 2. ¹H NMR (400 MHz, MeOD) δ8.28 (dd, J=10.6, 1.4 Hz, 2H), 7.39 (d, J=8.8 Hz, 1H), 7.27 (d, J=8.8 Hz, 1H), 4.07 (dt, J=13.9, 4.8 Hz, 2H), 3.54-3.43 (m, 2H), 2.91 (s, 2H), 2.41 (s, 3H), 1.60 (dt, J=8.4, 4.3 Hz, 4H), 1.20 (s, 3H); MS m/z: 431 [M+H]⁺.

Example 23: Synthesis of 6-((5-(4-(aminomethyl)-4-methylpiperidin-1-yl)pyrazin-2-yl)thio)-3-benzyl-5-chloro-2-methylquinazolin-4(3H)-one

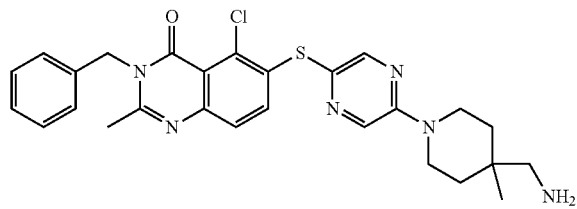 [SMILES: Cc1nc2ccc(Sc3cnc(N4CCC(C)(CN)CC4)cn3)c(Cl)c2c(=O)n1Cc1ccccc1]

The compound of Example 23 was synthesized in the same method as in Example 21, except that benzyl bromide was used instead of 3-(bromomethyl)benzenesulfonyl fluoride. ¹H NMR (400 MHz, MeOD) δ 8.29 (dd, J=9.0, 1.4 Hz, 2H), 7.54-7.45 (m, 1H), 7.45-7.17 (m, 5H), 7.11-7.01 (m, 1H), 5.41 (s, 2H), 4.07 (d, J=13.9 Hz, 2H), 3.55-3.48 (m, 1H), 3.47 (d, J=13.6 Hz, 1H), 2.91 (s, 2H), 2.52 (s, 3H), 1.65-1.57 (m, 4H), 1.20 (s, 3H); MS m/z: 521 [M+H]⁺.

Example 24: Synthesis of 1-(5-((7-chloro-2-methylbenzo[d]thiazol-6-yl)thio)pyrazin-2-yl)-4-methylpiperidin-4-amine

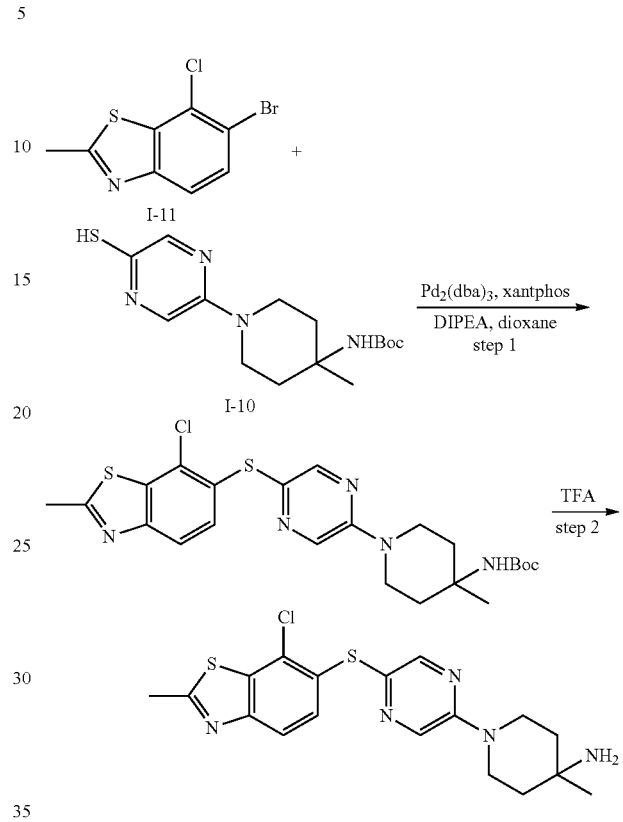

Step 1: tert-butyl (1-(54(7-chloro-2-methylbenzo[d]thiazol-6-yl)thio)pyrazin-2-yl)-4-methylpiperidin-4-yl)carbamate In a round bottom flask, Intermediate I-10 (100 mg, 0.31 mmol), Intermediate I-11 (89 mg, 0.34 mmol), Pd₂(dba)₃ (28 mg, 0.031 mmol) and XantPhos (18 mg, 0.031 mmol) were dissolved in 1,4-dioxane (2 mL, 0.15 M), and then DIPEA (0.11 mL, 0.62 mmol) was added thereto. The reaction was carried out at 150° C. for 30 minutes using a microwave instrument. The reaction mixture was washed with EA and filtered through celite, and then the filtrate was concentrated. The resulting product was separated by MPLC (EA:Hx=1:3) and concentrated to obtain tert-butyl(1-(5-((7-chloro-2-methylbenzo[d]thiazol-6-yl)thio)pyrazin-2-yl)-4-methylpiperidin-4-yl)carbamate (20 mg, 13%). MS m/z: 506 [M+H]⁺.

Step 2: 1-(5-((7-chloro-2-methylbenzo Id]thiazol-6-yl)thio)pyrazin-2-yl)-4-methylpiperidin-4-amine In a round bottom flask, tert-butyl (1-(5-((7-chloro-2-methylbenzo[d]thiazol-6-yl)thio)pyrazin-2-yl)-4-methylpiperidin-4-yl)carbamate (20 mg, 0.31 mmol) was dissolved in DCM (1 mL, 0.3 M). The reaction mixture was added with trifluoroacetic acid (0.5 mL, 0.62 M) and then stirred at room temperature for 1 hour. The reaction was terminated with aqueous NaHCO₃ solution, and the mixture was extracted with EA. The EA layer was dried over MgSO₄, filtered and then concentrated. The resulting product was separated by Prep-HPLC and concentrated to obtain the compound of Example 24 (4.5 mg, 28%). ¹H NMR (400 MHz, MeOD) δ8.26 (d, J=1.5 Hz, 1H), 8.19 (d, J=1.4 Hz, 1H), 7.73 (d, J=8.6 Hz, 1H), 7.33 (d, J=8.6 Hz, 1H), 4.17 (dt, J=14.2, 4.6 Hz, 2H), 3.47-3.32 (m, 2H), 2.83 (s, 3H), 1.89-1.80 (m, 2H), 1.49 (s, 3H), 1.41-1.27 (m, 2H); MS m/z: 406 [M+H]⁺.

Example 25: Synthesis of 1-(5-((4-chloro-2-methyl-2H-indazol-5-yl)thio)pyrazin-2-yl)-4-methylpiperidin-4-amine

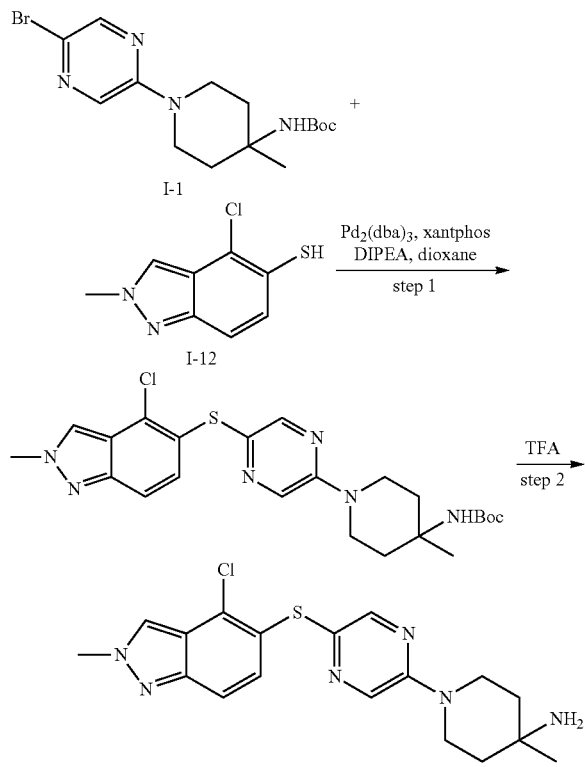

Step 1: tert-butyl (1-(5(4-chloro-2-methyl-2H-indazol-5-yl)thio)pyrazin-2-yl)-4-methylpiperidin-4-yl)carbamate In a round bottom flask, Intermediate I-1 (50 mg, 0.135 mmol), Intermediate I-12 (32 mg, 0.162 mmol), Pd₂(dba)₃ (12 mg, 0.0135 mmol) and XantPhos (8 mg, 0.0135 mmol) were dissolved in 1,4-dioxane (1 mL, 0.14 M), and then DIPEA (47 µL, 0.27 mmol) was added thereto. The reaction was carried out at 150° C. for 30 minutes using a microwave instrument. The reaction mixture was washed with EA and filtered through celite, and then the filtrate was concentrated. The resulting product was separated by MPLC (EA:Hx=1:3) and concentrated to obtain tert-butyl(1-(5-((4-chloro-2-methyl-2H-indazol-5-yl)thio)pyrazin-2-yl)-4-methylpiperidin-4-yl)carbamate (15 mg, 23%). MS m/z: 489 [M+H]⁺.

Step 2: 1-(5(4-chloro-2-methyl-2H-indazol-5-yl)thio)pyrazin-2-yl)-4-methylpiperidin-4-amine In a round bottom flask, tert-butyl (1-(5-((4-chloro-2-methyl-2H-indazol-5-yl)thio)pyrazin-2-yl)-4-methylpiperidin-4-yl)carbamate (15 mg, 0.03 mmol) was dissolved in DCM (1 mL, 0.03 M). The reaction mixture was added with trifluoro acetic acid (0.5 mL, 0.06 M) and then stirred at room temperature for 1 hour. The reaction was terminated with aqueous NaHCO₃ solution, and the mixture was extracted with EA. The EA layer was dried over MgSO₄, filtered and then concentrated. The resulting product was separated by Prep-HPLC and concentrated to obtain the compound of Example 25 (4.1 mg, 35%) as a TFA salt. ¹H NMR (400 MHz, MeOD) δ 8.31 (s, 1H), 8.20 (d, J=1.5 Hz, 1H), 8.06 (d, J=1.5 Hz, 1H), 7.48 (dd, J=8.9, 1.0 Hz, 1H), 7.21 (d, J=9.0 Hz, 1H), 4.22 (s, 3H), 4.13 (dt, J=14.2, 4.4 Hz, 2H), 3.43-3.32 (m, 2H), 1.84 (m, 4H), 1.48 (s, 3H); MS m/z: 389 [M+H]⁺.

Example 26: Synthesis of (3S,4S)-8-(5-((4-chloro-2-methyl-2H-indazol-5-yl)thio)pyrazin-2-yl)-3-methyl-2-oxa-8-azaspiro[4.5]decan-4-amine

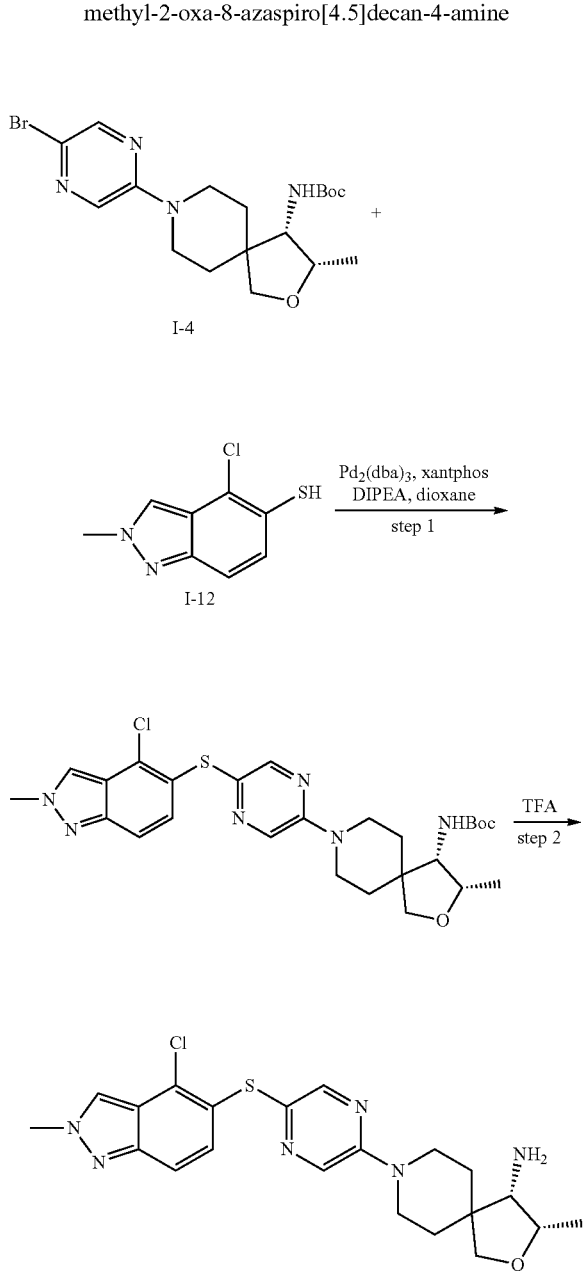

The compound of Example 26 was synthesized in the same method as in Example 25, except that Intermediate I-4 was used instead of Intermediate I-1. ¹H NMR (400 MHz, MeOD) δ 8.17 (d, J=1.5 Hz, 1H), 8.06 (d, J=1.4 Hz, 1H), 7.55 (d, J=9.0 Hz, 1H), 7.53-7.44 (m, 1H), 7.20 (d, J=9.0 Hz, 1H), 3.97 (s, 3H), 3.86-3.75 (m, 2H), 3.41-3.38 (m, 3H), 3.16-3.10 (m, 2H), 1.85-1.68 (m, 4H), 1.30 (d, J=6.5 Hz, 3H); MS m/z: 445 [M+H]⁺.

Example 27: Synthesis of 3-((4-amino-2-(4-amino-4-methylpiperidin-1-yl)-1-methyl-6-oxo-1,6-dihydropyrimidin-5-yl)thio)-2-chlorobenzoic acid

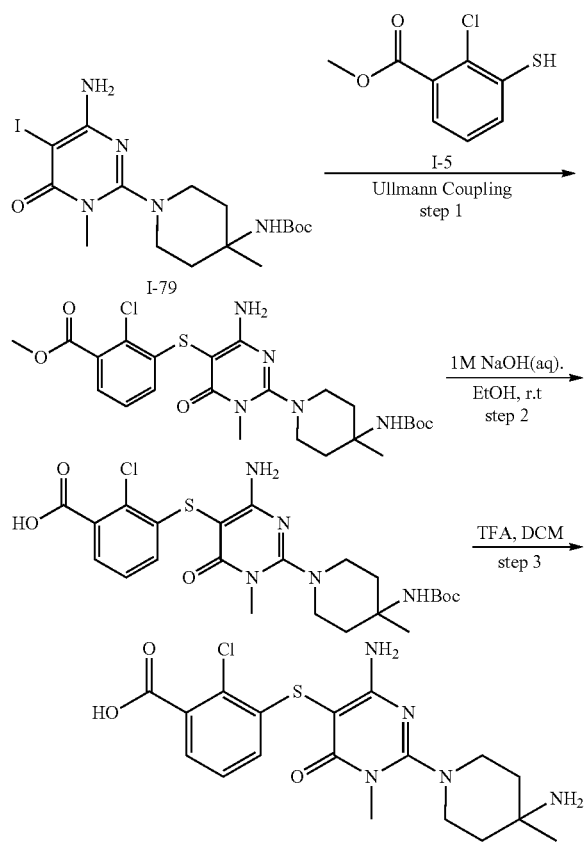

Step 1: methyl 3-((4-amino-2-(4-((tert-butoxycarbonyl)amino)-4-methylpiperidin-1-yl)-1-methyl-6-oxo-1,6-dihydropyrimidin-5-yl)thio)-2-chlorobenzoate In a round bottom flask, Intermediate I-79 (1.04 g, 2.13 mmol) was dissolved in 1,4-dioxane, and then Intermediate I-5 (763 mg, 4.26 mmol), $K_3PO_4$ (904 mg, 4.26 mmol), CuI (82 mg, 0.43 mmol) and (1R,2R)-N1, N2-dimethylcyclohexane-1,2-diamine (61 mg, 0.43 mmol) were added dropwise thereto. The reaction mixture was stirred at 90° C. for 16 hours. The reaction was terminated with $H_2O$, and the mixture was extracted with EA. The EA layer was dried over $MgSO_4$, filtered and then concentrated. The resulting product was separated by MPLC (MeOH:DCM=1:10) and concentrated to obtain methyl 3-((4-amino-2-(4-((tert-butoxycarbonyl)amino)-4-methylpiperidin-1-yl)-1-methyl-6-oxo-1,6-dihydropyrimidin-5-yl)thio)-2-chlorobenzoate (280 mg, 24%). MS m/z: 538.20 [M+H]$^+$.

Step 2: 3-((4-amino-2-(4-((tert-butoxycarbonyl)amino)-4-methylpiperidin-1-yl)-1-methyl-6-oxo-1,6-dihydropyrimidin-5-yl)thio)-2-chlorobenzoic acid In a round bottom flask, 1 M aqueous NaOH solution (0.5 mL, 0.50 mmol) was added dropwise to a reaction mixture of methyl 3-((4-amino-2-(4-((tert-butoxycarbonyl)amino)-4-methylpiperidin-1-yl)-1-methyl-6-oxo-1,6-dihydropyrimidin-5-yl)thio)-2-chlorobenzoate (134 mg, 0.25 mmol) dissolved in EtOH. The reaction mixture was stirred at room temperature for 4 hours. The reaction was terminated with 1 M aqueous HCl solution, and the mixture was extracted with EA. The EA layer was dried over $MgSO_4$, filtered and concentrated to obtain 3-((4-amino-2-(4-((tert-butoxycarbonyl)amino)-4-methylpiperidin-1-yl)-1-methyl-6-oxo-1,6-dihydropyrimidin-5-yl)thio)-2-chlorobenzoic acid (121 mg, 92%). MS m/z: 524.20 [M+H]$^+$.

Step 3: 3-((4-amino-2-(4-amino-4-methylpiperidin-1-yl)-1-methyl-6-oxo-1,6-dihydropyrimidin-5-yl)thio)-2-chlorobenzoic acid Tert-butyl N-[2-[4-[4-amino-5-[(2-amino-3-chloro-4-pyridyl)sulfanyl]-1-methyl-6-oxo-pyrimidin-2-yl]piperazin-1-yl]ethyl]carbamate (70.0 mg, 136 μmol) was dissolved in DCM (0.5 mL), and then TFA (2.69 g, 23.6 mmol) was added thereto. The reaction mixture was stirred at room temperature for 15 minutes. After completion of the reaction, the reaction mixture was concentrated and neutralized by addition of $NH_{3 1120}$. The resulting product was separated by Prep-HPLC to give the compound of Example 27 (7 mg, 18%). $^1$H NMR (400 MHz, MeOD) δ7.48 (dd, J=7.7, 1.6 Hz, 1H), 7.18 (t, J=7.8 Hz, 1H), 6.95 (dd, J=8.0, 1.6 Hz, 1H), 3.63 (d, J=14.2 Hz, 2H), 3.42 (d, J=1.5 Hz, 3H), 3.30-3.22 (m, 2H), 2.00 (td, J=11.8, 3.9 Hz, 2H), 1.89 (d, J=13.2 Hz, 2H); MS m/z: 424.10 [M+H]$^+$.

Example 28: Synthesis of 6-((5-(4-amino-4-methylpiperidin-1-yl)pyrazin-2-yl)thio)-5-chloro-3-phenylquinazolin-4(3H)-one

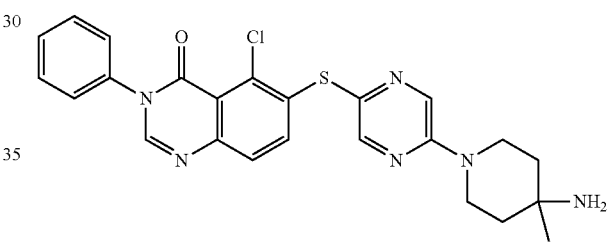

The compound of Example 28 (33 mg, 82%) was synthesized in the same method as in Example 26, except that Intermediate I-13 was used instead of Intermediate I-12. $^1$H NMR (400 MHz, MeOD) δ8.41-8.31 (m, 2H), 8.26 (s, 1H), 7.63-7.45 (m, 6H), 7.34 (d, J=8.8 Hz, 1H), 4.29-4.20 (m, 2H), 3.52-3.41 (m, 2H), 2.03-1.77 (m, 4H), 1.52 (s, 3H); MS m/z: 479.10 [M+H]$^+$.

Example 29: Synthesis of 6-((4-amino-2-(4-amino-4-methylpiperidin-1-yl)-1-methyl-6-oxo-1,6-dihydropyrimidin-5-yl)thio)-5-chloroquinazolin-4(3H)-one

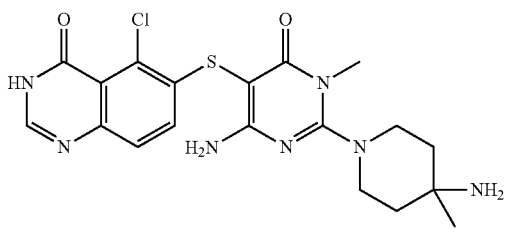 [SMILES: Cn1c(N2CCC(C)(N)CC2)nc(N)c(Sc2ccc3nc[nH]c(=O)c3c2Cl)c1=O]

The compound of Example 29 (8 mg, 20%) was synthesized in the same method as in Example 27, except that Intermediate I-8 was used instead of Intermediate I-6. $^1$H NMR (400 MHz, MeOD) δ8.18 (s, 1H), 7.98 (s, 1H), 7.45 (d, J=8.8 Hz, 1H), 7.26 (d, J=8.8 Hz, 1H), 3.65 (d, J=14.1 Hz, 2H), 3.43 (s, 3H), 3.30-3.16 (m, 2H), 2.07-1.98 (m, 2H), 1.94-1.85 (m, 2H); MS m/z: 448.10 [M+H]⁺.

Example 30: Synthesis of 6-((4-amino-2-(4-amino-4-methylpiperidin-1-yl)-1-methyl-6-oxo-1,6-dihydropyrimidin-5-yl)thio)-5-chloro-3-phenylquinazolin-4(3H)-one

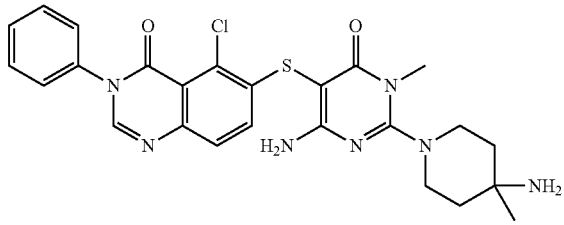 [SMILES: Cn1c(N2CCC(C)(N)CC2)nc(N)c(Sc2ccc3ncn(-c4ccccc4)c(=O)c3c2Cl)c1=O]

The compound of Example 30 (9 mg, 13%) was synthesized in the same method as in Example 27, except that Intermediate I-13 was used instead of Intermediate I-6. ¹H NMR (400 MHz, MeOD) δ8.22 (s, 1H), 7.63-7.45 (m, 6H), 7.28 (d, J=8.7 Hz, 1H), 3.65 (d, J=14.1 Hz, 2H), 3.44 (s, 3H), 3.34 (s, 3H), 3.32-3.17 (m, 2H), 2.07-1.96 (m, 2H), 1.95-1.87 (m, 2H); MS m/z: 524.20 [M+H]⁺.

Example 31: 3-((6-((5-((3S,4S)-4-amino-3-methyl-2-oxa-8-azaspiro[4.5]decan-8-yl)pyrazin-2-yl)thio)-5-chloro-4-oxoquinazolin-3(4H)-yl)methyl)benzonitrile

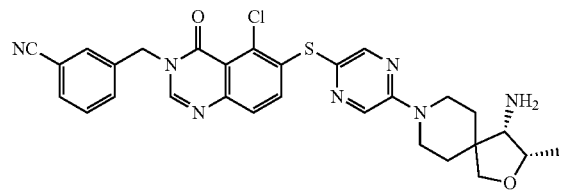 [SMILES: C[C@@H]1OCC2(CCN(c3cnc(Sc4ccc5ncn(Cc6cccc(C#N)c6)c(=O)c5c4Cl)cn3)CC2)[C@@H]1N]

The compound of Example 31 (18 mg, 97%) was synthesized in the same method as in Example 18, except that 3-(bromomethyl)benzonitrile was used instead of benzyl chloride. ¹H NMR (400 MHz, DMSO) δ 8.63 (s, 1H), 8.51 (d, J=1.5 Hz, 1H), 8.32 (d, J=1.3 Hz, 1H), 8.17 (bs, 3H), 7.90 (d, J=1.9 Hz, 1H), 7.79 (dt, J=7.7, 1.5 Hz, 1H), 7.74 (dt, J=8.0, 1.5 Hz, 1H), 7.80-7.73 (m, 2H), 7.26 (d, J=8.8 Hz, 1H), 5.20 (s, 2H), 4.33-4.17 (m, 3H), 3.94 (d, J=9.0 Hz, 1H), 3.69 (d, J=9.0 Hz, 1H), 3.43-3.36 (m, 1H), 3.19-3.12 (m, 2H), 1.85-1.70 (m, 3H), 1.63-1.59 (m, 1H), 1.24 (d, J=6.8 Hz, 3H); MS m/z: 573.17 [M+H]⁺.

Example 32: 6-((5-((3S,4S)-4-amino-3-methyl-2-oxa-8-azaspiro[4.5]decan-8-yl)pyrazin-2-yl)thio)-5-chloro-3-(1-phenylethyl)quinazolin-4(3H)-one

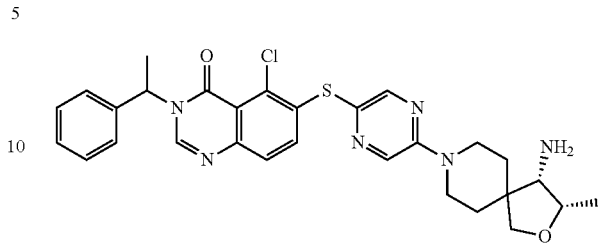

The compound of Example 32 (8.5 mg, 83%) was synthesized in the same method as in Example 18, except that 1-(bromoethyl)benzene was used instead of benzyl chloride. ¹H NMR (400 MHz, DMSO) δ 8.51 (d, J=1.5 Hz, 1H), 8.43 (s, 1H), 8.32 (d, J=1.3 Hz, 1H), 8.05 (bs, 3H), 7.53 (d, J=8.8 Hz, 1H), 7.46-7.30 (m, 4H), 7.33-7.22 (m, 1H), 7.25 (d, J=8.8 Hz, 1H), 6.05 (t, J=7.2 Hz, 1H), 4.32-4.17 (m, 3H), 3.92 (d, J=9.0 Hz, 1H), 3.70 (d, J=9.0 Hz, 1H), 3.42-3.40 (m, 1H), 1.84 (d, J=7.2 Hz, 3H), 1.79-1.71 (m, 3H), 1.61-1.58 (m, 1H), 1.61-1.58 (m, 1H), 1.23 (d, J=6.8 Hz, 3H); MS m/z: 562.19 [M+H]⁺.

Example 33: 6-((5-((3S,4S)-4-amino-3-methyl-2-oxa-8-azaspiro[4.5]decan-8-yl)pyrazin-2-yl)thio)-5-chloro-3-(3-fluorobenzyl)quinazolin-4(3H)-one

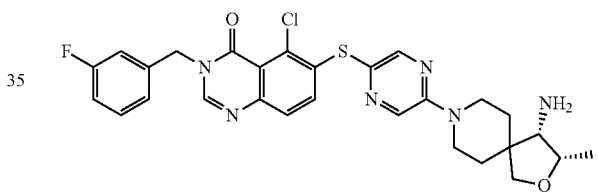

The compound of Example 33 (17 mg, 85%) was synthesized in the same method as in Example 18, except that 1-(bromomethyl)-3-fluorobenzene was used instead of benzyl chloride. ¹H NMR (400 MHz, DMSO) δ 8.61 (s, 1H), 8.51 (d, J=0.8 Hz, 1H), 8.32 (d, J=1.2 Hz, 1H), 8.12 (b, 3H), 7.56 (d, J=8.8 Hz, 1H), 7.44-7.39 (m, 1H), 7.29-7.20 (m, 3H), 7.15 (td, J=8.7, 2.7 Hz, 1H), 5.17 (s, 2H), 4.30-4.20 (m, 3H), 3.41-3.39 (m, 1H), 3.20-3.12 (m, 2H), 1.84-1.71 (m, 3H), 1.61 (d, J=13.2 Hz, 1H), 1.24 (d, J=6.8 Hz, 4H), 1.05 (s, 1H); MS m/z: 566.17 [M+H]⁺.

Example 34: 6-((5-((3S,4S)-4-amino-3-methyl-2-oxa-8-azaspiro[4.5]decan-8-yl)pyrazin-2-yl)thio)-5-chloro-3-(3-trifluoromethyl)benzyl)quinazolin-4(3H)-one

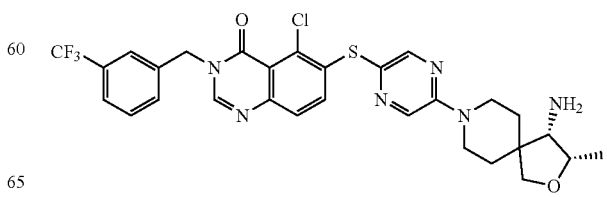

The compound of Example 34 (15.4 mg, 71%) was synthesized in the same method as in Example 18, except that 1-(bromomethyl)-3-(fluoromethyl)benzene was used instead of benzyl chloride. ¹H NMR (400 MHz, DMSO) δ 8.67 (s, 1H), 8.51 (d, J=1.2 Hz, 1H), 8.32 (d, J=1.2 Hz, 1H), 8.05 (b, 3H), 7.81 (s, 1H), 7.69-7.68 (m, 2H), 7.62 (d, J=7.6 Hz, 1H), 7.56 (d, J=8.8 Hz, 1H), 7.26 (d, J=8.8 Hz, 1H), 5.24 (s, 2H), 4.30-4.19 (m, 3H), 3.92 (d, J=8.8 Hz, 1H), 3.41-3.40 (m, 1H), 3.20-3.13 (m, 2H), 1.82-1.71 (m, 3H), 1.62-1.58 (m, 1H), 1.24-1.23 (m, 4H), 0.87 (t, J=6.8 Hz, 1H); MS m/z: 616.16 [M+H]⁺.

Example 35: 6-((5-((3S,4S)-4-amino-3-methyl-2-oxa-8-azaspiro[4.5]decan-8-yl)pyrazin-2-yl)thio)-5-chloro-3-(thiazol-2-ylmethyl)quinazolin-4(3H)-one

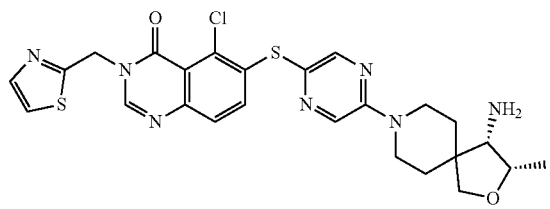 [SMILES: C[C@@H]1OCC2(CCN(c3cnc(Sc4ccc5ncn(Cc6nccs6)c(=O)c5c4Cl)cn3)CC2)[C@@H]1N]

The compound of Example 35 (27 mg, 91%) was synthesized in the same method as in Example 18, except that 2-(chloromethyl)thiazole was used instead of benzyl chloride. ¹H NMR (400 MHz, DMSO) δ 8.59 (d, J=1.6 Hz, 1H), 8.52 (s, 1H), 8.33 (s, 1H), 8.23 (b, 3H), 7.76-7.74 (m, 2H), 7.58 (dd, J=8.8 Hz, 1.6 Hz, 1H), 7.28 (dd, J=8.8 Hz, 2 Hz, 1H), 5.51 (s, 2H), 3.95 (d, J=8 Hz, 1H), 3.68 (d, J=8 Hz, 1H), 3.40 (b, 1H), 3.15 (b, 2H), 1.81 (b, 2H), 1.72 (d, J=13.2 Hz, 1H), 1.62 (d, J=13.2 Hz, 1H), 1.25 (m, 4H), 1.05 (d, J=1.6 Hz, 1H), 0.87-0.86 (m, 1H); MS m/z: 555.13 [M+H]⁺.

Example 36: 6-((5-((3S,4S)-4-amino-3-methyl-2-oxa-8-azaspiro[4.5]decan-8-yl)pyrazin-2-yl)thio)-5-chloro-3-(3-methoxybenzyl)quinazolin-4(3H)-one

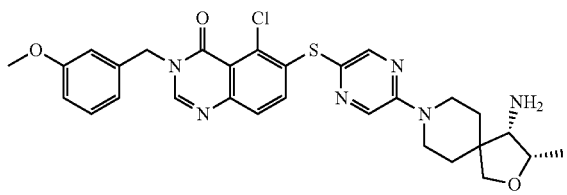

The compound of Example 36 (18.7 mg, 87%) was synthesized in the same method as in Example 18, except that 3-methoxybenzyl bromide was used instead of benzyl chloride. ¹H NMR (400 MHz, DMSO) δ 8.59 (s, 1H), 8.52 (s, 1H), 8.33 (s, 1H), 8.03 (bs, 3H), 7.55 (d, J=8.8 Hz, 1H), 7.32-7.22 (m, 2H), 6.96-6.88 (m, 3H), 5.13 (s, 2H), 4.30 (s, 1H), 4.30-4.21 (m, 3H), 3.92 (d, J=8.6 Hz, 1H), 3.75 (s, 3H), 3.70 (d, J=9.0 Hz, 1H), 3.18-3.13 (m, 3H), 1.79-1.76 (m, 3H), 1.61-1.58 (m, 1H), 1.23 (d, J=7.0 Hz, 3H); MS m/z: 578.19 [M+H]⁺.

Example 37: 3-((1H-benzo[d]imidazol-2-yl)methyl)-6-((5-((3S,4S)-4-amino-3-methyl-2-oxa-8-azaspiro[4.5]decan-8-yl)pyrazin-2-yl)thio)-5-chloroquinazolin-4(3H)-one

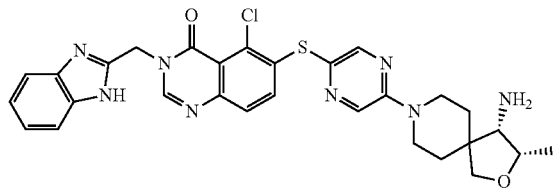

The compound of Example 37 (5.1 mg, 74%) was synthesized in the same method as in Example 18, except that 2-(chloromethyl)benzimidazole was used instead of benzyl chloride. ¹H NMR (400 MHz, DMSO) δ 8.65 (s, 1H), 8.59 (s, 1H), 8.52 (d, J=1.4 Hz, 1H), 8.33 (d, J=1.3 Hz, 1H), 8.12 (bs, 3H), 7.81-7.74 (m, 2H), 7.62 (d, J=8.8 Hz, 1H), 7.52-7.50 (m, 2H), 7.30 (d, J=8.8 Hz, 1H), 5.64 (s, 2H), 4.32-4.18 (m, 3H), 3.93 (d, J=8.8 Hz, 1H), 3.70 (d, J=9.0 Hz, 1H), 3.20-3.12 (m, 2H), 1.83-1.72 (m, 3H), 1.62-1.59 (m, 1H), 1.24 (d, J=6.6 Hz, 3H); MS m/z: 588.18 [M+H]⁺.

Example 38: 2-((6-((5-((3S,4S)-4-amino-3-methyl-2-oxa-8-azaspiro[4.5]decan-8-yl)pyrazin-2-yl)thio)-5-chloro-4-oxoquinazolin-3(4H)-yl)methyl)benzenesulfonyl fluoride

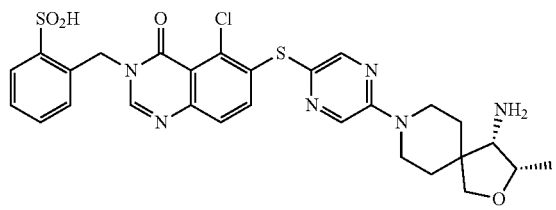

The compound of Example 38 (8 mg, 67%) was synthesized in the same method as in Example 18, except that 2-(bromomethyl)benzenesulfonyl fluoride was used instead of benzyl chloride. ¹H NMR (400 MHz, DMSO) δ 8.64 (s, 1H), 8.52 (s, 1H), 8.33 (s, 1H), 8.14-8.11 (m, 5H), 7.75 (d, J=7.6 Hz, 2H), 7.59-7.57 (m, 1H), 7.29-7.26 (m, 1H), 5.33 (s, 2H), 4.30-4.22 (m, 3H), 3.41 (m, 1H), 3.18-3.15 (m, 2H), 1.84-1.74 (m, 3H), 1.62-1.59 (m, 1H), 1.25-1.19 (m, 4H), 1.0 (d, J=1.2 Hz, 1H); MS m/z: 630.13 [M+H]⁺.

Example 39: 6-((5-((3S,4S)-4-amino-3-methyl-2-oxa-8-azaspiro[4.5]decan-8-yl)pyrazin-2-yl)thio)-5-chloro-3-(pyridin-4-ylmethyl)quinazolin-4(3H)-one

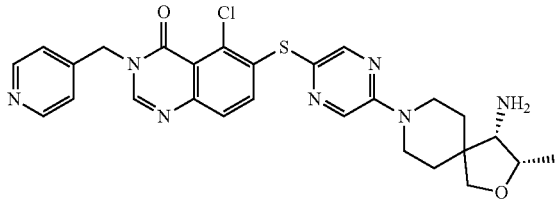 [SMILES: C[C@@H]1OCC2(CCN(c3cnc(Sc4ccc5ncn(Cc6ccncc6)c(=O)c5c4Cl)cn3)CC2)[C@@H]1N]

The compound of Example 39 (1.5 mg, 34%) was synthesized in the same method as in Example 18, except that 4-(bromomethyl)pyridine was used instead of benzyl chloride. $^1$H NMR (400 MHz, DMSO) δ 8.78 (d, J=6.5 Hz, 2H), 8.59 (s, 1H), 8.52 (d, J=1.5 Hz, 1H), 8.32 (d, J=1.3 Hz, 1H), 8.14 (bs, 3H), 7.82 (d, J=6.0 Hz, 2H), 7.59 (d, J=8.8 Hz, 1H), 7.28 (d, J=8.8 Hz, 1H), 5.37 (s, 2H), 4.33-4.20 (m, 3H), 3.93 (d, J=9.1 Hz, 1H), 3.69 (d, J=9.1 Hz, 1H), 3.20-3.13 (m, 3H), 1.91-1.71 (m, 3H), 1.63-1.59 (m. 1H), 1.24 (d, J=6.5 Hz, 3H); MS m/z: 549.17 [M+H]$^+$.

Example 40: 6-((5-((3S,4S)-4-amino-3-methyl-2-oxa-8-azaspiro[4.5]decan-8-yl)pyrazin-2-yl)thio)-5-chloro-3-(4-fluorobenzyl)quinazolin-4(3H)-one

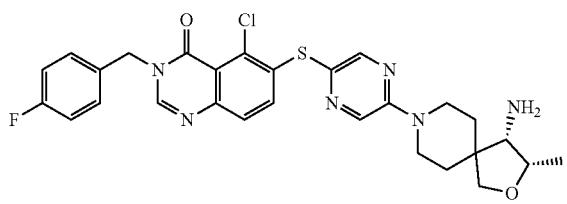 [SMILES: C[C@@H]1OCC2(CCN(c3cnc(Sc4ccc5ncn(Cc6ccc(F)cc6)c(=O)c5c4Cl)cn3)CC2)[C@@H]1N]

The compound of Example 40 (22 mg, 81%) was synthesized in the same method as in Example 18, except that 1-(bromomethyl)-4-fluorobenzene was used instead of benzyl chloride. $^1$H NMR (400 MHz, DMSO) δ 8.62 (s, 1H), 8.51 (d, J=1.1 Hz, 1H), 8.32 (d, J=1.2 Hz, 1H), 8.08 (s, 3H), 7.54 (d, J=8.8 Hz, 1H), 7.48-7.44 (m, 2H), 7.25 (d, J=8.8 Hz, 1H), 7.19 (t, J=8.9 Hz, 2H), 5.14 (s, 2H), 4.30-4.18 (m, 3H), 4.25-4.16 (m, 2H), 3.92 (d, J=9.1 Hz, 1H), 3.69 (d, J=9.1 Hz, 1H), 3.42-3.39 (m, 2H), 3.16 (q, J=10.1 Hz, 2H), 1.82-1.70 (m, 3H), 1.60 (d, J=13.3 Hz, 1H), 1.23 (d, J=6.6 Hz, 3H); MS m/z: 566.17 [M+E-1]$^+$.

Example 41: 6-((5-((3S,4S)-4-amino-3-methyl-2-oxa-8-azaspiro[4.5]decan-8-yl)pyrazin-2-yl)thio)-5-chloro-3-(4-methoxybenzyl)quinazolin-4(3H)-one

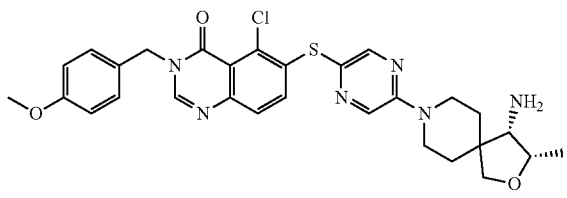

The compound of Example 41 (32 mg, 97%) was synthesized in the same method as in Example 18, except that 4-methoxybenzyl chloride was used instead of benzyl chloride. $^1$H NMR (400 MHz, DMSO) δ 8.60 (s, 1H), 8.51 (s, 1H), 8.32 (s, 1H), 8.09 (bs, 3H), 7.53 (d, J=8.7 Hz, 1H), 7.36 (d, J=8.5 Hz, 2H), 7.24 (d, J=8.8 Hz, 1H), 6.92 (d, J=8.3 Hz, 2H), 5.08 (s, 2H), 4.32-4.16 (m, 3H), 3.92 (d, J=9.1 Hz, 1H), 3.73 (s, 3H), 3.69 (d, J=9.2 Hz, 1H), 3.41-3.39 (m, 1H), 3.19-3.12 (m, 2H), 1.82-1.70 (m, 3H), 1.61-1.58 (m, 1H), 1.23 (d, J=6.6 Hz, 3H); MS m/z: 578.19 [M+H]$^+$.

Example 42: 3-((1H-pyrrolo[2,3-b]pyridin-6-yl)methyl)-6-((5-((3S,4S)-4-amino-3-methyl-2-oxa-8-azaspiro[4.5]decan-8-yl)pyrazin-2-yl)thio)-5-chloro-quinazolin-4(3H)-one

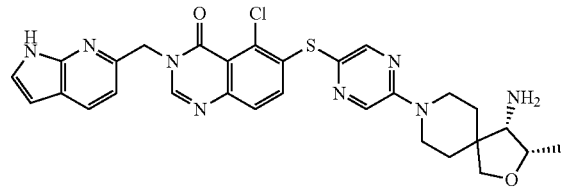 [SMILES: C[C@@H]1OCC2(CCN(c3cnc(Sc4ccc5ncn(Cc6ccc7cc[nH]c7n6)c(=O)c5c4Cl)cn3)CC2)[C@@H]1N]

The compound of Example 42 (24 mg, 87%) was synthesized in the same method as in Example 18, except that 6-(chloromethyl)-1H-pyrrolo[2,3-b]pyridine was used instead of benzyl chloride. $^1$H NMR (400 MHz, DMSO) δ 11.63 (s, 1H), 8.59 (s, 1H), 8.50 (s, 1H), 8.32 (s, 1H), 8.12(bs, 3H), 7.97 (d, J=7.9 Hz, 1H), 7.58 (d, J=8.8 Hz, 1H), 7.41 (t, J=2.8 Hz, 1H), 7.27 (d, J=8.8 Hz, 1H), 7.15 (d, J=8.0 Hz, 1H), 6.44 (s, 1H), 5.34 (s, 2H), 4.30-4.19 (m, 3H), 3.93 (d, J=9.1 Hz, 1H), 3.68-3.60 (m, 1H), 3.41-3.40 (m, 1H), 3.19-3.12 (m, 2H), 1.84-1.70 (m, 3H), 1.62-1.58 (m, 1H), 1.24 (d, J=6.4 Hz, 3H); MS m/z: 588.18 [M+H]$^+$.

Example 43: 6-((5-((3S,4S)-4-amino-3-methyl-2-oxa-8-azaspiro[4.5]decan-8-yl)pyrazin-2-yl)thio)-5-chloro-3-(2-fluorobenzyl)quinazolin-4(3H)-one

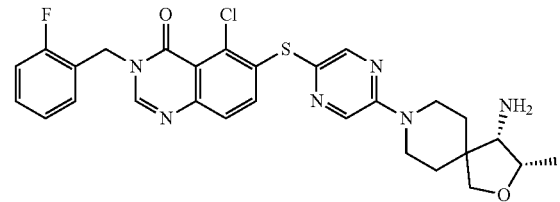 [SMILES: C[C@@H]1OCC2(CCN(c3cnc(Sc4ccc5ncn(Cc6ccccc6F)c(=O)c5c4Cl)cn3)CC2)[C@@H]1N]

The compound of Example 43 (18 mg, 90%) was synthesized in the same method as in Example 18, except that 1-(bromomethyl)-2-fluorobenzene was used instead of benzyl chloride. $^1$H NMR (400 MHz, DMSO) δ 8.55 (s, 1H), 8.51 (d, J=1.2 Hz, 1H), 8.32 (d, J=1.2 Hz, 1H), 8.06 (b, 3H), 7.56 (d, J=8.8 Hz, 1H), 7.40-7.31 (m, 2H), 7.27-7.17 (m, 3H), 5.20 (s, 2H), 4.29-4.19 (m, 3H), 3.92 (d, J=9 Hz, 1H), 3.70 (d, J=9.2 Hz, 1H), 3.42-3.40 (m, 2H), 3.20-3.12 (m, 2H), 1.83-1.70 (m, 3H), 1.60 (d, J=13 Hz, 1H), 1.23 (d, J=6.6 Hz, 3H); MS m/z: 566.17 [M+H]$^+$.

Example 44: 6-((5-((3S,4S)-4-amino-3-methyl-2-oxa-8-azaspiro[4.5]decan-8-yl)pyrazin-2-yl)thio)-5-chloro-3-(pyrazin-2-ylmethyl)quinazolin-4(3H)-one

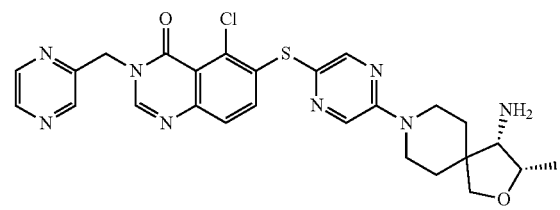 [SMILES: C[C@@H]1OCC2(CCN(c3cnc(Sc4ccc5ncn(Cc6cnccn6)c(=O)c5c4Cl)cn3)CC2)[C@@H]1N]

The compound of Example 44 (24.4 mg, 72%) was synthesized in the same method as in Example 18, except that 2-(chloromethyl)pyrazine and sodium hydride were used instead of benzyl chloride and cesium carbonate, and the reaction was carried out at 0° C. ¹H NMR (400 MHz, DMSO) δ 9.08 (d, J=1.2 Hz, 1H), 8.79 (d, J=5.3 Hz, 1H), 8.52-8.51 (m, 2H), 8.33 (d, J=1.2 Hz, 1H), 8.14(bs, 3H), 7.61-7.58 (m, 1H), 7.28 (d, J=8.8 Hz, 1H), 5.30 (s, 2H), 4.31-4.19 (m, 3H), 3.93 (d, J=9.1 Hz, 1H), 3.69 (d, J=9.3 Hz, 1H), 3.41-3.39 (m, 1H), 3.20-3.12 (m, 2H), 1.91-1.70 (m, 3H), 1.62-1.59 (m, 1H), 1.24 (d, J=6.6 Hz, 3H); MS m/z: 550.17 [M+H]⁺.

Example 45: 6-((5-((3S,4S)-4-amino-3-methyl-2-oxa-8-azaspiro[4.5]decan-8-yl)pyrazin-2-yl)thio)-5-chloro-3-(pyrimidin-4-ylmethyl)quinazolin-4(3H)-one

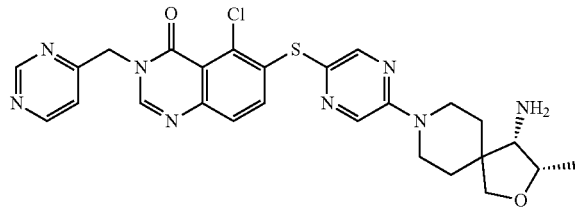 [SMILES: C[C@@H]1OCC2(CCN(c3cnc(Sc4ccc5ncn(Cc6ccncn6)c(=O)c5c4Cl)cn3)CC2)[C@@H]1N]

The compound of Example 45 (33 mg, 99%) was synthesized in the same method as in Example 18, except that 4-(bromomethyl)pyrimidine and sodiumhydride were used instead of benzyl chloride and cesium carbonate, and the reaction was carried out at 0° C. ¹H NMR (400 MHz, DMSO) δ 8.82 (d, J=1.5 Hz, 1H), 8.61-8.53 (m, 3H), 8.51 (d, J=1.5 Hz, 1H), 8.32 (d, J=1.3 Hz, 1H), 8.25 (bs, 3H), 7.57 (d, J=8.8 Hz, 1H), 7.27 (d, J=8.8 Hz, 1H), 5.35 (s, 2H), 4.22-4.20 (m, 3H), 3.94 (d, J=9.1 Hz, 1H), 3.68 (d, J=9.1 Hz, 1H), 3.43-3.37 (m, 1H), 3.20-3.09 (m, 2H), 1.85-1.79 (m, 2H), 1.71 (d, J=13.4 Hz, 1H), 1.62 (d, J=13.2 Hz, 1H), 1.25 (d, J=6.6 Hz, 3H); MS m/z: 550.17 [M+H]⁺.

Example 46: 6-((5-((3S,4S)-4-amino-3-methyl-2-oxa-8-azaspiro[4.5]decan-8-yl)pyrazin-2-yl)thio)-5-chloro-3-(pyrimidin-5-ylmethyl)quinazolin-4(3H)-one

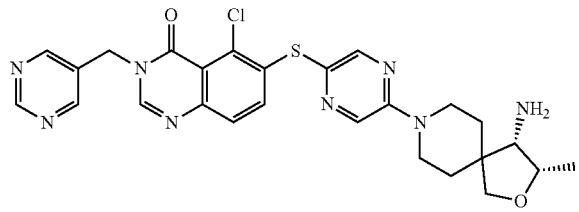 [SMILES: C[C@@H]1OCC2(CCN(c3cnc(Sc4ccc5ncn(Cc6cncnc6)c(=O)c5c4Cl)cn3)CC2)[C@@H]1N]

The compound of Example 46 (27 mg, 99%) was synthesized in the same method as in Example 18, except that 5-(chloromethyl)pyrimidine was used instead of benzyl chloride, and 1 equivalent of potassium iodide was added. ¹H NMR (400 MHz, DMSO) δ 9.13 (s, 1H), 8.91 (s, 2H), 8.68 (s, 1H), 8.50 (d, J=1.5 Hz, 1H), 8.31 (d, J=1.3 Hz, 1H), 8.16 (bs, 3H), 7.55 (d, J=8.8 Hz, 1H), 7.25 (d, J=8.8 Hz, 1H), 5.19 (s, 2H), 4.32-4.16 (m, 3H), 3.93 (d, J=9.0 Hz, 1H), 3.66-3.57 (m, 1H), 3.34-3.31 (m, 1H), 3.17-3.11 (m, 2H), 1.84-1.70 (m, 3H), 1.62-1.59 (m, 1H), 1.24 (d, J=6.5 Hz, 3H); MS m/z: 550.17 [M+H]⁺.

Example 47: 6-((5-((3S,4S)-4-amino-3-methyl-2-oxa-8-azaspiro[4.5]decan-8-yl)pyrazin-2-yl)thio)-3-(benzo oxazol-2-ylmethyl)-5-chloroquinazolin-4(3H)-one

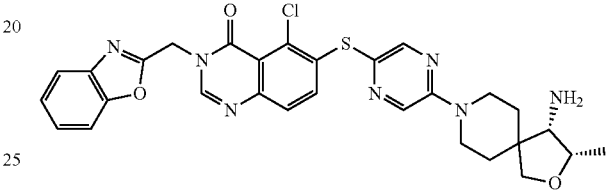

The compound of Example 47 (13.2 mg, 35%) was synthesized in the same method as in Example 18, except that 2-(chloromethyl)benzo[d]oxazol was used instead of benzyl chloride, and 1 equivalent of potassium iodide was added. ¹H NMR (400 MHz, DMSO) δ 8.61 (s, 1H), 8.52 (s, 1H), 8.38-8.33 (m, 1H), 8.16 (b s, 3H), 7.76-7.67 (m, 2H), 7.61 (d, J=8.8 Hz, 1H), 7.44-7.36 (m, 2H), 7.31 (d, J=8.8 Hz, 1H), 5.54 (s, 2H), 4.33-4.18 (m, 3H), 3.93 (d, J=9.1 Hz, 1H), 3.69 (d, J=9.1 Hz, 1H), 3.43-3.39 (m, 1H), 3.20-3.12 (m, 2H), 1.85-1.67 (m, 3H), 1.63-1.55 (m, 1H), 1.24 (d, J=6.4 Hz, 3H); MS m/z: 589.17 [M+H]⁺.

Example 48: 6-((5-((3S,4S)-4-amino-3-methyl-2-oxa-8-azaspiro[4.5]decan-8-yl)pyrazin-2-yl)thio)-3-((6-aminopyridin-3-yl)methyl)-5-chloroquinazolin-4(3H)-one

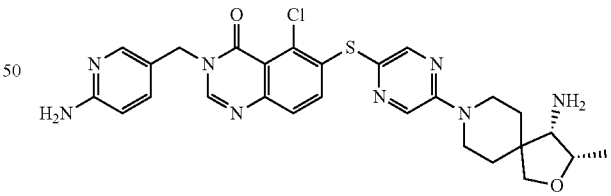

The compound of Example 48 (16 mg, 71%) was synthesized in the same method as in Example 18, except that 5-(bromomethyl)pyridin-2-amine was used instead of benzyl chloride. 1 H NMR (400 MHz, DMSO) δ 13.78-13.77 (b, 1H), 8.54 (s, 1H), 8.51 (s, 1H), 8.33 (s, 1H), 8.24 (b, 2H), 8.03 (b, 2H), 7.94 (d, J=6.3 Hz, 1H), 7.59 (d, J=8.8 Hz, 1H), 7.28 (d, J=8.8 Hz, 1H), 6.86 (d, J=6.6 Hz, 1H), 6.70 (s, 1H), 5.19 (s, 2H), 4.31-4.28 (m, 1H), 4.23-4.20 (m, 2H), 3.68 (d, J=9.1 Hz, 1H), 3.39 (m, 1H), 3.17 (m, 2H), 1.82-1.79 (m, 2H), 1.71 (d, J=13 Hz, 1H), 1.62 (d, J=13 Hz, 1H), 1.24 (d, J=6.3 Hz, 3H), 1.05 (s, 1H); MS m/z: 565.09 [M+H]⁺.

Example 49: (3S,4S)-8-(5-((2-benzyl-4-chloro-2H-indazol-5-yl)thio)pyrazin-2-yl)-3-methyl-2-oxa-8-azaspiro[4.5]decan-4-amine

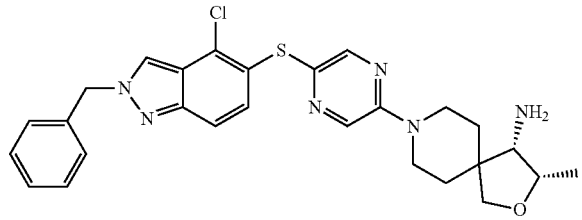 [SMILES: C[C@@H]1OCC2(CCN(c3cnc(Sc4ccc5nn(Cc6ccccc6)cc5c4Cl)cn3)CC2)[C@@H]1N]

The compound of Example 49 (3 mg, 20%) was synthesized in the same method as in Example 25 above, except that Intermediate I-16 was used instead of Intermediate I-1, and Intermediate I-17 was used instead of Intermediate I-2. $^1$H NMR (400 MHz, CDCl$_3$) δ 8.07 (s, 1H), 7.92 (d, J=12.8 Hz, 1H), 7.61-7.51 (m, 2H), 7.36-7.30 (m, 5H), 7.22 (d, J=8.9 Hz, 1H), 5.58 (s, 2H), 4.22-4.13 (m, 3H), 3.99 (d, J=9.7 Hz, 1H), 3.76 (d, J=9.5 Hz, 1H), 3.40-3.36 (m, 1H), 2.99-2.09 (m, 2H), 1.81-1.66 (m, 3H), 1.63-1.55 (m, 1H), 1.36 (d, J=6.5 Hz, 3H); MS m/z: 521 [M+H]$^+$.

Example 50: (3S,4S)-8-(5-((2-benzyl-7-chloro-1H-benzo[d]imidazol-6-yl)thio)pyrazin-2-yl)-3-methyl-2-oxa-8-azaspiro[4.5]decan-4-amine

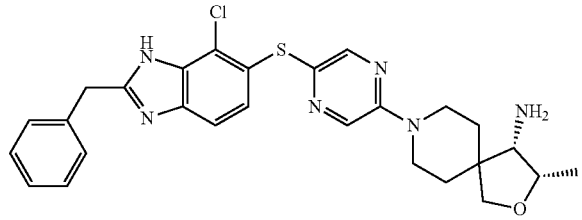 [SMILES: C[C@@H]1OCC2(CCN(c3cnc(Sc4ccc5nc(Cc6ccccc6)[nH]c5c4Cl)cn3)CC2)[C@@H]1N]

The compound of Example 50 (3 mg, 20%) was synthesized in the same method as in Example 25 above, except that Intermediate I-16 was used instead of Intermediate I-1, and Intermediate I-15 was used instead of Intermediate I-2. $^1$H NMR (400 MHz, MeOD) δ 8.22 (s, 1H), 8.14 (s, 1H), 8.00-7.93 (m, 2H), 7.57 (d, J=8.4, 1H), 7.50 (d, J=8.6 Hz, 1H), 7.43-7.29 (m, 5H), 4.20 (d, J=14.2 Hz, 2H), 3.97 (d, J=9.2 Hz, 1H), 3.86 (dd, J=9.3 Hz, 1H), 3.40-3.38 (m 1H), 3.24-3.06 (m, 2H), 2.23-2.15 (m, 2H), 1.69 (d, J=13.2 Hz, 3H), 1.60 (s, 1H), 1.30 (dd, J=6.5 Hz, 3H); MS m/z: 521 [M+H]$^+$.

Example 51: 6-((5-((3S,4S)-4-amino-3-methyl-2-oxa-8-azaspiro[4.5]decan-8-yl)pyrazin-2-yl)thio)-5-chloro-3-phenylquinazolin-4(3H)-one

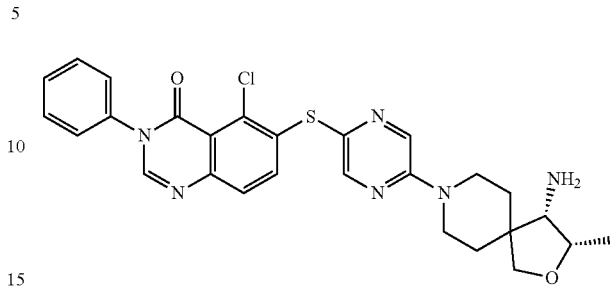

The compound of Example 51 (5 mg, 22%) was synthesized in the same method as in Example 26 above, except that Intermediate I-13 was used instead of Intermediate I-12. $^1$H NMR (400 MHz, MeOD) δ 8.34 (d, J=1.4 Hz, 1H), 8.30 (d, J=1.4 Hz, 1H), 8.26 (s, 1H), 7.62-7.43 (m, 6H), 7.31 (d, J=8.8 Hz, 1H), 4.43-4.20 (m, 3H), 4.00 (d, J=9.3 Hz, 1H), 3.89 (d, J=9.2 Hz, 1H), 3.49-3.38 (m, 1H), 3.29-3.11 (m, 2H), 1.91-1.80 (m, 3H), 1.78-1.69 (m, 1H), 1.32 (d, J=6.5 Hz, 3H); MS m/z: 535 [M+H]$^+$.

Example 52: 6-((5-((3S,4S)-4-amino-3-methyl-2-oxa-8-azaspiro[4.5]decan-8-yl)pyrazin-2-yl)thio)-3-((2-aminopyridin-3-yl)methyl)-5-chloroquinazolin-4(3H)-one

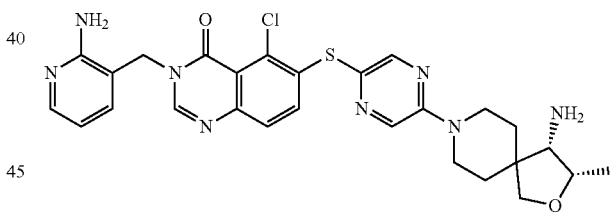

The compound of Example 52 (2.7 mg, 61%) was synthesized in the same method as in Example 18, except that 3-(chloromethyl)pyridin-2-amine hydrochloride (1:1) was used instead of benzyl chloride in step 2 of Example 18. $^1$H NMR (400 MHz, DMSO) δ 8.54 (s, 1H), 8.52 (s, 1H), 8.32 (d, J=1.3 Hz, 1H), 8.17-8.13 (m, 2H), 8.07 (br s, 2H), 7.98 (d, J=5.4 Hz, 1H), 7.76 (d, J=7.8 Hz, 1H), 7.58 (d, J=8.8 Hz, 1H), 7.26 (d, J=8.8 Hz, 1H), 6.86 (t, J=6.7 Hz, 1H), 5.07 (s, 2H), 4.30-4.19 (m, 3H), 3.92 (d, J=8.6 Hz, 1H), 3.70 (d, J=9.1 Hz, 1H), 3.17 (br s, 3H), 1.82-1.71 (m, 3H), 1.62-1.58 (m, 1H), 1.24 (br s, 3H); MS m/z: 565 [M+H]$^+$.

Example 53: 6-((5-((3S,4S)-4-amino-3-methyl-2-oxa-8-azaspiro[4.5]decan-8-yl)pyrazin-2-yl)thio)-5-chloro-3-((1-methyl-1H-pyrazol-3-yl)methyl)quinazolin-4(3H)-one

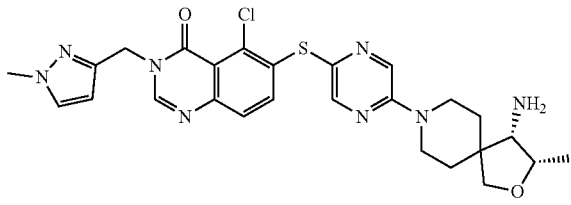

The compound of Example 53 (13 mg, 81%) was synthesized in the same method as in Example 18, except that, in step 2 of Example 18, 3-(chloromethyl)-1-methyl-1H-pyrazole was used instead of benzyl chloride, and 1 equivalent of potassium iodide was added. $^1$H NMR (400 MHz, DMSO) δ 8.51 (s, 1H), 8.46 (s, 1H), 8.32 (d, J=1.2 Hz, 1H), 8.02 (br s, 3H), 7.63 (d, J=2.2 Hz, 1H), 7.53 (d, J=8.8 Hz, 1H), 7.24 (d, J=8.8 Hz, 1H), 6.21 (d, J=2.2 Hz, 1H), 5.10(s 2H), 4.29-4.18 (m, 3H), 3.91 (d, J=9.1 Hz, 1H), 3.76 (s, 3H), 3.69 (d, J=9.2 Hz, 1H), 3.50-3.41 (m, 1H), 3.20-3.12 (m, 2H), 1.81-1.66 (m, 3H), 1.61-1.58 (m, 1H), 1.22 (d, J=6.6 Hz, 3H).

Example 54: 6-((5-((3S,4S)-4-amino-3-methyl-2-oxa-8-azaspiro[4.5]decan-8-yl)pyrazin-2-yl)thio)-5-chloro-3-(pyrrolidin-2-ylmethyl)quinazolin-4(3H)-one

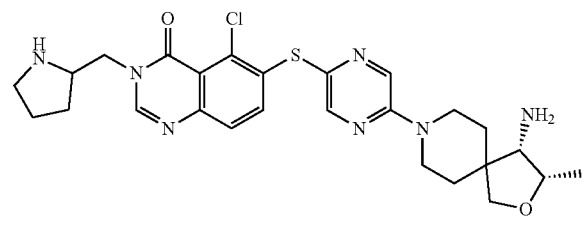 [SMILES: C[C@@H]1OCC2(CCN(c3cnc(Sc4ccc5ncn(CC6CCCN6)c(=O)c5c4Cl)cn3)CC2)[C@@H]1N]

The compound of Example 54 (25 mg, 80%) was synthesized in the same method as in Example 18, except that, in step 2 of Example 18, tert-butyl 2-(bromomethyl)pyrrolidine-1-carboxylate was used instead of benzyl chloride, and 1 equivalent of potassium iodide was added. $^1$H NMR (400 MHz, DMSO) δ 9.30-9.22 (m, 2H), 8.51 (s, 2H), 8.32 (d, J=1.2 Hz, 1H), 8.20 (br s, 3H), 7.55 (d, J=8.8 Hz, 1H), 7.26 (d, J=8.8 Hz, 1H), 4.32-4.19 (m, 5H), 3.94-3.91 (m, 1H), 3.68 (d, J=9.1 Hz, 1H), 3.40-3.37 (m, 1H), 3.34-3.28 (m, 1H), 3.19-3.11 (m, 4H), 2.17-2.11 (m, 1H), 2.02-1.89 (m, 2H), 1.84-1.78 (m, 2H), 1.75-1.67 (m, 2H), 1.63-1.59 (m, 1H), 1.24 (d, J=6.6 Hz, 3H).

Example 55: 6-((5-((3S,4S)-4-amino-3-methyl-2-oxa-8-azaspiro[4.5]decan-8-yl)pyrazin-2-yl)thio)-5-chloro-3-(pyrrolidin-3-ylmethyl)quinazolin-4(3H)-one

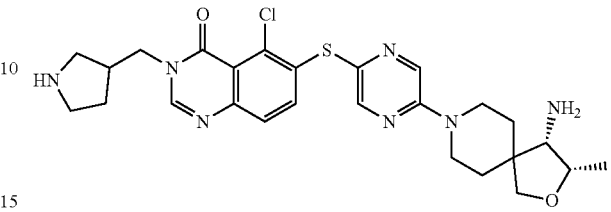

The compound of Example 55 (31 mg, 95%) was synthesized in the same method as in Example 18, except that, in step 2 of Example 18, tert-butyl 3-(bromomethyl)pyrrolidine-1-carboxylate was used instead of benzyl chloride, and 1 equivalent of potassium iodide was added. $^1$H NMR (400 MHz, DMSO) δ 9.26-9.09 (m, 2H), 8.51-8.48 (m, 2H), 8.32 (d, J=1.2 Hz, 1H), 8.20-8.16 (m, 3H), 7.53 (d, J=8.8 Hz, 1H), 7.24 (d, J=8.8 Hz, 1H), 4.30-4.27 (m, 1H), 4.23-4.19 (m, 2H), 4.03 (d, J=7.2 Hz, 2H), 3.93 (d, J=9.1 Hz, 1H), 3.68 (d, J=9.1 Hz, 1H), 3.40-3.37 (m, 1H), 3.28-3.24 (m, 2H), 3.19-3.12 (m, 3H), 2.99-2.91 (m, 1H), 2.78-2.72 (m, 1H), 2.06-1.98 (m, 1H), 1.81-1.65 (m, 4H), 1.60-1.59 (m, 1H), 1.24 (d, J=6.5 Hz, 3H).

Example 56: 6-((5-((3S,4S)-4-amino-3-methyl-2-oxa-8-azaspiro[4.5]decan-8-yl)pyrazin-2-yl)thio)-5-chloro-3-(isoxazol-3-ylmethyl)quinazolin-4(3H)-one

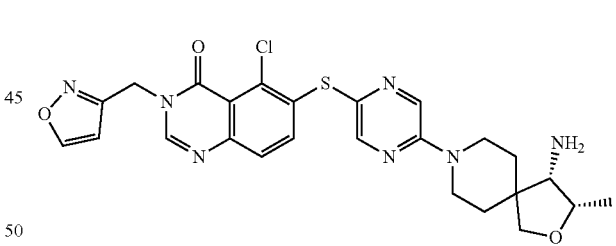

The compound of Example 56 (23 mg, 83%) was synthesized in the same method as in Example 18, except that, in step 2 of Example 18, 3-(chloromethyl)isoxazole was used instead of benzyl chloride, and 1 equivalent of potassium iodide was added. $^1$H NMR (400 MHz, DMSO) δ 8.91 (d, J=1.6 Hz, 1H), 8.53 (s, 1H), 8.51 (d, J=1.2 Hz, 1H), 8.33 (d, J=1.2 Hz, 1H), 8.05 (br s, 3H), 7.56 (d, J=8.8 Hz, 1H), 7.27 (d, J=8.8 Hz, 1H), 6.65 (d, J=1.7 Hz, 1H), 5.29(s 2H), 4.30-4.18 (m, 3H), 3.91 (d, J=9.0 Hz, 1H), 3.69 (d, J=9.0 Hz, 1H), 3.42-3.41 (m, 1H), 3.20-3.12 (m, 2H), 1.83-1.70 (m, 3H), 1.61-1.58 (m, 1H), 1.23 (d, J=6.5 Hz, 3H).

Example 57: 6-((5-((3S,4S)-4-amino-3-methyl-2-oxa-8-azaspiro[4.5]decan-8-yl)pyrazin-2-yl)thio)-5-chloro-3-(isoxazol-5-ylmethyl)quinazolin-4(3H)-one

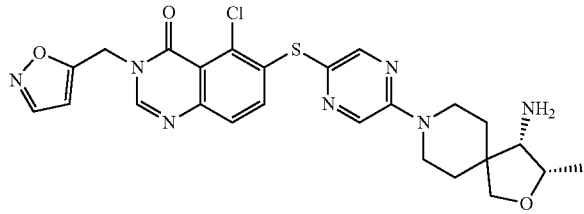 [SMILES: C[C@@H]1OCC2(CCN(c3cnc(Sc4ccc5ncn(Cc6ccno6)c(=O)c5c4Cl)cn3)CC2)[C@@H]1N]

The compound of Example 57 (44 mg, 94%) was synthesized in the same method as in Example 18, except that, in step 2 of Example 18, 5-(bromomethyl)isoxazol was used instead of benzyl chloride, and 1.5 equivalent of potassium iodide was added. $^1$H NMR (400 MHz, DMSO) δ 8.55 (d, J=2.5 Hz, 2H), 8.51 (s, 1H), 8.33 (s, 1H), 8.05 (br s, 2H), 7.56 (d, J=8.8 Hz, 1H), 7.27 (d, J=8.8 Hz, 1H), 6.53 (s, 1H), 5.37 (s, 2H), 4.29-4.19 (m, 3H), 3.91 (d, J=9.0 Hz, 1H), 3.69 (d, J=9.0 Hz, 1H), 3.20-3.12 (m, 3H), 1.82-1.70 (m, 3H), 1.61-1.58 (m, 1H), 1.23 (d, J=6.5 Hz, 3H); MS m/z: 540 [M+H]$^+$.

Example 58: 6-((5-((3S,4S)-4-amino-3-methyl-2-oxa-8-azaspiro[4.5]decan-8-yl)pyrazin-2-yl)thio)-5-chloro-3-(2-hydroxyethyl)quinazolin-4(3H)-one

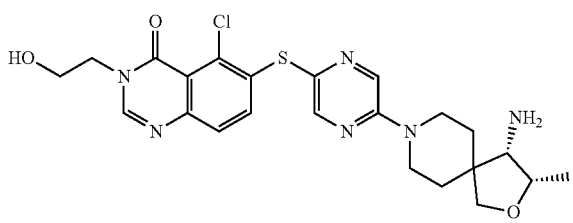 [SMILES: C[C@@H]1OCC2(CCN(c3cnc(Sc4ccc5ncn(CCO)c(=O)c5c4Cl)cn3)CC2)[C@@H]1N]

The compound of Example 58 (5 mg, 85%) was synthesized in the same method as in Example 18, except that, in step 2 of Example 18, 2-chloroethanol was used instead of benzyl chloride, and 1 equivalent of potassium iodide was added. $^1$H NMR (400 MHz, DMSO) δ 8.51 (s, 1H), 8.32 (d, J=1.5 Hz, 1H), 8.26 (s, 1H), 8.00 (br s, 3H), 7.52 (d, J=8.8 Hz, 1H), 7.24 (d, J=8.8 Hz, 1H), 4.29-4.18 (m, 3H), 4.01-3.99 (m, 2H), 3.91 (d, J=9.1 Hz, 1H), 3.71-3.61 (m, 4H), 3.21-3.12 (m, 3H), 1.78-1.71 (m, 3H), 1.61-1.58 (m, 1H), 1.22 (d, J=6.8 Hz, 3H).

Example 59: 6-((5-((3S,4S)-4-amino-3-methyl-2-oxa-8-azaspiro[4.5]decan-8-yl)pyrazin-2-yl)thio)-3-((6-aminopyridin-3-yl)methyl)-5-chloroquinazolin-4(3H)-one

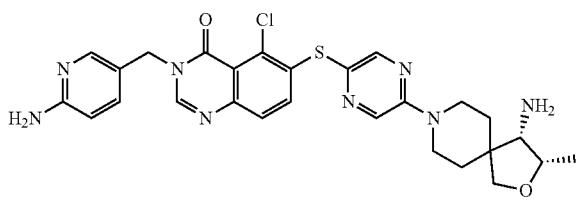 [SMILES: C[C@@H]1OCC2(CCN(c3cnc(Sc4ccc5ncn(Cc6ccc(N)nc6)c(=O)c5c4Cl)cn3)CC2)[C@@H]1N]

The compound of Example 59 (3.8 mg, 80%) was synthesized in the same method as in Example 18, except that 5-(chloromethyl)pyridin-2-amine hydrochloride (1:1) was used instead of benzyl chloride in step 2 of Example 18. $^1$H NMR (400 MHz, DMSO) δ 13.81-13.64 (m,1H), 8.60 (s, 1H), 8.50 (s, 1H), 8.31 (s, 1H), 8.11-8.08 (m, 5H), 8.02 (d, J=9.2 Hz, 1H), 7.54 (d, J=8.8 Hz, 1H), 7.23 (d, J=9.0 Hz, 1H), 6.98 (d, J=8.8 Hz, 1H), 5.03 (s, 2H), 4.30-4.18 (m, 3H), 3.92 (d, J=9.6 Hz, 1H), 3.69 (d, J=9.2 Hz, 1H), 3.19-3.11 (m, 3H), 1.80-1.70 (m, 3H), 1.62-1.58 (m, 1H), 1.24 (br s, 3H); MS m/z: 565 [M+H]$^+$.

Example 60: 6-((5-((3S,4S)-4-amino-3-methyl-2-oxa-8-azaspiro[4.5]decan-8-yl)pyrazin-2-yl)thio)-5-chloro-3-((2-chloropyridin-4-yl)methyl)quinazolin-4(3H)-one

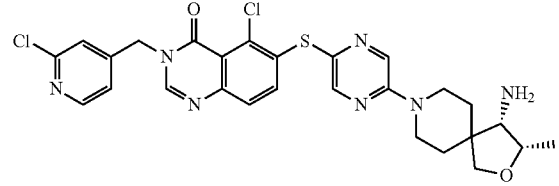 [SMILES: C[C@@H]1OCC2(CCN(c3cnc(Sc4ccc5ncn(Cc6ccnc(Cl)c6)c(=O)c5c4Cl)cn3)CC2)[C@@H]1N]

The compound of Example 60 was synthesized in the same method as in Example 18, except that 2-chloro-4-(chloromethyl)pyridine was used instead of benzyl chloride in step 2 of Example 18. $^1$H NMR (400 MHz, DMSO) δ 8.56 (s, 1H), 8.51 (s, 1H), 8.37 (d, J=5.1 Hz, 1H), 8.31 (s, 1H), 8.10 (br s, 3H), 7.56 (d, J=8.8 Hz, 1H), 7.52 (s, 1H), 7.35 (d, J=5.1 Hz, 1H), 7.26 (d, J=8.8 Hz, 1H), 5.18(s 2H), 4.29-4.18 (m, 3H), 3.91 (d, J=9.1 Hz, 1H), 3.76 (s, 3H), 3.69 (d, J=9.2 Hz, 1H), 3.50-3.41 (m, 1H), 3.20-3.12 (m, 2H), 1.81-1.66 (m, 3H), 1.61-1.58 (m, 1H), 1.22 (d, J=6.6 Hz, 3H).

Example 61: 6-((5-((3S,4S)-4-amino-3-methyl-2-oxa-8-azaspiro[4.5]decan-8-yl)pyrazin-2-yl)thio)-5-chloro-3-((tetrahydrofuran-3-yl)methyl)quinazolin-4(3H)-one

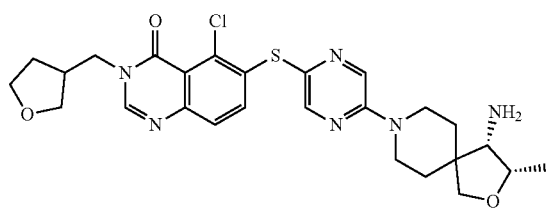 [SMILES: C[C@@H]1OCC2(CCN(c3cnc(Sc4ccc5ncn(CC6CCOC6)c(=O)c5c4Cl)cn3)CC2)[C@@H]1N]

The compound of Example 61 (57.7 mg, 88%) was synthesized in the same method as in Example 18, except that, in step 2 of Example 18, 3-(bromomethyl)tetrahydrofuran was used instead of benzyl chloride, and 1.5 equivalents of potassium iodide were added. $^1$H NMR (400 MHz, DMSO) δ 8.51 (s, 1H), 8.45 (s, 1H), 8.32 (d, J=1.2 Hz, 1H), 8.19 (br s, 2H), 7.53 (d, J=8.8 Hz, 1H), 7.24 (d, J=8.8 Hz, 1H), 4.31-4.27 (m, 1H), 4.23-4.20 (m, 2H), 3.99-3.94 (m, 3H), 3.83-3.78 (m, 1H), 3.71-3.60 (m, 3H), 3.47 (dd, J=2.9, 5.7 Hz, 1H), 3.39 (br s, 1H), 3.18-3.11 (m, 2H), 2.74-2.67 (m, 1H), 1.95-1.88 (m, 1H), 1.82-1.79 (m, 2H), 1.73-1.69 (m, 1H), 1.67-1.59 (m, 2H), 1.24 (d, J=6.5 Hz, 3H); MS m/z: 543 [M+H]$^+$.

Example 62: 6-((5-((3S,4S)-4-amino-3-methyl-2-oxa-8-azaspiro[4.5]decan-8-yl)pyrazin-2-yl)thio)-5-chloro-3-((tetrahydrofuran-2-yl)methyl)quinazolin-4(3H)-one

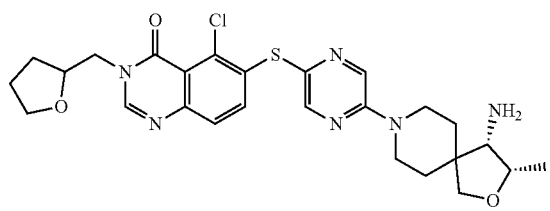 [SMILES: C[C@@H]1OCC2(CCN(c3cnc(Sc4ccc5ncn(CC6CCCO6)c(=O)c5c4Cl)cn3)CC2)[C@@H]1N]

The compound of Example 62 (24.5 mg, 70%) was synthesized in the same method as in Example 18, except that, in step 2 of Example 18, tetrahydrofurfuryl bromide was used instead of benzyl chloride, and 1.5 equivalents of potassium iodide were added. $^1$H NMR (400 MHz, DMSO) δ 8.51 (s, 1H), 8.33 (d, J=1.2 Hz, 1H), 8.29 (s, 1H), 7.96 (br s, 2H), 7.52 (d, J=8.8 Hz, 1H), 7.24 (d, J=8.8 Hz, 1H), 4.29-4.10 (m, 5H), 3.91-3.88 (m, 1H), 3.86-3.76 (m, 2H), 3.71-3.69 (m, 1H), 3.67-3.61 (m, 2H), 3.18-3.17 (m, 2H), 1.99-1.95 (m, 1H), 1.88-1.81 (m, 2H), 1.77-1.71 (m, 3H), 1.61-1.55 (m, 2H), 1.22 (d, J=6.6 Hz, 3H); MS m/z: 543 [M+H]$^+$.

Example 63: 6-((5-((3S,4S)-4-amino-3-methyl-2-oxa-8-azaspiro[4.5]decan-8-yl)pyrazin-2-yl)thio)-5-chloro-3-(3-hydroxypropyl)quinazolin-4(3H)-one

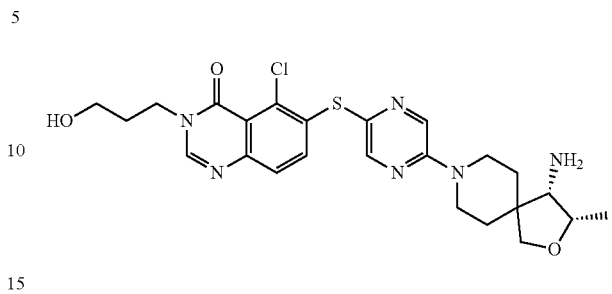

The compound of Example 63 (29 mg, 81%) was synthesized in the same method as in Example 18, except that, in step 2 of Example 18, 3-bromo-1-propanol was used instead of benzyl chloride, and 1 equivalent of potassium iodide was added. $^1$H NMR (400 MHz, DMSO) δ 8.51 (s, 1H), 8.56 (s, 1H), 8.32 (d, J=1.2 Hz, 1H), 8.09 (br s, 3H), 7.52 (d, J=8.8 Hz, 1H), 7.23 (d, J=8.8 Hz, 1H), 4.30-4.25 (m, 1H), 4.23-4.19 (m, 2H), 4.04-3.98 (m, 2H), 3.92 (d, J=9.2 Hz, 1H), 3.72-3.60 (m, 2H), 3.45 (t, J=6.0 Hz, 2H), 3.40-3.39 (m, 1H), 3.19-3.12 (m, 2H), 1.86-1.70 (m, 4H), 1.61-1.59 (m, 1H), 1.23 (d, J=6.5 Hz, 3H).

Example 64: 6-((5-((3S,4S)-4-amino-3-methyl-2-oxa-8-azaspiro[4.5]decan-8-yl)pyrazin-2-yl)thio)-5-chloro-3-(2-methoxyethyl)quinazolin-4(3H)-one

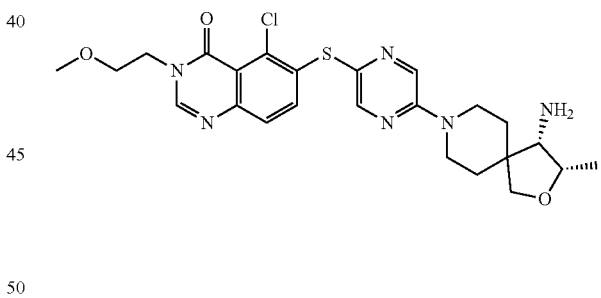

The compound of Example 64 (101 mg, 98%) was synthesized in the same method as in Example 18, except that 2-bromoethyl methyl ether was used instead of benzyl chloride in step 2 of Example 18. $^1$H NMR (400 MHz, DMSO) δ 8.51 (s, 1H), 8.32 (d, J=1.2 Hz, 1H), 8.29 (s, 1H), 8.11 (br s, 3H), 7.52 (d, J=8.8 Hz, 1H), 7.24 (d, J=8.8 Hz, 1H), 4.30-4.27 (m, 1H), 4.23-4.19 (m, 2H), 4.13 (t, J=5.0 Hz, 2H), 3.92 (d, J=9.0 Hz, 1H), 3.69 (d, J=8.9 Hz, 1H), 3.60 (t, J=5.1 Hz, 2H), 3.41-3.37 (m, 1H), 3.25 (s, 3H), 3.19-3.12 (m, 2H), 1.83-1.70 (m, 3H), 1.62-1.58 (m, 1H), 1.23 (d, J=6.5 Hz, 3H).

Example 65: 6-((5-((3S,4S)-4-amino-3-methyl-2-oxa-8-azaspiro[4.5]decan-8-yl)pyrazin-2-yl)thio)-5-chloro-3-((tetrahydro-2H-pyran-4-yl)methyl)quinazolin-4(3H)-one

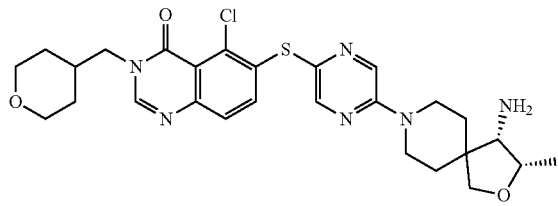

The compound of Example 65 (76 mg, 98%) was synthesized in the same method as in Example 18, except that, in step 2 of Example 18, 4-(bromomethyl)tetrahydro-2H-pyran was used instead of benzyl chloride, and 1.5 equivalents of potassium iodide were added. $^1$H NMR (400 MHz, DMSO) δ 8.51 (s, 1H), 8.36 (s, 1H), 8.32 (s, 1H), 7.99 (br s, 2H), 7.52 (d, J=8.7 Hz, 1H), 7.24 (d, J=7.7 Hz, 1H), 4.29-4.19 (m, 3H), 3.92-3.90 (m, 1H), 3.85-3.83 (m, 4H), 3.71-3.69 (m, 1H), 3.27-3.13 (m, 4H), 2.04-1.99 (m, 1H), 1.81-1.74 (m, 3H), 1.61-1.57 (m, 1H), 1.49-1.46 (m, 2H), 1.29-1.18 (m, 6H); MS m/z: 557 [M+H]$^+$.

Example 66: 6-((5-((3S,4S)-4-amino-3-methyl-2-oxa-8-azaspiro[4.5]decan-8-yl)pyrazin-2-yl)thio)-5-chloro-3-(3-hydroxybenzyl)quinazolin-4(3H)-one

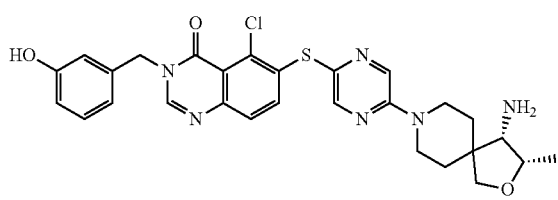 [SMILES: C[C@@H]1OCC2(CCN(c3cnc(Sc4ccc5ncn(Cc6cccc(O)c6)c(=O)c5c4Cl)cn3)CC2)[C@@H]1N]

The compound of Example 66 (48.8 mg, 81%) was synthesized in the same method as in Example 18, except that, in step 2 of Example 18, 3-(bromomethyl)phenol was used instead of benzyl chloride, and 1.5 equivalents of potassium iodide were added. $^1$H NMR (400 MHz, DMSO) δ 8.56 (s, 1H), 8.51 (s, 1H), 8.32 (s, 1H), 8.11 (br s, 2H), 7.55 (d, J=8.1 Hz, 1H), 7.25 (d, J=7.6 Hz, 1H), 7.16-7.13 (m, 1H), 6.78-6.67 (m, 3H), 5.08 (s, 2H), 4.30-4.22 (m, 3H), 3.93-3.91 (m, 2H), 3.40 (br s, 1H), 3.17-3.14 (m, 2H), 1.80-1.70 (m, 3H), 1.62-1.59 (m, 1H), 1.23 (d, J=5.2 Hz, 3H); MS m/z: 565 [M+H]$^+$.

Example 67: 6-((5-((3S,4S)-4-amino-3-methyl-2-oxa-8-azaspiro[4.5]decan-8-yl)pyrazin-2-yl)thio)-5-chloro-3-(2-(dimethylamino)ethyl)quinazolin-4(3H)-one

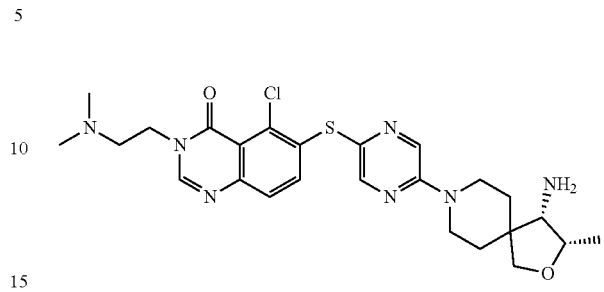

The compound of Example 67 (6 mg, 85%) was synthesized in the same method as in Example 18, except that, in step 2 of Example 18, 2-bromo-N,N-dimethylethylamine was used instead of benzyl chloride, and 1 equivalent of potassium iodide was added. $^1$H NMR (400 MHz, DMSO) δ 9.69 (br s, 1H), 8.51 (s, 1H), 8.40 (s, 1H), 8.33 (s, 1H), 8.07 (br s, 3H), 7.54 (d, J=9.2 Hz, 1H), 7.25 (d, J=8.7 Hz, 1H), 4.32-4.19 (m, 5H), 3.93-3.89 (m, 1H), 3.71-3.68 (m, 1H), 3.55-3.47 (m, 3H), 3.22-3.12 (m, 2H), 2.88 (s, 6H), 1.77-1.64 (m, 3H), 1.62-1.59 (m, 1H), 1.23 (d, J=4.4 Hz, 3H).

Example 68: 6-((5-((3S,4S)-4-amino-3-methyl-2-oxa-8-azaspiro[4.5]decan-8-yl)pyrazin-2-yl)thio)-5-chloro-3-(3-(dimethylamino)propyl)quinazolin-4(3H)-one

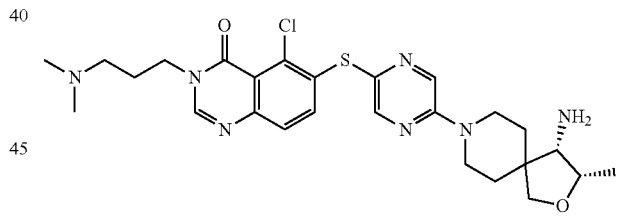

The compound of Example 68 (28 mg, 88%) was synthesized in the same method as in Example 18, except that, in step 2 of Example 18, 3-chloro-1-(N,N-dimethyl)propylamine was used instead of benzylchloride, and 1 equivalent of potassium iodide was added. $^1$H NMR (400 MHz, DMSO) δ 10.39 (br s, 1H), 8.51 (s, 1H), 8.45 (s, 1H), 8.32 (s, 1H), 8.24 (br s, 3H), 7.54 (d, J=8.8 Hz, 1H), 7.24 (d, J=8.8 Hz, 1H), 4.31-4.28 (m, 1H), 4.22-4.20 (m, 2H), J=5.9 Hz, 2H), 3.94 (d, J=8.8 Hz, 1H), 3.69-3.67 (m, 2H), 3.45-3.39 (m, 2H), 3.14-3.12 (m, 2H), 2.74 (s, 6H), 2.13-2.10 (m, 2H), 1.85-1.80 (m, 2H), 1.73-1.70 (m, 1H), 1.63-1.60 (m, 1H), 1.24 (d, J=6.0 Hz, 3H).

Example 69: 6-((5-((3S,4S)-4-amino-3-methyl-2-oxa-8-azaspiro[4.5]decan-8-yl)pyrazin-2-yl)thio)-5-chloro-3-(2-fluoro-4-methylbenzyl)quinazolin-4(3H)-one

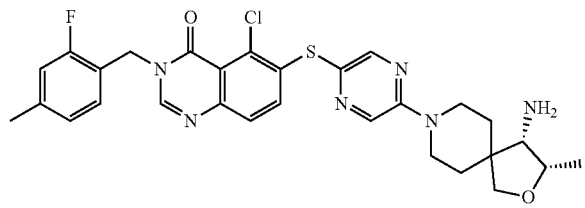

The compound of Example 69 (86 mg, 80%) was synthesized in the same method as in Example 18, except that, in step 2 of Example 18, 2-fluoro-4-methylbenzyl bromide was used instead of benzyl chloride, and 1.5 equivalents of potassium iodide were added. $^1$H NMR (400 MHz, DMSO) δ 8.50 (d, J=9.5 Hz, 2H), 8.31 (s, 1H), 8.09 (br s, 2H), 7.54 (d, J=8.8 Hz, 1H), 7.26-7.20 (m, 2H), 7.05 (d, J=11.6 Hz, 1H), 6.84 (d, J=7.8 Hz, 1H), 5.14 (s, 2H), 4.29-4.18 (m, 3H), 3.92 (d, J=9.1 Hz, 1H), 3.70 (br s, 1H), 3.39 (br s, 1H), 3.19-3.11 (m, 2H), 2.29 (s, 3H), 1.84-1.69 (m, 3H), 1.62-1.58 (m, 1H), 1.23 (d, J=6.5 Hz, 3H); MS m/z: 581 [M+H]$^+$.

Example 70: 6-((5-((3S,4S)-4-amino-3-methyl-2-oxa-8-azaspiro[4.5]decan-8-yl)pyrazin-2-yl)thio)-5-chloro-3-(2-fluoro-3-methoxybenzyl)quinazolin-4(3H)-one

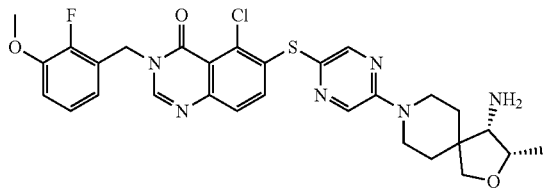

The compound of Example 70 (31 mg, 67%) was synthesized in the same method as in Example 18, except that, in step 2 of Example 18, 2-fluoro-3-methoxybenzyl bromide was used instead of benzyl chloride, and 1.5 equivalents of potassium iodide were added. $^1$H NMR (400 MHz, DMSO) δ 8.51 (d, J=11.2 Hz, 2H), 8.31 (s, 1H), 8.09 (br s, 2H), 7.55 (d, J=8.8 Hz, 1H), 7.26 (d, J=8.8 Hz, 1H), 7.14-7.07 (m, 2H), 6.83-6.80 (m, 1H), 5.19 (s, 2H), 4.29-4.18 (m, 3H), 3.92 (d, J=9.1 Hz, 1H), 3.83 (s, 3H), 3.72-3.67 (m, 1H), 3.40 (br s, 1H), 3.19-3.11 (m, 2H), 1.82-1.70 (m, 3H), 1.61-1.58 (m, 1H), 1.23 (d, J=6.5 Hz, 3H); MS m/z: 597 [M+H]$^+$.

Example 71: 4-((6-((5-((3S,4S)-4-amino-3-methyl-2-oxa-8-azaspiro[4.5]decan-8-yl)pyrazin-2-yl)thio)-5-chloro-4-oxoquinazolin-3(4H)-yl)methyl)picolinonitrile

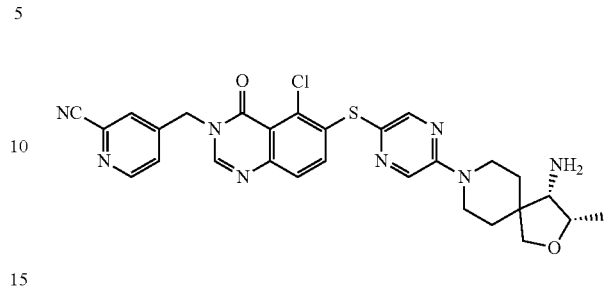

The compound of Example 71 (82 mg, 99%) was synthesized in the same method as in Example 18, except that, in step 2 of Example 18, 4-(bromomethyl)picolinonitrile was used instead of benzyl chloride, and 1 equivalent of potassium iodide was added. $^1$H NMR (400 MHz, DMSO) δ 8.71 (d, J=5.0 Hz, 1H), 8.54 (s, 1H), 8.50 (s, 1H), 8.31 (s, 1H), 8.13-8.07 (m, 4H), 7.70-7.68 (m, 1H), 7.57 (d, J=8.8 Hz, 1H), 7.28 (d, J=8.8 Hz, 1H), 5.24 (s, 2H), 4.29-4.18 (m, 3H), 3.92 (d, J=9.4 Hz, 1H), 3.69 (d, J=8.9 Hz, 1H), 3.41-3.40 (m, 1H), 3.20-3.12 (m, 2H), 1.82-1.66 (m, 3H), 1.62-1.58 (m, 1H), 1.23 (d, J=6.4 Hz, 3H).

Example 72: 6-((5-((3S,4S)-4-amino-3-methyl-2-oxa-8-azaspiro[4.5]decan-8-yl)pyrazin-2-yl)thio)-5-chloro-3-(2-fluoro-4-methoxybenzyl)quinazolin-4(3H)-one

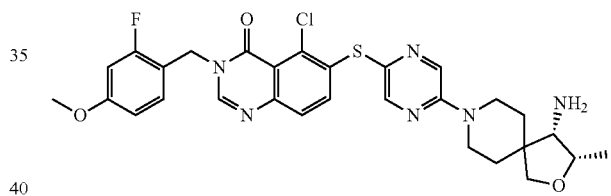

The compound of Example 72 was synthesized in the same method as in Example 18, except that 1-(bromomethyl)-2-fluoro-4-methoxybenzene was used instead of benzyl chloride in step 2 of Example 18. $^1$H NMR (400 MHz, DMSO) δ 8.51 (d, J=4.3 Hz, 2H), 8.31 (s, 1H), 8.02(br s, 3H), 7.53 (d, J=8.8 Hz, 1H), 7.13 (t, J=8.8 Hz, 1H), 7.24 (d, J=8.8 Hz, 1H), 6.85 (d, J=12.4 Hz, 2H), 6.76 (d, J=8.3 Hz, 1H), 5.10(s 2H), 4.28-4.17 (m, 3H), 3.91-3.89 (m, 1H), 3.41-3.39 (m, 1H), 3.19-3.11 (m, 2H), 1.81-1.73 (m, 3H), 1.60-1.55 (m, 1H), 1.22 (d, J=6.5 Hz, 3H), 1.04 (s, 3H).

Example 73: 6-((5-((3S,4S)-4-amino-3-methyl-2-oxa-8-azaspiro[4.5]decan-8-yl)pyrazin-2-yl)thio)-5-chloro-3-(3-fluoro-4-methoxybenzyl)quinazolin-4(3H)-one

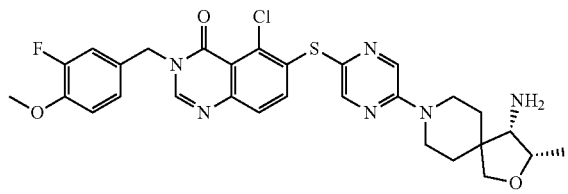

The compound of Example 73 (62 mg, 93%) was synthesized in the same method as in Example 18, except that, in step 2 of Example 18, 4-(bromomethyl)-2-fluoro-1-methoxybenzene was used instead of benzyl chloride, and 1.5 equivalents of potassium iodide were added. $^1$H NMR (400 MHz, DMSO) δ 8.60 (s, 1H), 8.50 (s, 1H), 8.31 (d, J=1.1 Hz, 1H), 8.14 (br s, 2H), 7.53 (d, J=8.8 Hz, 1H), 7.32-7.29 (m, 1H), 7.24 (d, J=8.8 Hz, 1H), 7.21-7.12 (m, 2H), 5.07 (s, 2H), 4.29-4.18 (m, 3H), 3.93 (d, J=9.0 Hz, 1H), 3.81 (s, 3H), 3.68 (d, J=9.3 Hz, 1H), 3.39 (br s, 1H), 3.19-3.11 (m, 2H), 1.84-1.69 (m, 3H), 1.60 (d, J=12.7 Hz, 1H), 1.23 (d, J=6.5 Hz, 3H); MS m/z: 597 [M+H]$^+$.

Example 74: 6-((5-((3S,4S)-4-amino-3-methyl-2-oxa-8-azaspiro[4.5]decan-8-yl)pyrazin-2-yl)thio)-5-chloro-3-((l-methylpyrrolidin-2-yl)methyl)quinazolin-4(3H)-one

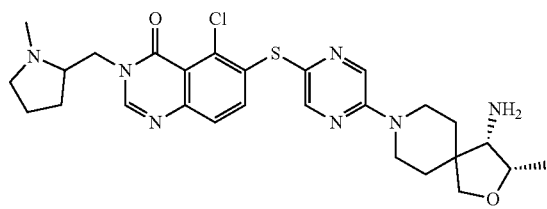 [SMILES: C[C@@H]1OCC2(CCN(c3cnc(Sc4ccc5ncn(CC6CCCN6C)c(=O)c5c4Cl)cn3)CC2)[C@@H]1N]

The compound of Example 74 was synthesized in the same method as in Example 18, except that 2-(bromomethyl)-1-methylpyrrolidin hydrochloride was used instead of benzyl chloride in step 2 of Example 18. $^1$H NMR (400 MHz, DMSO) δ 8.50(d, J=7.2 Hz 2H), 8.32 (s, 1H), 8.07 (br s, 3H), 7.56 (d, J=8.8 Hz, 1H), 7.25 (d, J=8.8 Hz, 1H), 4.46-4.41 (m, 1H), 4.30-4.19 (m, 4H), 3.92-3.90 (m, 1H), 3.70-3.68 (m, 3H), 3.56 (s, 2H), 3.21-3.08 (m, 5H), 2.90 (d, J=4.4 Hz, 3H), 2.22-2.18 (m, 1H), 2.02-1.98 (m, 2H), 1.84-1.70 (m, 3H), 1.62-1.55 (m, 1H), 1.22 (d, J=6.2 Hz, 3H).

Example 75: 6-((5-((3S,4S)-4-amino-3-methyl-2-oxa-8-azaspiro[4.5]decan-8-yl)pyrazin-2-yl)thio)-5-chloro-3-(2,2,2-trifluoroethyl)quinazolin-4(3H)-one

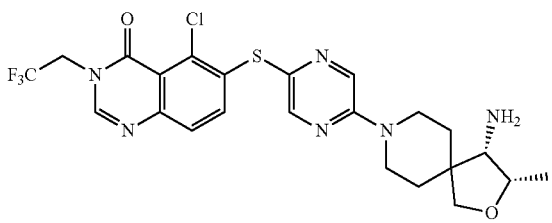 [SMILES: C[C@@H]1OCC2(CCN(c3cnc(Sc4ccc5ncn(CC(F)(F)F)c(=O)c5c4Cl)cn3)CC2)[C@@H]1N]

The compound of Example 75 was synthesized in the same method as in Example 18, except that 2-bromo-1,1,1-trifluoroethane was used instead of benzyl chloride in step 2 of Example 18. MS m/z: 542 [M+H]$^+$.

Example 76: 6-((5-((3S,4S)-4-amino-3-methyl-2-oxa-8-azaspiro[4.5]decan-8-yl)pyrazin-2-yl)thio)-5-chloro-3-(3-fluoro-2-hydroxypropyl)quinazolin-4(3H)-one

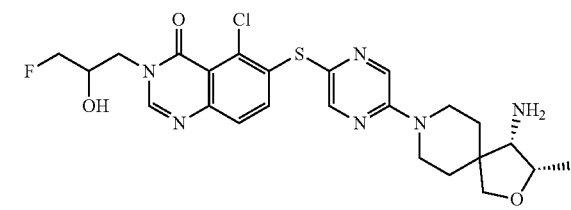 [SMILES: C[C@@H]1OCC2(CCN(c3cnc(Sc4ccc5ncn(CC(O)CF)c(=O)c5c4Cl)cn3)CC2)[C@@H]1N]

The compound of Example 76 (60 mg, 87%) was synthesized in the same method as in Example 18, except that, in step 2 of Example 18, 1-chloro-3-fluoroisopropanol was used instead of benzyl chloride, and 1 equivalent of potassium iodide was added. $^1$H NMR (400 MHz, DMSO) δ 8.51 (s, 1H), 8.32 (s, 1H), 8.26 (s, 1H), 8.15 (br s, 2H), 7.53 (d, J=8.8 Hz, 1H), 7.25 (d, J=8.9 Hz, 1H), 4.53-4.45 (m, 1H), 4.42-4.32 (m, 1H), 4.30-4.27 (m, 1H), 4.22-4.16 (m, 3H), 4.08-4.02 (m, 2H), 3.93 (d, J=9.3 Hz, 1H), 3.80-3.75 (m, 1H), 3.68 (d, J=9.2 Hz, 1H), 3.40 (br s, 1H), 3.16-3.14 (m, 2H), 1.81-1.69 (m, 3H), 1.62-1.59 (m, 1H), 1.23 (d, J=6.3 Hz, 3H).

Example 77: 6-((5-((3S,4S)-4-amino-3-methyl-2-oxa-8-azaspiro[4.5]decan-8-yl)pyrazin-2-yl)thio)-5-chloro-3-(3-fluoropropyl)quinazolin-4(3H)-one

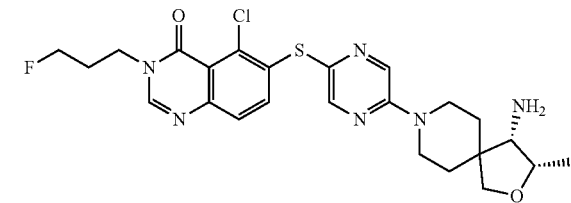 [SMILES: C[C@@H]1OCC2(CCN(c3cnc(Sc4ccc5ncn(CCCF)c(=O)c5c4Cl)cn3)CC2)[C@@H]1N]

The compound of Example 77 (77 mg, 99%) was synthesized in the same method as in Example 18, except that, in step 2 of Example 18, 1-iodo-3-fluoropropane was used instead of benzyl chloride, and 1 equivalent of potassium iodide was added. $^1$H NMR (400 MHz, DMSO) δ 8.51 (s, 1H), 8.41 (s, 1H), 8.32 (s, 1H), 8.15 (br s, 2H), 7.53 (d, J=9.2 Hz, 1H), 7.24 (d, J=8.6 Hz, 1H), 4.60 (t, J=5.2 Hz, 1H), 4.48 (t, J=5.2 Hz, 1H), 4.30-4.27 (m, 1H), 4.22-4.19 (m, 2H), 4.08-4.05 (m, 2H), 3.93 (d, J=9.4 Hz, 1H), 3.68 (d, J=9.5 Hz, 1H), 3.40 (br s, 1H), 3.16-3.14 (m, 2H), 2.14-2.03 (m, 2H), 1.81-1.70 (m, 3H), 1.62-1.59 (m, 1H), 1.23 (d, J=6.1 Hz, 3H).

Example 78: 6-((5-((3S,4S)-4-amino-3-methyl-2-oxa-8-azaspiro[4.5]decan-8-yl)pyrazin-2-yl)thio)-5-chloro-3-(morpholinomethyl)quinazolin-4(3H)-one

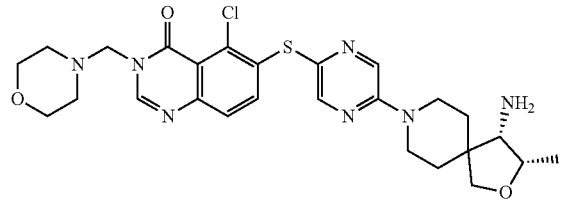 [SMILES: C[C@@H]1OCC2(CCN(c3cnc(Sc4ccc5ncn(CN6CCOCC6)c(=O)c5c4Cl)cn3)CC2)[C@@H]1N]

The compound of Example 78 (101.7 mg, 100%) was synthesized in the same method as in Example 18, except that, in step 2 of Example 18, 4-(2-chloroethyl)morpholine was used instead of benzylchloride, and 1.5 equivalents of potassium iodide were added. $^1$H NMR (400 MHz, DMSO) δ 10.69-10.65 (m, 1H), 8.51 (s, 1H), 8.43 (s, 1H), 8.32 (s, 1H), 8.14 (br s, 2H), 7.55 (d, J=9.5 Hz, 1H), 7.25 (d, J=8.7 Hz, 1H), 4.36 (br s, 2H), 4.04-3.99 (m, 2H), 3.93 (d, J=8.4 Hz, 1H), 3.77-3.68 (m, 4H), 3.59-3.55 (m, 4H), 3.40 (br s, 1H), 3.16-3.14 (m, 4H), 1.83-1.70 (m, 3H), 1.62-1.59 (m, 1H), 1.23 (d, J=6.2 Hz, 3H); MS m/z: 558 [M+H]$^+$.

Example 79: 6-((5-((3S,4S)-4-amino-3-methyl-2-oxa-8-azaspiro[4.5]decan-8-yl)pyrazin-2-yl)thio)-5-chloro-3-((4-fluorotetrahydro-2H-pyran-4-yl)methyl)quinazolin-4(3H)-one

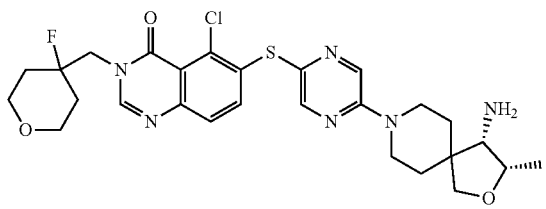 [SMILES: C[C@@H]1OCC2(CCN(c3cnc(Sc4ccc5ncn(CC6(F)CCOCC6)c(=O)c5c4Cl)cn3)CC2)[C@@H]1N]

The compound of Example 79 (31 mg, 99%) was synthesized in the same method as in Example 18, except that, in step 2 of Example 18, 4-(bromomethyl)-4-fluorooxane was used instead of benzyl chloride, and 1 equivalent of potassium iodide was added. $^1$H NMR (400 MHz, DMSO) δ 8.52 (s, 1H), 8.32 (d, J=1.2 Hz, 1H), 8.24 (d, J=1.8 Hz, 1H), 8.12 (br s, 2H), 7.53 (d, J=8.8 Hz, 1H), 7.24 (d, J=8.8 Hz, 1H), 4.27 (s, 2H), 4.23-4.19 (m, 3H), 3.92 (d, J=9.0 Hz, 1H), 3.76-3.74 (m, 2H), 3.69 (d, J=9.1 Hz, 1H), 3.53-3.45 (m, 2H), 3.40-3.37 (m, 1H), 3.19-3.12 (m, 2H), 1.91-1.55 (m, 8H), 1.23 (d, J=6.5 Hz, 3H).

Example 80: 6-((5-((3S,4S)-4-amino-3-methyl-2-oxa-8-azaspiro[4.5]decan-8-yl)pyrazin-2-yl)thio)-5-chloro-3-((3-fluorooxetan-3-yl)methyl)quinazolin-4(3H)-one

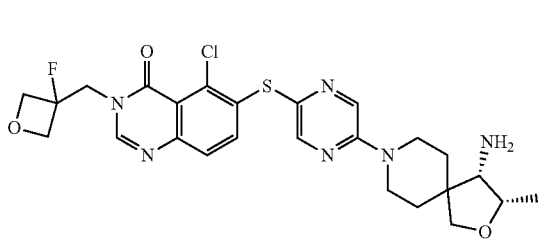 [SMILES: C[C@@H]1OCC2(CCN(c3cnc(Sc4ccc5ncn(CC6(F)COC6)c(=O)c5c4Cl)cn3)CC2)[C@@H]1N]

The compound of Example 80 (34 mg, 99%) was synthesized in the same method as in Example 18, except that, in step 2 of Example 18, 3-(bromomethyl)-3-fluoro oxetane was used instead of benzylchloride, and 1 equivalent of potassium iodide was added. $^1$H NMR (400 MHz, DMSO) δ 8.51 (s, 1H), 8.32 (d, J=1.2 Hz, 1H), 8.20 (d, J=1.5 Hz, 1H), 8.07 (br s, 2H), 7.53 (d, J=8.8 Hz, 1H), 7.24 (d, J=8.8 Hz, 1H), 4.30-4.27 (m, 1H), 4.23-4.19 (m, 2H), 3.94-3.93 (m, 2H), 3.91-3.89 (m, 2H), 3.70-3.63 (m, 4H), 3.43-3.40 (m, 1H), 3.20-3.12 (m, 2H), 1.82-1.70 (m, 3H), 1.61-1.58 (m, 1H), 1.23 (d, J=6.5 Hz, 3H).

Example 81: 6-((5-((3S,4S)-4-amino-3-methyl-2-oxa-8-azaspiro[4.5]decan-8-yl)pyrazin-2-yl)thio)-5-chloro-3-(2-hydroxy-2-methylpropyl)quinazolin-4(3H)-one

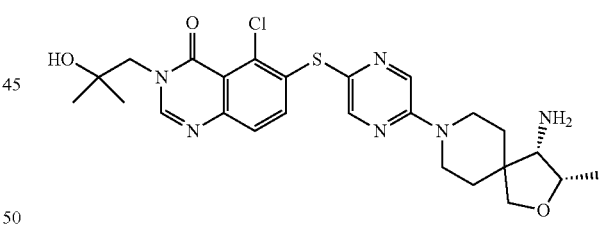

The compound of Example 81 (33 mg, 89%) was synthesized in the same method as in Example 18, except that, in step 2 of Example 18, 1-chloro-2-methyl-2-propanol was used instead of benzyl chloride, and 1 equivalent of potassium iodide was added. $^1$H NMR (400 MHz, DMSO) δ 8.51 (s, 1H), 8.33 (d, J=1.2 Hz, 1H), 8.24 (s, 1H), 8.08 (br s, 2H), 7.52 (d, J=8.8 Hz, 1H), 7.23 (d, J=8.8 Hz, 1H), 4.30-4.25 (m, 1H), 4.23-4.19 (m, 2H), 3.96 (s, 2H), 3.92 (d, J=9.1 Hz, 1H), 3.69 (d, J=9.2 Hz, 1H), 3.41-3.40 (m, 1H), 3.20-3.12 (m, 2H), 1.83-1.70 (m, 3H), 1.61-1.58 (m, 1H), 1.23 (d, J=6.6 Hz, 3H), 1.11 (s, 6H).

Example 82: 6-((5-((3S,4S)-4-amino-3-methyl-2-oxa-8-azaspiro[4.5]decan-8-yl)pyrazin-2-yl)thio)-5-chloro-3-(2-(methylsulfonyl)ethyl)quinazolin-4(3H)-one

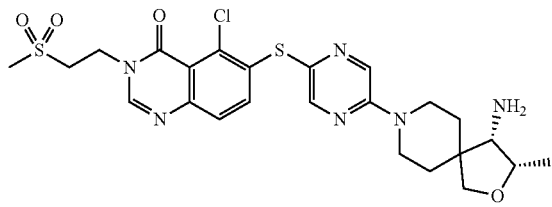

The compound of Example 82 (77 mg, 99%) was synthesized in the same method as in Example 18, except that, in step 2 of Example 18, 2-bromomethyl-methylsulfon was used instead of benzyl chloride, and 1 equivalent of potassium iodide was added. $^1$H NMR (400 MHz, DMSO) δ 8.51 (d, J=1.1 Hz, 1H), 8.40 (s, 1H), 8.33 (d, J=1.2 Hz, 1H), 8.11 (br s, 2H), 7.53 (d, J=8.8 Hz, 1H), 7.25 (d, J=8.8 Hz, 1H), 4.37 (t, J=6.8 Hz, 2H), 4.30-4.26 (m, 2H), 4.23-4.19 (m, 2H), 3.92 (d, J=9.2 Hz, 1H), 3.69 (d, J=9.0 Hz, 1H), 3.63 (t, J=6.8 Hz, 2H), 3.45-3.40 (m, 1H), 3.19-3.15 (m, 2H), 3.10 (s, 3H), 1.83-1.70 (m, 3H), 1.62-1.58 (m, 1H), 1.23 (d, J=6.6 Hz, 3H).

Example 83: 6-((5-((3S,4S)-4-amino-3-methyl-2-oxa-8-azaspiro[4.5]decan-8-yl)pyrazin-2-yl)thio)-5-chloro-3-((4-hydroxytetrahydro-2H-pyran-4-yl)methyl)quinazolin-4(3H)-one

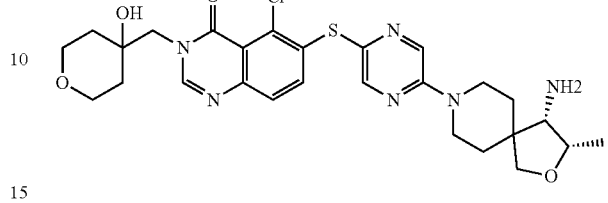

The compound of Example 83 (6.5 mg, 59%) was synthesized in the same method as in Example 18, except that 1,6-dioxaspiro[2,5]octane was used instead of benzyl chloride in step 2 of Example 18. $^1$H NMR (400 MHz, DMSO) δ 8.51 (s, 1H), 8.32 (d, J=1.2 Hz, 1H), 8.25 (s, 1H), 8.06 (br s, 2H), 7.52 (d, J=8.7 Hz, 1H), 7.23 (d, J=8.8 Hz, 1H), 4.30-4.23 (m, 1H), 4.22-4.19 (m, 3H), 4.00 (s, 2H), 3.91 (d, J=9.0 Hz, 1H), 3.69 (d, J=9.1 Hz, 1H), 3.65-3.55 (m, 4H), 3.41 (br s, 1H), 3.20-3.12 (m, 2H), 1.82-1.70 (m, 3H), 1.65-1.58 (m, 3H), 1.35 (d, J=13.6 Hz, 2H), 1.23 (d, J=6.6 Hz, 3H); MS m/z: 573 [M+H]$^+$.

Example 84: (S)-6-((5-(1-amino-1,3-dihydrospiro(indene-2,4'-piperidin]-1'-yl)pyrazin-2-yl)thio)-5-chloro-3-(2-methoxyethyl)quinazolin-4(3H)-one

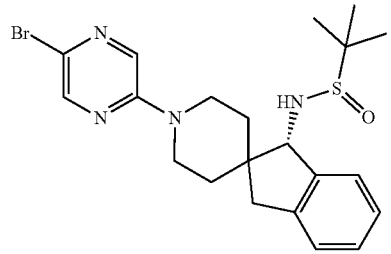

I-21

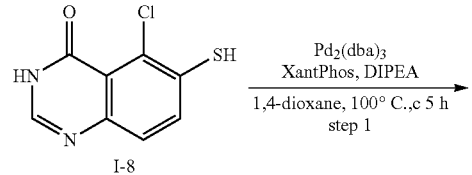

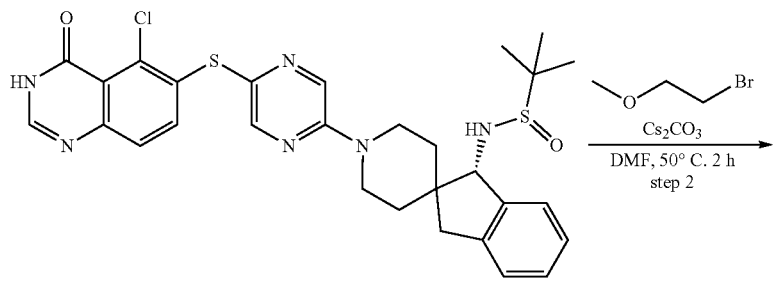

-continued

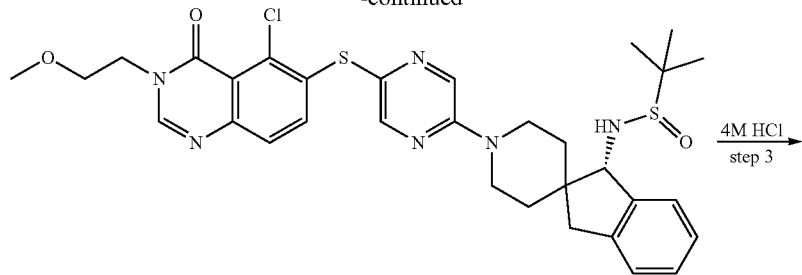

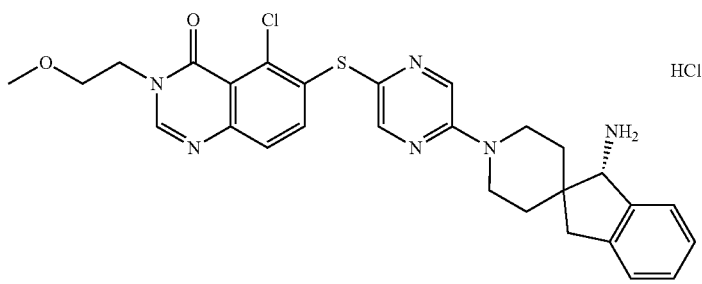

Step 1: N—((S)-1'-(5-((5-chloro-4-oxo-3,4-dihydroquinazolin-6-yl) thio)pyrazin-2-yl)-1,3-dihydrospiro[indene-2,4'-piperidin]-1-yl)-2-methylpropane-2-sulfinamide Intermediate I-21 (150 mg, 0.32 mmol), Intermediate I-8 (106 mg, 0.42 mmol), Pd$_2$(dba)$_3$ (30 mg, 0.032 mmol) and XantPhos (18.5 mg, 0.032 mmol) were dissolved in 1,4-dioxane (3.2 mL, 0.2M), and then DIPEA (0.11 mL, 0.64 mmol) was added thereto. The reaction mixture was purged with nitrogen and stirred at 100° C. for 5 hours. The reaction was terminated with H$_2$O, and the mixture was extracted with EA. The EA layer was dried over MgSO$_4$, filtered and then concentrated. The resulting product was separated by MPLC (MeOH:MC=1:50) and concentrated to obtain N—((S)-1'-(5-((5-chloro-4-oxo-3,4-dihydroquinazolin-6-yl)thio)pyrazin-2-yl)-1,3-dihydrospiro[indene-2,4'-piperidin]-1-yl)-2-methylpropane-2-sulfinamide (140 mg, 73%). MS m/z: 596.1 [M+H]$^+$.

Step 2: N—((S)-1'-(5-((5-chloro-3-(2-methoxyethyl)-4-oxo-3,4-dihydroquinazolin-6-yl)thio)pyrazin-2-yl)-1,3-dihydrospiro[indene-2,4'-piperidin]-1-yl)-2-methylpropane-2-sulfinamide N—((S)-1'-(5-((5-chloro-4-oxo-3,4-dihydroquinazolin-6-yl)thio)pyrazin-2-yl)-1,3-dihydrospiro[indene-2,4'-piperidin]-1-yl)-2-methylpropane-2-sulfinamide (50 mg, 0.084 mmol), 1-bromo-2-methoxyethane (17.5 mg, 0.126 mmol) and cesium carbonate (54.7 mg, 0.168 mmol) were dissolved in DMF (0.84 mL, 0.1 M). The reaction mixture was stirred at 50° C. for 2 hours. The reaction was terminated with aqueous NaHCO$_3$ solution, and the mixture was extracted with EA. The EA layer was dried over MgSO$_4$, filtered and then concentrated. The resulting product was separated by MPLC (MeOH:MC=1:50) to obtain N—((S)-1'-(5-((5-chloro-3-(2-methoxyethyl)-4-oxo-3,4-dihydroquinazolin-6-yl)thio)pyrazin-2-yl)-1,3-dihydrospiro[indene-2,4'-piperidin]-1-yl)-2-methylpropane-2-sulfinamide (9.6 mg, 17%). MS m/z: 654.1 [M+H]$^+$.

Step 3: (S)-6-((5-(1-amino-1,3-dihydrospiro[indene-2,4'-piperidin]1'-yl)pyrazin-2-yl)thio)-5-chloro-3-(2-methoxyethyl)quinazolin-4(3H)-one N—((S)-1'-(5-((5-chloro-3-(2-m ethoxy ethyl)-4-oxo-3,4-dihydroquinazolin-6-yl)thio)pyrazin-2-yl)-1,3-dihydrospiro [indene-2,4'-piperidin]-1-yl)-2-methylpropane-2-sulfinamide (9.6 mg, 0.0146 mol) was dissolved in DCM (0.1 mL, 0.1M). The reaction mixture was added with 4M HCl (0.0036 mL, 4 M in dioxane) and stirred at 40° C. for 1 hour. After completion of the reaction, the reaction mixture was concentrated using a concentrator. The reaction mixture was washed with EA, and the solid was collected by filtration to obtain the compound of Example 84 (6.3 mg, 74%). $^1$H NMR (400 MHz, DMSO) δ 8.52 (s, 1H), 8.32-8.28 (m, 5H), 7.53 (d, J=8.5 Hz, 2H), 7.37-7.31 (m, 3H), 7.26-7.24 (d, J=8.8 Hz, 1H), 4.42-4.34 (m, 2H), 4.30-4.24 (m, 1H), 4.14-4.11 (m, 2H), 3.74-3.70 (m, 2H), 3.62-3.59 (m, 2H), 1.78-1.74 (m, 2H), 1.60-1.56 (m, 2H), 1.23 (s, 3H).

Example 85: 7-((5-((3S,4S)-4-amino-3-methyl-2-oxa-8-azaspiro[4.5]decan-8-yl)pyrazin-2-yl)thio)-2-benzyl-8-chloro-3,4-dihydroisoquinolin-1(2H)-one

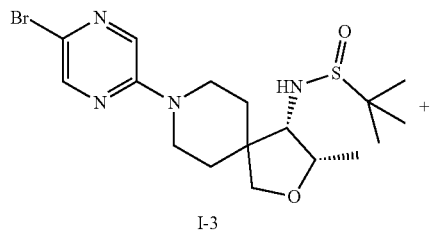

I-3

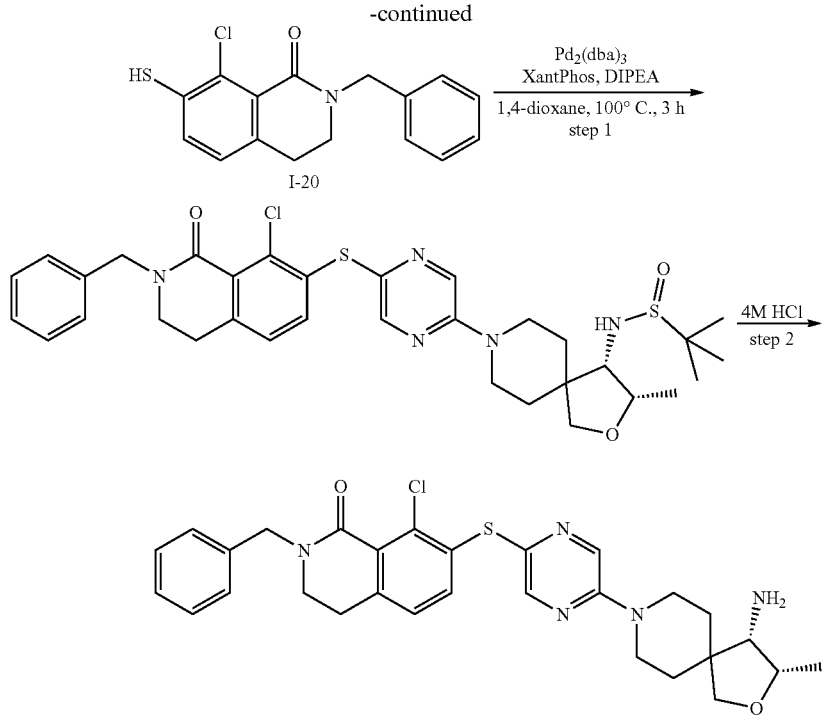

Step 1: N-((3S,4S)-8-(54(2-benzyl-8-chloro-1-oxo-1,2,3,4-tetrahydroisoquinolin-7-yl)thio)pyrazin-2-yl)-3-methyl-2-oxa-8-azaspiro[4.5]decan-4-yl)-2-methylpropane-2-sulfonamide Intermediate I-20 (0.25 mmol), Intermediate I-3 (160 mg, 0.37 mmol), Pd$_2$(dba)$_3$ (23 mg, 0.02 mmol), XantPhos (14 mg, 0.02 mmol) and DIPEA (0.09 mL, 0.5 mmol) were dissolved in 1,4-dioxane (1.0 mL, 0.25M). The reaction mixture was purged with nitrogen and stirred at 100° C. for 3 hours. The reaction was terminated with H$_2$O, and the mixture was extracted with EA. The EA layer was dried over MgSO$_4$, filtered and then concentrated. The resulting product was separated by MPLC (MeOH:MC=1:50) and concentrated to obtain N-((3S,4S)-8-(5-((2-benzyl-8-chloro-1-oxo-1,2,3,4-tetrahydroisoquinolin-7-yl)thio)pyrazin-2-yl)-3-methyl-2-oxa-8-azaspiro[4.5]decan-4-yl)-2-methylpropane-2-sulfonamide (74 mg, 47%). MS m/z: 655.1 [M+H]$^+$.

Step 2: 74(54(3S,4S)-4-amino-3-methyl-2-oxa-8-azaspiro[4.5]decan-8-yl)pyrazin-2-yl)thio)-2-benzyl-8-chloro-3,4-dihydroisoquinolin-1(2H)-one N-((3 S,4S)-8-(5-((2-benzyl-8-chloro-1-oxo-1,2,3,4-tetrahydroisoquinolin-7-yl)thio)pyrazin-2-yl)-3-methyl-2-oxa-8-azaspiro[4.5]decan-4-yl)-2-methylpropane-2-sulfonamide (74 mg, 0.12 mmol) was dissolved in DCM (1.2 mL, 0.1M). The reaction mixture was added with hydrochloric acid aqueous solution (0.3 mL, 4 M in dioxane) and stirred at room temperature for 1 hour. After completion of the reaction, the reaction mixture was concentrated using a concentrator. The reaction mixture was washed with EA, and the solid was collected by filtration to obtain the compound of Example 85 (60 mg, 88%). $^1$H NMR (400 MHz, DMSO) δ 8.39 (s, 1H), 8.21 (s, 1H), 8.07 (br s, 3H), 7.75 (s, 1H), 7.45-7.27 (m, 6H), 4.66 (s, 2H), 4.23-4.19 (m, 2H), 4.16-4.12 (m, 1H), 3.90 (d, J=9.0 Hz, 1H), 3.67 (d, J=9.0 Hz, 1H), 3.49 (t, J=6.4 Hz, 2H), 3.38-3.37 (m, 1H), 3.14-3.07 (m, 2H), 2.93 (t, J=6.2 Hz, 2H), 1.79-1.67 (m, 3H), 1.60-1.56 (m, 1H), 1.22 (d, J=6.4 Hz, 3H).

Example 86: 4-((5-((3S,4S)-4-amino-3-methyl-2-oxa-8-azaspiro[4.5]decan-8-yl)pyrazin-2-yl)thio)-N-benzyl-3-chloropicolinamide

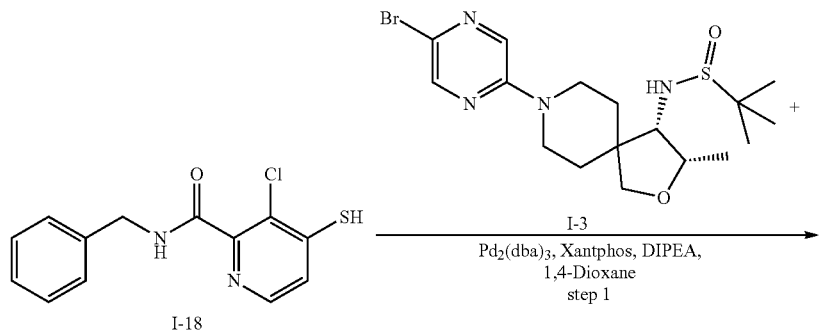

-continued

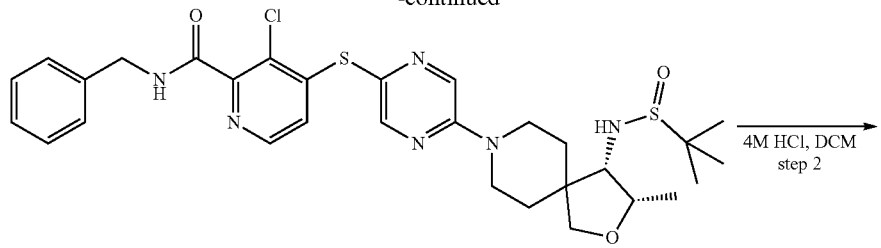

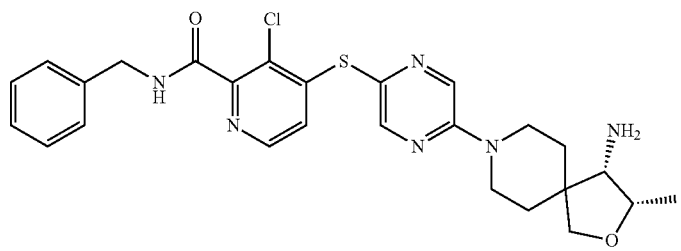

Step 1: N-benzyl-44(54(3S,4S)-4-((tert-butylsulfinyl) amino)-3-methyl-2-oxa-8-azaspiro[4.5]decan-8-yl)pyrazin-2-yl)thio)-3-chloropicolinamide Intermediate I-18 (0.32 mmol), Intermediate I-3 (117 mg, 0.27 mmol), Pd$_2$(dba)$_3$ (25 mg, 0.027 mmol) and XantPhos (16 mg, 0.027 mmol) were dissolved in 1,4-dioxane (1.4 mL, 0.2M), and then DIPEA (94 μL, 0.54 mmol) was added thereto. The reaction mixture was purged with nitrogen and stirred at 110° C. for 5 hours. The reaction was terminated with H$_2$O, and the mixture was extracted with EA. The EA layer was dried over MgSO$_4$, filtered and then concentrated. The resulting product was separated by MPLC (EA:Hx=1:1) and concentrated to obtain N-benzyl-4-((5-((3 S,4S)-4-((tert-butylsulfinyl)amino)-3-methyl-2-oxa-8-azaspiro[4.5] decan-8-yl)pyrazin-2-yl)thio)-3-chloropicolinamide (44 mg, 22%). MS m/z: 279 [M+H]$^+$.

Step 2: 4-054(3S,4S)-4-amino-3-methyl-2-oxa-8-azaspiro[4.5]decan-8-yl)pyrazin-2-yl)thio)-N-benzyl-3-chloropicolinamide N-benzyl-4-((5-((3 S,4S)-4-((tert-butylsulfinyl)amino)-3-methyl-2-oxa-8-azaspiro[4.5]decan-8-yl)pyrazin-2-yl)thio)-3-chloropicolinamide (44 mg, 0.07 mmol) was dissolved in MC (0.7 mL, 0.1 M). The reaction mixture was added dropwise with 4M HCl (84 μL, 0.35 mmol) in dioxane and stirred at 40° C. for 10 minutes. The reaction mixture was concentrated and added with MC to precipitate a solid, and then the precipitated solid was filtered to obtain the compound of Example 86 (33.2 mg, 90%) in the form of a hydrochloride salt. $^1$H NMR (400 MHz, DMSO) δ 9.17 (t, J=6.3 Hz, 1H), 8.57 (d, J=0.9 Hz, 1H), 8.37 (d, J=1.2 Hz, 1H), 8.27 (d, J=5.3 Hz, 1H), 8.16 (br s, 2H), 7.36-7.35 (m, 4H), 7.30-7.24 (m, 1H), 6.81 (d, J=5.3 Hz, 1H), 4.47 (d, J=6.1 Hz, 2H), 4.33-4.30 (m, 1H), 4.25-4.19 (m, 2H), 3.70 (t, J=9.2 Hz, 1H), 3.40 (br s, 1H), 3.22-3.17 (m, 3H), 1.85-1.70 (m, 3H), 1.63-1.60 (m, 1H), 1.24 (d, J=6.5 Hz, 3H); MS m/z: 525 [M+H]$^+$.

Example 87: 4-((5-((3S,4S)-4-amino-3-methyl-2-oxa-8-azaspiro[4.5]decan-8-yl)pyrazin-2-yl)thio)-3-chloro-N-(pyridin-3-ylmethyl)picolinamide

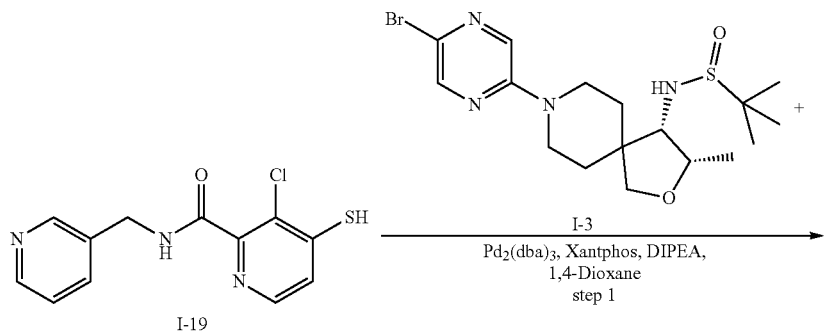

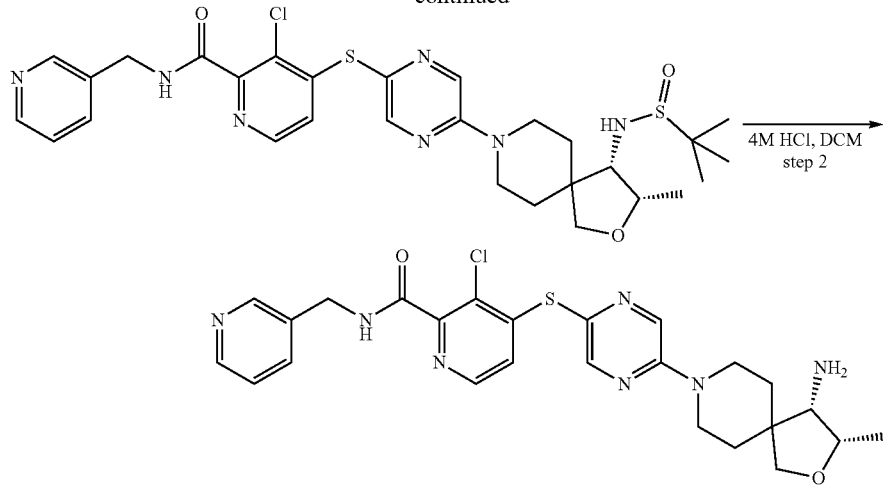

Step 1: 4-054(3S,4S)-4-((tert-butylsulfinyl)amino)-3-methyl-2-oxa-8-azaspiro[4.5]decan-8-yl)pyrazin-2-yl)thio)-3-chloro-N-(pyridin-3-ylmethyl)picolinamide Intermediate I-19 (0.45 mmol), Intermediate I-3 (162 mg, 0.38 mmol), Pd$_2$(dba)$_3$ (34 mg, 0.038 mmol) and XantPhos (22 mg, 0.038 mmol) were dissolved in 1,4-dioxane (2.3 mL, 0.2M), and then DIPEA (130 μL, 0.75 mmol) was added thereto. The reaction mixture was purged with nitrogen and stirred at 110° C. for 5 hours. The reaction was terminated with H$_2$O, and the mixture was extracted with EA. The EA layer was dried over MgSO$_4$, filtered and then concentrated. The resulting product was separated by MPLC (EA:Hx=1:1) and concentrated to obtain 4-((5-((3S,4S)-4-((tert-butylsulfinyl)amino)-3-methyl-2-oxa-8-azaspiro[4.5]decan-8-yl)pyrazin-2-yl)thio)-3-chloro-N-(pyridin-3-ylmethyl)picolinamide (27 mg, 10%). MS m/z: 630 [M+H]$^+$.

Step 2: 4-((5((3S,4S)-4-amino-3-methyl-2-oxa-8-azaspiro[4.5]decan-8-yl)pyrazin-2-yl)thio)-3-chloro-N-(pyridin-3-ylmethyl)picolinamide 4-((5-((3 S,4 S)-4-((tert-butyl sulfinyl)amino)-3-methyl-2-oxa-8-azaspiro[4.5]decan-8-yl)pyrazin-2-yl)thio)-3-chloro-N-(pyridin-3-ylmethyl)picolinamide (27 mg, 0.043 mmol) was dissolved in MC (0.43 ml, 0.1 M). The reaction mixture was added dropwise with 4M HCl in dioxane (54 μL, 0.22 mmol) and stirred at 40° C. for 10 minutes. The reaction mixture was concentrated and was added with MC to precipitate a solid, and then the precipitated solid was filtered to obtain the compound of Example 87 (25 mg, 100%) in the form of a hydrochloride salt. $^1$H NMR (400 MHz, DMSO) δ 9.46-9.43 (m, 1H), 8.84 (s, 1H), 8.81 (d, J=5.6 Hz, 1H), 8.57 (s, 1H), 8.42-8.39 (m, 1H), 8.38 (d, J=1.1 Hz, 1H), 8.29 (d, J=5.3 Hz, 1H), 8.14 (br s, 2H), 7.98 (br s, 1H), 6.85 (d, J=5.3 Hz, 1H), 4.65 (d, J=5.5 Hz, 2H), 4.33-4.29 (m, 1H), 4.25-4.21 (m, 2H), 3.93 (d, J=9.2 Hz, 2H), 3.20-3.17 (m, 3H), 1.82-1.71 (m, 3H), 1.63-1.60 (m, 1H), 1.24 (d, J=6.5 Hz, 3H); MS m/z: 526 [M+H]$^+$.

Example 88: 6-((5-((3S,4S)-4-amino-3-methyl-2-oxa-8-azaspiro[4.5]decan-8-yl)pyrazin-2-yl)thio)-5-chloro-3-(pyridin-2-ylmethyl)quinazolin-4(3H)-one

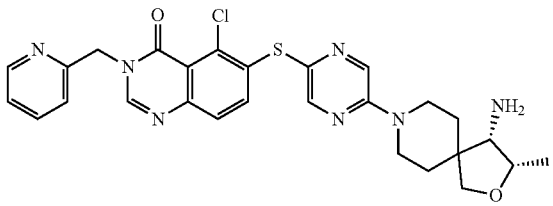 [SMILES: C[C@@H]1OCC2(CCN(c3cnc(Sc4ccc5ncn(Cc6ccccn6)c(=O)c5c4Cl)cn3)CC2)[C@@H]1N]

The compound of Example 88 (5 mg, 30%) was synthesized in the same method as in Example 18, except that 2-(chloromethyl)pyridine was used instead of benzyl chloride in step 2 of Example 18. $^1$H NMR(400 MHz, MeOD) δ 8.58 (s, 1H), 8.46 (s, 1H), 8.33 (s, 1H), 8.29 (s, 1H), 8.05 (t, J=7.9 Hz, 1H), 7.67 (d, J=8.1 Hz, 1H), 7.56-7.47 (m, 2H), 7.29 (d, J=8.7 Hz, 1H), 5.36 (s, 2H), 4.37 (d, J=14.0 Hz, 1H), 4.28 (d, J=14.5 Hz, 2H), 4.00 (d, J=9.0 Hz, 1H), 3.89 (d, J=8.9 Hz, 1H), 3.44 (s, 1H), 3.21 (dd, J=15.9, 10.9 Hz, 3H), 1.93 (s, 1H), 1.91-1.78 (m, 3H), 1.72 (d, J=12.9 Hz, 1H), 1.32 (d, J=6.7 Hz, 3H); MS(O) m/z: 550.1 [M+H]$^+$.

Example 89: 6-((5-((3S,4S)-4-amino-3-methyl-2-oxa-8-azaspiro[4.5]decan-8-yl)pyrazin-2-yl)thio)-5-chloro-3-(2-(pyrrolidin-1-yl]ethylquinazolin-4(3H)-one

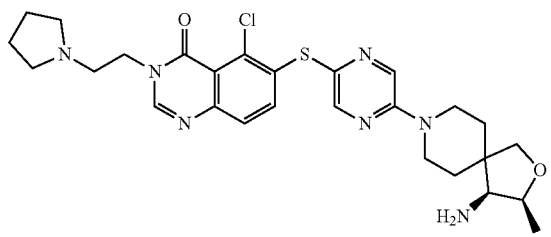 [SMILES: C[C@@H]1OCC2(CCN(c3cnc(Sc4ccc5ncn(CCN6CCCC6)c(=O)c5c4Cl)cn3)CC2)[C@@H]1N]

The compound of Example 89 (6.1 mg, 35%) was synthesized in the same method as in Example 18, except that 1-(2-chloroethyl)pyrrolidine hydrochloride was used instead of benzyl chloride in step 2 of Example 18. $^1$H NMR (400 MHz, MeOD) δ 8.37-8.27 (m, 3H), 7.49 (d, J=8.8 Hz, 1H), 7.28 (d, J=8.8 Hz, 1H), 4.44-4.30 (m, 4H), 4.33-4.25 (m, 2H), 4.00 (d, J=9.2 Hz, 1H), 3.89 (d, J=9.3 Hz, 1H), 3.83 (s, 3H), 3.65 (t, J=6.2 Hz, 2H), 3.45 (d, J=4.1 Hz, 1H), 3.22 (s, 6H), 2.19 (s, 3H), 2.05 (s, 3H), 1.96-1.79 (m, 4H), 1.73 (d, J=13.3 Hz, 1H), 1.32 (d, J=6.5 Hz, 3H); MS (EI) m/z: 556.3 [M+H]$^+$.

Example 90: 6-((5-((3S,4S)-4-amino-3-methyl-2-oxa-8-azaspiro[4.5]decan-8-yl)pyrazin-2-yl)thio)-5-chloro-3-(2-oxo-2-(pyridin-3-yl)ethyl)quinazolin-4(3H)-one

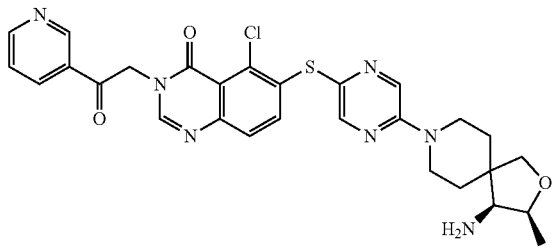 [SMILES: C[C@@H]1OCC2(CCN(c3cnc(Sc4ccc5ncn(CC(=O)c6cccnc6)c(=O)c5c4Cl)cn3)CC2)[C@@H]1N]

The compound of Example 90 (27 mg, 13%) was synthesized in the same method as in Example 18, except that 2-bromo-1-(pyridin-3-yl)ethan-1-one was used instead of benzyl chloride in step 2 of Example 18. $^1$H NMR (400 MHz, MeOD) δ 9.15 (s, 1H), 8.54 (d, J=7.9 Hz, 1H), 8.4(s, 1H), 8.32 (d, J=13.8 Hz, 2H), 8.25 (s, 1H), 7.74 (s, 1H), 7.53 (d, J=8.8 Hz, 1H), 7.34 (d, J=8.8 Hz, 1H), 5.59 (s, 2H), 4.38 (d, J=14.0 Hz, 1H), 4.34-4.25 (m, 3H), 4.00 (d, J=9.2 Hz, 1H), 3.96-3.86 (m, 1H), 3.44 (d, J=4.2 Hz, 1H), 3.28-3.14 (m, 2H), 1.96-1.78 (m, 4H), 1.72 (d, J=13.1 Hz, 1H), 1.30 (d, J=6.5 Hz, 3H); MS (EI) m/z: 578.9 [M+H]$^+$.

Example 91: 6-((5-((3S,4S)-4-amino-3-methyl-2-oxa-8-azaspiro[4.5]decan-8-yl)pyrazin-2-yl)thio)-5-chloro-3-cyclohexylquinazolin-4(3H)-one

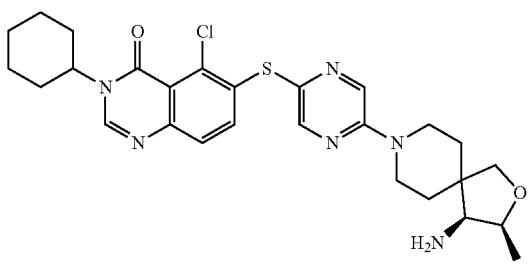 [SMILES: C[C@@H]1OCC2(CCN(c3cnc(Sc4ccc5ncn(C6CCCCC6)c(=O)c5c4Cl)cn3)CC2)[C@@H]1N]

The compound of Example 91 (7 mg, 18%) was synthesized in the same method as in Example 18, except that bromocyclohexane was used instead of benzyl chloride in step 2 of Example 18. $^1$H NMR (400 MHz, MeOD) δ 8.35-8.26 (m, 3H), 7.46 (d, J=8.8 Hz, 1H), 7.28 (d, J=8.8 Hz, 1H), 4.30 (s, 2H), 4.00 (d, J=9.3 Hz, 1H), 3.89 (d, J=9.3 Hz, 1H), 3.43 (d, J=4.0 Hz, 1H), 2.18 (d, J=7.6 Hz, 1H), 2.01-1.92 (m, 6H), 1.89 (s, 1H), 1.80 (s, 9H), 1.53 (d, J=12.5 Hz, 2H), 1.35-1.26 (m, 8H), 0.89 (d, J=6.9 Hz, 1H); MS (EI) m/z: 541.1 [M+H]$^+$.

Example 92: 6-((5-((3S,4S)-4-amino-3-methyl-2-oxa-8-azaspiro[4.5]decan-8-yl)pyrazin-2-yl)thio)-5-chloro-3-(2-oxopropyl)quinazolin-4(3H)-one

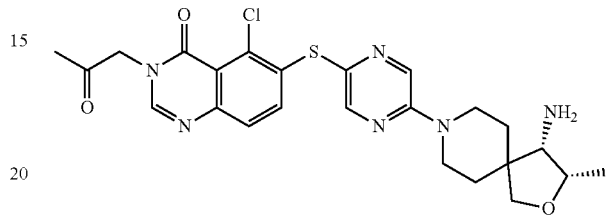

The compound of Example 92 (13 mg, 45%) was synthesized in the same method as in Example 18, except that chloroacetone was used instead of benzyl chloride in step 2 of Example 18. $^1$H NMR (400 MHz, DMSO) δ 8.51 (d, J=1.4 Hz, 1H), 8.33 (d, J=1.3 Hz, 1H), 8.22 (s, 1H), 7.93 (s, 3H), 7.55 (d, J=8.8 Hz, 1H), 7.27 (d, J=8.8 Hz, 1H), 4.91 (s, 2H), 4.31-4.16 (m, 2H), 3.90 (d, J=9.0 Hz, 1H), 3.71 (d, J=9.0 Hz, 1H), 3.20 (d, J=10.1 Hz, 1H), 3.14 (d, J=11.5 Hz, 1H), 2.26 (s, 3H), 1.74 (s, 3H), 1.59 (d, J=13.3 Hz, 1H), 1.22 (d, J=6.5 Hz, 3H); MS (EI) m/z: 515.3 [M+H]$^+$.

Example 93: 6-((5-((3S,4S)-4-amino-3-methyl-2-oxa-8-azaspiro[4.5]decan-8-yl)pyrazin-2-yl)thio)-5-chloro-3-(2-methoxy-5-methylbenzyl)quinazolin-4(3H)-one

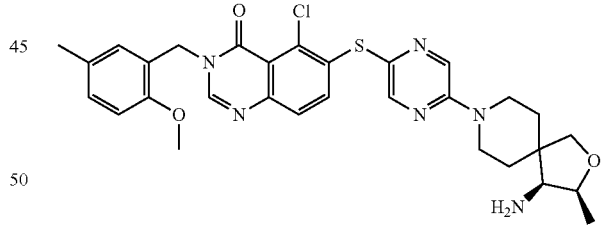

The compound of Example 93 (8.5 mg, 30%) was synthesized in the same method as in Example 18, except that 2-(chloromethyl)-1-methoxy-4-methylbenzene was used instead of benzyl chloride in step 2 of Example 18. $^1$H NMR(400 MHz, MeOD) δ 8.37 (s, 1H), 8.29 (dd, J=16.5, 1.4 Hz, 2H), 7.44 (d, J=8.8 Hz, 1H), 7.26 (d, J=8.7 Hz, 1H), 7.21 (d, J=2.2 Hz, 1H), 7.15-7.08 (m, 1H), 6.88 (d, J=8.4 Hz, 1H), 5.10 (s, 2H), 4.40-4.23 (m, 1H), 4.00 (d, J=9.2 Hz, 1H), 3.98 (s, 3H), 3.88 (d, J=9.3 Hz, 1H), 3.82 (s, 3H), 3.43 (d, J=4.1 Hz, 1H), 3.35 (s, 6H), 3.29-3.12 (m, 1H), 2.27 (s, 3H), 1.90-1.77 (m, 4H), 1.72 (d, J=13.0 Hz, 1H), 1.32 (d, J=6.5 Hz, 3H); MS (EI) m/z: 593.4 [M+H]$^+$.

Example 94: 6-((5-((3S,4S)-4-amino-3-methyl-2-oxa-8-azaspiro[4.5]decan-8-yl)pyrazin-2-yl)thio)-5-chloro-3-(3-methoxypropyl)quinazolin-4(3H)-one

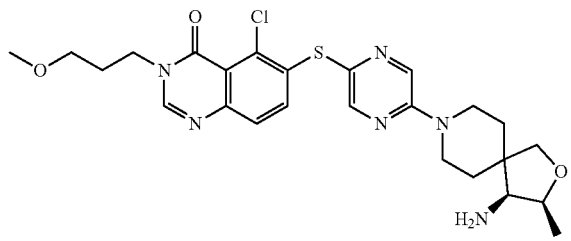 [SMILES: COCCCn1cnc2ccc(Sc3cnc(N4CCC5(CC4)CO[C@@H](C)[C@H]5N)cn3)c(Cl)c2c1=O]

The compound of Example 94 (10 mg, 31%) was synthesized in the same method as in Example 18, except that 1-chloro-3-methoxypropane was used instead of benzyl chloride in step 2 of Example 18. $^1$H NMR (400 MHz, DMSO) δ 8.51 (d, J=1.5 Hz, 1H), 8.36-8.30 (m, 2H), 7.96 (s, 3H), 7.52 (d, J=8.8 Hz, 1H), 7.23 (d, J=8.8 Hz, 1H), 4.48 (s, 32H), 4.31-4.16 (m, 2H), 3.99 (t, J=7.0 Hz, 2H), 3.90 (d, J=9.1 Hz, 1H), 3.71 (d, J=9.1 Hz, 1H), 3.42 (t, J=5.3 Hz, 1H), 3.38 (t, J=6.0 Hz, 2H), 3.21-3.10 (m, 2H), 1.92 (p, J=6.4 Hz, 2H), 1.74 (s, 2H), 1.59 (d, J=13.2 Hz, 1H), 1.22 (d, J=6.5 Hz, 3H); MS(O) m/z: 531.7 [M+H]$^+$.

Example 95: 6-((5-((3S,4S)-4-amino-3-methyl-2-oxa-8-azaspiro[4.5]decan-8-yl)pyrazin-2-yl)thio)-5-chloro-3-(2-oxo-(2-piperidin-1-yl]ethyl)quinazolin-4(3H)-one

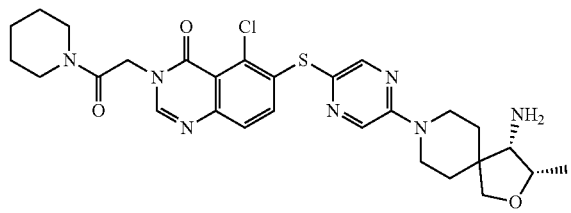 [SMILES: C[C@@H]1OCC2(CCN(c3cnc(Sc4ccc5ncn(CC(=O)N6CCCCC6)c(=O)c5c4Cl)cn3)CC2)[C@@H]1N]

The compound of Example 95 (15 mg, 50%) was synthesized in the same method as in Example 18, except that 2-chloro-1-(piperidin-1-yl)ethan-1-one was used instead of benzyl chloride in step 2 of Example 18. $^1$H NMR (400 MHz, DMSO) δ 8.52 (d, J=1.5 Hz, 1H), 8.34 (d, J=1.3 Hz, 1H), 8.27 (s, 1H), 7.93 (s, 3H), 7.55 (d, J=8.8 Hz, 1H), 7.28 (d, J=8.8 Hz, 1H), 4.88 (s, 2H), 4.31-4.16 (m, 3H), 3.70 (s, 6H), 3.64 (s, 54H), 3.54-3.39 (m, 7H), 3.25-3.10 (m, 2H), 1.74 (s, 3H), 1.61 (d, J=8.2 Hz, 6H), 1.47 (s, 2H), 1.22 (d, J=6.5 Hz, 3H); MS(O) m/z: 584.4 [M+H]$^+$.

Example 96: 6-((5-((3S,4S)-4-amino-3-methyl-2-oxa-8-azaspiro[4.5]decan-8-yl)pyrazin-2-yl)thio)-5-chloro-3-(2-(trifluoromethoxy)ethyl)quinazolin-4(3H)-one

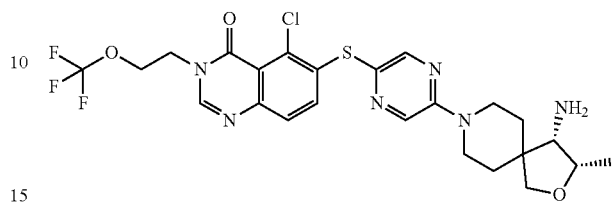

The compound of Example 96 (4.5 mg, 20%) was synthesized in the same method as in Example 18, except that 1-bromo-2-(trifluoromethoxy)ethane was used instead of benzyl chloride in step 2 of Example 18. $^1$H NMR(400 MHz, DMSO) δ 8.52 (d, J=1.4 Hz, 1H), 8.38-8.31 (m, 2H), 7.91 (s, 3H), 7.54 (d, J=8.7 Hz, 1H), 7.25 (d, J=8.7 Hz, 1H), 4.41 (t, J=5.2 Hz, 2H), 4.30 (t, J=5.1 Hz, 2H), 4.27-4.16 (m, 2H), 3.90 (d, J=9.1 Hz, 1H), 3.71 (d, J=9.1 Hz, 1H), 3.43 (d, J=5.4 Hz, 1H), 3.19 (s, 1H), 3.19-3.11 (m, 1H), 1.74 (s, 3H), 1.59 (d, J=13.3 Hz, 1H), 1.22 (d, J=6.5 Hz, 3H); MS(O) m/z: 571.2 [M+H]$^+$.

Example 97: 2-(6-((5-((3S,4S)-4-amino-3-methyl-2-oxa-8-azaspiro[4.5]decan-8-yl)pyrazin-2-yl)thio)-5-chloro-4-oxoquinazolin-3(4H)-yl)acetamide

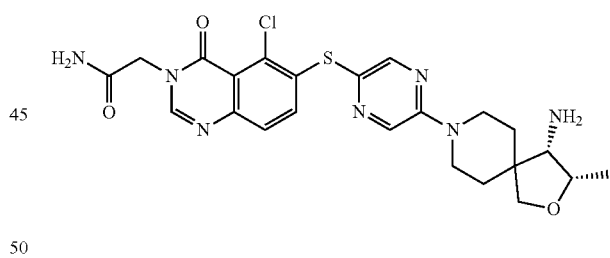

The compound of Example 97 (4.8 mg, 30%) was synthesized in the same method as in Example 18, except that 2-chloroacetamide was used instead of benzyl chloride in step 2 of Example 18. $^1$H NMR (400 MHz, DMSO) δ 8.51 (d, J=1.4 Hz, 1H), 8.36-8.27 (m, 2H), 7.96 (s, 3H), 7.78 (d, J=1.9 Hz, 1H), 7.54 (d, J=8.7 Hz, 1H), 7.32 (s, 1H), 7.26 (d, J=8.8 Hz, 1H), 5.94 (s, 8H), 4.57 (s, 2H), 4.31-4.16 (m, 3H), 3.90 (d, J=9.1 Hz, 1H), 3.71 (d, J=9.1 Hz, 1H), 3.17 (q, J=10.8 Hz, 2H), 1.76 (dd, J=6.3, 3.2 Hz, 1H), 1.74 (s, 2H), 1.59 (d, J=13.3 Hz, 1H), 1.22 (d, J=6.5 Hz, 3H); MS(O) m/z: 516.1 [M+H]$^+$.

Example 98: 3-(6-((5-((3S,4S)-4-amino-3-methyl-2-oxa-8-azaspiro[4.5]decan-8-yl)pyrazin-2-yl)thio)-5-chloro-4-oxoquinazolin-3(4H)-yl)propanamide

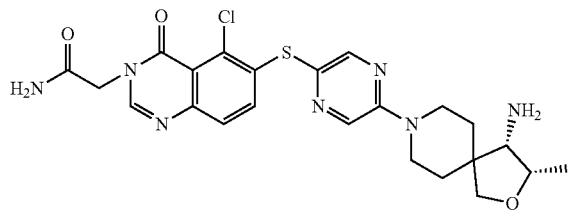 [SMILES: C[C@@H]1OCC2(CCN(c3cnc(Sc4ccc5ncn(CC(N)=O)c(=O)c5c4Cl)cn3)CC2)[C@@H]1N]

The compound of Example 98 (18 mg, 50%) was synthesized in the same method as in Example 18, except that 3-chloropropanamide was used instead of benzyl chloride in step 2 of Example 18. $^1$H NMR (400 MHz, DMSO) δ 8.51 (d, J=1.4 Hz, 1H), 8.35-8.28 (m, 2H), 7.93 (s, 3H), 7.51 (d, J=8.7 Hz, 1H), 7.45-7.40 (m, 1H), 7.22 (d, J=8.8 Hz, 1H), 6.94 (s, 1H), 4.31-4.16 (m, 2H), 4.11 (t, J=6.5 Hz, 2H), 3.90 (d, J=9.0 Hz, 1H), 3.71 (d, J=9.1 Hz, 1H), 3.46-3.39 (m, 1H), 3.14 (d, J=11.8 Hz, 1H), 2.57 (t, J=6.5 Hz, 2H), 1.74 (s, 3H), 1.59 (d, J=13.2 Hz, 1H), 1.22 (d, J=6.5 Hz, 3H); MS(O) m/z: 530.4 [M+H]$^+$.

Example 99: (S)-6-((5-(1-amino-1,3-dihydrospiro(indene-2,4'-piperidin]-1'-yl)pyrazin-2-yl)thio)-3-benzyl-5-chloroquinazolin-4(3H)-one

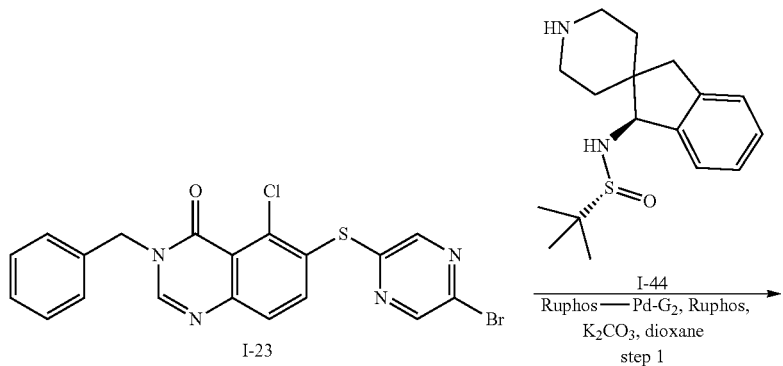

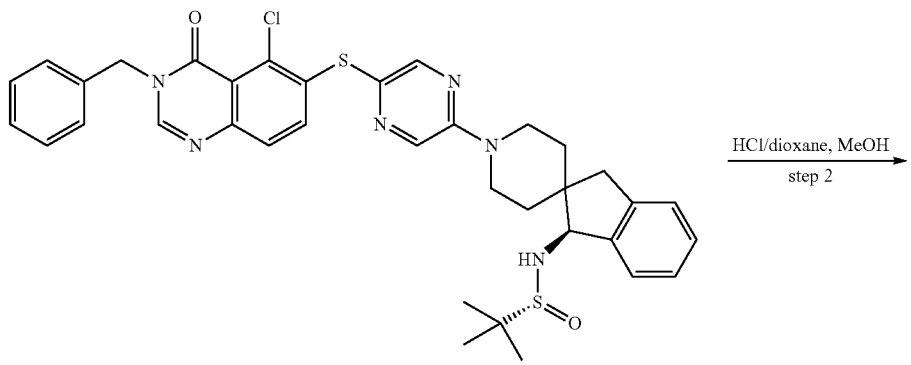

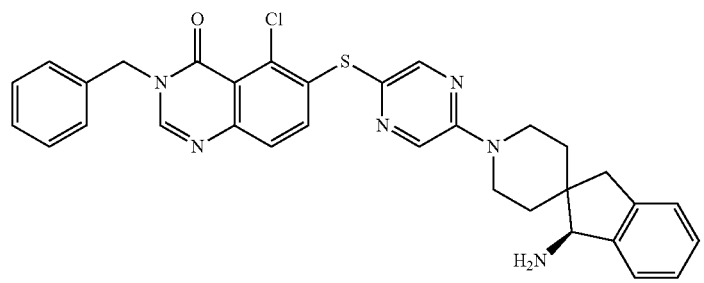

Step 1: (R)-N-((S)-1'-(5-((3-benzyl-5-chloro-4-oxo-3,4-dihydroquinazolin-6-yl)thio)pyrazin-2-yl)-1,3-dihydrospiro[indene-2,4'-piperidin]-1-yl)-2-methylpropane-2-sulfinamide A mixture of Intermediate I-23 (100 mg, 217 μmol), Intermediate I-44 (70.0 mg, 228 μmol), RuPhos (20.3 mg, 43.5 μmol), RuPhos-Pd-G2 (33.7 mg, 43.5 μmol) and K₂CO₃ (90.1 mg, 652.5 μmol) in dioxane (2.00 mL) was stirred under N₂ at 100° C. for 16 hours. The reaction mixture was filtered, and the filtrate was concentrated under vacuum to obtain a residue. The residue was purified by reverse phase flash column chromatography (0.1% FA) to obtain (R)-N-((S)-1'-(5-((3-benzyl-5-chloro-4-oxo-3,4-dihydroquinazolin-6-yl)thio)pyrazin-2-yl)-1,3-dihydrospiro[indene-2,4'-piperidin]-1-yl)-2-methylpropane-2-sulfinamide (70.0 mg, 46% yield) as a yellow solid. MS (E SI) m/z: 685.2 [M+H]⁺.

Step 2: (S)-6-((5-(1-amino-1,3-dihydrospiro[indene-2,4'-piperidin]-1'-yl)pyrazin-2-yl)thio)-3-benzyl-5-chloroquinazolin-4(3H)-one To a mixture of (R)-N-((S)-1'-(5-((3-benzyl-5-chloro-4-oxo-3,4-dihydroquinazolin-6-yl)thio)pyrazin-2-yl)-1,3-dihydrospiro[indene-2,4'-piperidin]-1-yl)-2-methylpropane-2-sulfinamide (70.0 mg, 102 μmol) in MeOH (3 mL) was added HCl/dioxane (0.3 mL), followed by stirring at 25° C. for 1 hour. The reaction mixture was concentrated under vacuum to obtain a residue. The residue was purified by Prep-HPLC (Column: Phenomenex Luna C18 150*25 mm*10 um; mobile phase: [water (FA)-ACN]; B %: 21%-51%, 10 minutes) to obtain the compound of Example 99 (12 mg, 20% yield) as a yellow solid. ¹H NMR (400 MHz, CDCl₃) δ =8.27 (d, J=1.2 Hz, 1H), 8.23 (d, J=1.2 Hz, 1H), 8.05 (s, 1H), 7.46 (d, J=8.8 Hz, 1H), 7.40-7.29 (m, 6H), 7.28 (s, 1H), 7.26-7.23 (m, 3H), 5.16 (s, 2H), 4.25 (d, J=13.6 Hz, 2H), 4.05 (s, 1H), 3.33-3.22 (m, 2H), 3.13 (d, J=15.6 Hz, 1H), 2.80 (d, J=15.6 Hz, 1H), 1.90-1.83 (m, 2H), 1.70-1.63 (m, 1H), 1.50-1.45 (m, 1H); MS (EI) m/z: 581.1 [M+H]⁺.

Example 100: 6-151(1R)-1-aminospiro[indene-2,4'-piperidin]-1'-yl]pyrazin-2-yl]sulfanyl-3-benzyl-5-chloro-quinazolin-4-one

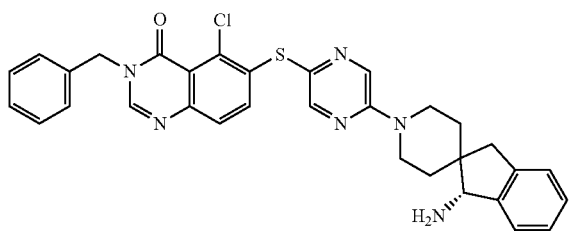 [SMILES: N[C@H]1c2ccccc2CC12CCN(c1cnc(Sc3ccc4ncn(Cc5ccccc5)c(=O)c4c3Cl)cn1)CC2]

The compound of Example 100 (6 mg, 35%) was synthesized in the same method as in Example 99, except that Intermediate I-24 was used instead of Intermediate I-44 in step 1 of Example 99. ¹H NMR (400 MHz, CDCl₃) δ=8.28 (d, J=0.8 Hz, 1H), 8.22 (s, 1H), 8.07 (s, 1H), 7.46 (d, J=8.8 Hz, 1H), 7.42-7.30 (m, 6H), 7.29 (s, 1H), 7.26-7.24 (m, 3H), 5.17 (s, 2H), 4.29-4.16 (m, 2H), 4.07 (s, 1H), 3.33-3.23 (m, 2H), 3.14 (d, J=15.6 Hz, 1H), 2.82 (d, J=15.6 Hz, 1H), 1.87-1.79 (m, 2H), 1.70-1.65 (m, 1H), 1.52-1.50 (m, 1H); MS (E SI) m/z: 581.1 [M+H]⁺.

Example 101: (R)-6-((5-(5-amino-5,7-dihydrospiro[cyclopenta[b]pyridine-6,4'-piperidin]-1'-yl)pyrazin-2-yl)thio)-3-benzyl-5-chloroquinazolin-4(3H)-one

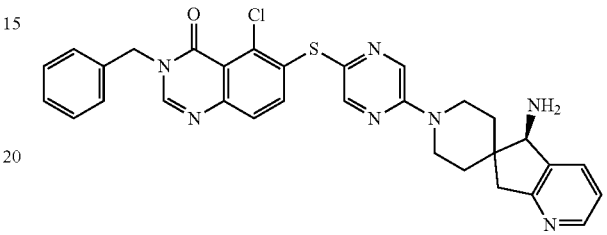

The compound of Example 101 (11 mg, 43%) was synthesized in the same method as in Example 99, except that Intermediate I-26 was used instead of Intermediate I-44 in step 1 of Example 99. ¹H NMR (400 MHz, CDCl₃) δ=8.30 (d, J=4.4 Hz, 1H), 8.26 (s, 1H), 8.22 (s, 1H), 8.05 (s, 1H), 7.70 (d, J=8.8 Hz, 1H), 7.44 (d, J=8.8 Hz, 1H), 7.40-7.33 (m, 5H), 7.32-7.27 (m, 1H), 7.22-7.14 (m, 1H), 5.16 (s, 2H), 4.36-4.26 (m, 2H), 4.06 (s, 1H), 3.33-3.18 (m, 3H), 2.96-2.86 (m, 1H), 1.97-1.87 (m, 1H), 1.84-1.76 (m, 1H), 1.74-1.64 (m, 1H), 1.45-1.41 (m, 1H); MS (EI) m/z: 582.1 [M+H]⁺.

Example 102: (S)-6-((5-(5-amino-5,7-dihydrospiro[yclopenta[b]pyridine-6,4'-piperidin]-1'-yl)pyrazin-2-yl)thio)-3-benzyl-5-chloroquinazolin-4(3H)-one

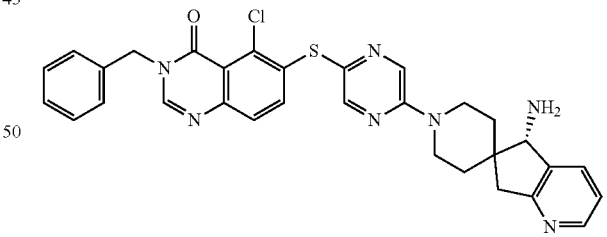

The compound of Example 102 (11 mg, 42%) was synthesized in the same method as in Example 99, except that Intermediate I-25 was used instead of Intermediate I-44 in step 1 of Example 99. ¹H NMR (400 MHz, CDCl₃) δ=8.44 (d, J=2.8 Hz, 1H), 8.26 (s, 1H), 8.22 (s, 1H), 8.05 (s, 1H), 7.71 (d, J=8.8 Hz, 1H), 7.43 (d, J=8.8 Hz, 1H), 7.40-7.33 (m, 5H), 7.32-7.25 (m, 1H), 7.17-7.15 (m, 1H), 5.16 (s, 2H), 4.35-4.26 (m, 2H), 4.10 (s, 1H), 3.33-3.20 (m, 3H), 2.96-2.90 (m, 1H), 1.98-1.83 (m, 2H), 1.70-1.68 (m, 1H), 1.52-1.48 (m, 1H); MS (EI) m/z: 582.1 [M+H]⁺.

Example 103: 6-((5-((S)-1-amino-1,3-dihydrospiro [indene-2,4'-piperidin]-1'-yl]pyrazin-2-yl]thio)-5-chloro-3-((tetrahydrofuran-3-yl)methyl)quinazolin-4(3H)-one

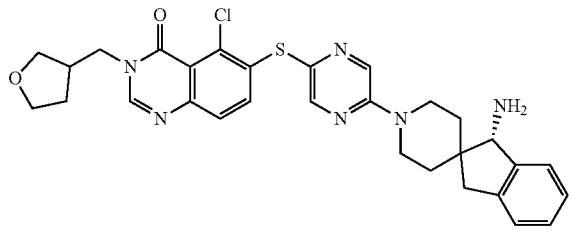 [SMILES: N[C@@H]1c2ccccc2CC12CCN(c1cnc(Sc3ccc4ncn(CC5CCOC5)c(=O)c4c3Cl)cn1)CC2]

The compound of Example 103 (20 mg, 52%) was synthesized in the same method as in Example 99, except that Intermediate I-27 was used instead of Intermediate I-23 in step 1 of Example 99. $^1$H NMR (400 MHz, CDCl$_3$) δ=8.30 (d, J=1.2 Hz, 1H), 8.25 (d, J=1.2 Hz, 1H), 7.98 (s, 1H), 7.47 (d, J=8.8 Hz, 1H), 7.39-7.34 (m, 1H), 7.29 (s, 1H), 7.27-7.23 (m, 3H), 4.29-4.21 (m, 2H), 4.04 (s, 1H), 4.02-3.95 (m, 2H), 3.93-3.86 (m, 1H), 3.82-3.76 (m, 2H), 3.63 (dd, J=4.8, 9.2 Hz, 1H), 3.33-3.23 (m, 2H), 3.13 (d, J=15.6 Hz, 1H), 2.95-2.87 (m, 1H), 2.80 (d, J=15.6 Hz, 1H), 2.11-2.08 (m, 1H), 1.89-1.80 (m, 2H), 1.73-1.64 (m, 2H), 1.47 (d, J=13.2 Hz, 1H); m/z ES+: 575.2 [M+H]$^+$.

Example 104: 6-((5-((R)-1-amino-1,3-dihydrospiro (indene-2,4'-piperidin]-1'-yl]pyrazin-2-yl]thio)-5-chloro-3-((tetrahydrofuran-3-yl)methyl)quinazolin-4(3H)-one

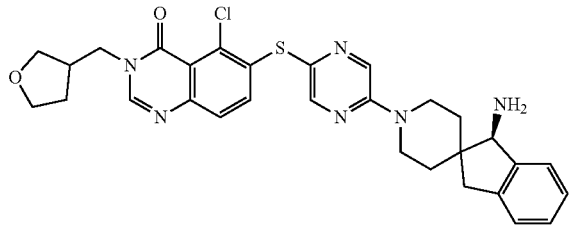 [SMILES: N[C@H]1c2ccccc2CC12CCN(c1cnc(Sc3ccc4ncn(CC5CCOC5)c(=O)c4c3Cl)cn1)CC2]

The compound of Example 104 (15 mg, 30%) was synthesized in the same method as in Example 99, using Intermediate I-24 and Intermediate I-27 as starting materials in step 1 of Example 99. $^1$H NMR (400 MHz, MeOD-d$_4$) δ=8.30 (s, 1H), 8.23 (s, 1H), 7.97 (s, 1H), 7.59-7.52 (m, 1H), 7.47 (d, J=8.8 Hz, 1H), 7.38-7.27 (m, 4H), 4.20 (s, 1H), 4.18-4.07 (m, 2H), 4.04-3.94 (m, 2H), 3.93-3.85 (m, 1H), 3.83-3.74 (m, 2H), 3.67-3.59 (m, 1H), 3.38-3.28 (m, 1H), 3.27-3.15 (m, 2H), 2.97-2.85 (m, 2H), 2.14-2.04 (m, 1H), 1.91-1.66 (m, 4H), 1.61-1.58 (m, 1H); MS (EI) m/z: 575.3 [M+H]$^+$.

Example 105: (S)-6-((5-(5-amino-5,7-dihydrospiro [yclopenta[b]pyridine-6,4'-piperidin]-1'-yl)pyrazin-2-yl)thio)-5-chloro-(3-pyridin-3-ylmethyl)quinazolin-4(3H)-one

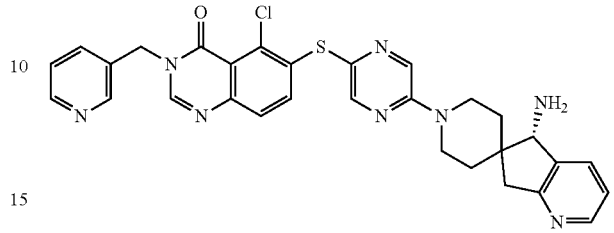

The compound of Example 105 (2.1 mg, 23%) was synthesized in the same method as in Example 99, using Intermediate I-25 and Intermediate I-28 as starting materials in step 1 of Example 99. $^1$H NMR (400 MHz, CDCl$_3$) δ=8.69 (d, J=1.6 Hz, 1H), 8.59 (dd, J=1.2, 4.8 Hz, 1H), 8.47-8.43 (m, 1H), 8.29-8.27 (m, 1H), 8.25-8.22 (m, 1H), 8.11-8.09 (m, 1H), 7.80-7.76 (m, 1H), 7.71-7.66 (m, 1H), 7.49-7.45 (m, 1H), 7.34-7.30 (m, 1H), 7.29 (s, 1H), 7.20-7.15 (m, 1H), 5.18-5.15 (m, 2H), 4.37-4.29 (m, 2H), 4.08 (s, 1H), 3.32-3.20 (m, 3H), 2.96-2.90 (m, 1H), 1.88-1.78 (m, 2H), 1.69 (d, J=13.2 Hz, 1H), 1.49-1.41 (m, 1H); MS (EI) m/z: 583.2 [M+H]$^+$.

Example 106: (R)-6-((5-(5-amino-5,7-dihydrospiro [yclopenta[b]pyridine-6,4'-piperidin]-1'-yl)pyrazin-2-yl)thio)-5-chloro-(3-pyridin-3-ylmethyl)quinazolin-4(3H)-one

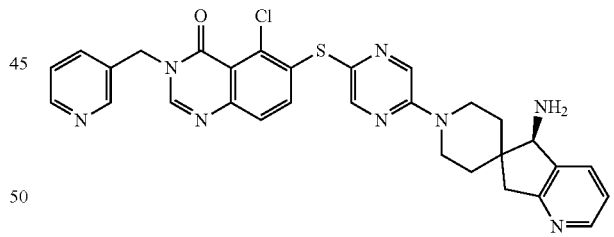

The compound of Example 106 (20 mg, 76%) was synthesized in the same method as in Example 99, using Intermediate I-26 and Intermediate I-28 as starting materials in step 1 of Example 99. $^1$H NMR (400 MHz, CDCl$_3$) δ=8.69 (d, J=2.0 Hz, 1H), 8.60 (dd, J=1.2, 4.8 Hz, 1H), 8.45 (d, J=4.8 Hz, 1H), 8.28 (s, 1H), 8.24 (s, 1H), 8.10 (s, 1H), 7.78 (d, J=7.6 Hz, 1H), 7.70-7.66 (m, 1H), 7.47 (d, J=8.8 Hz, 1H), 7.34-7.29 (m, 2H), 7.17 (dd, J=5.2, 7.6 Hz, 1H), 5.18 (s, 2H), 4.32 (d, J=13.6 Hz, 2H), 4.10 (s, 1H), 3.34-3.22 (m, 3H), 2.96-2.88 (m, 1H), 1.89-1.79 (m, 2H), 1.73-1.66 (m, 1H), 1.46 (d, J=12.4 Hz, 1H); MS (EI) m/z: 583.2 [M+H]$^+$.

Example 107: 6-((5-((S)-5-amino-5,7-dihydrospiro [yclopenta[b]pyridine-6,4'-piperidin]-1'-yl)pyrazin-2-yl]thio)-5-chloro-3-((tetrahydrofuran-3-yl)methyl) quinazolin-4(3H)-one

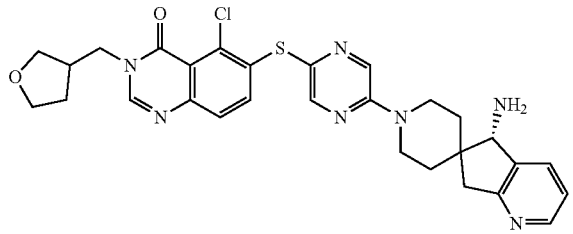 [SMILES: N[C@@H]1c2cccnc2CC12CCN(c1cnc(Sc3ccc4ncn(CC5CCOC5)c(=O)c4c3Cl)cn1)CC2]

The compound of Example 107 (15 mg, 53%) was synthesized in the same method as in Example 99, using Intermediate I-27 and Intermediate I-25 as starting materials in step 1 of Example 99. $^1$H NMR (400 MHz, CDCl$_3$) δ=8.49 (s, 1H), 8.28 (d, J=1.2 Hz, 1H), 8.23 (s, 1H), 7.97 (s, 1H), 7.74 (d, J=7.2 Hz, 1H), 7.49-7.44 (m, 1H), 7.28 (s, 1H), 7.19-7.15 (m, 1H), 4.34-4.25 (m, 2H), 4.15 (s, 1H), 4.04-3.94 (m, 2H), 3.93-3.86 (m, 1H), 3.83-3.75 (m, 2H), 3.68-3.63 (m, 1H), 3.32-3.20 (m, 3H), 2.99-2.88 (m, 2H), 2.14-2.06 (m, 1H), 1.94-1.79 (m, 2H), 1.74-1.66 (m, 2H), 1.53-1.45 (m, 1H); MS (EI) m/z: 576.2 [M+H]$^+$.

Example 108: (S)-6-((5-(5-amino-5,7-dihydrospiro [yclopenta[b]pyridine]-6,4'-piperidin]-1'-yl)pyrazin-2-yl]thio)-5-chloro-3-(2-methoxyethyl)quinazolin-4 (3H)-one

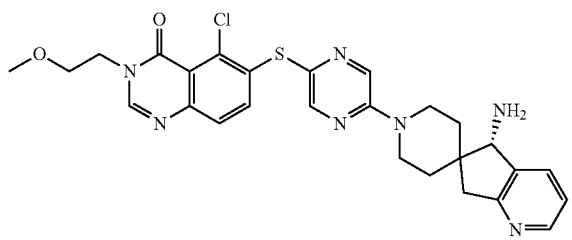 [SMILES: COCCn1cnc2ccc(Sc3cnc(N4CCC5(CC4)Cc4ncccc4[C@H]5N)cn3)c(Cl)c2c1=O]

The compound of Example 108 (135 mg, 49%) was synthesized in the same method as in Example 99, using Intermediate I-25 and Intermediate I-29 as starting materials in step 1 of Example 99. $^1$H NMR (400 MHz, CDCl$_3$) δ=8.46 (d, J=4.4 Hz, 1H), 8.28-8.26 (m, 1H), 8.23 (s, 1H), 8.13 (s, 1H, FA), 8.04 (s, 1H), 7.74 (d, J=7.2 Hz, 1H), 7.47 (d, J=8.8 Hz, 1H), 7.29-7.27 (m, 1H), 7.20 (dd, J=5.2, 7.6 Hz, 1H), 4.36-4.25 (m, 2H), 4.19-4.10 (m, 3H), 3.68 (t, J=4.8 Hz, 2H), 3.33 (s, 3H), 3.30-3.21 (m, 3H), 2.97 (d, J=16.4 Hz, 1H), 1.93-1.78 (m, 2H), 1.70-1.64 (m, 1H), 1.53-1.49 (m, 1H); MS (EI) m/z: 550.2 [M+H]$^+$.

Example 109: (S)-6-((5-(5-amino-5,7-dihydrospiro [yclopenta[b]pyridine]-6,4'-piperidin]-1'-yl)pyrazin-2-yl]thio)-5-chloro-3-(3-hydroxypropyl)quinazolin-4 (3H)-one

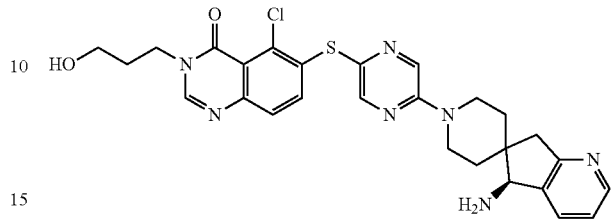

The compound of Example 109 (5.72 mg, 26%) was synthesized in the same method as in Example 99, using Intermediate I-25 and Intermediate I-30 as starting materials in step 1 of Example 99. $^1$H NMR (400 MHz, CDCl$_3$) δ=8.45 (d, J=4.8 Hz, 1H), 8.29 (d, J=1.2 Hz, 1H), 8.24 (s, 1H), 8.04 (s, 1H), 7.66 (d, J=7.2 Hz, 1H), 7.48 (d, J=8.8 Hz, 1H), 7.30 (d, J=8.8 Hz, 1H), 7.20-7.15 (m, 1H), 4.40-4.26 (m, 2H), 4.17 (t, J=6.4 Hz, 2H), 4.07 (s, 1H), 3.71-3.61 (m, 2H), 3.34-3.19 (m, 3H), 2.92 (d, J=16.8 Hz, 1H), 2.08-1.99 (m, 2H), 1.97-1.85 (m, 2H), 1.69-1.65 (m, 1H), 1.45-1.43 (m, 1H); MS (EI) m/z: 550.2 [M+H]$^+$.

Example 110: (S)-6-((5-(5-amino-5,7-dihydrospiro [yclopenta[b]pyridine]-6,4'-piperidin]-1'-yl)pyrazin-2-yl]thio)-5-chloro-3-(3-fluoropropyl)quinazolin-4 (31-1)-one

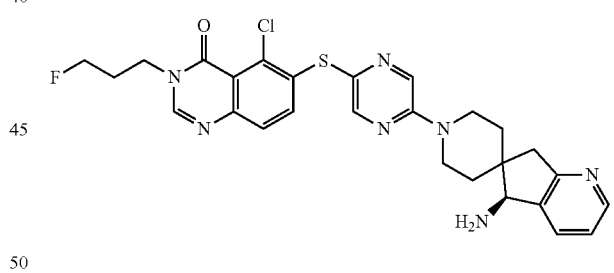

The compound of Example 110 (22 mg, 85%) was synthesized in the same method as in Example 99, using Intermediate I-25 and Intermediate I-31 as starting materials in step 1 of Example 99. $^1$H NMR (400 MHz, DMSO-d$_6$) δ=8.49 (d, J=1.2 Hz, 1H), 8.38 (s, 1H), 8.36-8.34 (m, 1H), 8.31 (d, J=1.2 Hz, 1H), 7.72-7.68 (m, 1H), 7.54-7.50 (m, 1H), 7.23 (d, J=8.8 Hz, 1H), 7.21-7.18 (m, 1H), 4.60 (t, J=5.6 Hz, 1H), 4.48 (t, J=5.6 Hz, 1H), 4.32 (br s, 1H), 4.30-4.28 (m, 1H), 4.06 (t, J=6.8 Hz, 2H), 3.99 (s, 1H), 3.28-3.21 (m, 2H), 3.19-3.11 (m, 1H), 2.85-2.80 (m, 1H), 2.17-2.10 (m, 1H), 2.08-2.02 (m, 1H), 1.85-1.68 (m, 2H), 1.62-1.54 (m, 1H), 1.25-1.19 (m, 1H); MS (EI) m/z: 552.2 [M+H]$^+$.

Example 111: (6-((5-((S)-5-amino-5,7-dihydrospiro[yclopenta[b]pyridine]-6,4'-piperidin]-1'-yl)pyrazin-2-yl]thio)-5-chloro-3-(3-hydroxybutyl)quinazolin-4(3H)-one

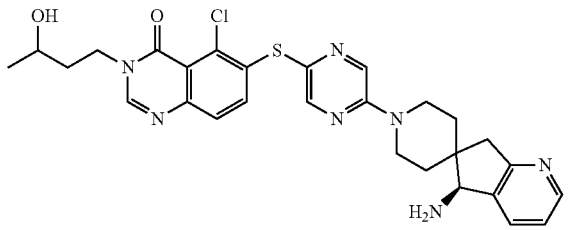 [SMILES: CC(O)CCn1cnc2ccc(Sc3cnc(N4CCC5(CC4)Cc4ncccc4[C@H]5N)cn3)c(Cl)c2c1=O]

The compound of Example 111 (22 mg, 69%) was synthesized in the same method as in Example 99, using Intermediate I-25 and Intermediate I-32 as starting materials in step 1 of Example 99. ¹H NMR (400 MHz, CDCl₃) δ=8.44 (d, J=4.4 Hz, 1H), 8.28 (s, 1H), 8.24 (s, 1H), 8.04 (s, 1H), 7.67 (d, J=7.6 Hz, 1H), 7.47 (d, J=8.8 Hz, 1H), 7.30 (s, 1H), 7.17 (dd, J=4.8, 7.6 Hz, 1H), 4.38-4.23 (m, 3H), 4.09-3.99 (m, 2H), 3.84-3.74 (m, 1H), 3.33-3.20 (m, 3H), 2.92 (d, J=16.4 Hz, 1H), 1.95-1.84 (m, 2H), 1.83-1.75 (m, 2H), 1.72-1.65 (m, 1H), 1.44 (d, J=12.8 Hz, 1H), 1.24 (d, J=6.0 Hz, 3H); MS (EI) m/z: 564.2 [M+H]⁺.

Example 112: (S)-6-((5-(5-amino-5,7-dihydrospiro[cyclopenta[b]pyridine]-6,4'-piperidin]-1'-yl)pyrazin-2-yl]thio)-5-chloro-3-(2-oxopropyl)quinazolin-4(3H)-one Step 1: (R)-N-((S)-1'-(5-((5-chloro-4-oxo-3-(2-oxopropyl)-3,4-dihydroquinazolin-6-yl)thio)pyrazin-2-yl)-5,7-dihydrospiro[cyclopenta[b]pyridine-6,4'-piperidin]-5-yl)-2-methylpropane-2-sulfinamide To a solution of Intermediate I-39 (80.0 mg, 134 μmol) and 1-bromopropan-2-one (36.8 mg, 268 μmol) in DMF (3 mL), K₂CO₃(55.6 mg, 403 μmol) and tetra-n-butylammonium iodide(TBAI) (4.96 mg, 13.4 μmol) were added, and the mixture was stirred at 20° C. for 12 hours. The reaction mixture was quenched by addition of aqueous ammonium chloride (10 mL) at 25° C., diluted with water (20 mL) and extracted with EA (30 mL×3). The combined organic layers were washed with brine (20 mL×3), dried over anhydrous sodium sulfate, and then filtered and concentrated under reduced pressure to obtain a residue. The residue was purified by reverse phase flash column chromatography (0.1% FA) to obtain (R)-N-((S)-1'-(5-((5-chloro-4-oxo-3-(2-oxopropyl)-3,4-dihydroquinazolin-6-yl)thio)pyrazin-2-yl)-5,7-dihydrospiro[cyclopenta[b]pyridine-6,4'-piperidin]-5-yl)-2-methylpropane-2-sulfinamide (60 mg, 69% yield) as a yellow solid. MS (EI) m/z: 652.1 [M+H]⁺.

Step 2: (S)-6-((5-(5-amino-5,7-dihydrospiro[cyclopenta[b]pyridine]-6,4% piperidin]-1'-yl)pyrazin-2-yl]thio)-5-chloro-3-(2-oxopropyl)quinazolin-4(3H)-one To a solution of (R)-N-((S)-1'-(5-((5-chloro-4-oxo-3-(2-oxopropyl)-3,4-dihydroquinazolin-6-yl)thio)pyrazin-2-yl)-5,7-dihydrospiro[cyclopenta[b]pyridine-6,4'-piperidin]-5-yl)-2-methylpropane-2-sulfinamide (50 mg, 76.7 μmol) in MeOH (5 mL) was added HCl/dioxane(4 M), and then the mixture was stirred at 25° C. for 0.5 hours. The reaction

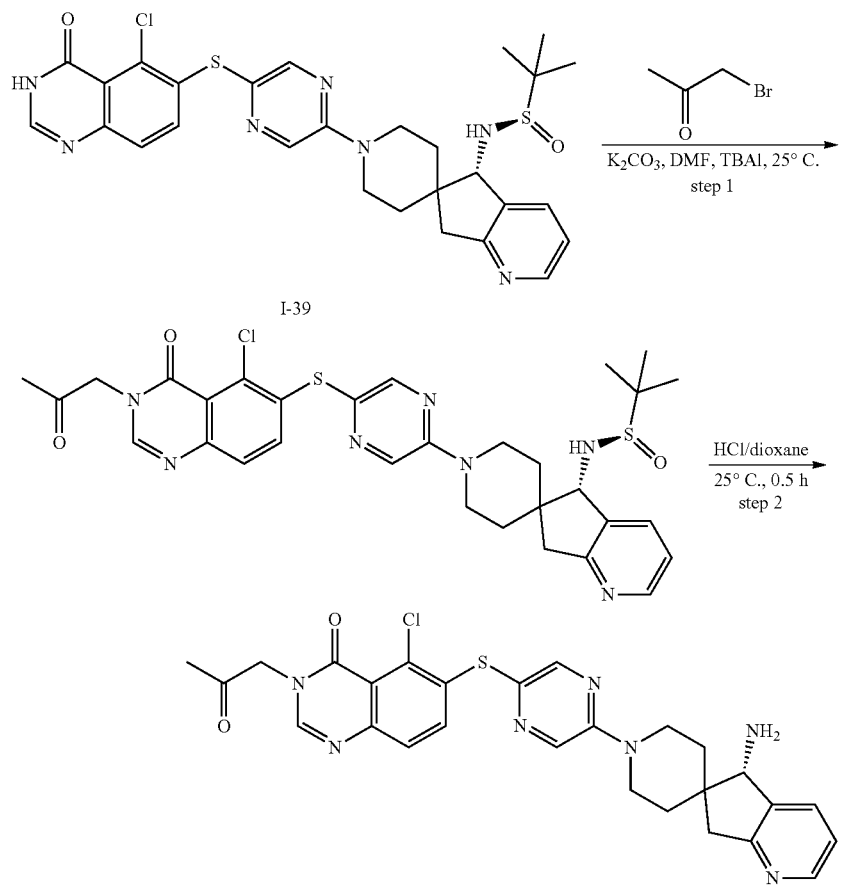

mixture was concentrated under reduced pressure to obtain a residue. The residue was purified by Prep-HPLC (Column: Phenomenex C18 75*30 mm*3 um; mobile phase: [water (FA)-ACN]; B %: 8%-38%, 7 minutes) to obtain the compound of Example 112 (12 mg, 25% yield, FA) as a yellow solid. $^1$H NMR (400 MHz, CDCl$_3$) δ=8.45 (d, J=4.8 Hz, 1H), 8.28 (s, 1H), 8.24 (s, 1H), 8.15 (s, 1H, FA), 7.84 (s, 1H), 7.70 (d, J=7.6 Hz, 1H), 7.49 (d, J=8.8 Hz, 1H), 7.32-7.28 (m, 1H), 7.21-7.16 (m, 1H), 4.75-4.70 (m, 2H), 4.32 (d, J=13.2 Hz, 2H), 4.10 (s, 1H), 3.33-3.20 (m, 3H), 2.97-2.89 (m, 1H), 2.36 (s, 3H), 1.96-1.88 (m, 1H), 1.82-1.78 (m, 1H), 1.71-1.67 (m, 1H), 1.48-1.44 (m, 1H); MS (EI) m/z: 548.1 [M+H]$^+$.

Example 113: 6-((5-(3S,4S)-4-amino-3-methyl-2-oxa-8-azaspiro[4,5]decan-8-yl)pyrazin-2-yl)thio)-5-chloro-3-(3,3,3-trifluoropropyl)quinazolin-4(3H)one

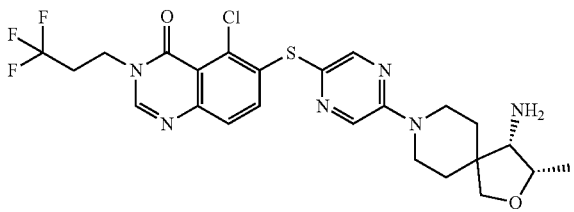 [SMILES: C[C@@H]1OCC2(CCN(c3cnc(Sc4ccc5ncn(CCC(F)(F)F)c(=O)c5c4Cl)cn3)CC2)[C@@H]1N]

The compound of Example 113 (40 mg, 73%) was synthesized in the same method as in Example 18, except that 3-chloro-1,1,1-trifluoro-propane was used instead of benzyl chloride in step 2 of Example 18. $^1$H NMR (400 MHz, CDCl$_3$) δ=8.28 (d, J=1.2 Hz, 1H), 8.22 (d, J=1.2 Hz, 1H), 8.10 (s, 1H, FA), 7.97 (s, 1H), 7.47 (d, J=8.8 Hz, 1H), 7.30 (s, 1H), 4.24-4.17 (m, 3H), 4.05-3.95 (m, 2H), 3.86 (d, J=8.8 Hz, 1H), 3.76-3.72 (m, 1H), 3.50-3.43 (m, 1H), 3.40-3.32 (m, 1H), 3.08 (d, J=4.4 Hz, 1H), 2.76-2.65 (m, 2H), 1.96-1.87 (m, 1H), 1.84-1.73 (m, 3H), 1.27 (d, J=6.4 Hz, 3H); MS (E SI) m/z: 555.1 [M+H]$^+$.

Example 114: 3-(2-6-((5-(3S,4S)-4-amino-3-methyl-2-oxa-8-azaspiro[4,5]decan-8-yl)pyrazin-2-yl)thio)-5-chloro-4-oxoquinazolin-3(4H)-yl)ethyl)oxazolidin-2-one

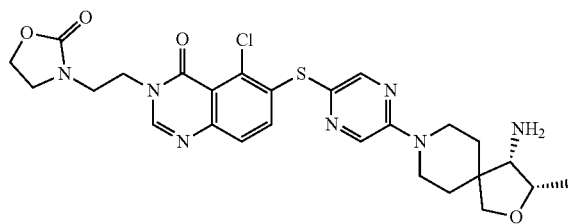 [SMILES: C[C@@H]1OCC2(CCN(c3cnc(Sc4ccc5ncn(CCN6CCOC6=O)c(=O)c5c4Cl)cn3)CC2)[C@@H]1N]

The compound of Example 114 (60 mg, 79%) was synthesized in the same method as in Example 18, except that 3-(2-chloroethyl)oxazolidin-2-one was used instead of benzyl chloride in step 2 of Example 18. $^1$H NMR (400 MHz, DMSO-d$_6$) δ=8.47 (d, J=1.2 Hz, 1H), 8.35 (s, 1H), 8.30 (d, J=1.2 Hz, 1H), 7.49 (d, J=8.8 Hz, 1H), 7.20 (d, J=8.8 Hz, 1H), 4.23 (t, J=8.0 Hz, 2H), 4.12-4.07 (m, 3H), 4.02-3.92 (m, 2H), 3.72 (d, J=8.8 Hz, 1H), 3.66 (t, J=8.0 Hz, 2H), 3.55-3.50 (m, 3H), 3.47-3.41 (m, 1H), 3.39 (d, J=2.8 Hz, 1H), 3.01 (d, J=4.8 Hz, 1H), 1.80-1.71 (m, 1H), 1.70-1.63 (m, 1H), 1.61-1.55 (m, 1H), 1.54-1.47 (m, 1H), 1.10 (d, J=6.4 Hz, 3H); MS(O) m/z: 572.2 [M+H]$^+$.

Example 115: N-(2-(6-((5-(3S,4S)-4-amino-3-methyl-2-oxa-8-azaspiro[4,5]decan-8-yl)pyrazin-2-yl)thio)-5-chloro-4-oxoquinazolin-3(4H)-yl]ethyl) acetamide

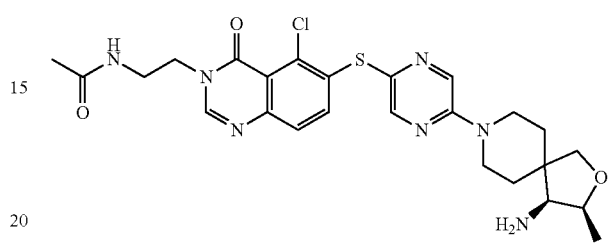

The compound of Example 115 (45 mg, 45%) was synthesized in the same method as in Example 18, except that N-(2-bromoethyl) acetamide was used instead of benzyl chloride in step 2 of Example 18. $^1$H NMR (400 MHz, CDCl$_3$) δ=8.30 (d, J=1.2 Hz, 1H), 8.24 (d, J=1.2 Hz, 1H), 7.95 (s, 1H), 7.47 (d, J=8.8 Hz, 1H), 7.26 (d, J=8.8 Hz, 1H), 5.98 (t, J=5.6 Hz, 1H), 4.27-4.15 (m, 3H), 4.04-3.92 (m, 2H), 3.87-3.83 (m, 1H), 3.73 (d, J=8.8 Hz, 1H), 3.68-3.64 (m, 2H), 3.56-3.48 (m, 1H), 3.44-3.41 (m, 1H), 3.04 (d, J=4.4 Hz, 1H), 2.00 (s, 3H), 1.95-1.90 (m, 1H), 1.83-1.68 (m, 3H), 1.27 (d, J=6.4 Hz, 3H); MS(O) m/z: 544.2 [M+H]$^+$.

Example 116: 6-((5-(3S,4S)-4-amino-3-methyl-2-oxa-8-azaspiro[4,5]decan-8-yl)pyrazin-2-yl)thio)-5-chloro-(3-(2-isopropoxyethyl)quinazolin-4(3H)-one

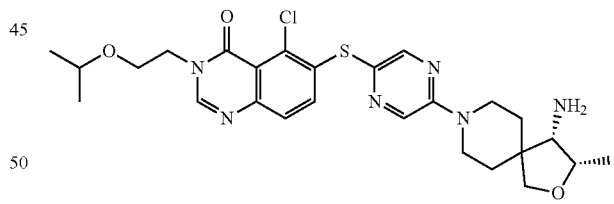

The compound of Example 116 (43 mg, 53%) was synthesized in the same method as in Example 18, except that 2-(2-bromoethoxy)propane was used instead of benzyl chloride in step 2 of Example 18. $^1$H NMR (400 MHz, CDCl$_3$) δ=8.27 (s, 1H), 8.21 (s, 1H), 8.16 (s, 1H, FA), 8.09 (s, 1H), 7.46 (d, J=8.8 Hz, 1H), 7.28 (s, 1H), 4.28-4.19 (m, 1H), 4.14 (t, J=4.8 Hz, 2H), 4.10-3.96 (m, 2H), 3.89 (d, J=8.8 Hz, 1H), 3.75 (d, J=9.2 Hz, 1H), 3.72 (t, J=4.8 Hz, 2H), 3.57-3.47 (m, 1H), 3.40 (t, J=10.8 Hz, 1H), 3.31 (t, J=10.8 Hz, 1H), 3.12 (d, J=3.6 Hz, 1H), 2.00-1.88 (m, 1H), 1.87-1.72 (m, 3H), 1.30 (d, J=6.4 Hz, 3H), 1.08 (d, J=6.0 Hz, 6H); MS (EI) m/z: 545.3 [M+H]$^+$.

Example 117: 6-((5-(3S,4S)-4-amino-3-methyl-2-oxa-8-azaspiro[4,5]decan-8-yl)pyrazin-2-yl)thio)-5-chloro-(3-((3,6-dihydro-2H-pyran-4-yl)methyl)quinazolin-4(3H)-one

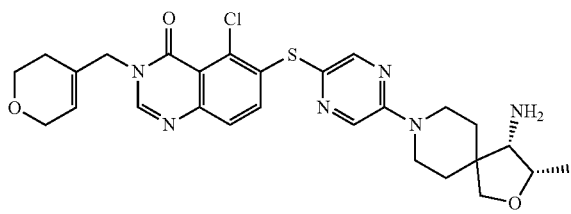 [SMILES: C[C@@H]1OCC2(CCN(c3cnc(Sc4ccc5ncn(CC6=CCOCC6)c(=O)c5c4Cl)cn3)CC2)[C@@H]1N]

The compound of Example 117 (8 mg, 63%) was synthesized in the same method as in Example 18, except that 4-(chloromethyl)-3,6-dihydro-2H-pyran was used instead of benzyl chloride in step 2 of Example 18. $^1$H NMR (400 MHz, CDCl$_3$) δ=8.25 (s, 1H), 8.21 (s, 1H), 8.02 (br s, 1H, FA), 7.95 (s, 1H), 7.46 (d, J=8.8 Hz, 1H), 7.25 (s, 1H), 5.66 (s, 1H), 4.55 (br s, 2H), 4.35-4.29 (m, 2H), 4.26-4.21 (m, 1H), 4.17-4.12 (m, 3H), 3.80 (t, J=5.6 Hz, 3H), 3.49 (d, J=4.4 Hz, 1H), 3.18-3.07 (m, 2H), 2.23-2.15 (m, 1H), 2.11 (s, 2H), 2.07-2.01 (m, 1H), 1.96 (d, J=11.4 Hz, 1H), 1.85-1.79 (m, 1H), 1.54 (d, J=6.4 Hz, 3H); MS (EI) m/z: 555.2 [M+H]$^+$.

Example 118: 5-((6-((5-(3S,4S)-4-amino-3-methyl-2-oxa-8-azaspiro[4,5]decan-8-yl)pyrazin-2-yl)thio)-5-chloro-4-oxoquinazolin-3(4H)-yl)methyl)oxazolidin-2-one

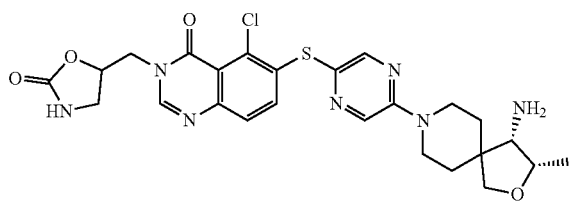 [SMILES: C[C@@H]1OCC2(CCN(c3cnc(Sc4ccc5ncn(CC6CNC(=O)O6)c(=O)c5c4Cl)cn3)CC2)[C@@H]1N]

The compound of Example 118 (25 mg, 59%) was synthesized in the same method as in Example 18, except that 5-(bromomethyl)oxazolidin-2-one was used instead of benzyl chloride in step 2 of Example 18. $^1$H NMR (400 MHz, CDCl$_3$) δ=8.29 (s, 1H), 8.23 (s, 1H), 8.06 (s, 1H), 7.49 (d, J=8.8 Hz, 1H), 7.29 (s, 1H), 5.12-5.00 (m, 2H), 4.49 (dd, J=2.4, 14.0 Hz, 1H), 4.24-4.17 (m, 1H), 4.07-3.89 (m, 3H), 3.86-3.78 (m, 2H), 3.71 (d, J=8.8 Hz, 1H), 3.55-3.48 (m, 1H), 3.46-3.39 (m, 2H), 3.02 (d, J=4.4 Hz, 1H), 1.95-1.88 (m, 1H), 1.83-1.67 (m, 3H), 1.25 (d, J=6.4 Hz, 3H); MS (EI) m/z: 558.2 [M+H]$^+$.

Example 119: 6-((5-(3S,4S)-4-amino-3-methyl-2-oxa-8-azaspiro[4,5]decan-8-yl)pyrazin-2-yl)thio)-5-chloro-3-(furan-3-ylmethyl)quinazolin-4(3H-1)-one

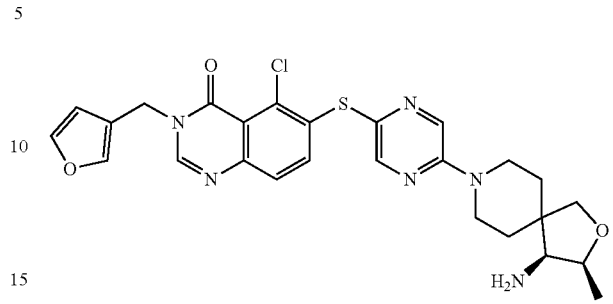

The compound of Example 119 (20 mg, 30%) was synthesized in the same method as in Example 18, except that 3-(bromomethyl)furan was used instead of benzyl chloride in step 2 of Example 18. $^1$H NMR(400 MHz, CDCl$_3$) δ=8.25 (s, 1H), 8.23-8.19 (m, 1H), 8.05-8.02 (m, 1H), 7.57 (s, 1H), 7.46-7.39 (m, 2H), 7.26-7.20 (m, 1H), 6.46-6.43 (m, 1H), 5.02-4.98 (m, 2H), 4.25-4.16 (m, 1H), 4.06-3.95 (m, 2H), 3.91-3.84 (m, 1H), 3.72 (d, J=8.8 Hz, 1H), 3.43-3.32 (m, 1H), 3.31-3.21 (m, 1H), 3.17-3.06 (m, 1H), 2.00-1.89 (m, 2H), 1.84-1.76 (m, 2H), 1.29 (d, J=6.4 Hz, 3H); MS(O) m/z: 539.2 [M+H]$^+$.

Example 120: 6-((5-(3S,4S)-4-amino-3-methyl-2-oxa-8-azaspiro[4,5]decan-8-yl)pyrazin-2-yl)thio)-5-chloro-3-(2-methoxypropyl)quinazolin-4(3H)-one

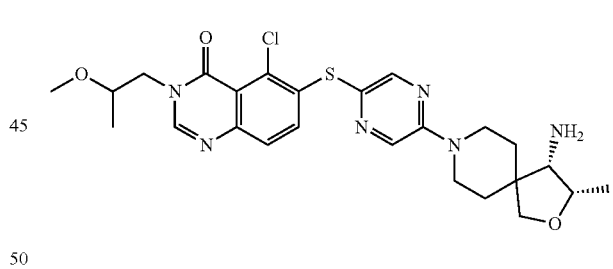

The compound of Example 120 (22 mg, 61%) was synthesized in the same method as in Example 18, except that 1-chloro-2-methoxypropane was used instead of benzyl chloride in step 2 of Example 18. $^1$H NMR(400 MHz, CDCl$_3$) δ=8.27 (d, J=1.2 Hz, 1H), 8.21 (s, 1H), 8.04 (s, 1H), 7.46 (d, J=8.8 Hz, 1H), 7.29 (d, J=8.8 Hz, 1H), 4.38-4.31 (m, 1H), 4.26-4.17 (m, 1H), 4.06-3.91 (m, 2H), 3.86 (d, J=8.8 Hz, 1H), 3.71 (s, 2H), 3.57-3.50 (m, 1H), 3.50-3.42 (m, 1H), 3.40-3.31 (m, 1H), 3.27 (s, 3H), 3.06 (d, J=4.4 Hz, 1H), 1.96-1.89 (m, 1H), 1.84-1.73 (m, 3H), 1.28 (d, J=6.4 Hz, 3H), 1.24 (d, J=6.4 Hz, 3H); MS (EI) m/z: 531.2 [M+H]$^+$.

Example 121: 6-((5-(3S,4S)-4-amino-3-methyl-2-oxa-8-azaspiro[4,5]decan-8-yl)pyrazin-2-yl)thio)-5-chloro-3-((4-oxocyclohexyl)methyl)quinazolin-4(3H)-one

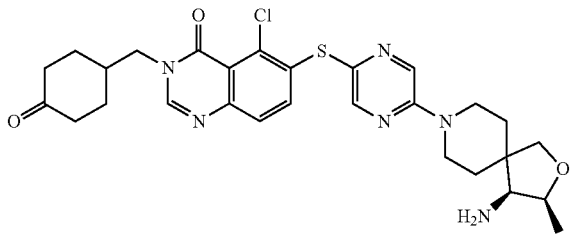 [SMILES: C[C@@H]1OCC2(CCN(c3cnc(Sc4ccc5ncn(CC6CCC(=O)CC6)c(=O)c5c4Cl)cn3)CC2)[C@@H]1N]

The compound of Example 121 (14 mg, 54%) was synthesized in the same method as in Example 18, except that (4-oxocyclohexyl)methyl 4-methylbenzenesulfonate was used instead of benzyl chloride in step 1 of Example 18. $^1$H NMR(400 MHz, CDCl$_3$) δ=8.26 (s, 1H), 8.21 (s, 1H), 8.11 (s, 1H, FA), 7.94 (s, 1H), 7.47 (d, J=8.8 Hz, 1H), 7.30 (d, J=8.8 Hz, 1H), 4.28-4.17 (m, 1H), 4.06-3.94 (m, 2H), 3.90 (d, J=7.2 Hz, 2H), 3.86 (d, J=8.8 Hz, 1H), 3.73 (d, J=8.8 Hz, 1H), 3.51-3.41 (m, 1H), 3.41-3.29 (m, 1H), 3.07 (d, J=3.6 Hz, 1H), 2.52-2.41 (m, 3H), 2.40-2.30 (m, 2H), 2.13-2.06 (m, 2H), 1.82-1.68 (m, 4H), 1.59-1.47 (m, 2H), 1.33-1.23 (m, 3H); MS (EI) m/z: 569.3 [M+H]$^+$.

Example 122: 6-((5-((3S,4S)-4-amino-3-methyl-2-oxa-8-azaspiro[4,5]decan-8-yl)pyrazin-2-yl)thio)-5-chloro-3-(2,3-dihydroxypropyl)quinazolin-4(3H)-one

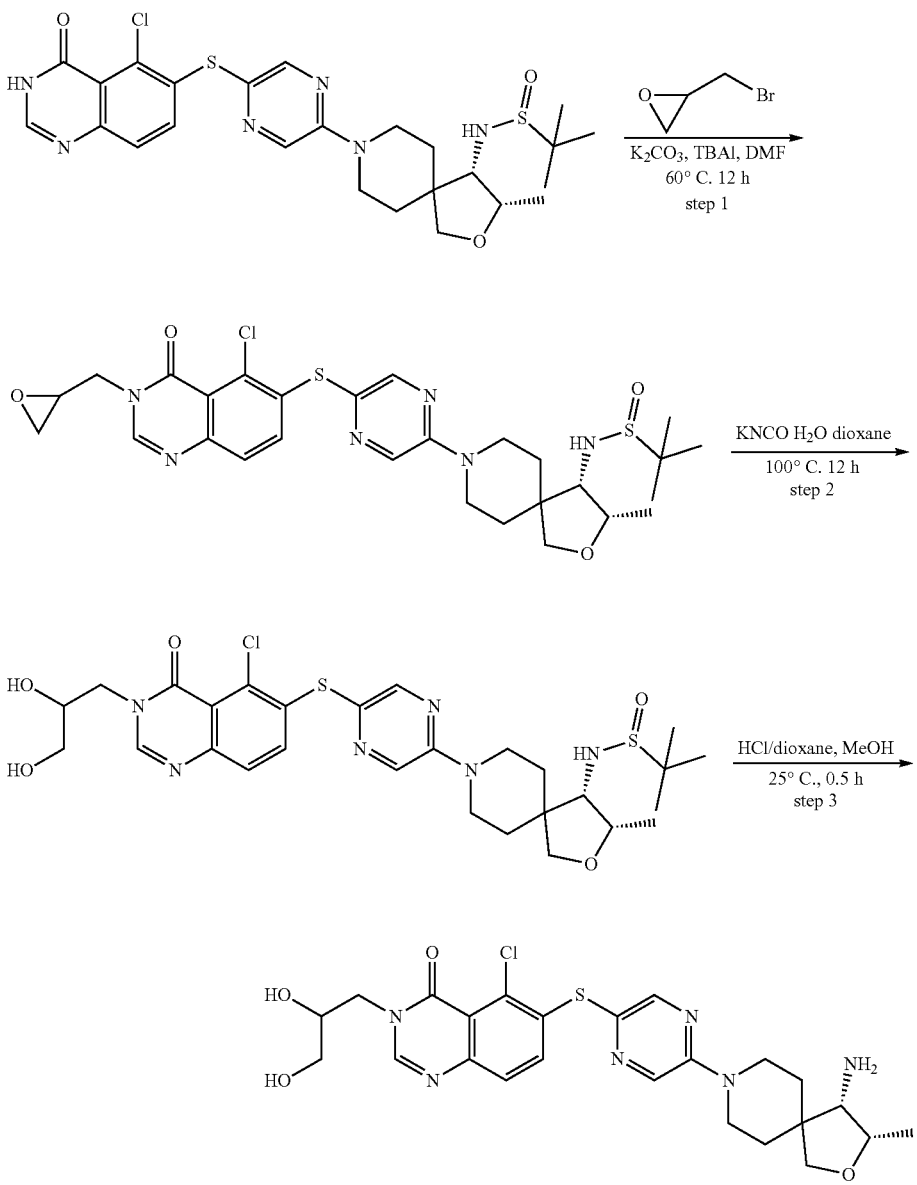

Step 1: N-((3S,4S)-8-(5-((5-chloro-3-(oxiran-2-ylmethyl)-4-oxo-3,4-dihydroquinazolin-6-yl)thio)pyrazin-2-yl)-3-methyl-2-oxa-8-azaspiro[4.5]decan-4-yl)-2-methylpropane-2-sulfinamide To a solution of N-((3S,4S)-8-(5-((5-chloro-4-oxo-3,4-dihydroquinazolin-6-yl)thio)pyrazin-2-yl)-3-methyl-2-oxa-8-azaspiro[4.5]decan-4-yl)-2-methylpropane-2-sulfinamide (100 mg, 178 μmol) obtained in step 1 of Example 18 and 2-(bromomethyl)oxirane (36.5 mg, 266 μmol) in DMF (2 mL), K$_2$CO$_3$ (73.6 mg, 533 μmol) and TBAI (6.56 mg, 17.8 μmol) were added. The mixture was stirred at 60° C. for 12 hours. The reaction mixture was quenched by addition of aqueous ammonium chloride (10 mL) at 25° C., diluted with water (20 mL) and extracted with EA (3×30 mL). The combined organic layers were washed with brine (3×20 mL), dried over anhydrous sodium sulfate, and then filtered and concentrated under reduced pressure to obtain a residue. The residue was purified by Prep-TLC (EA/MeOH=10/1) to obtain N-((3S,4S)-8-(5-((5-chloro-3-(oxiran-2-ylmethyl)-4-oxo-3,4-dihydroquinazolin-6-yl)thio)pyrazin-2-yl)-3-methyl-2-oxa-8-azaspiro[4.5]decan-4-yl)-2-methylpropane-2-sulfinamide (100 mg, 91% yield) as a yellow solid. 1 I-1 NMR (400 MHz, CDCl$_3$) δ=8.27 (d, J=1.2 Hz, 1H), 8.20 (d, J=1.2 Hz, 1H), 7.98 (s, 1H), 7.48 (d, J=8.8 Hz, 1H), 7.25 (d, J=8.8 Hz, 1H), 4.59-4.53 (m, 1H), 4.29-4.22 (m, 2H), 4.20-4.14 (m, 1H), 3.92 (d, J=9.2 Hz, 1H), 3.82-3.73 (m, 1H), 3.69 (d, J=9.2 Hz, 1H), 3.57-3.51 (m, 1H), 3.41-3.36 (m, 2H), 3.27-3.13 (m, 2H), 2.64-2.59 (m, 1H), 2.11-1.93 (m, 2H), 1.75 (d, J=13.6 Hz, 1H), 1.64 (d, J=13.2 Hz, 2H), 1.27 (s, 9H), 1.23 (d, J=6.4 Hz, 3H); MS (EI) m/z: 619.1 [M+H]$^+$.

Step 2: N-43S,4S)-8-(5-((5-chloro-3-(2,3-dihydroxypropyl)-4-oxo-3,4-dihydroquinazolin-6-yl)thio)pyrazin-2-yl)-3-methyl-2-oxa-8-azaspiro[4.5]decan-4-yl)-2-methylpropane-2-sulfinamide To a solution of N-((3S,4S)-8-(5-((5-chloro-3-(oxiran-2-ylmethyl)-4-oxo-3,4-dihydroquinazolin-6-yl)thio)pyrazin-2-yl)-3-methyl-2-oxa-8-azaspiro[4.5]decan-4-yl)-2-methylpropane-2-sulfinamide (100 mg, 161 μmol) in H$_2$O (6 mL) and dioxane (3 mL) was added potassium cyanate (26.2 mg, 323 μmol), and then the mixture was stirred at 100° C. for 12 hours. The reaction mixture was quenched by addition of aqueous ammonium chloride (10 mL) at 25° C., diluted with water (20 mL) and extracted with DCM (3×30 mL). The combined organic layers were washed with brine (3×20 mL), dried over anhydrous sodium sulfate, and then filtered and concentrated under reduced pressure to obtain N-((3S,4S)-8-(5-((5-chloro-3-(2,3-dihy droxypropyl)-4-oxo-3,4-dihydroquinazolin-6-yl)thio)pyrazin-2-yl)-3-methyl-2-oxa-8-azaspiro[4.5]decan-4-yl)-2-methylpropane-2-sulfinamide (80 mg, 78% yield) as a yellow solid. $^1$H NMR (400 MHz, CDCl$_3$) δ=8.27 (s, 1H), 8.20 (s, 1H), 8.05 (s, 1H), 7.45 (d, J=8.8 Hz, 1H), 7.23 (d, J=8.8 Hz, 1H), 4.30-4.22 (m, 3H), 4.17 (d, J=14.0 Hz, 1H), 4.12-4.07 (m, 1H), 3.95-3.88 (m, 2H), 3.62-3.57 (m, 1H), 3.53-3.48 (m, 1H), 3.40 (d, J=10.4 Hz, 1H), 3.26-3.13 (m, 3H), 2.10-1.94 (m, 3H), 1.78-1.70 (m, 2H), 1.67-1.58 (m, 2H), 1.27-1.25 (m, 9H), 1.22 ((d, J=6.4 Hz, 3H); MS (EI) m/z: 637.1 [M+H]$^+$.

Step 3: 6-((5-((3S,4S)-4-amino-3-methyl-2-oxa-8-azaspiro[4.5]decan-8-yl)pyrazin-2-yl)thio)-5-chloro-3-(2,3-dihydroxypropyl)quinazolin-4(3H)-one To a solution of N-((3S,4S)-8-(5-((5-chloro-3-(2,3-dihydroxypropyl)-4-oxo-3,4-dihydroquinazolin-6-yl)thio)pyrazin-2-yl)-3-methyl-2-oxa-8-azaspiro[4.5]decan-4-yl)-2-methylpropane-2-sulfinamide (80 mg, 126 μmol) in MeOH (10 mL) was added HCl/dioxane(4M, 1.57 mL), and then the mixture was stirred at 25° C. for 0.5 hours. The reaction mixture was concentrated under reduced pressure to obtain a residue. The residue was purified by Prep-HPLC (Column: Unisil 3-100 C18 Ultra 150*50 mm*3 um; mobile phase: [water(FA)-ACN]; B %: 4%-34%, 7 minutes) to obtain the compound of Example 122 (37 mg, 55% yield) as a off-white solid. $^1$H NMR (400 MHz, DMSO-d$_6$) δ=8.46 (d, J=1.2 Hz, 1H), 8.29 (d, J=1.2 Hz, 1H), 8.21 (s, 1H), 7.51 (d, J=8.8 Hz, 1H), 7.22 (d, J=8.8 Hz, 1H), 5.10-4.98 (m, 1H), 4.82-4.70 (m, 1H), 4.27 (dd, J=3.2, 13.2 Hz, 1H), 4.13-4.04 (m, 1H), 4.01-3.89 (m, 2H), 3.81-3.75 (m, 1H), 3.74-3.70 (m, 1H), 3.63-3.57 (m, 1H), 3.53 (d, J=8.8 Hz, 1H), 3.48-3.42 (m, 2H), 3.41-3.37 (m, 2H), 3.00 (d, J=4.8 Hz, 1H), 1.80-1.71 (m, 1H), 1.69-1.64 (m, 1H), 1.62-1.47 (m, 2H), 1.11 (d, J=6.4 Hz, 3H); MS (EI) m/z: 533.2 [M+H]$^+$.

Example 123: N-(2-(6-((5-((3S,4S)-4-amino-3-methyl-2-oxa-8-azaspiro[4,5]decan-8-yl)pyrazin-2-yl)thio)-5-chloro-4-oxoquinazolin-3(4H)-yl]ethyl)-N-methylmethanesulfonamide

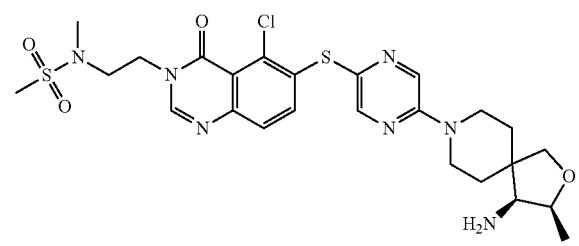 [SMILES: C[C@@H]1OCC2(CCN(c3cnc(Sc4ccc5ncn(CCN(C)S(C)(=O)=O)c(=O)c5c4Cl)cn3)CC2)[C@@H]1N]

The compound of Example 123 (40 mg, 62%) was synthesized in the same method as in Example 18, except that N-(2-bromoethyl)-N-methyl methanesulfonamide was used instead of benzyl chloride in step 2 of Example 18. $^1$H NMR (400 MHz, DMSO-d$_6$) δ=8.47 (s, 1H), 8.30 (s, 1H), 8.26 (s, 1H), 8.24 (s, 1H, FA), 7.50 (d, J=8.8 Hz, 1H), 7.20 (d, J=8.8 Hz, 1H), 4.14-4.06 (m, 3H), 4.02-3.90 (m, 3H), 3.73 (d, J=8.8 Hz, 1H), 3.53 (d, J=8.8 Hz, 1H), 3.45-3.40 (m, 1H), 3.39-3.32 (m, 2H), 3.04-3.00 (m, 1H), 2.86 (s, 3H), 2.82 (s, 3H), 1.81-1.65 (m, 2H), 1.61-1.47 (m, 2H), 1.11 (d, J=6.4 Hz, 3H); MS (EI) m/z: 594.1 [M+H]$^+$.

Example 124: 7-((5-((3S,4S)-4-amino-3-methyl-2-oxa-8-azaspiro[4,5]decan-8-yl)pyrazin-2-yl)thio)-2-benzyl-8-chloro-2H-benzo[e][1,2,4]thiadiazine 1,1-dioxide

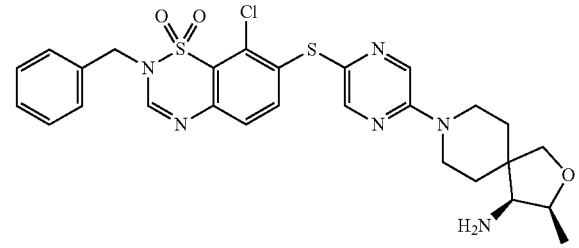 [SMILES: C[C@@H]1OCC2(CCN(c3cnc(Sc4ccc5c(c4Cl)S(=O)(=O)N(Cc4ccccc4)C=N5)cn3)CC2)[C@@H]1N]

The compound of Example 124 (7 mg, 38%) was synthesized in the same method as in steps 1 and 3 of Example 18, using Intermediate I-33 and Intermediate I-34 as starting materials. $^1$H NMR (400 MHz, CDCl$_3$) δ=8.27 (s, 1H), 8.20 (s, 1H), 7.45-7.38 (m, 5H), 7.32-7.23 (m, 3H), 5.03 (s, 2H), 4.27-4.17 (m, 1H), 4.06-3.92 (m, 2H), 3.86 (d, J=8.8 Hz, 1H), 3.72 (d, J=8.8 Hz, 1H), 3.55-3.44 (m, 1H), 3.43-3.33 (m, 1H), 3.06 (d, J=4.6 Hz, 1H), 1.96-1.89 (m, 1H), 1.83-1.74 (m, 3H), 1.28 (d, J=6.4 Hz, 3H); MS (EI) m/z: 585.1 [M+H]+.

Example 125: (3S,4S)-8-(5-((7-chloro-2-phenoxy-1H-benzo[d]imidazol-6-yl)thio)pyrazin-2-yl-3-methyl-2-oxa-8-azaspiro[4,5]decan-4-amine

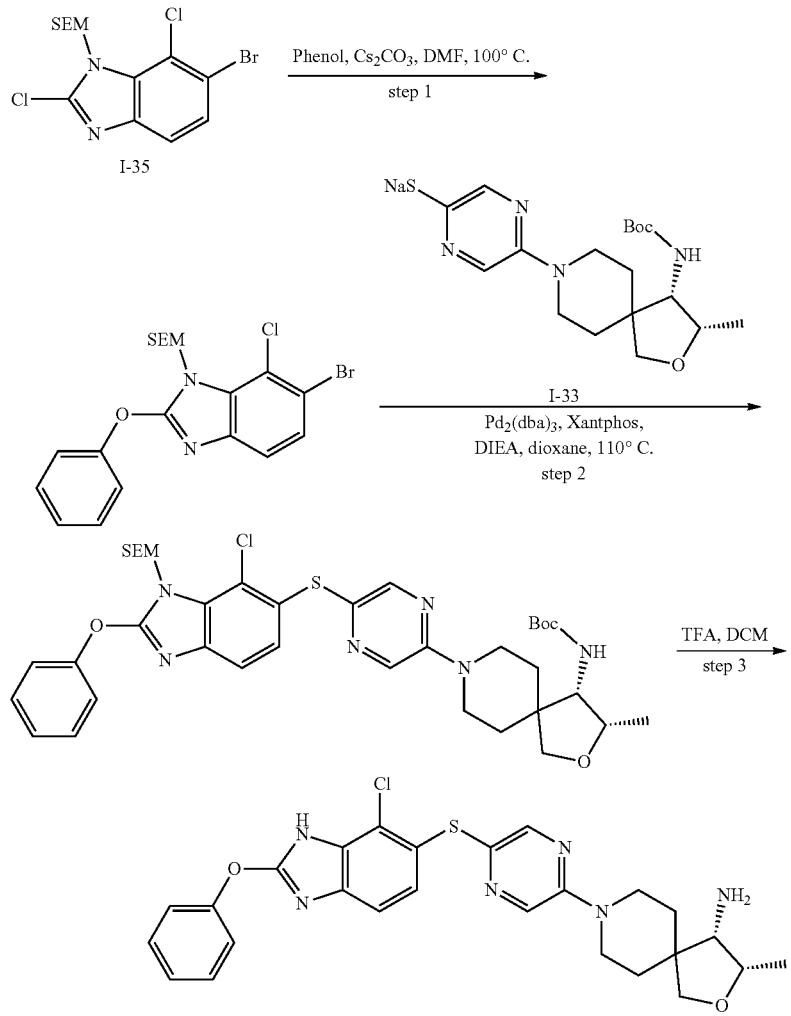

Step 1: 2-1(6-bromo-7-chloro-2-phenoxy-benzimidazol-1-yl)methoxy]ethyl-trimethyl-silane To a solution of Intermediate I-35 (380 mg, 959 μmol) in DMF (5 mL), Cs$_2$CO$_3$ (938 mg, 2.88 mmol) and phenol (181 mg, 1.92 mmol) were added. The mixture was stirred at 100° C. for 12 hours. The reaction mixture was quenched by addition of aqueous ammonium chloride (20 mL) at 25° C., diluted with water (30 mL) and extracted with EA (3×50 mL). The combined organic layers were washed with brine (3×20 mL), dried over anhydrous sodium sulfate, and then filtered and concentrated under reduced pressure to obtain a residue. The residue was purified by reverse phase flash column chromatography (0.1% FA) to obtain 2-[(6-bromo-7-chloro-2-phenoxy-benzimidazol-1-yl)methoxy]ethyl-trimethyl-silane (300 mg, 69% yield) as a yellow oil. $^1$H NMR (400 MHz, CDCl$_3$) δ=7.49-7.41 (m, 5H), 7.30-7.27 (m, 1H), 7.22-7.18 (m, 1H), 3.64-3.60 (m, 4H), 0.95-0.93 (m, 2H), 0.03 (d, J=2.4 Hz, 9H).

Step 2: tert-butyl ((3S,4S)-8-(5-((7-chloro-2-phenoxy-14 (2-(trimethylsilyl)ethoxy)methyl)-1H-benzo[d]imidazol-6-yl)thio)pyrazin-2-yl)-3-methyl-2-oxa-8-azaspiro[4.5]decan-4-yl)carbamate A mixture of 2-[(6-bromo-7-chloro-2-phenoxy-benzimidazol-1-yl)methoxy]ethyl-trimethyl-silane (150 mg, 331 μmol), Intermediate I-33 (160 mg, 397 μmol), Pd$_2$(dba)$_3$ (30.3 mg, 33.1 μmol), XantPhos (38.3 mg, 66.1 μmol) and DIEA (128 mg, 992 μmol) in dioxane (3 mL) was degassed and purged 3 times with N2. Then, the mixture was stirred under N$_2$ atmosphere at 110° C. for 12 hours. The reaction mixture was filtered, and the filtrate was concentrated under reduced pressure to obtain a residue. The residue was purified by reverse phase flash column chromatography (0.1% FA) to obtain tert-butyl ((3S,4S)-8-(5-((7-chloro-2-phenoxy-1-((2-(trimethylsilyl)ethoxy)methyl)-1H-benzo[d]imidazol-6-yl)thio)pyrazin-2-yl)-3-methyl-2-oxa-8-azaspiro[4.5]decan-4-yl)carbamate (25 mg, 10% yield) as a yellow solid. $^1$H NMR (400 MHz, CDCl$_3$) δ=8.07-7.97 (m, 2H), 7.47-7.44 (m, 1H), 7.42-7.38 (m, 2H), 7.39-7.35 (m, 1H), 7.29-7.26 (m, 2H), 7.26-7.23 (m, 1H), 4.68-4.54 (m, 1H), 4.21-4.14 (m, 1H), 4.03-3.96 (m, 1H), 3.85-3.68 (m, 3H), 3.68-3.64 (m, 3H), 3.64-3.55 (m, 2H), 3.54-3.46 (m, 1H), 3.44-3.33 (m, 1H), 1.89-1.80 (m, 2H), 1.78-1.73 (m, 2H), 1.45 (s, 9H), 1.22-1.18 (m, 3H), 0.98-0.89 (m, 2H), 0.04 (m, 9H).

Step 3: (3S,4S)-8-(5-((7-chloro-2-phenoxy-1H-benzo[d]imidazol-6-yl)thio)pyrazin-2-yl-3-methyl-2-oxa-8-azaspiro[4,5]decan-4-amine To a solution of tert-butyl ((3S,4S)-8-(5-((7-chloro-2-phenoxy-1-((2-(trimethylsilyl)ethoxy)methyl)-1H-benzo[d]imidazol-6-yl)thio)pyrazin-2-yl)-3-methyl-2-oxa-8-azaspiro[4,5]decan-4-yl)carbamate (20 mg, 26.6 μmol) in DCM (3 mL) was added TFA (303 mg, 2.65 mmol), and then the mixture was stirred at 25° C. for 2 hours. The reaction mixture was concentrated under reduced pressure to obtain a residue. The residue was purified by Prep-HPLC (Column: Unisil 3-100 C18 Ultra 150*50 mm*3 um; mobile phase: [water(FA)-ACN]; B %: 10%-40%, 10 minutes) to obtain the compound of Example 125 (10 mg, 72% yield) as a yellow solid. $^1$H NMR (400 MHz, MeOD) δ=8.12 (s, 1H), 7.96 (s, 1H), 7.51-7.44 (m, 2H), 7.36-7.29 (m, 3H), 7.29-7.23 (m, 2H), 4.31-4.21 (m, 1H), 4.18-4.03 (m, 2H), 3.92 (d, J=8.8 Hz, 1H), 3.79 (d, J=8.8 Hz, 1H), 3.24 (d, J=4.4 Hz, 1H), 3.23-3.17 (m, 1H), 3.16-3.09 (m, 1H), 1.84-1.75 (m, 3H), 1.70-1.62 (m, 1H), 1.26 (d, J=6.4 Hz, 3H); MS(O) m/z: 523.2 [M+H]$^+$.

Example 126: (3S,4S)-8-(5-((7-chloro-2-((tetrahydrofuran-3-yl)oxy)-1H-benzo[d]imidazol-6-yl)thio)pyrazin-2-yl)-3-methyl-2-oxa-8-azaspiro[4,5]decan-4-amine

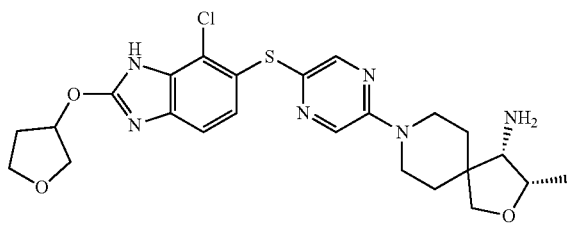 [SMILES: C[C@@H]1OCC2(CCN(c3cnc(Sc4ccc5nc(OC6CCOC6)[nH]c5c4Cl)cn3)CC2)[C@@H]1N]

The compound of Example 126 (9.03 mg, 79%) was synthesized in the same method as in Example 125, except that tetrahydrofuran-3-ol was used instead of phenol in step 1 of Example 125. $^1$H NMR (400 MHz, MeOD-d$_4$) δ=8.53 (s, 1H, FA), 8.11 (d, J=1.2 Hz, 1H), 7.93 (d, J=1.2 Hz, 1H), 7.25 (s, 2H), 5.62 (s, 1H), 4.28-4.21 (m, 1H), 4.13-3.93 (m, 6H), 3.93-3.88 (m, 2H), 3.76 (d, J=8.8 Hz, 1H), 3.28-3.21 (m, 1H), 3.20-3.12 (m, 2H), 2.44-2.32 (m, 1H), 2.30-2.20 (m, 1H), 1.85-1.78 (m, 1H), 1.78-1.72 (m, 2H), 1.70-1.60 (m, 1H), 1.25 (d, J=6.4 Hz, 3H); MS (EI) m/z: 516.9 [M+H]$^+$.

Example 127: (3S,4S)-8-(5-((7-chloro-2-(2-methoxyethoxy)-1H-benzo[d]imidazol-6-yl)thio)pyrazin-2-yl-3-methyl-2-oxa-8-azaspiro[4,5]decan-4-amine

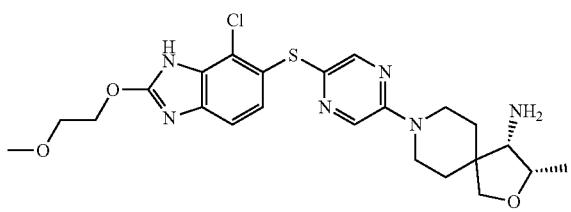

The compound of Example 127 (18.7 mg, 68%) was synthesized in the same method as in Example 125, except that 2-methoxyethanol was used instead of phenol in step 1 of Example 125. $^1$H NMR (400 MHz, MeOD-d$_4$) δ=8.11 (d, J=1.2 Hz, 1H), 7.92 (d, J=1.2 Hz, 1H), 7.25 (s, 2H), 4.66-4.60 (m, 2H), 4.29-4.21 (m, 1H), 4.12-3.98 (m, 2H), 3.89 (d, J=9.2 Hz, 1H), 3.81-3.77 (m, 2H), 3.75 (d, J=9.2 Hz, 1H), 3.42 (s, 3H), 3.29-3.23 (m, 1H), 3.23-3.16 (m, 1H), 3.15 (d, J=4.8 Hz, 1H), 1.84-1.70 (m, 3H), 1.69-1.60 (m, 1H), 1.24 (d, J=6.4 Hz, 3H); MS (EI) m/z: 505.2 [M+H]$^+$.

Example 128: (3S,4S)-8-(5-((7-chloro-2-(pyridin-3-yloxy)-1H-benzo[d]imidazol-6-yl)thio)pyrazin-2-yl-3-methyl-2-oxa-8-azaspiro[4,5]decan-4-amine

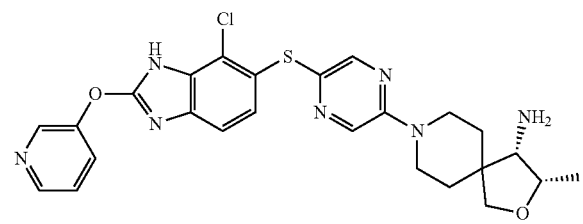 [SMILES: C[C@@H]1OCC2(CCN(c3cnc(Sc4ccc5nc(Oc6cccnc6)[nH]c5c4Cl)cn3)CC2)[C@@H]1N]

The compound of Example 128 (23.7 mg, 68%) was synthesized in the same method as in Example 125, except that pyridin-3-ol was used instead of phenol in step 1 of Example 125. $^1$H NMR (400 MHz, MeOD-d$_4$) δ=8.67 (d, J=2.4 Hz, 1H), 8.52-8.48 (m, 1H), 8.13 (d, J=1.2 Hz, 1H), 7.99-7.91 (m, 2H), 7.60-7.54 (m, 1H), 7.33-7.24 (m, 2H), 4.30-4.22 (m, 1H), 4.19-4.04 (m, 2H), 3.93 (d, J=9.2 Hz, 1H), 3.80 (d, J=8.8 Hz, 1H), 3.26 (d, J=4.4 Hz, 1H), 3.24-3.18 (m, 1H), 3.18-3.09 (m, 1H), 1.84-1.73 (m, 3H), 1.70-1.61 (m, 1H), 1.27 (d, J=6.4 Hz, 3H); MS (EI) m/z: 524.2 [M+H]$^+$.

Example 129: (3S,4S)-8-(5-((7-chloro-1-methyl-2-((tetrahydrofuran-3-yl)oxy)-1H-benzo[d]imidazol-6-yl)thio)pyrazin-2-yl)-3-methyl-2-oxa-8-azaspiro[4.5]decan-4-amine

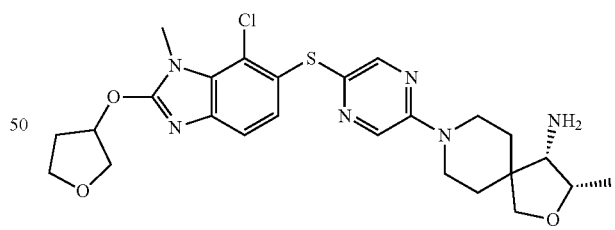

The compound of Example 129 (45.8 mg, 53%) was synthesized in the same method as in steps 1 and 3 of Example 18, using Intermediate I-33 and Intermediate I-36 as starting materials. $^1$H NMR (400 MHz, MeOD-d$_4$) δ=8.47 (s, 1H, FA), 8.14 (d, J=1.6 Hz, 1H), 7.96 (d, J=1.6 Hz, 1H), 7.36-7.31 (m, 1H), 7.24 (d, J=8.4 Hz, 1H), 5.63-5.56 (m, 1H), 4.31-4.24 (m, 1H), 4.23-4.16 (m, 1H), 4.16-4.10 (m, 1H), 4.09-3.99 (m, 3H), 3.96-3.90 (m, 2H), 3.89 (s, 3H), 3.83 (d, J=9.2 Hz, 1H), 3.33 (s, 1H), 3.21-3.07 (m, 2H), 2.45-2.35 (m, 1H), 2.33-2.23 (m, 1H), 1.82 (t, J=4.4 Hz, 2H), 1.80 (s, 1H), 1.71-1.62 (m, 1H), 1.29 (d, J=6.4 Hz, 3H); MS (EI) m/z: 531.2 [M+H]$^+$.

Example 130: (3S,4S)-8-(5-((4-chloro-1-methyl-2-(tetrahydrofuran-3-yl)oxy)-1H-benzo[d]imidazol-5-yl)thio)pyrazin-2-yl)-3-methyl-2-oxa-8-azaspiro[4,5]decan-4-amine

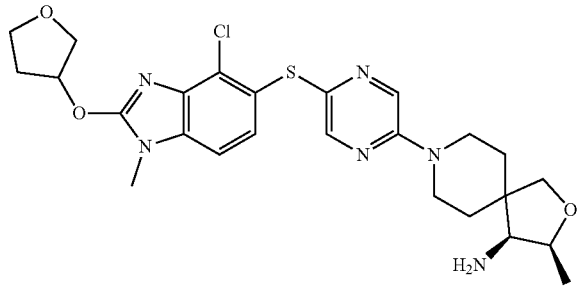 [SMILES: C[C@@H]1OCC2(CCN(c3cnc(Sc4ccc5c(nc(OC6CCOC6)n5C)c4Cl)cn3)CC2)[C@@H]1N]

The compound of Example 130 (13 mg, 50%) was synthesized in the same method as in steps 1 and 3 of Example 18, using Intermediate I-33 and Intermediate I-37 as starting materials. $^1$H NMR (400 MHz, MeOD) δ=8.10 (s, 1H), 7.91 (s, 1H), 7.31-7.21 (m, 2H), 5.72 (t, J=4.8 Hz, 1H), 4.28-4.22 (m, 1H), 4.11-4.07 (m, 1H), 4.04 (s, 2H), 4.03-4.00 (m, 1H), 3.96-3.88 (m, 2H), 3.76 (d, J=8.8 Hz, 1H), 3.64-3.60 (m, 1H), 3.59-3.56 (m, 3H), 3.27-3.20 (m, 1H), 3.14-3.10 (m, 2H), 2.45-2.34 (m, 1H), 2.32-2.24 (m, 1H), 1.84-1.71 (m, 3H), 1.64-1.61 (m, 1H), 1.27-1.23 (m, 3H); MS (EI) m/z: 531.3 [M+H]$^+$.

Example 131: 6-((5-(3S,4S)-4-amino-3-methyl-2-oxa-8-azaspiro[4,5]decan-8-yl)-6-(hydroxymethyl)-3-methylpyrazin-2-yl)thio)-5-chloro-3-(2-methoxyethyl)quinazolin-4(3H)-one Step 1: tert-butyl ((3S,4S)-8-(5-((5-chloro-3-(2-methoxyethyl)-4-oxo-3,4-dihydroquinazolin-6-yl)thio)-3-(hydroxymethyl)-6-methylpyrazin-2-yl)-3-methyl-2-oxa-8-azaspiro[4.5]decan-4-yl)carbamate A mixture of Intermediate I-38 (120 mg, 255 µmol), [5-chloro-3-(2-methoxyethyl)-4-oxo-quinazolin-6-yl]sulfanyl sodium (111 mg, 382 µmol) obtained in step 2 of Preparation Example 28, Pd$_2$(dba)$_3$ (23.3 mg, 25.5 XantPhos (29.5 mg, 50.9 µmol) and DIEA (98.7 mg, 764 µmol) in dioxane (5 mL) was degassed and purged 3 times with N2, and then the mixture was stirred under N$_2$ atmosphere at 100° C. for 12 hours. The reaction mixture was filtered, and the filtrate was concentrated under reduced pressure to obtain a residue. The residue was purified by Pre-TLC(PE/EA=1:10) to obtain tert-butyl ((3S,4S)-8-(5-((5-chloro-3-(2-methoxyethyl)-4-oxo-3,4-dihydroquinazolin-6-yl)thio)-3-(hydroxymethyl)-6-methylpyrazin-2-yl)-3-methyl-2-oxa-8-azaspiro[4.5]decan-4-yl)carbamate(60 mg, 36% yield) as a yellow solid. MS (EI) m/z: 661.2 [M+H]$^+$.

Step 2: 6-((5-(3S,4S)-4-amino-3-methyl-2-oxa-8-azaspiro[4.5]decan-8-yl)-6-(hydroxymethyl)-3-methylpyrazin-2-yl)thio)-5-chloro-3-(2-methoxyethyl)quinazolin-4(3H)-one To a solution of tert-butyl ((3S,4S)-8-(5-((5-chloro-3-(2-methoxyethyl)-4-oxo-3,4-dihydroquinazolin-6-yl)thio)-3-(hydroxymethyl)-6-methylpyrazin-2-yl)-3-methyl-2-oxa-8-azaspiro[4.5]decan-4-yl)carbamate(60 mg, 90.7 µmol) in DCM (3 mL) was added TFA (1.03 g, 9.07 mmol), and the mixture was stirred at 25° C. for 0.5 hours. The reaction mixture was concentrated under reduced pressure to obtain a residue. The residue was purified by Prep-HPLC (Column: Unisil 3-100 C18 Ultra 150*50 mm*3 um; mobile phase: [water(FA)-ACN]; B %: 11%-41%, 7 minutes) to obtain the

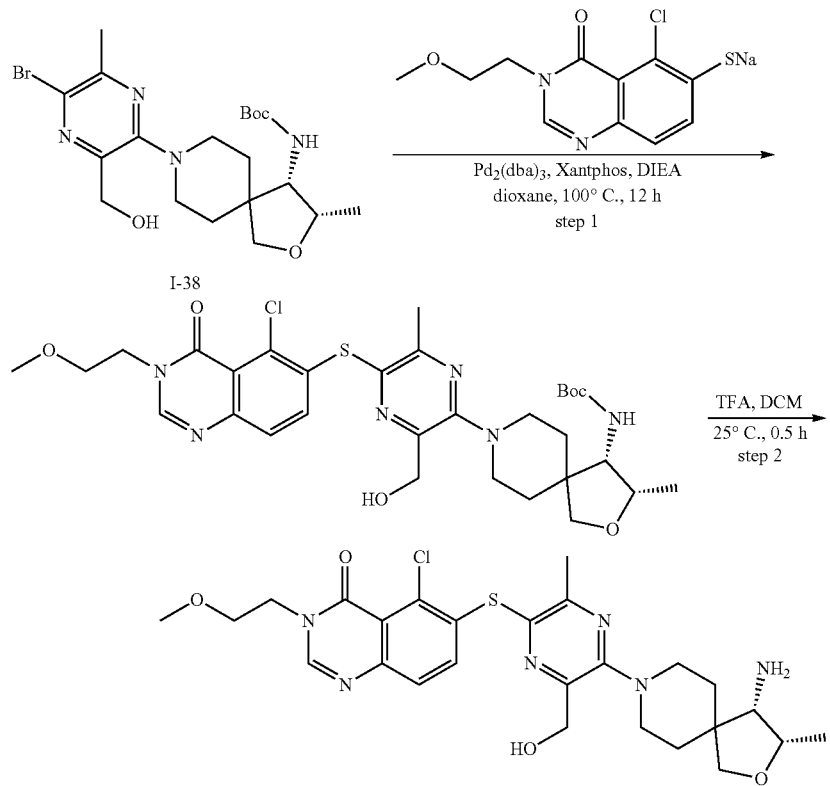

compound of Example 131 (42 mg, 82% yield) as a white solid. 1 H NMR (400 MHz, CDCl$_3$) δ=8.07 (s, 1H), 7.48 (d, J=8.8 Hz, 1H), 7.33 (d, J=8.8 Hz, 1H), 4.56 (s, 2H), 4.22 (d, J=5.2 Hz, 1H), 4.16 (t, J=4.8 Hz, 2H), 3.92 (d, J=9.2 Hz, 1H), 3.78-3.73 (m, 1H), 3.68 (t, J=4.8 Hz, 2H), 3.49 (d, J=13.2 Hz, 2H), 3.34 (s, 3H), 3.23 (d, J=4.0 Hz, 1H), 3.07-2.90 (m, 2H), 2.53-2.47 (m, 3H), 2.02-1.87 (m, 2H), 1.76 (d, J=12.4 Hz, 2H), 1.31 (d, J=6.0 Hz, 3H); MS (EI) m/z: 561.2 [M+H]$^+$.

Example 132: 7-((5-(3S,4S)-4-amino-3-methyl-2-oxa-8-azaspiro[4,5]decan-8-yl)-pyrazin-2-yl)thio)-3-benzyl-8-chloroquinazolin-4(3H)-one

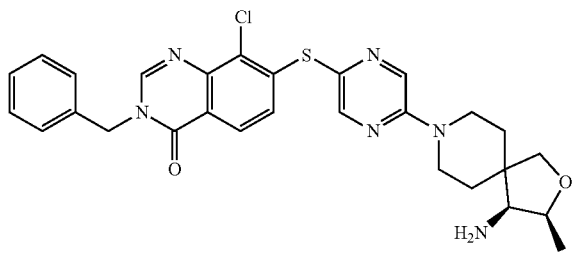 [SMILES: C[C@@H]1OCC2(CCN(c3cnc(Sc4ccc5c(=O)n(Cc6ccccc6)cnc5c4Cl)cn3)CC2)[C@@H]1N]

The compound of Example 132 (16 mg, 61% yield) was obtained as a white solid in the same method as in Example 131, using Intermediate I-40 and Intermediate I-33 as starting materials. $^1$H NMR (400 MHz, CDCl$_3$) δ=8.30 (s, 1H), 8.24 (s, 1H), 8.21 (s, 1H), 8.01 (d, J=8.8 Hz, 1H), 7.40-7.28 (m, 5H), 6.92 (d, J=8.8 Hz, 1H), 5.18 (s, 2H), 4.27-4.18 (m, 1H), 4.07-4.01 (m, 2H), 3.88 (d, J=8.8 Hz, 1H), 3.74 (d, J=8.8 Hz, 1H), 3.47-3.31 (m, 2H), 3.11 (d, J=4.0 Hz, 1H), 1.96-1.90 (m, 1H), 1.80-1.68 (m, 3H), 1.28 (d, J=6.4 Hz, 3H); MS (EI) m/z: 549.1 [M+H]$^+$.

Example 133: 6-((5-((3S,4S)-4-amino-3-methyl-2-oxa-8-azaspiro[4,5]decan-8-yl)-pyrazin-2-yl)thio)-2-benzyl-7-chloroisoindolin-1-one

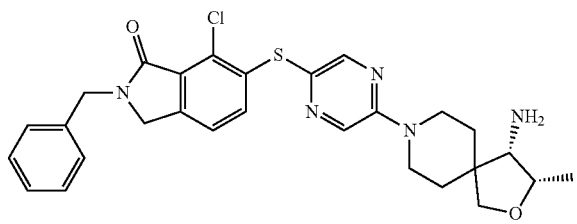 [SMILES: C[C@@H]1OCC2(CCN(c3cnc(Sc4ccc5c(c4Cl)C(=O)N(Cc4ccccc4)C5)cn3)CC2)[C@@H]1N]

The compound of Example 133 (13 mg, 50%) was synthesized in the same method as in Example 131, using Intermediate I-41 and Intermediate I-33 as starting materials. $^1$H NMR (400 MHz, CDCl$_3$) δ 8.21-8.18 (m, 1H), 8.14-8.11 (m, 1H), 7.37-7.28 (m, 6H), 7.17-7.12 (m, 1H), 4.77 (s, 2H), 4.25-4.23 (m, 1H), 4.21 (s, 2H), 4.04-3.90 (m, 2H), 3.89-3.85 (m, 1H), 3.74-3.69 (m, 1H), 3.43-3.34 (m, 1H), 3.32-3.21 (m, 1H), 3.11-3.06 (m, 1H), 1.81-1.69 (m, 4H), 1.32-1.25 (m, 3H); MS (EI) m/z: 536.1 [M+H]$^+$.

Example 134: (S)-6-((3-amino-5-(5-amino-5,7-dihydrospiro[cyclopenta[b]pyridine]-6,4'-piperidin]-1'-yl)pyrazin-2-yl]thio)-5-chloro-3-(2-methoxyethyl)quinazolin-4(3H)-one

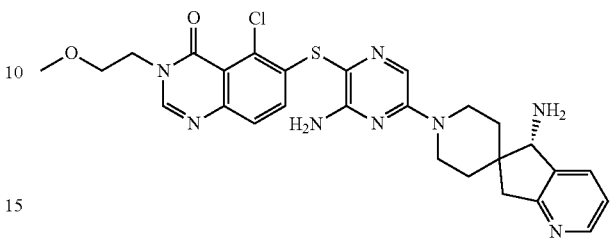

The compound of Example 134 (13 mg, 25%) was synthesized in the same method as in Example 99 using Intermediate I-25 and Intermediate I-42. $^1$H NMR (400 MHz, CDCl$_3$) δ=8.46-8.42 (m, 1H), 8.03-8.01 (m, 1H), 7.71-7.69 (m, 1H), 7.66 (d, J=7.6 Hz, 1H), 7.46 (d, J=8.8 Hz, 1H), 7.20-7.13 (m, 2H), 4.85 (br s, 2H), 4.32-4.25 (m, 2H), 4.15 (t, J=4.8 Hz, 2H), 4.05 (s, 1H), 3.69 (t, J=4.8 Hz, 2H), 3.34-3.31 (m, 3H), 3.24 (d, J=8.4 Hz, 1H), 3.22-3.15 (m, 2H), 2.90 (d, J=16.4 Hz, 1H), 1.82 (s, 2H), 1.66 (d, J=12.0 Hz, 1H), 1.39 (d, J=13.2 Hz, 1H); MS (EI) m/z: 565.2 [M+H]$^+$.

Example 135: (3S,4S)-8-(5-((7-chloro-2-(3-methoxybenzyl)-1H-benzo[d]imidazol-6-yl)thio)pyrazin-2-yl-3-methyl-2-oxa-8-azaspiro[4.5]decan-4-amine

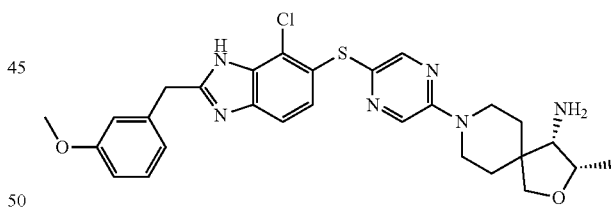

The compound of Example 135 (18 mg, 50%) was synthesized in the same method as in Example 131, using Intermediate I-43 and Intermediate I-33 as starting materials. $^1$H NMR (400 MHz, MeOD) δ 8.19 (d, J=1.5 Hz, 1H), 8.11 (d, J=1.4 Hz, 1H), 7.48 (d, J=8.6 Hz, 1H), 7.29 (dd, J=16.9, 8.3 Hz, 2H), 6.97-6.84 (m, 3H), 4.39-4.24 (m, 5H), 4.19 (d, J=13.9 Hz, 1H), 4.00-3.94 (m, 1H), 3.86 (d, J=9.2 Hz, 1H), 3.78 (s, 4H), 3.41 (d, J=4.2 Hz, 1H), 3.23-3.05 (m, 2H), 1.83 (dd, J=10.3, 4.4 Hz, 2H), 1.79 (dd, J=11.5, 4.6 Hz, 1H), 1.68 (d, J=13.1 Hz, 1H), 1.31 (d, J=6.6 Hz, 6H); MS (EI) m/z: 551.1 [M+H]$^+$.

Example 136: (3S,4S)-8-(5-((7-chloro-2-(pyrazin-2-ylmethyl)-1H-benzo[d]imidazol-6-yl)thio)pyrazin-2-yl)-3-methyl-2-oxa-8-azaspiro[4.5]decan-4-amine

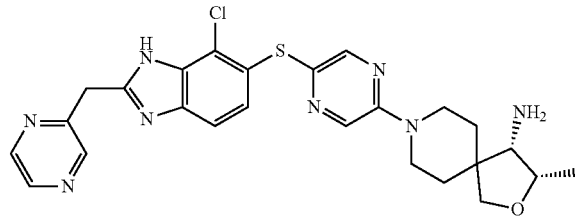 [SMILES: C[C@@H]1OCC2(CCN(c3cnc(Sc4ccc5nc(Cc6cnccn6)[nH]c5c4Cl)cn3)CC2)[C@@H]1N]

The compound of Example 136 (6 mg, 33%) was synthesized in the same method as in Example 135 above, except that Intermediate I-45 was used instead of Intermediate I-43. ¹H NMR (400 MHz, MeOD) δ 8.77 (s, 1H), 8.58 (s, 2H), 8.21 (s, 1H), 8.15 (s, 1H), 7.55 (d, J=8.6 Hz, 1H), 7.38-7.31 (m, 1H), 4.28 (d, J=4.8 Hz, 2H), 4.21 (d, J=14.3 Hz, 1H), 3.98 (d, J=9.3 Hz, 1H), 3.87 (d, J=9.3 Hz, 1H), 3.42 (s, 1H), 3.24-3.07 (m, 3H), 1.86 (s, 3H), 1.69 (d, J=13.3 Hz, 1H), 1.31 (d, J=6.5 Hz, 4H); MS (EI) m/z: 523.6 [M+H]⁺.

Example 137: (3S,4S)-8-(5-((7-chloro-2-(pyridin-3-ylmethyl)-1H-benzo[d]imidazol-6-yl)thio)pyrazin-2-yl)-3-methyl-2-oxa-8-azaspiro[4.5]decan-4-amine

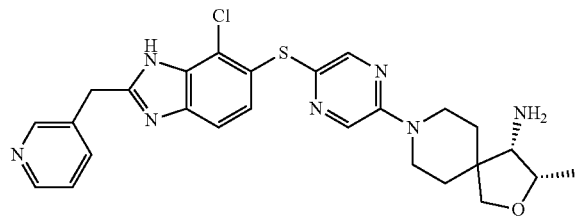 [SMILES: C[C@@H]1OCC2(CCN(c3cnc(Sc4ccc5nc(Cc6cccnc6)[nH]c5c4Cl)cn3)CC2)[C@@H]1N]

The compound of Example 137 (5.1 mg, 31%) was synthesized in the same method as in Example 135 above, except that Intermediate I-46 was used instead of Intermediate I-43. ¹H NMR (400 MHz, MeOD) δ 8.71 (s, 1H), 8.60 (d, J=5.3 Hz, 1H), 8.15 (d, J=1.4 Hz, 1H), 8.02 (d, J=1.3 Hz, 1H), 7.68 (s, 1H), 7.43 (d, J=8.5 Hz, 1H), 7.28 (d, J=8.4 Hz, 1H), 4.44 (s, 2H), 4.32-4.21 (m, 1H), 4.16 (d, J=14.0 Hz, 1H), 3.96 (d, J=9.2 Hz, 1H), 3.85 (d, J=9.2 Hz, 1H), 3.40 (d, J=4.1 Hz, 1H), 3.21-3.03 (m, 2H), 1.84 (s, 2H), 1.83-1.74 (m, 1H), 1.67 (d, J=12.9 Hz, 1H), 1.30 (d, J=6.5 Hz, 4H); MS (EI) m/z: 522.7 [M+H]⁺.

Example 138: (S)-6-((5-(5-amino-5,7-dihydrospiro[cyclopenta[b]pyridine]-6,4'-piperidin]-1'-yl)pyrazin-2-yl]thio)-5-chloro-3-(furan-3-ylmethyl)quinazolin-4(3H)-one

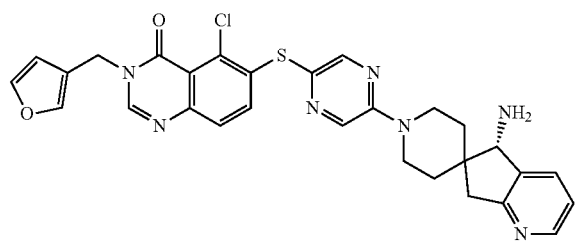 [SMILES: N[C@@H]1c2cccnc2CC12CCN(c1cnc(Sc3ccc4ncn(Cc5ccoc5)c(=O)c4c3Cl)cn1)CC2]

The compound of Example 138 (7.8 mg, 38%) was synthesized in the same method as in Example 112, except that 3-(bromomethyl)furan was used instead of 1-bromopropan-2-one in step 1 of Example 112. ¹H NMR (400 MHz, CDCl₃) δ=8.46 (d, J=4.4 Hz, 1H), 8.27 (s, 1H), 8.23 (s, 1H), 8.04 (s, 1H), 7.73-7.69 (m, 1H), 7.57 (s, 1H), 7.45 (d, J=8.8 Hz, 1H), 7.41 (t, J=1.6 Hz, 1H), 7.29 (s, 1H), 7.18 (dd, J=5.2, 7.2 Hz, 1H), 6.45 (s, 1H), 5.00 (s, 2H), 4.35-4.26 (m, 2H), 4.12-4.08 (m, 1H), 3.31-3.21 (m, 3H), 2.95 (d, J=16.4 Hz, 1H), 1.93-1.79 (m, 2H), 1.68 (d, J=12.8 Hz, 1H), 1.49 (d, J=12.4 Hz, 1H); MS (EI) m/z: 572.2 [M+H]⁺.

Example 139: 6-((5-((3S,4S)-4-amino-3-methyl-2-oxa-8-azaspiro[4.5]decan-8-yl)pyrazin-2-yl)thio)-5-chloro-3-(2-fluoro-2-methylpropyl)quinazolin-4(3H)-one

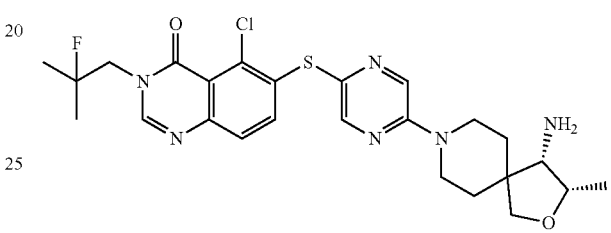

The compound of Example 139 (9.1 mg, 69%) was synthesized in the same method as in Example 18, except that, in step 2 of Example 18, 1-bromo-2-fluoro-2-methylpropane was used instead of benzyl chloride, and 1.5 equivalents of potassium iodide were added. ¹H NMR (400 MHz, DMSO) δ 8.52 (s, 1H), 8.33 (d, J=1.1 Hz, 1H), 8.21 (d, J=1.8 Hz, 1H), 8.14-8.09 (m, 2H), 7.54 (d, J=8.8 Hz, 1H), 7.24 (d, J=8.8 Hz, 1H), 4.28-4.19 (m, 4H), 3.92 (d, J=9.1 Hz, 1H), 3.69 (d, J=9.0 Hz, 1H), 3.20-3.12 (m, 4H), 1.83-1.70 (m, 3H), 1.59 (d, J=16 Hz, 1H), 1.37 (s, 3H), 1.32 (s, 3H), 1.23 (d, J=6.6 Hz, 3H); MS m/z: 533 [M+H]⁺.

Example 140: (S)-6-((5-(5-amino-5,7-dihydrospiro[yclopenta[b]pyridine-6,4'-piperidin]-1'-yl)pyrazin-2-yl)thio)-5-chloro-3-((3-fluorooxetan-3-yl)methyl)quinazolin-4(3H)-one

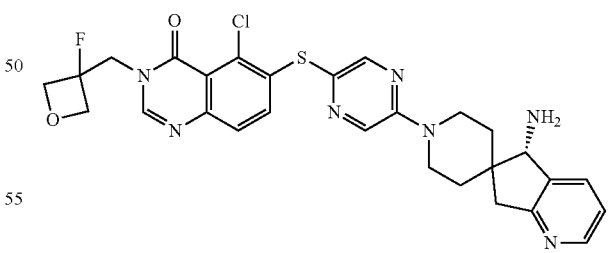

The compound of Example 140 (16 mg, 75%) was synthesized in the same method as in Example 112, except that 3-(fluorooxetan-3-yl)methyl 4-methylbenzenesulfonate was used instead of 1-bromopropan-2-one in step 1 of Example 112. ¹H NMR (400 MHz, CDCl₃) δ=8.48-8.44 (m, 1H), 8.27 (s, 1H), 8.21 (s, 1H), 7.95 (d, J=1.6 Hz, 1H), 7.73 (d, J=7.2 Hz, 1H), 7.44 (d, J=8.8 Hz, 1H), 7.25 (s, 1H), 7.17 (dd, J=5.2, 7.2 Hz, 1H), 4.87-4.77 (m, 4H), 4.60-4.52 (m, 2H), 4.34-4.27 (m, 2H), 4.15 (s, 1H), 3.31-3.27 (m, 1H), 3.25 (s, 2H), 3.00 (d, J=16.4 Hz, 1H), 1.90-1.81 (m, 2H), 1.70-1.63 (m, 1H), 1.59-1.54 (m, 1H);

Example 141: (S)-6-((5-(5-amino-5,7-dihydrospiro[yclopenta[b]pyridine-6,4'-piperidin]-1'-yl)pyrazin-2-yl)thio)-5-chloro-3-(pyrimidin-4-ylmethyl)quinazolin-4(3H)-one

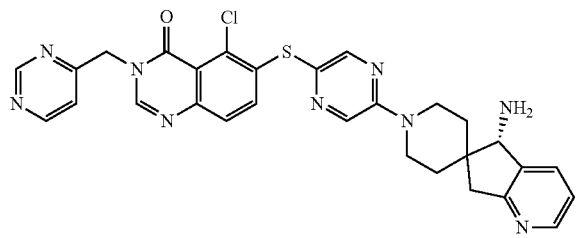 [SMILES: N[C@@H]1c2cccnc2CC12CCN(c1cnc(Sc3ccc4ncn(Cc5ccncn5)c(=O)c4c3Cl)cn1)CC2]

The compound of Example 141 (26 mg, 87%) was synthesized in the same method as in Example 112, except that 4-(chloromethyl)pyrimidine was used instead of 1-bromopropan-2-one in step 1 of Example 112. $^1$H NMR (400 MHz, CDCl$_3$) δ=9.15 (s, 1H), 8.74 (d, J=5.2 Hz, 1H), 8.44 (d, J=4.4 Hz, 1H), 8.27 (s, 1H), 8.22 (d, J=3.2 Hz, 2H), 7.66 (d, J=8.8 Hz, 1H), 7.51 (d, J=8.8 Hz, 1H), 7.46 (d, J=4.8 Hz, 1H), 7.30 (d, J=8.8 Hz, 1H), 7.20-7.16 (m, 1H), 5.17 (s, 2H), 4.37-4.28 (m, 2H), 4.06 (s, 1H), 3.32-3.19 (m, 3H), 2.91 (d, J=16.4 Hz, 1H), 1.92-1.87 (m, 1H), 1.82-1.80 (m, 1H), 1.71-1.67 (m, 1H), 1.46-1.38 (m, 1H); MS (EI) m/z: 584.1 [M+H]$^+$.

Example 142: 6-((5-((S)-5-amino-5,7-dihydrospiro[yclopenta[b]pyridine-6,4'-piperidin]-1'-yl)pyrazin-2-yl)thio)-5-chloro-3-(2-methoxypropyl)quinazolin-4(3H)-one

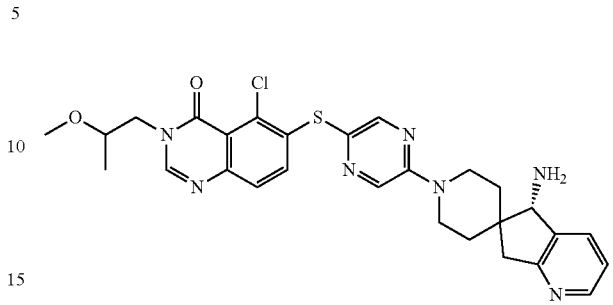

The compound of Example 142 (26 mg, 87%) was synthesized in the same method as in Example 112, except that 2-methoxypropyl-4-methylbenzenesulfonate was used instead of 1-bromopropan-2-one in step 1 of Example 112. $^1$H NMR (400 MHz, CDCl$_3$) δ=8.45 (d, J=4.4 Hz, 1H), 8.28 (s, 1H), 8.24 (s, 1H), 8.04 (s, 1H), 7.68 (d, J=5.6 Hz, 1H), 7.48 (d, J=8.8 Hz, 1H), 7.30 (d, J=8.8 Hz, 1H), 7.18 (t, J=6.0 Hz, 1H), 4.40-4.26 (m, 3H), 4.08 (s, 1H), 3.76-3.64 (m, 1H), 3.58-3.49 (m, 1H), 3.36-3.19 (m, 6H), 2.93 (d, J=16.8 Hz, 1H), 1.95-1.88 (m, 1H), 1.86-1.78 (m, 1H), 1.70 (d, J=12.0 Hz, 1H), 1.51-1.37 (m, 1H), 1.24 (d, J=6.0 Hz, 3H); MS (EI) m/z: 564.2 [M+H]$^+$.

Example 143: 6-((3-amino-5-((3S,4S)-4-amino-3-methyl-2-oxa-8-azaspiro[4.5]decan 8-yl)pyrazin-2-yl)thio)-5-chloro-3-(2-methoxyethyl)quinazolin-4(3H)-one

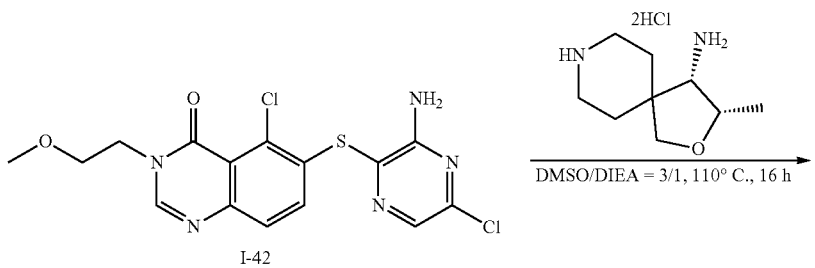

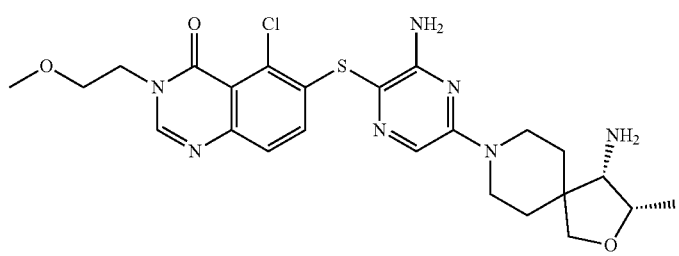

Intermediate I-42 (40 mg, 101 μmol), (3S,4S)-3-methyl-2-oxa-8-azaspiro[4.5]decan-4-amine (29.6 mg, 151 μmol) were dissolved in DMSO (3 mL), and DIEA (649 mg, 5.02 mmol) was added thereto, followed by stirring at 110° C. for 12 hours. After completion of the reaction, the reaction mixture was extracted with water and EA. The EA layer was dried over MgSO$_4$, filtered and then concentrated. The resulting product was separated by prep-HPLC and concentrated to obtain the compound of Example 143 (20 mg, 37% yield). $^1$H NMR (400 MHz, DMSO-d$_6$) δ =8.26 (s, 1H, FA), 8.25 (s, 1H), 7.67 (s, 1H), 7.52 (d, J=8.8 Hz, 1H), 6.99 (d, J=8.8 Hz, 1H), 6.14 (s, 2H), 4.13 (t, J=5.2 Hz, 2H), 4.10-4.05 (m, 1H), 3.88 (dd, J=4.0, 8.8 Hz, 2H), 3.70 (d, J=8.8 Hz, 1H), 3.62-3.59 (m, 2H), 3.51 (d, J=8.8 Hz, 2H), 3.33 (s, 2H), 3.26 (s, 3H), 2.95 (d, J=5.2 Hz, 1H), 1.78-1.70 (m, 1H), 1.64-1.62 (m, 1H), 1.55-1.44 (m, 2H), 1.10 (d, J=6.4 Hz, 3H); MS (EI) m/z: 532.2 [M+H]$^+$.

Example 144: 6-[5-[(6S)-6-aminospiro[4,6-dihydrocyclopenta[d]thiazole-5,4'-piperidin]-1'-yl]pyrazin-2-yl]sulfanyl-5-chloro-3-(2-methoxyethyl)quinazolin-4-one Step 1: (R)-N-[(6S)-1'-[5-[5-chloro-3-(2-methoxyethyl)-4-oxo-quinazolin-6-yl]sulfanylpyrazin-2-yl]spiro[4,6-dihydrocyclopenta[d]thiazole-5,4'-piperidin]-6-yl]-2-methyl-propane-2-sulfinamide To a solution of Intermediate I-29 (50 mg, 117 μmol) in dioxane(3 mL), Intermediate I-48 (36.7 mg, 117 μmol), [2-(2-aminophenyl)phenyl]-chloro-palladium; dicyclohexyl-[2-(2,6-diisopropoxyphenyl)phenyl]phosphane(9.08 mg, 11.7 μmol), RuPhos (10.9 mg, 23.4 μmol) and K$_2$CO$_3$ (48.8 mg, 351 μmol) were added. The mixture was stirred at 100° C. for 12 hours and filtered, and then the filtrate was concentrated under reduced pressure. The filtrate was purified by reverse phase flash column chromatography (0.1% FA) to obtain (R)—N-[(6S)-1'-[5-[5-chloro-3-(2-methoxyethyl)-4-oxo-quinazolin-6-yl]sulfanylpyrazin-2-yl]spiro[4,6-dihydrocyclopenta[d]thiazole-5,4'-piperidin]-6-yl]-2-methyl-propane-2-sulfinamide (20 mg, 26%) as a yellow solid. $^1$H NMR (400 MHz, CDCl$_3$) δ=8.82 (s, 1H), 8.29-8.27 (m, 1H), 8.24 (d, J=1.2 Hz, 1H), 8.03 (s, 1H), 7.50-7.46 (m, 1H), 7.25 (s, 1H), 4.66 (d, J=9.2 Hz, 1H), 4.42-4.30 (m, 2H), 4.16 (d, J=4.4 Hz, 2H), 3.70-3.68 (m, 2H), 3.66 (s, 1H), 3.33 (s, 3H), 3.27-3.18 (m, 2H), 3.10-3.04 (m, 1H), 2.99-2.92 (m, 1H), 2.08 (d, J=12.4 Hz, 2H), 1.89-1.82 (m, 1H), 1.77-1.73 (m, 1H), 1.24 (s, 9H).

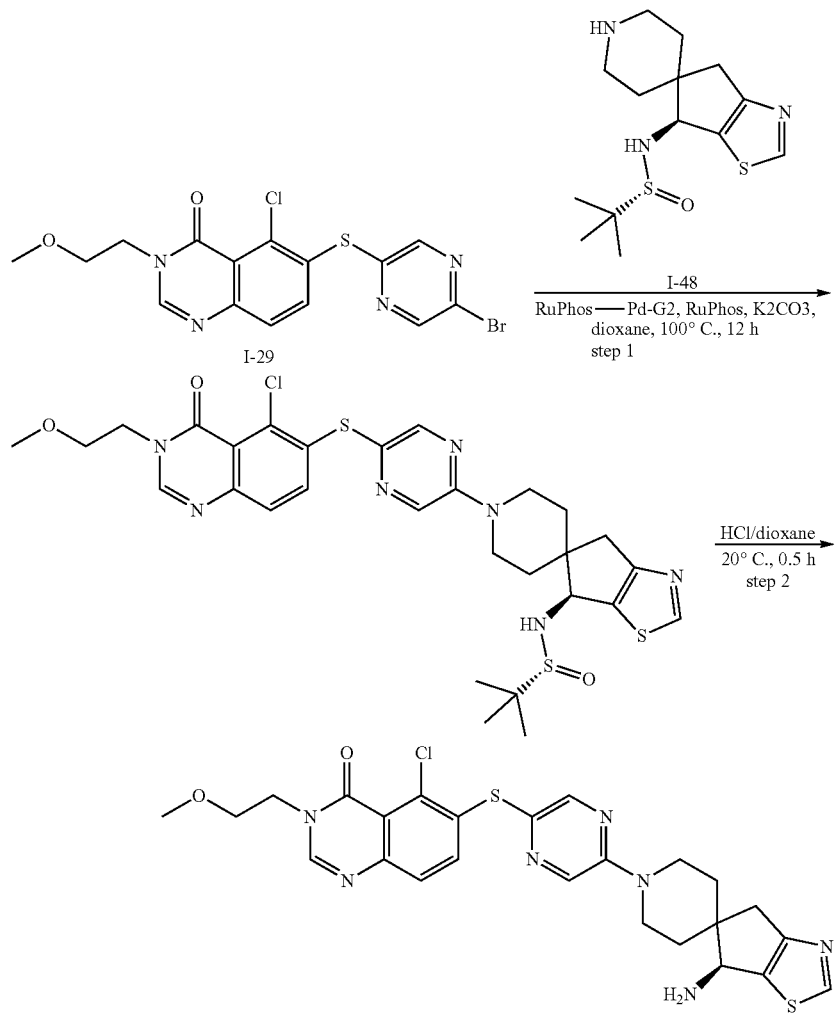

Step 2: 6-[5-[(6S)-6-aminospiro[4,6-dihydrocyclopenta[d]thiazole-5,4'-piperidin]-1'-yl]pyrazin-2-yl]sulfanyl-5-chloro-3-(2-methoxyethyl)quinazolin-4-one To a solution of (R)—N-[(6S)-1'-[5-[5-chloro-3-(2-methoxyethyl)-4-oxo-quinazolin-6-yl]sulfanylpyrazin-2-yl]spiro[4,6-dihydrocyclopenta[d]thiazole-5,4'-piperidin]-6-yl]-2-methyl-propane-2-sulfinamide (20 mg, 30.3 µmol) in methanol (3 mL) was added HCl/dioxane (4 M, 757 µL), followed by stirring at 25° C. for 0.5 hours. The reaction mixture was filtered, and then the filtrate was concentrated under reduced pressure. The filtrate was purified by column chromatography to obtain the compound of Example 144 (12 mg, 66% yield) as a yellow-white solid. $^1$H NMR (400 MHz, CDCl$_3$) δ=8.77 (s, 1H), 8.31-8.18 (m, 2H), 8.03 (s, 1H), 7.47 (d, J=8.8 Hz, 1H), 7.32-7.27 (m, 1H), 4.30-4.16 (m, 5H), 3.68 (br s, 2H), 3.42-3.24 (m, 5H), 3.01-2.89 (m, 2H), 2.01-1.78 (m, 4H); MS (EI) m/z: 556.0 [M+H]$^+$.

Example 145: 6-[5-[(6R)-6-aminospiro[4,6-dihydrocyclopenta[d]thiazole-5,4'-piperidin]-1'-yl]pyrazin-2-yl]sulfanyl-5-chloro-3-(2-methoxyethyl)quinazolin-4-one Step 1: (S)-N-[(6R)-1'-[5-[5-chloro-3-(2-methoxyethyl)-4-oxo-quinazolin-6-yl]sulfanylpyrazin-2-yl]spiro[4,6-dihydrocyclopenta[d]thiazole-5,4'-piperidin]-6-yl]-2-methyl-propane-2-sulfinamide TBAI (2.36 mg, 6.39 µmol), K$_2$CO$_3$ (26.5 mg, 191 µmol) and 1-bromo-2-methoxy-ethane (9.77 mg, 70.3 µmol) were added to Intermediate I-51 (55 mg, 63.9 µmol) in DMF (0.5 mL). The reaction mixture was stirred at 60° C. for 16 hours. The reaction mixture was diluted with water (10 mL) and extracted with EtOAc (3×5 mL). The combined organic layers were washed with brine (2×20 mL), dried over Na$_2$SO$_4$ and filtered, and the filtrate was concentrated under reduced pressure. The filtrate was purified by column chromatography to obtain (S)-N-[(6R)-1'-[5-[5-chloro-3-(2-methoxy ethyl)-4-oxo-quinazolin-6-yl]sulfanylpyrazin-2-yl]spiro[4,6-dihydrocyclopenta[d]thiazole-5,4'-piperidin]-6-yl]-2-methyl-propane-2-sulfinamide(30 mg, 63% yield) as a pale yellow solid. $^1$H NMR (400 MHz, CDCl$_3$) δ=8.82 (s, 1H), 8.28 (s, 1H), 8.24 (s, 1H), 8.04 (s, 1H), 7.49 (d, J=8.8 Hz, 1H), 7.25 (s, 1H), 4.67 (d, J=9.2 Hz, 1H), 4.45-4.30 (m, 2H), 4.14-4.10 (m, 1H), 3.72-3.62 (m, 3H), 3.33 (s, 3H), 3.31-3.17 (m, 2H), 3.09-3.03 (m, 1H), 2.98 (s, 1H), 2.94 (s, 1H), 2.13-2.06 (m, 2H), 1.90-1.81 (m, 1H), 1.78-1.71 (m, 1H), 1.24 (s, 9H); MS (EI) m/z: 660.3 [M+H]$^+$.

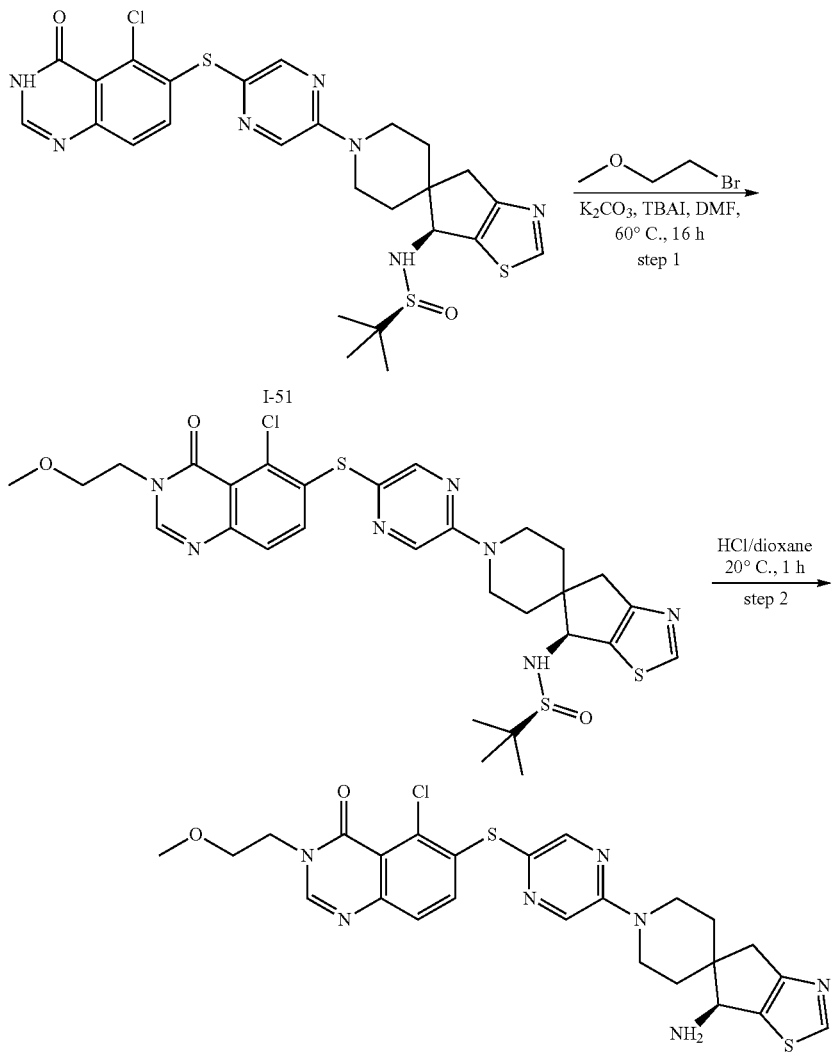

Step 2: 6-[5-[(6R)-6-aminospiro[4,6-dihydrocyclopenta[d]thiazole-5,4'-piperidin]-1'-yl]pyrazin-2-yl]sulfanyl-5-chloro-3-(2-methoxyethyl)quinazolin-4-one HCl/dioxane (4 M, 0.5 mL) was added to (S)—N-R6R)-1'4545-chloro-3-(2-methoxyethyl)-4-oxo-quinazolin-6-yl]sulfanylpyrazin-2-yl]spiro[4,6-dihydrocyclopenta[d]thiazole-5,4'-piperidin]-6-yl]-2-methyl-propane-2-sulfinamide (30 mg, 45.4 µmol) in methanol (0.5 mL). The reaction mixture was stirred at 20° C. for 1 hour. The reaction mixture was concentrated under reduced pressure and purified by column chromatography to obtain the compound of Example 145 (11.55 mg, 45.71% yield) as a pale yellow solid. $^1$H NMR (400 MHz, CDCl$_3$) δ=8.77 (s, 1H), 8.28 (s, 1H), 8.24 (s, 1H), 8.03 (s, 1H), 7.47 (d, J=8.8 Hz, 1H), 7.29 (d, J=8.8 Hz, 1H), 4.31-4.23 (m, 1H), 4.23-4.11 (m, 4H), 3.69 (t, J=4.8 Hz, 2H), 3.43-3.29 (m, 5H), 3.04-2.87 (m, 2H), 2.02-1.88 (m, 4H); MS (EI) m/z: 556.0 [M+H]$^+$.

Example 146: 6-]5-](6R)-6-aminospiro[4,6-d]hydrocyclopenta[d]thiazole-5,4'-pyrazin-2-yl]sulfanyl-5-chloro-3-(2-hydroxy-2-methyl-propyl)quinazolin-4-one

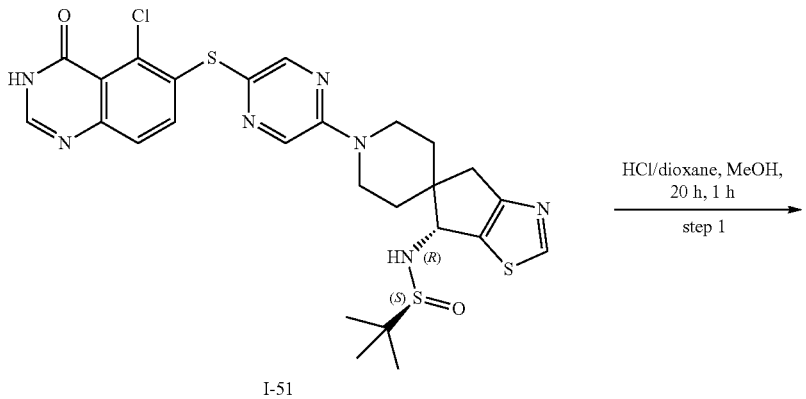

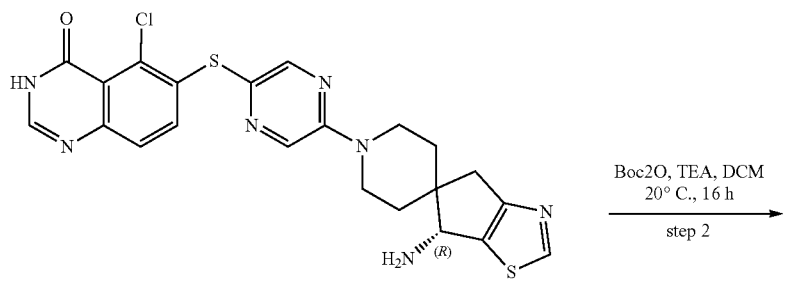

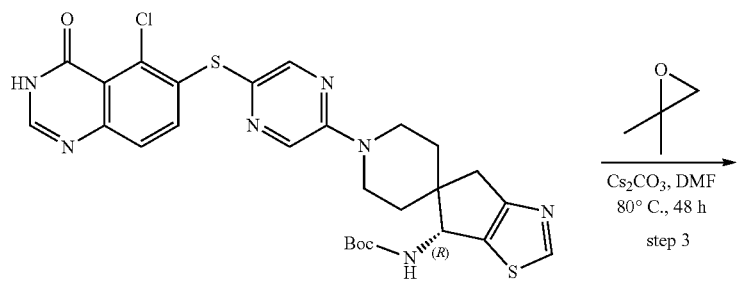

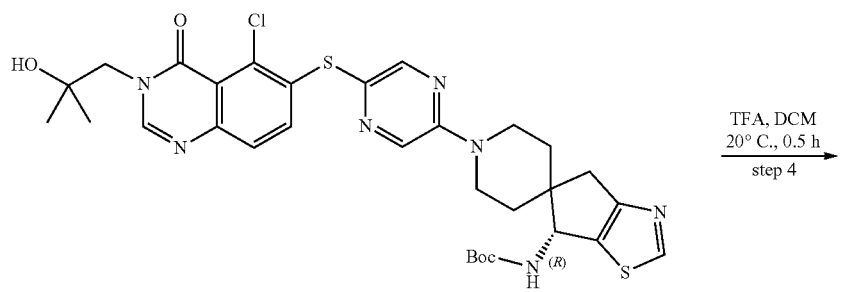

-continued

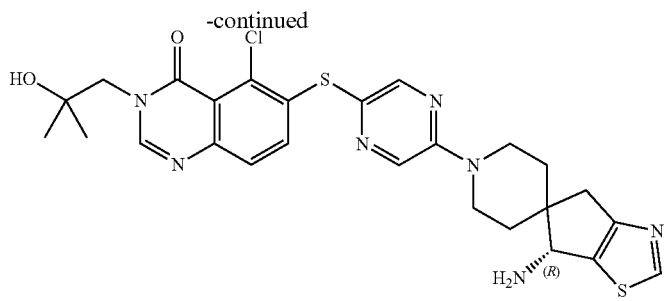

Step 1: 6-[5-[(6R)-6-aminospiro[4,6-dihydrocyclopenta[d]thiazole-5,4'-piperidin]-1'-yl]pyrazin-2-yl]sulfanyl-5-chloro-3H-quinazolin-4-one HCl/dioxane (4 M, 2 mL) was added to Intermediate I-51 (180 mg, 299 μmol) in methanol (2 mL). The reaction mixture was stirred at 20° C. for 1 hour. The reaction mixture was concentrated under reduced pressure to obtain 6-[5-[(6R)-6-aminospiro[4,6-dihydrocyclopenta[d]thiazole-5,4'-piperidin]-1'-yl]pyrazin-2-yl]sulfanyl-5-chloro-3H-quinazolin-4-one (150 mg, crude product, HCl) as a pale yellow solid. MS (EI) m/z: 520.2 [M+Na]$^+$.

Step 2: tert-butyl (R)-(1'-(5-((5-chloro-4-oxo-3,4-dihydroquinazolin-6-yl)thio)pyrazin-2-yl)-4,6-dihydrospiro[cyclopenta[d]thiazole-5,4'-piperidin]-6-yl)carbamate TEA (85.2 mg, 842 μmol) and tert-butoxycarbonyl tert-butyl carbonate (91.9 mg, 421 μmol) were added to 6-[5-[(6R)-6-aminospiro[4,6-dihydrocyclopenta[d]thiazole-5,4'-piperidin]-1'-yl]pyrazin-2-yl]sulfanyl-5-chloro-3H-quinazolin-4-one (150 mg, 281 HCl) in DCM (5 mL). The reaction mixture was stirred at 20° C. for 16 hours. The reaction mixture was diluted with water (20 mL) and extracted with EtOAc (3×5 mL). The combined organic layers were washed with brine (2×20 mL), dried over Na$_2$SO$_4$ and filtered, and then the filtrate was concentrated under reduced pressure. The filtrate was purified by column chromatography to obtain tert-butyl (R)-(1'-(5-((5-chloro-4-oxo-3,4-dihydroquinazolin-6-yl)thio)pyrazin-2-yl)-4,6-dihydrospiro[cyclopenta[d]thiazole-5,4'-piperidin]-6-yl)carbamate (100 mg, 46%) as a pale yellow solid. $^1$H NMR (400 MHz, CDCl$_3$) δ=8.82 (s, 1H), 8.32 (s, 1H), 8.29 (s, 1H), 8.24 (s, 1H), 7.46 (d, J=8.8 Hz, 1H), 7.25 (s, 1H), 5.05 (d, J=9.6 Hz, 1H), 4.71 (d, J=9.6 Hz, 1H), 4.26-4.16 (m, 2H), 3.54-3.43 (m, 1H), 3.42-3.31 (m, 1H), 2.99-2.88 (m, 2H), 1.99-1.91 (m, 2H), 1.87-1.79 (m, 2H), 1.67 (s, 9H); MS(O) m/z: 698.3 [M+H]$^+$.

Step 3: tert-butyl (R)-(1'-(54(5-chloro-3-(2-hydroxy-2-methylpropyl)-4-oxo-3,4-dihydroquinazolin-6-yl)thio)pyrazin-2-yl)-4,6-dihydrospiro[cyclopenta[d]thiazole-5,4'-piperidin]-6-yl)carbamate Cs$_2$CO$_3$ (74.7 mg, 229 μmol) and 2,2-dimethyloxirane (496 mg, 6.87 mmol) were added to tert-butyl (R)-(1'-(5-((5-chloro-4-oxo-3,4-dihydroquinazolin-6-yl)thio)pyrazin-2-yl)-4,6-dihydrospiro[cyclopenta[d]thiazole-5,4'-piperidin]-6-yl)carbamate (80 mg, 115 μmol) in DMF (2 mL). The reaction mixture was stirred at 80° C. for 48 hours. The reaction mixture was concentrated under reduced pressure and purified by column chromatography to obtain tert-butyl (R)-(1'-(5-((5-chloro-3-(2-hydroxy-2-methylpropyl)-4-oxo-3,4-dihydroquinazolin-6-yl)thio)pyrazin-2-yl)-4,6-dihydrospiro[cyclopenta[d]thiazole-5,4'-piperidin]-6-yl)carbamate (35 mg, 31% yield) as a pale yellow oil. $^1$H NMR (400 MHz, CDCl$_3$) δ=8.74 (s, 1H), 8.28-8.00 (m, 3H), 7.41 (d, J=8.8 Hz, 1H), 7.21 (d, J=9.6 Hz, 1H), 4.97 (d, J=9.6 Hz, 1H), 4.68-4.59 (m, 1H), 4.17-4.09 (m, 1H), 4.04-3.98 (m, 2H), 3.48-3.23 (m, 2H), 2.95-2.78 (m, 2H), 1.93-1.81 (m, 2H), 1.80-1.69 (m, 2H), 1.39 (s, 9H), 1.29-1.22 (m, 6H); MS (EI) m/z: 670.4 [M+H]$^+$.

Step 4: (R)-64(5-(6-amino-4,6-dihydrospiro[cyclopenta[d]thiazole-5,4'-piperidin-]-1'-yl)pyrazin-2-yl)thio)-5-chloro-3-(2-hydroxy-2-methylpropyl)quinazolin-4(3H)-one TFA (0.5 mL) was added to tert-butyl (R)-(1'-(5-((5-chloro-3-(2-hydroxy-2-methylpropyl)-4-oxo-3,4-dihydroquinazolin-6-yl)thio)pyrazin-2-yl)-4,6-dihydrospiro[cyclopenta[d]thiazole-5,4'-piperidin]-6-yl)carbamate (35 mg, 52.2 μmol) in DCM (1.5 mL). The reaction mixture was stirred at 20° C. for 0.5 hours. The reaction mixture was concentrated under reduced pressure and purified by column chromatography to obtain the compound of Example 146 (13.78 mg, 46%) as a white solid. $^1$H NMR (400 MHz, DMSO-d$_6$) δ =8.98 (s, 1H), 8.50 (s, 1H), 8.31 (d, J=1.2 Hz, 1H), 8.22-8.20 (m, 1H), 7.52 (d, J=8.8 Hz, 1H), 7.22 (d, J=8.8 Hz, 1H), 4.91-4.65 (m, 1H), 4.28-4.13 (m, 2H), 4.02 (s, 1H), 3.95 (s, 2H), 3.43-3.37 (m, 2H), 2.93-2.85 (m, 1H), 2.82-2.74 (m, 1H), 1.91-1.80 (m, 1H), 1.75-1.57 (m, 3H), 1.11 (s, 6H); MS (EI) m/z: 570.1 [M+H]$^+$.

Example 147: 6-[5-[(6S)-6-aminospiro[4,6-dihydrocyclopenta[d]thiazole-5,4'piperidin]1'-yl]pyrazin-2-yl]sulfanyl-5-chloro-3-(2-hydroxy-2-methyl-propyl)quinazolin-4-one

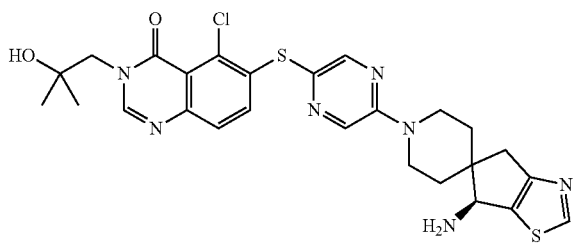 [SMILES: CC(C)(O)Cn1cnc2ccc(Sc3cnc(N4CCC5(CC4)Cc4ncsc4[C@H]5N)cn3)c(Cl)c2c1=O]

The compound of Example 147 (1.4 mg, 16%) was synthesized in the same method as in Example 146, except that Intermediate I-52 was used instead of Intermediate I-51 in step 1 of Example 146. $^1$H NMR (400 MHz, CDCl$_3$) δ=8.76 (s, 1H), 8.30 (s, 1H), 8.25 (s, 1H), 8.12 (s, 1H), 7.48 (d, J=8.8 Hz, 1H), 7.31 (s, 1H), 4.31-4.25 (m, 1H), 4.23-4.17 (m, 1H), 4.15 (s, 1H), 4.07 (s, 2H), 3.42-3.30 (m, 2H), 3.02-2.96 (m, 1H), 2.94-2.89 (m, 1H), 2.04-1.91 (m, 2H), 1.82-1.79 (m, 2H), 1.33 (s, 6H); MS (EI) m/z: 570.2 [M+H]$^+$.

Example 148: 6-[5-[(6R)-6-aminospiro[4,6-dihydro-cyclopenta[d]thiazole-5,4'piperidin]1'-yl]-pyrazin-2-yl]sulfanyl-5-chloro-3-(tetrahydropyran-4-ylmethyl)quinazolin-4-one

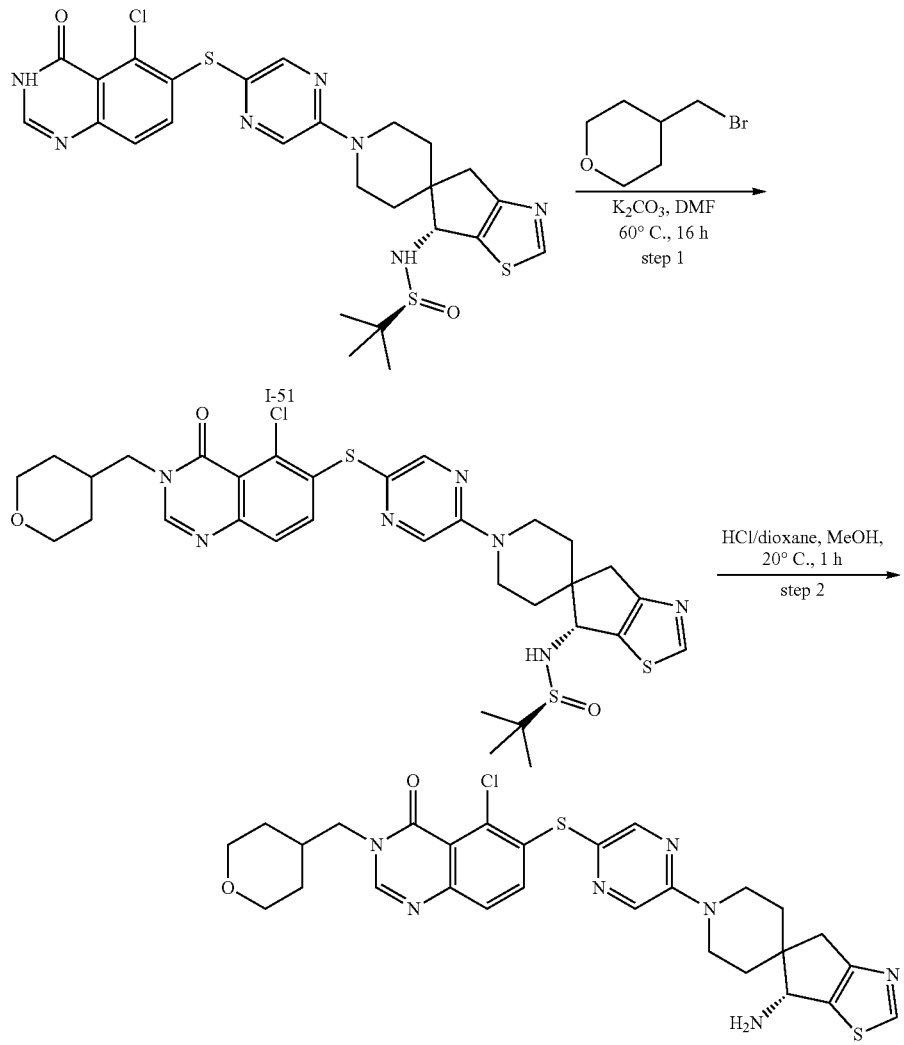

Step 1: (S)-N-[(6R)-1'-[5-[5-chloro-4-oxo-3-(tetrahydropyran-4-ylmethyl)quinazolin-6-yl]sulfanylpyrazin-2-yl]spiro[4,6-dihydrocyclopenta[d]thiazole-5,4'-piperidine-6-yl]-2-methyl-propane-2-sulfinamide $K_2CO_3$ (26.5 mg, 191 μmol) and 4-(bromomethyl)tetrahydropyran (12.5 mg, 70.3 μmol) were added to Intermediate I-51 (55 mg, 63.9 μmol) in DMF (0.5 mL). The reaction mixture was stirred at 60° C. for 16 hours. The reaction mixture was concentrated under reduced pressure, diluted with water (10 mL) and extracted with EtOAc (3×5 mL). The combined organic layers were washed with water (3×5 mL), dried over $Na_2SO_4$ and filtered, and then the filtrate was concentrated under reduced pressure. The residue was purified by column chromatography to obtain (S)-N-[(6R)-1'-[5-[5-chloro-4-oxo-3-(tetrahydropyran-4-ylmethyl)quinazolin-6-yl]sulfanylpyrazin-2-yl]spiro[4,6-dihydrocyclopenta[d]thiazole-5,4'-piperidine-6-yl]-2-methyl-propane-2-sulfinamide (25 mg, 44% yield) as a light yellow solid. $^1$H NMR (400 MHz, $CDCl_3$) δ=8.83 (s, 1H), 8.29 (s, 1H), 8.25 (s, 1H), 7.94 (s, 1H), 7.49 (d, J=8.8 Hz, 1H), 7.28-7.25 (m, 1H), 4.71-4.64 (m, 1H), 4.45-4.31 (m, 2H), 4.00 (dd, J=3.6, 11.6 Hz, 2H), 3.84 (d, J=7.2 Hz, 2H), 3.66 (d, J=9.2 Hz, 1H), 3.44-3.32 (m, 2H), 3.32-3.18 (m, 2H), 3.12-2.91 (m, 2H), 2.26-2.07 (m, 2H), 1.89-1.82 (m, 1H), 1.79-1.71 (m, 1H), 1.65-1.62 (m, 2H), 1.48-1.38 (m, 2H), 1.25 (s, 9H); MS (EI) m/z: 700.3 [M+H]$^+$.

Step 2: 6-[5-[(6R)-6-aminospiro[4,6-dihydrocyclopenta[d]thiazole-5,4'-piperidin]-1'-yl]pyrazin-2-yl]sulfanyl-5-chloro-3-(tetrahydropyran-4-ylmethyl)quinazolin-4-one HCl/dioxane (4 M, 0.5 mL) was added to (S)-N-[(6R)-1'-[5-[5-chloro-4-oxo-3-(tetrahydropyran-4-ylmethyl)quinazolin-6-yl]sulfanylpyrazin-2-yl]spiro[4,6-dihydrocyclopenta[d]thiazole-5,4'-piperidine-6-yl]-2-methyl-propane-2-sulfinamide (25 mg, 35.7 μmol) in methanol (0.5 mL). The reaction mixture was stirred at 20° C. for 1 hour. The reaction mixture was concentrated under reduced pressure and purified by column chromatography to obtain the compound of Example 148 (12.39 mg, 58%) as a white solid. $^1$H NMR (400 MHz, $CDCl_3$) δ=8.77 (s, 1H), 8.32-8.19 (m, 2H), 7.92 (s, 1H), 7.46 (d, J=8.8 Hz, 1H), 7.29 (d, J=8.8 Hz, 1H), 4.33-4.13 (m, 3H), 3.99 (dd, J=3.6, 11.2 Hz, 2H), 3.84 (d, J=7.2 Hz, 2H), 3.45-3.27 (m, 4H), 3.04-2.87 (m, 2H), 2.29-2.14 (m, 1H), 2.02-1.84 (m, 4H), 1.62 (d, J=11.2 Hz, 2H), 1.43-1.39 (m, 2H); MS (EI) m/z: 596.4 [M+H]$^+$.

Example 149: 6-[5-](6S)-6-aminospiro[4,6-dihydro-cyclopenta[d]thiazole-5,4'-piperidin]-1'-yl]pyrazin-2-yl]sulfanyl-5-chloro-3-(tetrahydropyran-4-ylmethyl)quinazolin-4-one

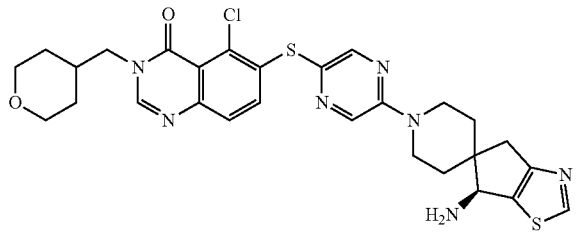 [SMILES: N[C@@H]1c2scnc2CC12CCN(c1cnc(Sc3ccc4ncn(CC5CCOCC5)c(=O)c4c3Cl)cn1)CC2]

The compound of Example 149 (3.97 mg, 31%) was synthesized in the same method as in Example 148, except that Intermediate I-52 was used instead of Intermediate I-51 in step 1 of Example 148. $^1$H NMR (400 MHz, CDCl$_3$) δ=8.79 (s, 1H), 8.29 (s, 1H), 8.25 (s, 1H), 7.93 (s, 1H), 7.46 (d, J=8.8 Hz, 1H), 7.29 (s, 1H), 4.30 (d, J=13.2 Hz, 1H), 4.26-4.16 (m, 2H), 3.99 (dd, J=3.2, 11.2 Hz, 2H), 3.84 (d, J=7.2 Hz, 2H), 3.42-3.27 (m, 4H), 3.04-2.92 (m, 2H), 2.29-2.15 (m, 1H), 2.00-1.91 (m, 1H), 1.87-1.74 (m, 3H), 1.62 (d, J=11.4 Hz, 2H), 1.32-1.47 (m, 2H); MS (EI) m/z: 596.1 [M+H]$^+$.

Example 150: 6-[5-[(4R)-4-aminospiro[4,6-dihydro-cyclopenta[d]thiazole-5,4'-piperidin]-1'-yl]pyrazin-2-yl]sulfanyl-5-chloro-3-(2-methoxyethyl)quinazolin-4-one

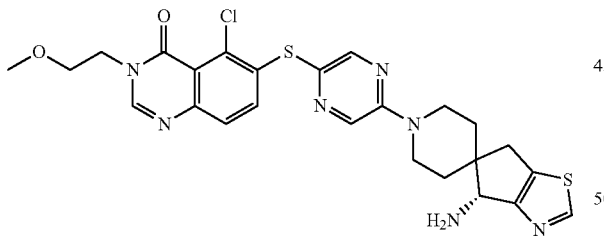

The compound of Example 150 (12.6 mg, 72%) was synthesized in the same method as in Example 144, except that Intermediate I-54 was used instead of Intermediate I-48 in step 1 of Example 144. $^1$H NMR (400 MHz, CDCl$_3$) δ=8.74 (s, 1H), 8.28 (s, 1H), 8.24 (s, 1H), 8.04 (s, 1H), 7.47 (d, J=8.8 Hz, 1H), 7.29 (d, J=8.8 Hz, 1H), 4.18-4.04 (m, 5H), 3.69 (t, J=4.8 Hz, 2H), 3.54-3.40 (m, 2H), 3.33 (s, 3H), 3.08-2.99 (m, 1H), 2.92-2.83 (m, 1H), 2.14-2.03 (m, 1H), 1.97-1.85 (m, 1H), 1.84-1.74 (m, 2H); MS (EI) m/z: 556.0 [M+H]$^+$.

Example 151: 6-[5-[(4S)-4-aminospiro[4,6-dihydro-cyclopenta[d]thiazole-5,4'-piperidin]-1'-yl]pyrazin-2-yl]sulfanyl-5-chloro-3-(2-methoxyethyl)quinazolin-4-one

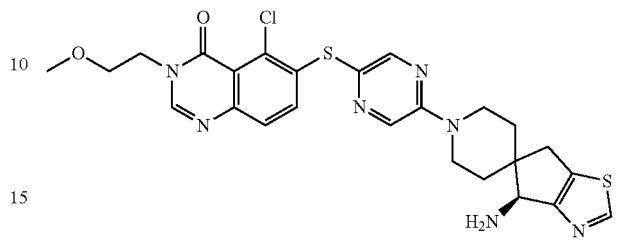

The compound of Example 151 (5.37 mg, 42%) was synthesized in the same method as in Example 150, except that Intermediate I-55 was used instead of Intermediate I-54 in step 1 of Example 150. $^1$H NMR (400 MHz, CDCl$_3$) δ=8.73 (s, 1H), 8.28 (s, 1H), 8.24 (s, 1H), 8.04 (s, 1H), 7.47 (d, J=8.8 Hz, 1H), 7.30-7.27 (m, 1H), 4.18-4.11 (m, 3H), 4.11-4.05 (m, 2H), 3.69 (t, J=4.8 Hz, 2H), 3.53-3.41 (m, 2H), 3.33 (s, 3H), 3.05-2.98 (m, 1H), 2.91-2.84 (m, 1H), 2.06 (s, 1H), 1.94-1.87 (m, 1H), 1.79 (d, J=13.6 Hz, 2H); MS (EI) m/z: 556.2 [M+H]$^+$.

Example 152: 6-[5-[(4R)-4-aminospiro[4,6-dihydro-cyclopenta[d]thiazole-5,4'-piperidin]-1'-yl]pyrazin-2-yl]sulfanyl-5-chloro-3-(2-hydroxy-2-methyl-propyl)quinazolin-4-one

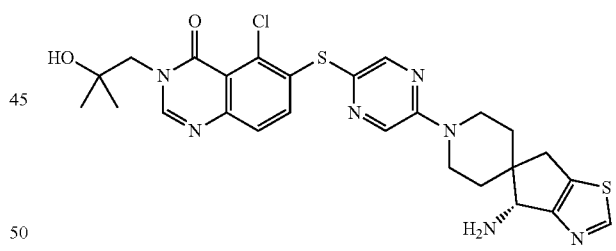

The compound (5.98 mg, 54%) of Example 152 was synthesized in the same method as in Example 146, except that Intermediate I-56 was used instead of Intermediate I-51 in step 1 of Example 146. $^1$H NMR (400 MHz, DMSO-d$_6$) δ=8.98 (s, 1H), 8.50 (s, 1H), 8.32-8.21 (m, 2H), 7.52 (d, J=8.8 Hz, 1H), 7.22 (d, J=8.8 Hz, 1H), 4.23-4.03 (m, 3H), 4.01-3.91 (m, 4H), 3.51-3.33 (m, 3H), 2.99-2.83 (m, 2H), 1.98-1.83 (m, 1H), 1.75-1.56 (m, 3H), 1.11 (s, 6H); MS (EI) m/z: 570.4 [M+H]$^+$.

Example 153: 6-[5-[(3S,4S)-4-amino-3-methyl-2-oxa-8-azaspiro[4.5]decan-8-yl]-6-(hydroxymethyl)pyrazin-2-yl]sulfanyl-5-chloro-3-(2-methoxyethyl)quinazolin-4-one

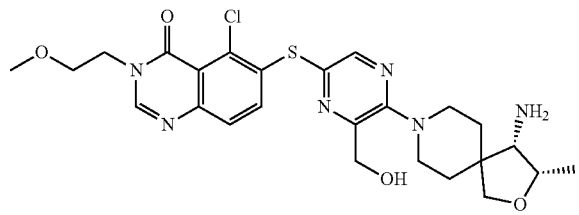

The compound of Example 153 (66.33 mg, 60% yield) was synthesized in the same method as in step 1 and step 3 of Example 18, except that Intermediate I-57 was used instead of Intermediate I-3 in step 1 of Example 18, and the product obtained in step 2 of Preparation Example 28 was used instead of Intermediate I-8. $^1$H NMR (400 MHz, CDCl$_3$) δ=8.32 (br s, 1H), 8.14 (s, 1H), 8.07 (s, 1H), 7.46-7.38 (m, 1H), 7.32 (d, J=8.4 Hz, 1H), 4.65-4.61 (m, 2H), 4.21 (s, 1H), 4.15 (s, 2H), 3.92 (d, J=8.4 Hz, 1H), 3.75-3.70 (m, 1H), 3.67 (t, J=4.8 Hz, 2H), 3.52 (d, J=8.4 Hz, 2H), 3.38 (s, 1H), 3.31 (s, 3H), 3.03-2.82 (m, 2H), 2.09-1.86 (m, 2H), 1.84-1.68 (m, 2H), 1.31 (s, 3H); MS (EI) m/z: 547.2 [M+H]$^+$.

Example 154: 5-amino-3-[(3S,4S)-4-amino-3-methyl-2-oxa-8-azaspiro[4.5]decan-8-yl]-6-[5-chloro-3-(2-methoxyethyl)-4-oxo-quinazolin-6-yl]sulfanyl-pyrazine-2-carboxamide

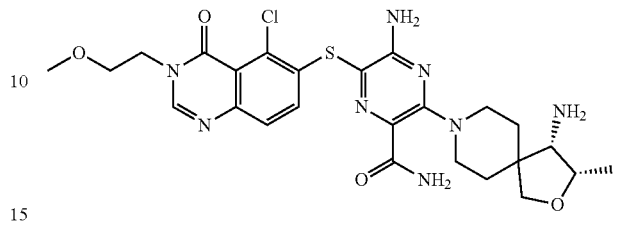

The compound of Example 154 (6.29 mg, 49%) was synthesized in the same method as in Example 153, except that Intermediate I-58 was used instead of Intermediate I-57 of Example 153. $^1$H NMR (400 MHz, CDCl$_3$) δ=8.04 (s, 1H), 7.47 (d, J=8.8 Hz, 1H), 7.27-7.23 (m, 1H), 7.17 (d, J=8.8 Hz, 1H), 5.35 (s, 1H), 5.23 (s, 2H), 4.25-4.12 (m, 3H), 3.87-3.75 (m, 3H), 3.72 (d, J=8.8 Hz, 1H), 3.69 (t, J=4.8 Hz, 2H), 3.33 (s, 3H), 3.32-3.19 (m, 2H), 3.06 (d, J=4.0 Hz, 1H), 2.02-1.93 (m, 1H), 1.84-1.81 (m, 1H), 1.72 (d, J=4.0 Hz, 2H), 1.26 (d, J=6.4 Hz, 3H); MS (EI) m/z: 575.0 [M+H]$^+$.

Example 155: 6-[6-acetyl-3-amino-5-1(3S,4S)-4-amino-3-methyl-2-oxa-8-azaspiro[4.5]decan-8-yl]pyrazin-2-yl]sulfanyl-5-chloro-3-(2-methoxyethyl)quinazolin-4-one

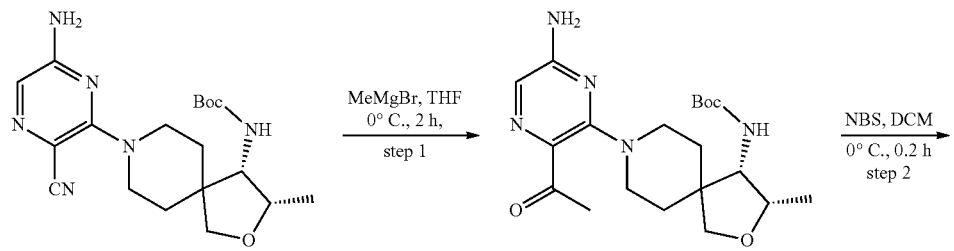

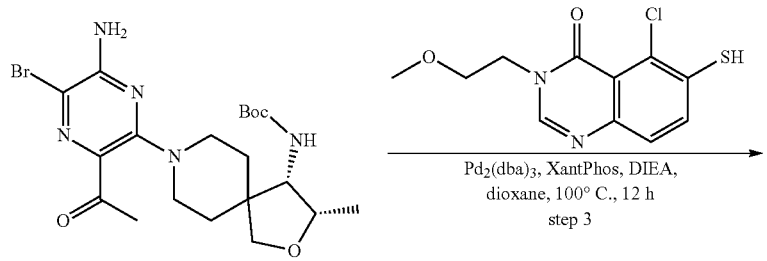

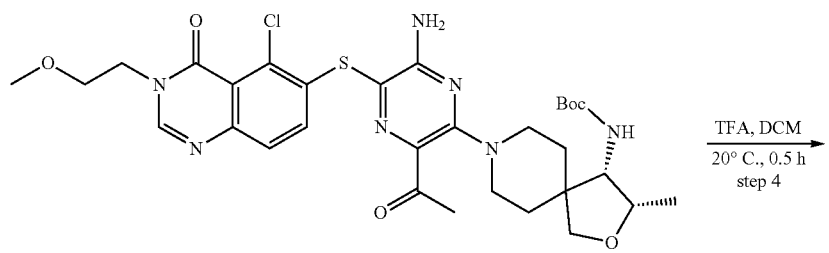

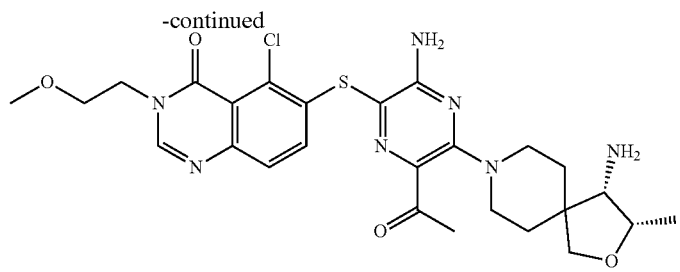

Step 1: tert-butyl N-[(3S,4S)-8-(3-acetyl-6-amino-pyrazin-2-yl)-3-methyl-2-oxa-8-azaspiro[4.5]decan-4-yl] carbamate MeMgBr (1 M, 7.72 mL) was added to tert-butyl N-[(3S,4S)-8-(6-amino-3-cyano-pyrazin-2-yl)-3-methyl-2-oxa-8-azaspiro[4.5]decan-4-yl]carbamate (300 mg, 772 μmol, the product obtained in step 3 of Preparation Example 56) in THF (2 mL), and then the reaction mixture was stirred at 0° C. for 2 hours. The reaction mixture was quenched with aqueous ammonium chloride solution (20 mL), diluted with water (30 mL) and then extracted with EtOAc (3×5 mL). The combined organic layers were washed with brine (3×20 mL), dried over $Na_2SO_4$ and filtered, and then the filtrate was concentrated under reduced pressure. The residue was purified by column chromatography to obtain tert-butyl N-[(3S,4S)-8-(3-acetyl-6-amino-pyrazin-2-yl)-3-methyl-2-oxa-8-azaspiro[4.5]decan-4-yl]carbamate (110 mg, 35% yield) as a yellow solid. $^1$H NMR (400 MHz, $CDCl_3$) δ=7.37 (s, 1H), 4.77 (s, 2H), 4.61 (d, J=10.8 Hz, 1H), 4.14-4.10 (m, 1H), 3.95 (dd, J=4.6, 10.7 Hz, 1H), 3.67 (t, J=3.6 Hz, 1H), 3.63-3.57 (m, 1H), 3.53-3.47 (m, 1H), 3.36-3.29 (m, 1H), 3.27-3.19 (m, 1H), 2.56 (s, 3H), 1.87-1.82 (m, 1H), 1.77 (d, J=4.8 Hz, 1H), 1.67-1.60 (m, 2H), 1.44 (s, 9H), 1.19 (d, J=6.4 Hz, 3H).

Step 2: tert-butyl N-[(3S,4S)-8-(3-acetyl-6-amino-5-bromo-pyrazin-2-yl)-3-methyl-2-oxa-8-azaspiro[4.5]decan-4-yl]carbamate NBS (46.1 mg, 259 μmol) was added to tert-butyl N-[(3S,4S)-8-(3-acetyl-6-amino-pyrazin-2-yl)-3-methyl-2-oxa-8-azaspiro[4.5]decan-4-yl]carbamate (100 mg, 247 μmol) in DCM (2 mL), followed by stirring at 0° C. for 0.2 hours. The reaction mixture was quenched with aqueous ammonium chloride solution (10 mL), diluted with water (20 mL) and then extracted with DCM (3×30 mL). The combined organic layers were washed with brine (3×20 mL), dried over $Na_2SO_4$ and filtered, and then the filtrate was concentrated under reduced pressure. The residue was purified by column chromatography to obtain tert-butyl N-[(3S,4S)-8-(3-acetyl-6-amino-5-bromo-pyrazin-2-yl)-3-methyl-2-oxa-8-azaspiro[4.5]decan-4-yl]carbamate (100 mg, 84% yield) as a yellow solid. $^1$H NMR (400 MHz, $CDCl_3$) δ=5.20 (s, 2H), 4.60 (d, J=10.8 Hz, 1H), 3.95 (dd, J=4.4, 10.8 Hz, 1H), 3.70-3.65 (m, 2H), 3.59-3.51 (m, 1H), 3.50-3.42 (m, 1H), 3.35-3.31 (m, 1H), 3.27-3.19 (m, 1H), 2.53 (s, 3H), 1.85-1.80 (m, 1H), 1.79-1.76 (m, 1H), 1.67-1.59 (m, 2H), 1.46-1.43 (m, 9H), 1.18 (d, J=6.4 Hz, 3H).

Step 3 and Step 4: 6-[6-acetyl-3-amino-5-1(3S,4S)-4-amino-3-methyl-2-oxa-8-azaspiro[4.5]decan-8-yl]pyrazin-2-yl]sulfanyl-5-chloro-3-(2-methoxyethyl)quinazolin-4-one The compound of Example 155 (6.78 mg, 53%) was synthesized in the same method as in step 1 and step 2 of Example 153. $^1$H NMR (400 MHz, $CDCl_3$) δ=8.04 (s, 1H), 7.48 (d, J=8.8 Hz, 1H), 7.26-7.23 (m, 1H), 5.48 (s, 2H), 4.28-4.22 (m, 1H), 4.16 (t, J=4.4 Hz, 2H), 3.91 (d, J=8.8 Hz, 1H), 3.83-3.77 (m, 1H), 3.73 (d, J=8.8 Hz, 2H), 3.68 (t, J=4.8 Hz, 2H), 3.33 (s, 3H), 3.29-3.24 (m, 1H), 3.15 (s, 2H), 2.54 (s, 3H), 2.10-2.00 (m, 1H), 1.97-1.88 (m, 1H), 1.78-1.68 (m, 2H), 1.34 (d, J=6.4 Hz, 3H); MS (EI) m/z: 574.2 [M+H]$^+$.

Example 156: 6-[5-[(3S,4S)-4-amino-3-methyl-2-oxa-8-azaspiro[4.5]decan-8-yl]pyrazin-2-yl]sulfanyl-5-fluoro-3-(2-methoxyethyl)quinazolin-4-one

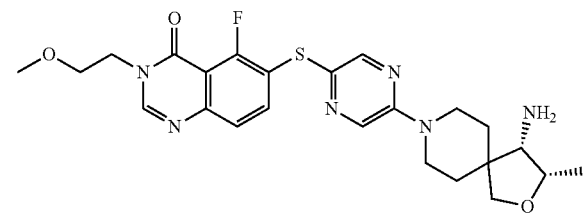

The compound of Example 156 (16.87 mg, 52%) was synthesized in the same method as in Example 153, except that Intermediate I-33 was used instead of Intermediate I-57, and Intermediate I-59 was used instead of the product obtained in step 2 of Preparation Example 28, sodium[5-chloro-3-(2-methoxyethyl)-4-oxo-quinazolin-6-yl]sulfanyl. $^1$H NMR (400 MHz, $CDCl_3$) δ=8.29-8.21 (m, 1H), 8.19 (s, 1H), 8.10-8.01 (m, 2H), 7.71-7.62 (m, 1H), 7.43 (d, J=8.8 Hz, 1H), 4.25-4.20 (m, 1H), 4.17-4.11 (m, 3H), 4.04-3.92 (m, 3H), 3.88 (d, J=8.8 Hz, 1H), 3.73 (d, J=8.8 Hz, 1H), 3.66 (t, J=4.8 Hz, 2H), 3.35-3.25 (m, 4H), 3.25-3.10 (m, 2H), 1.96-1.65 (m, 4H), 1.29 (d, J=6.4 Hz, 3H); MS (EI) m/z: 501.2 [M+H]$^+$.

Example 157: 6-[5-[(6R)-6-amino-2-chloro-spiro[4,6-dihydrocyclopenta[d]thiazole-5,4'-piperidin]-1'-yl]pyrazin-2-yl]sulfanyl-5-chloro-3-(2-methoxyethyl)quinazolin-4-one

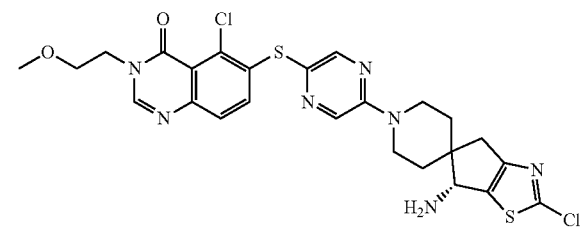 [SMILES: COCCn1cnc2ccc(Sc3cnc(N4CCC5(CC4)Cc4nc(Cl)sc4[C@@H]5N)cn3)c(Cl)c2c1=O]

The compound of Example 157 (11.89 mg, 46%) was synthesized in the same method as in Example 144, except that Intermediate I-60 was used instead of Intermediate I-48 in Example 144. $^1$H NMR (400 MHz, CDCl$_3$) δ=8.28 (s, 1H), 8.23 (s, 1H), 8.03 (s, 1H), 7.47 (d, J=8.8 Hz, 1H), 7.29 (d, J=8.8 Hz, 1H), 4.29-4.21 (m, 1H), 4.19 (d, J=4.0 Hz, 4H), 3.68 (t, J=4.8 Hz, 2H), 3.42-3.25 (m, 5H), 2.96-2.80 (m, 2H), 1.98-1.87 (m, 1H), 1.85-1.76 (m, 3H); MS (EI) m/z: 612.1 [M+Na]$^+$.

Example 158: 6-[5-[(1S)-1-amino-6-methoxy-spiro [indane-2,4'-piperidin]-1'-yl]pyrazin-2-yl]sulfanyl-5-chloro-3-(2-methoxyethyl)quinazolin-4-one

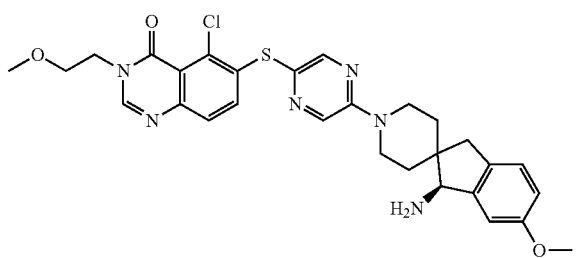

The compound of Example 158 (18 mg, 69%) was synthesized in the same method as in Example 144, except that Intermediate I-61 was used instead of Intermediate I-48 in Example 144. $^1$H NMR (400 MHz, CDCl$_3$) δ=8.29 (d, J=1.2 Hz, 1H), 8.26 (s, 1H), 8.04 (s, 1H), 7.48 (d, J=8.8 Hz, 1H), 7.30-7.28 (m, 1H), 7.14 (d, J=8.8 Hz, 1H), 7.00 (s, 1H), 6.82 (dd, J=2.4, 8.0 Hz, 1H), 4.29-4.20 (m, 2H), 4.16 (t, J=4.8 Hz, 2H), 4.03 (s, 1H), 3.82 (s, 3H), 3.70 (t, J=4.8 Hz, 2H), 3.34 (s, 3H), 3.31-3.21 (m, 2H), 3.07 (d, J=15.6 Hz, 1H), 2.76 (d, J=15.6 Hz, 1H), 1.90-1.77 (m, 2H), 1.65 (d, J=13.2 Hz, 1H), 1.48 (d, J=12.4 Hz, 1H); MS (EI) m/z: 579.2 [M+H]$^+$.

Example 159: 6-[5-[(5R)-5-aminospiro[5,7-dihydro-cyclopenta[b]pyridine-6,4'-piperidin]-1'-yl]pyrazin-2-yl]sulfanyl-5-chloro-3-(2-hydroxy-2-methylpropyl)quinazolin-4-one

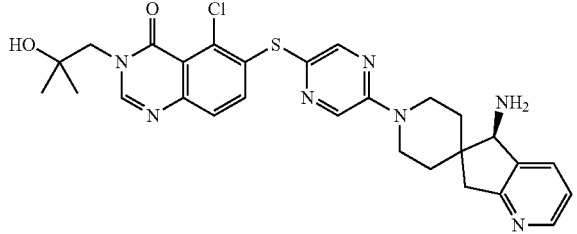 [SMILES: CC(C)(O)Cn1cnc2ccc(Sc3cnc(N4CCC5(CC4)Cc4ncccc4[C@@H]5N)cn3)c(Cl)c2c1=O]

The compound of Example 159 (3.36 mg, 26% yield) was synthesized in the same method as in step 3 and step 4 of Example 146, except that Intermediate I-39 was used as a starting material in step 3 of Example 146. $^1$H NMR (400 MHz, CDCl$_3$) δ=8.44 (d, J=4.8 Hz, 1H), 8.29 (d, J=1.2 Hz, 1H), 8.24 (d, J=1.2 Hz, 1H), 8.12 (s, 1H), 7.66 (d, J=7.8 Hz, 1H), 7.47 (d, J=8.8 Hz, 1H), 7.29 (d, J=8.8 Hz, 1H), 7.17 (dd, J=5.0, 7.6 Hz, 1H), 4.36-4.27 (m, 2H), 4.12-3.99 (m, 3H), 3.29-3.21 (m, 3H), 2.91 (d, J=16.4 Hz, 1H), 1.85-1.82 (m, 2H), 1.69 (dd, J=2.0, 13.3 Hz, 1H), 1.43 (d, J=11.2 Hz, 1H), 1.32 (s, 6H); MS (EI) m/z: 564.2 [M+H]$^+$.

Example 160: 6-[5-[(4S)-4-amino[4,6-dihydrocyclopenta[d]thiazole-5,4'-piperidin]-1'-yl]pyrazin-2-yl] sulfanyl-5-chloro-3-(2-hydroxy-2-methyl-propyl) quinazolin-4-one

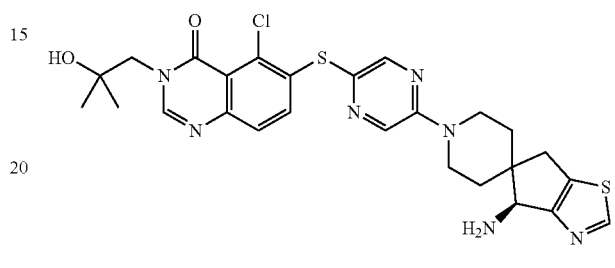

The compound of Example 160 (7 mg, 55% yield) was synthesized in the same method as in Example 146, except that Intermediate I-62 was used instead of Intermediate I-51 in step 1 of Example 146. $^1$H NMR (400 MHz, CDCl$_3$) δ=8.72 (s, 1H), 8.29 (s, 1H), 8.25 (s, 1H), 8.12 (s, 1H), 7.48 (d, J=8.8 Hz, 1H), 7.31-7.28 (m, 1H), 4.15-4.08 (m, 2H), 4.08-4.04 (m, 3H), 3.56-3.43 (m, 2H), 3.04-2.95 (m, 1H), 2.90-2.82 (m, 1H), 2.13-2.04 (m, 1H), 1.92-1.86 (m, 1H), 1.32 (s, 6H), 1.31-1.23 (m, 2H); MS (EI) m/z: 570.2 [M+H]$^+$.

Example 161: 6-[5-[(6S)-6-amino-2-chloro-spiro[4, 6-dihydrocyclopenta[d]thiazole-5,4'-piperidin]-1'-yl] pyrazin-2-yl]sulfanyl-5-chloro-3-(2-methoxyethyl) quinazolin-4-one

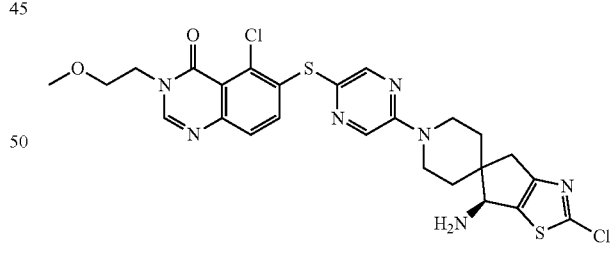

The compound of Example 161 (13 mg, 50% yield) was synthesized as a white solid in the same method as in Example 144, except that Intermediate I-63 was used instead of Intermediate 1-48 in Example 144. $^1$H NMR (400 MHz, CDCl$_3$) δ=8.28 (d, J=1.2 Hz, 1H), 8.24 (s, 1H), 8.04 (s, 1H), 7.47 (d, J=8.8 Hz, 1H), 7.30 (d, J=8.8 Hz, 1H), 4.29-4.22 (m, 1H), 4.21-4.13 (m, 3H), 4.11 (s, 1H), 3.69 (t, J=4.8 Hz, 2H), 3.41-3.35 (m, 1H), 3.33 (s, 3H), 3.33-3.28 (m, 1H), 2.95-2.82 (m, 2H), 1.91 (dd, J=3.6, 10.8 Hz, 1H), 1.85-1.79 (m, 2H), 1.75-1.72 (m, 1H); MS (EI) m/z: 612.1 [M+Na]$^+$.

Example 162: (S)-6-((5-(1-amino-6-methoxy-1,3-dihydrospiro[indene-2,4'-piperidin]-1'-yl)pyrazin-2-yl)thio)-5-chloro-3-(2-hydroxy-2-methylpropyl)quinazolin-4(3H)-one
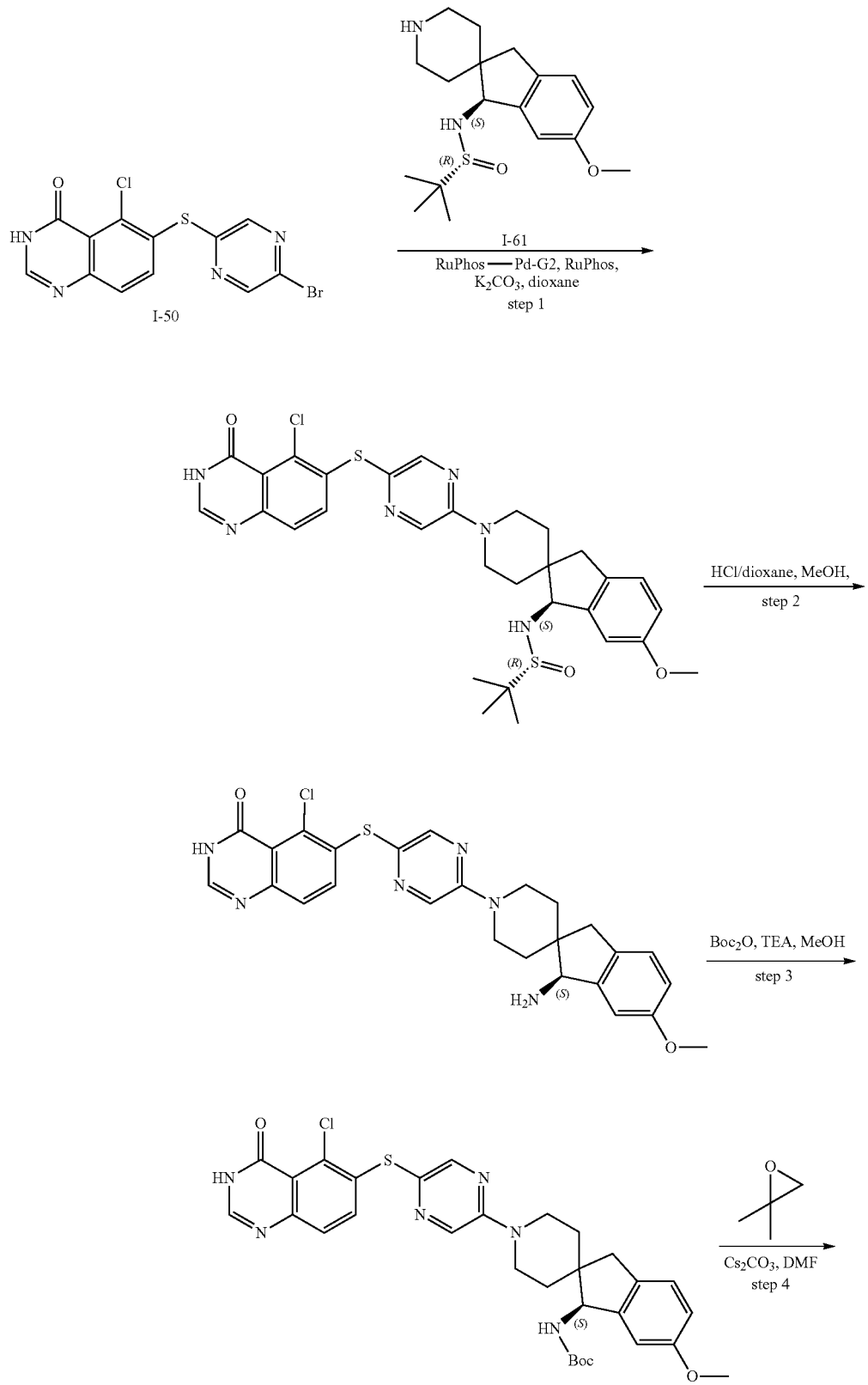

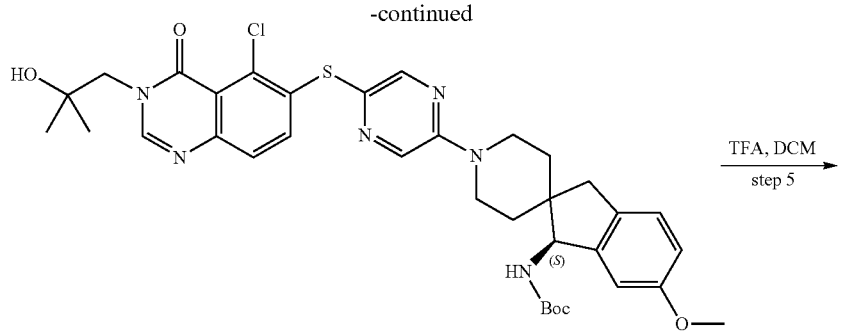

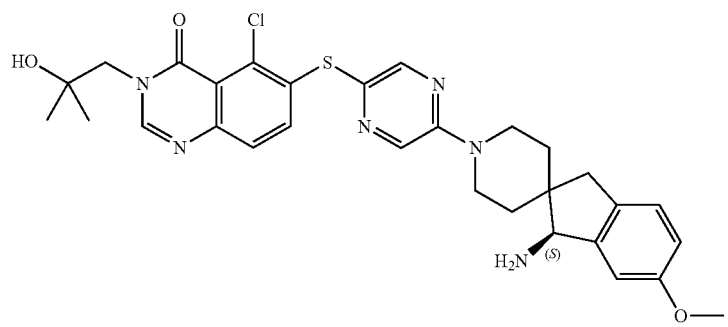

Step 1 and Step 2: (S)-6-((5-(1-amino-6-methoxy-1,3-dihydrospiro[indene-2,4'-piperidin]-1'-yl)pyrazin-2-yl)thio)-5-chloroquinazolin-4(3H)-one (S)-6-((5-(1-amino-6-methoxy-1,3-dihydrospiro[indene-2,4'-piperidin]-1'-yl)pyrazin-2-yl)thio)-5-chloroquinazolin-4(3H)-one (250 mg, crude product) was synthesized as a yellow solid in the same method as in Example 144, except that, in Example 144, Intermediate I-50 was used instead of Intermediate I-29, and Intermediate I-61 was used instead of Intermediate I-48. MS (EI) m/z: 521.3 [M+H]⁺.

Step 3 to Step 5: (S)-tert-butyl (1'-(5-((5-chloro-3-(2-hydroxy-2-methylpropyl)-4-oxo-3,4-dihydroquinazolin-6-yl)thio)pyrazin-2-yl)-5-methoxy-1,3-dihydrospiro[indene-2,4'-piperidin]-3-yl)carbamate The compound of Example 162 (9.53 mg, 45% yield) was synthesized as a white solid in the same method as in steps 2 to 4 of Example 146, except that (S)-6-((5-(1-amino-6-methoxy-1,3-dihydrospiro[indene-2,4'-piperidin]-1'-yl)pyrazin-2-yl)thio)-5-chloroquinazolin-4(3H)-one was used as a starting material in step 3 of Example 146. ¹H NMR (400 MHz, CDCl₃) δ=8.28 (s, 1H), 8.23-8.21 (m, 1H), 8.11 (s, 1H), 7.46 (d, J=8.8 Hz, 1H), 7.25 (s, 1H), 7.12 (d, J=8.0 Hz, 1H), 6.93 (d, J=1.6 Hz, 1H), 6.79 (dd, J=2.0, 8.0 Hz, 1H), 4.30-4.21 (m, 2H), 4.06 (s, 2H), 4.00 (s, 1H), 3.79 (s, 3H), 3.29-3.19 (m, 2H), 3.05 (d, J=15.6 Hz, 1H), 2.73 (d, J=15.6 Hz, 1H), 1.90-1.75 (m, 2H), 1.68-1.62 (m, 1H), 1.51-1.44 (m, 1H), 1.32 (s, 6H); MS (EI) m/z: 615.2 [M+Na]⁺.

Example 163: (S)-6-((5-(1-amino-6-hydroxy-1,3-dihydrospiro(indene-2,4'-piperidin]-1'-yl)pyrazin-2-yl)thio)-5-chloro-3-(2-methoxyethyl)quinazolin-4 (31-1)-one

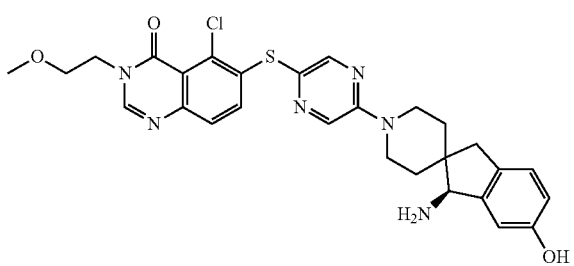 [SMILES: COCCn1cnc2ccc(Sc3cnc(N4CCC5(CC4)Cc4ccc(O)cc4[C@H]5N)cn3)c(Cl)c2c1=O]

The compound of Example 163 (7.14 mg, 85% yield) was synthesized as a yellow solid in the same method as in Example 144, except that Intermediate I-64 was used instead of Intermediate 1-48 in Example 144. ¹H NMR (400 MHz, MeOD-d₄) δ=8.38-8.24 (m, 2H), 8.22-8.12 (m, 1H), 7.51-7.39 (m, 1H), 7.34-7.20 (m, 1H), 7.17-7.07 (m, 1H), 6.95-6.84 (m, 1H), 6.81-6.70 (m, 1H), 4.79-4.76 (m, 1H), 4.44-4.27 (m, 2H), 4.25-4.12 (m, 3H), 3.75-3.61 (m, 2H), 3.29-3.22 (m, 3H), 3.16-2.88 (m, 3H), 1.88-1.75 (m, 2H), 1.71-1.59 (m, 2H); MS (EI) m/z: 564.2 [M+H]⁺.

Example 164: (S)-6-((3-amino-5-(6-amino-4,6-dihydrospiro[cyclopenta[d]thiazole-5,4'-piperidin]-1'-yl)pyrazin-2-yl)thio)-5-chloro-3-(2-methoxyethyl)quinazolin-4(3H)-one

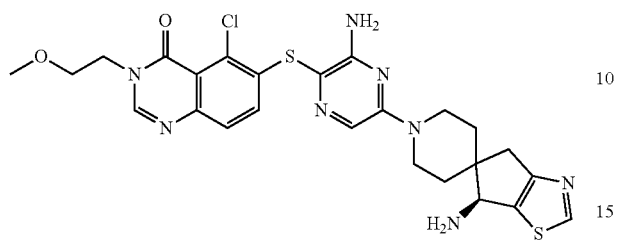

The compound of Example 164 (14.6 mg, 34% yield) was synthesized as a yellow solid in the same method as in Example 144, except that Intermediate I-42 was used instead of Intermediate I-29 in Example 144. $^1$H NMR (400 MHz, CDCl$_3$) δ=8.76 (s, 1H), 8.02 (s, 1H), 7.70 (s, 1H), 7.45 (d, J=8.8 Hz, 1H), 7.19-7.14 (m, 1H), 4.88 (s, 2H), 4.26-4.19 (m, 1H), 4.18-4.10 (m, 4H), 3.69 (t, J=4.8 Hz, 2H), 3.37-3.27 (m, 5H), 3.01-2.86 (m, 2H), 1.96-1.87 (m, 1H), 1.84-1.79 (m, 1H), 1.71-1.64 (m, 2H); MS (EI) m/z: 571.2 [M+H]$^+$.

Example 165: (S)-6-((3-amino-5-(4-amino-4,6-dihydrospiro[cyclopenta[d]thiazole-5,4'-piperidin]-1'-yl)pyrazin-2-yl)thio)-5-chloro-3-(2-hydroxy-2-methylpropyl)quinazolin-4(3H)-one

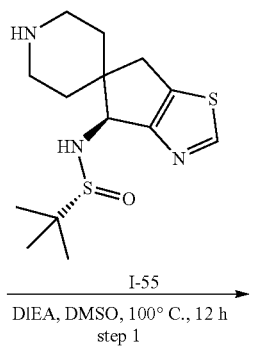

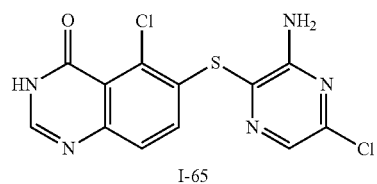
I-65

I-55
DIEA, DMSO, 100° C., 12 h
step 1

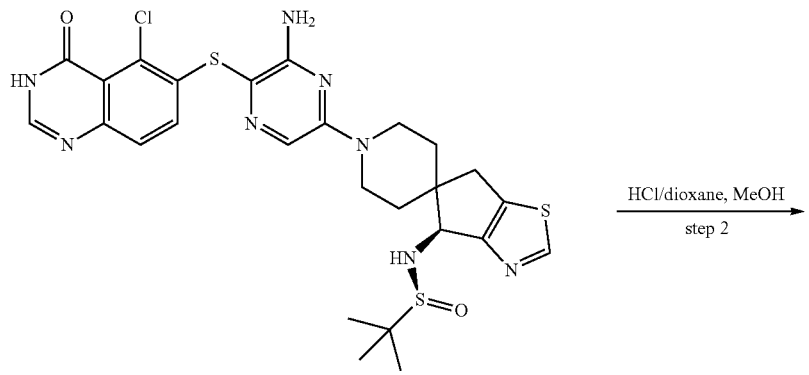

HCl/dioxane, MeOH
step 2

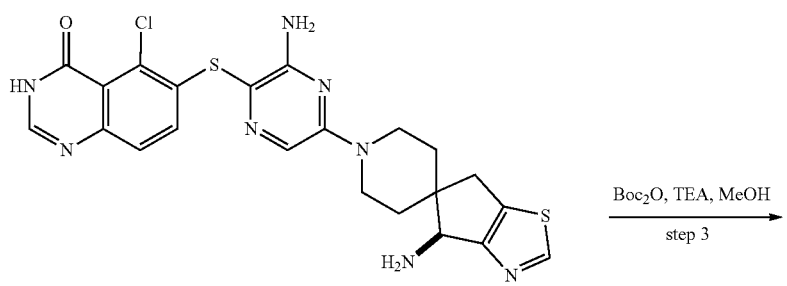

Boc$_2$O, TEA, MeOH
step 3

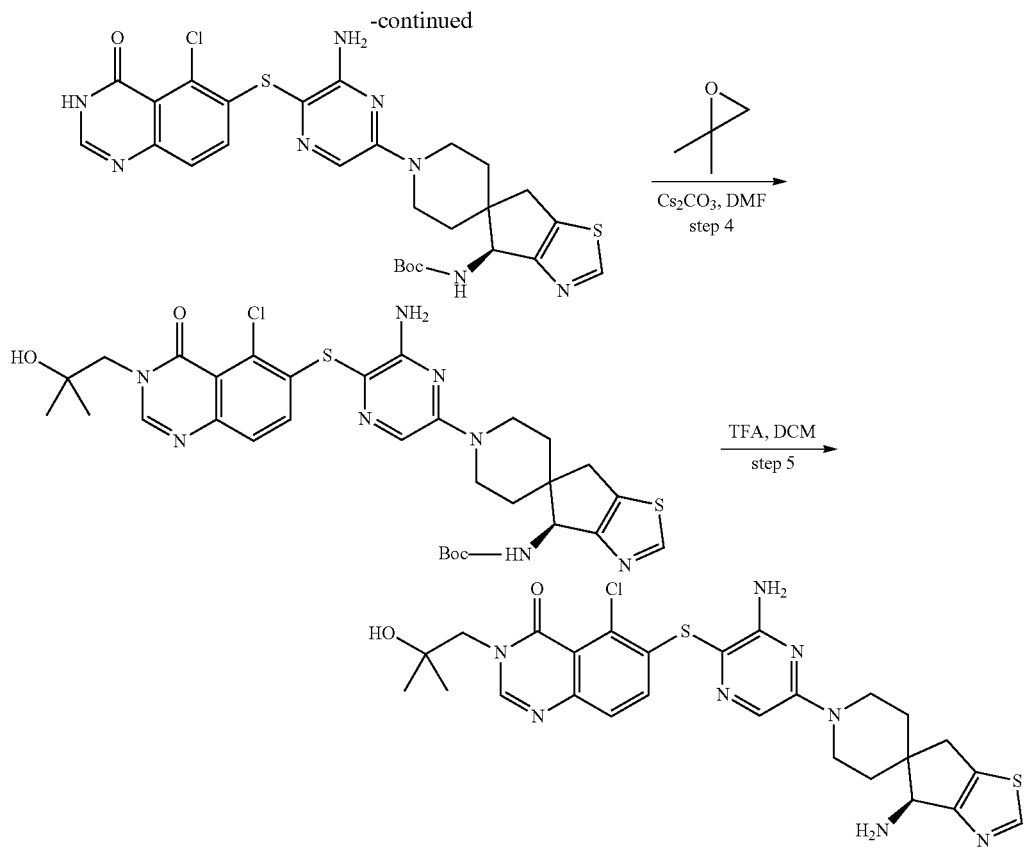

Step 1: (R)-N-((S)-1'-(6-amino-5-((5-chloro-4-oxo-3,4-dihydroquinazolin-6-yl)thio)pyrazin-2-yl)-4,6-dihydrospiro[cyclopenta[d]thiazole-5,4'-piperidin]-4-yl)-2-methylpropane-2-sulfinamide To a solution of Intermediate I-65 (200 mg, 588 μmol) in DMSO (3 mL), DIEA (2.28 g, 17.6 mmol) and Intermediate I-55 (184 mg, 588 μmol) were added, and then the mixture was stirred at 100° C. for 12 hours. The reaction mixture was quenched with aqueous ammonium chloride solution (10 mL), diluted with water (30 mL) and then extracted with EtOAc (3×10 mL). The combined organic layers were washed with brine (3×10 mL), dried over Na$_2$SO$_4$ and filtered, and then the filtrate was concentrated under reduced pressure. The residue was purified by column chromatography to obtain (R)-N-((S)-1'-(6-amino-5-((5-chloro-4-oxo-3,4-dihydroquinazolin-6-yl)thio)pyrazin-2-yl)-4,6-dihydrospiro[cyclopenta[d]thiazole-5,4'-piperidin]-4-yl)-2-methylpropane-2-sulfinamide (180 mg, 50% yield) as a brown solid. $^1$H NMR (400 MHz, CDCl$_3$) δ=10.87-10.74 (m, 1H), 8.76 (s, 1H), 7.96 (s, 1H), 7.65 (s, 1H), 7.49-7.40 (m, 2H), 7.15-7.10 (m, 1H), 4.96-4.87 (m, 2H), 4.60-4.54 (m, 1H), 4.28-4.21 (m, 1H), 4.19-4.12 (m, 1H), 4.02 (d, J=9.2 Hz, 1H), 3.30-3.18 (m, 2H), 3.07-3.03 (m, 1H), 2.92-2.85 (m, 1H), 2.19-2.11 (m, 1H), 2.09-2.01 (m, 1H), 1.83-1.74 (m, 2H), 1.30 (s, 9H).

Steps 2 to 5: (S)-6-((3-amino-5-(4-amino-4,6-dihydrospiro[cyclopenta[d]thiazole-5,4'-piperidin]-1'-yl)pyrazin-2-yl)thio)-5-chloro-3-(2-hydroxy-2-methylpropyl)quinazolin-4(3H)-one The compound of Example 165 (12 mg, 47% yield) was synthesized in the same method as in step 1 to step 4 of Example 146, using the product obtained in step 1 above. $^1$H NMR (400 MHz, CCl$_3$) δ=8.77 (s, 1H), 8.12 (s, 1H), 7.72 (s, 1H), 7.48 (d, J=8.8 Hz, 1H), 7.18 (d, J=8.8 Hz, 1H), 4.89 (s, 2H), 4.10-4.01 (m, 5H), 3.47-3.41 (m, 2H), 3.01-2.97 (m, 2H), 2.87-2.82 (m, 1H), 1.86-1.84 (m, 1H), 2.09-2.03 (m, 1H), 1.77-1.74 (m, 2H), 1.33 (s, 6H); MS (EI)m/z: 585.2 [M+H]$^+$.

Example 166: (S)-6-((3-amino-5-(6-amino-4,6-dihydrospiro[cyclopenta[d]thiazole-5,4'-piperidin]-1'-yl)pyrazin-2-yl)thio)-5-chloro-3-(2-hydroxy-2-methylpropyl)quinazolin-4(3H)-one

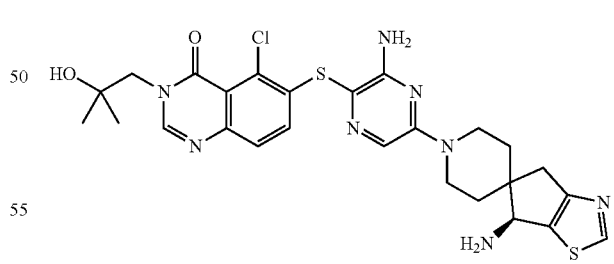

The compound of Example 166 (20 mg, 58% yield) was synthesized as a yellow solid in the same method as in Example 165, except that Intermediate I-48 was used instead of Intermediate I-55 in Example 165. $^1$H NMR (400 MHz, CDCl$_3$) δ=8.76 (s, 1H), 8.11 (s, 1H), 7.71 (s, 1H), 7.46 (d, J=8.8 Hz, 1H), 7.18 (d, J=8.8 Hz, 1H), 4.94-4.84 (m, 2H), 4.26-4.15 (m, 2H), 4.14-4.12 (m, 1H), 4.07 (s, 2H), 3.38-3.23 (m, 2H), 3.01-2.85 (m, 2H), 1.96-1.83 (m, 2H), 1.75-1.70 (m, 2H), 1.33 (s, 6H); MS (EI) m/z: 585.2 [M+H]$^+$.

Example 167: (S)-6-((3-amino-5-(4-amino-4,6-dihydrospiro[cyclopenta[d]thiazole-5,4'-piperidin]-1'-yl)pyrazin-2-yl)thio)-5-chloro-3-(2-methoxyethyl)quinazolin-4(3H)-one

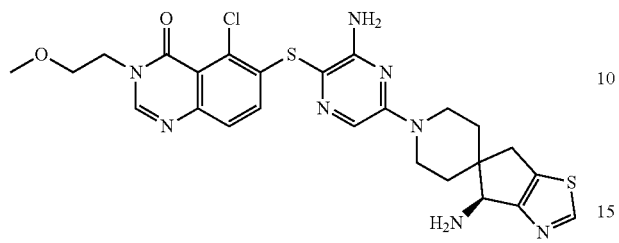

The compound of Example 167 (15.8 mg, 36% yield) was synthesized as a yellow solid in the same method as in Example 164, except that Intermediate I-55 was used instead of Intermediate I-48 in Example 164. $^1$H NMR (400 MHz, CDCl$_3$) δ=8.74-8.69 (m, 1H), 8.04-8.00 (m, 1H), 7.70 (s, 1H), 7.46 (d, J=8.8 Hz, 1H), 7.17 (d, J=8.8 Hz, 1H), 4.92-4.85 (m, 2H), 4.19-4.12 (m, 2H), 4.11-3.99 (m, 3H), 3.69 (t, J=4.4 Hz, 2H), 3.49-3.37 (m, 2H), 3.33 (s, 3H), 3.02-2.95 (m, 1H), 2.89-2.80 (m, 1H), 2.11-2.00 (m, 1H), 1.89-1.83 (m, 1H), 1.76-1.69 (m, 2H); MS (EI) m/z: 571.3 [M+H]$^+$.

Example 168: (S)-6-((5-(5-amino-5,7-dihydrospiro[cyclopenta[b]pyridine-6,4'-piperidin]-1'-yl)-6-(hydroxymethyl)pyrazin-2-yl)thio)-5-chloro-3-(2-methoxyethyl)quinazolin-4(3H)-one

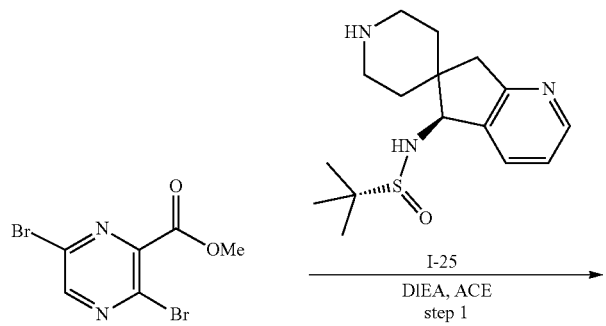

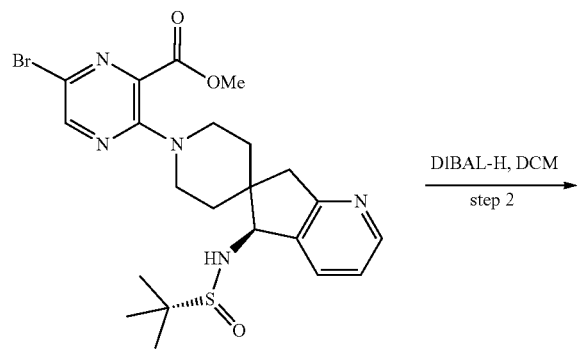

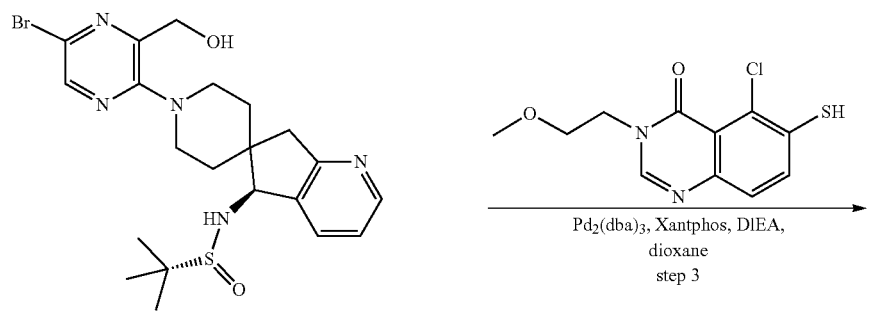

-continued

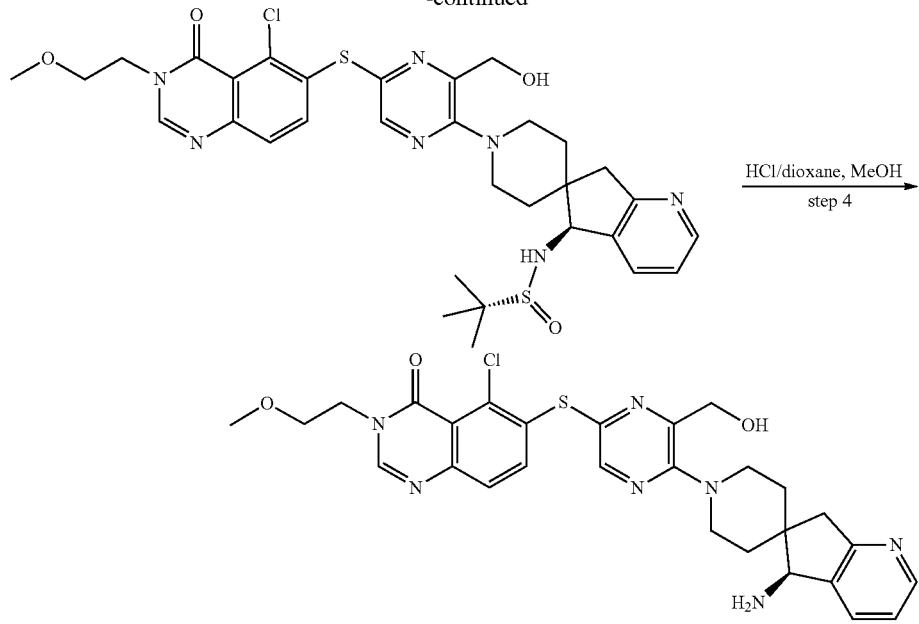

Step 1: methyl 6-bromo-3-((S)-5-(((S)-tert-butylsulfinyl)amino)-5,7-dihydrospiro[cyclopenta[b]pyridine-6,4'-piperidin]-1'-yl)pyrazine-2-carboxylate Methyl 6-bromo-34(S)-54(S)-tert-butylsulfinyl)amino)-5,7-dihydrospiro[cyclopenta[b]pyridine-6,4'-piperidin]-1'-yl)pyrazine-2-carboxylate (520 mg, 61% yield) was synthesized as a yellow solid in the same method as in step 1 of Preparation Example 55, except that Intermediate I-25 was used instead of (3S,4S)-3-methyl-2-oxa-8-azaspiro[4.5]decan-4-amine in step 1 of Preparation Example 55. $^1$H NMR (400 MHz, CDCl$_3$) δ=8.46 (d, J=4.4 Hz, 1H), 8.22 (s, 1H), 7.98 (d, J=7.6 Hz, 1H), 7.20-7.15 (m, 1H), 4.54 (d, J=10.0 Hz, 1H), 4.28 (s, 1H), 4.13 (q, J=7.2 Hz, 1H), 3.96 (s, 3H), 3.92-3.78 (m, 2H), 3.36-3.31 (m, 1H), 3.30-3.21 (m, 2H), 2.90 (d, J=16.4 Hz, 1H), 1.96-1.91 (m, 1H), 1.82-1.75 (m, 1H), 1.69 (dd, J=3.2, 7.2 Hz, 2H), 1.29 (s, 9H).

Step 2: (S)—N—((S)-1'-(5-bromo-3-(hydroxymethyl)pyrazin-2-yl)-5,7-dihydrospiro[cyclopenta[b]pyridine-6,4'-piperidin]-5-yl)-2-methylpropane-2-sulfinamide To a solution of methyl 6-bromo-34(S)-5-4(S)-tert-butylsulfinyl)amino)-5,7-dihydrospiro[cyclopenta[b]pyridine-6,4'-piperidin]-1'-yl)pyrazine-2-carboxylate (500 mg, 957 μmol) in DCM (10 mL) was added DIBAL-H (1 M, 2.87 mL) at −60° C., and then the mixture was stirred at 20° C. for 16 hours. The reaction mixture was quenched with methanol (5 mL) at −60° C., and then filtered. The filtrate was concentrated under reduced pressure, and the residue was purified by column chromatography to give (S)-N4S)-1'-(5-bromo-3-(hydroxymethyl)pyrazin-2-yl)-5,7-dihydrospiro[cyclopenta[b]pyridine-6,4'-piperidin]-5-yl)-2-methylpropane-2-sulfinamide (230 mg, 49% yield) as a yellow solid. $^1$H NMR (400 MHz, CDCl$_3$) δ=8.62-8.53 (m, 2H), 8.22 (s, 1H), 7.61 (dd, J=6.0, 7.6 Hz, 1H), 4.67-4.63 (m, 3H), 4.06-4.01 (m, 1H), 3.60 (d, J=17.6 Hz, 1H), 3.50-3.37 (m, 2H), 3.18-3.07 (m, 3H), 2.02-1.85 (m, 2H), 1.75 (d, J=13.2 Hz, 1H), 1.48 (d, J=13.2 Hz, 1H), 1.31 (s, 9H).

Step 3: (S)—N—((S)-1'-(5-((5-chloro-3-(2-methoxyethyl)-4-oxo-3,4-dihydroquinazolin-6-yl)thio)-3-(hydroxymethyl)pyrazin-2-yl)-5,7-dihydrospiro[cyclopenta[b]pyridine-6,4'-piperidin]-5-yl)-2-methylpropane-2-sulfinamide To a solution of (S)—N—((S)-1'-(5-bromo-3-(hydroxymethyl)pyrazin-2-yl)-5,7-dihydrospiro[cyclopenta[b]pyridine-6,4'-piperidin]-5-yl)-2-methylpropane-2-sulfinamide (100 mg, 202 μmol) in dioxane (4 mL), Pd$_2$(dba)$_3$ (18.5 mg, 20.2 μmol), XantPhos (23.4 mg, 40.5 μmol) and DIEA (78.4 mg, 607 μmol) were added, followed by stirring at 100° C. for 12 hours. The reaction mixture was filtered, the filtrate was concentrated under reduced pressure, and then the residue was purified by column chromatography to give (S)—N—((S)-1'-(5-((5-chloro-3-(2-methoxyethyl)-4-oxo-3,4-dihydroquinazolin-6-yl)thio)-3-(hydroxymethyl)pyrazin-2-yl)-5,7-dihydrospiro[cyclopenta[b]pyridine-6,4'-piperidin]-5-yl)-2-methylpropane-2-sulfinamide (100 mg, 72% yield) as a yellow solid. $^1$H NMR (400 MHz, CDCl$_3$) δ=8.45 (d, J=4.4 Hz, 1H), 8.18 (s, 1H), 8.09 (s, 1H), 8.01 (d, J=7.2 Hz, 1H), 7.54-7.50 (m, 2H), 7.20 (dd, J=5.2, 7.6 Hz, 1H), 4.66-4.63 (m, 2H), 4.56 (d, J=9.6 Hz, 1H), 4.16 (t, J=4.8 Hz, 2H), 3.69 (t, J=4.8 Hz, 2H), 3.60-3.52 (m, 2H), 3.35-3.32 (m, 3H), 3.30-3.22 (m, 2H), 3.21-3.11 (m, 2H), 2.89-2.84 (m, 1H), 2.05-1.97 (m, 1H), 1.86-1.82 (m, 1H), 1.77-1.71 (m, 1H), 1.40 (d, J=12.4 Hz, 1H), 1.30 (s, 9H).

Step 4: (S)-6-((5-(5-amino-5,7-dihydrospiro[cyclopenta[b]pyridine-6,4'-piperidin]-1'-yl)-6-(hydroxymethyl)pyrazin-2-yl)thio)-5-chloro-3-(2-methoxyethyl)quinazolin-4(3H)-one HCl/dioxane (4M, 2.56 mL) was added to (S)-N4S)-1'-(5-((5-chloro-3-(2-methoxyethyl)-4-oxo-3,4-dihydroquinazolin-6-yl)thio)-3-(hydroxymethyl)pyrazin-2-yl)-5, 7-dihydrospiro[cyclopenta[b]pyridine-6,4'-piperidin]-5-yl)-2-methylpropane-2-sulfinamide (70 mg, 102 μmol) in MeOH (6 mL). The reaction mixture was stirred at 25° C. for 0.5 hours. The reaction mixture was concentrated under reduced pressure and purified by column chromatography to give the compound of Example 168 (26.8 mg, 45% yield) as a yellow solid. $^1$H NMR (400 MHz, CDCl$_3$) δ=8.42 (d, J=4.4 Hz, 1H), 8.19 (s, 1H), 8.07 (s, 1H), 7.67 (d, J=6.4 Hz, 1H), 7.54-7.45 (m, 2H), 7.18-7.11 (m, 1H), 4.66 (s, 2H), 4.16 (t, J=4.4 Hz, 2H), 4.08 (s, 1H), 3.68 (t, J=4.4 Hz, 2H), 3.57 (s, 2H), 3.33 (s, 3H), 3.23-3.11 (m, 3H), 2.88 (d, J=16.8 Hz, 1H), 2.03-1.83 (m, 2H), 1.67 (d, J=12.4 Hz, 1H), 1.47-1.38 (m, 1H); MS (EI) m/z: 580.2 [M+H]$^+$.

Example 169: (S)-6-((5-(6-amino-4,6-dihydrospiro [yclopenta[d]thiazole-5,4'-piperidin]-1'-yl)-6-(hydroxymethyl)pyrazin-2-yl)thio)-5-chloro-3-(2-methoxyethyl)quinazolin-4(3H)-one

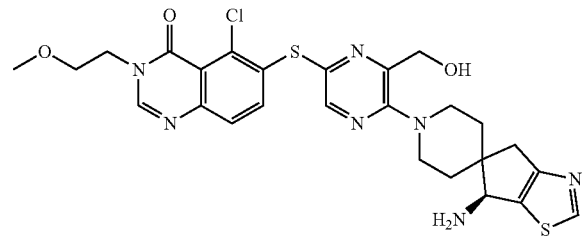 [SMILES: COCCn1cnc2ccc(Sc3cnc(N4CCC5(CC4)Cc4ncsc4[C@H]5N)c(CO)n3)c(Cl)c2c1=O]

The compound of Example 169 (1.51 mg, 18% yield) was synthesized as a yellow solid in the same method as in Example 168, except that Intermediate I-48 was used instead of Intermediate I-25 in Example 168. $^1$H NMR (400 MHz, MeOD) δ=9.14-9.12 (m, 1H), 8.25-8.24 (m, 2H), 7.58-7.51 (m, 2H), 5.39-5.34 (m, 1H), 4.69 (s, 1H), 4.61 (s, 2H), 4.46 (s, 1H), 4.23 (t, J=4.8 Hz, 2H), 3.96-3.89 (m, 1H), 3.81 (dd, J=3.2, 12.0 Hz, 1H), 3.71 (t, J=4.8 Hz, 2H), 3.37 (s, 3H), 3.27-3.18 (m, 1H), 3.17-3.11 (m, 1H), 3.06-2.98 (m, 1H), 2.02-1.90 (m, 2H), 1.83-1.76 (m, 1H), 1.66-1.59 (m, 1H); MS (EI) m/z: 586.1 [M+H]$^+$.

Example 170: (S)-6-((5-(4-amino-4,6-dihydrospiro [yclopenta[d]thiazole-5,4'-piperidin]-1'-yl)-6-(hydroxymethyl)pyrazin-2-yl)thio)-5-chloro-3-(2-methoxyethyl)quinazolin-4(3H)-one

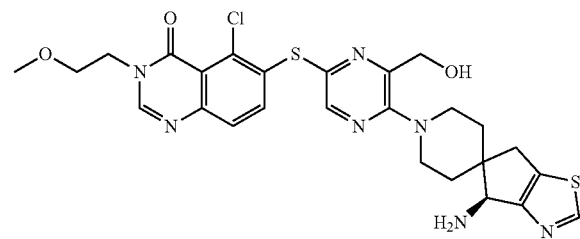 [SMILES: COCCn1cnc2ccc(Sc3cnc(N4CCC5(CC4)Cc4scnc4[C@H]5N)c(CO)n3)c(Cl)c2c1=O]

The compound of Example 170 (11.02 mg, 43% yield) was synthesized as a yellow solid in the same method as in Example 168, except that Intermediate I-55 was used instead of Intermediate I-25 in Example 168. $^1$H NMR (400 MHz, CDCl$_3$) δ=8.77-8.70 (m, 1H), 8.20-8.16 (m, 1H), 8.07 (s, 1H), 7.51-7.42 (m, 2H), 4.67 (s, 2H), 4.23-4.10 (m, 3H), 3.72-3.65 (m, 2H), 3.61-3.49 (m, 2H), 3.33 (s, 3H), 3.25-3.09 (m, 3H), 2.98 (s, 2H), 2.19-2.09 (m, 1H), 2.02-1.92 (m, 1H), 1.88-1.73 (m, 2H); MS (EI) m/z: 586.1 [M+H]$^+$.

Example 171: (S)-3-(6-amino-4,6-dihydrospiro[cyclopenta[d]thiazole-5,4'-piperidin]-1'-yl)-6-((5-chloro-3-(2-methoxyethyl)-4-oxo-3,4-dihydroquinazolin-6-yl)thio)pyrazine-2-carboxamide

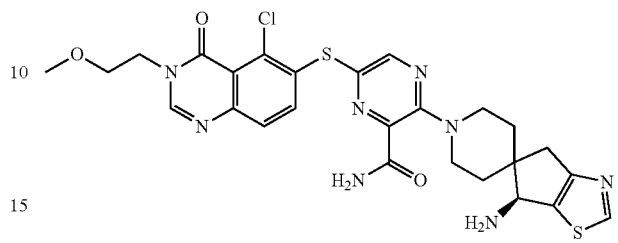

The compound of Example 171 (13 mg, 51% yield) was synthesized in the same method as in step 1 and step 3 of Example 18, except that Intermediate I-66 was used instead of Intermediate I-3 in step 1 of Example 18, and the product obtained in step 2 of Preparation Example 28 was used instead of Intermediate I-8. $^1$H NMR (400 MHz, CDCl$_3$) δ=8.79-8.74 (m, 1H), 8.22 (d, J=3.2 Hz, 1H), 8.06 (d, J=2.4 Hz, 1H), 7.54-7.43 (m, 2H), 7.38 (d, J=7.6 Hz, 1H), 6.40-6.07 (m, 1H), 4.27 (s, 1H), 4.18-4.13 (m, 2H), 4.03-3.93 (m, 2H), 3.69-3.64 (m, 2H), 3.32 (d, J=2.4 Hz, 3H), 3.29-3.19 (m, 2H), 2.95-2.91 (m, 2H), 2.11-2.03 (m, 1H), 1.91-1.79 (m, 2H), 1.71-1.69 (m, 1H); MS (EI) m/z: 599.1 [M+H]$^+$.

Example 172: (S)-3-(4-amino-4,6-dihydrospiro[cyclopenta[d]thiazole-5,4'-piperidin]-1'-yl)-6-((5-chloro-3-(2-methoxyethyl)-4-oxo-3,4-dihydroquinazolin-6-yl)thio)pyrazine-2-carboxamide

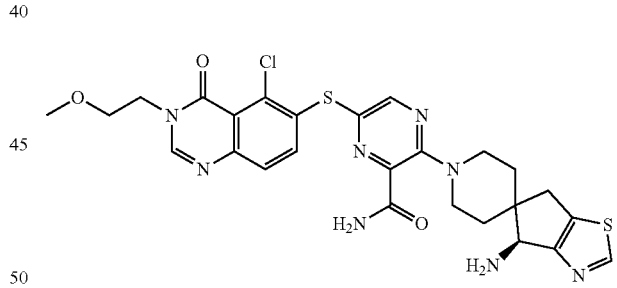

The compound of Example 172 (5 mg, 59% yield) was synthesized as a yellow solid in the same method as in step 1 and step 3 of Example 18, except that Intermediate I-67 was used instead of Intermediate I-3 in step 1 of Example 18, and the product obtained in step 2 of Preparation Example 28 was used instead of Intermediate I-8. $^1$H NMR (400 MHz, CDCl$_3$) δ=8.75 (s, 1H), 8.23 (s, 1H), 8.06 (s, 1H), 7.51 (d, J=8.8 Hz, 1H), 7.43-7.36 (m, 2H), 6.42-6.19 (m, 1H), 4.23 (s, 1H), 4.16 (t, J=4.4 Hz, 2H), 4.04-3.89 (m, 2H), 3.69 (t, J=4.4 Hz, 2H), 3.43-3.38 (m, 1H), 3.37-3.35 (m, 1H), 3.33 (s, 3H), 3.06 (s, 1H), 2.93-2.90 (m, 1H), 2.26-2.17 (m, 1H), 2.02-1.88 (m, 2H), 1.76 (d, J=12.8 Hz, 1H); MS (EI) m/z: 599.1 [M+H]$^+$.

Example 173: (S)-3-(5-amino-5,7-dihydrospiro[cyclopenta[d]pyridine-6,4'-piperidin]-1'-yl)-6-((5-chloro-3-(2-methoxyethyl)-4-oxo-3,4-dihydroquinazolin-6-yl)thio)pyrazine-2-carboxamide

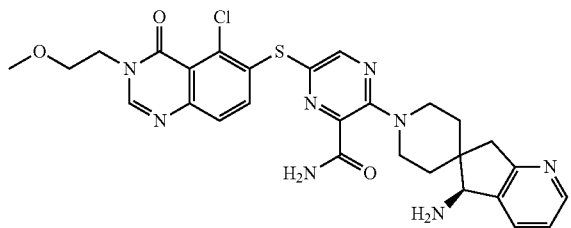 [SMILES: COCCn1cnc2ccc(Sc3cnc(N4CCC5(CC4)Cc4ncccc4[C@H]5N)c(C(N)=O)n3)c(Cl)c2c1=O]

The compound of Example 173 (18 mg, 71% yield) was synthesized as a yellow solid in the same method as in step 1 and step 3 of Example 18, except that Intermediate I-68 was used instead of Intermediate I-3 in step 1 of Example 18, and the product obtained in step 2 of Preparation Example 28 was used instead of Intermediate I-8. $^1$H NMR (400 MHz, CDCl$_3$) δ =8.41 (d, J=4.4 Hz, 1H), 8.24 (s, 1H), 8.06 (s, 1H), 7.67 (d, J=7.2 Hz, 1H), 7.51 (d, J=8.8 Hz, 1H), 7.41 (d, J=8.8 Hz, 1H), 7.29 (s, 1H), 7.17-7.12 (m, 1H), 5.69-5.51 (m, 1H), 4.86-4.77 (m, 2H), 4.75-4.63 (m, 1H), 4.16 (s, 2H), 4.05 (d, J=15.6 Hz, 2H), 3.72-3.65 (m, 2H), 3.33 (s, 3H), 3.24-3.19 (m, 1H), 2.89 (d, J=16.4 Hz, 1H), 1.97 (s, 2H), 1.62 (s, 1H), 1.39 (d, J=10.8 Hz, 1H); MS (EI) m/z: 593.2 [M+H]$^+$.

Example 174: (S)-3-(6-amino-4,6-dihydrospiro[cyclopenta[d]thiazole-5,4'-piperidin]-1'-yl)-6-((5-chloro-4-oxo-3-((tetrahydro-2H-pyran-4-yl)methyl)-3,4-dihydroquinazolin-6-yl)thio)pyrazine-2-carboxamide

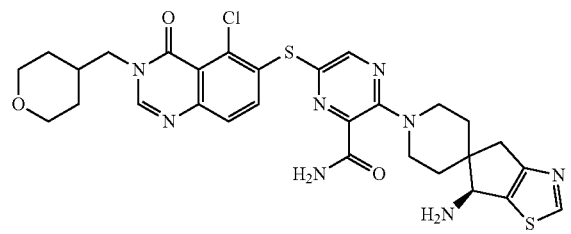 [SMILES: NC(=O)c1nc(Sc2ccc3ncn(CC4CCOCC4)c(=O)c3c2Cl)cnc1N1CCC2(CC1)Cc1ncsc1[C@H]2N]

The compound of Example 174 (12 mg, 47% yield) was synthesized as a yellow solid in the same method as in step 1 and step 3 of Example 18, except that Intermediate I-66 was used instead of Intermediate I-3 in step 1 of Example 18, and Intermediate I-69 was used instead of Intermediate I-8. $^1$H NMR (400 MHz, CDCl$_3$) δ=8.76 (s, 1H), 8.25 (s, 1H), 7.98-7.94 (m, 1H), 7.51 (d, J=8.8 Hz, 1H), 7.40 (d, J=8.8 Hz, 1H), 7.33 (s, 1H), 5.87-5.59 (m, 1H), 4.21 (s, 1H), 4.03-3.97 (m, 4H), 3.85 (d, J=7.2 Hz, 2H), 3.42-3.30 (m, 4H), 2.94 (d, J=8.4 Hz, 2H), 2.27-2.15 (m, 2H), 1.89 (d, J=9.2 Hz, 1H), 1.74 (d, J=13.2 Hz, 2H), 1.62 (d, J=11.6 Hz, 2H), 1.46-1.38 (m, 2H); MS (EI) m/z: 639.1 [M+H]$^+$.

Example 175: (S)-6-((5-(6-amino-4,6-dihydrospiro[cyclopenta[d]thiazole-5,4'-piperidin]-1'-yl)pyrazin-2-yl)thio)-5-chloro-3-(2-fluoro-2-methylpropyl)quinazolin-4(3H)-one

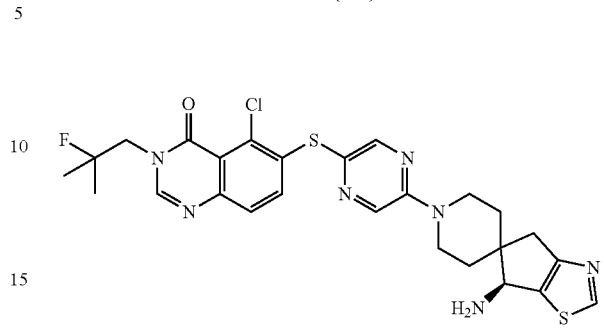

The compound of Example 175 (18 mg, 67% yield) was synthesized as a white solid in the same method as in Example 144, except that Intermediate I-70 was used instead of Intermediate I-29 in step 1 of Example 144. $^1$H NMR (400 MHz, CDCl$_3$) δ=8.82-8.78 (m, 1H), 8.48 (s, 1H), 8.29 (s, 1H), 8.11-8.06 (m, 1H), 7.74 (d, J=8.8 Hz, 1H), 7.61 (d, J=8.8 Hz, 1H), 4.35-4.27 (m, 1H), 4.26-4.16 (m, 2H), 3.40-3.30 (m, 2H), 3.28-3.26 (m, 1H), 3.24-3.22 (m, 1H), 3.05-3.00 (m, 1H), 2.97-2.92 (m, 1H), 2.03-1.94 (m, 1H), 1.90-1.79 (m, 2H), 1.77-1.71 (m, 1H), 1.57 (s, 3H), 1.51 (s, 3H); MS (EI) m/z: 572.1 [M+H]$^+$.

Example 176: 64(3-amino-5-((S)-6-amino-4,6-dihydrospiro[cyclopenta[d]thiazole-5,4'-piperidin]-1'-yl)pyrazin-2-yl)thio)-5-chloro-3-(2-methoxypropyl)quinazolin-4(3H)-one

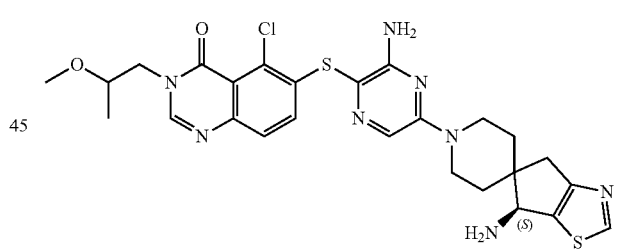

The compound of Example 176 (5.38 mg, 30% yield) was synthesized as a white solid in the same method as in Example 144, except that Intermediate I-71 was used instead of Intermediate I-29 in step 1 of Example 144. $^1$H NMR (400 MHz, CDCl$_3$) δ=8.77 (s, 1H), 8.04 (s, 1H), 7.71 (s, 1H), 7.46 (d, J=8.8 Hz, 1H), 7.18 (d, J=8.8 Hz, 1H), 4.89 (s, 2H), 4.35 (dd, J=2.4, 13.6 Hz, 1H), 4.27-4.20 (m, 1H), 4.20-4.13 (m, 2H), 3.70 (d, J=3.2 Hz, 1H), 3.54 (dd, J=8.8, 13.6 Hz, 1H), 3.38-3.32 (m, 1H), 3.31 (s, 1H), 3.27 (s, 3H), 3.01-2.95 (m, 1H), 2.94-2.88 (m, 1H), 1.91 (d, J=2.0 Hz, 2H), 1.77 (s, 2H), 1.24 (d, J=6.0 Hz, 3H); MS (EI) m/z: 607.2 [M+Na]$^+$.

Example 177: 6-((3-amino-54(S)-4-amino-4,6-dihydrospiro[cyclopenta[d]thiazole-5,4'-piperidin]-1'-yl)pyrazin-2-yl)thio)-5-chloro-3-(2-methoxypropyl)quinazolin-4(3H)-one

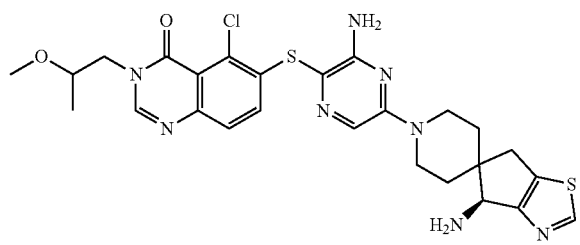 [SMILES: COC(C)Cn1cnc2ccc(Sc3ncc(N4CCC5(CC4)Cc4scnc4[C@H]5N)nc3N)c(Cl)c2c1=O]

The compound of Example 177 (12.38 mg, 70% yield) was synthesized as a white solid in the same method as in Example 144, except that, in step 1 of Example 144, Intermediate I-71 was used instead of Intermediate I-29, and Intermediate I-55 was used instead of Intermediate I-48. $^1$H NMR (400 MHz, CDCl$_3$) δ=8.75 (s, 1H), 8.04 (s, 1H), 7.70 (s, 1H), 7.47-7.41 (m, 1H), 7.18-7.13 (m, 1H), 4.94 (s, 2H), 4.38-4.32 (m, 1H), 4.17-4.09 (m, 2H), 4.08-4.01 (m, 1H), 3.74-3.68 (m, 1H), 3.58-3.51 (m, 1H), 3.45-3.34 (m, 2H), 3.27 (d, J=1.2 Hz, 3H), 3.06-2.99 (m, 1H), 2.91-2.85 (m, 1H), 1.92-1.70 (m, 4H), 1.24 (d, J=6.0 Hz, 3H); MS (EI) m/z: 585.0 [M+H]$^+$.

Example 178: Synthesis of 6-((6-((3S,4S)-4-amino-3-methyl-2-oxa-8-azaspiro[4.5]decan-8-yl)-1H-pyrazolo[3,4-b]pyrazin-3-yl)thio)-5-chloro-3-(2-methoxyethyl)quinazolin-4(3H)-one

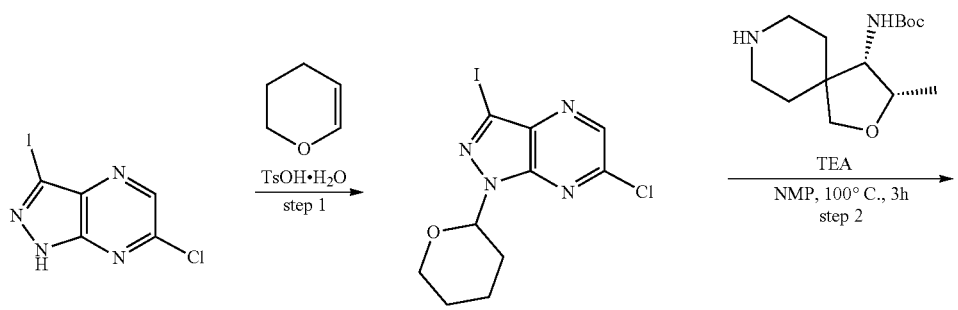

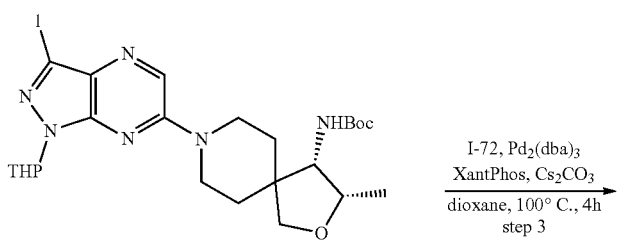

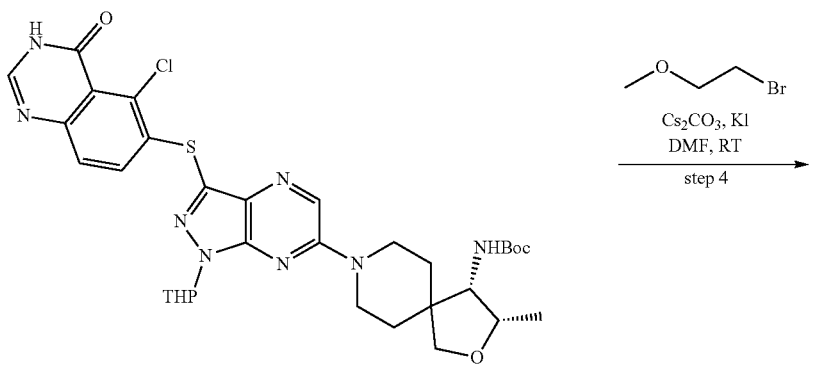

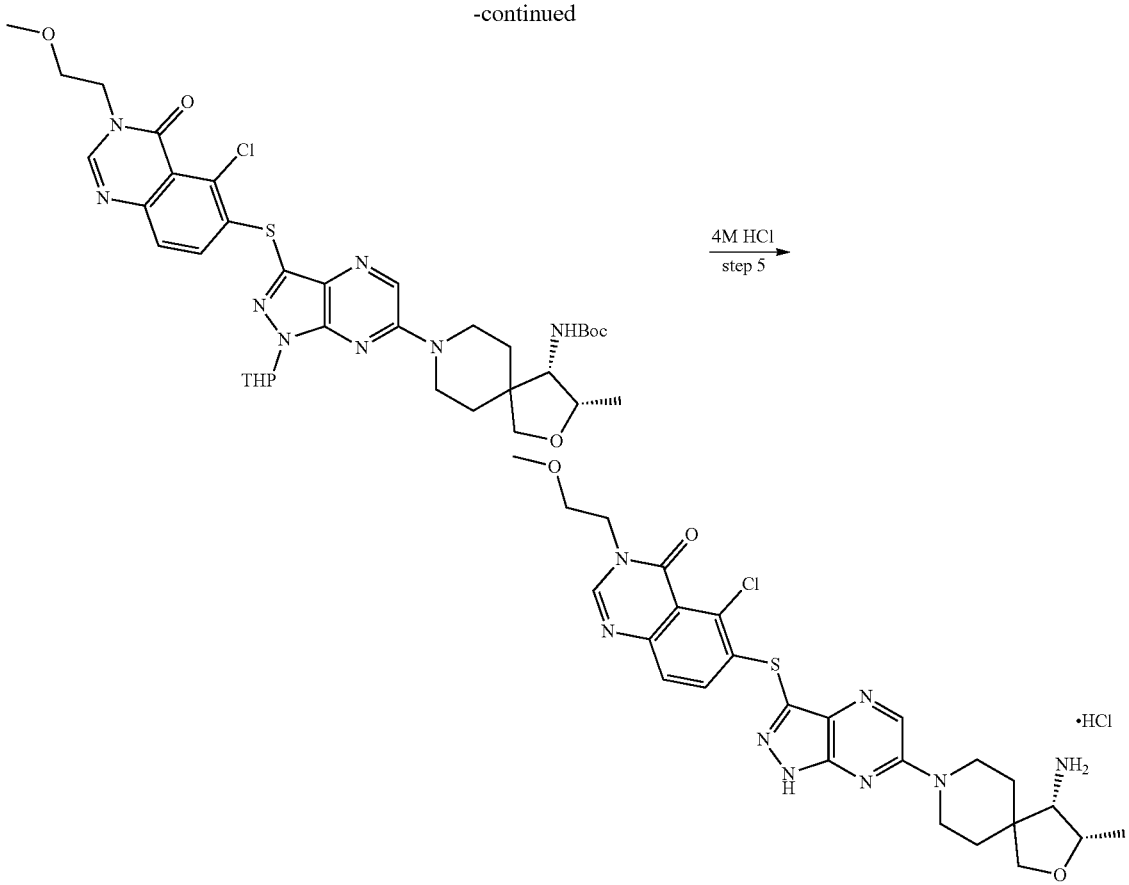

Step 1: 6-chloro-3-iodo-1-(tetrahydro-2H-pyran-2-yl)-1H-pyrazolo[3,4-b]pyrazine

In a round bottom flask, 6-chloro-3-iodo-1H-pyrazolo[3,4-b]pyrazine (500 mg, 1.78 mmol), 3,4-dihydro-2H-furan (0.5 ml, 5.35 mmol) and p-toluenesulfonic acid (102 mg, 0.53 mmol) were dissolved in DCM (9 ml, 0.2M) and stirred at room temperature for 10 minutes. The reaction mixture was added with 15 mL of aqueous sodium bicarbonate solution and stirred at room temperature for 10 minutes. The reaction was terminated with $H_2O$, and the DCM layer was washed with brine. The DCM layer was dried over $MgSO_4$, filtered and then concentrated to obtain 6-chloro-3-iodo-1-(tetrahydro-2H-pyran-2-yl)-1H-pyrazolo[3,4-b]pyrazine (620 mg, 96%). MS m/z: 365.5 [M+H]$^+$.

Step 2: tert-butyl ((3S,4S)-8-(3-iodo-1-(tetrahydro-2H-pyran-2-yl)-1H-pyrazolo[3,4-b]pyrazin-6-yl)-3-methyl-2-oxaspiro[4.5]decan-4-yl)carbamate In a round bottom flask, 6-chloro-3-iodo-1-(tetrahydro-2H-pyran-2-yl)-1H-pyrazolo[3,4-b]pyrazine (550 mg, 1.51 mmol) was dissolved in NMP (1.5 ml, 1.0M), and then triethylamine (0.42 ml, 3.02 mmol) was added to, followed by stirring at 120° C. for 2 hours. The reaction was terminated with $H_2O$, and the mixture was extracted with EA. The EA layer was dried over $MgSO_4$, filtered and then concentrated. The resulting product was separated by MPLC (EA:Hx=1:2) and concentrated to obtain tert-butyl ((3S,4S)-8-(3-iodo-1-(tetrahydro-2H-pyran-2-yl)-1H-pyrazolo[3,4-b]pyrazin-6-yl)-3-methyl-2-oxaspiro[4.5]decan-4-yl)carbamate (780 mg, 96%). MS m/z: 599.5 [M+H]$^+$.

Step 3: tert-butyl ((3S,4S)-8-(34(5-chloro-4-oxo-3,4-dihydroquinazolin-6-yl)thio)-1-(tetrahydro-2H-pyran-2-yl)-1H-pyrazolo[3,4-b]pyrazin-6-yl)-3-methyl-2-oxaspiro[4.5]decan-4-yl)carbamate In a round bottom flask, tert-butyl ((3 S,4S)-8-(3-iodo-1-(tetrahydro-2H-pyran-2-yl)-1H-pyrazolo[3,4-b]pyrazin-6-yl)-3-methyl-2-oxa-8-azaspiro[4.5]decan-4-yl)carbamate (780 mg, 1.31 mmol), Intermediate I-72 (500 mg, 1.96 mmol), Pd$_2$(dba)$_3$ (120 mg, 0.13 mmol), XantPhos (150 mg, 0.26 mmol) and cesium carbonate (850 mg, 2.62 mmol) were dissolved in 1,4-dioxane (22 ml, 0.06M). The reaction mixture was purged with nitrogen and stirred at 100° C. for 5 hours. The reaction was terminated with $H_2O$, and the mixture was extracted with EA. The EA layer was dried over $MgSO_4$, filtered and then concentrated. The resulting product was separated by MPLC (MeOH:MC=1:100) and concentrated to obtain tert-butyl ((3 S,4S)-8-(3-((5-chloro-4-oxo-3,4-dihydroquinazolin-6-yl)thio)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (680 mg, 76%). MS m/z: 649.5 [M+H]$^+$.

Step 4: tert-butyl ((3S,4S)-8-(34(5-chloro-3-(2-methoxyethyl)-4-oxo-3,4-dihydroquinazolin-6-yl)thio)-1-(tetrahydro-2H-pyran-2-yl)-1H-pyrazolo[3,4-b]pyrazin-6-yl)-3-methyl-2-oxa-8-azaspiro[4.5]decan-4-yl)carbamate In a round bottom flask, tert-butyl ((3 S,4S)-8-(3-((5-chloro-4-oxo-3,4-dihydroquinazolin-6-yl)thio)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (85 mg, 0.13 mmol), 2-bromoethyl methyl ether (18 µL, 0.19 mmol), cesium carbonate (81 mg, 0.25 mmol) and potassium iodide (21 mL, 0.13 mmol) were dissolved in DMF (1.3 mL, 0.1M) and stirred at 50° C. for 1 hour. The reaction was terminated with H₂O, and the mixture was extracted with EA. The EA layer was dried over MgSO₄, filtered and then concentrated. The resulting product was separated by MPLC (EA:Hx=1: 20) and concentrated to obtain tert-butyl ((3 S,4 S)-8-(3-((5-chloro-3-(2-m ethoxy ethyl)-4-oxo-3,4-dihydroquinazo-lin-6-yl)thio)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (80 mg, 85%). MS m/z: 707.5 [M+H]⁺.

Step 5: 64(64(3S,4S)-4-amino-3-methyl-2-oxa-8-azaspiro[4.5]decan-8-yl)-1H-pyrazolo[3,4-b]pyrazin-3-yl)thio)-5-chloro-3-(2-methoxyethyl)quinazolin-4(3H)-one In a round bottom flask, tert-butyl ((3S,4S)-8-(3-((5-chloro-3-(2-methoxyethyl)-4-oxo-3,4-dihydroquinazolin-6-yl)thio)-1-(tetrahydro-2H-pyran-2-yl)-1H-pyrazolo[3,4-b]pyrazin-6-yl)-3-methyl-2-oxa-8-azaspiro[4.5]decan-4-yl)carbamate (80 mg, 0.12 mmol) was dissolved in DCM (1.1 ml, 0.1M) and cooled to 0. The reaction mixture was added with aqueous hydrochloric acid solution (0.3 ml, 4M in dioxane) and stirred at room temperature for 3 hours. After completion of the reaction, the reaction mixture was concentrated using a concentrator. The reaction mixture was washed with EA, and the solid was collected by filtration to obtain the compound of Example 178 (63 mg, 99%) as an HCl salt. ¹H NMR (400 MHz, DMSO) δ 13.87 (br s, 1H), 8.47 (s, 1H), 8.28 (s, 1H), 8.12 (br s, 2H), 7.42 (d, J=8.8 Hz, 1H), 7.08 (d, J=8.8 Hz, 1H), 4.36-4.32 (m, 1H), 4.28-4.12 (m, 2H), 4.13 (t, J=5.0 Hz, 2H), 3.93 (d, J=9.0 Hz, 1H), 3.69 (d, J=9.2 Hz, 1H), 3.61 (t, J=5.0 Hz, 2H), 3.39-3.37 (m, 1H), 3.26 (s, 3H), 3.23-3.17 (m, 2H), 1.81-1.71 (m, 3H), 1.63-1.59 (m, 1H), 1.23 (d, J=6.6 Hz, 3H).

Example 179: Synthesis of 6-((6-((3S,4S)-4-amino-3-methyl-2-oxa-8-azaspiro[4.5]decan-8-yl)-1H-pyrazolo[3,4-b]pyrazin-3-yl)thio)-5-chloro-3-((tetrahydrofuran-3-yl)methyl)quinazolin-4(3H)-one

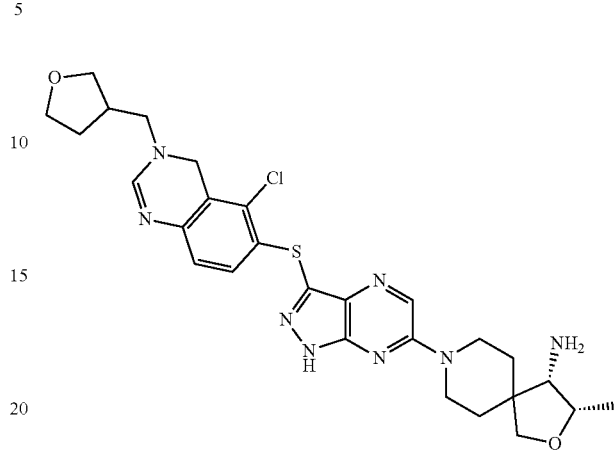

The compound of Example 179 (53 mg, 99%) was synthesized in the same method as in Example 178, except that 3-(bromomethyl)tetrahydrofuran was used instead of 2-bromoethyl methyl ether in step 4 of Example 178. ¹H NMR (400 MHz, DMSO) δ 13.88 (br s, 1H), 8.49 (s, 1H), 8.44 (s, 1H), 8.12 (br s, 2H), 7.43 (d, J=8.8 Hz, 1H), 7.07 (d, J=8.8 Hz, 1H), 4.36-4.20 (m, 3H), 4.00-3.92 (m, 3H), 3.84-3.78 (m, 1H), 3.71-3.60 (m, 3H), 3.50-3.46 (m, 1H), 3.39-3.38 (m, 1H), 3.25-3.17 (m, 2H), 2.75-2.67 (m, 1H), 1.95-1.89 (m, 1H), 1.81-1.70 (m, 3H), 1.67-1.59 (m, 2H), 1.23 (d, J=6.5 Hz, 3H).

Example 180: Synthesis of (R)-6-((5-(1-amino-8-azaspiro[4.5]decan-8-yl)pyrazin-2-yl)thio)-5-chloro-3-(2-methoxyethyl)quinazolin-4(3H)-one

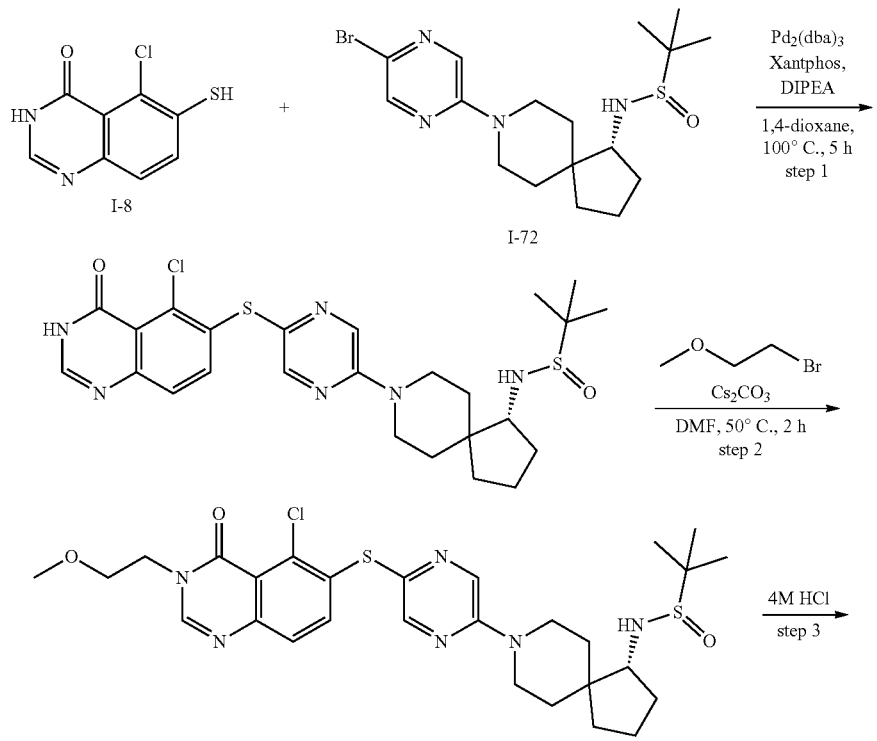

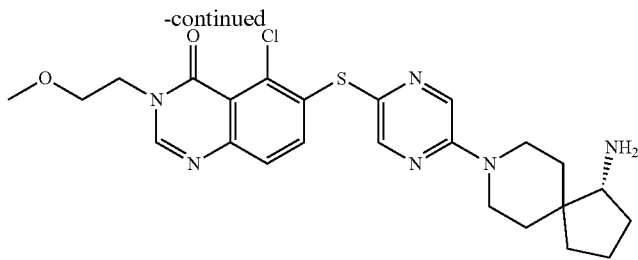

Step 1: N-OR)-8-(5-((5-chloro-4-oxo-3,4-dihydroquinazolin-6-yl)thio)pyrazin-2-yl)-8-azaspiro[4.5]decan-1-yl)-2-methylpropane-2-sulfinamide In a round bottom flask, Intermediate I-8 (158 mg, 0.63 mmol), Intermediate I-72 (200 mg, 0.48 mmol), Pd$_2$(dba)$_3$ (44 mg, 0.048 mmol) and XantPhos (28 mg, 0.048 mmol) were dissolved in 1,4-dioxane (2.4 mL, 0.2 M), and then DIPEA (0.17 mL, 0.96 mmol) was added thereto. The reaction mixture was purged with nitrogen and stirred at 120° C. for 4 hours. The reaction was terminated with H$_2$O, and the mixture was extracted with EA. The EA layer was dried over MgSO$_4$, filtered and then concentrated. The resulting product was separated by MPLC (MeOH:MC=1:50) and concentrated to obtain N-((R)-8-(5-((5-chloro-4-oxo-3,4-dihydroquinazolin-6-yl)thio)pyrazin-2-yl)-8-azaspiro[4.5]decan-1-yl)-2-methylpropane-2-sulfinamide (55 mg, 21%). MS m/z: 548.1 [M+H]$^+$.

Step 2: N-((R)-8-(5-((5-chloro-3-(2-methoxyethyl)-4-oxo-3,4-dihydroquinazolin-6-yl)thio)pyrazin-2-yl)-8-azaspiro[4.5]decan-1-yl)-2-methylpropane-2-sulfinamide In a round bottom flask, N-((R)-8-(5-((5-chloro-4-oxo-3,4-dihydroquinazolin-6-yl)thio)pyrazin-2-yl)-8-azaspiro[4.5]decan-1-yl)-2-methylpropane-2-sulfinamide (55 mg, 0.1 mmol), 1-bromo-2-methoxyethane (0.014 mL, 0.15 mmol), potassium iodide (16.6 mg, 0.1 mmol) and cesium carbonate (65 mg, 0.2 mmol) were dissolved in DMF (1 mL, 0.1 M). The reaction mixture was stirred at 50° C. for 6 hours. The reaction was terminated with aqueous NaHCO$_3$ solution, and the mixture was extracted with EA. The EA layer was dried over MgSO$_4$, filtered and then concentrated. The resulting product was separated by MPLC (amine column, EA:Hex=80: 20) to obtain N-((R)-8-(5-((5-chloro-3-(2-m ethoxy ethyl)-4-oxo-3,4-dihydroquinazolin-6-yl)thio)pyrazin-2-yl)-8-azaspiro[4.5]decan-1-yl)-2-methylpropane-2-sulfinamide (7.9 mg, 13%). MS m/z: 606.1 [M+H]$^+$.

Step 3: (R)-64(5-(1-amino-8-azaspiro[4.5]decan-8-yl)pyrazin-2-yl)thio)-5-chloro-3-(2-methoxyethyl)quinazolin-4(3H)-one In a round bottom flask, N-((R)-8-(5-((5-chloro-3-(2-methoxyethyl)-4-oxo-3,4-dihydroquinazolin-6-yl)thio)pyrazin-2-yl)-8-azaspiro[4.5]decan-1-yl)-2-methylpropane-2-sulfinamide (7.9 mg, 0.013 mmol) was dissolved in DCM (0.13 mL, 0.1 M). The reaction mixture was added with 4M HCl in dioxane (0.016 mL, 0.0652 mmol) and stirred at 40° C. for 10 minutes. After completion of the reaction, the reaction mixture was concentrated using a concentrator. The reaction mixture was washed with MC/EA, and the solid was collected by filtration to obtain the compound of Example 180 (2.1 mg, 30%). $^1$H NMR (400 MHz, DMSO) δ 8.50 (d, J=1.1 Hz, 1H), 8.32 (d, J=1.1 Hz, 1H), 8.28 (s, 1H), 7.97 (brs, 2H), 7.52 (d, J=8.8 Hz, 1H), 7.23 (d, J=8.8 Hz, 1H), 4.27 (dd, J=26.6, 13.6 Hz, 2H), 4.13 (t, J=5.2 Hz, 2H), 3.60 (t, J=5.2 Hz, 2H), 3.25 (s, 3H), 3.18-3.12 (m, 3H), 2.08-2.01 (m, 1H), 1.83-1.74 (m, 2H), 1.72-1.39 (m, 7H), 1.23 (s, 1H)

Example 181: Synthesis of 6-((5-((3S,4S)-4-amino-3-methyl-2-oxa-8-azaspiro[4.5]decan-8-yl)pyridin-2-yl)thio)-5-chloro-3-(2-methoxyethyl)quinazolin-4(3H)-one

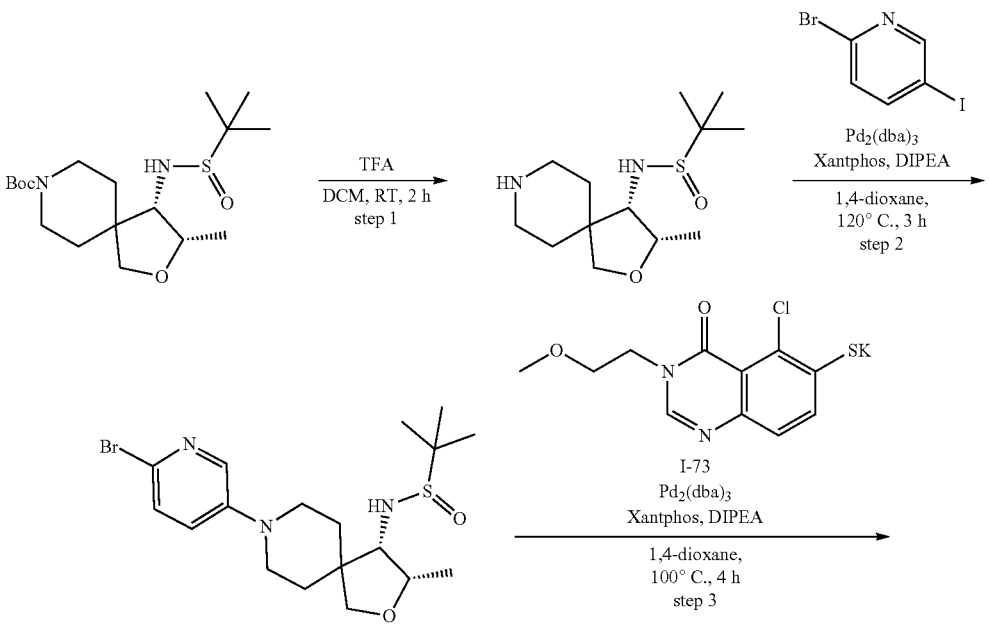

-continued

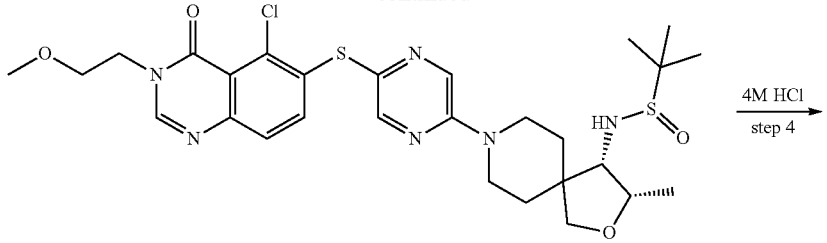

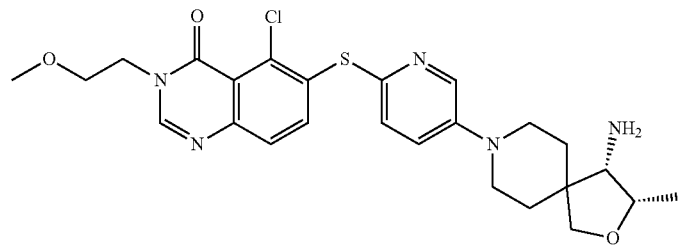

Step 1: 2-methyl-N4(3S,4S)-3-methyl-2-oxa-8-azaspiro[4.5]decan-4-yl)propane-2-sulfinamide Tert-butyl (3 S,4S)-4-((tert-butylsulfinyl)amino)-3-methyl-2-oxa-8-azaspiro[4.5]decan-8-carboxylate (200 mg, 0.53 mmol) was dissolved in DCM (13 ml, 0.04 M). The reaction mixture was slowly added dropwise with TFA (0.4 ml, 5.3 M) and stirred at room temperature for 3 hours. The reaction mixture was poured into aqueous 1N NaOH and then extracted with EA/MeOH. The combined organic layers were dried over anhydrous sodium sulfate, and then filtered and concentrated under reduced pressure to obtain 2-methyl-N-((3S,4S)-3-methyl-2-oxa-8-azaspiro[4.5]decan-4-yl)propane-2-sulfinamide. MS m/z: 275.5 [M+H]$^+$.

Step 2: N4(3S,4S)-8-(6-bromopyridin-3-yl)-3-methyl-2-oxa-8-azaspiro[4.5]decan-4-yl)-2-methylpropane-2-sulfinamide A mixture of 2-methyl-N-((3S,4S)-3-methyl-2-oxa-8-azaspiro[4.5]decan-4-yl)propane-2-sulfinamide (100 mg, 0.36 mmol), 2-bromo-5-iodopyridine (114 mg, 0.40 mmol), Pd$_2$(dba)$_3$ (33 mg, 0.036 mmol), XantPhos (21 mg, 0.036 mmol) and cesium carbonate (235 mg, 0.72 mmol) in dioxane (2.3 mL) was degassed and purged 3 times with N2, and stirred under N$_2$ atmosphere at 120° C. for 3 hours. The reaction mixture was filtered through celite and then concentrated under reduced pressure to obtain a residue. The mixture was added with H$_2$O and extracted with EA. The EA layer was dried over MgSO$_4$, filtered and then concentrated. The resulting product was purified by column chromatography (EA/Hex=80:20) to obtain N-((3S,4S)-8-(6-bromopyridin-3-yl)-3-methyl-2-oxa-8-azaspiro[4.5]decan-4-yl)-2-methylpropane-2-sulfinamide (47 mg, 31%). MS m/z: 431.5 [M+H]$^+$.

Step 3: N4(3S,4S)-8-(64(5-chloro-3-(2-methoxyethyl)-4-oxo-3,4-dihydroquinazolin-6-yl)thio)pyridin-3-yl)-3-methyl-2-oxa-8-azaspiro[4.5]decan-4-yl)-2-methylpropane-2-sulfinamide A mixture of N-((3 S,4S)-8-(6-bromopyridin-3-yl)-3-methyl-2-oxa-8-azaspiro[4.5]decan-4-yl)-2-methylpropane-2-sulfinamide (47 mg, 0.11 mmol), potassium 5-chloro-3-(2-methoxyethyl)-4-oxo-3,4-dihydroquinazolin-6-thiolate (40.3 mg, 0.13 mmol), Pd$_2$(dba) (10.1 mg, 0.011 mmol), XantPhos (6.4 mg, 0.011 mmol) and DIPEA (0.038 mL, 0.22 mmol) in dioxane (2.3 mL) was degassed and purged 3 times with N2, and stirred under N$_2$ atmosphere at 110° C. for 4 hours. The reaction mixture was filtered through celite and then concentrated under reduced pressure to obtain a residue. The residue was added with aqueous NaHCO$_3$ and extracted with EA. The combined organic layers were dried over MgSO$_4$, filtered and then concentrated. The resulting product was purified by column chromatography (MeOH:MC=1:50) to obtain N-((3 S,4 S)-8-(6-((5-chloro-3-(2-methoxyethyl)-4-oxo-3,4-dihydroquinazolin-6-yl)thio)pyridin-3-yl)-3-methyl-2-oxa-8-azaspiro[4.5]decan-4-yl)-2-methylpropane-2-sulfinamide (16 mg, 24%). MS m/z: 621.5 [M+H]$^+$.

Step 4: 6-((5-((3S,4S)-4-amino-3-methyl-2-oxa-8-azaspiro[4.5]decan-8-yl)pyridin-2-yl)thio)-5-chloro-3-(2-methoxyethyl)quinazolin-4(3H)-one N-((3 S,4 S)-8-(6-((5-chloro-3-(2-methoxyethyl)-4-oxo-3,4-dihydroquinazolin-6-yl)thio)pyridin-3-yl)-3-methyl-2-oxa-8-azaspiro[4.5]decan-4-yl)-2-methylpropane-2-sulfinamide (16 mg, 0.026 mmol) was dissolved in DCM (0.26 mL, 0.1 M). The reaction mixture was added with hydrochloric acid (0.032 mL, 4 M in dioxane) and then stirred at 50° C. for 10 minutes. After completion of the reaction, the reaction mixture was concentrated using a concentrator. The reaction mixture was washed with EA, and then filtered to obtain the compound of Example 181 (8.3 mg, 58%) as an HCl salt. $^1$H NMR (500 MHz, DMSO) δ 8.38 (d, J=2.4 Hz, 1H), 8.30 (s, 1H), 8.10-8.06 (m, 2H), 7.54 (d, J=8.7 Hz, 1H), 7.44-7.36 (m, 3H), 4.21 (quin, J=6.7, 5.6 Hz, 1H), 4.13 (t, J=4.9 Hz, 2H), 3.86 (d, J=9.0 Hz, 1H), 3.78 (d, J=13.6 Hz, 1H), 3.70 (d, J=13.5 Hz, 1H), 3.66 (d, J=9.1 Hz, 1H), 3.61 (t, J=5.1 Hz, 2H), 3.39 (br s, 1H), 2.90(q, J=13.6, 12.6 Hz, 2H), 1.85-1.80 (m, 2H), 1.72 (d, J=13.5 Hz, 1H), 1.60 (d, J=12.7 Hz, 1H), 1.23 (d, J=6.6 Hz, 3H).

Example 182: Synthesis of 6-((5-((3S,4S)-4-amino-3-methyl-2-oxa-8-azaspiro[4.5]decan-8-yl)imidazo[1,2-c]pyrimidin-8-yl)thio)-5-chloro-3-(2-methoxyethyl)quinazolin-4(3H)-one
Step 1: 5-bromo-2-chloro-N-(2,2-dimethoxyethyl)pyrimidin-4-amine
At 0° C., triethylamine(TEA) (6.1 mL, 43.9 mmol) and aminoacetaldehyde dimethyl acetal (3.1 mL, 28.5 mmol)
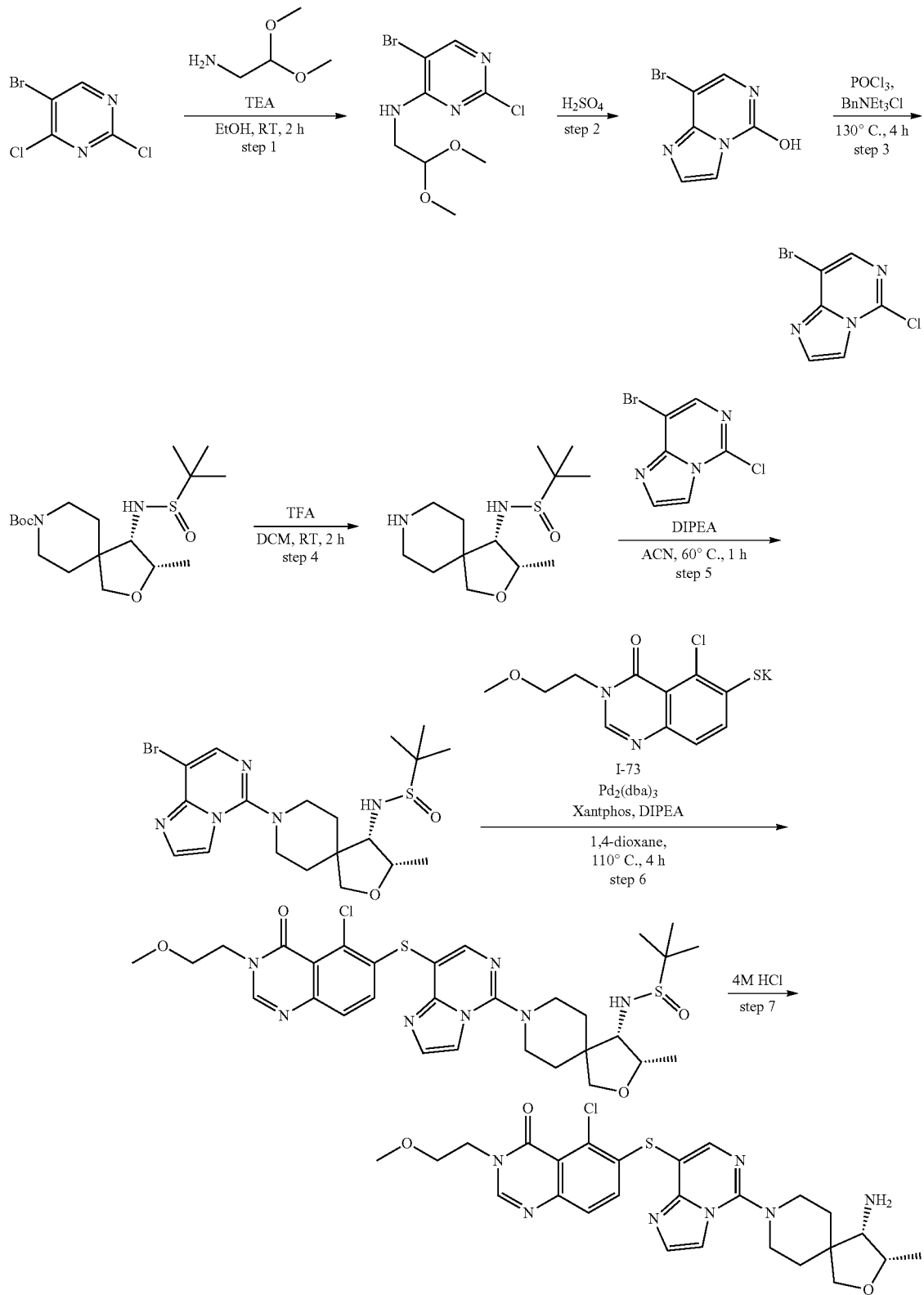

were added to 5-bromo-2,4-dichloropyrimidine (5 g, 21.9 mmol) in EtOH, followed by stirring for 15 minutes. The reaction mixture was stirred at room temperature for 2 hours and then concentrated. At 0° C., the mixture was added with diethyl ether and diluted, and then filtered through celite to remove solid. The filtered material was dried over MgSO₄, filtered and then concentrated to obtain 5-bromo-2-chloro-N-(2,2-dimethoxyethyl)pyrimidin-4-amine (6.94 g, 100%). MS m/z: 297.5 [M+H]⁺.

Step 2: 8-bromoimidazo[1,2-c]pyrimidin-5-ol 5-bromo-2-chloro-N-(2,2-dimethoxyethyl)pyrimidin-4-amine (2 g, 6.74 mmol) in sulfuric acid(20 ml, 20 V) was stirred at 75° C. for 2 hours. The reaction mixture was poured into cold distilled water, and aqueous 5M NaOH was slowly added dropwise to adjust the pH to 6. The precipitated solid was filtered and washed with MC. The resulting solid was dried to obtain 8-bromoimidazo[1,2-c]pyrimidin-5-ol (320 mg, 22%). MS m/z: 215.1 [M+H]⁺.

Step 3: 8-bromo-5-chloroimidazo[1,2-c]pyrimidine 8-bromoimidazo[1,2-c]pyrimidin-5-ol (100 mg, 0.47 mmol), POCl₃ (1.3 mL, 14 mmol), and benzyl triethyl ammonium chloride (321 mg, 1.41 mmol) were put into a round bottom flask, and then stirred at 130° C. for 4 hours. After completion of the reaction, the reaction mixture was concentrated using a concentrator. The mixture was slowly added dropwise with aqueous NaHCO₃ and extracted with EA. The organic layer was washed with brine, dried over MgSO₄, filtered and then concentrated to obtain 8-bromo-5-chloroimidazo[1,2-c]pyrimidine (72.9 mg, 67%). MS m/z: 233.5 [M+H]⁺.

Step 4: 2-methyl-N-((S5,S5)-3-methyl-2-oxa-8-azaspiro[4.5]decan-4-yl)propane-2-sulfinamide Tert-butyl (3 S,4S)-4-((tert-butylsulfinyl)amino)-3-methyl-2-oxa-8-azaspiro[4.5]decan-8-carboxylate (112 mg, 0.3 mmol) was dissolved in dichloromethane (DCM)(7.5 mL, 0.04 M). The reaction mixture was slowly added dropwise with trifluoroacetic acid (TFA) (0.23 mL, 3.0 mmol) and then stirred at room temperature for 2 hours. After completion of the reaction, the resulting product was concentrated to obtain 2-methyl-N-((3S,4S)-3-methyl-2-oxa-8-azaspiro[4.5]decan-4-yl)propane-2-sulfinamide. MS m/z: 275.5 [M+H]⁺.

Step 5: N-((3S,4S)-8-(8-bromoimidazo[1,2-c]pyrimidin-5-yl)-3-methyl-2-oxa-8-azaspiro[4.5]decan-4-yl)-2-methylpropane-2-sulfinamide DIPEA (0.52 mL, 3.0 mmol) was added to [2-methyl-N-((3S,4S)-3-methyl-2-oxa-8-azaspiro[4.5]decan-4-yl)propane-2-sulfinamide](crude product, 0.3 mmol) and 8-bromo-5-chloroimidazo[1,2-c]pyrimidine (72.9 mg, 0.31 mmol) in ACN, followed by stirring at 60° C. for 1 hour. The reaction was terminated with distilled water, and the mixture was extracted with EA. The combined organic layers were washed with brine, dried over MgSO₄, filtered and then concentrated. The resulting product was purified by column chromatography (MeOH:MC=1:15) to obtain N-((3S,4S)-8-(8-bromoimidazo[1,2-c]pyrimidin-5-yl)-3-methyl-2-oxa-8-azaspiro[4.5]decan-4-yl)-2-methylpropane-2-sulfinamide (131 mg, 93%). MS m/z: 471.5 [M+H]⁺.

Step 6: N-((3S,4S)-8-(8-((5-chloro-3-(2-methoxyethyl)-4-oxo-3,4-dihydroquinazolin-6-yl)thio)imidazo[1,2-c]pyrimidin-5-yl)-3-methyl-2-oxa-8-azaspiro[4.5]decan-4-yl)-2-methylpropane-2-sulfinamide A mixture of N-((3S,4S)-8-(8-bromoimidazo[1,2-c]pyrimidin-5-yl)-3-methyl-2-oxa-8-azaspiro[4.5]decan-4-yl)-2-methylpropane-2-sulfinamide (100 mg, 0.21 mmol), potassium 5-chloro-3-(2-m ethoxy ethyl)-4-oxo-3,4-dihydroquinazolin-6-thiolate (78 mg, 0.26 mmol), Pd₂(dba)₃ (9.6 mg, 0.01 mmol), XantPhos (12.2 mg, 0.021 mmol) and DIPEA (0.109 mL, 0.63 mmol) in dioxane (1.1 mL) was degassed and purged 3 times with N2, and then stirred under N₂ atmosphere at 120° C. for 4 hours. The reaction mixture was filtered through celite and then concentrated under reduced pressure to obtain a residue. The residue was added with aqueous NaHCO₃ and extracted with EA. The combined organic layers were dried over MgSO₄, filtered and then concentrated. The resulting product was purified by column chromatography (MeOH:MC=1:20) to obtain N-((3 S,4S)-8-(8-((5-chloro-3-(2-methoxyethyl)-4-oxo-3,4-dihydroquinazolin-6-yl)thio)imidazo[1,2-c]pyrimidin-5-yl)-3-methyl-2-oxa-8-azaspiro[4.5]decan-4-yl)-2-methylpropane-2-sulfinamide (9.6 mg, 7.1%). MS m/z: 661.1 [M+H]⁺.

Step 7: 64(54(3S,4S)-4-amino-3-methyl-2-oxa-8-azaspiro[4.5]decan-8-yl)imidazo[1,2-c]pyrimidin-8-yl)thio)-5-chloro-3-(2-methoxyethyl)quinazolin-4(3H)-one N-((3 S,4S)-8-(8-((5-chloro-3-(2-methoxyethyl)-4-oxo-3,4-dihydroquinazolin-6-yl)thio)imidazo[1,2-c]pyrimidin-5-yl)-3-methyl-2-oxa-8-azaspiro[4.5]decan-4-yl)-2-methylpropane-2-sulfinamide (9.6 mg, 0.015 mmol) was dissolved in DCM (0.15 mL, 0.1 M). The reaction mixture was added with hydrochloric acid (0.019 mL, 4 M in dioxane) and then stirred at 50° C. for 10 minutes. After completion of the reaction, the reaction mixture was concentrated using a concentrator. The reaction mixture was washed with EA, and then filtered to obtain the compound of Example 182 (3.5 mg, 39%) as an HCl salt. ¹H NMR (500 MHz, DMSO) δ 8.28 (s, 1H), 8.19 (br s, 1H), 8.10-8.07 (m, 2H), 7.93 (s, 1H), 7.74 (br s, 1H), 7.40 (d, J=8.8 Hz, 1H), 7.16 (d, J=8.7 Hz, 1H), 4.26 (t, J=5.5 Hz, 1H), 4.14 (t, J=5.0 Hz, 2H), 3.97-3.90 (m, 4H), 3.75 (d, J=9.2 Hz, 2H), 3.61 (t, J=5.1 Hz, 2H), 3.26 (s, 3H), 1.99-1.98 (m, 3H), 1.83 (d, J=12.9 Hz, 1H), 1.72 (d, J=13.2 Hz, 1H), 1.25 (d, J=6.45 Hz, 3H), 1.05 (s, 1H)

Example 183: Synthesis of 6-((3-((3S,4S)-4-amino-3-methyl-2-oxa-8-azaspiro[4.5]decan-8-yl)-1,2,4-triazin-6-yl)thio)-5-chloro-3-(2-methoxyethyl)quinazolin-4(3H)-one

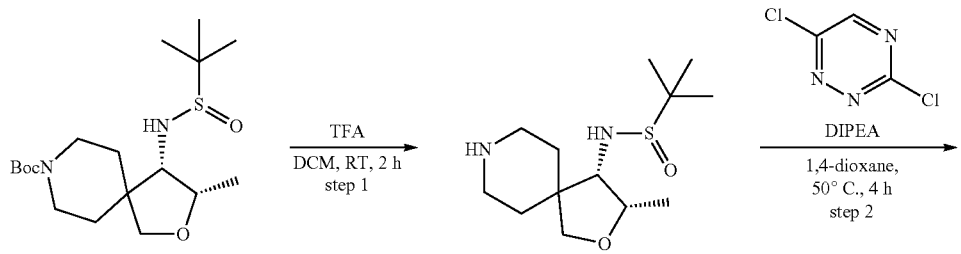

-continued

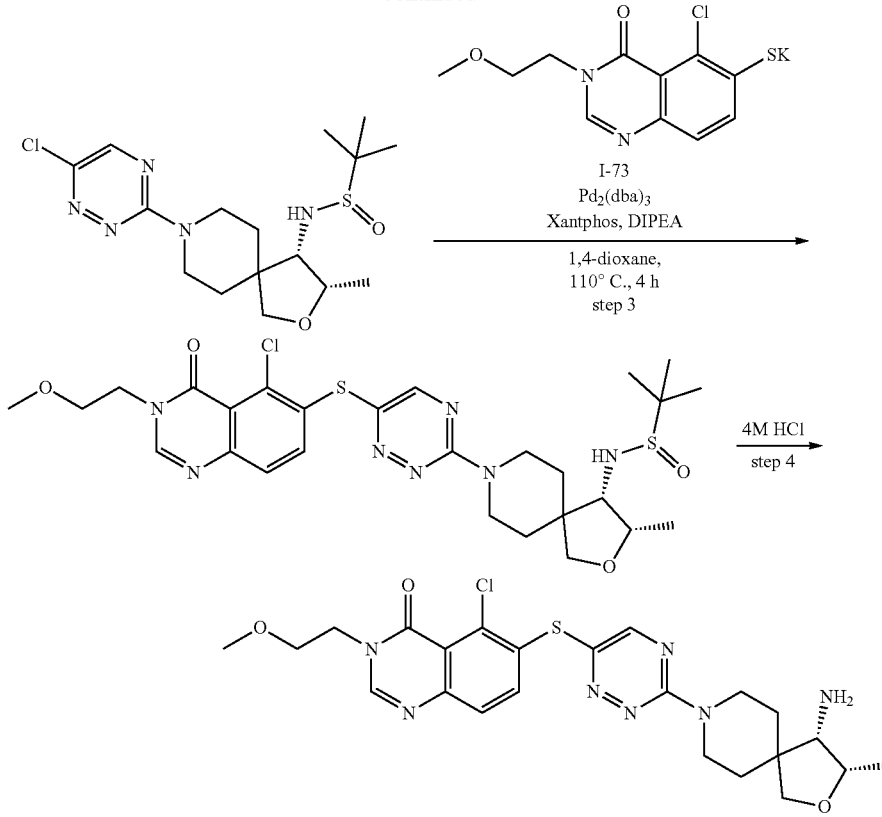

Step 1: 2-methyl-N-((S5,S5)-3-methyl-2-oxa-8-azaspiro[4.5]decan-4-yl)propane-2-sulfinamide Tert-butyl (3 S,4S)-4-((tert-butylsulfinyl)amino)-3-methyl-2-oxa-8-azaspiro[4.5]decan-8-carboxylate (300 mg, 2.0 mmol) was dissolved in dichloromethane(DCM) (6.7 mL, 0.3 M). The reaction mixture was slowly added dropwise with trifluoroacetic acid(TFA) (1.53 mL, 20.0 mmol) and then stirred at room temperature for 2 hours. After completion of the reaction, the resulting product was concentrated to obtain 2-methyl-N-((3S,4S)-3-methyl-2-oxa-8-azaspiro[4.5]decan-4-yl)propane-2-sulfinamide. MS m/z: 275.5 [M+H]$^+$.

Step 2: N-((S5,S5)-8-(6-chloro-1,2,4-triazin-3-yl)-3-methyl-2-oxa-8-azaspiro[4.5]decan-4-yl)-2-methylpropane-2-sulfinamide 2-methyl-N-((3 S,4S)-3-methyl-2-oxa-8-azaspiro[4.5]decan-4-yl)propane-2-sulfinamide (crude product, 2.0 mmol) and 3,6-dichloro-1,2,4-triazine (300 mg, 2.0 mmol) were dissolved in 1,4-dioxane (10 mL, 0.2 M). The reaction mixture was added with DIPEA (1.22 mL, 7.0 mmol) and then stirred at 50° C. for 4 hours. The reaction was terminated with H$_2$O, and the mixture was extracted with EA. The EA layer was dried over MgSO$_4$, filtered and then concentrated. The resulting product was purified by MPLC (EA:hexane(Hx)=4:1) and concentrated to obtain N-((3 S,4S)-8-(6-chloro-1,2,4-triazin-3-yl)-3-methyl-2-oxa-8-azaspiro[4.5]decan-4-yl)-2-methylpropane-2-sulfinamide (119 mg, 15%). MS m/z: 388.5 [M+H]$^+$.

Step 3: N-43S,4S)-8-(6-((5-chloro-3-(2-methoxyethyl)-4-oxo-3,4-dihydroquinazolin-6-yl)thio)-1,2,4-triazin-3-yl)-3-methyl-2-oxa-8-azaspiro[4.5]decan-4-yl)-2-methylpropane-2-sulfinamide A mixture of N-((3 S,4 S)-8-(6-chloro-1,2,4-triazin-3-yl)-3-methyl-2-oxa-8-azaspiro[4.5]decan-4-yl)-2-methylpropane-2-sulfinamide (97 mg, 0.25 mmol), potassium 5-chloro-3-(2-methoxyethyl)-4-oxo-3,4-dihydroquinazolin-6-thiolate (93 mg, 0.3 mmol), Pd$_2$(dba)$_3$ (11 mg, 0.012 mmol), XantPhos (15 mg, 0.025 mmol) and DIPEA (0.087 mL, 0.5 mmol) in dioxane (1.25 mL) was degassed and purged 3 times with N2, and stirred under N$_2$ atmosphere at 120° C. for 4 hours. The reaction mixture was filtered through celite and then concentrated under reduced pressure to obtain a residue. The residue was added with aqueous NaHCO$_3$ and extracted with EA. The combined organic layers were dried over MgSO$_4$, filtered and then concentrated. The resulting product was purified by column chromatography (amine column, EA:Hex=3:1) to obtain N-((3 S,4 S)-8-(6-((5-chloro-3-(2-methoxyethyl)-4-oxo-3,4-dihydroquinazolin-6-yl)thio)-1,2,4-triazin-3-yl)-3-methyl-2-oxa-8-azaspiro[4.5]decan-4-yl)-2-methylpropane-2-sulfinamide (13.1 mg, 8.4%). MS m/z: 623.1 [M+H]$^+$.

Step 4: 6-034(3S,4S)-4-amino-3-methyl-2-oxa-8-azaspiro[4.5]decan-8-yl)-1,2,4-triazin-6-yl)thio)-5-chloro-3-(2-methoxyethyl)quinazolin-4(3H)-one N-((3 S,4 S)-8-(6-((5-chloro-3-(2-methoxyethyl)-4-oxo-3,4-dihydroquinazolin-6-yl)thio)-1,2,4-triazin-3-yl)-3-methyl-2-oxa-8-azaspiro[4.5]decan-4-yl)-2-methylpropane-2-sulfinamide (13.1 mg, 0.02 mmol) was dissolved in DCM (0.2 mL, 0.1 M). The reaction mixture was added with hydrochloric acid (0.025 mL, 4 M in dioxane) and then stirred at 50° C. for 10 minutes. After completion of the reaction, the reaction mixture was concentrated using a concentrator. The reaction mixture was washed with EA/Hex, and then filtered to obtain the compound of Example 183 (5.9 mg, 53%) as an HCl salt. $^1$H NMR (500 MHz, DMSO) δ 8.40 (s, 1H), 8.32 (s, 1H), 8.10 (dd, J=5.6, 3.5 Hz, 1H), 7.98-7.95 (m, 2H), 7.66 (t, J=7.9 Hz, 1H), 4.31 (q, J=14.9, 13.2 Hz, 1H), 4.16-4.14 (m, 3H), 4.02 (d, J=15.1 Hz, 1H), 3.94-3.92 (m, 1H), 3.84 (d, J=9.3 Hz, 2H), 3.37(br s, 2H), 3.27 (s, 3H), 3.22-3.14 (m, 1H), 3.03 (dd, J=14.2, 12.4 Hz, 1H), 1.66-1.45 (m, 5H), 1.20 (d, J=6.6 Hz, 3H).

Example 184: Synthesis of (S)-6-((3-(1-amino-1,3-dihydrospiro[indene-2,4'-piperidin]-1'-yl)-1,2,4-triazin-6-yl)thio)-5-chloro-3-(2-methoxyethyl)quinazolin-4(3H)-one

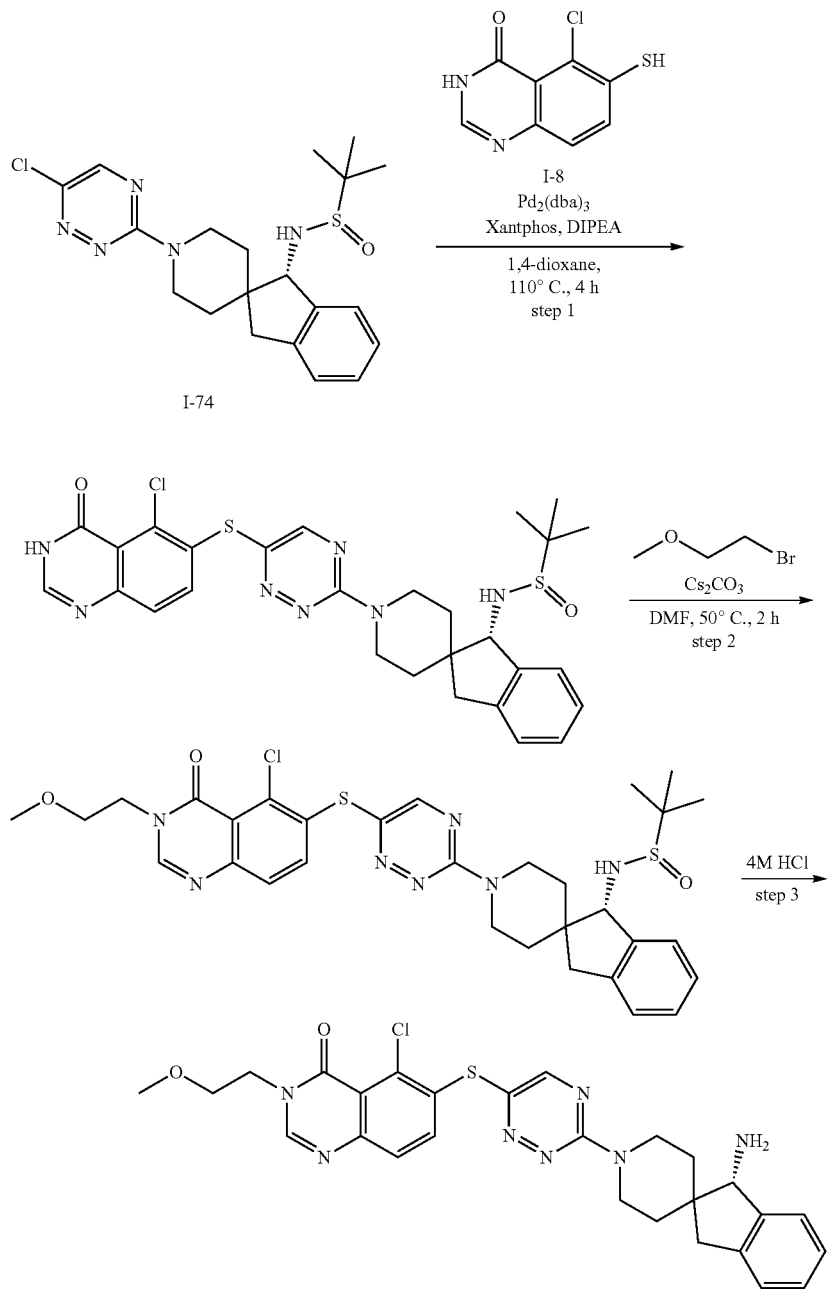

Step 1: N—((S)-1'-(6-((5-chloro-4-oxo-3,4-dihydroquinazolin-6-yl)thio)-1,2,4-triazin-3-yl)-1,3-dihydrospiro[indene-2,4'-piperidin]-1-yl)-2-methylpropane-2-sulfinamide A mixture of Intermediate I-74 (42 mg, 0.1 mmol), Intermediate I-8 (33 mg, 0.13 mmol), Pd$_2$(dba)$_3$ (4.6 mg, 0.005 mmol), XantPhos (5.8 mg, 0.01 mmol) and DIPEA (0.035 mL, 0.2 mmol) in dioxane (0.5 mL) was degassed and purged 3 times with N2, and stirred under N$_2$ atmosphere at 120° C. for 4 hours. The reaction mixture was filtered through celite and then concentrated under reduced pressure to obtain a residue. The residue was added with aqueous NaHCO$_3$ and extracted with EA. The combined organic layers were dried over MgSO$_4$, filtered and then concentrated. The resulting product was purified by column chromatography (MeOH:MC=1:20) to obtain N—((S)-1'-(6-((5-chloro-4-oxo-3,4-dihydroquinazolin-6-yl)thio)-1,2,4-triazin-3-yl)-1,3-dihydrospiro[indene-2,4'-piperidin]-1-yl)-2-methylpropane-2-sulfinamide (45 mg, 76%). MS m/z: 597.1 [M+H]$^+$.

Step 2: N—((S)-1'-(6-((5-chloro-3-(2-methoxyethyl)-4-oxo-3,4-dihydroquinazolin-6-yl)thio)-1,2,4-triazin-3-yl)-1,3-dihydrospiro[indene-2,4'-piperidin]-1-yl)-2-methylpropane-2-sulfinamide In a round bottom flask, N—((S)-1'-(6-((5-chloro-4-oxo-3,4-dihydroquinazolin-6-yl)thio)-1,2,4-triazin-3-yl)-1,3-dihydrospiro[indene-2,4'-piperidin]-1-yl)-2-methylpropane-2-sulfinamide (45.1 mg, 0.076 mmol), 1-bromo-2-methoxyethane (0.011 mL, 0.11 mmol) and cesium carbonate (50 mg, 0.15 mmol) were dissolved in DMF (0.76 mL, 0.1 M). The reaction mixture was stirred at 50° C. for 3 hours. The reaction was terminated with aqueous NaHCO₃ solution, and the mixture was extracted with EA. The EA layer was dried over MgSO₄, filtered and then concentrated. The resulting product was separated by MPLC (amine column, EA:Hex=1:1) to obtain N—((S)-1'-(6-((5-chloro-3-(2-m ethoxy ethyl)-4-oxo-3,4-dihydroquinazolin-6-yl)thio)-1,2,4-triazin-3-yl)-1,3-dihydrospiro[indene-2,4'-piperidin]-1-yl)-2-methylpropane-2-sulfinamide (33 mg, 67%). MS m/z: 655.1 [M+H]⁺.

Step 3: (S)-64(3-(1-amino-1,3-dihydrospiro[indene-2,4'-piperidin]-1'-yl)-1,2,4-triazin-6-yl)thio)-5-chloro-3-(2-methoxyethyl)quinazolin-4(3H)-one N—((S)-1'-(6-((5-chloro-3-(2-m ethoxy ethyl)-4-oxo-3,4-dihydroquinazolin-6-yl)thio)-1,2,4-triazin-3-yl)-1,3-dihydrospiro[indene-2,4'-piperidin]-1-yl)-2-methylpropane-2-sulfinamide (33 mg, 0.05 mmol) was dissolved in DCM (0.5 mL, 0.1 M). The reaction mixture was added with 4 M hydrochloric acid (0.064 mL, 4 M in dioxane) and then stirred at 50° C. for 10 minutes. After completion of the reaction, the reaction mixture was concentrated using a concentrator. The reaction mixture was washed with EA/Hex, and then filtered to obtain the compound of Example 184 (31.3 mg, 100%) as an HCl salt. ¹H NMR (500 MHz, DMSO) δ 8.41-8.33 (m, 4H), 8.11 (d, J=4.35 Hz, 1H), 7.68-7.64 (m, 1H), 7.55 (br s, 1H), 7.34-7.30 (m, 3H), 4.47-4.40 (m, 1H), 4.33 (br s, 1H), 4.12 (br s, 2H), 4.03-4.00 (m, 1H), 3.25 (br s, 2H), 3.18 (s, 3H), 3.12-3.08 (m, 1H), 2.94 (d, J=16.2 Hz, 1H), 1.71-1.50 (m, 3H), 1.42-1.39 (m, 1H), 1.25-1.17 (m, 1H), 1.05 (s, 1H).

Example 185: Synthesis of (S)-6-((6-(1-amino-1,3-dihydrospiro(indene-2,4'-piperidin]-1'-yl)-1,2,4-triazin-3-yl)thio)-5-chloro-3-(2-methoxyethyl)quinazolin-4(3H)-one

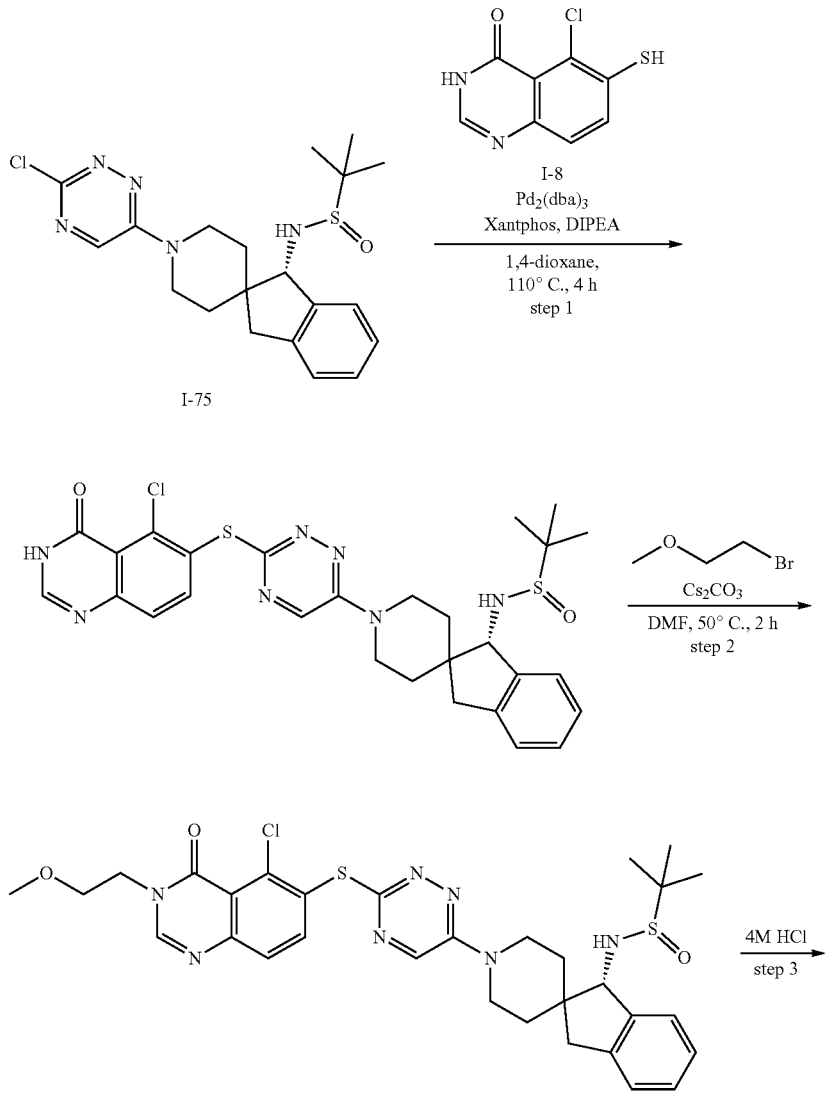

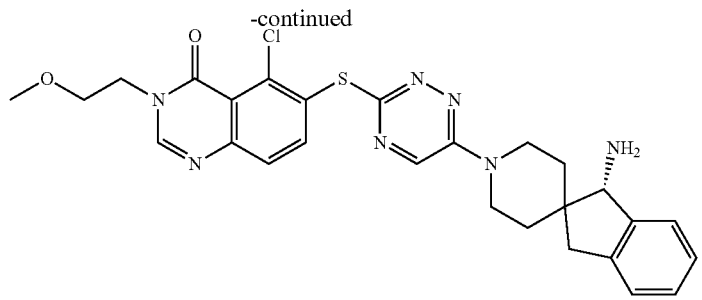

Step 1: N—((S)-1'-(3-((5-chloro-4-oxo-3,4-dihydroquinazolin-6-yl)thio)-1,2,4-triazin-6-yl)-1,3-dihydrospiro[indene-2,4'-piperidin]-1-yl)-2-methylpropane-2-sulfinamide A mixture of Intermediate I-75 (42 mg, 0.1 mmol), Intermediate I-8 (33 mg, 0.13 mmol), Pd₂(dba)₃ (4.6 mg, 0.005 mmol), XantPhos (5.8 mg, 0.01 mmol) and DIPEA (0.035 mL, 0.2 mmol) in dioxane (0.5 mL) was degassed and purged 3 times with N2, and stirred under N₂ atmosphere at 120° C. for 4 hours. The reaction mixture was filtered through celite and then concentrated under reduced pressure to obtain a residue. The residue was added with aqueous NaHCO₃ and extracted with EA. The combined organic layers were dried over MgSO₄, filtered and then concentrated. The resulting product was purified by column chromatography (MeOH:MC=1:20) to obtain N—((S)-1'-(3-((5-chloro-4-oxo-3,4-dihydroquinazolin-6-yl)thio)-1,2,4-triazin-6-yl)-1,3-dihydrospiro[indene-2,4'-piperidin]-1-yl)-2-methylpropane-2-sulfinamide (41 mg, 69%). MS m/z: 597.1 [M+H]⁺.

Step 2: N—((S)-1'-(3-((5-chloro-3-(2-methoxyethyl)-4-oxo-3,4-dihydroquinazolin-6-yl)thio)-1,2,4-triazin-6-yl)-1,3-dihydrospiro[indene-2,4'-piperidin]-1-yl)-2-methylpropane-2-sulfinamide In a round bottom flask, N—((S)-1'-(3-((5-chloro-4-oxo-3,4-dihydroquinazolin-6-yl)thio)-1,2,4-triazin-6-yl)-1,3-dihydrospiro[indene-2,4'-piperidin]-1-yl)-2-methylpropane-2-sulfinamide (41 mg, 0.069 mmol), 1-bromo-2-methoxyethane (0.010 mL, 0.103 mmol) and cesium carbonate (50 mg, 0.15 mmol) were dissolved in DMF (0.69 mL, 0.1 M). The reaction mixture was stirred at 50° C. for 3 hours. The reaction was terminated with aqueous NaHCO₃ solution, and the mixture was extracted with EA. The EA layer was dried over MgSO₄, filtered and then concentrated. The resulting product was separated by MPLC (amine column, EA:Hex=1:1) to obtain N—((S)-1'-(3-((5-chloro-3-(2-m ethoxy ethyl)-4-oxo-3,4-dihydroquinazolin-6-yl)thio)-1,2,4-triazin-6-yl)-1,3-dihydrospiro[indene-2,4'-piperidin]-1-yl)-2-methylpropane-2-sulfinamide (34.1 mg, 75%). MS m/z: 655.1 [M+H]⁺.

Step 3: (S)-6-((6-(1-amino-1,3-dihydrospiro[indene-2,4'-piperidin]-1'-yl)-1,2,4-triazin-3-yl)thio)-5-chloro-3-(2-methoxyethyl)quinazolin-4(3H)-one N—((S)-1'-(3-((5-chloro-3-(2-m ethoxy ethyl)-4-oxo-3,4-dihydroquinazolin-6-yl)thio)-1,2,4-triazin-6-yl)-1,3-dihydrospiro[indene-2,4'-piperidin]-1-yl)-2-methylpropane-2-sulfinamide (34 mg, 0.05 mmol) was dissolved in DCM (0.5 mL, 0.1 M). The reaction mixture was added with hydrochloric acid (0.065 mL, 4 M in dioxane) and then stirred at 50° C. for 10 minutes. After completion of the reaction, the reaction mixture was concentrated using a concentrator. The reaction mixture was washed with EA/Hex, and then filtered to obtain the compound of Example 185 (32 mg, 100%) as an HCl salt. ¹H NMR (500 MHz, DMSO) δ 8.39-8.37 (m, 3H), 8.33 (d, J=5.0 Hz, 1H), 8.11 (t, J=7.45 Hz, 1H), 7.69-7.64(m. 1H), 7.54 (d, J=6.25 Hz, 1H), 7.37-7.29 (m, 3H), 4.49-4.33 (m, 2H), 4.14-4.12 (m, 2H), 4.02 (d, J=12.6 Hz, 1H), 3.25 (s, 3H), 3.21-3.08 (m, 3H), 2.95 (d, J=16.2 Hz, 1H), 1.73-1.59 (m, 2H), 1.51 (d, J=12.5 Hz, 1H), 1.39 (t, J=14.1 Hz, 1H), 1.29-1.25 (m, 1H), 1.05 (s, 1H).

Example 186: Synthesis of (R)-6-amino-2-(4-(2-amino-3-(pyridin-4-yl)propyl)piperazin-1-yl)-5-((2,3-dichlorophenyl)thio)-3-methylpyrimidin-4(3H)-one

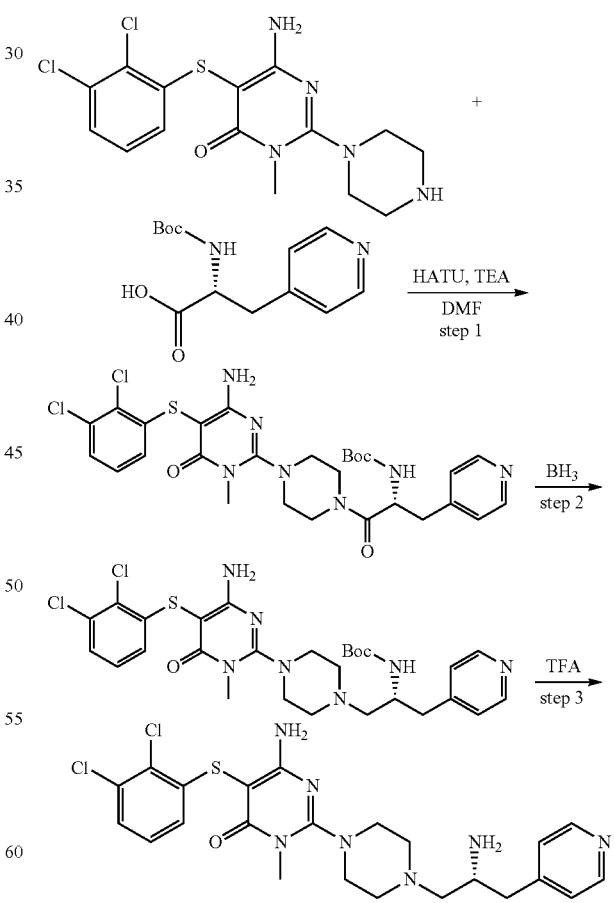

Step 1: tert-butyl (R)-(1-(4-(4-amino-5-((2,3-dichlorophenyl)thio)-1-methyl-6-oxo-1,6-dihydropyrimidin-2-yl)piperazin-1-yl)-1-oxo-3-(pyridin-4-yl)propan-2-yl)carbamate 6-amino-5-((2,3-dichlorophenyl)thio)-3-methyl-2-

(piperazin-1-yl)pyrimidin-4(3H)-one (200 mg, 0.52 mmol) and HATU (14bis(dimethylamino)methylene]-1H-1,2,3-triazolo[4,5-b]pyridinium 3-oxide hexafluorophosphate, 395 mg, 1.04 mmol), TEA (0.15 mL, 1.04 mmol) were dissolved in DMF (5 mL, 0.1 M), and then (R)-2-((tert-butoxycarbonyl)amino)-3-(pyridin-4-yl)propanoic acid (277 mg, 1.04 mmol) was added thereto. The reaction mixture was stirred at room temperature for 4 hours. The reaction mixture was added with brine (10 mL) and EtOAc (10 mL×3) and extracted. The organic layer was dried over $Na_2SO_4$, filtered and then concentrated. The resulting product was separated by MPLC to obtain tert-butyl (R)-(1-(4-(4-amino-5-((2,3-dichlorophenyl)thio)-1-methyl-6-oxo-1,6-dihydropyrimidin-2-yl)piperazin-1-yl)-1-oxo-3-(pyridin-4-yl)propan-2-yl)carbamate (150 mg, 45%). MS m/z: 634 [M+H]$^+$.

Step 2: tert-butyl (R)-(1-(4-(4-amino-5-((2,3-dichlorophenyl)thio)-1-methyl-6-oxo-1,6-dihydropyrimidin-2-yl)piperazin-1-yl)-3-(pyridin-4-yl)propan-2-yl)carbamate Tert-butyl (R)-(1-(4-(4-amino-5-((2,3-di chlorophenyl)thio)-1-methyl-6-oxo-1,6-dihydropyrimidin-2-yl)piperazin-1-yl)-1-oxo-3-(pyridin-4-yl)propan-2-yl)carbamate (150 mg, 0.24 mmol) was dissolved in THF (3 mL), and then $BH_3$-$Me_2$S (30 μL) was added thereto at 0° C. The reaction mixture was stirred at room temperature for 1 hour. At 0° C., The reaction was terminated with MeOH (5 mL), and the mixture was concentrated. The resulting product was separated by MPLC to obtain tert-butyl (R)-(1-(4-(4-amino-5-((2,3-dichlorophenyl)thio)-1-methyl-6-oxo-1,6-dihydropyrimidin-2-yl)piperazin-1-yl)-3-(pyridin-4-yl)propan-2-yl)carbamate (50 mg, 34%). MS m/z: 620 [M+H]$^+$.

Step 3: (R)-6-amino-2-(4-(2-amino-3-(pyridin-4-yl)propyl)piperazin-1-yl)-54(2,3-dichlorophenyl)thio)-3-methylpyrimidin-4(3H)-one Tert-butyl (R)-(1-(4-(4-amino-5-((2,3-di chlorophenyl)thio)-1-methyl-6-oxo-1,6-dihydropyrimidin-2-yl)piperazin-1-yl)-3-(pyridin-4-yl)propan-2-yl)carbamate (50 mg, 0.08 mmol) was dissolved in DCM (1 mL, 0.08 M). The reaction mixture was added with trifluoroacetic acid (TFA, 0.5 mL, 0.16 M) and then stirred at room temperature for 1 hour. The reaction was terminated with aqueous $NaHCO_3$ solution, and the mixture was extracted with EA. The EA layer was dried over $MgSO_4$, filtered and then concentrated. The resulting product was separated by Prep-HPLC and concentrated to obtain the compound of Example 186 (30 mg, 72%) as a TFA salt. $^1$H NMR (400 MHz, $CD_3OD$) δ 8.87-8.79 (m, 2H), 8.12-8.01 (m, 2H), 7.29-7.21 (m, 1H), 7.18-7.05 (m, 1H), 6.75 (dd, J=8.1, 1.4 Hz, 1H), 4.02 (s, 1H), 3.41 (d, J=5.4 Hz, 8H), 3.31-3.21 (m, 1H), 2.97-2.89 (m, 2H), 2.93-2.78 (m, 1H), 2.81-2.67 (m, 3H); MS m/z: 520 [M+H]$^+$.

Example 187: Synthesis of (S)-6-amino-2-(4-(2-amino-3-(pyridin-4-yl)propyl)piperazin-1-yl)-5-((2,3-dichlorophenyl)thio)-3-methylpyrimidin-4(3H)-one

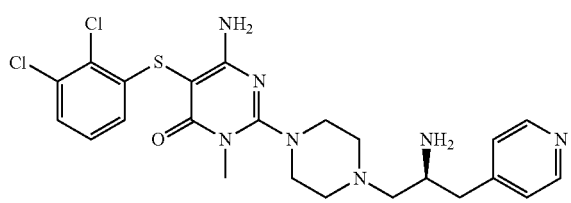 [SMILES: Cn1c(N2CCN(C[C@@H](N)Cc3ccncc3)CC2)nc(N)c(Sc2cccc(Cl)c2Cl)c1=O]

The compound of Example 187 was synthesized in the same method as in Example 186 above, except that (S)-2-((tert-butoxycarbonyl)amino)-3-(pyridin-4-yl)propanoic acid was used instead of (R)-2-((tert-butoxycarbonyl)amino)-3-(pyridin-4-yl)propanoic acid. $^1$H NMR (400 MHz, $CD_3OD$) δ 8.87-8.79 (m, 2H), 8.12-8.01 (m, 2H), 7.29-7.21 (m, 1H), 7.18-7.05 (m, 1H), 6.75 (dd, J=8.1, 1.4 Hz, 1H), 4.02 (s, 1H), 3.41 (d, J=5.4 Hz, 8H), 3.31-3.21 (m, 1H), 2.97-2.89 (m, 2H), 2.93-2.78 (m, 1H), 2.81-2.67 (m, 3H); MS m/z: 520 [M+H]$^+$.

Example 188: Synthesis of 6-amino-2-(4-(2-amino-3-(pyridin-3-yl)propyl)piperazin-1-yl)-5-((2,3-dichlorophenyl)thio)-3-methylpyrimidin-4(3H)-one

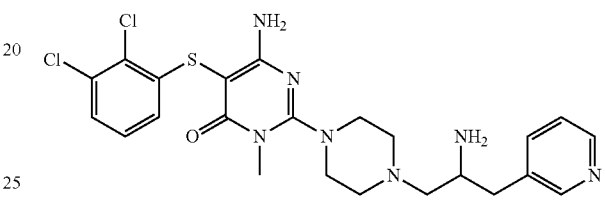

The compound of Example 188 was synthesized in the same method as in Example 186 above, except that 2-((tert-butoxycarbonyl)amino)-3-(pyridin-3-yl)propanoic acid was used instead of (R)-2-((tert-butoxycarbonyl)amino)-3-(pyridin-4-yl)propanoic acid. $^1$H NMR (400 MHz, $CD_3OD$) δ 8.65 (d, J=5.5 Hz, 2H), 8.14 (d, J=8.1 Hz, 1H), 7.76-7.69 (m, 1H), 7.24 (dd, J=7.9, 1.4 Hz, 1H), 7.08 (t, J=8.0 Hz, 1H), 6.74 (dd, J=8.0, 1.4 Hz, 1H), 4.02 (s, 1H), 3.42-3.32 (m, 8H), 3.26-3.21 (m, 3H), 3.09 (d, J=7.0 Hz, 2H), 2.62 (d, J=7.4 Hz, 2H); MS m/z: 520 [M+H]$^+$.

Example 189: Synthesis of 6-amino-2-(4-(2-amino-4-phenylbutyl)piperazin-1-yl)-5-((2,3-dichlorophenyl)thio)-3-methylpyrimidin-4(3H)-one

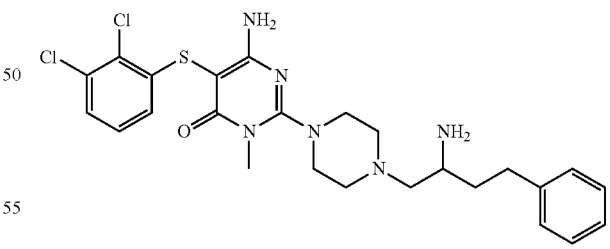

The compound of Example 189 was synthesized in the same method as in Example 186 above, except that 2-((tert-butoxycarbonyl)amino)-4-phenylbutanoic acid was used instead of (R)-2-((tert-butoxycarbonyl)amino)-3-(pyridin-4-yl)propanoic acid. $^1$H NMR (400 MHz, $CD_3OD$) δ 7.30 (d, J=7.3 Hz, 2H), 7.23 (dd, J=8.9, 7.5 Hz, 4H), 7.11-7.07 (m, 1H), 6.76-6.74 (m, 1H), 3.41-3.35 (m, 4H), 3.26-3.25 (m, 3H), 2.79-2.75 (m, 5H), 2.58-2.54 (m, 4H) 1.93-1.92 (m, 2H); MS m/z: 533 [M+H]$^+$.

Example 190: Synthesis of 6-amino-2-(4-(2-amino-2-phenylethyl)piperazin-1-yl)-5-((2,3-dichlorophenyl)thio)-3-methylpyrimidin-4(3H)-one

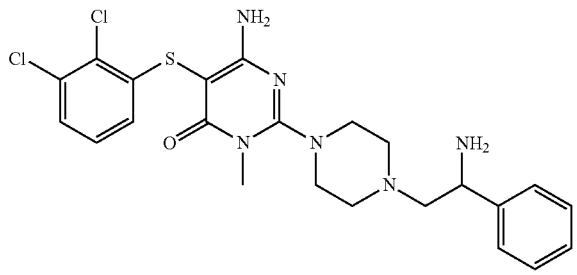 [SMILES: Cn1c(N2CCN(CC(N)c3ccccc3)CC2)nc(N)c(Sc2cccc(Cl)c2Cl)c1=O]

The compound of Example 190 was synthesized in the same method as in Example 186 above, except that 2-((tert-butoxycarbonyl)amino)-2-phenylacetic acid was used instead of (R)-2-((tert-butoxycarbonyl)amino)-3-(pyridin-4-yl)propanoic acid. $^1$H NMR (400 MHz, CD$_3$OD) δ 7.53-7.41 (m, 5H), 7.24 (dd, J=8.0, 1.4 Hz, 1H), 7.09 (t, J=8.0 Hz, 1H), 6.75 (dd, J=8.0, 1.5 Hz, 1H), 4.55 (dd, J=10.9, 4.0 Hz, 1H), 3.47-3.44 (m, 4H), 3.43 (s, 3H), 3.04-2.77 (m, 4H), 2.71-2.64 (m, 2H); MS m/z: 505 [M+H]$^+$.

Example 191: Synthesis of (S)-6-amino-2-(4-(2-amino-2-phenylethyl)piperazin-1-yl)-5-((2,3-dichlorophenyl)thio)-3-methylpyrimidin-4(3H)-one

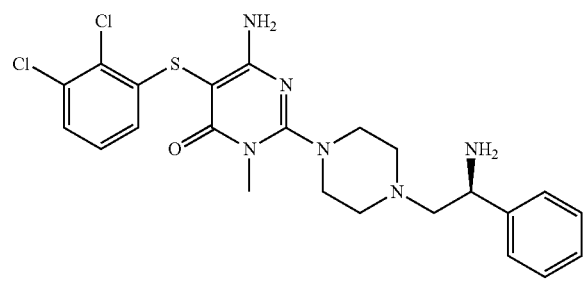 [SMILES: Cn1c(N2CCN(C[C@@H](N)c3ccccc3)CC2)nc(N)c(Sc2cccc(Cl)c2Cl)c1=O]

The compound of Example 191 was synthesized in the same method as in Example 186 above, except that (S)-2-((tert-butoxycarbonyl)amino)-2-phenylacetic acid was used instead of (R)-2-((tert-butoxycarbonyl)amino)-3-(pyridin-4-yl)propanoic acid. $^1$H NMR (400 MHz, CD$_3$OD) δ 7.53-7.41 (m, 5H), 7.24 (dd, J=8.0, 1.4 Hz, 1H), 7.09 (t, J=8.0 Hz, 1H), 6.75 (dd, J=8.0, 1.5 Hz, 1H), 4.55 (dd, J=10.9, 4.0 Hz, 1H), 3.47-3.44 (m, 4H), 3.43 (s, 3H), 3.04-2.77 (m, 4H), 2.71-2.64 (m, 2H); MS m/z: 505 [M+H]$^+$.

Example 192: Synthesis of 6-amino-5-((2-amino-3-chloropyridin-4-yl)thio)-2-(4-(2-aminoethyl)piperazin-1-yl-3-methylpyrimidin-4(3H)-one

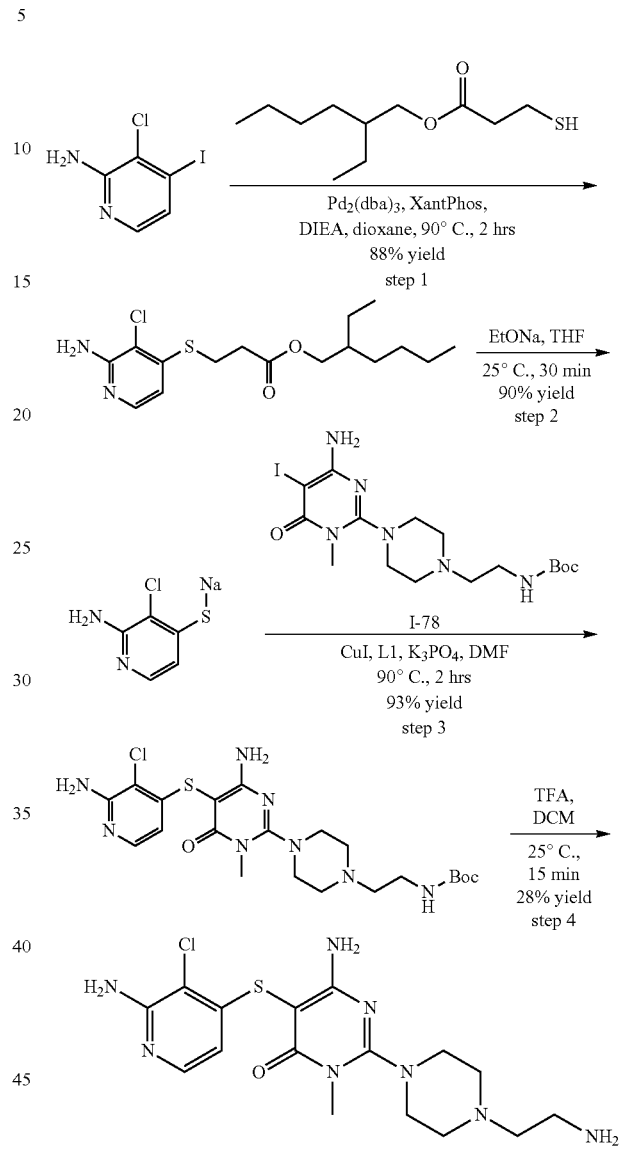

Step 1: 2-ethylhexyl 3-[(2-amino-3-chloro-4-pyridyl)sulfanyl]propanoate 3-chloro-4-iodo-pyridin-2-amine (1.00 g, 3.93 mmol) and 2-ethylhexyl-3-sulfanylpropanoate (943 mg, 4.32 mmol), Pd$_2$(dba)$_3$ (359 mg, 393 μmol), XantPhos (227 mg, 393 DIEA (1.02 g, 7.86 mmol) were dissolved in dioxane (2 mL), followed by stirring at 90° C. for 2 hours. After completion of the reaction, the mixture was filtered, and the filtrate was concentrated. The resulting product was separated by column chromatography (petroleum ether/ethyl acetate=15/1 to 0/1) to obtain 2-ethylhexyl 3-[(2-amino-3-chloro-4-pyridyl)sulfanyl]propanoate (1.20 g, 88% yield) as a yellow solid. $^1$H NMR (400 MHz, DMSO-d$_6$) δ=7.80 (d, J=5.2 Hz, 1H) 6.55 (d, J=5.2 Hz, 1H) 6.25 (s, 2H) 3.97 (d, J=5.6 Hz, 2H) 3.21 (t, J=6.8 Hz, 2H) 2.71 (t, J=6.8 Hz, 2H) 1.59-1.45 (m, 1H) 1.31-1.21 (m, 8H) 0.86-0.81 (m, 6H); MS m/z: 345.1 [M+H]$^+$.

Step 2: (2-amino-3-chloro-4-pyridyl)sulfanyl sodium 2-ethylhexyl 3-[(2-amino-3-chloro-4-pyridyl)sulfanyl]propanoate (500 mg, 1.45 mmol) was dissolved in THF (10 mL), and then EtONa (295 mg, 4.35 mmol) was added thereto. The reaction mixture was stirred at room temperature for 30 minutes. After completion of the reaction, DCM (10 mL) was added to the mixture, and the resulting solid was filtered. The solid was dried under vacuum to obtain (2-amino-3-chloro-4-pyridyl)sulfanyl sodium (550 mg, 90% yield) as a yellow solid. $^1$H NMR (400 MHz, DMSO-d$_6$) δ=7.02 (d, J=5.6 Hz, 1H) 6.45 (d, J=5.6 Hz, 1H); MS m/z: 161.0 [M+H]$^+$.

Step 3: tert-butyl N-[2-[4-14-amino-5-1(2-amino-3-chloro-4-pyridyl)sulfanyl]-1-methyl-6-oxo-pyrimidin-2-yl]piperazin-1-yl]ethyl]carbamate (2-amino-3-chloro-4-pyridyl)sulfanyl sodium (95.4 mg, 522 μmol) and Intermediate I-78 (50.0 mg, 104 μmol), CuI (1.99 mg, 10.4 μmol), K$_3$PO$_4$ (110 mg, 522 μmol), (1S,2S)-N1,N2-dimethylcyclohexane-1,2-diamine (1.49 mg, 10.45 μmol) were dissolved in DMF (1 mL), followed by stirring at 90° C. for 2 hours. After completion of the reaction, the mixture was filtered, and the filtrate was concentrated under reduced pressure. The resulting product was separated by reverse phase flash (0.1% FA codition) to obtain tert-butyl N-[24444-amino-5-[(2-amino-3-chloro-4-pyridyl)sulfanyl]-1-methyl-6-oxo-pyrimidin-2-yl]piperazin-1-yl]ethyl]carbamate (100 mg, 93% yield). MS m/z: 511.3 [M+H]$^+$.

Step 4: 6-amino-5-((2-amino-3-chloropyridin-4-yl)thio)-2-(4-(2-aminoethyl)piperazin-1-yl-3-methylpyrimidin-4(3H)-one Tert-butyl N-[2-[4-[4-amino-5-[(2-amino-3-chloro-4-pyridyl)sulfanyl]-1-methyl-6-oxo-pyrimidin-2-yl]piperazin-1-yl]ethyl]carbamate (70.0 mg, 136 μmol) was dissolved in DCM (0.5 mL), and then TFA (2.69 g, 23.6 mmol) was added thereto. The reaction mixture was stirred at room temperature for 15 minutes. After completion of the reaction, the reaction mixture was concentrated and neutralized by addition of NH$_3$·H$_2$O. The resulting product was separated by Prep-HPLC to obtain the compound of Example 192 (17.4 mg, 28% yield). $^1$H NMR (400 MHz, MeOD-d$_4$) δ=8.85-7.85 (m, 1H), 7.59 (d, J=5.2 Hz, 1H) 6.15 (d, J=5.2 Hz, 1H) 3.43 (s, 3H) 3.41 (d, J=4.4 Hz, 4H) 3.10 (t, J=5.6 Hz, 2H) 2.69 (d, J=5.2 Hz, 6H); MS m/z: 411.1 [M+H]$^+$.

Example 193: Synthesis of 6-amino-2-(4-(2-aminoethyl)piperazin-1-yl)-5-((2,3-dichloropyridin-4-yl)thio)-3-methylpyrimidin-4(3H)-one

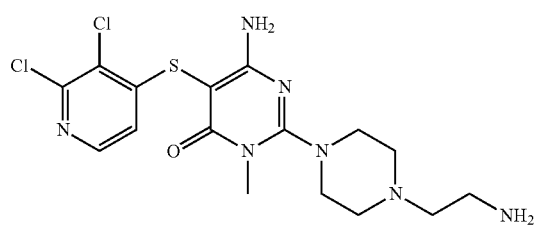 [SMILES: Cn1c(N2CCN(CCN)CC2)nc(N)c(Sc2ccnc(Cl)c2Cl)c1=O]

The compound of Example 193 was synthesized in the same method as in Example 192 above, except that 2,3-dichloro-4-iodo-pyridine was used instead of 3-chloro-4-iodo-pyridin-2-amine. $^1$H NMR (400 MHz, MeOD-d$_4$) δ=8.54 (s, 1H), 7.98 (d, J=5.2 Hz, 1H), 6.83 (d, J=5.2 Hz, 1H), 3.48-3.37 (m, 7H), 3.09 (t, J=5.6 Hz, 2H), 2.75-2.62 (m, 6H); MS m/z: 430.1 [M+H]$^+$.

Example 194: Synthesis of 6-amino-2-(4-(2-aminoethyl)piperazin-1-yl)-5-((2,3-dichlorophenyl)thio)-3-methylpyrimidin-4(3H)-one

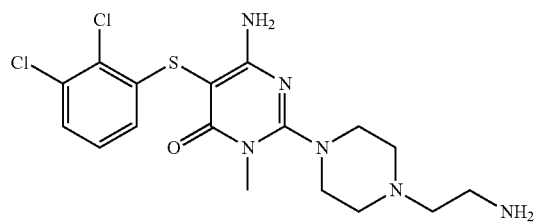 [SMILES: Cn1c(N2CCN(CCN)CC2)nc(N)c(Sc2cccc(Cl)c2Cl)c1=O]

The compound of Example 194 was synthesized in the same method as in Example 192 above, except that 2,3-dichlorobenzenethiol was used instead of 3-chloro-4-iodo-pyridin-2-amine. $^1$H NMR (400 MHz, MeOD-d$_4$) δ=7.25 (dd, J=7.6, 1.2 Hz, 1H) 7.10 (t, J=8.0 Hz, 1H) 6.76 (dd, J=8.0, 1.2 Hz, 1H) 3.42 (s, 3H) 3.41-3.40 (m, 4H) 3.04-3.14 (m, 2H) 2.62-2.74 (m, 6H); MS m/z: 429.1 [M+H]$^+$.

Example 195: Synthesis of 6-amino-2-(4-(2-aminoethyl)piperazin-1-yl)-5-((2,3-dichlorophenyl)-3-methylpyrimidin-4(3H)-one

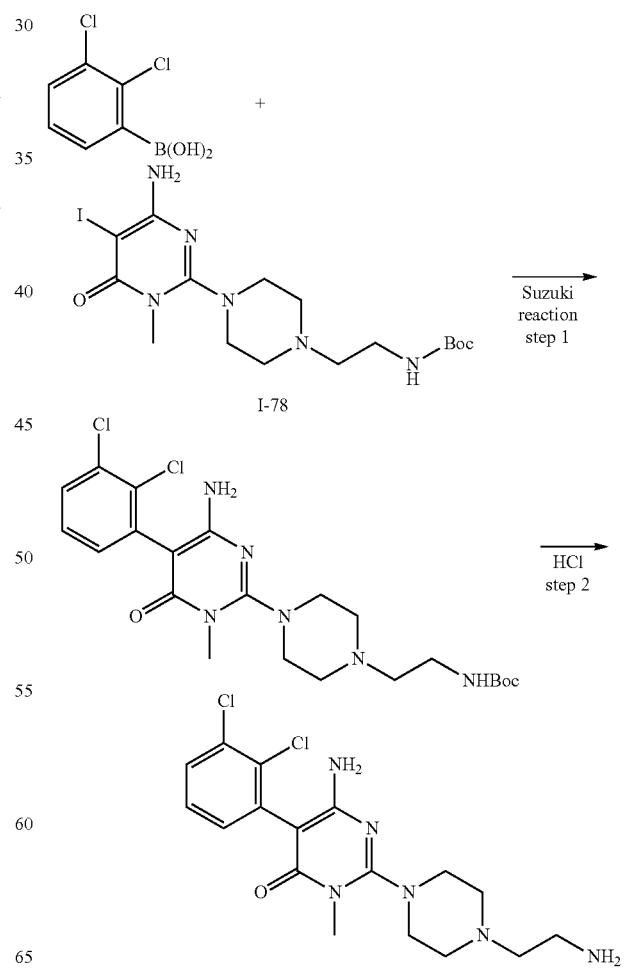

Step 1: tert-butyl N-[2-[4-[4-amino-5-(2,3-dichlorophenyl)-1-methyl-6-oxo-pyrimidin-2-yl]piperazin-1-yl]ethyl]carbamate Intermediate I-78 (150.0 mg, 313.59 μmol), (2,3-dichlorophenyl)boronic acid (89.76 mg, 470.39 μmol), and $K_2CO_3$ (65.01 mg, 470.39 μmol) were dissolved in dioxane (2.0 mL) and $H_2O$ (0.2 mL), and then $Pd(PPh_3)_4$ (36.24 mg, 31.36 μmol) was added thereto. The reaction mixture was stirred at 90 t for 16 hours. After completion of the reaction, the reaction mixture was filtered, and the filtrate was concentrated and then separated by Prep-TLC (EtOAc). Then, tert-Butyl N-[2-[4-[4-amino-5-(2,3-dichlorophenyl)-1-methyl-6-oxo-pyrimidin-2-yl]piperazin-1-yl]ethyl]carbamate (100.0 mg, 34.36% yield) was obtained. MS m/z: 497.4 $[M+H]^+$.

Step 2: 6-amino-2-(4-(2-aminoethyl)piperazin-1-yl)-54 (2,3-dichlorophenyl)-3-methylpyrimidin-4(3H)-one HCl/EtOAc (4 M, 1 mL) was added to tert-butyl N-[2-[4-[4-amino-5-(2,3-dichlorophenyl)-1-methyl-6-oxo-pyrimidin-2-yl]piperazin-1-yl]ethyl]carbamate (100.0 mg, 107.76 μmol), followed by stirring at room temperature for 30 minutes. The reaction mixture was concentrated and separated by Prep-HPLC (neutral) to obtain the compound of Example 195 (25.45 mg, 56.82% yield). $^1$H NMR (400 MHz, CHLOROFORM-d) δ=7.50-7.43 (m, 1H), 7.28 (s, 1H), 7.26 (d, J=1.1 Hz, 1H), 4.37 (s, 2H), 3.47 (s, 3H), 3.33-3.25 (m, 4H), 2.85 (br d, J=5.3 Hz, 2H), 2.63 (br s, 4H), 2.53 (br t, J=5.7 Hz, 2H); MS m/z: 397.3 $[M+H]^+$.

Example 196: Synthesis of 6-amino-2-1(3S)-3-(aminomethyl)piperazin-1-yl]-5-(2,3-dichlorophenyl)sulfanyl-3-methyl-pyrimidin-4-one

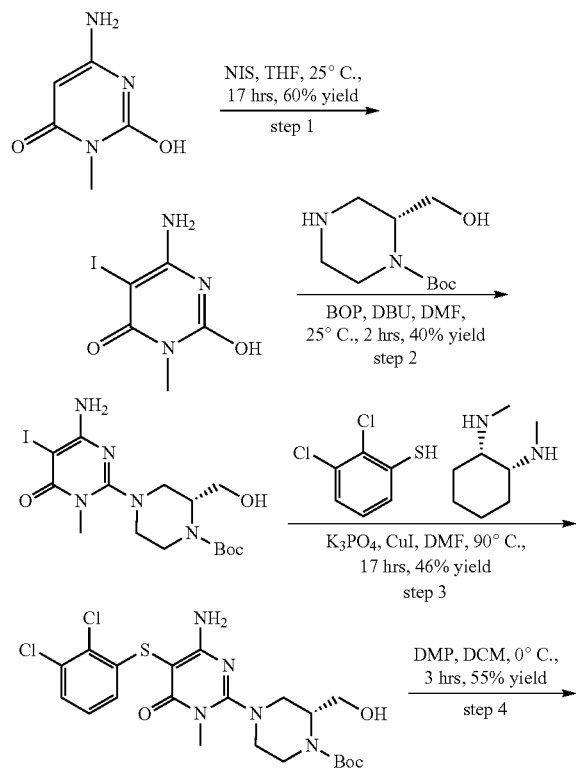

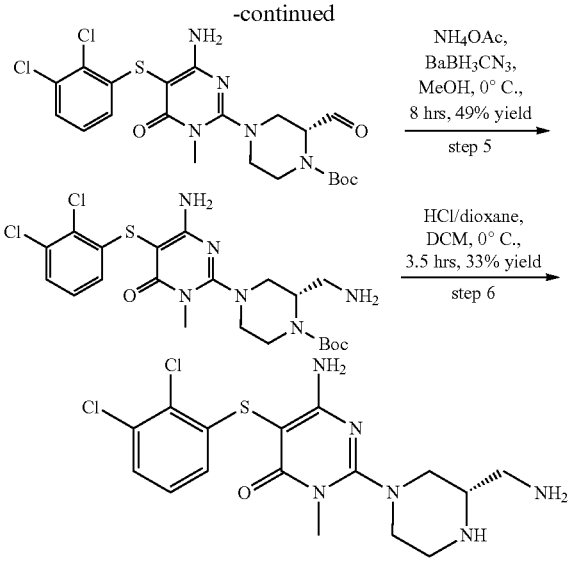

Step 1: 6-amino-2-hydroxy-5-iodo-3-methyl-pyrimidin-4-one 6-amino-3-methyl-1H-pyrimidine-2,4-dione (1.0 g, 7.09 mmol) was dissolved in THF (50 mL), and then NIS (1.91 g, 8.50 mmol) was added thereto. The reaction mixture was stirred at room temperature for 17 hours. After completion of the reaction, the mixture was added with water (100 mL) and saturated $Na_2S_2O_3$ (100 mL) and filtered. The filter cake was dried under vacuum to obtain 6-amino-2-hydroxy-5-iodo-3-methyl-pyrimidin-4-one (1.2 g, 63% yield). $^1$H NMR (400 MHz, DMSO-$d_6$) 10.85 (br s, 1H), 6.35 (s, 2H), 3.10 (s, 3H).

Step 2: tert-butyl (2R)-4-(4-amino-5-iodo-1-methyl-6-oxo-pyrimidin-2-yl)-2-(hydroxymethyl)piperazine-1-carboxylate 6-amino-2-hydroxy-5-iodo-3-methyl-pyrimidin-4-one (500 mg, 1.87 mmol), tert-butyl (2R)-2-(hydroxymethyl)piperazine-1-carboxylate (445 mg, 2.06 mmol), BOP (1.08 g, 2.43 mmol) and DBU (570 mg, 3.74 mmol) were dissolved in DMF (5 mL) and stirred at room temperature for 2 hours. After completion of the reaction, the mixture was added with water (0.5 mL) and concentrated under reduced pressure. The resulting product was separated by reverse phase flash (0.1% FA) to obtain tert-butyl (2R)-4-(4-amino-5-iodo-1-methyl-6-oxo-pyrimidin-2-yl)-2-(hydroxymethyl)piperazine-1-carboxylate (350 mg, 40% yield). $^1$H NMR (400 MHz, DMSO-$d_6$) δ=3.97 (br s, 1H), 3.82-3.72 (m, 1H), 3.69-3.59 (m, 2H), 3.51-3.40 (m, 2H), 3.32 (s, 3H), 2.83-2.67 (m, 2H), 2.52 (s, 2H), 1.41 (s, 9H).

Step 3: tert-butyl (2R)-4-[4-amino-5-(2,3-dichlorophenyl)sulfanyl-1-methyl-6-oxo-pyrimidin-2-yl]-2-(hydroxymethyl)piperazine-1-carboxylate Tert-butyl (2R)-4-(4-amino-5-iodo-1-methyl-6-oxo-pyrimidin-2-yl)-2-(hydroxymethyl)piperazine-1-carboxylate (350 mg, 752 μmol), 2,3-dichlorobenzenethiol (161 mg, 902 μmol), CuI (14.3 mg, 75.2 μmol), (1S,2S)-N1,N2-dimethylcyclohexane-1,2-diamine (10.7 mg, 75.2 μmol), $K_3PO_4$ (479 mg, 2.26 mmol) were dissolved in DMF (10 mL), and then stirred at 90° C. for 17 hours. The reaction mixture was filtered, and the filtrate was concentrated under reduced pressure. The resulting product was separated by reverse phase flash (0.1% FA) to obtain tert-butyl (2R)-4-[4-amino-5-(2,3-dichlorophenyl)sulfanyl-1-methyl-6-oxo-pyrimidin-2-yl]-2-(hydroxymethyl)piperazine-1-carboxylate (180 mg, 46% yield). $^1$H NMR (400 MHz, DMSO-$d_6$) δ=7.34 (d, J=8.0 Hz, 1H), 7.20 (t, J=8.0 Hz, 1H), 6.71 (d, J=8.0 Hz, 1H), 4.00 (br s, 1H), 3.85-3.72 (m, 2H), 3.69-3.55 (m, 2H), 3.46-3.30 (m, 3H), 3.30 (s, 3H), 2.97-2.89 (m, 1H), 2.86-2.75 (m, 1H), 1.42 (s, 9H).

Step 4: tert-butyl (2R)-4-[4-amino-5-(2,3-dichlorophenyl)sulfanyl-1-methyl-6-oxo-pyrimidin-2-yl]-2-formyl-piperazine-1-carboxylate Tert-butyl (2R)-4-[4-amino-5-(2,3-di chlorophenyl)sulfanyl-1-methyl-6-oxo-pyrimidin-2-yl]-2-(hydroxymethyl)piperazine-1-carboxylate (90 mg, 174 μmol) was dissolved in DCM (5 mL), and then DMP (110 mg, 261 μmol) was added thereto at 0° C. The reaction mixture was stirred at 0° C. for 3 hours. After completion of the reaction, the mixture was added with aqueous Na$_2$S$_2$O$_3$ (10 mL) and extracted with DCM (3×20 mL). The organic layer was concentrated under reduced pressure, and the resulting product was separated by reverse phase flash (0.1% FA) to obtain tert-butyl (2R)-4-[4-amino-5-(2,3-di chlorophenyl)sulfanyl-1-methyl-6-oxo-pyrimidin-2-yl]-2-formyl-piperazine-1-carboxylate (50 mg, 55% yield). MS m/z: 458.0 [M+H]$^+$.

Step 5: tert-butyl (2R)-4-[4-amino-5-(2,3-dichlorophenyl)sulfanyl-1-methyl-6-oxo-pyrimidin-2-yl]-2-formyl-piperazine-1-carboxylate At 0° C., tert-butyl (2R)-4-[4-amino-5-(2,3-di chlorophenyl)sulfanyl-1-methyl-6-oxo-pyrimidin-2-yl]-2-formyl-piperazine-1-carboxylate (40.0 mg, 77.7 μmol) and NH$_4$OAc (599 mg, 7.78 mmol) were dissolved in MeOH (5 mL), and then NaBH$_3$CN (7.33 mg, 116 μmol) was added thereto. The reaction mixture was stirred at 0° C. for 8 hours. After completion of the reaction, the reaction mixture was concentrated under reduced pressure and separated by reverse phase flash (0.1% FA) to obtain tert-butyl (2R)-4-[4-amino-5-(2,3-di chlorophenyl)sulfanyl-1-methyl-6-oxo-pyrimidin-2-yl]-2-formyl-piperazine-1-carboxylate (20 mg, 49% yield). MS m/z: 515.2 [M+H]$^+$.

Step 6: 6-amino-2-1(3S)-3-(aminomethyl)piperazin-1-yl]-5-(2,3-dichlorophenyl)sulfanyl-3-methyl-pyrimidin-4-one At 0° C., tert-Butyl (2R)-4-[4-amino-5-(2,3-di chlorophenyl)sulfanyl-1-methyl-6-oxo-pyrimidin-2-yl]-2-formyl-piperazine-1-carboxylate (20 mg, 38.8 μmol) was dissolved in MeOH (4 mL), and then HCl/MeOH (4 M, 5 mL) was added thereto. The reaction mixture was stirred at 0° C. for 3.5 hours. After completion of the reaction, the reaction mixture was concentrated under reduced pressure. After being dissolved in MeOH (5 mL), the mixture was added with 10% aqueous NH$_3$·H$_2$O to neutralize until the pH became 8, and concentrated under reduced pressure. The resulting product was separated by Prep-HPLC to obtain the compound of Example 196 (6.1 mg, 33%, FA salt). $^1$H NMR (400 MHz, MeOD-d$_4$) δ=8.42 (br s, 1H, FA), 7.25 (dd, J=1.6, 8.0 Hz, 1H), 7.09 (t, J=8.0 Hz, 1H), 6.75 (dd, J=1.6, 8.0 Hz, 1H), 3.61 (dd, J=1.6, 13.2 Hz, 1H), 3.57-3.49 (m, 1H), 3.42 (s, 3H), 3.20-2.84 (m, 7H); MS m/z: 415.1 [M+H]$^+$.

Example 197: Synthesis of (R)-6-amino-2-(3-(aminomethyl)piperazin-1-yl)-5-((2,3-dichlorophenyl)thio)-3-methylpyrimidin-4(3H)-one

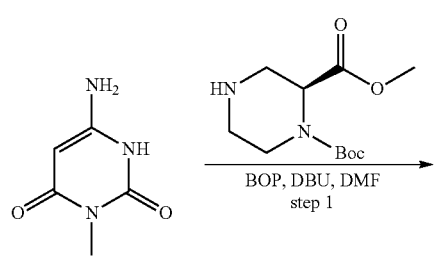

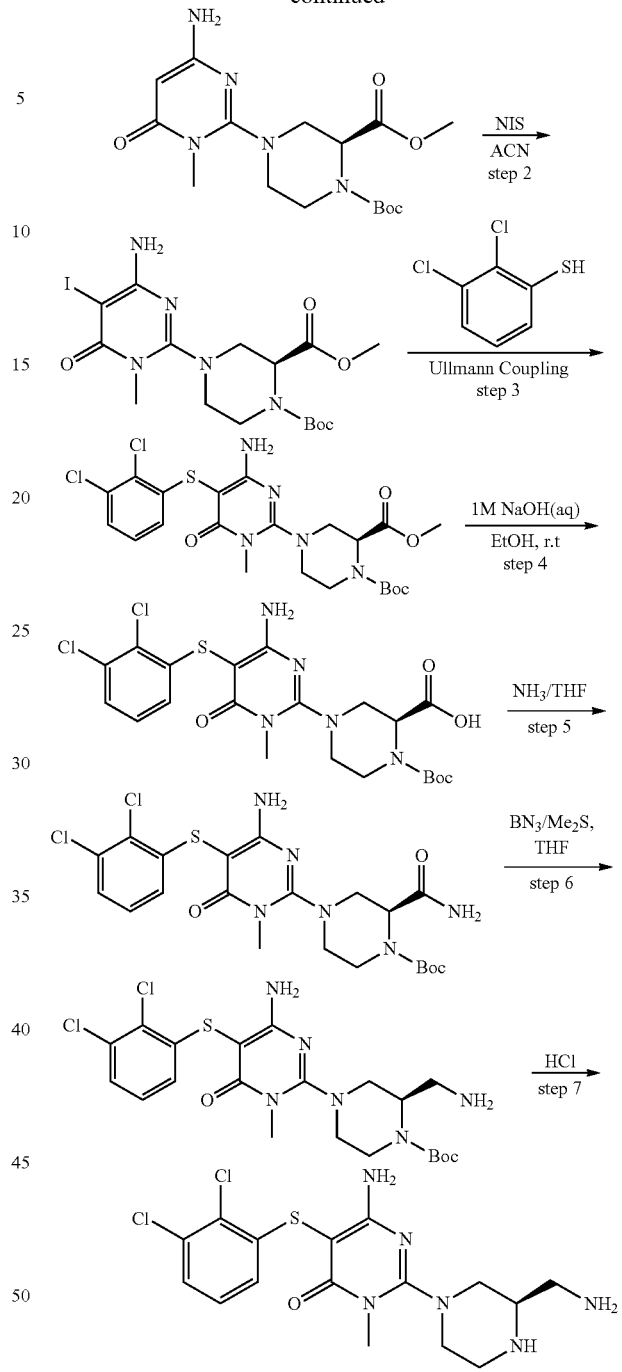

Step 1: 1-(tert-butyl) 2-methyl(R)-4-(4-amino-1-methyl-6-oxo-1,6-dihydropyrimidin-2-yl)piperazine-1,2-dicarboxylate In a round bottom flask, 6-amino-3-methylpyrimidine-2,4 (1H, 3H)-dione (300 mg, 2.13 mmol) and BOP (942 mg, 2.13 mmol) were dissolved in DMF, and then 1-(tert-butyl) 2-methyl (S)-piperazine-1,2-dicarboxylate (520 mg, 2.13 mmol) was added dropwise to a reaction mixture. The reaction mixture was stirred at room temperature for 16 hours. The reaction was terminated with H$_2$O, and the mixture was extracted with EA. The EA layer was dried over MgSO$_4$, filtered and then concentrated. The resulting product was separated by MPLC (MeOH:DCM=1:10) and concentrated to obtain 1-(tert-butyl) 2-methyl (R)-4-(4-amino-1-methyl-6-oxo-1,6-dihydropyrimidin-2-yl)piperazine-1,2-dicarboxylate (760 mg, 97%). MS m/z: 368.20 [M+H]$^+$.

Step 2: 1-(tert-butyl) 2-methyl (R)-4-(4-amino-5-iodo-1-methyl-6-oxo-1,6-dihydropyrimidin-2-yl)piperazine-1,2-dicarboxylate In a round bottom flask, NIS (567 mg, 2.52 mmol) was added dropwise to 1-(tert-butyl) 2-methyl(R)-4-(4-amino-1-methyl-6-oxo-1,6-dihydropyrimidin-2-yl)piperazine-1,2-dicarboxylate (772 mg, 2.52 mmol) dissolved in DMF. The reaction mixture was stirred at room temperature for 2 hours. The reaction was terminated with H$_2$O, and the mixture was extracted with EA. The EA layer was dried over MgSO$_4$, filtered and concentrated. The resulting product was separated by MPLC (MeOH:DCM=1:10) and concentrated to obtain 1-(tert-butyl) 2-methyl (R)-4-(4-amino-5-iodo-1-methyl-6-oxo-1,6-dihydropyrimidin-2-yl)piperazine-1,2-dicarboxylate (981 mg, 94%). MS m/z: 494.10 [M+H]$^+$.

Step 3: 1-(tert-butyl) 2-methyl (R)-4-(4-amino-5-((2,3-dichlorophenyl)thio)-1-methyl-6-oxo-1,6-dihydropyrimidin-2-yl)piperazine-1,2-dicarboxylate In a round bottom flask, 1-(tert-butyl) 2-methyl (R)-4-(4-amino-5-iodo-1-methyl-6-oxo-1,6-dihydropyrimidin-2-yl)piperazine-1,2-dicarboxylate (1.04 g, 2.13 mmol) was dissolved in 1,4-dioxane, and then 2,3-dichloro benzenethiol (763 mg, 4.26 mmol), K$_3$PO$_4$ (904 mg, 4.26 mmol), CuI (82 mg, 0.43 mmol) and (1R,2R)-N1, N2-dimethylcyclohexane-1,2-diamine (61 mg, 0.43 mmol) were added dropwise thereto. The reaction mixture was stirred at 90° C. for 16 hours. The reaction was terminated with H$_2$O, and the mixture was extracted with EA. The EA layer was dried over MgSO$_4$, filtered and then concentrated. The resulting product was separated by MPLC (MeOH:DCM=1:10) and concentrated to obtain 1-(tert-butyl) 2-methyl (R)-4-(4-amino-5-((2,3-di chlorophenyl)thio)-1-methyl-6-oxo-1,6-dihydropyrimidin-2-yl)piperazine-1,2-dicarboxylate (280 mg, 24%). MS m/z: 544.20 [M+H]$^+$.

Step 4: (R)-4-(4-amino-5-((2,3-dichlorophenyl)thio)-1-methyl-6-oxo-1,6-dihydropyrimidin-2-yl)-1-(tert-butoxycarbonyl)piperazine-2-carboxylic acid In a round bottom flask, 1-(tert-butyl) 2-methyl (R)-4-(4-amino-5-((2,3-di chlorophenyl)thio)-1-methyl-6-oxo-1,6-dihydropyrimidin-2-yl)piperazine-1,2-dicarboxylate (220 mg, 0.40 mmol) was dissolved in EtOH, and then 1 M NaOH aqueous solution (1.83 mL, 1.83 mmol) was added dropwise thereto. The reaction mixture was stirred at room temperature for 3 hours. The reaction was terminated with 1 M HCl aqueous solution, and the mixture was extracted with EA. The EA layer was dried over MgSO$_4$, filtered and then concentrated to obtain (R)-4-(4-amino-5-((2,3-di chlorophenyl)thio)-1-methyl-6-oxo-1,6-dihydropyrimidin-2-yl)-1-(tert-butoxycarbonyl)piperazine-2-carboxylic acid (210 mg, 99%). MS m/z: 530.20 [M+H]$^+$.

Step 5: tert-butyl (R)-4-(4-amino-5-((2,3-dichlorophenyl)thio)-1-methyl-6-oxo-1,6-dihydropyrimidin-2-yl)-2-carbamoylpiperazine-1-carboxylate In a round bottom flask, (R)-4-(4-amino-5-((2,3-di chlorophenyl)thio)-1-methyl-6-oxo-1,6-dihydropyrimidin-2-yl)-1-(tert-butoxycarbonyl)piperazine-2-carboxylic acid (212 mg, 0.40 mmol) was dissolved in DMF, and then HATU (182 mg, 0.48 mmol), DIPEA (0.21 mL, 1.20 mmol) were added dropwise thereto. The reaction mixture was stirred at room temperature for 30 minutes. After 30 minutes of stirring, the mixture was added dropwise with NH$_4$Cl (32 mg, 0.60 mmol) and stirred at room temperature for 16 hours. The reaction was terminated with H$_2$O, and the mixture was extracted with EA. The EA layer was dried over MgSO$_4$, filtered and then concentrated. The resulting product was separated by MPLC (MeOH:DCM=1:10) and concentrated to obtain tert-butyl (R)-4-(4-amino-5-((2,3-dichlorophenyl)thio)-1-methyl-6-oxo-1,6-dihydropyrimidin-2-yl)-2-carbamoylpiperazine-1-carboxylate (191 mg, 90%). MS m/z: 529.20 [M+H]$^+$.

Step 6: tert-butyl (R)-4-(4-amino-5-((2,3-dichlorophenyl)thio)-1-methyl-6-oxo-1,6-dihydropyrimidin-2-yl)-2-(aminomethyl)piperazine-1-carboxylate In a round bottom flask, tert-butyl (R)-4-(4-amino-5-((2, 3-dichlorophenyl)thio)-1-methyl-6-oxo-1,6-dihydropyrimidin-2-yl)-2-carbamoylpiperazine-1-carboxylate (24 mg, 0.05 mmol) was dissolved in THF, and then BH$_3$-S(CH$_3$)$_2$ (0.02 mL, 0.23 mmol) was added dropwise thereto. The reaction mixture was stirred at room temperature for 16 hours. After 30 minutes of stirring, the mixture was added dropwise with NH$_4$Cl (32 mg, 0.60 mmol) and stirred at room temperature for 16 hours. The reaction was terminated with H$_2$O, and the mixture was extracted with EA. The EA layer was dried over MgSO$_4$, filtered and then concentrated. The resulting product was separated by MPLC (MeOH:DCM=1:10) and concentrated to obtain tert-butyl (R)-4-(4-amino-5-((2,3-dichlorophenyl)thio)-1-methyl-6-oxo-1,6-dihydropyrimidin-2-yl)-2-(aminomethyl)piperazine-1-carboxylate (6 mg, 60%). MS m/z: 515.10 [M+H]$^+$.

Step 7: (R)-6-amino-2-(3-(aminomethyl)piperazin-1-yl)-54(2,3-dichlorophenyl)thio)-3-methylpyrimidin-4(3H)-one In a round bottom flask, tert-butyl (R)-4-(4-amino-5-((2, 3-dichlorophenyl)thio)-1-methyl-6-oxo-1,6-dihydropyrimidin-2-yl)-2-(aminomethyl)piperazine-1-carboxylate (10 mg, 0.02 mmol) was dissolved in dioxane. The reaction mixture was added dropwise with 4 M HCl in dioxane (0.19 mL, 0.78 mmol) and then stirred at room temperature for 6 hours. The reaction was terminated with saturated aqueous NaHCO$_3$ solution, and the mixture was extracted with EA. The EA layer was dried over MgSO$_4$, filtered and then concentrated. The resulting product was separated by Prep-HPLC and concentrated to obtain the compound of Example 197 (3 mg, 38%). $^1$H NMR (400 MHz, MeOD) δ7.29-7.22 (m, 1H), 7.09 (t, J=8.0 Hz, 1H), 6.77 (dd, J=8.0, 1.4 Hz, 1H), 3.92 (d, J=14.1 Hz, 1H), 3.84-3.76 (m, 2H), 3.55-3.46 (m, 1H), 3.44 (s, 3H), 3.44-3.30 (m, 5H), 3.28-3.23 (m, 1H); MS m/z: 415.10 [M+H]$^+$.

Example 198: Synthesis of 6-amino-2-(2-(aminomethyl)morpholino)-5-((2,3-dichlorophenyl)thio)-3-methylpyrimidin-4(3H)-one

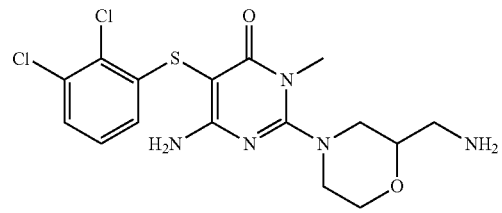 [SMILES: Cn1c(N2CCOC(CN)C2)nc(N)c(Sc2cccc(Cl)c2Cl)c1=O]

The compound of Example 198 was synthesized in the same method as in Example 197 above, except that methylmorpholine-2-carboxylate was used instead of 1-(tert-butyl) 2-methyl (S)-piperazine-1,2-dicarboxylate. $^1$H NMR (400 MHz, MeOD) δ7.25 (dd, J=7.9, 1.4 Hz, 1H), 7.09 (t, J=8.0 Hz, 1H), 6.76 (dd, J=8.0, 1.4 Hz, 1H), 4.08-4.01 (m, 1H), 3.96-3.77 (m, 2H), 3.69-3.57 (m, 2H), 3.43 (s, 3H), 3.21-3.13 (m, 2H), 3.00 (dd, J=13.1, 9.4 Hz, 1H), 2.89 (dd, J=12.9, 10.4 Hz, 1H); MS m/z: 416.10 [M+H]⁺.

Example 199: Synthesis of 6-amino-2-(4-(3-amino-propyl)piperazin-1-yl)-5-((2,3-dichlorophenyl)thio)-3-methylpyrimidin-4(3H)-one

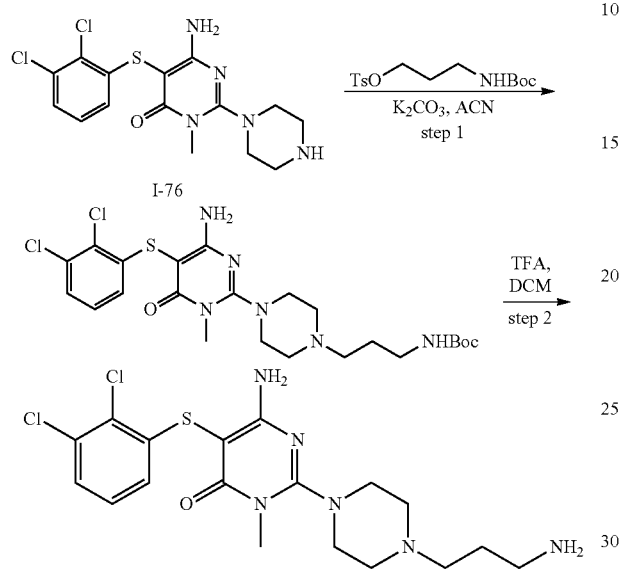

Step 1: tert-butyl (3-(4-(4-amino-5-((2,3-dichlorophenyl)thio)-1-methyl-6-oxo-1,6-dihydropyrimidin-2-yl)piperazin-1-yl)propyl)carbamate In a round bottom flask, 3-((tert-butoxycarbonyl)amino) propyl 4-methylbenzenesulfonate (128 mg, 0.39 mmol) was added dropwise to Intermediate I-76 (100 mg, 0.26 mmol) dissolved in MeCN. The reaction mixture was stirred at 100° C. for 16 hours. The reaction was terminated with H₂O, and the mixture was extracted with EA. The EA layer was dried over MgSO₄, filtered and then concentrated. The resulting product was separated by MPLC (MeOH:DCM=1:10) and concentrated to obtain tert-butyl (3-(4-(4-amino-5-((2,3-dichlorophenyl)thio)-1-methyl-6-oxo-1,6-dihydropyrimidin-2-yl)piperazin-1-yl)propyl)carbamate (132 mg, 94%). MS m/z: 543.20 [M+H]⁺.

Step 2: 6-amino-2-(4-(3-aminopropyl)piperazin-1-yl)-54 (2,3-dichlorophenyl)thio)-3-methylpyrimidin-4(3H)-one In a round bottom flask, TFA (0.9 mL) was added dropwise to tert-butyl (3-(4-(4-amino-5-((2,3-di chlorophenyl)thio)-1-methyl-6-oxo-1, 6-dihydropyrimidin-2-yl)piperazin-1-yl)propyl)carbamate (15 mg, 0.03 mmol) dissolved in DCM. The reaction mixture was stirred at room temperature for 3 hours. The reaction was terminated with saturated aqueous NaHCO₃ solution, and the mixture was extracted with EA. The EA layer was dried over MgSO₄, filtered and then concentrated. The resulting product was separated by MPLC (MeOH:DCM=1:10) and concentrated to obtain the compound of Example 199 (5 mg, 41%). ¹H NMR (400 MHz, MeOD) δ7.25 (dd, J=7.9, 1.4 Hz, 1H), 7.09 (t, J=8.0 Hz, 1H), 6.78 (dd, J=8.0, 1.4 Hz, 1H), 3.65 (s, 4H), 3.44 (s, 3H), 3.42-3.31 (m, 1H), 3.30-3.19 (m, 5H), 3.13-2.97 (m, 2H), 2.22-2.10 (m, 2H); MS m/z: 443.10 [M+H]⁺.

Example 200: Synthesis of 6-amino-2-(4-(2-amino-ethyl)-1,4-diazepan-1-yl)-5-((2,3-dichlorophenyl)thio)-3-methylpyrimidin-4(3H)-one

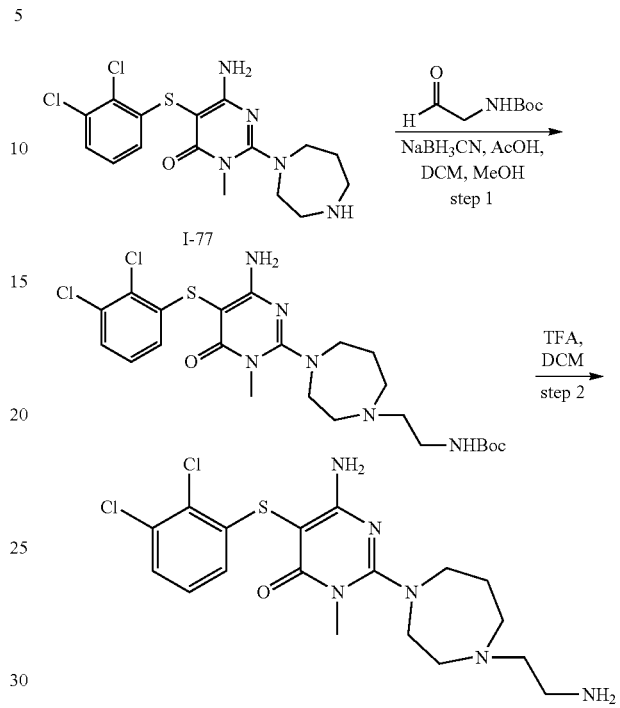

Step 1: tert-butyl (2-(4-(4-amino-5-((2,3-dichlorophenyl)thio)-1-methyl-6-oxo-1,6-dihydropyrimidin-2-yl)-1,4-diazepan-1-yl)ethyl)carbamate In a round bottom flask, tert-butyl (2-oxoethyl)carbamate (7 mg, 0.04 mmol) was added to Intermediate I-77 (12 mg, 0.03 mmol) and AcOH (0.07 mL, 0.12 mmol) in DCM. The reaction mixture was stirred at room temperature for 1 hour. After 1 hour of stirring, NaBH₃CN (2 mg, 0.03 mmol) was added dropwise to the reaction mixture. The reaction was terminated with H₂O, and the mixture was extracted with EA. The EA layer was dried over MgSO₄, filtered and then concentrated. The resulting product was separated by MPLC (MeOH:DCM=1:10) and concentrated to obtain tert-butyl (2-(4-(4-amino-5-((2,3-di chlorophenyl)thio)-1-methyl-6-oxo-1,6-dihydropyrimidin-2-yl)-1,4-diazepan-1-yl)ethyl) carbamate (132 mg, 94%). MS m/z: 543.20 [M+H]⁺.

Step 2: 6-amino-2-(4-(2-aminoethyl)-1,4-diazepan-1-yl)-54(2,3-dichlorophenyl)thio)-3-methylpyrimidin-4(3H)-one In a round bottom flask, TFA (0.92 mL, 11.99 mmol) was added dropwise to tert-butyl (2-(4-(4-amino-5-((2,3-di chlorophenyl)thio)-1-methyl-6-oxo-1,6-dihydropyrimidin-2-yl)-1,4-diazepan-1-yl)ethyl)carbamate (132 mg, 0.243 mmol) dissolved in DCM. The reaction mixture was stirred at room temperature for 3 hours. The reaction was terminated with saturated aqueous NaHCO₃ solution, and the mixture was extracted with EA. The EA layer was dried over MgSO₄, filtered and then concentrated. The resulting product was separated by MPLC (MeOH:DCM=1:10) and concentrated to obtain the compound of Example 200 (121 mg, 76%). ¹H NMR (400 MHz, MeOD) δ7.24 (dd, J=8.0, 1.5 Hz, 1H), 7.09 (t, J=7.9 Hz, 1H), 6.82-6.75 (m, 1H), 3.91-3.86 (m, 2H), 3.75-3.52 (m, 4H), 3.51-3.32 (m, 8H), 2.31 (t, J=5.7 Hz, 2H); MS m/z: 443.10 [M+H]⁺.

Example 201: Synthesis of 6-amino-2-(4-(3-aminopropyl)-1,4-diazepan-1-yl)-5-((2,3-dichlorophenyl)thio)-3-methylpyrimidin-4(3H)-one

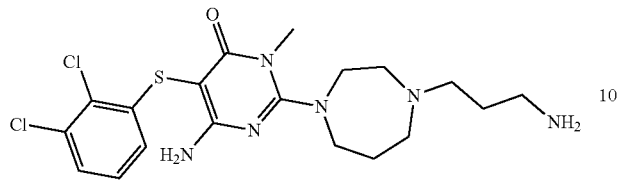

The compound of Example 201 was synthesized in the same method as in Example 199 above, except that Intermediate I-77 was used instead of Intermediate I-76. $^1$H NMR (400 MHz, MeOD) δ7.25 (dd, J=7.9, 1.4 Hz, 1H), 7.09 (t, J=8.0 Hz, 1H), 6.79 (dd, J=8.0, 1.5 Hz, 1H), 3.69 (s, 2H), 3.52-3.33 (m, 8H), 3.26 (q, J=1.7 Hz, 3H), 3.05 (t, J=7.6 Hz, 2H), 2.31 (s, 2H), 2.14 (s, 2H); MS m/z: 457 [M+H]$^+$.

Example 202: Synthesis of 6-amino-2-(4-(2-aminopropyl)piperazin-1-yl)-5-((2,3-dichlorophenyl)thio)-3-methylpyrimidin-4(3H)-one

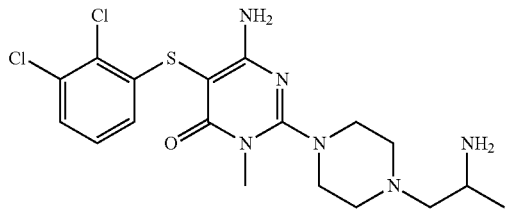 [SMILES: CC(N)CN1CCN(c2nc(N)c(Sc3cccc(Cl)c3Cl)c(=O)n2C)CC1]

The compound of Example 202 was synthesized in the same method as in Example 200 above, except that tert-butyl (1-oxopropan-2-yl)carbamate was used instead of tert-butyl (2-oxoethyl)carbamate. $^1$H NMR (400 MHz, CD$_3$OD) δ 7.27-7.18 (m, 1H), 7.09 (t, J=8.0 Hz, 1H), 6.75 (d, J=7.0 Hz, 1H), 3.41-3.35 (m, 7H), 2.81-2.78 (m, 3H), 2.60-2.52 (m, 4H), 1.31 (m, 3H); MS m/z: 443-[M+H]$^+$.

Experimental Example

Experimental Example 1: Phosphatase assay (IC$_{50}$) IC$_{50}$ values were measured using 6,8-difluoro-4-methylumbelliferyl phosphate (DiFMU) as a substrate. The reaction was performed in a 384-well plate, and fluorescence measurement values were obtained using an EnVision plate reader from PerkinElmer.

SHP2 (full length, diluted to 100 pM final concentration in reaction buffer, BPS bioscience, US) was incubated with the SHP2 activating peptide in reaction buffer (60 mM HEPES (pH 7.2), 75 mM NaCl, 75 mM KCl, 1 mM EDTA, 5 mM DTT, 0.05% P-20) for 30 minutes to activate SHP2. After activation, DMSO [1% (V/V) or the compound of the present invention (concentration ranging from 0.6 nM to 10 pM)] was added. As a positive control group, the selective SHP2 inhibitors SHP099 (6-(4-amino-4-methylpiperidin-1-yl)-3-(2,3-dichlorophenyl)pyrazin-2-amine, FOCUS bioscience, Austrailia; concentration ranging from 0.6 nM to 10 μM) and TNO155 ((3S,4S)-8-(6-amino-5-((2-amino-3-chloropyridin-4-yl)thio)pyrazin-2-yl)-3-methyl-2-oxa-8-azaspiro[4.5]decan-4-amine, Chemietek, US; concentration ranging from 0.6 nM to 10 μM) were used.

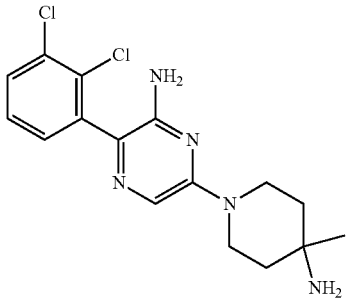

SHP099

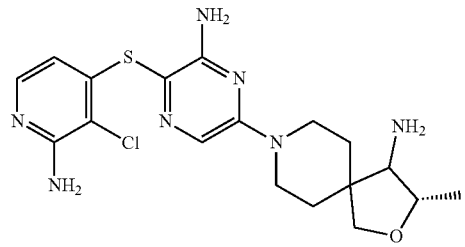

TNO155

DiFMUP (80 μM) was added to the reaction and incubated for a total of 2 hours to allow for the reaction to proceed. Thereafter, fluorescence (340 nm excitation, 450 nm emission) values were measured. IC$_{50}$ values were obtained using Graphad's Prism from the measured values depending on the concentration. The IC$_{50}$ values of the compounds of the present invention as obtained are summarized in Table 1 below.

In the phosphatase assay (PTPase assay), when an IC$_{50}$ value was 100 nM or more, + was indicated, when an IC$_{50}$ value was 3 nM or more and less than 100 nM, ++ was indicated, and when an IC$_{50}$ value was less than 3 nM, +++ was indicated.

TABLE 1

| Example No. | IC50 (PTPase aS say, nM) |
| --- | --- |
| 1 | ++ |
| 2 | + |
| 3 | ++ |
| 4 | ++ |
| 5 | ++ |
| 6 | ++ |
| 7 | ++ |
| 8 | ++ |
| 9 | +++ |
| 10 | ++ |
| 11 | +++ |
| 12 | ++ |
| 13 | ++ |
| 14 | ++ |
| 15 | ++ |
| 16 | +++ |
| 17 | ++ |
| 18 | +++ |
| 19 | +++ |
| 20 | +++ |
| 21 | ++ |
| 22 | ++ |
| 23 | ++ |
| 24 | ++ |
| 25 | ++ |

TABLE 1-continued

| Example No. | IC50 (PTPase aS say, nM) |
|---|---|
| 26 | +++ |
| 27 | + |
| 28 | ++ |
| 29 | + |
| 30 | + |
| 31 | +++ |
| 32 | +++ |
| 33 | +++ |
| 34 | ++ |
| 35 | +++ |
| 36 | +++ |
| 37 | +++ |
| 38 | +++ |
| 39 | ++ |
| 40 | +++ |
| 41 | +++ |
| 42 | +++ |
| 43 | +++ |
| 44 | +++ |
| 45 | +++ |
| 46 | ++ |
| 47 | +++ |
| 48 | +++ |
| 49 | ++ |
| 50 | ++ |
| 51 | +++ |
| 52 | ++ |
| 53 | ++ |
| 54 | ++ |
| 55 | ++ |
| 56 | +++ |
| 57 | +++ |
| 58 | ++ |
| 59 | +++ |
| 60 | +++ |
| 61 | +++ |
| 62 | +++ |
| 63 | +++ |
| 64 | +++ |
| 65 | +++ |
| 66 | +++ |
| 67 | ++ |
| 68 | ++ |
| 69 | +++ |
| 70 | +++ |
| 71 | +++ |
| 72 | +++ |
| 73 | +++ |
| 74 | ++ |
| 75 | ++ |
| 76 | ++ |
| 77 | +++ |
| 78 | +++ |
| 79 | +++ |
| 80 | +++ |
| 81 | +++ |
| 82 | +++ |
| 83 | +++ |
| 84 | +++ |
| 85 | ++ |
| 86 | ++ |
| 87 | ++ |
| 88 | +++ |
| 89 | ++ |
| 90 | +++ |
| 91 | ++ |
| 92 | +++ |
| 93 | +++ |
| 94 | +++ |
| 95 | +++ |
| 96 | ++ |
| 97 | +++ |
| 98 | ++ |
| 99 | +++ |
| 100 | ++ |
| 101 | ++ |
| 102 | +++ |
| 103 | +++ |
| 104 | +++ |
| 105 | +++ |
| 106 | ++ |
| 107 | +++ |
| 108 | ++ |
| 109 | +++ |
| 110 | +++ |
| 111 | +++ |
| 112 | +++ |
| 113 | +++ |
| 114 | +++ |
| 115 | +++ |
| 116 | +++ |
| 117 | ++ |
| 118 | +++ |
| 119 | +++ |
| 120 | +++ |
| 121 | +++ |
| 122 | +++ |
| 123 | +++ |
| 124 | +++ |
| 125 | +++ |
| 126 | ++ |
| 127 | +++ |
| 128 | +++ |
| 129 | +++ |
| 130 | +++ |
| 131 | ++ |
| 132 | +++ |
| 133 | ++ |
| 134 | ++ |
| 135 | + |
| 136 | +++ |
| 137 | ++ |
| 138 | +++ |
| 139 | ++ |
| 140 | +++ |
| 141 | +++ |
| 142 | +++ |
| 143 | +++ |
| 144 | +++ |
| 145 | ++ |
| 146 | ++ |
| 147 | +++ |
| 148 | ++ |
| 149 | +++ |
| 150 | +++ |
| 151 | +++ |
| 152 | ++ |
| 153 | +++ |
| 154 | ++ |
| 155 | ++ |
| 156 | ++ |
| 157 | ++ |
| 158 | +++ |
| 159 | +++ |
| 160 | +++ |
| 161 | +++ |
| 162 | +++ |
| 163 | +++ |
| 164 | +++ |
| 165 | +++ |
| 166 | +++ |
| 167 | +++ |
| 168 | +++ |
| 169 | +++ |
| 170 | +++ |
| 171 | +++ |
| 172 | +++ |
| 173 | N.A. |
| 174 | +++ |
| 175 | N.A. |
| 176 | +++ |
| 177 | +++ |
| 178 | +++ |
| 179 | +++ |
| 180 | +++ |
| 181 | ++ |

TABLE 1-continued

| Example No. | IC50 (PTPase aS say, nM) |
| --- | --- |
| 182 | ++ |
| 183 | N.A. |
| 184 | N.A. |
| 185 | N.A. |
| 186 | + |
| 187 | + |
| 188 | + |
| 189 | + |
| 190 | + |
| 191 | + |
| 192 | + |
| 193 | + |
| 194 | + |
| 195 | + |
| 196 | + |
| 197 | ++ |
| 198 | + |
| 199 | + |
| 200 | + |
| 201 | + |
| 202 | + |
| SHP099 (positive control group) | + |
| TNO155 (positive control group) | +++ |

Experimental Example 2: Phospho-ERK Assay

MIA PaCa2 or H358 [20,000 cell/well] was contained in 40 μL of the cell culture solution (DMEM/RPMI, 10% FBS, penicillin, streptomycin) and placed on a 384-well plate. After 24 hours, the serially diluted compound of the present invention (concentration of minimum 0.13 nM, maximum 10 μM) was contained in 10 μL of the cell culture solution, put into wells containing cells, and incubated in a cell incubator for 1.5 hours. As a positive control group, the selective SHP2 inhibitors, SHP099 (FOCUS bioscience, Austrailia; concentration ranging from 0.6 nM to 10 μM) and TNO155 (Chemietek, US; concentration ranging from 0.6 nM to 10 μM) were used.

Thereafter, phospho-ERK was labeled using an AlphaLisa system from PerkinElmer according to the manufacturer's instructions, and then fluorescence (680 nm excitation wavelength, 615 nm emission wavelength) values were measured using a Varioskan equipment from Thermo. $IC_{50}$ values were obtained using Graphad's Prism from the measured values depending on the concentration. The $IC_{50}$ values of the compounds of the present invention as obtained are summarized in Table 2 below. In the phospho-ERK assay, when an $IC_{50}$ value was 1.5 μM or more, + was indicated, when an $IC_{50}$ value was 45 nM or more and less than 1.5 μM, ++ was indicated, and when an $IC_{50}$ value was less than 45 nM, +++ was indicated.

TABLE 2

| Example No. | $IC_{50}$ (p-ERK, nM) |
| --- | --- |
| 1 | ++ |
| 2 | ++ |
| 3 | ++ |
| 4 | ++ |
| 5 | ++ |
| 6 | ++ |
| 7 | ++ |
| 8 | + |
| 9 | +++ |
| 10 | +++ |
| 11 | +++ |
| 12 | ++ |
| 13 | ++ |
| 14 | ++ |
| 15 | ++ |
| 16 | ++ |
| 17 | ++ |
| 18 | +++ |
| 19 | ++ |
| 20 | +++ |
| 21 | ++ |
| 22 | ++ |
| 23 | ++ |
| 24 | + |
| 25 | ++ |
| 26 | +++ |
| 27 | + |
| 28 | ++ |
| 29 | + |
| 30 | + |
| 31 | +++ |
| 32 | ++ |
| 33 | ++ |
| 34 | ++ |
| 35 | +++ |
| 36 | +++ |
| 37 | +++ |
| 38 | ++ |
| 39 | ++ |
| 40 | ++ |
| 41 | +++ |
| 42 | +++ |
| 43 | +++ |
| 44 | +++ |
| 45 | +++ |
| 46 | +++ |
| 47 | +++ |
| 48 | +++ |
| 49 | + |
| 50 | ++ |
| 51 | ++ |
| 52 | ++ |
| 53 | +++ |
| 54 | N.A. |
| 55 | N.A. |
| 56 | N.A. |
| 57 | N.A. |
| 58 | N.A. |
| 59 | N.A. |
| 60 | +++ |
| 61 | +++ |
| 62 | +++ |
| 63 | +++ |
| 64 | +++ |
| 65 | +++ |
| 66 | +++ |
| 67 | ++ |
| 68 | ++ |
| 69 | +++ |
| 70 | +++ |
| 71 | +++ |
| 72 | +++ |
| 73 | +++ |
| 74 | ++ |
| 75 | ++ |
| 76 | ++ |
| 77 | +++ |
| 78 | +++ |
| 79 | +++ |
| 80 | +++ |
| 81 | +++ |
| 82 | +++ |
| 83 | +++ |
| 84 | +++ |
| 85 | + |
| 86 | N.A. |
| 87 | ++ |
| 88 | +++ |
| 89 | ++ |

TABLE 2-continued

| Example No. | IC$_{50}$ (p-ERK, nM) |
|---|---|
| 90 | +++ |
| 91 | ++ |
| 92 | +++ |
| 93 | +++ |
| 94 | + |
| 95 | ++ |
| 96 | +++ |
| 97 | +++ |
| 98 | ++ |
| 99 | N.A. |
| 100 | N.A. |
| 101 | N.A. |
| 102 | +++ |
| 103 | +++ |
| 104 | +++ |
| 105 | +++ |
| 106 | ++ |
| 107 | +++ |
| 108 | ++ |
| 109 | +++ |
| 110 | +++ |
| 111 | +++ |
| 112 | +++ |
| 113 | +++ |
| 114 | +++ |
| 115 | +++ |
| 116 | +++ |
| 117 | ++ |
| 118 | +++ |
| 119 | +++ |
| 120 | +++ |
| 121 | +++ |
| 122 | +++ |
| 123 | +++ |
| 124 | +++ |
| 125 | +++ |
| 126 | ++ |
| 127 | +++ |
| 128 | +++ |
| 129 | +++ |
| 130 | +++ |
| 131 | ++ |
| 132 | +++ |
| 133 | ++ |
| 134 | ++ |
| 135 | + |
| 136 | +++ |
| 137 | ++ |
| 138 | +++ |
| 139 | ++ |
| 140 | +++ |
| 141 | +++ |
| 142 | +++ |
| 143 | +++ |
| 144 | +++ |
| 145 | ++ |
| 146 | ++ |
| 147 | +++ |
| 148 | ++ |
| 149 | +++ |
| 150 | ++ |
| 151 | +++ |
| 152 | ++ |
| 153 | +++ |
| 154 | ++ |
| 155 | + |
| 156 | +++ |
| 157 | ++ |
| 158 | +++ |
| 159 | +++ |
| 160 | +++ |
| 161 | +++ |
| 162 | N.A. |
| 163 | +++ |
| 164 | N.A. |
| 165 | +++ |
| 166 | +++ |
| 167 | ++ |
| 168 | +++ |
| 169 | +++ |
| 170 | +++ |
| 171 | +++ |
| 172 | +++ |
| 173 | N.A. |
| 174 | +++ |
| 175 | N.A. |
| 176 | +++ |
| 177 | +++ |
| 178 | +++ |
| 179 | ++ |
| 180 | ++ |
| 181 | ++ |
| 182 | ++ |
| 183 | + |
| 184 | N.A. |
| 185 | N.A. |
| 186 | ++ |
| 187 | N.A. |
| 188 | + |
| 189 | + |
| 190 | + |
| 191 | + |
| 192 | N.A. |
| 193 | + |
| 194 | + |
| 195 | + |
| 196 | + |
| 197 | ++ |
| 198 | + |
| 199 | + |
| 200 | + |
| 201 | + |
| 202 | + |
| SHP099 (positive control group) | ++ |
| TNO155 (positive control group) | +++ |

The invention claimed is:

1. A compound of Formula 1A-1, or a stereoisomer, solvate or pharmaceutically acceptable salt thereof:

[Formula 1A-1]

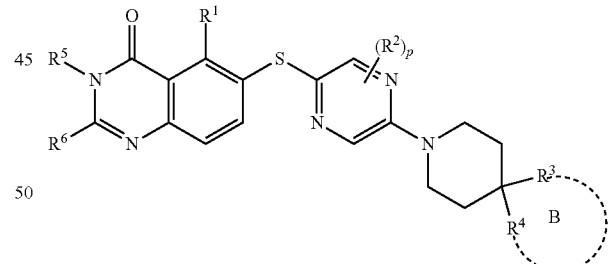

wherein,
$R^1$ is H, halogen, hydroxy, cyano or $C_1$-$C_6$ haloalkyl;
$R^2$ is selected from a group consisting of H, halogen, hydroxy, oxo, $C_1$-$C_{20}$ alkyl, $C_1$-$C_{20}$ alkoxy, $C_1$-$C_{20}$ haloalkyl, hydroxy-($C_1$-$C_{20}$ alkyl)-, ($C_1$-$C_{10}$ alkoxy)-($C_1$-$C_{10}$ alkyl)-, $H_2N$—($C_1$-$C_{20}$ alkyl)-, —$NH_2$, —NH($C_1$-$C_{20}$ alkyl), —N($C_1$-$C_{20}$ alkyl)$_2$, nitro, cyano, amidino, —C(O)$NH_2$, —C(O)($C_1$-$C_{20}$ alkyl), —C(O)O($C_1$-$C_{20}$ alkyl), and carboxy or a salt thereof;
$R^3$ and $R^4$ are each independently H, $C_1$-$C_6$ alkyl, —$NH_2$, —NH($C_1$-$C_6$ alkyl), —N($C_1$-$C_6$ alkyl)$_2$, or $H_2N$—($C_1$-$C_6$ alkyl)-, or $R^3$ and $R^4$ are connected to each other to form Ring B, Ring B is a 3- to 8-membered cyclic ring group optionally containing one oxygen atom and optionally substituted, wherein Ring B can be optionally fused with a cycloalkyl, aryl or heteroaryl ring, and the cycloalkyl, aryl and heteroaryl rings fused with Ring B can be optionally substituted;

$R^5$ is each independently selected from:
(i) H, halogen, hydroxy, —$NH_2$, =NH, —$C(O)NH_2$, nitro, cyano, amidino, or carboxy or a salt thereof;
(ii) $C_1$-$C_{20}$ alkyl or $C_1$-$C_{20}$ alkoxy, which is optionally substituted with at least one substituent selected from a group consisting of halogen, hydroxy, $C_1$-$C_{20}$ alkyl, $C_1$-$C_{20}$ haloalkyl, $C_1$-$C_{20}$ alkoxy, $C_1$-$C_{20}$ haloalkoxy, —NR'R", R'C(O)—, R'S(O)$_2$—, R'S(O)$_2$NR"—, R"R'NC(O)—, and R' C(O)NR"—;
(iii) $C_6$-$C_{20}$ aryl, ($C_6$-$C_{12}$ aryl)-($C_1$-$C_8$ alkyl)-, $C_6$-$C_{20}$ aryloxy, ($C_6$-$C_{12}$ aryloxy)-($C_1$-$C_8$ alkyl)-, $C_6$-$C_{20}$ arylcarbonyl, ($C_6$-$C_{12}$ arylcarbonyl)-($C_1$-$C_8$ alkyl)-, —CONH—($C_6$-$C_{12}$ aryl), —CONH—($C_1$-$C_8$ alkyl)-($C_6$-$C_{12}$ aryl), —NHCO—($C_6$-$C_{12}$ aryl), or —NHCO—($C_1$-$C_8$ alkyl)-($C_6$-$C_{12}$ aryl);
(iv) heteroaryl, heteroaryl-($C_1$-$C_8$ alkyl)-, heteroaryloxy, heteroaryloxy-($C_1$-$C_8$ alkyl)-, heteroarylcarbonyl, heteroaryl carb onyl-($C_1$-$C_8$ alkyl)-, —CONH-heteroaryl, —CONH—($C_1$-$C_8$ alkyl)-heteroaryl, —NHCO-heteroaryl, or —NHCO—($C_1$-$C_8$ alkyl)-heteroaryl, wherein the heteroaryl ring is 4- to 10-membered heteroaryl containing at least one heteroatom selected from N, O and S;
(v) heterocycloalkyl, heterocycloalkyl-($C_1$-$C_8$ alkyl)-, heterocycloalkyloxy, heterocycloalkyloxy-($C_1$-$C_8$ alkyl)-, heterocycloalkylcarbonyl, heterocycloalkylcarbonyl-($C_1$-$C_8$ alkyl)-, —CONH-heterocycloalkyl, —CONH—($C_1$-$C_8$ alkyl)-heterocycloalkyl, —NHCO— heterocycloalkyl, or —NHCO—($C_1$-$C_8$ alkyl)-heterocycloalkyl, wherein the heterocycloalkyl ring is 3- to 10-membered fully saturated or partially unsaturated heterocycloalkyl containing at least one heteroatom selected from N, O and S; or
(vi) $C_3$-$C_{10}$ cycloalkyl, ($C_3$-$C_{10}$ cycloalkyl)-($C_1$-$C_8$ alkyl)-, $C_3$-$C_{10}$ cycloalkyloxy, ($C_3$-$C_{10}$ cycloalkyloxy)-($C_1$-$C_8$ alkyl)-, $C_3$-$C_{10}$ cycloalkylcarbonyl, ($C_3$-$C_{10}$ cycloalkylcarbonyl)-($C_1$-$C_8$ alkyl)-, —CONH—($C_3$-$C_{10}$ cycloalkyl), —CONH—($C_1$-$C_8$ alkyl)-($C_3$-$C_{10}$ cycloalkyl), —NHCO—($C_3$-$C_{10}$ cycloalkyl), or —NHCO—($C_1$-$C_8$ alkyl)-($C_3$-$C_{10}$ cycloalkyl);
wherein the aryl ring, heteroaryl ring, heterocycloalkyl ring and cycloalkyl ring as described in (iii) to (vi) can be each optionally substituted;
R' and R" are each independently H or $C_1$-$C_{10}$ alkyl;
$R^6$ is H or $C_1$-$C_6$ alkyl; and
p is an integer from 0 to 2.

2. The compound according to claim 1, or a stereoisomer, solvate or pharmaceutically acceptable salt thereof, wherein $R^1$ is halogen or $C_1$-$C_3$ haloalkyl;
$R^2$ is selected from a group consisting of H, halogen, hydroxy, oxo, $C_1$-$C_6$ alkyl, $C_1$-$C_6$ alkoxy, $C_1$-$C_6$ haloalkyl, hydroxy-($C_1$-$C_6$ alkyl)-, ($C_1$-$C_6$ alkoxy)-($C_1$-$C_6$ alkyl)-, $H_2N$—($C_1$-$C_6$ alkyl)-, —$NH_2$, —NH($C_1$-$C_6$ alkyl), —N($C_1$-$C_6$ alkyl)$_2$, nitro, cyano, amidino, —$C(O)NH_2$, —C(O)($C_1$-$C_6$ alkyl), —C(O)O($C_1$-$C_6$ alkyl), and carboxy or a salt thereof;
$R^3$ and $R^4$ are each independently H, $C_1$-$C_6$ alkyl, —$NH_2$, —NH($C_1$-$C_6$ alkyl), —N($C_1$-$C_6$ alkyl)$_2$, or $H_2N$—($C_1$-$C_6$ alkyl)-, or $R^3$ and $R^4$ are connected to each other to form Ring B, Ring B is a $C_3$-$C_8$ cycloalkyl or 3- to 8-membered heterocycloalkyl ring that optionally contains one oxygen atom and is optionally substituted with at least one R B,
Ring B can be optionally fused with Ring BB selected from $C_3$-$C_8$ cycloalkyl, $C_6$-$C_{10}$ aryl, and 5- to 10-membered heteroaryl containing one or two heteroatoms selected from N, O and S, and Ring BB can be optionally substituted with at least one $R^{BB}$,
$R^B$ is selected from a group consisting of deuterium, ($C_1$-$C_6$ alkyl), —$NH_2$, —NH($C_1$-$C_6$ alkyl), —N($C_1$-$C_6$ alkyl)$_2$, and $H_2N$—($C_1$-$C_6$ alkyl)-;
$R^{BB}$ is selected from a group consisting of halogen, hydroxy, oxo, $C_1$-$C_6$ alkyl, $C_1$-$C_6$ alkoxy, $C_1$-$C_6$ haloalkyl, hydroxy-($C_1$-$C_6$ alkyl)-, ($C_1$-$C_6$ alkoxy)-($C_1$-$C_6$ alkyl)-, $H_2N$—($C_1$-$C_6$ alkyl)-, —$NH_2$, —NH($C_1$-$C_6$ alkyl), —N($C_1$-$C_6$ alkyl)$_2$, nitro, cyano and amidino;
wherein $R^5$ is each independently selected from:
(i) H, halogen, hydroxy, —$NH_2$, =NH, —$C(O)NH_2$, nitro, cyano, amidino, or carboxy or a salt thereof;
(ii) $C_1$-$C_6$ alkyl or $C_1$-$C_6$ alkoxy, which is optionally substituted with at least one substituent selected from a group consisting of halogen, hydroxy, $C_1$-$C_6$ alkyl, $C_1$-$C_6$ haloalkyl, $C_1$-$C_6$ alkoxy, $C_1$-$C_6$ haloalkoxy, —NR'R", R'C(O)—, R'S(O)$_2$—, R'S(O)$_2$NR"—, R"R'NC(O)—, and R' C(O)NR"—;
(iii) $C_6$-$C_{10}$ aryl, ($C_6$-$C_{10}$ aryl)-($C_1$-$C_8$ alkyl)-, $C_6$-$C_{10}$ aryloxy, ($C_6$-$C_{10}$ aryloxy)-($C_1$-$C_5$ alkyl)-, $C_6$-$C_{10}$ arylcarbonyl, ($C_6$-$C_{10}$ arylcarbonyl)-($C_1$-$C_8$ alkyl)-, —CONH—($C_6$-$C_{10}$ aryl), —CONH—($C_1$-$C_8$ alkyl)-($C_6$-$C_{10}$ aryl), —NHCO—($C_6$-$C_{10}$ aryl) or —NHCO—($C_1$-$C_8$ alkyl)-($C_6$-$C_{10}$ aryl), wherein the aryl ring can be optionally substituted with at least one $R^{5a}$;
(iv) heteroaryl, heteroaryl-($C_1$-$C_5$ alkyl)-, heteroaryloxy, heteroaryloxy-($C_1$-$C_5$ alkyl)-, heteroarylcarbonyl, heteroaryl carb onyl-($C_1$-$C_5$ alkyl)-, —CONH-heteroaryl, —CONH—($C_1$-$C_5$ alkyl)-heteroaryl, —NHCO-heteroaryl, or —NHCO—($C_1$-$C_8$ alkyl)-heteroaryl, wherein the heteroaryl ring is 5- to 10-membered heteroaryl containing one to three heteroatoms selected from N, O and S, and can be optionally substituted with at least one $R^{5a}$;
(v) heterocycloalkyl, heterocycloalkyl-($C_1$-$C_5$ alkyl)-, heterocycloalkyloxy, heterocycloalkyloxy-($C_1$-$C_5$ alkyl)-, heterocycloalkylcarbonyl, heterocycloalkylcarbonyl-($C_1$-$C_5$ alkyl)-, —CONH-heterocycloalkyl, —CONH—($C_1$-$C_5$ alkyl)-heterocycloalkyl, —NHCO— heterocycloalkyl, or —NHCO—($C_1$-$C_5$ alkyl)-heterocycloalkyl, wherein the heterocycloalkyl ring is 3- to 10-membered fully saturated or partially unsaturated heterocycloalkyl containing one or three heteroatom selected from N, O and S, and can be optionally substituted with at least one $R^{5a}$; or
(vi) $C_3$-$C_8$ cycloalkyl, ($C_3$-$C_8$ cycloalkyl)-($C_1$-$C_5$ alkyl)-, $C_3$-$C_8$ cycloalkyloxy, ($C_3$-$C_8$ cycloalkyloxy)-($C_1$-$C_5$ alkyl)-, $C_3$-$C_8$ cycloalkylcarbonyl, ($C_3$-$C_8$ cycloalkylcarbonyl)-($C_1$-$C_5$ alkyl)-, —CONH—($C_3$-$C_8$ cycloalkyl), —CONH—($C_1$-$C_5$ alkyl)-($C_3$-$C_8$ cycloalkyl), —NHCO—($C_3$-$C_8$ cycloalkyl), or —NHCO—($C_1$-$C_5$ alkyl)-($C_3$-$C_8$ cycloalkyl), wherein the cycloalkyl ring can be optionally substituted with at least one $R^{5a}$;
R' and R" are each independently H or $C_1$-$C_6$ alkyl;
$R^{5a}$ is selected from a group consisting of halogen, hydroxy, —$NH_2$, —NH($C_1$-$C_6$ alkyl), —N($C_1$-$C_6$ alkyl)$_2$, cyano, oxo, nitro, $C_1$-$C_6$ alkyl, $C_1$-$C_6$ alkoxy; $C_1$-$C_6$ alkyl substituted with halogen, hydroxy, $C_1$-$C_6$ alkoxy, —$NH_2$ or cyano; $C_1$-$C_6$ alkoxy substituted with halogen, hydroxy, $C_1$-$C_6$ alkyl, —$NH_2$ or cyano; and halogen-$SO_2$—, ($C_1$-$C_6$ alkyl)-$SO_2$—, —$SO_2NH_2$, —$SO_2NH(C_1$-$C_6$ alkyl), and —$SO_2N(C_1$-$C_6$ alkyl)$_2$;

wherein $R^6$ is H or $C_1$-$C_6$ alkyl; and p is an integer from 0 to 2.

3. The compound according to claim 2, or a stereoisomer, solvate or pharmaceutically acceptable salt thereof, wherein $R^1$ is halogen;

$R^2$ is selected from a group consisting of H, halogen, hydroxy, oxo, $C_1$-$C_3$ alkyl, $C_1$-$C_3$ alkoxy, $C_1$-$C_3$ haloalkyl, hydroxy-($C_1$-$C_3$ alkyl)-, ($C_1$-$C_3$ alkoxy)-($C_1$-$C_3$ alkyl)-, $H_2N$—($C_1$-$C_3$ alkyl)-, —$NH_2$, —$NH(C_1$-$C_3$ alkyl), —$N(C_1$-$C_3$ alkyl)$_2$, nitro, cyano, —$C(O)NH_2$, —$C(O)(C_1$-$C_3$ alkyl), —$C(O)O(C_1$-$C_3$ alkyl), and carboxy or a salt thereof;

$R^3$ and $R^4$ are each independently H, $C_1$-$C_3$ alkyl, —$NH_2$, —$NH(C_1$-$C_3$ alkyl), —$N(C_1$-$C_3$ alkyl)$_2$, or $H_2N$—($C_1$-$C_3$ alkyl)-, or $R^3$ and $R^4$ are connected to each other to form Ring B, Ring B is $C_4$-$C_6$ cycloalkyl or a 4- to 6-membered heterocycloalkyl ring that optionally contains one oxygen atom and is optionally substituted with at least one R B, wherein $R^B$ is selected from a group consisting of deuterium, ($C_1$-$C_3$ alkyl), —$NH_2$, —$NH(C_1$-$C_3$ alkyl), —$N(C_1$-$C_3$ alkyl)$_2$, and $H_2N$—($C_1$-$C_3$ alkyl)-, Ring B can be optionally fused with Ring BB, and Ring BB is selected from $C_3$-$C_6$ cycloalkyl, $C_6$-$C_{10}$ aryl, and 5- to 7-membered heteroaryl containing one or two heteroatom selected from N, O and S, and Ring BB can be optionally substituted with at least one R BB, wherein $R^{BB}$ is selected from a group consisting of halogen, hydroxy, oxo, $C_1$-$C_3$ alkyl, $C_1$-$C_3$ alkoxy, $C_1$-$C_3$ haloalkyl, hydroxy-($C_1$-$C_3$ alkyl)-, ($C_1$-$C_3$ alkoxy)-($C_1$-$C_3$ alkyl)-, $H_2N$—($C_1$-$C_3$ alkyl)-, —$NH_2$, —$NH(C_1$-$C_3$ alkyl)-, —$N(C_1$-$C_3$ alkyl)$_2$, nitro and cyano;

wherein $R^5$ is each independently selected from the following (i) to (vi):

(i) H, halogen, hydroxy, —$NH_2$, —$C(O)NH_2$, nitro, cyano or carboxy or a salt thereof;

(ii) $C_1$-$C_6$ alkyl or $C_1$-$C_6$ alkoxy, which is optionally substituted with at least one substituent selected from a group consisting of halogen, hydroxy, $C_1$-$C_6$ alkyl, $C_1$-$C_6$ haloalkyl, $C_1$-$C_6$ alkoxy, $C_1$-$C_6$ haloalkoxy, —NR'R", R'C(O)—, R'S(O)$_2$—, R'S(O)$_2$NR"—, R"R'NC(O)—, and R' C(O)NR"—;

(iii) $C_6$-$C_{10}$ aryl, ($C_6$-$C_{10}$ aryl)-($C_1$-$C_3$ alkyl)-, $C_6$-$C_{10}$ aryloxy, ($C_6$-$C_{10}$ aryloxy)-($C_1$-$C_3$ alkyl)-, $C_6$-$C_{10}$ arylcarbonyl or ($C_6$-$C_{10}$ arylcarbonyl)-($C_1$-$C_3$ alkyl)-, wherein the aryl ring can be optionally substituted with at least one $R^{5a}$;

(iv) heteroaryl, heteroaryl-($C_1$-$C_3$ alkyl)-, heteroaryloxy, heteroaryloxy-($C_1$-$C_3$ alkyl)-, heteroarylcarbonyl or heteroarylcarbonyl-($C_1$-$C_3$ alkyl)-, wherein the heteroaryl ring is a 5- to 6-membered monocyclic heteroaryl or 9- to 10-membered bicyclic heteroaryl ring containing one or two heteroatom selected from N, O and S, and can be optionally substituted with at least one $R^{5a}$;

(v) heterocycloalkyl, heterocycloalkyl-($C_1$-$C_3$ alkyl)-, heterocycloalkyloxy, heterocycloalkyloxy-($C_1$-$C_3$ alkyl)-, heterocycloalkylcarbonyl, or heterocycloalkylcarbonyl-($C_1$-$C_3$ alkyl)-, wherein the heterocycloalkyl ring is 4- to 7-membered fully saturated or partially unsaturated heterocycloalkyl containing one or two heteroatom selected from N, O and S, and can be optionally substituted with at least one $R^{5a}$; or (vi) $C_4$-$C_8$ cycloalkyl, ($C_4$-$C_8$ cycloalkyl)-($C_1$-$C_3$ alkyl)-, $C_4$-$C_8$ cycloalkyloxy, ($C_4$-$C_8$ cycloalkyloxy)-($C_1$-$C_3$ alkyl)-, $C_4$-$C_8$ cycloalkylcarbonyl, or ($C_4$-$C_8$ cycloalkylcarbonyl)-($C_1$-$C_3$ alkyl)-, wherein the cycloalkyl ring can be optionally substituted with at least one $R^{5a}$;

R' and R" are each independently H or $C_1$-$C_6$ alkyl;

$R^{5a}$ is selected from a group consisting of halogen, hydroxy, oxo, $C_1$-$C_6$ alkyl, $C_1$-$C_6$ alkoxy, $C_1$-$C_6$ haloalkyl, hydroxy-($C_1$-$C_6$ alkyl)-, ($C_1$-$C_6$ alkoxy)-($C_1$-$C_6$ alkyl)-, —$NH_2$, —$NH(C_1$-$C_6$ alkyl), —$N(C_1$-$C_6$ alkyl)$_2$, nitro, cyano, halogen-$SO_2$—, ($C_1$-$C_6$ alkyl)-$SO_2$- and —$SO_2NH_2$;

$R^6$ is H or $C_1$-$C_6$ alkyl;

p is an integer from 0 to 2.

4. The compound according to claim 1, or a stereoisomer, solvate or pharmaceutically acceptable salt thereof, wherein $R^1$ is F or Cl.

5. The compound according to claim 1, or a stereoisomer, solvate or pharmaceutically acceptable salt thereof, wherein $R^2$ is selected from a group consisting of H, halogen, hydroxy, cyano, $C_1$-$C_6$ alkyl, $C_1$-$C_6$ alkoxy, hydroxy-($C_1$-$C_6$ alkyl)-, —$NH_2$, —$C(O)NH_2$ and —$C(O)(C_1$-$C_6$ alkyl).

6. The compound according to claim 3, or a stereoisomer, solvate or pharmaceutically acceptable salt thereof, wherein $R^2$ is selected from a group consisting of H, $C_1$-$C_3$ alkyl, hydroxy-($C_1$-$C_3$ alkyl)-, —$NH_2$, —$C(O)NH_2$ and —$C(O)(C_1$-$C_3$ alkyl).

7. The compound according to claim 1, or a stereoisomer, solvate or pharmaceutically acceptable salt thereof, wherein $R^1$ is F or Cl; and $R^2$ is H, —$CH_3$, —$CH_2OH$, —$NH_2$, —$C(O)NH_2$ or -$C(O)CH_3$.

8. The compound according to claim 1, or a stereoisomer, solvate or pharmaceutically acceptable salt thereof, wherein one of $R^3$ and $R^4$ is $C_1$-$C_3$ alkyl, and the other is —$NH_2$ or $H_2N$—($C_1$-$C_3$ alkyl)-, or $R^3$ and $R^4$ are connected to each other to form Ring B, wherein Ring B is a cyclopentane ring or a tetrahydrofuran ring, and Ring B can be optionally substituted with at least one $R^B$ selected from deuterium, $C_1$-$C_3$ alkyl and —$NH_2$;

Ring B can be optionally fused with Ring BB selected from a $C_3$-$C_6$ cycloalkyl ring, a benzene ring, a pyridine ring or a thiazole ring;

Ring BB can be optionally substituted with at least one $R^{BB}$ selected from a group consisting of halogen, cyano, hydroxy, $C_1$-$C_3$ alkyl and $C_1$-$C_3$ alkoxy.

9. The compound according to claim 8, or a stereoisomer, solvate or pharmaceutically acceptable salt thereof,

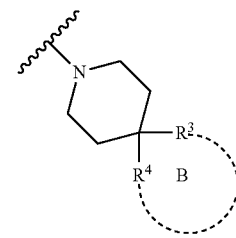

of Formula 1A-1 is selected from the following structures:

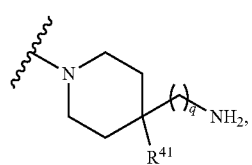 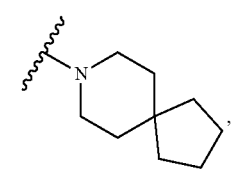

-continued

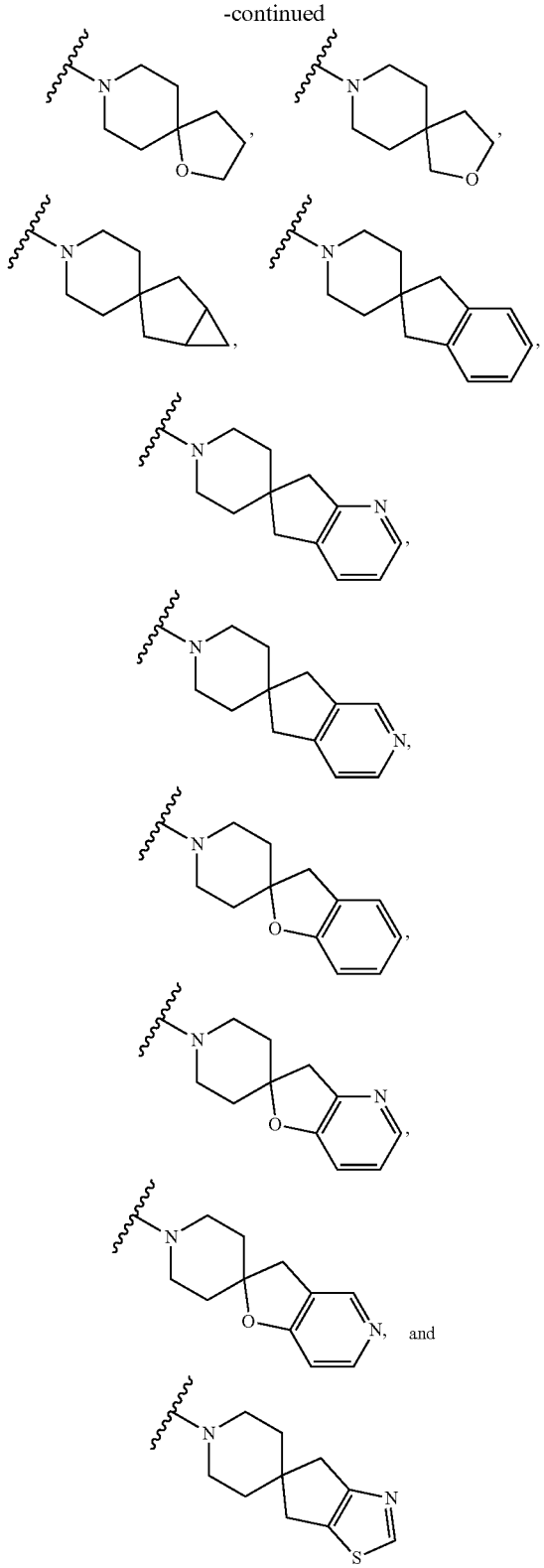

wherein, $R^{41}$ is $C_1$-$C_3$ alkyl, and q is an integer from 0 to 3; and wherein Ring B in the above structures can be optionally substituted with at least one $R^B$ selected from deuterium, methyl and —$NH_2$, and Ring BB can be optionally substituted with at least one $R^{BB}$ selected from a group consisting of halogen, cyano, hydroxy, methyl and methoxy.

10. The compound according to claim 9, or a stereoisomer, solvate or pharmaceutically acceptable salt thereof, wherein

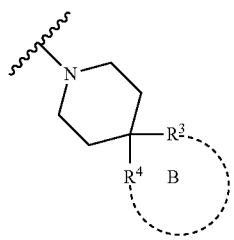

of Formula 1A-1 is selected from the following structures:

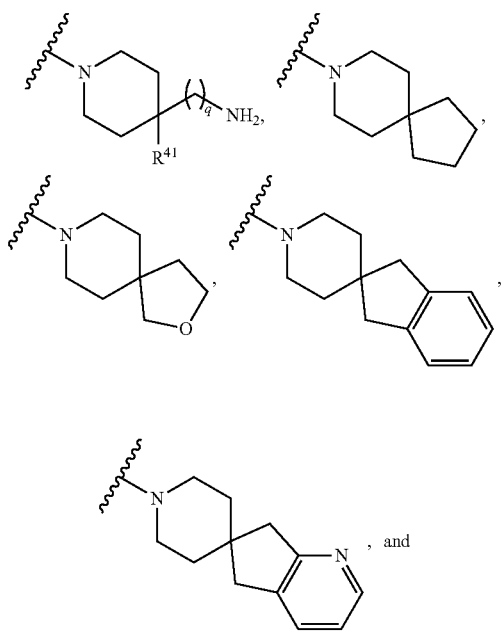

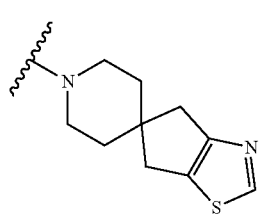

wherein, $R^{41}$ is methyl, and q is 0 or 1; and wherein Ring B in the above structures can be optionally substituted with at least one $R^B$ selected from methyl and —$NH_2$, and Ring BB is optionally substituted with at least one $R^{BB}$ selected from a group consisting of halogen, cyano, hydroxy, methyl and methoxy.

11. The compound according to claim 9, or a stereoisomer, solvate or pharmaceutically acceptable salt thereof, wherein

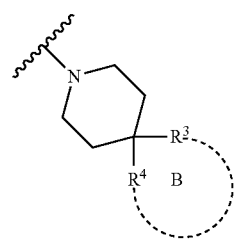
of Formula 1A-1 is selected from the following structures:
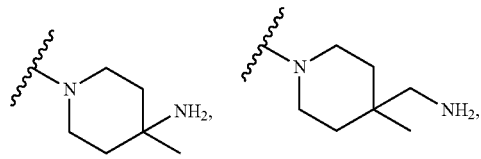
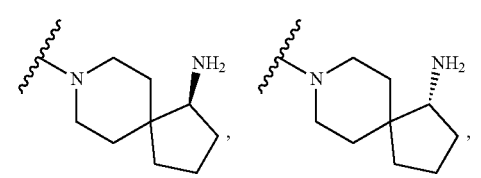
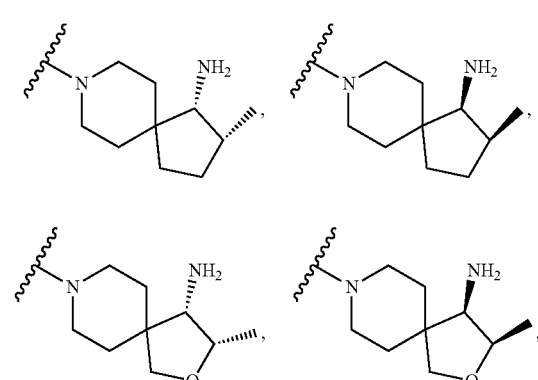
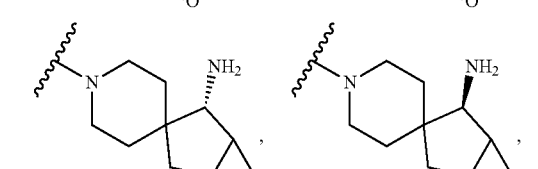
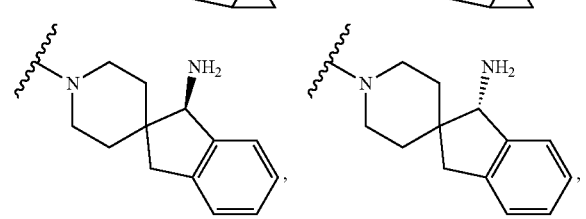
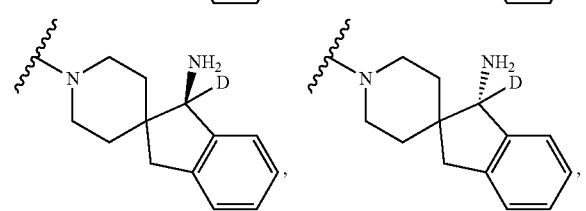
-continued
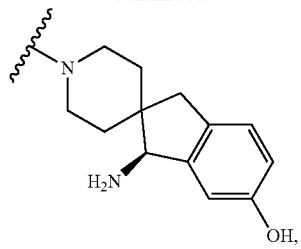
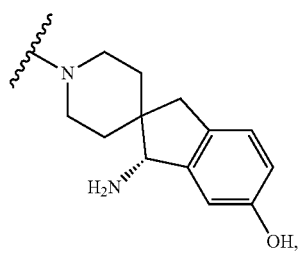
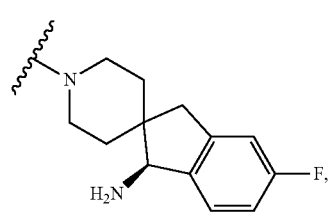
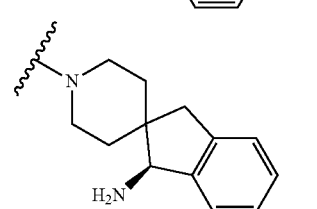
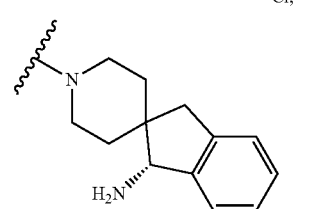
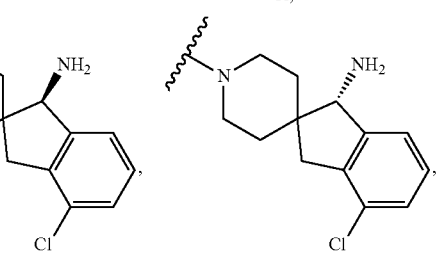

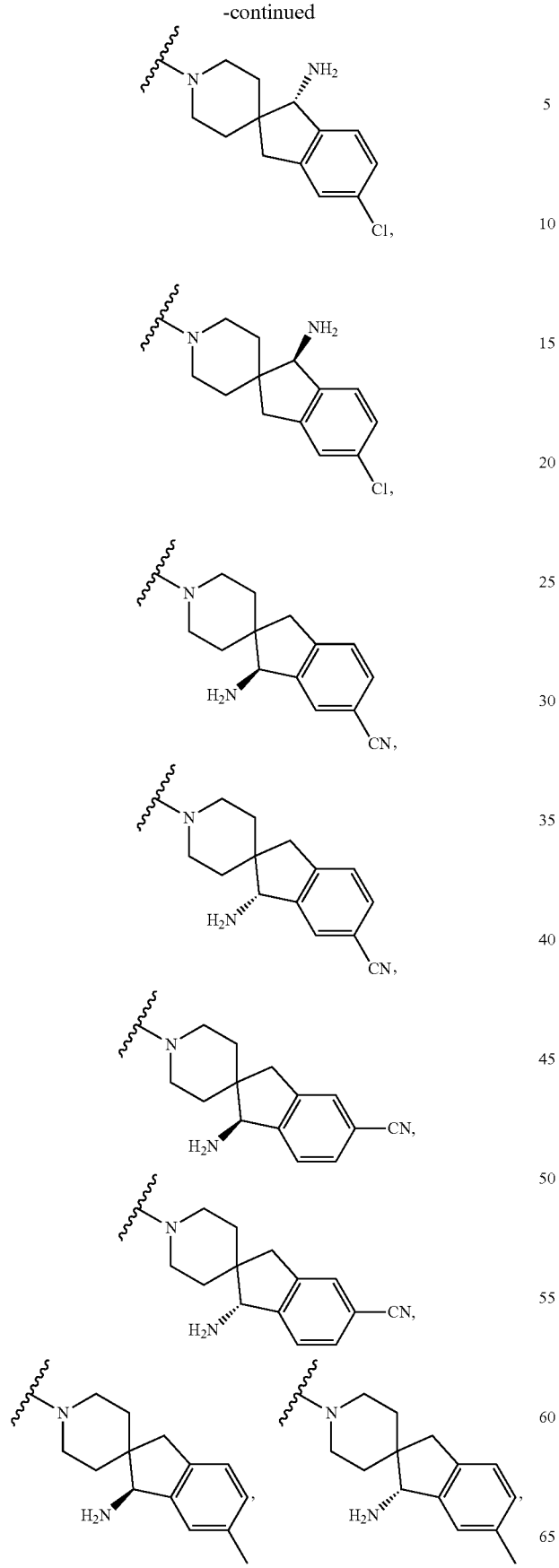
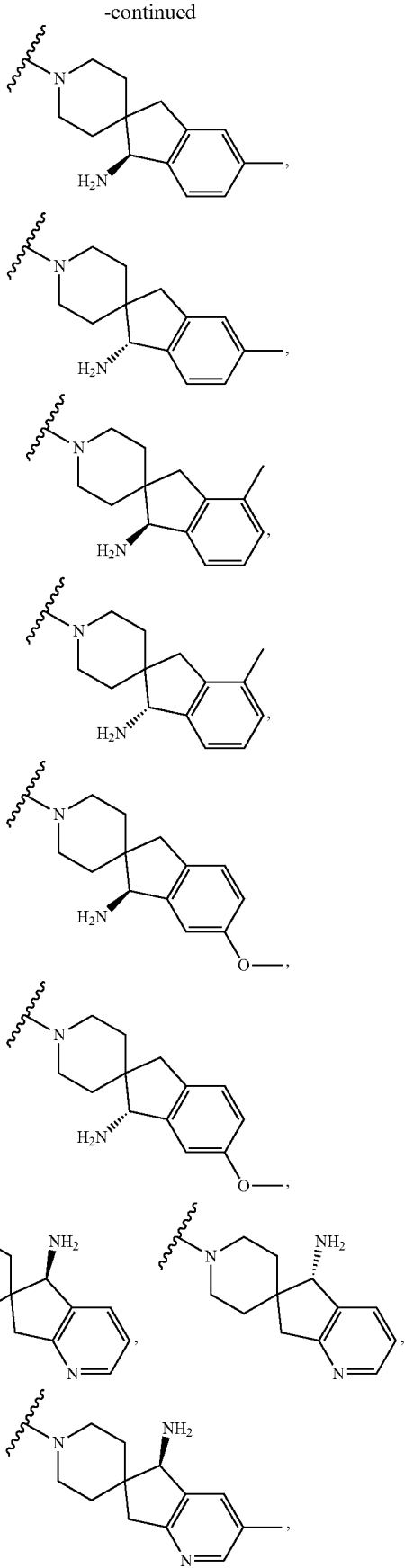

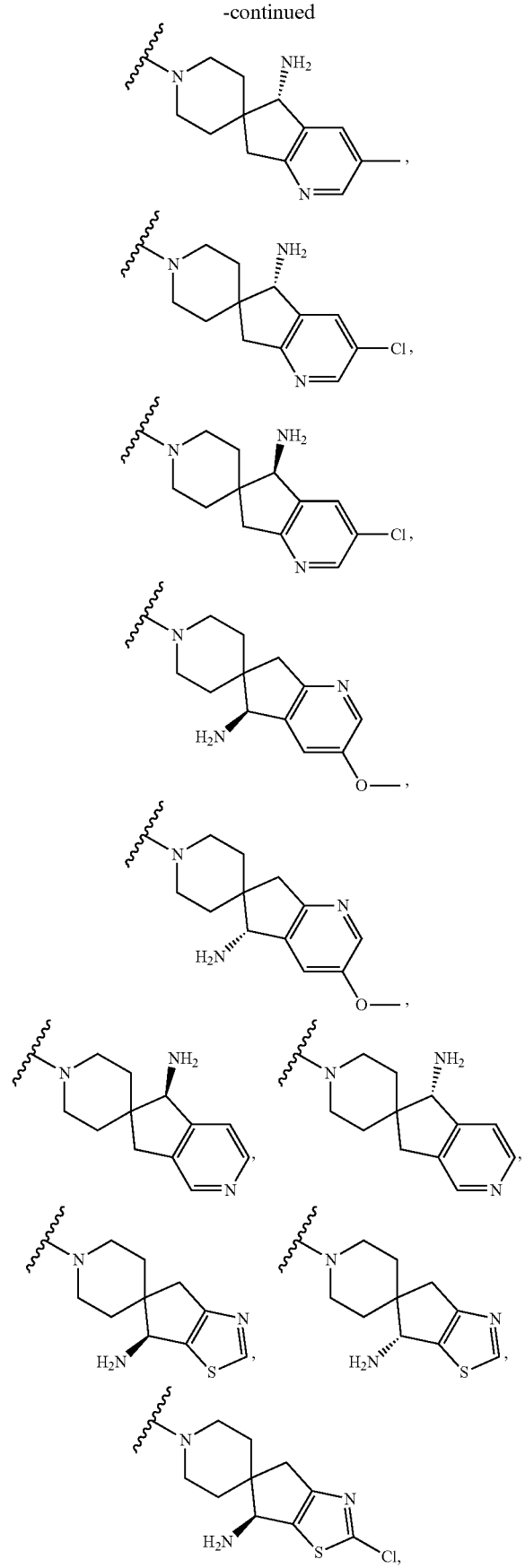
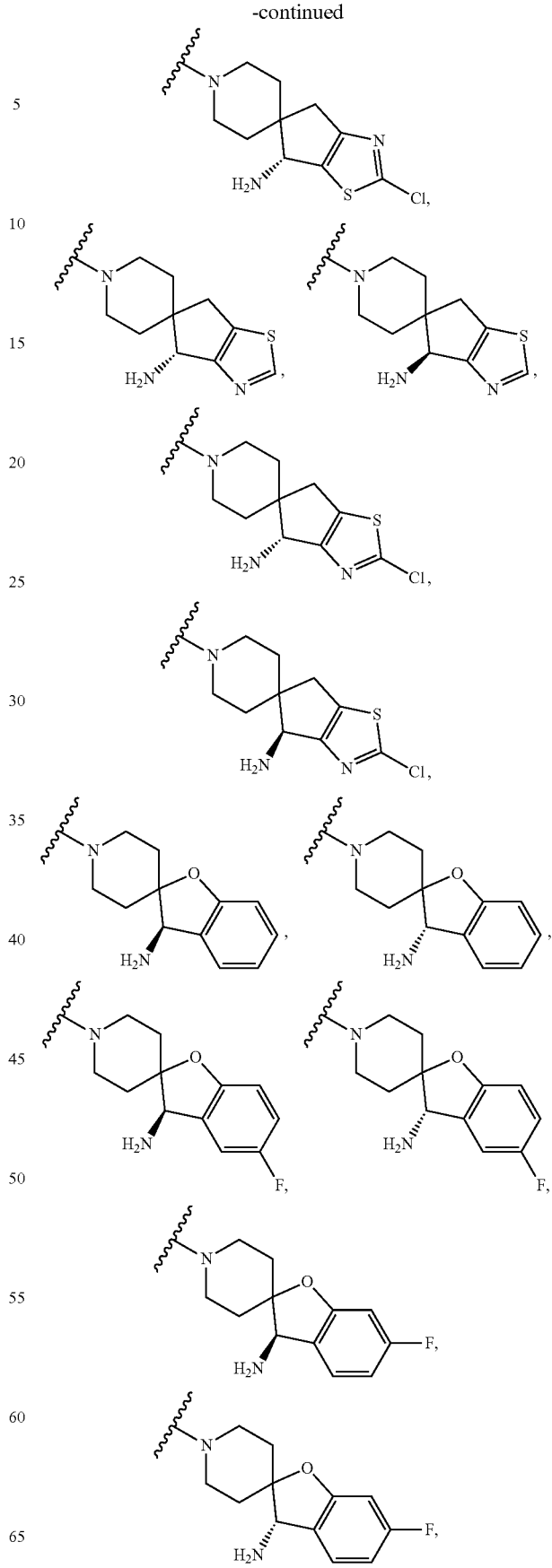

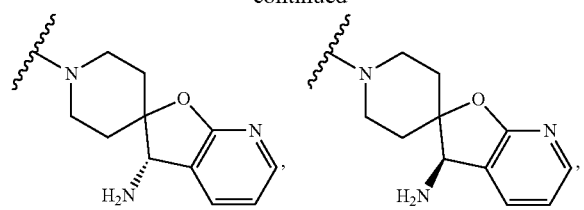 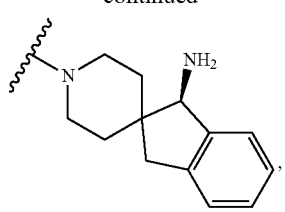
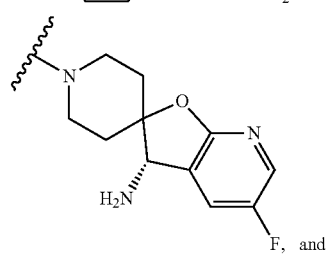 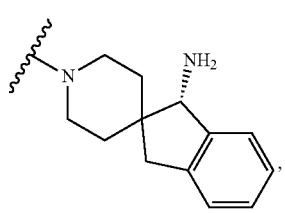
F, and
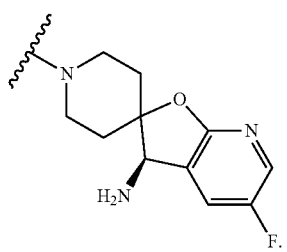 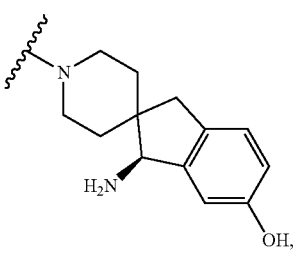
F.
12. The compound according to claim 11, or a stereoisomer, solvate or pharmaceutically acceptable salt thereof, wherein
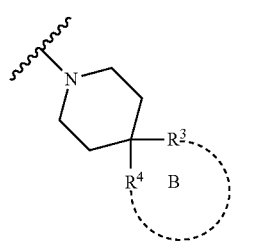
of Formula 1A-1 is selected from the following structures:
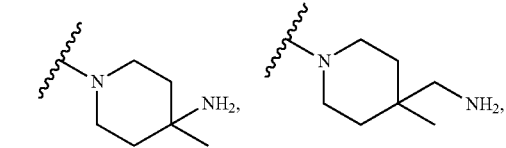
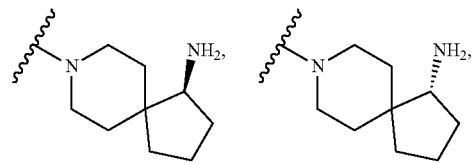
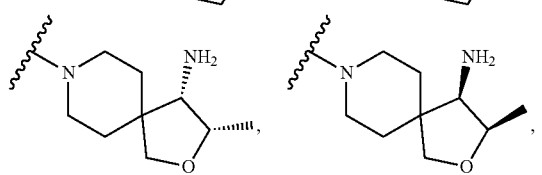
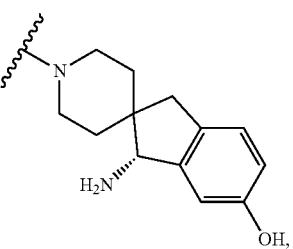
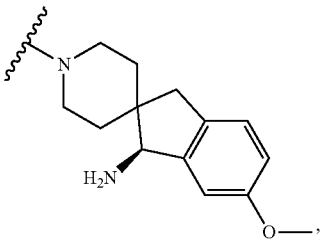
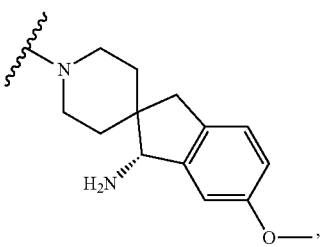
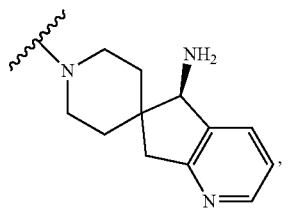

-continued

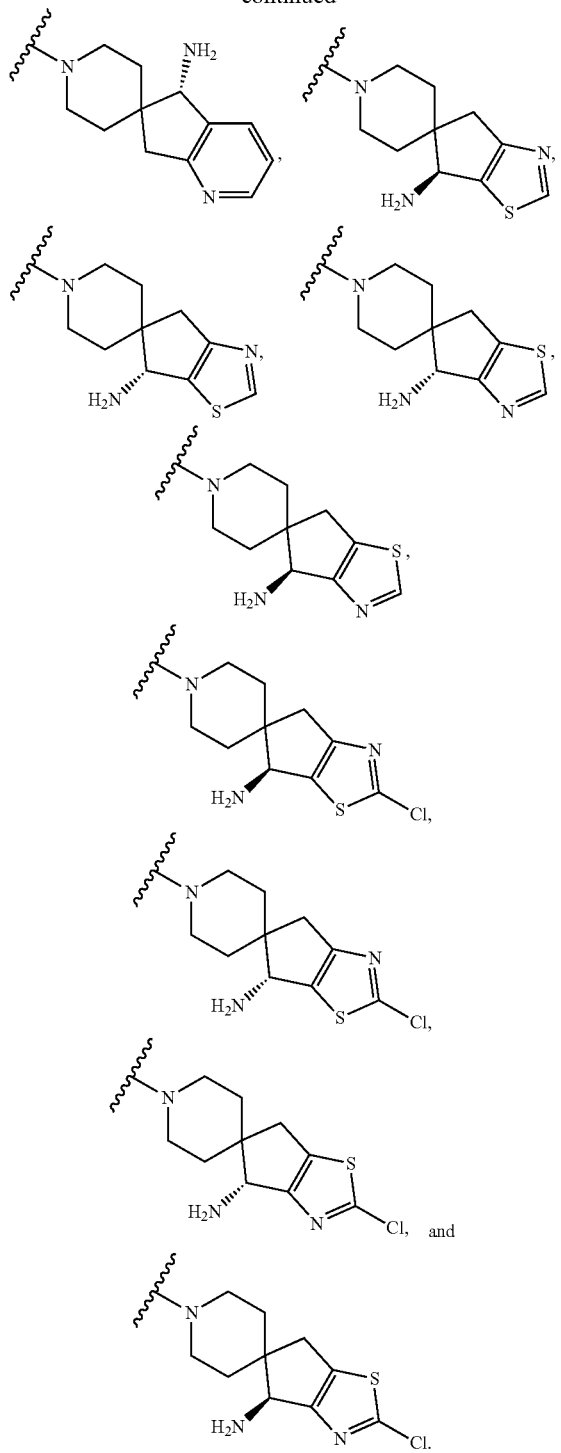

13. The compound according to claim 1, or a stereoisomer, solvate or pharmaceutically acceptable salt thereof, wherein
  $R^5$ is each independently selected from the following (i) to (vi):
  (i) H, halogen, hydroxy, —$NH_2$, —$C(O)NH_2$, nitro, cyano or carboxy or a salt thereof;
  (ii) $C_1$-$C_6$ alkyl, which is optionally substituted with at least one substituent selected from a group consisting of halogen, hydroxy, $C_1$-$C_6$ haloalkyl, $C_1$-$C_6$ alkoxy, $C_1$-$C_6$ haloalkoxy, -NR'R",R'C(O)—, R'S(O)$_2$—, R'S(O)$_2$NR"—, R"R'NC(O)- and R'C(O)NR"—; $C_1$-$C_6$ alkoxy; or ($C_1$-$C_6$ alkoxy)-($C_1$-$C_6$ alkoxy)-, wherein the R' and R" are each independently H or $C_1$-$C_3$ alkyl;
  (iii) phenyl, phenyl-($C_1$-$C_3$ alkyl)-, phenyloxy, phenyloxy-($C_1$-$C_3$ alkyl)-, phenylcarbonyl, or phenylcarbonyl-($C_1$-$C_3$ alkyl)-, wherein the phenyl ring can be optionally substituted with at least one $R^{5a}$;
  (iv) heteroaryl, heteroaryl-($C_1$-$C_3$ heteroaryloxy, heteroaryloxy-($C_1$-$C_3$ heteroarylcarbonyl, or heteroarylcarbonyl-($C_1$-$C_3$ alkyl)-, wherein the heteroaryl ring is selected from a group consisting of pyrrolyl, furanyl, thiophenyl, pyrazolyl, imidazolyl, isoxazolyl, oxazolyl, thiazolyl, isothiazolyl, pyridinyl, pyrimidinyl, pyrazinyl, pyridazinyl, indolyl, benzofuranyl, benzothiophenyl, benzopyrazolyl, benzimidazolyl, benzooxazolyl, benzoisoxazolyl, benzothiazolyl, benzoisothiazolyl and 1H-pyrrolo[2,3-b]pyridinyl, and can be optionally substituted with at least one $R^{5a}$;
  (v) heterocycloalkyl, heterocycloalkyl-($C_1$-$C_3$ heterocycloalkyloxy, heterocycloalkyloxy-($C_1$-$C_3$ heterocycloalkylcarbonyl, or heterocycloalkylcarbonyl-($C_1$-$C_3$ alkyl)-, wherein the heterocycloalkyl ring is selected from a group consisting of oxetanyl, azetidinyl, pyrrolidinyl, tetrahydrofuranyl, tetrahydrothiophenyl, piperidinyl, tetrahydropyranyl, 4H-pyranyl, 3,6-dihydro-2H-pyranyl, 3,4-dihydro-2H-pyranyl, 1,2-dihydropyridinyl, 1,4-dihydropyridinyl, 1,2,3,6-tetrahydropyridinyl, 1,2,3,4-tetrahydropyridinyl, piperazinyl, morpholinyl, thiomorpholinyl, oxazolidinyl and 2-oxo-oxazolidinyl, and can be optionally substituted with at least one $R^{5a}$; or
  (vi) $C_5$-$C_7$ cycloalkyl, ($C_5$-$C_7$ cycloalkyl)-($C_1$-$C_3$ alkyl)-, $C_5$-$C_7$ cycloalkyloxy, ($C_5$-$C_7$ cycloalkyloxy)-($C_1$-$C_3$ alkyl)-, $C_5$-$C_7$ cycloalkylcarbonyl, or ($C_5$-$C_7$ cycloalkylcarbonyl)-($C_1$-$C_3$ alkyl)-, wherein the cycloalkyl ring can be optionally substituted with at least one $R^{5a}$, and
  wherein $R^{5a}$ is selected from a group consisting of halogen, hydroxy, oxo, $C_1$-$C_3$ alkyl, $C_1$-$C_3$ alkoxy, $C_1$-$C_3$ haloalkyl, hydroxy-($C_1$-$C_3$ alkyl)-, —$NH_2$, —NH($C_1$-$C_3$ alkyl), —N($C_1$-$C_3$ alkyl)$_2$, nitro, cyano, —$SO_2$F and —$SO_2$Cl.

14. The compound according to claim 13, or a stereoisomer, solvate or pharmaceutically acceptable salt thereof, wherein the heteroaryl ring is selected from a group consisting of pyridinyl, pyrazolyl, isoxazolyl, furanyl, pyrimidinyl, thiazolyl, pyrazinyl, benzimidazolyl, benzooxazolyl and 1H-pyrrolo[2,3-b]pyridinyl; and the heterocycloalkyl ring is selected from a group consisting of pyrrolidinyl, tetrahydrofuranyl, tetrahydropyranyl, 3,6-dihydro-2H-pyranyl, morpholinyl, oxetanyl, piperidinyl and 2-oxo-oxazolidinyl.

15. The compound according to claim 13, or a stereoisomer, solvate or pharmaceutically acceptable salt thereof, wherein $R^5$ is selected from a group consisting of phenyl, benzyl, 1-phenylethyl, phenoxy, pyridinylmethyl, pyridinyloxy, pyridinylcarbonylmethyl, pyrazolylmethyl, pyrrolidinylmethyl, pyrrolidinylethyl, isoxazolylmethyl, tetrahydrofuranylmethyl, tetrahydrofuranyloxy, tetrahydropyranylmethyl, 3,6-dihydro-2H-pyranylmethyl, morpholinylmethyl, oxetanylmethyl, piperidinylcarbonylmethyl, 2-oxo-oxazolidinylethyl, 2-oxo-oxazolidinylmethyl, furanylmethyl, pyrimidinylmethyl, thiazolylmethyl, pyrazinylmethyl, benzimidazolylmethyl, benzooxazolylmethyl, 1H-pyrrolo[2,3-b]pyridinylmethyl and cyclohexyl; and wherein $R^5$ is optionally substituted with at least one $R^{5a}$ selected from a group consisting of at least one F, Cl, OH, —CH₃, —OCH₃, cyano, oxo, —NH₂, NO₂, SO₂F and CF₃.
16. The compound according to claim 13, or a stereoisomer, solvate or pharmaceutically acceptable salt thereof, wherein R⁵ is selected from:
H, CH₃—, HOCH₂CH₂—, HOCH₂CH₂CH₂—, CF₃CH₂—, CF₃CH₂CH₂—, FCH₂CH₂CH₂—,
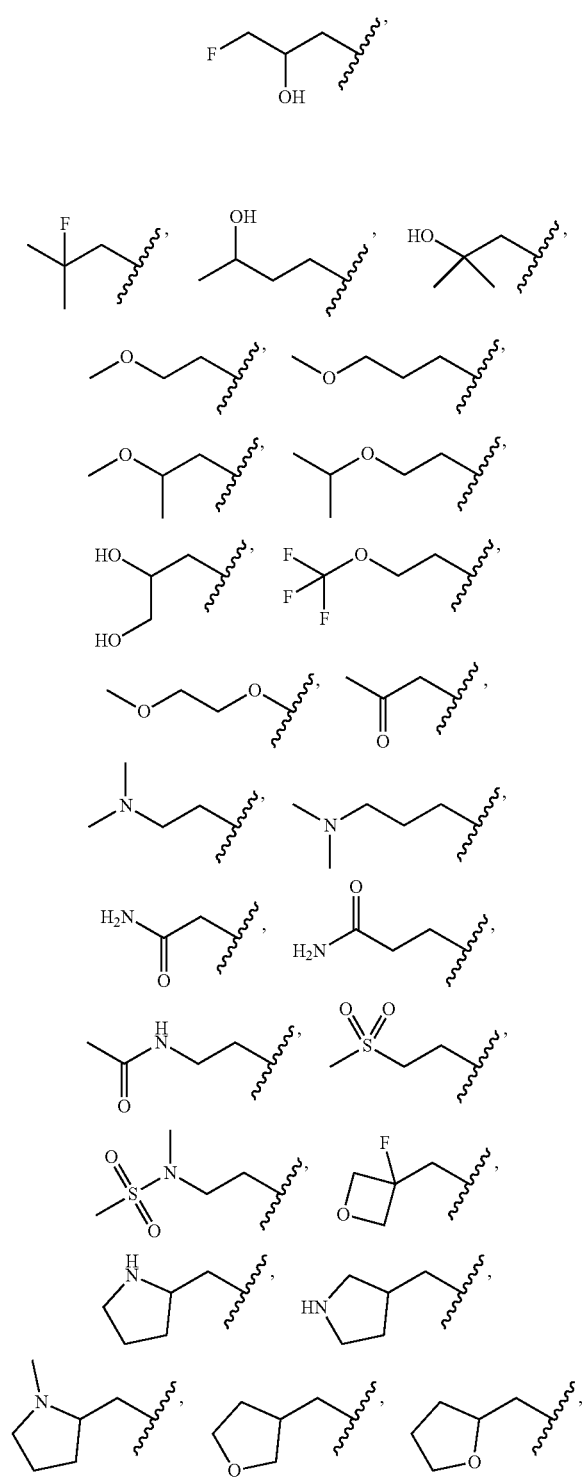
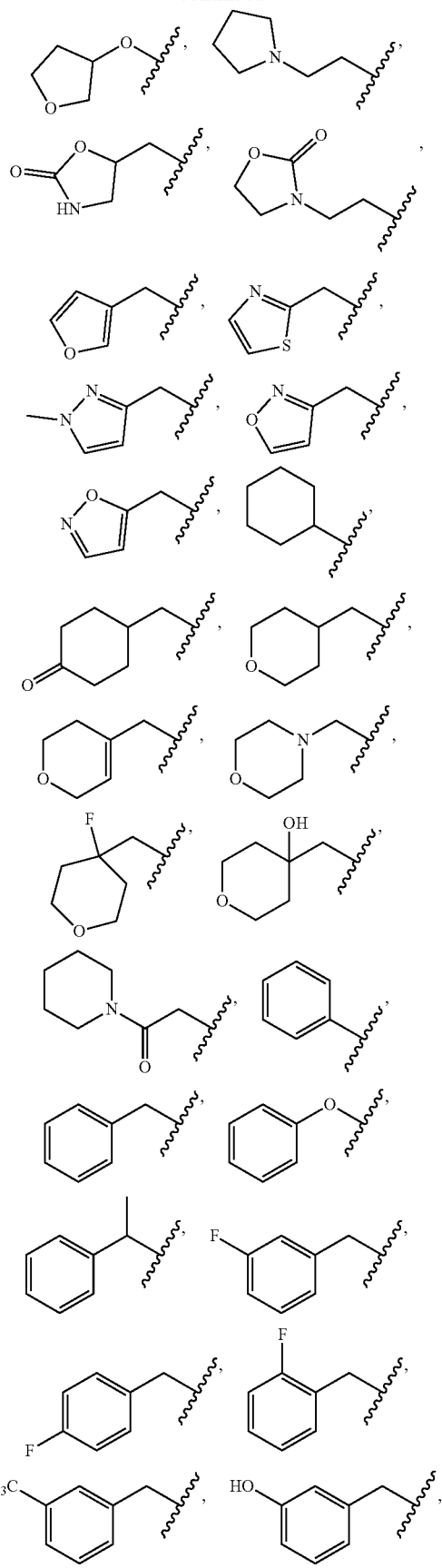

-continued
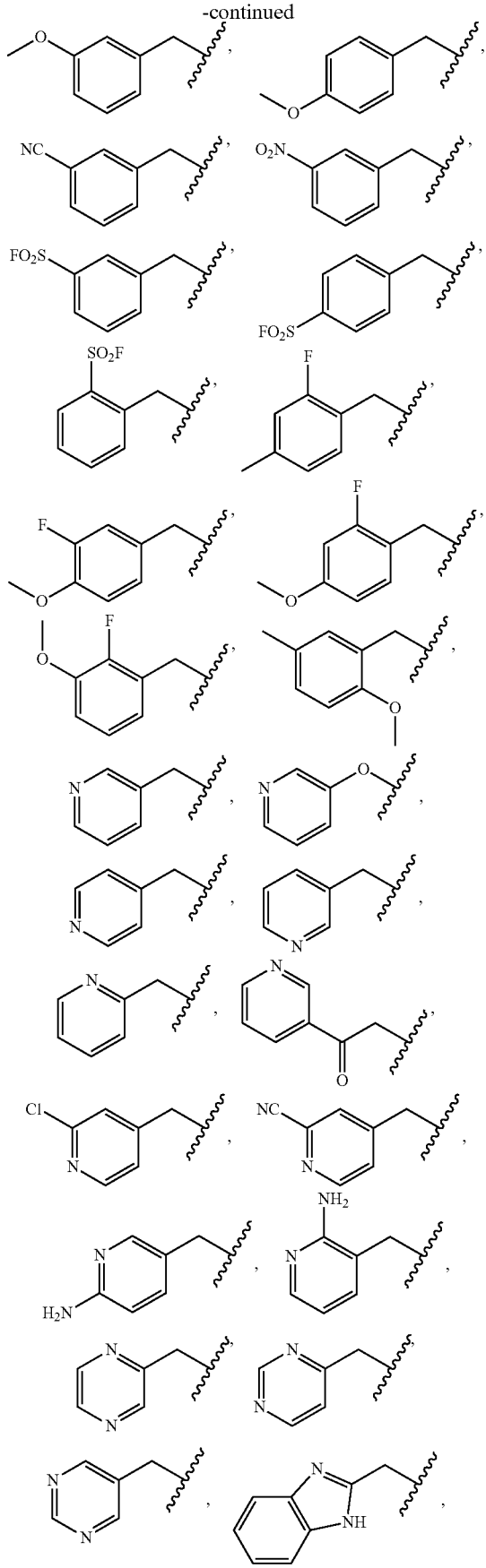
-continued
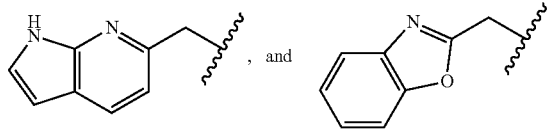, and
(In the above structures,
represents a binding position with the remaining residue of the compound).
17. The compound according to claim 1, or a stereoisomer, solvate or pharmaceutically acceptable salt thereof, wherein the compound is selected from:
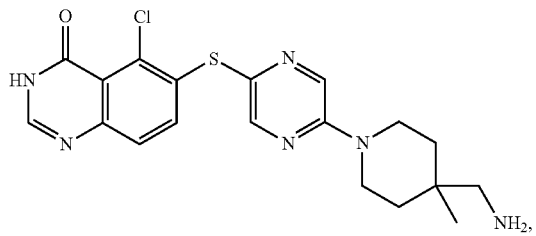
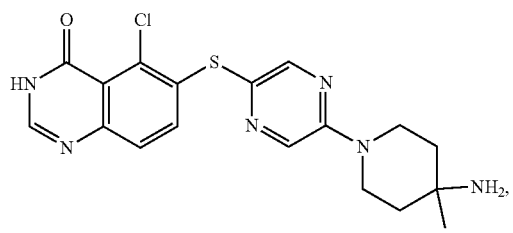
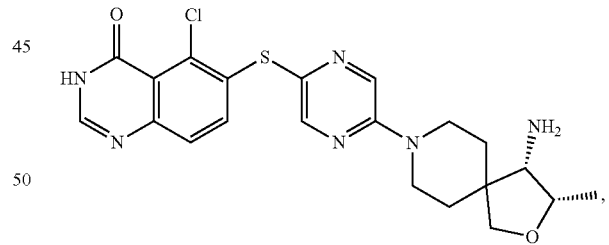
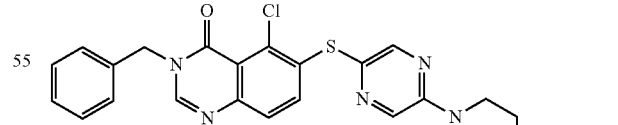
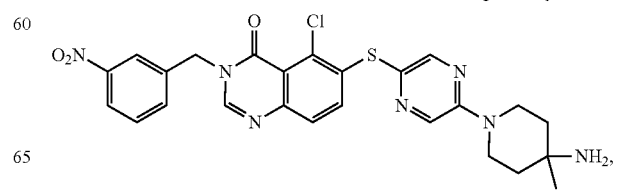

353
-continued
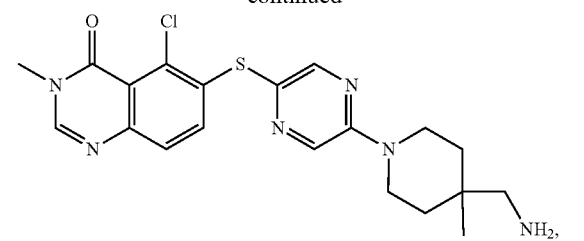
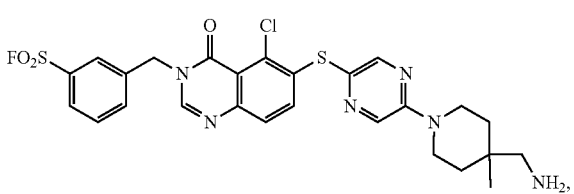
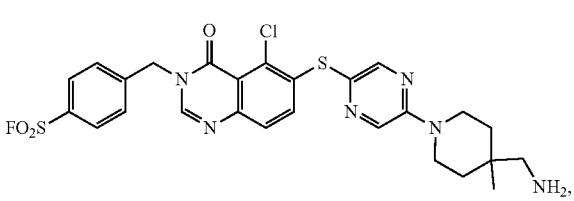
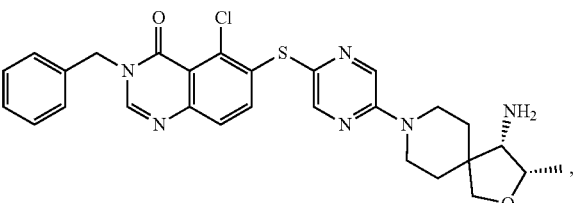
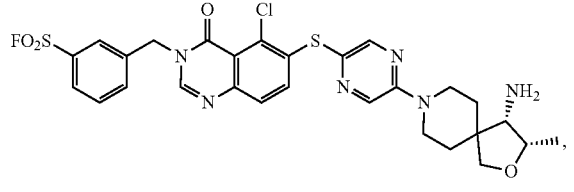
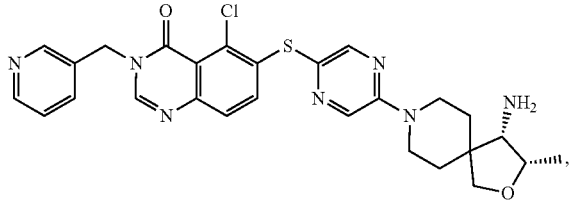
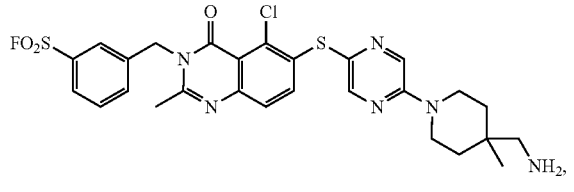
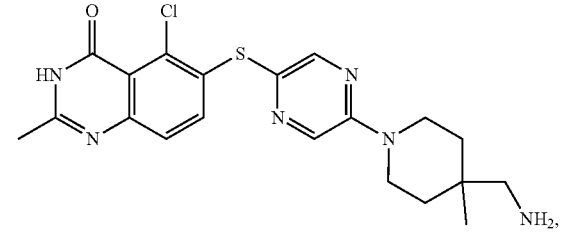
354
-continued
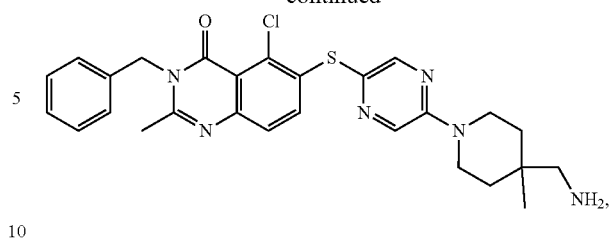
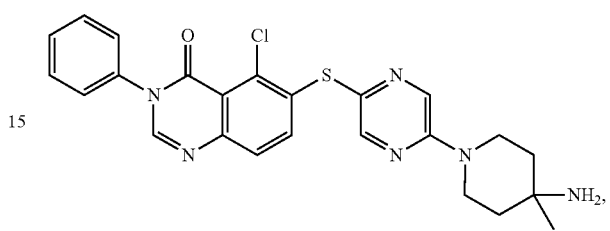
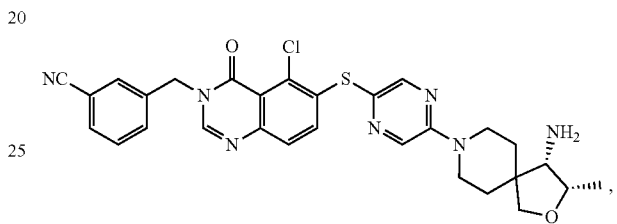
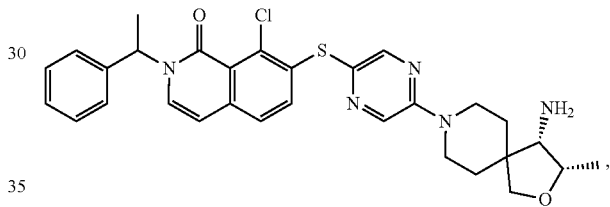
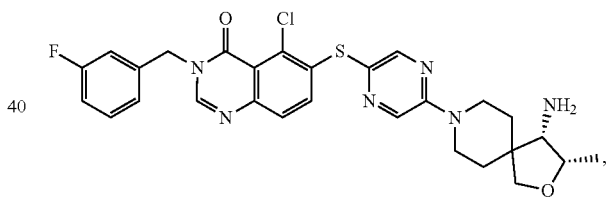
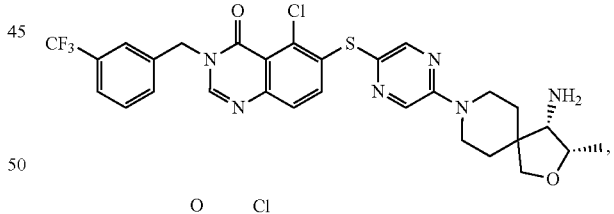
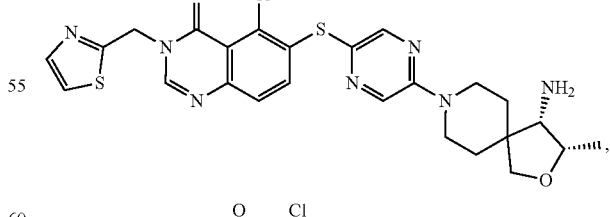
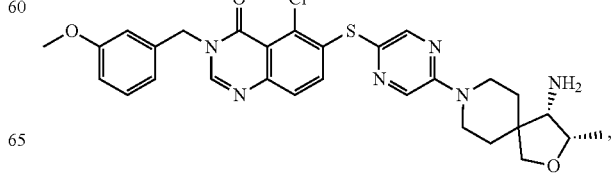

355
-continued
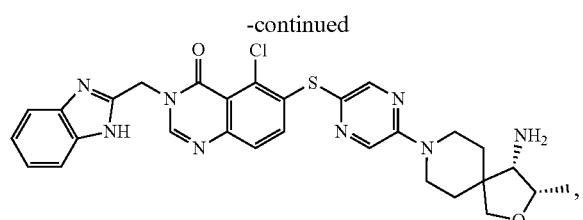
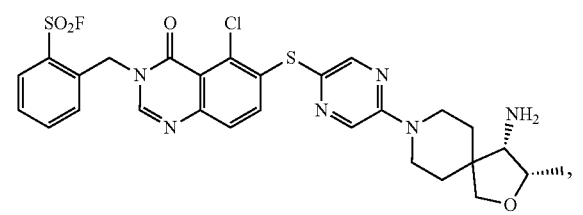
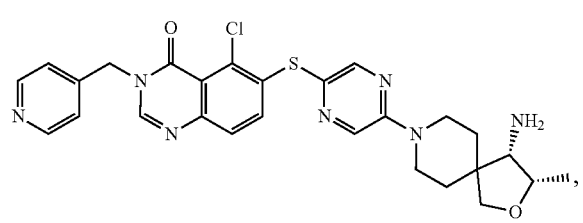
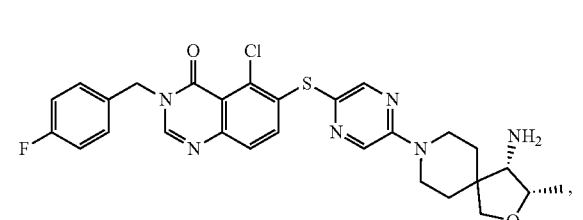
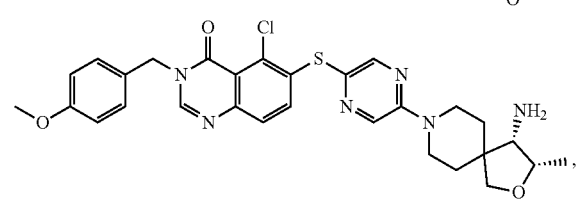
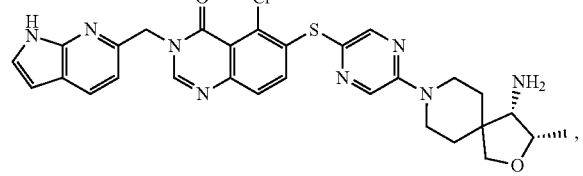
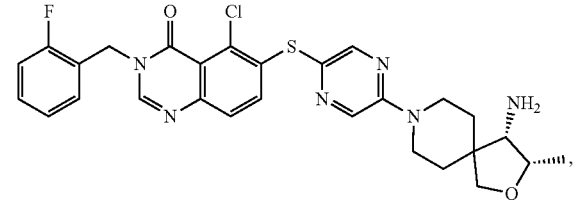
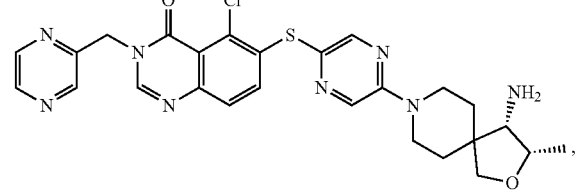
356
-continued
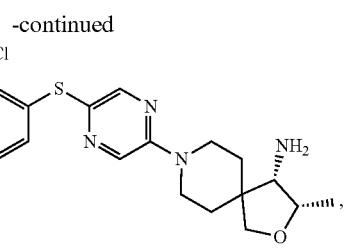
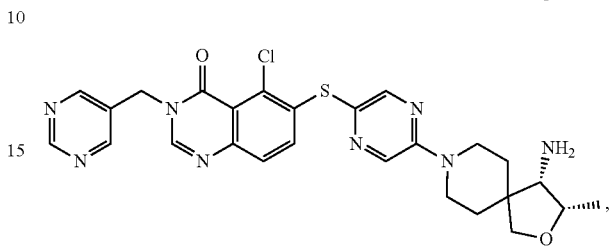
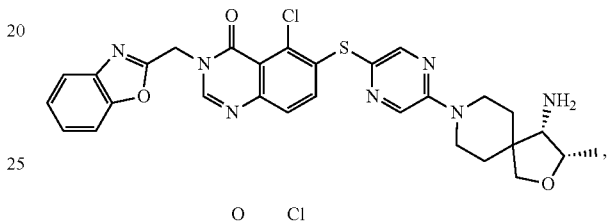
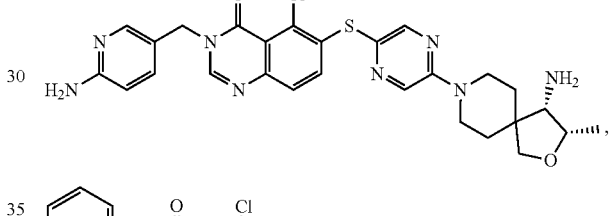
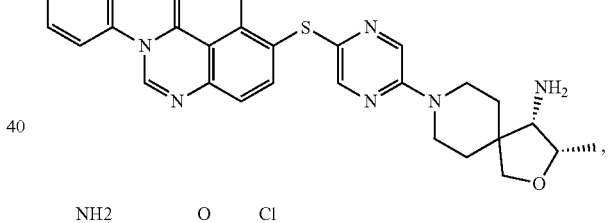
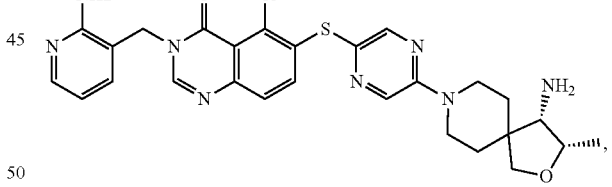
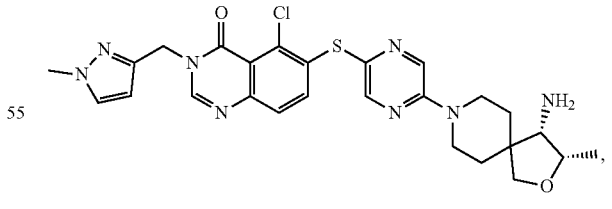
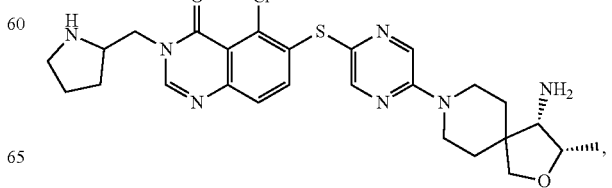

357
-continued
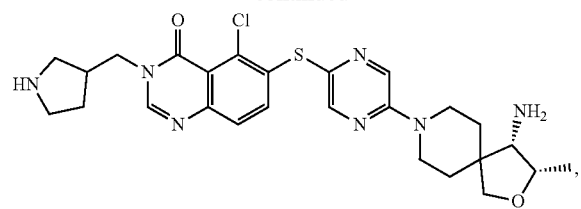
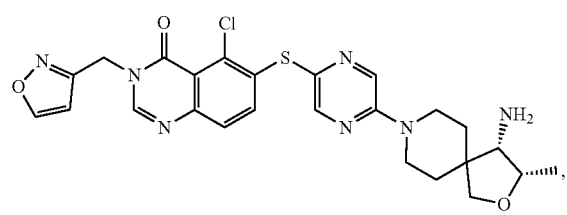
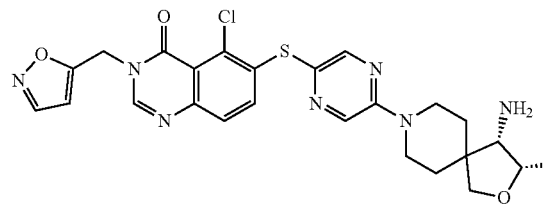
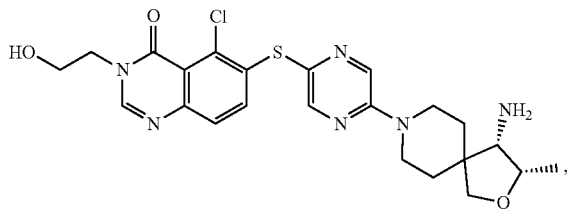
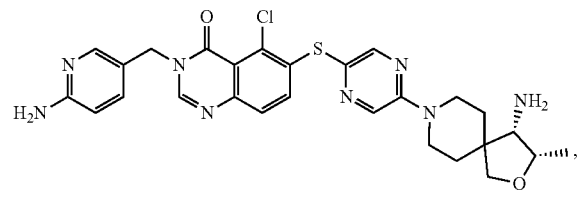
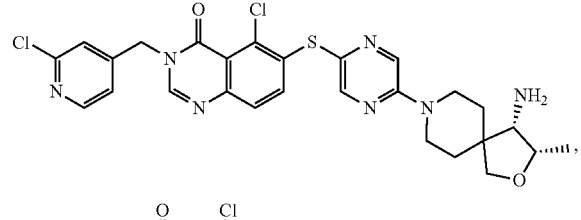
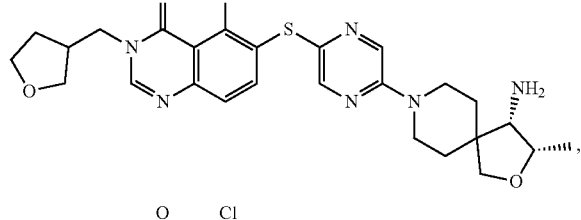
358
-continued
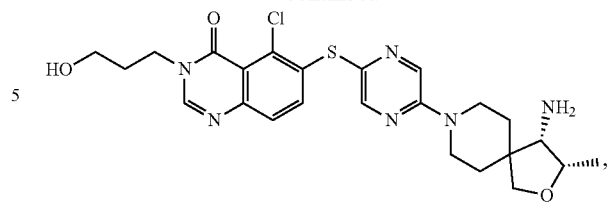
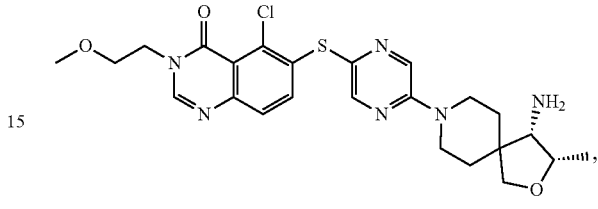
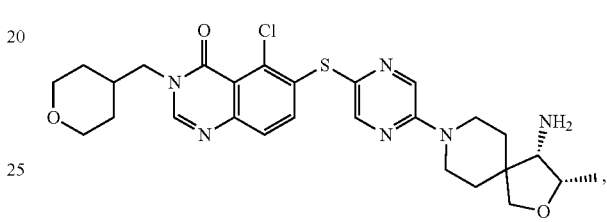
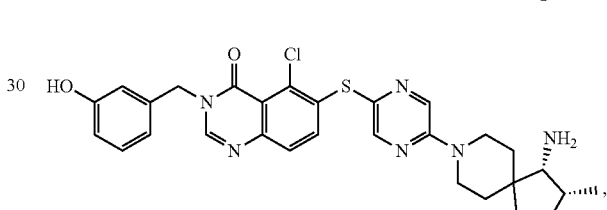
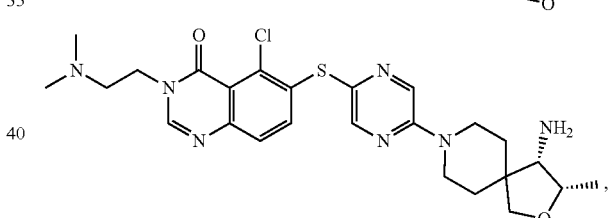
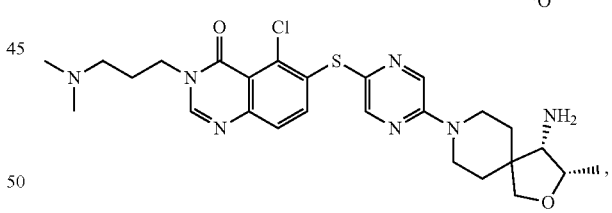
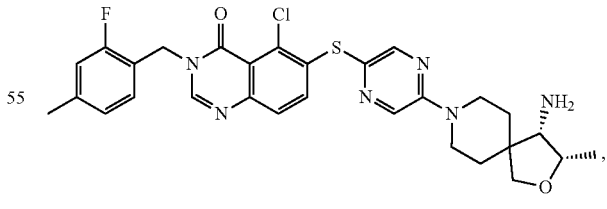

359
-continued
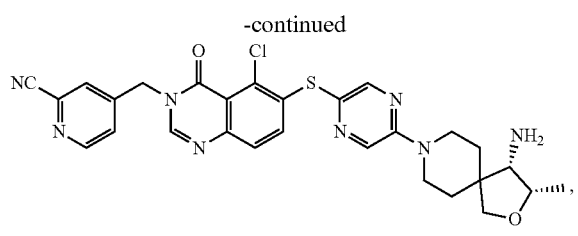
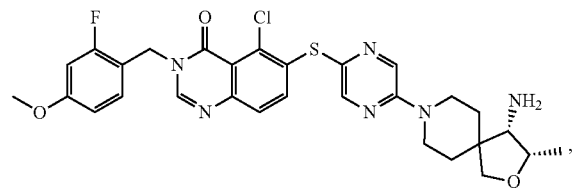
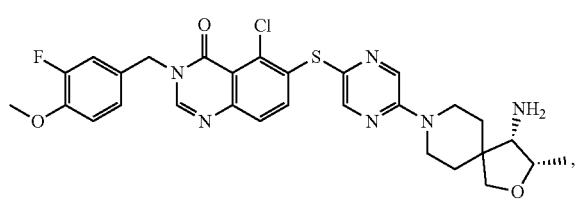
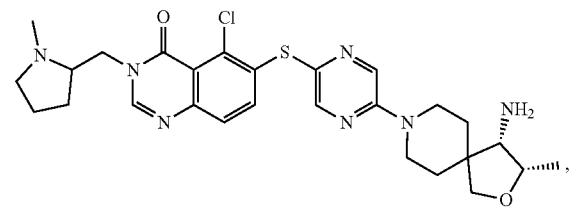
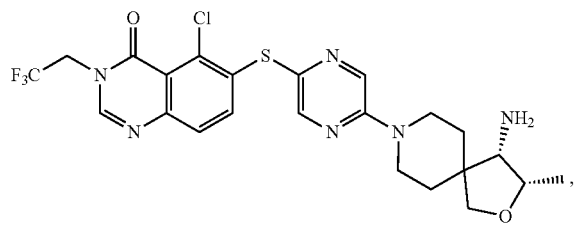
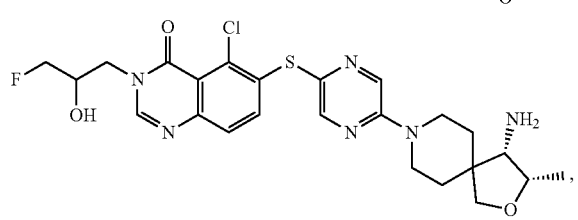
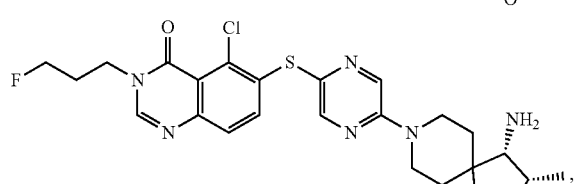
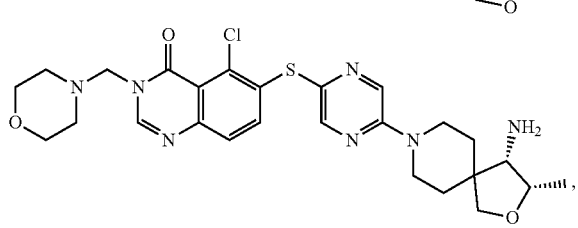
360
-continued
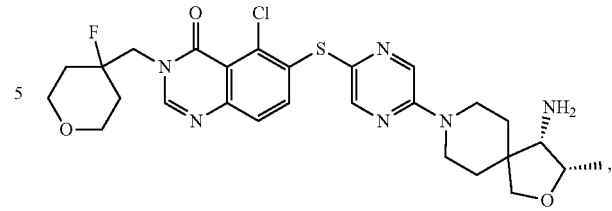
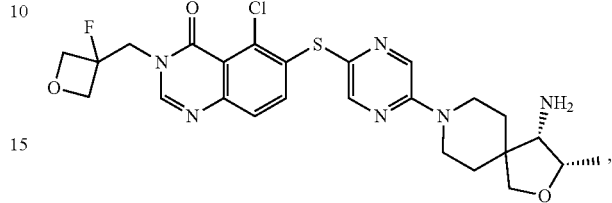
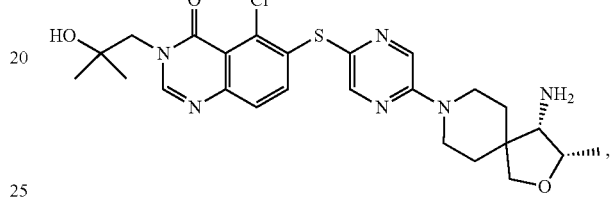
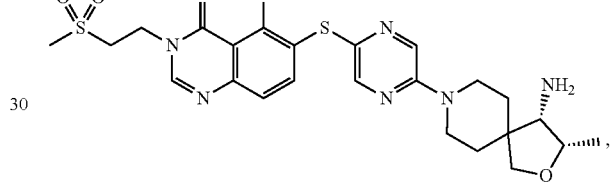
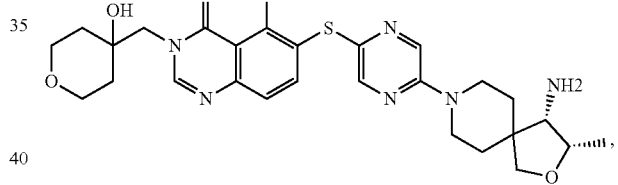
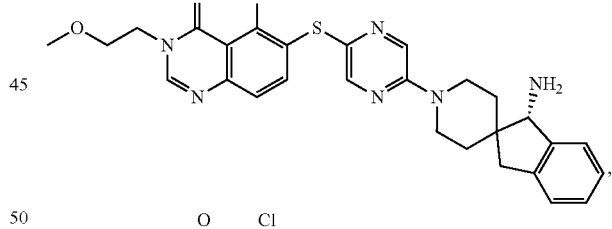
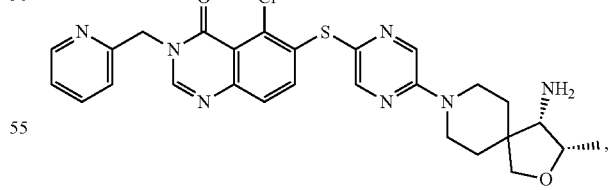
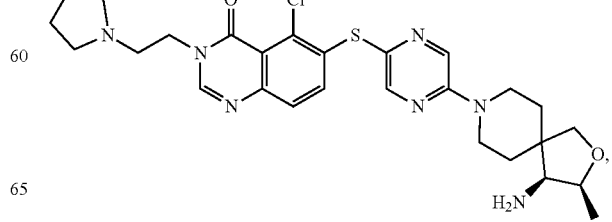

361
-continued
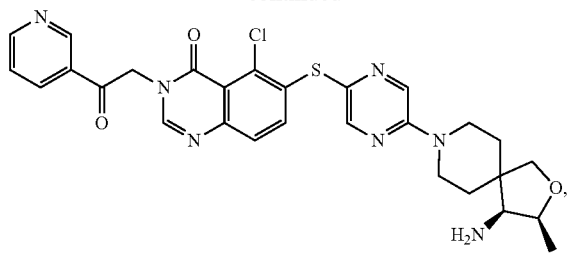
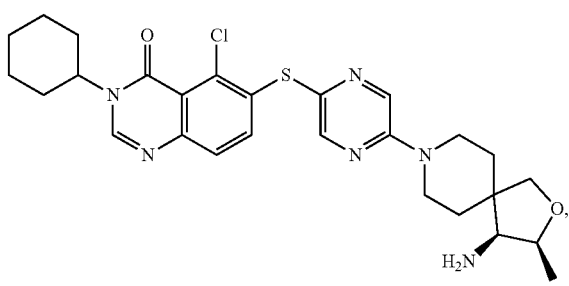
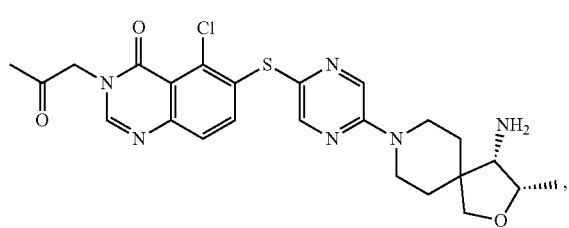 [SMILES: CC(=O)Cn1cnc2ccc(Sc3cnc(N4CCC5(CC4)CO[C@@H](C)[C@H]5N)cn3)c(Cl)c2c1=O]
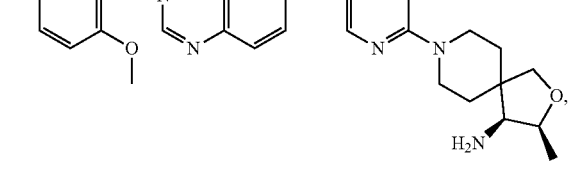
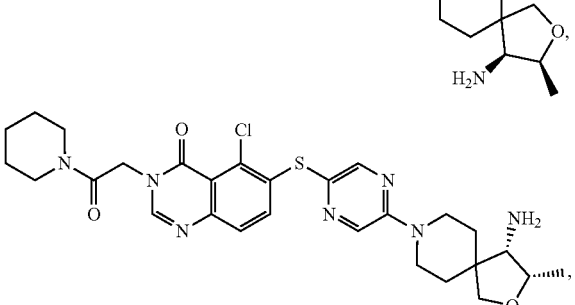
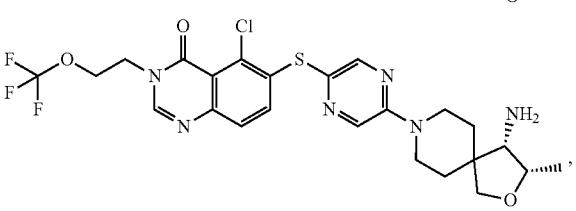
362
-continued
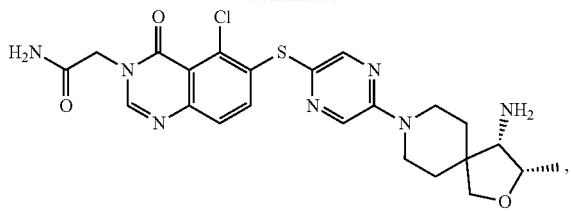
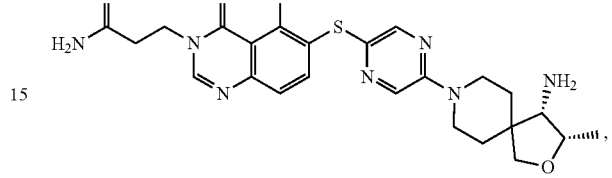
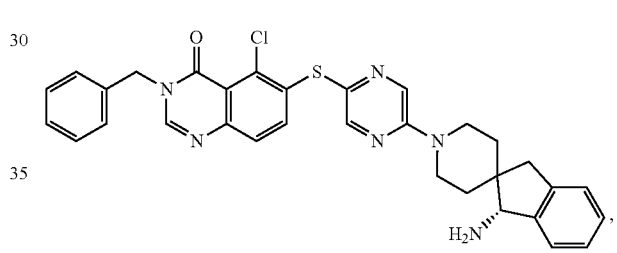
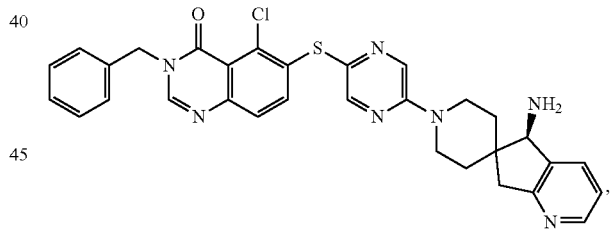
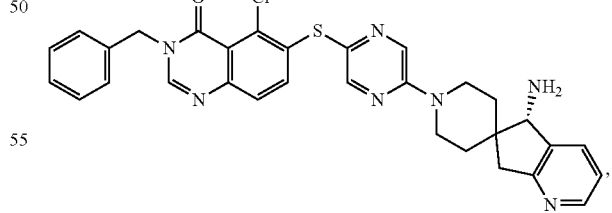
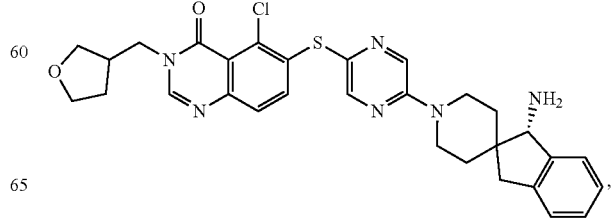

363                                   364
-continued                          -continued
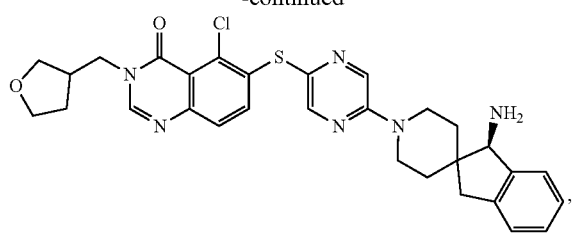
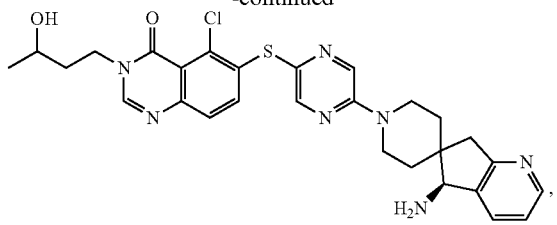
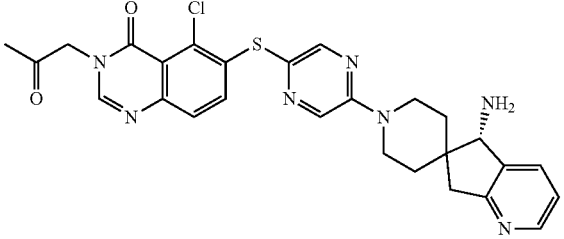
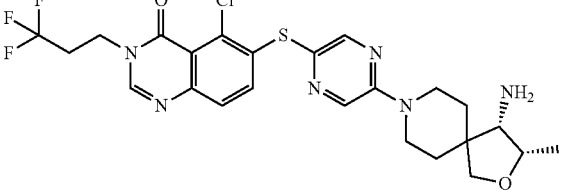
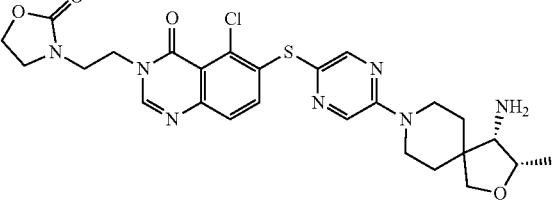
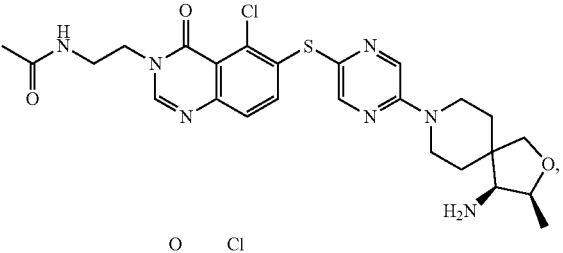
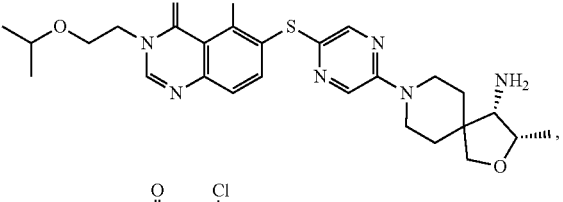
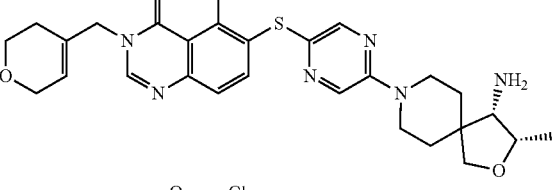
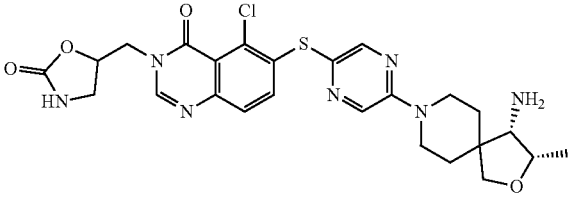

365
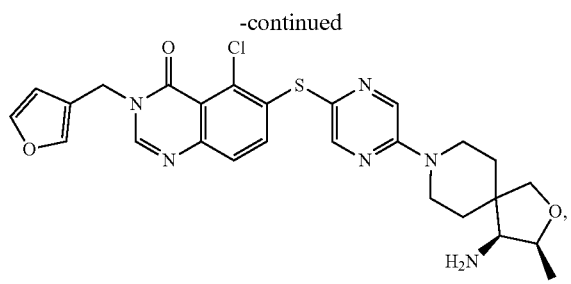
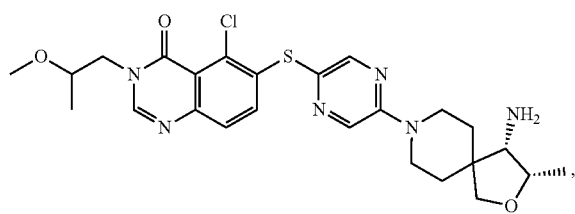
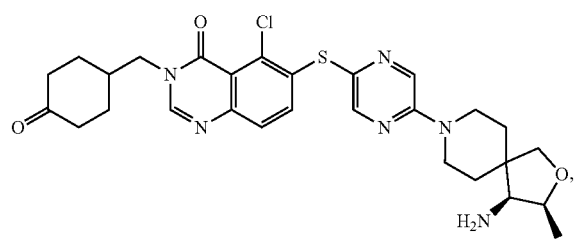
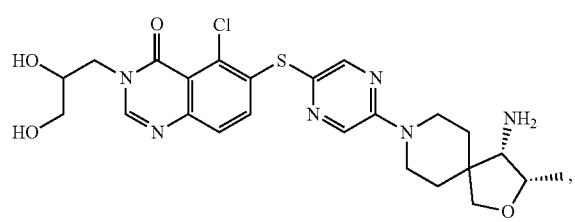
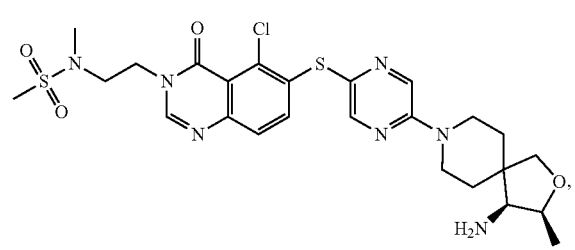
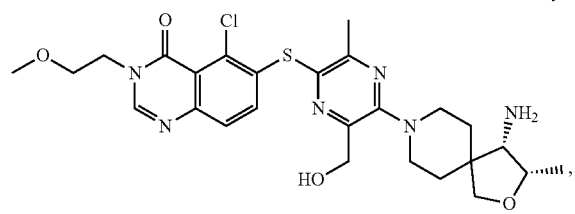
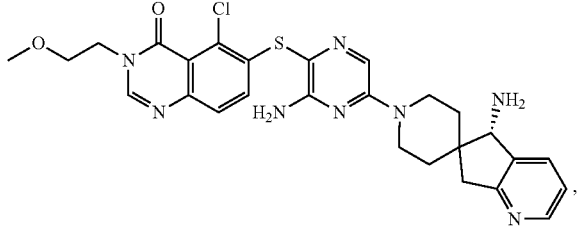
366
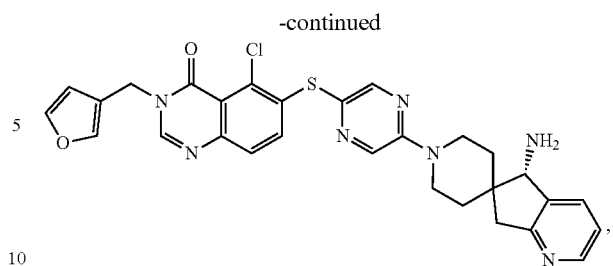
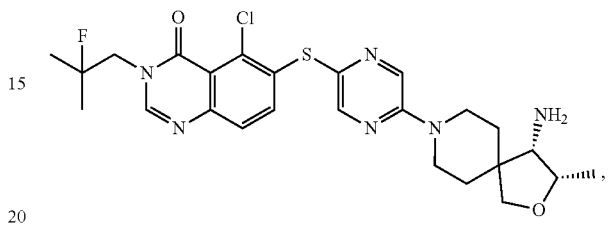
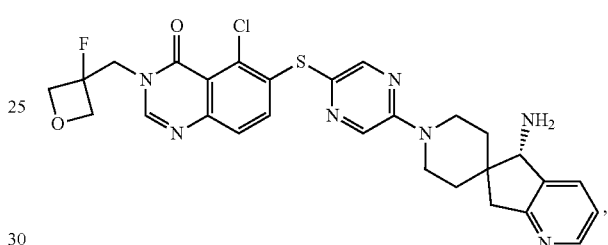
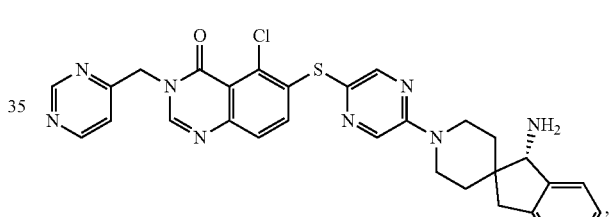
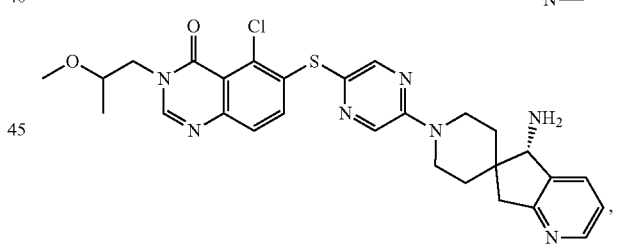
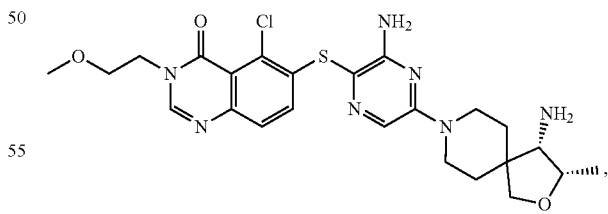
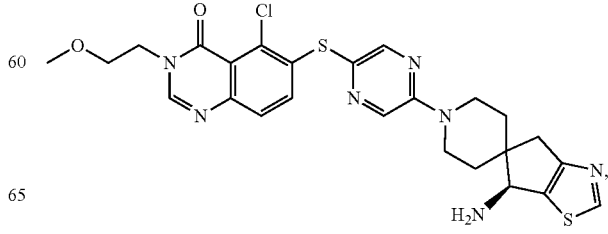

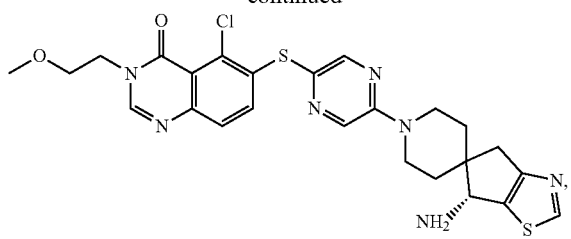
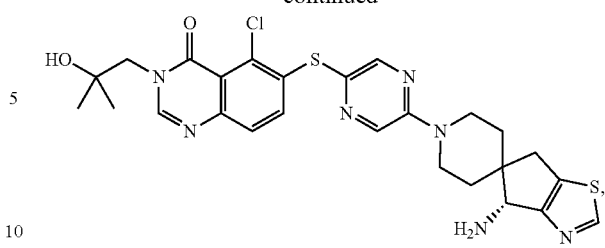
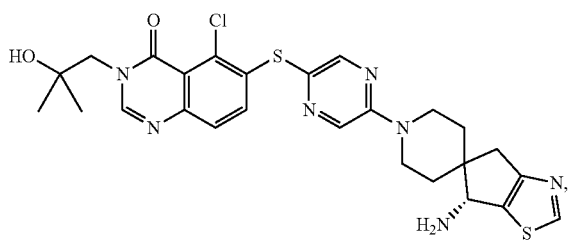
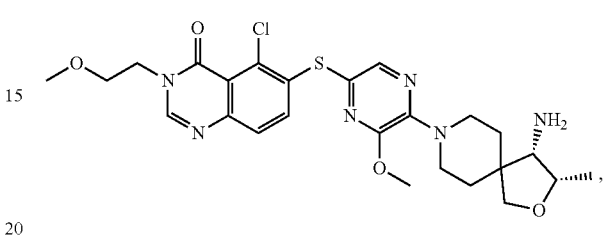
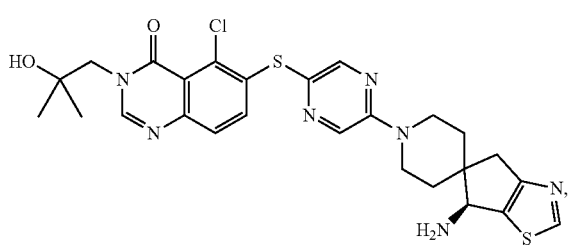
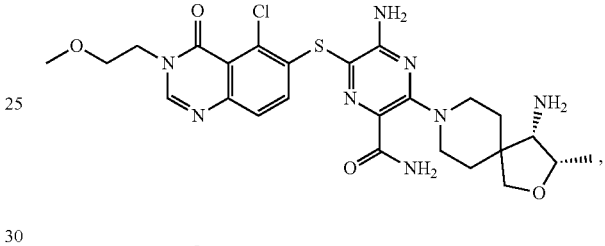
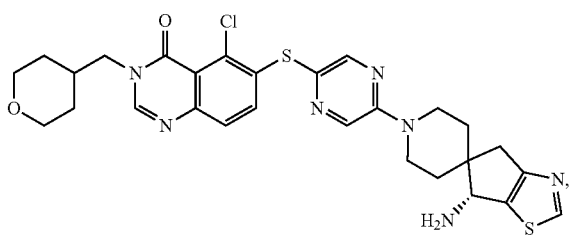
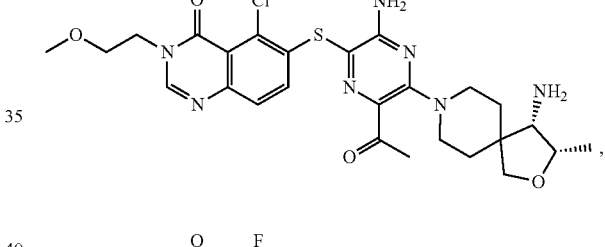
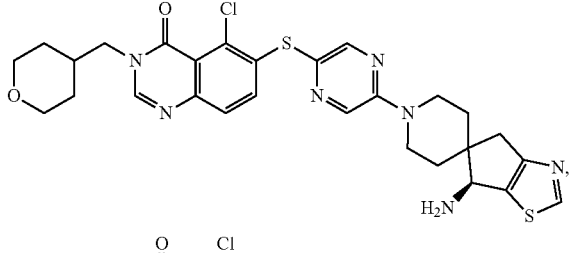
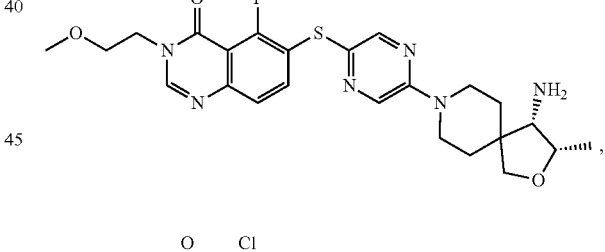
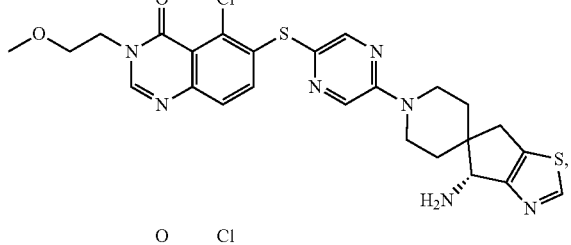
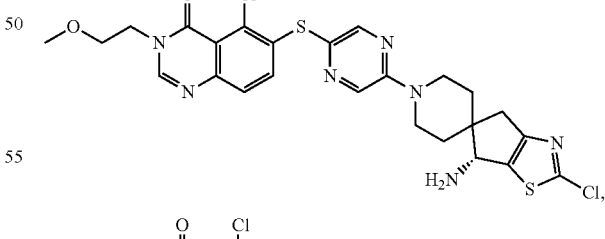
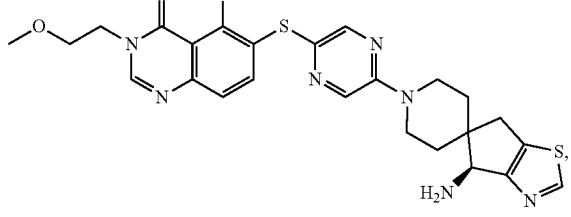
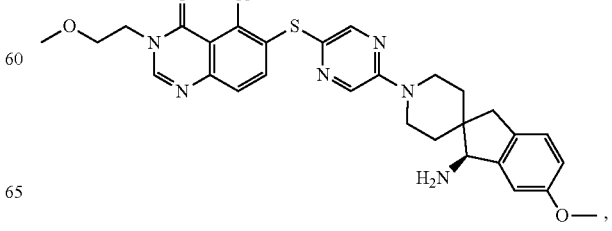

369
-continued
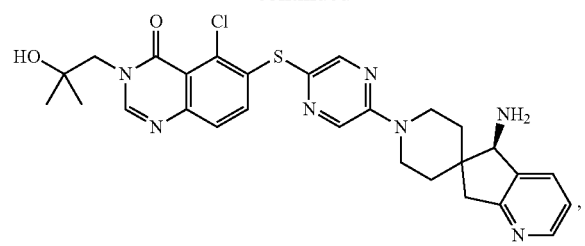
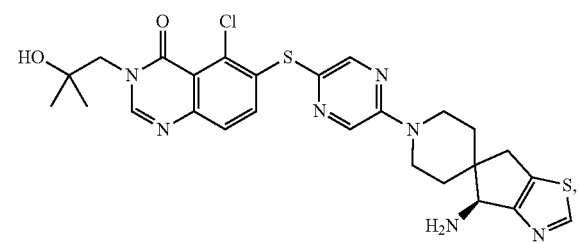
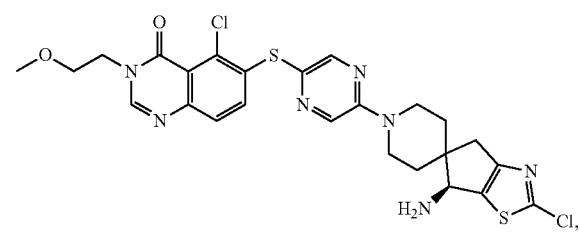
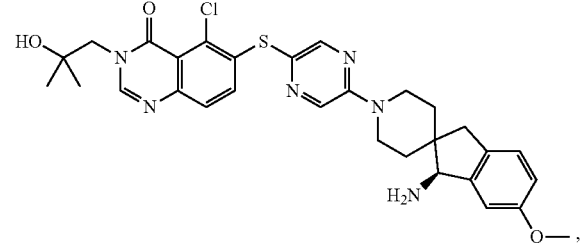
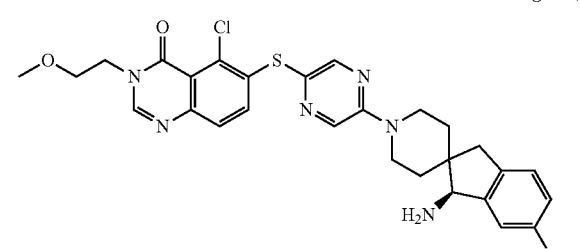
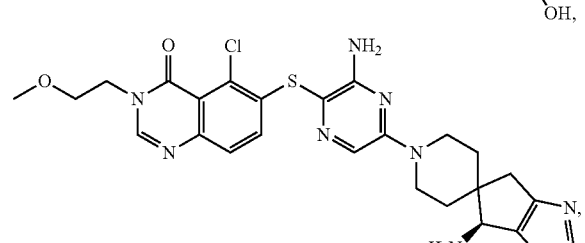
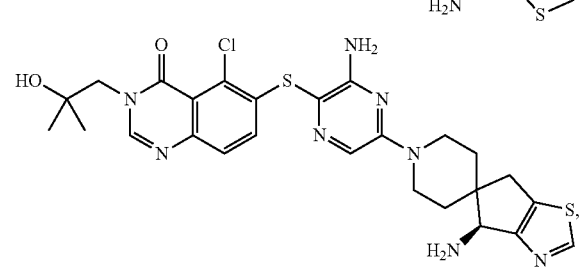
370
-continued
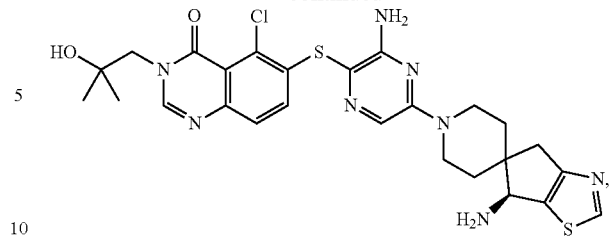
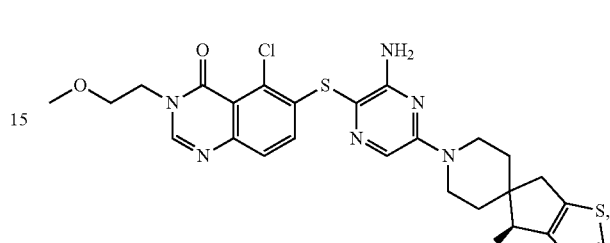
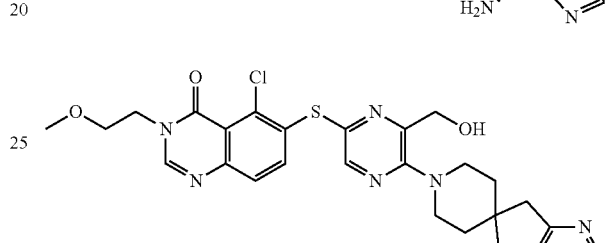
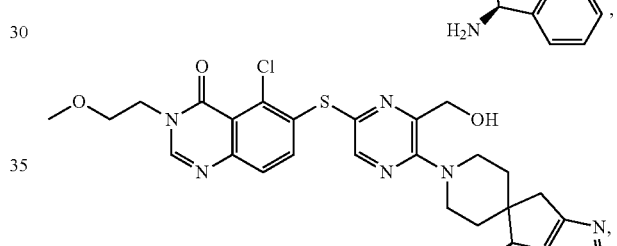
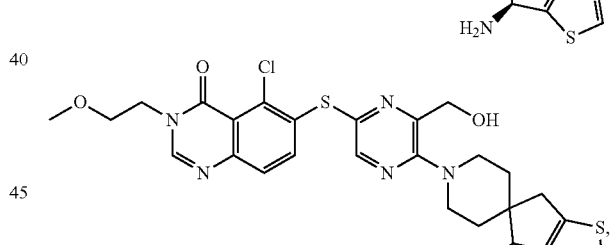
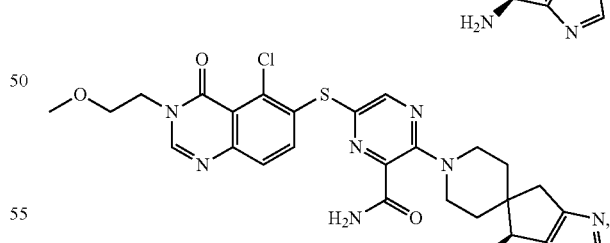
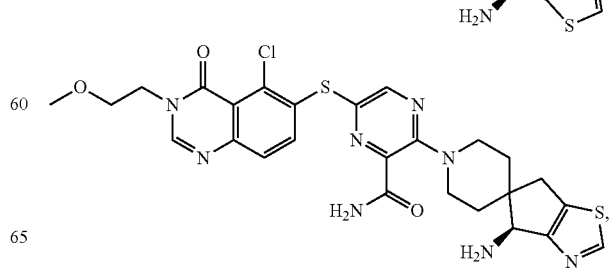

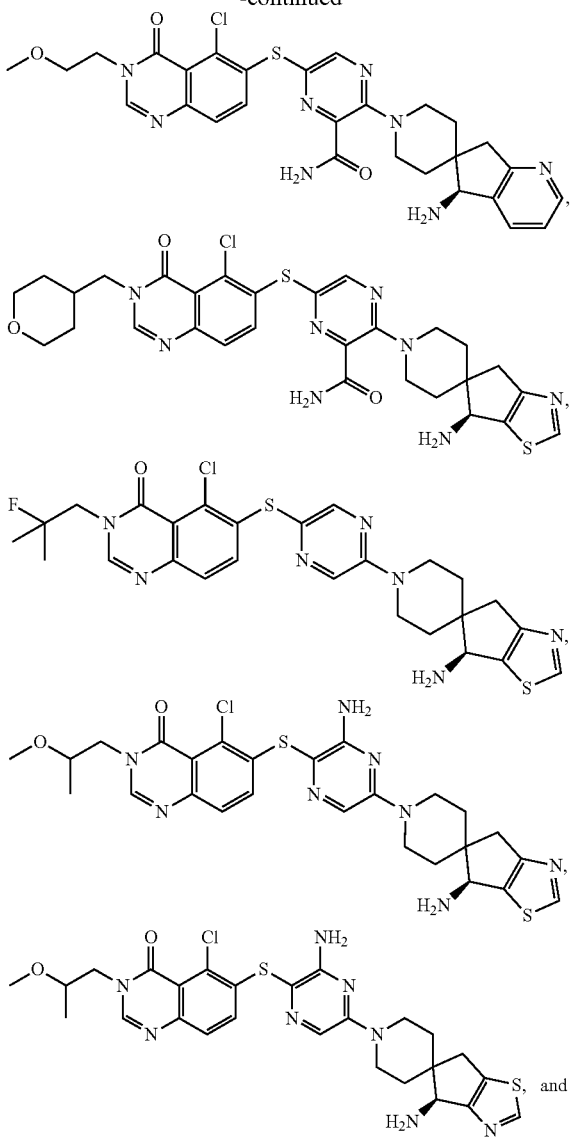

18. A pharmaceutical composition comprising the compound of claim 1, or a stereoisomer, solvate or pharmaceutically acceptable salt thereof.

19. A method for preventing or treating a disease associated with the abnormal activity of Src homology region 2 domain-containing phosphatase-2 (SHP2) in a subject in need thereof, the method comprising administering to the subject a therapeutically effective amount of the compound of claim 1, or a stereoisomer, solvate or pharmaceutically acceptable salt thereof.

20. The method according to claim 19, wherein the disease associated with the abnormal activity of SHP2 is selected from a group consisting of cancer, cancer metastasis, cardiovascular disease, immune disorder, fibrosis, and ocular disorder.

21. The method according to claim 19, wherein the disease associated with the abnormal activity of SHP2 is selected from a group consisting of Noonan syndrome, Leopard syndrome, juvenile myelomonocytic leukemia, neuroblastoma, melanoma, acute myeloid leukemia, breast cancer, esophageal cancer, lung cancer, large intestinal cancer, head cancer, squamous cell carcinoma of the head and neck, gastric carcinoma, anaplastic large cell lymphoma, glioblastoma, pancreatic cancer, biliary tract cancer, uterine cancer, endometrial cancer, liver cancer and neurofibromatosis type 1.

* * * * *

UNITED STATES PATENT AND TRADEMARK OFFICE
CERTIFICATE OF CORRECTION

PATENT NO. : 12,029,739 B2
APPLICATION NO. : 18/407400
DATED : July 9, 2024
INVENTOR(S) : Miyeon Kim et al.

Page 1 of 4

It is certified that error appears in the above-identified patent and that said Letters Patent is hereby corrected as shown below:

In the Claims

Column 333, Claim 1, Lines 24-25:
"heteroaryl carb onyl-($C_1$-$C_8$ alkyl)-,"
Should read:
-- heteroarylcarbonyl-($C_1$-$C_8$ alkyl)-, --.

Column 334, Claim 2, Line 4:
"R B,"
Should read:
-- $R^B$, --.

Column 334, Claim 2, Line 27:
"($C_6$-$C_{10}$ aryl)-($C_1$-$C_8$ alkyl)-,"
Should read:
-- ($C_6$-$C_{10}$ aryl)-($C_1$-$C_5$ alkyl)-, --.

Column 334, Claim 2, Line 29:
"($C_6$-$C_{10}$ arylcarbonyl)-($C_1$-$C_8$ alkyl)-,"
Should read:
-- ($C_6$-$C_{10}$ arylcarbonyl)-($C_1$-$C_5$ alkyl)-, --.

Column 334, Claim 2, Lines 30-31:
"-CONH-($C_1$-$C_8$ alkyl)-($C_6$-$C_{10}$ aryl),"
Should read:
-- -CONH-($C_1$-$C_5$ alkyl)-($C_6$-$C_{10}$ aryl), --.

Column 334, Claim 2, Lines 31-32:
"or -NHCO-($C_1$-$C_8$ alkyl)-($C_6$-$C_{10}$ aryl),"

Signed and Sealed this
Twenty-ninth Day of October, 2024

Katherine Kelly Vidal
*Director of the United States Patent and Trademark Office*

Should read:
-- or -NHCO-($C_1$-$C_5$ alkyl)-($C_6$-$C_{10}$ aryl), --.

Column 334, Claim 2, Lines 35-36:
"heteroaryl carb onyl-($C_1$-$C_5$ alkyl)-,"
Should read:
-- heteroarylcarbonyl-($C_1$-$C_5$ alkyl)-, --.

Column 334, Claim 2, Line 38:
"or -NHCO-($C_1$-$C_8$ alkyl)-heteroaryl,"
Should read:
-- or -NHCO-($C_1$-$C_5$ alkyl)-heteroaryl, --.

Column 335, Claim 3, Line 23:
"R B, wherein"
Should read:
-- $R^B$, wherein --.

Column 335, Claim 3, Line 30:
"one R BB,"
Should read:
-- one $R^{BB}$, --.

Column 339, Claim 11, Lines 30-35, Structure 1:

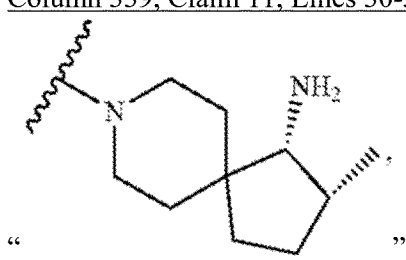

"                    "

Should read:

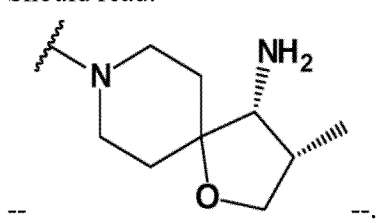

--                    --.

Column 339, Claim 11, Lines 30-35, Structure 2:

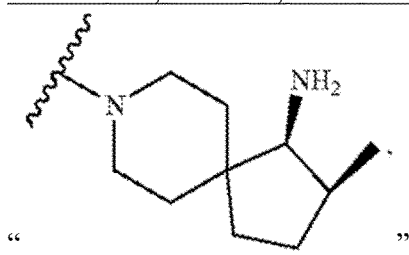

"                    "

CERTIFICATE OF CORRECTION (continued)
U.S. Pat. No. 12,029,739 B2

Should read:

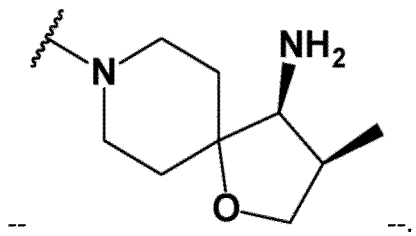

--.

Column 348, Claim 13, Line 9:
"heteroaryl-($C_1$-$C_3$ heteroaryloxy,"
Should read:
-- heteroaryl-($C_1$-$C_3$ alkyl)-, heteroaryloxy, --.

Column 348, Claim 13, Lines 10-11:
"heteroaryloxy-($C_1$-$C_3$ heteroarylcarbonyl, or"
Should read:
-- heteroaryloxy-($C_1$-$C_3$ alkyl)-, heteroarylcarbonyl, or --.

Column 348, Claim 13, Line 20:
"heterocycloalkyl-($C_1$-$C_3$ heterocycloalkyloxy,"
Should read:
-- heterocycloalkyl-($C_1$-$C_3$ alkyl)-, heterocycloalkyloxy, --.

Column 348, Claim 13, Lines 21-22:
"heterocycloalkyloxy-($C_1$-$C_3$ heterocycloalkylcarbonyl,"
Should read:
-- heterocycloalkyloxy-($C_1$-$C_3$ alkyl)-, heterocycloalkylcarbonyl, --.

Column 354, Claim 17, Lines 30-35:

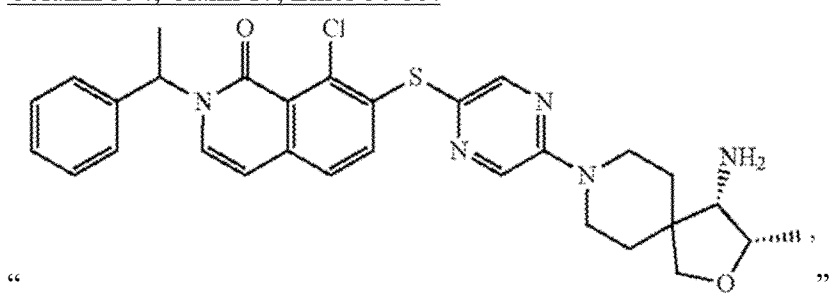

" "

Should read:

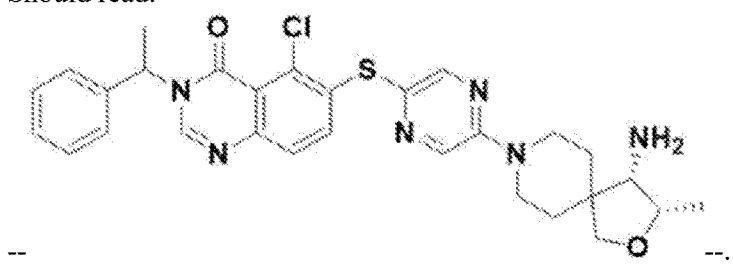

--.

CERTIFICATE OF CORRECTION (continued)
U.S. Pat. No. 12,029,739 B2

Column 368, Claim 17, Lines 14-20:

"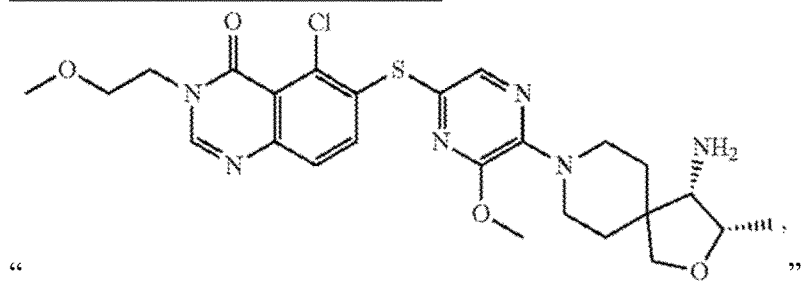"

Should read:

--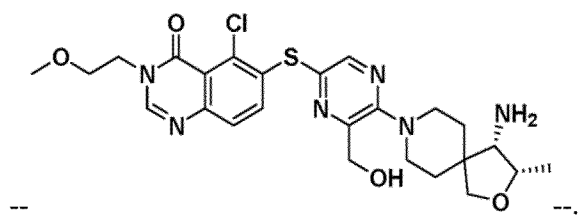--.